(12) United States Patent
Kinsella et al.

(10) Patent No.: US 11,352,360 B2
(45) Date of Patent: Jun. 7, 2022

(54) TGF-BETA INHIBITORS

(71) Applicants: Rigel Pharmaceuticals, Inc., South San Francisco, CA (US); Bristol-Myers Squibb Company, Princeton, NJ (US)

(72) Inventors: Todd Kinsella, Redwood City, CA (US); Marina Gelman, San Francisco, CA (US); Hui Hong, Foster City, CA (US); Ihab S. Darwish, San Carlos, CA (US); Rajinder Singh, Belmont, CA (US); Jiaxin Yu, San Carlos, CA (US); Robert M. Borzilleri, Carversville, PA (US); Upender Velaparthi, Cheshire, CT (US); Peiying Liu, Madison, CT (US); Chetan Padmakar Dame, Orange, CT (US); Hasibur Rahaman, Bangalore (IN); Jayakumar Sankara Warrier, Bangalore (IN)

(73) Assignees: Rigel Pharmaceuticals, hic., South San Francisco, CA (US); Bristol-Myers Squibb Company, Princeton, NJ (US)

( * ) Notice: Subject to any disclaimer, the term of this patent is extended or adjusted under 35 U.S.C. 154(b) by 184 days.

(21) Appl. No.: 16/360,162

(22) Filed: Mar. 21, 2019

(65) Prior Publication Data

US 2020/0031832 A1    Jan. 30, 2020

Related U.S. Application Data

(63) Continuation of application No. 15/860,379, filed on Jan. 2, 2018, now Pat. No. 10,287,295, which is a continuation of application No. 15/054,895, filed on Feb. 26, 2016, now Pat. No. 9,884,868.

(60) Provisional application No. 62/127,109, filed on Mar. 2, 2015.

(51) Int. Cl.

| C07D 487/04 | (2006.01) |
|---|---|
| C07D 401/04 | (2006.01) |
| C07D 403/04 | (2006.01) |
| C07D 471/04 | (2006.01) |
| A61P 35/00 | (2006.01) |
| C07D 417/04 | (2006.01) |

(52) U.S. Cl.
CPC ......... *C07D 487/04* (2013.01); *C07D 401/04* (2013.01); *C07D 403/04* (2013.01); *C07D 417/04* (2013.01); *C07D 471/04* (2013.01); *A61P 35/00* (2018.01)

(58) Field of Classification Search
CPC ... C07D 487/04; C07D 401/04; C07D 403/04
See application file for complete search history.

(56) References Cited

U.S. PATENT DOCUMENTS

| 2008/0227839 A1 | 9/2008 | Bonjouklian et al. |
|---|---|---|
| 2013/0137740 A1 | 5/2013 | Schobert et al. |
| 2014/0357612 A1 | 12/2014 | Zhang et al. |
| 2018/0127426 A1 | 5/2018 | Kinsella et al. |

FOREIGN PATENT DOCUMENTS

| CN | 103936730 | 7/2014 |
|---|---|---|
| EP | 2543372 | 1/2013 |
| WO | 2004/014900 | 2/2004 |
| WO | 2007/016392 | 2/2007 |
| WO | 2007/076348 | 7/2007 |
| WO | 2008/154241 | 12/2008 |
| WO | 2005/075478 | 1/2009 |
| WO | 2009/005675 | 1/2009 |
| WO | 2014/055955 | 4/2014 |
| WO | 2014/100533 | 6/2014 |

OTHER PUBLICATIONS

Vogelstein et al. Nature Medicine (2004), vol. 10, pp. 789-799 (Year: 2004).*
Clinical Cancer Res (2012), vol. 18, pp. 4514-4521 (Year: 2012).*
Gellibert et al., "Identification of 1,5-Naphthyridine Derivatives as a Novel Series of Potent and Selective TGF-[beta] Type 1 Receptor Inhibitors," Journal of medicinal Chemistry, vol. 47, No. 18, Apr. 8, 2004, pp. 4494-4506.
Wang et al., "Potent, orally, active heterocycle-based combretastatin A-4 analogues: synthesis, structure-activity relationship, pharmacokinetics, and in vivo antitumor activity evaluation," Journal of Medicinal Chemistry, American Chemical Society, vol. 45, Jan. 1, 2002, pp. 1697-1711.
De Dios et al., "Design of potent and selective 2-aminobenzimidazole-based p38alpha MAP kinase inhibitors with excellent in vivo efficacy," Journal of Medicinal Chemistry, American Chemical Society, US, vol. 48, No. 7, Feb. 19, 2005, pp. 2270-2273.

(Continued)

*Primary Examiner* — Samira J Jean-Louis
(74) *Attorney, Agent, or Firm* — Klarquist Sparkman, LLP

(57) ABSTRACT

Disclosed are imidazole and thiazole compounds, as well as pharmaceutical compositions and methods of use thereof. One embodiment is a compound having the structure

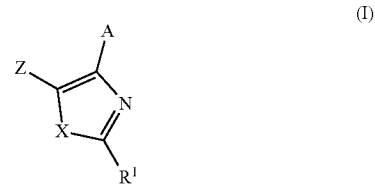

(I)

and pharmaceutically acceptable salts, prodrugs and N-oxides thereof (and solvates and hydrates thereof), wherein X, A, Z, $R^1$ and R' are as described herein. In certain embodiments, a compound disclosed herein inhibits TGF-β, and can be used to treat disease by blocking TGF-β signaling.

21 Claims, No Drawings

(56) References Cited

OTHER PUBLICATIONS

Liu et al., "Benzothiazole based inhibitors of p38alpha MAP kinase," Bioorganic & Medicinal Chemistry Letters, Pergamon, Amsterdam, NL, vol. 18, No. 6, Mar. 15, 2008, pp. 1874-1879.
Mader et al., "Imidazolyl benzimidazoles and imidazo[4,5-b]pyridines as potent p38alpha MAP kinase inhibitors with excellent in vivo antiinflammatory properties," Bioorganic & Medicinal Chemistry Letters, Pergamon, Amsterdam, NL, vol. 18, No. 1, Nov. 1, 2007, pp. 179-183.
Schobert et al., "4-(3-Halo/amino-4,5-dimethoxyphenyl)-5-aryloxazoles and -N-methylimidazoles That are Cytotoxic against Combretatstatin A Resistant Tumor Cells and Vascular Disrupting in a Cisplatin Resistant Germ Cell Tumor Model".
Akhurst et al., Nature (2012) vol. 11, pp. 790-811.
Lippard The Art of Chemistry, Nature 2002, vol. 416, pp. 587.
Irini Akritopoulou-Zanze et al., "Scaffold Oriented Synthesis Part 4: Design, Synthesis and Biological Evaluation of Novel 5-Substituted Indazoles as Potent and Selective Kinase Inhibitors Employing Heterocycle Forming and Multicomponent Reactions," *Bioorganic & Medicinal Chemistry Letters*, vol. 21 (2011) pp. 1480-1483.
Ji-Xia Ren et al., "Pharmacophore Modeling and Virtual Screening for the Discovery of New Transforming Growth Factor-β type I Receptor (ALK5) Inhibitors," *European Journal of Medicinal Chemistry*, vol. 44 (2009), pp. 4259-4265.

* cited by examiner

TGF-BETA INHIBITORS

CROSS-REFERENCE TO RELATED APPLICATIONS

This application is a continuation of U.S. application Ser. No. 15/860,379, filed Jan. 2, 2018, which is a continuation of U.S. application Ser. No. 15/054,895, filed Feb. 26, 2016, now U.S. Pat. No. 9,884,868, which claims the benefit of priority of US provisional application no. 62/127,109, filed Mar. 2, 2015, the entire contents of which are hereby incorporated by reference into this specification.

BACKGROUND

Field of Invention

This invention relates to the field of compounds, pharmaceutical compositions comprising them, and methods of using the compounds and compositions. This invention relates more particularly to the field of imidazole and thiazole compounds and pharmaceutical compositions thereof, methods of inhibiting TGF-β with the compounds, and methods of treating and/or preventing disease with the compounds.

Technical Background

Growth and Differentiation Factor-8 (GDF-8), also known as myostatin, and TGF-β1 are members of the Transforming Growth Factor-beta (TGF-β) superfamily of structurally related growth factors, all of which possess physiologically important growth-regulatory and morphogenetic properties (Kingsley et al. (1994) Genes Dev., 8: 133-46; Hoodless et al. (1998) Curr. Topics Microbiol. Immunol., 228: 235-72). For example, activation of TGF-β1 signaling and expansion of extracellular matrix are early and persistent contributors to the development and progression of fibrotic disorders, such as involved in chronic renal disease and vascular disease. Border W. A., et al, N. Engl. J. Med., 1994; 331(19), 1286-92. GDF-8 is a negative regulator of skeletal muscle mass. For example, GDF-8 is highly expressed in the developing and adult skeletal muscle. The GDF-8 null mutation in transgenic mice is characterized by a marked hypertrophy and hyperplasia of the skeletal muscle (McPherron et al. (1997) Nature, 387: 83-90). Similar increases in skeletal muscle mass are evident in naturally occurring mutations of GDF-8 in cattle (Ashmore et al. (1974) Growth, 38: 501 507; Swatland and Kieffer (1994) J. Anim. Sci., 38: 752-757; McPherron and Lee (1997) Proc. Natl. Acad. Sci. USA, 94: 12457-12461; and Kambadur et al. (1997) Genome Res., 7: 910-915). Because GDF-8 is expressed in both developing and adult muscles, it is not clear whether it regulates muscle mass during development or in adults. Recent studies have also shown that muscle wasting associated with HIV-infection in humans is accompanied by increases in GDF-8 protein expression (Gonzalez-Cadavid et al. (1998) PNAS, 95: 14938-43). In addition, GDF-8 can modulate the production of muscle-specific enzymes (e.g., creatine kinase) and modulate myoblast cell proliferation (WO 00/43781).

A number of human and animal disorders are associated with loss or functional impairment of muscle tissue, including muscular dystrophy, muscle atrophy, congestive obstructive pulmonary disease, muscle wasting syndrome, sarcopenia, and cachexia. To date, very few reliable or effective therapies exist for these disorders. However, the terrible symptoms associated with these disorders may be substantially reduced by employing therapies that increase the amount of muscle tissue in patients suffering from the disorders. While not curing the conditions, such therapies would significantly improve the quality of life for these patients and could ameliorate some of the effects of these diseases.

In addition to its growth-regulatory and morphogenetic properties in skeletal muscle, GDF-8 may also be involved in a number of other physiological processes, including glucose homeostasis in the development of type 2 diabetes and adipose tissue disorders, such as obesity. For example, GDF-8 modulates pre-adipocyte differentiation to adipocytes (Kim et al. (2001) BBRC, 281: 902-906).

Alteration in TGF-β signaling are associated with a wide variety of human disorders including fibrosis, inflammatory, skeletal, muscular and cardiovascular disorders as well as cancer (Harradine, et al, 2006, Annals of Medicine 38:403-14). In human cancer, TGF-β signaling alterations can occur in the germline or arise spontaneously in various cancer types. TGF-β is also a potent inducer of angiogenesis, which provides a critical support system for solid tumors as well as a mechanism for tumor cell dissemination (Buijs et al., 2011, Curr Pharmaceutical Biotech, 12:2121-37). Therefore multiple strategies to inhibit TGF-β signaling have been exploited in various disease states.

There are also a number of conditions associated with a loss of bone, including osteoporosis, especially in the elderly and/or postmenopausal women. Currently available therapies for these conditions work by inhibiting bone resorption.

Like TGF-β-1, -2, and -3, the GDF-8 protein is synthesized as a precursor protein consisting of an amino-terminal propeptide and a carboxy-terminal mature domain (McPherron and Lee, (1997) Proc. Natl. Acad. Sci. USA, 94: 12457-12461). Before cleavage, the precursor GDF-8 protein forms a homodimer. The amino-terminal propeptide is then cleaved from the mature domain. The cleaved propeptide may remain noncovalently bound to the mature domain dimer, inactivating its biological activity (Miyazono et al. (1988) J. Biol. Chem., 263: 6407-6415; Wakefield et al. (1988) J. Biol. Chem., 263; 7646-7654; and Brown et al. (1990) Growth Factors, 3: 35-43). It is believed that two GDF-8 propeptides bind to the GDF-8 mature dimer (Thies et al. (2001) Growth Factors, 18: 251-259). Due to this inactivating property, the propeptide is known as the "latency-associated peptide" (LAP), and the complex of mature domain and propeptide is commonly referred to as the "small latent complex" (Gentry and Nash (1990) Biochemistry, 29: 6851-6857; Derynck et al. (1995) Nature, 316: 701-705; and Massague (1990) Ann. Rev. Cell Biol., 12: 597-641). Other proteins are also known to bind to GDF-8 or structurally related proteins and inhibit their biological activity. Such inhibitory proteins include follistatin, and potentially, follistatin-related proteins (Gamer et al. (1999) Dev. Biol., 208: 222-232). The mature domain is believed to be active as a homodimer when the propeptide is removed.

GDF-8 is highly conserved in sequence and in function across species. The amino acid sequence of murine and human GDF-8 is identical, as is the pattern of mRNA expression (McPherron et al. (1997) Nature 387: 83-90; Gonzalez-Cadavid et al. (1998) Proc. Natl. Acad. Sci. USA 95: 14938-14943). This conservation of sequence and function suggests that inhibition of GDF-8 in humans is likely to have a similar effect to inhibition of GDF-8 in mice.

U.S. Pat. No. 7,320,789 shows that GDF-8 antibodies in mouse models can increase muscle strength (e.g., for treating sarcopenia), increase muscle mass and strength in dystrophic muscle (e.g., for treating Duchenne's muscular dystrophy), increase bone mass and bone density (e.g., for prevention and treatment of osteoporosis), augment bone healing (e.g., for treating an established muscle or bone degenerative disease (e.g., fracture repair and spine fusion, preventing the decline in bone mass, microarchitecture and strength associated with estrogen deficiency, increasing trabecular bone density), and are useful for treatment of metabolic disorders such as type 2 diabetes, impaired glucose tolerance, metabolic syndrome (e.g., syndrome X), insulin resistance induced by trauma (e.g., burns), and adipose tissue disorders (e.g., obesity).

SUMMARY

In view of the foregoing, we recognized that new therapeutic agents that inhibit the activity of one or more members of the TGF-β superfamily may useful and therefore desirable for treating human or animal disorders in which an increase in muscle tissue would be therapeutically beneficial, particularly muscle and adipose tissue disorders, bone degenerative diseases, neuromuscular disorders, and diabetes.

Accordingly, the present invention comprises compounds, pharmaceutical compositions comprising them, and methods of using them to inhibit TGF-β superfamily activity both in vitro and in vivo and to treat and/or prevent disease by inhibiting TGF-β superfamily activity.

Disclosed herein are compounds having structural formula (I):

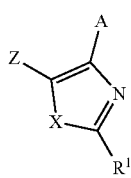

(I)

and pharmaceutically acceptable salts, prodrugs, and N-oxides thereof (and solvates and hydrates thereof), wherein X, A, Z, $R^1$ and R' are as described herein.

Also disclosed herein are pharmaceutical compositions. Examples of such compositions include those having at least one pharmaceutically acceptable carrier, diluent, and/or excipient together with a compound, pharmaceutically acceptable salt, prodrug, or N-oxide (or solvate or hydrate) as described herein.

Another aspect of the present invention comprises methods for treating and/or preventing disease by blocking GDF 8, TGF-β, activin or combinations thereof. Accordingly, the invention also comprises methods for treating disease using the presently disclosed compounds and pharmaceutical compositions.

Another aspect of the invention is the use of the compounds described herein to block TGF-β superfamily activity in vitro and in vivo for the purpose of studying their role in biological processes.

All publications referenced herein are incorporated by reference in their entirety to the extent they are not inconsistent with the teachings presented herein.

DETAILED DESCRIPTION

In one aspect, the invention comprises compounds that inhibit TGF-β.

In embodiment I°$_1$ of this first aspect, the compounds have structural formula (I°):

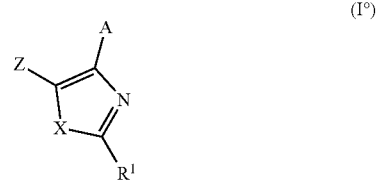

(I°)

or a pharmaceutically acceptable salt, prodrug, or N-oxide thereof, or a solvate or hydrate thereof, wherein X is —S— or —N(R')—;

R' is hydrogen, $C_1$-$C_6$alkyl, $C_1$-$C_6$ haloalkyl, $C_1$-$C_6$alkyloxy, —($C_0$-$C_{12}$alkyl)-Cak or —($C_0$-$C_6$alkyl)-Hca, each optionally substituted with 1 to 3 moieties that are each independently $C_1$-$C_6$alkyl, halogen, $C_1$-$C_6$ haloalkyl, —OR$^{S0}$, $C_1$-$C_6$alkyl-OR$^{S0'}$, C(O)OR$^{S0}$, —C(O)$^{S0}$, —C(O)NR$^{S0}$$_2$, —R$^{S0}$ or cyano;

wherein each R$^{S0}$ is independently hydrogen, $C_1$-$C_6$alkyl, $C_1$-$C_6$ haloalkyl, —($C_0$-$C_6$alkyl)-Ar, —($C_0$-$C_6$alkyl)-Het, —($C_0$-$C_6$alkyl)-Cak, or —($C_0$-$C_6$alkyl)-Hca, wherein Ar, Het, Cak, Hca, alkyl, and haloalkyl are optionally substituted with $C_1$-$C_6$alkyl, halogen, $C_1$-$C_6$ haloalkyl or cyano;

$R^1$ is hydrogen, $C_1$-$C_6$alkyl, $C_1$-$C_6$ haloalkyl, $C_1$-$C_6$alkyloxy, —OR$^{S1}$, —NR$^{S1}$$_2$, —SR$^{S1}$ or —N(R$^{S1}$)C(O)R$^{S1}$, each optionally substituted with 1 to 3 moieties that are each independently $C_1$-$C_6$alkyl, halogen, $C_1$-$C_6$ haloalkyl or cyano;

wherein each R$^{S1}$ is independently hydrogen, $C_1$-$C_6$alkyl, $C_1$-$C_6$ haloalkyl, —($C_0$-$C_6$alkyl)-Ar, —($C_0$-$C_6$alkyl)-Het, —($C_0$-$C_6$alkyl)-Cak, or —($C_0$-$C_6$alkyl)-Hca, wherein Ar, Het, Cak, Hca, alkyl, and haloalkyl are optionally substituted with $C_1$-$C_6$alkyl, halogen, $C_1$-$C_6$ haloalkyl or cyano;

or R' and $R^1$ combined with the atoms to which they are attached form a five- to eight-membered ring;

A is phenyl optionally substituted with one to five $R^2$ groups, wherein each $R^2$ is independently halogen, —$C_1$-$C_6$alkyl, —$C_1$-$C_6$ haloalkyl, —$C_1$-$C_6$alkoxy, —$C_1$-$C_6$ haloalkoxy, —NO$_2$, —N(R$^{S2}$)C(O)R$^{S2}$, —OR$^{S2}$, —C(O)NR$^{S2}$$_2$, —N(R$^{S2}$)S(O)$_2$R$^{S2}$, —S(O)$_2$R$^{S2}$, —($C_0$-$C_6$alkyl)-Ar or —CN, wherein each alkyl, haloalkyl and alkoxy are optionally substituted with 1, 2, 3, or 4 groups that are each independently halogen, cyano, nitro, —OR$^{S2}$, —SR$^{S2}$, —NR$^{S2}$$_2$, —C(O)OR$^{S2}$, —C(O)NR$^{S2}$$_2$, —C(O)R$^{S2}$, —S(O)R$^{S2}$, —S(O)$_2$R$^{S2}$, —S(O)OR$^{S2}$, —S(O)$_2$OR$^{S2}$, —S(O)NR$^{S2}$$_2$, —S(O)$^2$NR$^{S2}$$_2$, —OC(O)R$^{S2}$, —OC(O)OR$^{S2}$, —OC(O)NR$^{S2}$$_2$, —N(R$^{S2}$)C(O)R$^{S2}$, —N(R$^{S2}$)C(O)OR$^{S2}$, —N(R$^{S1}$)C(O)NR$^{S2}$$_2$, —N(R$^{S2}$)S(O)R$^{S2}$, —N(R$^{S2}$)S(O)$_2$R$^{S2}$, $C_1$-$C_6$alkyl, or $C_1$-$C_6$ haloalkyl;

wherein each R$^{S2}$ is independently hydrogen, $C_1$-$C_6$alkyl, $C_1$-$C_6$ haloalkyl, —($C_0$-$C_6$alkyl)-Ar, —($C_0$-$C_6$alkyl)-Het, —($C_0$-$C_6$alkyl)-Cak, or —($C_0$-$C_6$alkyl)-Hca, wherein Ar, Het, Cak, Hca, alkyl, and haloalkyl are optionally substituted with $C_1$-$C_6$alkyl, halogen, $C_1$-$C_6$ haloalkyl or cyano;

Z is
a fused bicyclic ring of the formula,

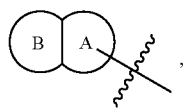

wherein
ring A is Ar or 5- or 6-membered Het,
ring B is 5- or 6-membered Het,
wherein
Z is optionally substituted by one or two —$R^Z$ groups that are each independently halogen, cyano, $C_{1-6}$alkyl, $C_{1-6}$alkenyl, $C_{1-6}$ haloalkyl, —$C_1$-$C_6$alkoxy, —($C_0$-$C_6$alkyl)-Het, —($C_0$-$C_6$alkyl)-Hca, —$OR^{S3}$, —$SR^{S3}$, —$NR^{S3}_2$, —$C(O)R^{S3}$, —$C(O)OR^{S3}$, —$C(O)NR^{S3}_2$, —$C(NR^{S3})NR^{S3}OR^{S3}$, —$S(O)_2NR^{S3}_2$, —$S(O)_2R^{S3}$, —$OC(O)R^{S3}$, —$N(R^{S3})C(O)R^{S3}$, —$OC(O)OR^{S3}$, —$OC(O)NR^{S3}_2$, —$N(R^{S3})C(O)OR^{S3}$, —$N(R^{S3})C(O)NR^{S3}_2$, —$N(R^{S3f})S(O)_2R^{S3}$, —$OP(O)(OR^{S3})_2$ or —$CH_2$—$OP(O)(OR^{S3})$, wherein each alkyl, haloalkyl and alkoxy is optionally substituted by one or two —$R^{Z2}$ groups;
wherein each $R^{S3}$ is independently hydrogen, —$NR^{S3}_2$, —$OR^{S3}$, $C_1$-$C_6$alkyl, $C_1$-$C_6$ haloalkyl, —($C_0$-$C_6$alkyl)-Ar, —($C_0$-$C_6$alkyl)-Het, —($C_0$-$C_6$alkyl)-Cak, or —($C_0$-$C_6$alkyl)-Hca, wherein Ar, Het, Cak, Hca, alkyl, and haloalkyl are optionally substituted with $C_1$-$C_6$alkyl, halogen, $C_1$-$C_6$ haloalkyl, —$C(O)NR^{S4}_2$ or cyano; and
each —$R^{Z2}$ is independently halogen, cyano, $C_{1-6}$alkyl, $C_{1-6}$ haloalkyl, —$C_1$-$C_6$alkoxy, —$OR^{S4}$, —$SR^{S4}$, —$NR^{S4}_2$, —$C(O)R^{S4}$, —$C(O)OR^{S4}$, —$C(O)NR^{S4}_2$, —$S(O)_2NR^{S4}_2$, —$S(O)_2R^{S4}$, —$OC(O)R^{S4}$, —$N(R^{S4})C(O)R^{S4}$, —$OC(O)OR^{S4}$, —$OC(O)NR^{S4}_2$, —$N(R^{S4})C(O)OR^{S4}$, —$N(R^{S4})C(O)NR^{S4}_2$, —$N(R^{S4})S(O)_2R^{S4}$, —$OP(O)(OR^{S4})_2$ or —$CH_2$—$OP(O)(OR^{S4})$; and
wherein each $R^{S4}$ is independently hydrogen, $C_1$-$C_6$alkyl, $C_1$-$C_6$ haloalkyl, —($C_0$-$C_6$alkyl)-Ar, —($C_0$-$C_6$alkyl)-Het, —($C_0$-$C_6$alkyl)-Cak, or —($C_0$-$C_6$alkyl)-Hca,
wherein Ar, Het, Cak, Hca, alkyl, and haloalkyl are optionally substituted with one or two $C_1$-$C_6$alkyl, halogen, $C_1$-$C_6$ haloalkyl or cyano.

In embodiment I°$_1$', the compounds are of embodiment I°$_1$, provided that the compound is not any compound expressly recited in "Benzothiazole Based Inhibitors of p38a MAP Kinase" Liu, C. et al. Bioorganic & Medicinal Chemistry Letters (2008), 18(6), 1874-1879; International Publication No. WO 2004014900 A1; International Publication No. WO 2002072576 A1; or "Potent, Orally Active Heterocycle-Based Combretastatin A-4 Analogues: Synthesis, Structure-Activity Relationship" Wang, L. et al. Journal of Medicinal Chemistry (2002), 45(8), 1697-1711.

In embodiment I°$_2$, the compounds are of embodiment I°$_1$, provided that the compound is not:
6-(4-phenyl-1H-imidazol-5-yl)-1H-benzo[d]imidazol-2-amine;
5-(4-(m-tolyl)-1H-imidazol-5-yl)-1,3-dihydro-2H-benzo[d]imidazol-2-one;
1-methyl-6-(4-phenyl-1H-imidazol-5-yl)-1H-benzo[d][1,2,3]triazole;
6-(4-phenyl-1H-imidazol-5-yl)benzo[d]thiazol-2-amine;
1-isopropyl-6-(4-phenyl-1H-imidazol-5-yl)-1H-benzo[d][1,2,3]triazole;
N-benzyl-6-(4-phenyl-1H-imidazol-5-yl)-1H-benzo[d]imidazol-2-amine;
1-ethyl-6-(4-(m-tolyl)-1H-imidazol-5-yl)-1H-benzo[d][1,2,3]triazole;
6-(4-(4-fluorophenyl)-1H-imidazol-5-yl)-1-methyl-1H-benzo[d][1,2,3]triazole;
1-ethyl-6-(4-(4-fluorophenyl)-1H-imidazol-5-yl)-1H-benzo[d][1,2,3]triazole;
1-methyl-5-(4-(m-tolyl)-1H-imidazol-5-yl)-1,3-dihydro-2H-benzo[d]imidazol-2-one;
1,3-dimethyl-5-(4-phenyl-1H-imidazol-5-yl)-1,3-dihydro-2H-benzo[d]imidazol-2-one;
N-isopropyl-6-(4-phenyl-1H-imidazol-5-yl)benzo[d]thiazol-2-amine;
1-methyl-6-(4-(m-tolyl)-1H-imidazol-5-yl)-1,3-dihydro-2H-benzo[d]imidazol-2-one;
6-(4-(4-fluorophenyl)-1H-imidazol-5-yl)-1-isopropyl-1H-benzo[d][1,2,3]triazole;
6-(4-(4-fluoro-3-methylphenyl)-1H-imidazol-5-yl)-1-methyl-1H-benzo[d][1,2,3]triazole;
1-ethyl-6-(4-(m-tolyl)-1H-imidazol-5-yl)-1,3-dihydro-2H-benzo[d]imidazol-2-one;
1,3-dimethyl-5-(4-(m-tolyl)-1H-imidazol-5-yl)-1,3-dihydro-2H-benzo[d]imidazol-2-one;
1,3-diethyl-5-(4-phenyl-1H-imidazol-5-yl)-1,3-dihydro-2H-benzo[d]imidazol-2-one;
1-isopropyl-6-(4-(m-tolyl)-1H-imidazol-5-yl)-1,3-dihydro-2H-benzo[d]imidazol-2-one;
6-(4-(4-fluoro-3-methylphenyl)-1H-imidazol-5-yl)-1-isopropyl-1H-benzo[d][1,2,3]triazole;
5-(4-(4-fluorophenyl)-1H-imidazol-5-yl)-1,3-dimethyl-1,3-dihydro-2H-benzo[d]imidazol-2-one;
6-(4-(4-fluoro-3-methylphenyl)-1H-imidazol-5-yl)-1-isopropyl-1H-benzo[d][1,2,3]triazole;
3-ethyl-1-methyl-5-(4-(m*-tolyl)-1H-imidazol-5-yl)-1,3-dihydro-2H-benzo[d]imidazol-2-one;
1-ethyl-3-methyl-5-(4-(m-tolyl)-1H-imidazol-5-yl)-1,3-dihydro-2H-benzo[d]imidazol-2-one;
1-phenyl-6-(4-(m-tolyl)-1H-imidazol-5-yl)-1,3-dihydro-2H-benzo[d]imidazol-2-one;
1,3-diethyl-5-(4-(m-tolyl)-1H-imidazol-5-yl)-1,3-dihydro-2H-benzo[d]imidazol-2-one;
1-isopropyl-3-methyl-5-(4-(m-tolyl)-1H-imidazol-5-yl)-1,3-dihydro-2H-benzo[d]imidazol-2-one;
3-isopropyl-1-methyl-5-(4-(m-tolyl)-1H-imidazol-5-yl)-1,3-dihydro-2H-benzo[d]imidazol-2-one;
3-methyl-1-phenyl-5-(4-(m-tolyl)-1H-imidazol-5-yl)-1,3-dihydro-2H-benzo[d]imidazol-2-one;
3-ethyl-1-isopropyl-5-(4-(m-tolyl)-1H-imidazol-5-yl)-1,3-dihydro-2H-benzo[d]imidazol-2-one;
6-(5-(2-fluorophenyl)-1H-imidazol-4-yl)-N-isopropylbenzo[d]thiazol-2-amine;
1,3-dipropyl-5-(4-(m-tolyl)-1H-imidazol-5-yl)-1,3-dihydro-2H-benzo[d]imidazol-2-one;
1,3-diisopropyl-5-(4-(m-tolyl)-1H-imidazol-5-yl)-1,3-dihydro-2H-benzo[d]imidazol-2-one;
1,3-diethyl-5-(4-(4-fluorophenyl)-1H-imidazol-5-yl)-1,3-dihydro-2H-benzo[d]imidazol-2-one;
3-methyl-1-(m-tolyl)-5-(4-(m-tolyl)-1H-imidazol-5-yl)-1,3-dihydro-2H-benzo[d]imidazol-2-one;
1-cyclopropyl-3-methyl-5-(4-(m-tolyl)-1H-imidazol-5-yl)-1,3-dihydro-2H-benzo[d]imidazol-2-one;
1-(isopropylsulfonyl)-5-(4-phenyl-1H-imidazol-5-yl)-1H-benzo[d]imidazol-2-amine;
1-(isopropylsulfonyl)-6-(4-phenyl-1H-imidazol-5-yl)-1H-benzo[d]imidazol-2-amine;

1-cyclobutyl-3-methyl-5-(4-(m-tolyl)-1H-imidazol-5-yl)-1,3-dihydro-2H-benzo[d]imidazol-2-one;
1-cyclohexyl-3-methyl-5-(4-(m-tolyl)-1H-imidazol-5-yl)-1,3-dihydro-2H-benzo[d]imidazol-2-one;
3-methyl-1-(o-tolyl)-5-(4-(m-tolyl)-1H-imidazol-5-yl)-1,3-dihydro-2H-benzo[d]imidazol-2-one;
5-(4-(4-fluorophenyl)-1H-imidazol-5-yl)-3-methyl-1-phenyl-1,3-dihydro-2H-benzo[d]imidazol-2-one;
1-cyclopentyl-3-methyl-5-(4-(m-tolyl)-1H-imidazol-5-yl)-1,3-dihydro-2H-benzo[d]imidazol-2-one;
(R)—N-(sec-butyl)-6-(5-(2-fluorophenyl)-1H-imidazol-4-yl)benzo[d]thiazol-2-amine;
1-(3,4-dimethylphenyl)-3-methyl-5-(4-(m-tolyl)-1H-imidazol-5-yl)-1,3-dihydro-2H-benzo[d]imidazol-2-one;
1,3-diethyl-5-(5-(3-methoxyphenyl)-1H-imidazol-4-yl)-1,3-dihydro-2H-benzo[d]imidazol-2-one;
1-cyclobutyl-3-ethyl-5-(4-(m-tolyl)-1H-imidazol-5-yl)-1,3-dihydro-2H-benzo[d]imidazol-2-one;
1-cyclopentyl-3-ethyl-5-(4-(m-tolyl)-1H-imidazol-5-yl)-1,3-dihydro-2H-benzo[d]imidazol-2-one;
1-(3-chlorophenyl)-3-methyl-5-(4-(m-tolyl)-1H-imidazol-5-yl)-1,3-dihydro-2H-benzo[d]imidazol-2-one;
1-(3-fluorophenyl)-3-methyl-5-(4-(m-tolyl)-1H-imidazol-5-yl)-1,3-dihydro-2H-benzo[d]imidazol-2-one;
1-(4-fluorophenyl)-3-methyl-5-(4-(m-tolyl)-1H-imidazol-5-yl)-1,3-dihydro-2H-benzo[d]imidazol-2-one;
1-(4-chlorophenyl)-3-methyl-5-(4-(m-tolyl)-1H-imidazol-5-yl)-1,3-dihydro-2H-benzo[d]imidazol-2-one;
6-(4-(4-fluorophenyl)-1H-imidazol-5-yl)-1-(isopropylsulfonyl)-1H-benzo[d]imidazol-2-amine;
1-(4-methoxyphenyl)-3-methyl-5-(4-(m-tolyl)-1H-imidazol-5-yl)-1,3-dihydro-2H-benzo[d]imidazol-2-one;
1-(2-fluorophenyl)-3-methyl-5-(4-(m-tolyl)-1H-imidazol-5-yl)-1,3-dihydro-2H-benzo[d]imidazol-2-one;
1-(2-chlorophenyl)-3-methyl-5-(4-(m-tolyl)-1H-imidazol-5-yl)-1,3-dihydro-2H-benzo[d]imidazol-2-one;
6-(5-(3-fluorophenyl)-1H-imidazol-4-yl)-1-(isopropylsulfonyl)-1H-benzo[d]imidazol-2-amine;
1,3-bis(cyclopropylmethyl)-5-(4-(m-tolyl)-1H-imidazol-5-yl)-1,3-dihydro-2H-benzo[d]imidazol-2-one;
6-(5-(2-fluorophenyl)-1H-imidazol-4-yl)-1-(isopropylsulfonyl)-1H-benzo[d]imidazol-2-amine;
3-(4-methoxybenzyl)-1-methyl-5-(4-(m-tolyl)-1H-imidazol-5-yl)-1,3-dihydro-2H-benzo[d]imidazol-2-one;
1-(3,4-difluorophenyl)-3-methyl-5-(4-(m-tolyl)-1H-imidazol-5-yl)-1,3-dihydro-2H-benzo[d]imidazol-2-one;
3-methyl-5-(4-(m-tolyl)-1H-imidazol-5-yl)-1-(4-(trifluoromethyl)phenyl)-1,3-dihydro-2H-benzo[d]imidazol-2-one;
3-methyl-5-(4-(m-tolyl)-1H-imidazol-5-yl)-1-(3-(trifluoromethyl)phenyl)-1,3-dihydro-2H-benzo[d]imidazol-2-one;
3-methyl-1-(thiophen-3-yl)-5-(4-(m-tolyl)-1H-imidazol-5-yl)-1,3-dihydro-2H-benzo[d]imidazol-2-one;
3-methyl-5-(4-(m-tolyl)-1H-imidazol-5-yl)-1-(2-(trifluoromethyl)phenyl)-1,3-dihydro-2H-benzo[d]imidazol-2-one;
N-benzyl-1-(isopropylsulfonyl)-6-(4-phenyl-1H-imidazol-5-yl)-1H-benzo[d]imidazol-2-amine;
6-(5-(2,4-difluorophenyl)-1H-imidazol-4-yl)-1-(isopropylsulfonyl)-1H-benzo[d]imidazol-2-amine;
6-(5-(2,3-difluorophenyl)-1H-imidazol-4-yl)-1-(isopropylsulfonyl)-1H-benzo[d]imidazol-2-amine;
1-(3,4-dimethoxyphenyl)-3-methyl-5-(4-(m-tolyl)-1H-imidazol-5-yl)-1,3-dihydro-2H-benzo[d]imidazol-2-one;
1-(benzo[d][1,3]dioxol-5-yl)-3-methyl-5-(4-(m-tolyl)-1H-imidazol-5-yl)-1,3-dihydro-2H-benzo[d]imidazol-2-one;
1-(isopropylsulfonyl)-6-(4-(3-(trifluoromethyl)phenyl)-1H-imidazol-5-yl)-1H-benzo[d]imidazol-2-amine;
3-methyl-5-(4-(m-tolyl)-1H-imidazol-5-yl)-1-(3,4,5-trimethoxyphenyl)-1,3-dihydro-2H-benzo[d]imidazol-2-one;

or a pharmaceutically acceptable salt thereof.

In embodiment I°₃, the compounds are of embodiment I°₁, provided that (a) when ring A is Ar, ring B is not triazolyl or imidazolidin-2-onyl; and (b) Z is not (1)
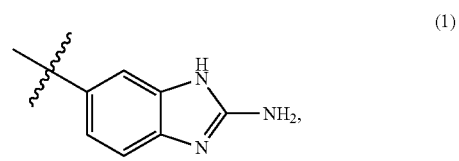

(2)
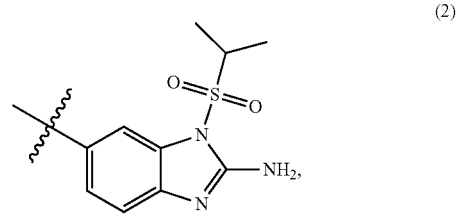

(3)
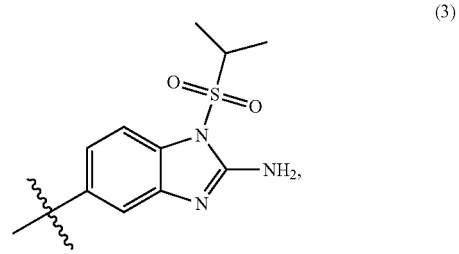

(4)
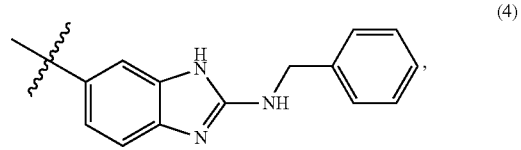

(5)
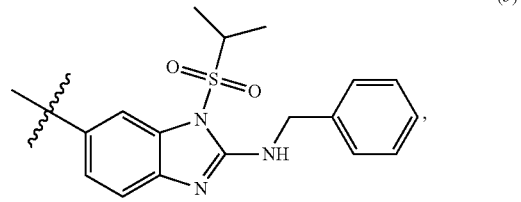

(6)
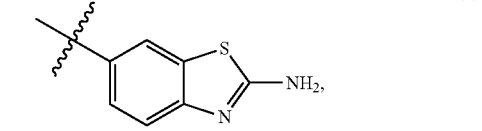

(7)
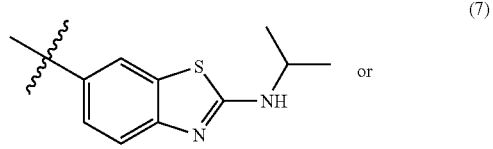

or (8)

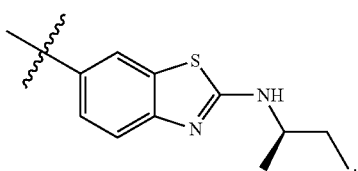

In embodiment I°4, the compounds are of embodiment I°1, provided that
(a) when ring A is Ar, ring B is not triazolyl or imidazolidin-2-onyl; and
(b) Z is not

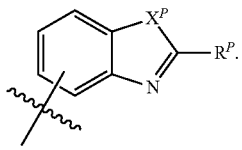

In embodiment I°5, the compounds are of embodiment I°1, wherein
Z is
(a) a fused bicyclic ring of the formula,

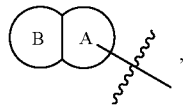

wherein
(1) ring A is —Ar, and
ring B is a 6-membered Het; or
(2) ring A is 6-membered Het, and
ring B is a 5-membered Het; or
(b)

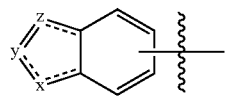

wherein
z is CH, O, S or N;
y is CH, CH$_2$, or N; and
x is CH, O, S, N(R$^a$);
provided that when z is N and x is N(R$^a$), y is not N;
wherein R$^a$ is hydrogen, —C$_1$-C$_6$alkyl, —C$_1$-C$_6$ haloalkyl, —C(O)OR, —C(O)NR$_2$, —C(O)R, —S(O)R, —S(O)$_2$R, —S(O)OR, —S(O)$_2$OR, —S(O)NR$_2$, —S(O)$_2$NR$_2$, —OC(O)R, —OC(O)OR, —OC(O)NR$_2$;
wherein each R is independently hydrogen, C$_1$-C$_6$alkyl, C$_1$-C$_6$ haloalkyl, —(C$_0$-C$_6$alkyl)-Ar, —(C$_0$-C$_6$alkyl)-Het, —(C$_0$-C$_6$alkyl)-Cak, or —(C$_0$-C$_6$alkyl)-Hca,
wherein Ar, Het, Cak, Hca, alkyl, and haloalkyl are optionally substituted with C$_1$-C$_6$alkyl, halogen, C$_1$-C$_6$ haloalkyl or cyano;
wherein Z is optionally substituted by one or two —R$^Z$ groups.

In embodiment I°6, the compounds are of embodiment I°1, wherein
Z is
(a) a fused bicyclic ring of the formula,

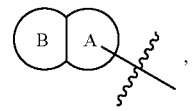

wherein
(1) ring A is —Ar, and
ring B is a 6-membered Het; or
(2) ring A is 6-membered Het, and
ring B is a 5-membered Het; or
(b)

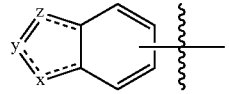

wherein
z is CH, O, S or N;
y is CH, CH$_2$, or N; and
x is CH, O, S, N(R$^a$);
provided that when z is N and x is N(R$^a$), y is not N;
wherein
Z is optionally substituted by one or two —R$^Z$ groups that are each independently halogen, cyano, C$_{1-6}$alkyl, C$_{1-6}$haloalkyl, —C$_1$-C$_6$alkoxy, —OR$^{S3}$, —SR$^{S3}$, —C(O)R$^{S3}$, —C(O)OR$^{S3}$, —C(O)NR$^{S3}$$_2$, —S(O)$_2$NR$^{S3}$$_2$, —OC(O)R$^{S3}$, —N(R$^{S3}$)C(O)R$^{S3}$, —OC(O)OR$^{S3}$, —OC(O)NR$^{S3}$$_2$, —N(R$^{S3}$)C(O)OR$^{S3}$, —N(R$^{S3}$)C(O)$_{NR}$$^{S3}$$_2$, —N(R$^{S3}$)S(O)$_2$R$^{S3}$, —OP(O)OR$^{S3}$)$_2$ or —CH$_2$—OP(O)(OR$^{S3}$), wherein each alkyl, haloalkyl and alkoxy is optionally substituted by one or two —R$^{Z2}$ groups.

In embodiment I°7, the compounds are of any one of embodiments I$_1$-I$_6$ or I', wherein
R' is hydrogen or C$_1$-C$_6$alkyl; and
R$^1$ is hydrogen or C$_1$-C$_6$alkyl.

In embodiment I$_8$, the compounds are of any one of embodiments I°$_1$-I°$_6$ or I°', wherein X is —S—.

In embodiment I°$_8$, the compounds are of any one of embodiments I°$_1$-I°$_6$ or I°', wherein X is —N(R')—.

In embodiment I$_1$ of this first aspect, the compounds have structural formula (I):

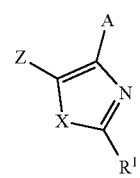

(I)

or a pharmaceutically acceptable salt, prodrug, or N-oxide thereof, or a solvate or hydrate thereof,
wherein
X is —S— or —N(R')—;
R' is hydrogen, C$_1$-C$_6$alkyl, C$_1$-C$_6$ haloalkyl, C$_1$-C$_6$alkyloxy, each optionally substituted with 1 to 3 moieties that are each independently C$_1$-C$_6$alkyl, halogen, C$_1$-C$_6$ haloalkyl or cyano;

R$^1$ is hydrogen, C$_1$-C$_6$alkyl, C$_1$-C$_6$ haloalkyl, C$_1$-C$_6$alkyloxy, —OR$^{S1}$, —NR$^{S1}$$_2$, —SR$^{S1}$, each optionally substituted with 1 to 3 moieties that are each independently C$_1$-C$_6$alkyl, halogen, C$_1$-C$_6$ haloalkyl or cyano;
  wherein each R$^{S1}$ is independently hydrogen, C$_1$-C$_6$alkyl, C$_1$-C$_6$ haloalkyl, —(C$_0$-C$_6$alkyl)-Ar, —(C$_0$-C$_6$alkyl)-Het, —(C$_0$-C$_6$alkyl)-Cak, or —(C$_0$-C$_6$alkyl)-Hca, wherein Ar, Het, Cak, Hca, alkyl, and haloalkyl are optionally substituted with C$_1$-C$_6$alkyl, halogen, C$_1$-C$_6$ haloalkyl or cyano;

A is phenyl optionally substituted with one to five R$^2$ groups, wherein
  each R$^2$ is independently halogen, —C$_1$-C$_6$alkyl, —C$_1$-C$_6$ haloalkyl, —C$_1$-C$_6$alkoxy, —NO$_2$ or —CN, wherein each alkyl, haloalkyl and alkoxy are optionally substituted with 1, 2, 3, or 4 groups that are each independently halogen, cyano, nitro, —OR$^{S2}$, —SR$^{S2}$, —NR$^{S2}$$_2$, —C(O)OR$^{S2}$, —C(O)NR$^{S2}$$_2$, —C(O)R$^{S2}$, —S(O)R$^{S2}$, —S(O)$_2$R$^{S2}$, —S(O)OR$^{S2}$, —S(O)$_2$OR$^{S2}$, —S(O)NR$^{S2}$$_2$, —S(O)$_2$NR$^{S2}$$_2$, —OC(O)R$^{S2}$, —OC(O)OR$^{S2}$, —OC(O)NR$^{S2}$$_2$, —N(R$^{S2}$)C(O)R$^{S2}$, —N(R$^{S2}$)C(O)OR$^{S2}$, —N(R$^{S2}$)C(O)NR$^{S2}$$_2$, —N(R$^{S2}$)S(O)R$^{S2}$, —N(R$^{S2}$)S(O)$_2$R$^{S2}$, C$_1$-C$_6$alkyl, or C$_1$-C$_6$ haloalkyl;
  wherein each R$^{S2}$ is independently hydrogen, C$_1$-C$_6$alkyl, C$_1$-C$_6$ haloalkyl, —(C$_0$-C$_6$alkyl)-Ar, —(C$_0$-C$_6$alkyl)-Het, —(C$_0$-C$_6$alkyl)-Cak, or —(C$_0$-C$_6$alkyl)-Hca, wherein Ar, Het, Cak, Hca, alkyl, and haloalkyl are optionally substituted with C$_1$-C$_6$alkyl, halogen, C$_1$-C$_6$ haloalkyl or cyano;

Z is
a fused bicyclic ring of the formula,

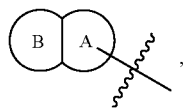

wherein
  ring A is Ar or 5- or 6-membered Het,
  ring B is 5- or 6-membered Het,
  wherein
  Z is optionally substituted by one or two —R$^Z$ groups that are each independently halogen, cyano, C$_{1-6}$alkyl, C$_{1-6}$ haloalkyl, —C$_1$-C$_6$alkoxy, —OR$^{S3}$, —SR$^{S3}$, —NR$^{S3}$$_2$, —C(O)R$^{S3}$, —C(O)OR$^{S3}$, —C(O)NR$^{S3}$$_2$, —S(O)$_2$NR$^{S3}$$_2$, —S(O)$_2$R$^{S3}$, —OC(O)R$^{S3}$, —N(R$^{S3}$)C(O)R$^{S3}$, —OC(O)OR$^{S3}$, —OC(O)NR$^{S3}$$_2$, —N(R$^{S3}$)C(O)OR$^{S3}$, —N(R$^{S3}$)C(O)NR$^{S3}$$_2$, —N(R$^{S3}$)S(O)$_2$R$^{S3}$, —OP(O)(OR$^{S3}$)$_2$ or —CH$_2$—OP(O)(OR$^{S3}$), wherein each alkyl, haloalkyl and alkoxy is optionally substituted by one or two —R$^{Z2}$ groups;
    wherein each R$^{S3}$ is independently hydrogen, C$_1$-C$_6$alkyl, C$_1$-C$_6$ haloalkyl, —(C$_0$-C$_6$alkyl)-Ar, —(C$_0$-C$_6$alkyl)-Het, —(C$_0$-C$_6$alkyl)-Cak, or —(C$_0$-C$_6$alkyl)-Hca, wherein Ar, Het, Cak, Hca, alkyl, and haloalkyl are optionally substituted with C$_1$-C$_6$alkyl, halogen, C$_1$-C$_6$ haloalkyl or cyano; and
    each —R$^{Z2}$ is independently halogen, cyano, C$_{1-6}$alkyl, C$_{1-6}$ haloalkyl, —C$_1$-C$_6$alkoxy, —OR$^{S4}$, —SR$^{S4}$, —NR$^{S4}$$_2$, —C(O)R$^{S4}$, —C(O)OR$^{S4}$, —C(O)NR$^{S4}$$_2$, —S(O)$_2$NR$^{S4}$$_2$, —S(O)$_2$R$^{S4}$, —OC(O)R$^{S4}$, —N(R$^{S4}$)C(O)R$^{S4}$, —OC(O)OR$^{S4}$, —N(R$^{S4}$)C(O)NR$^{S4}$$_2$, —N(R$^{S4}$)C(O)OR$^{S4}$, —N(R$^{S4}$)S(O)$_2$R$^{S4}$, —OP(O)(OR$^{S4}$)$_2$ or —CH$_2$—OP(O)(OR$^{S4}$); and wherein each R$^{S4}$ is independently hydrogen, C$_1$-C$_6$alkyl, C$_1$-C$_6$ haloalkyl, —(C$_0$-C$_6$alkyl)-Ar, —(C$_0$-C$_6$alkyl)-Het, —(C$_0$-C$_6$alkyl)-Cak, or —(C$_0$-C$_6$alkyl)-Hca,
wherein Ar, Het, Cak, Hca, alkyl, and haloalkyl are optionally substituted with C$_1$-C$_6$alkyl, halogen, C$_1$-C$_6$ haloalkyl or cyano.

In some embodiments of formulae (I°) and (I), R$^{S0}$, R$^{S1}$, R$^{S2}$, R$^{S3}$ and R$^{S4}$ are optionally substituted with one C$_1$-C$_6$alkyl, halogen, C$_1$-C$_6$ haloalkyl or cyano.

In embodiment I', the compounds are of embodiment I$_1$, provided that the compound is not any compound expressly recited in "Benzothiazole Based Inhibitors of p38a MAP Kinase" Liu, C. et al. Bioorganic & Medicinal Chemistry Letters (2008), 18(6), 1874-1879; International Publication No. WO 2004014900 A1; International Publication No. WO 2002072576 A1; or "Potent, Orally Active Heterocycle-Based Combretastatin A-4 Analogues: Synthesis, Structure-Activity Relationship" Wang, L. et al. Journal of Medicinal Chemistry (2002), 45(8), 1697-1711.

In embodiment I$_2$, the compounds are of embodiment I$_1$, provided that the compound is not:
6-(4-phenyl-1H-imidazol-5-yl)-1H-benzo[d]imidazol-2-amine;
5-(4-(m-tolyl)-1H-imidazol-5-yl)-1,3-dihydro-2H-benzo[d]imidazol-2-one;
1-methyl-6-(4-phenyl-1H-imidazol-5-yl)-1H-benzo[d][1,2,3]triazole;
6-(4-phenyl-1H-imidazol-5-yl)benzo[d]thiazol-2-amine;
1-isopropyl-6-(4-phenyl-1H-imidazol-5-yl)-1H-benzo[d][1,2,3]triazole;
N-benzyl-6-(4-phenyl-1H-imidazol-5-yl)-1H-benzo[d]imidazol-2-amine;
1-ethyl-6-(4-(m-tolyl)-1H-imidazol-5-yl)-1H-benzo[d][1,2,3]triazole;
6-(4-(4-fluorophenyl)-1H-imidazol-5-yl)-1-methyl-1H-benzo[d][1,2,3]triazole;
1-ethyl-6-(4-(4-fluorophenyl)-1H-imidazol-5-yl)-1H-benzo[d][1,2,3]triazole;
1-methyl-5-(4-(m-tolyl)-1H-imidazol-5-yl)-1,3-dihydro-2H-benzo[d]imidazol-2-one;
1,3-dimethyl-5-(4-phenyl-1H-imidazol-5-yl)-1,3-dihydro-2H-benzo[d]imidazol-2-one;
N-isopropyl-6-(4-phenyl-1H-imidazol-5-yl)benzo[d]thiazol-2-amine;
1-methyl-6-(4-(m-tolyl)-1H-imidazol-5-yl)-1,3-dihydro-2H-benzo[d]imidazol-2-one;
6-(4-(4-fluorophenyl)-1H-imidazol-5-yl)-1-isopropyl-1H-benzo[d][1,2,3]triazole;
6-(4-(4-fluoro-3-methylphenyl)-1H-imidazol-5-yl)-1-methyl-1H-benzo[d][1,2,3]triazole;
1-ethyl-6-(4-(m-tolyl)-1H-imidazol-5-yl)-1,3-dihydro-2H-benzo[d]imidazol-2-one;
1,3-dimethyl-5-(4-(m-tolyl)-1H-imidazol-5-yl)-1,3-dihydro-2H-benzo[d]imidazol-2-one;
1,3-diethyl-5-(4-phenyl-1H-imidazol-5-yl)-1,3-dihydro-2H-benzo[d]imidazol-2-one;
1-isopropyl-6-(4-(m-tolyl)-1H-imidazol-5-yl)-1,3-dihydro-2H-benzo[d]imidazol-2-one;
6-(4-(4-fluoro-3-methylphenyl)-1H-imidazol-5-yl)-1-isopropyl-1H-benzo[d][1,2,3]triazole;
5-(4-(4-fluorophenyl)-1H-imidazol-5-yl)-1,3-dimethyl-1,3-dihydro-2H-benzo[d]imidazol-2-one;
6-(4-(4-fluoro-3-methylphenyl)-1H-imidazol-5-yl)-1-isopropyl-1H-benzo[d][1,2,3]triazole;
3-ethyl-1-methyl-5-(4-(m-tolyl)-1H-imidazol-5-yl)-1,3-dihydro-2H-benzo[d]imidazol-2-one;

1-ethyl-3-methyl-5-(4-(m-tolyl)-1H-imidazol-5-yl)-1,3-dihydro-2H-benzo[d]imidazol-2-one;
1-phenyl-6-(4-(m-tolyl)-1H-imidazol-5-yl)-1,3-dihydro-2H-benzo[d]imidazol-2-one;
1,3-diethyl-5-(4-(m-tolyl)-1H-imidazol-5-yl)-1,3-dihydro-2H-benzo[d]imidazol-2-one;
1-isopropyl-3-methyl-5-(4-(m-tolyl)-1H-imidazol-5-yl)-1,3-dihydro-2H-benzo[d]imidazol-2-one;
3-isopropyl-1-methyl-5-(4-(m-tolyl)-1H-imidazol-5-yl)-1,3-dihydro-2H-benzo[d]imidazol-2-one;
3-methyl-1-phenyl-5-(4-(m-tolyl)-1H-imidazol-5-yl)-1,3-dihydro-2H-benzo[d]imidazol-2-one;
3-ethyl-1-isopropyl-5-(4-(m-tolyl)-1H-imidazol-5-yl)-1,3-dihydro-2H-benzo[d]imidazol-2-one;
6-(5-(2-fluorophenyl)-1H-imidazol-4-yl)-N-isopropylbenzo[d]thiazol-2-amine;
1,3-dipropyl-5-(4-(m-tolyl)-1H-imidazol-5-yl)-1,3-dihydro-2H-benzo[d]imidazol-2-one;
1,3-diisopropyl-5-(4-(m-tolyl)-1H-imidazol-5-yl)-1,3-dihydro-2H-benzo[d]imidazol-2-one;
1,3-diethyl-5-(4-(4-fluorophenyl)-1H-imidazol-5-yl)-1,3-dihydro-2H-benzo[d]imidazol-2-one;
3-methyl-1-(m-tolyl)-5-(4-(m-tolyl)-1H-imidazol-5-yl)-1,3-dihydro-2H-benzo[d]imidazol-2-one;
1-cyclopropyl-3-methyl-5-(4-(m-tolyl)-1H-imidazol-5-yl)-1,3-dihydro-2H-benzo[d]imidazol-2-one;
1-(isopropylsulfonyl)-5-(4-phenyl-1H-imidazol-5-yl)-1H-benzo[d]imidazol-2-amine;
1-(isopropylsulfonyl)-6-(4-phenyl-1H-imidazol-5-yl)-1H-benzo[d]imidazol-2-amine;
1-cyclobutyl-3-methyl-5-(4-(m-tolyl)-1H-imidazol-5-yl)-1,3-dihydro-2H-benzo[d]imidazol-2-one;
1-cyclohexyl-3-methyl-5-(4-(m-tolyl)-1H-imidazol-5-yl)-1,3-dihydro-2H-benzo[d]imidazol-2-one;
3-methyl-1-(o-tolyl)-5-(4-(m-tolyl)-1H-imidazol-5-yl)-1,3-dihydro-2H-benzo[d]imidazol-2-one;
5-(4-(4-fluorophenyl)-1H-imidazol-5-yl)-3-methyl-1-phenyl-1,3-dihydro-2H-benzo[d]imidazol-2-one;
1-cyclopentyl-3-methyl-5-(4-(m-tolyl)-1H-imidazol-5-yl)-1,3-dihydro-2H-benzo[d]imidazol-2-one;
(R)—N-(sec-butyl)-6-(5-(2-fluorophenyl)-1H-imidazol-4-yl)benzo[d]thiazol-2-amine;
1-(3,4-dimethylphenyl)-3-methyl-5-(4-(m-tolyl)-1H-imidazol-5-yl)-1,3-dihydro-2H-benzo[d]imidazol-2-one;
1,3-diethyl-5-(5-(3-methoxyphenyl)-1H-imidazol-4-yl)-1,3-dihydro-2H-benzo[d]imidazol-2-one;
1-cyclobutyl-3-ethyl-5-(4-(m-tolyl)-1H-imidazol-5-yl)-1,3-dihydro-2H-benzo[d]imidazol-2-one;
1-cyclopentyl-3-ethyl-5-(4-(m-tolyl)-1H-imidazol-5-yl)-1,3-dihydro-2H-benzo[d]imidazol-2-one;
1-(3-chlorophenyl)-3-methyl-5-(4-(m-tolyl)-1H-imidazol-5-yl)-1,3-dihydro-2H-benzo[d]imidazol-2-one;
1-(3-fluorophenyl)-3-methyl-5-(4-(m-tolyl)-1H-imidazol-5-yl)-1,3-dihydro-2H-benzo[d]imidazol-2-one;
1-(4-fluorophenyl)-3-methyl-5-(4-(m-tolyl)-1H-imidazol-5-yl)-1,3-dihydro-2H-benzo[d]imidazol-2-one;
1-(4-chlorophenyl)-3-methyl-5-(4-(m-tolyl)-1H-imidazol-5-yl)-1,3-dihydro-2H-benzo[d]imidazol-2-one;
6-(4-(4-fluorophenyl)-1H-imidazol-5-yl)-1-(isopropylsulfonyl)-1H-benzo[d]imidazol-2-amine;
1-(4-methoxyphenyl)-3-methyl-5-(4-(m-tolyl)-1H-imidazol-5-yl)-1,3-dihydro-2H-benzo[d]imidazol-2-one;
1-(2-fluorophenyl)-3-methyl-5-(4-(m-tolyl)-1H-imidazol-5-yl)-1,3-dihydro-2H-benzo[d]imidazol-2-one;
1-(2-chlorophenyl)-3-methyl-5-(4-(m-tolyl)-1H-imidazol-5-yl)-1,3-dihydro-2H-benzo[d]imidazol-2-one;
6-(5-(3-fluorophenyl)-1H-imidazol-4-yl)-1-(isopropylsulfonyl)-1H-benzo[d]imidazol-2-amine;
1,3-bis(cyclopropylmethyl)-5-(4-(m-tolyl)-1H-imidazol-5-yl)-1,3-dihydro-2H-benzo[d]imidazol-2-one;
6-(5-(2-fluorophenyl)-1H-imidazol-4-yl)-1-(isopropylsulfonyl)-1H-benzo[d]imidazol-2-amine;
3-(4-methoxybenzyl)-1-methyl-5-(4-(m-tolyl)-1H-imidazol-5-yl)-1,3-dihydro-2H-benzo[d]imidazol-2-one;
1-(3,4-difluorophenyl)-3-methyl-5-(4-(m-tolyl)-1H-imidazol-5-yl)-1,3-dihydro-2H-benzo[d]imidazol-2-one;
3-methyl-5-(4-(m-tolyl)-1H-imidazol-5-yl)-1-(4-(trifluoromethyl)phenyl)-1,3-dihydro-2H-benzo[d]imidazol-2-one;
3-methyl-5-(4-(m-tolyl)-1H-imidazol-5-yl)-1-(3-(trifluoromethyl)phenyl)-1,3-dihydro-2H-benzo[d]imidazol-2-one;
3-methyl-1-(thiophen-3-yl)-5-(4-(m-tolyl)-1H-imidazol-5-yl)-1,3-dihydro-2H-benzo[d]imidazol-2-one;
3-methyl-5-(4-(m-tolyl)-1H-imidazol-5-yl)-1-(2-(trifluoromethyl)phenyl)-1,3-dihydro-2H-benzo[d]imidazol-2-one;
N-benzyl-1-(isopropylsulfonyl)-6-(4-phenyl-1H-imidazol-5-yl)-1H-benzo[d]imidazol-2-amine;
6-(5-(2,4-difluorophenyl)-1H-imidazol-4-yl)-1-(isopropylsulfonyl)-1H-benzo[d]imidazol-2-amine;
6-(5-(2,3-difluorophenyl)-1H-imidazol-4-yl)-1-(isopropylsulfonyl)-1H-benzo[d]imidazol-2-amine;
1-(3,4-dimethoxyphenyl)-3-methyl-5-(4-(m-tolyl)-1H-imidazol-5-yl)-1,3-dihydro-2H-benzo[d]imidazol-2-one;
1-(benzo[d][1,3]dioxol-5-yl)-3-methyl-5-(4-(m-tolyl)-1H-imidazol-5-yl)-1,3-dihydro-2H-benzo[d]imidazol-2-one;
1-(isopropylsulfonyl)-6-(4-(3-(trifluoromethyl)phenyl)-1H-imidazol-5-yl)-1H-benzo[d]imidazol-2-amine;
3-methyl-5-(4-(m-tolyl)-1H-imidazol-5-yl)-1-(3,4,5-trimethoxyphenyl)-1,3-dihydro-2H-benzo[d]imidazol-2-one;
or a pharmaceutically acceptable salt thereof.

In embodiment I$_3$, the compounds are of embodiment I$_1$, provided that
(a) when ring A is Ar, ring B is not triazolyl or imidazolidin-2-onyl; and
(b) Z is not

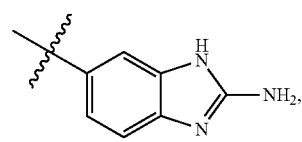

(1)

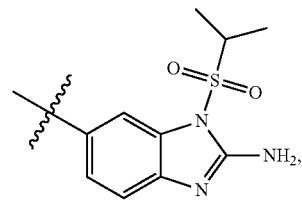

(2)

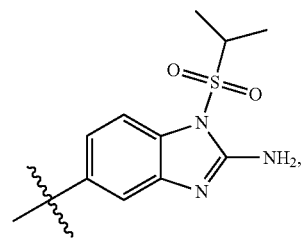

(3)

-continued (4)
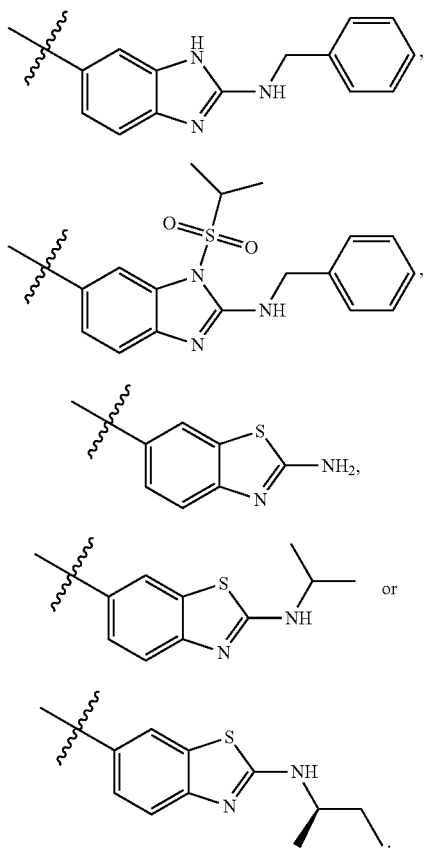
(5)

(6)

(7)

(8)

In embodiment I₄, the compounds are of embodiment I₁, provided that (a) when ring A is Ar, ring B is not triazolyl or imidazolidin-2-onyl; and (b) Z is not

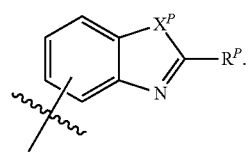

In embodiment I₅, the compounds are of embodiment I₁, wherein

Z is (a) a fused bicyclic ring of the formula,

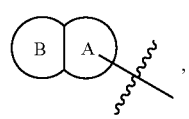

wherein (1) ring A is —Ar, and
    ring B is a 6-membered Het; or (2) ring A is 6-membered Het, and
    ring B is a 5-membered Het; or (b)

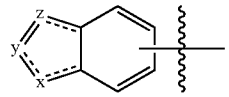

wherein
z is CH, O, S or N;
y is CH, CH₂, or N; and
x is CH, O, S, N(R$^a$);
provided that when z is N and x is N(R$^a$), y is not N;
wherein R$^a$ is hydrogen, —C₁-C₆alkyl, —C₁-C₆ haloalkyl, —C(O)OR, —C(O)NR₂, —C(O)R, —S(O)R, —S(O)₂R, —S(O)OR, —S(O)₂OR, —S(O)NR₂, —S(O)₂NR₂, —OC(O)R, —OC(O)OR, —OC(O)NR₂;
wherein each R is independently hydrogen, C₁-C₆alkyl, C₁-C₆ haloalkyl, —(C₀-C₆alkyl)-Ar, —(C₀-C₆alkyl)-Het, —(C₀-C₆alkyl)-Cak, or —(C₀-C₆alkyl)-Hca,
wherein Ar, Het, Cak, Hca, alkyl, and haloalkyl are optionally substituted with C₁-C₆alkyl, halogen, C₁-C₆ haloalkyl or cyano;
wherein Z is optionally substituted by one or two —R$^Z$ groups.

In embodiment I₆, the compounds are of embodiment I₁, wherein

Z is (a) a fused bicyclic ring of the formula,

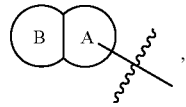

wherein (1) ring A is —Ar, and
    ring B is a 6-membered Het; or (2) ring A is 6-membered Het, and
    ring B is a 5-membered Het; or (b)

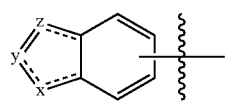

wherein
z is CH, O, S or N;
y is CH, CH₂, or N; and
x is CH, O, S, N(R$^a$);
provided that when z is N and x is N(R$^a$), y is not N;
wherein
Z is optionally substituted by one or two —R$^Z$ groups that are each independently halogen, cyano, C₁₋₆alkyl, C₁₋₆ haloalkyl, —C₁-C₆alkoxy, —OR$^{S3}$, —SR$^{S3}$, —C(O)R$^{S3}$, —C(O)OR$^{S3}$, —C(O)NR$^{S3}$₂, —S(O)₂NR$^{S3}$₂, —OC(O)R$^{S3}$, —N(R$^{S3}$)C(O)R$^{S3}$, —OC(O)OR$^{S3}$, —OC(O)NR$^{S3}$₂, —N(R$^{S3}$)C(O)OR$^{S3}$, —N(R$^{S3}$)C(O)NR$^{S3}$₂, —N(R$^{S3}$)S(O)₂R$^{S3}$, —OP(O)(OR$^{S3}$)₂ or —CH₂—OP(O)(OR$^{S3}$), wherein each alkyl, haloalkyl and alkoxy is optionally substituted by one or two —R$^{Z2}$ groups.

In embodiment I₇, the compounds are of any one of embodiments I₁-I₆ or I', wherein R' is hydrogen or $C_1$-$C_6$alkyl; and R¹ is hydrogen or $C_1$-$C_6$alkyl.

In embodiment I₈, the compounds are of any one of embodiments I₁-I₆ or I', wherein X is —S—.

In embodiment I₈, the compounds are of any one of embodiments I₁-I₆ or I', wherein X is —N(R')—.

The invention further comprises subgenera of formula (I) in which structural formula (I), A, Z, R' and R¹ are any group or combinations of groups as defined hereinbelow (e.g., wherein the compound is of structural formula (I) as defined in any of the above embodiments and A is phenyl optionally substituted with one R² group, wherein R² is halogen; or the compound is formula (Ib), A is group (1c), Z is group (2b), R' is group (3i) and R¹ is group (4a)):

Structural Formulae (Ia)-(Ix) Under Formula (I):

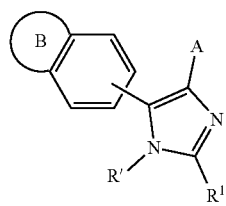
(Ia)

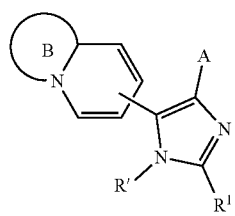
(Ib)

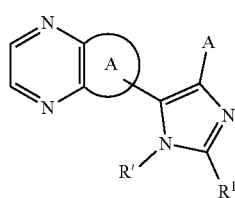
(Ic)

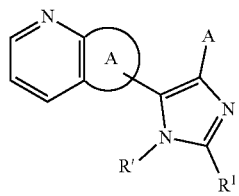
(Id)

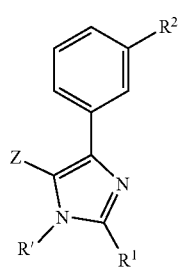
(Ie)

-continued

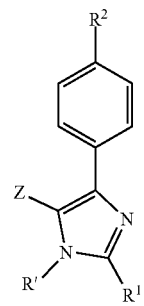
(If)

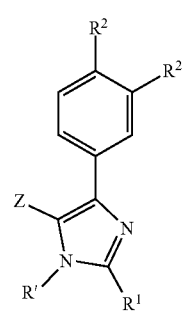
(Ig)

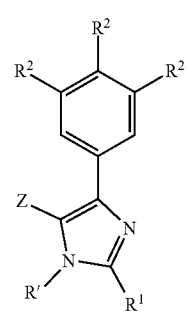
(Ih)

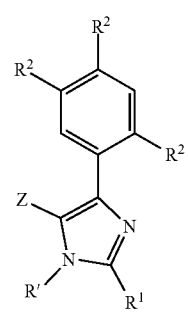
(Ii)

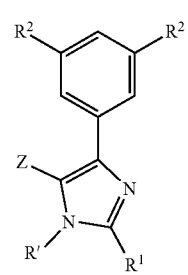
(Ij)

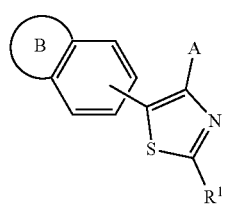
(Ik)
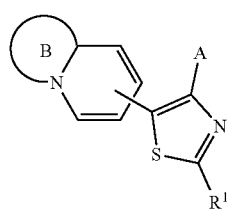
(Il)
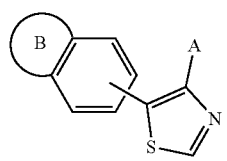
(Im)
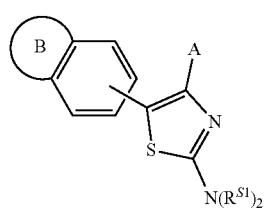
(In)
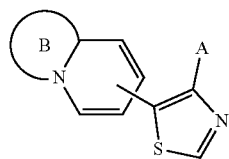
(Io)
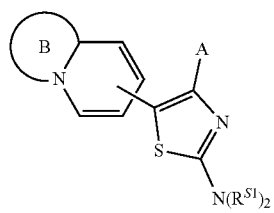
(Ip)
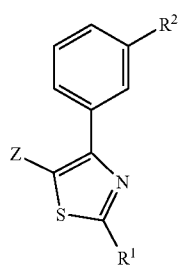
(Iq)
(Ir)
(Is)
(It)
(Iu)
(Iv)

-continued

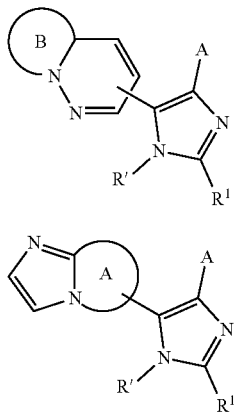

A is Selected from One of the Following Groups (1a)-(1ddd):

(1a) A is phenyl optionally substituted with one to five R² groups, wherein
  each R² is independently halogen, —$C_1$-$C_6$alkyl, —$C_1$-$C_6$ haloalkyl, —$C_1$-$C_6$alkoxy, —$NO_2$ or —CN, wherein each alkyl, haloalkyl and alkoxy are optionally substituted with 1, 2, 3, or 4 groups that are each independently halogen, cyano, nitro, —$OR^{S2}$, —$SR^{S2}$, —$NR^{S2}_2$, —$C(O)OR^{S2}$, —$C(O)NR^{S2}_2$, —$C(O)R^{S2}$, —$S(O)R^{S2}$, —$S(O)_2R^{S2}$, —$S(O)OR^{S2}$, —$S(O)_2OR^{S2}$, —$S(O)NR^{S2}_2$, —$S(O)_2NR^{S2}_2$, —$OC(O)R^{S2}$, —$OC(O)OR^{S2}$, —$OC(O)NR^{S2}_2$, —$N(R^{S2})C(O)R^{S2}$, —$N(R^{S2})C(O)OR^{S2}$, —$N(R^{S2})C(O)NR^{S2}_2$, —$N(R^{S2})S(O)R^{S2}$, —$N(R^{S2})S(O)_2R^{S2}$, $C_1$-$C_6$alkyl, or $C_1$-$C_6$ haloalkyl;
  wherein each $R^{S2}$ is independently hydrogen, $C_1$-$C_6$alkyl, $C_1$-$C_6$ haloalkyl, —($C_0$-$C_6$alkyl)-Ar, —($C_0$-$C_6$alkyl)-Het, —($C_0$-$C_6$alkyl)-Cak, or —($C_0$-$C_6$alkyl)-Hca,
  wherein Ar, Het, Cak, Hca, alkyl, and haloalkyl are optionally substituted with $C_1$-$C_6$alkyl, halogen, $C_1$-$C_6$ haloalkyl or cyano.
(1b) The group of (1a), wherein A is phenyl substituted with one to five R² groups.
(1c) The group of (1a), wherein A is phenyl substituted with one to three R² groups.
(1d) The group of (1a), wherein A is phenyl substituted with one or two R² groups.
(1e) The group of (1a), wherein A is phenyl substituted with one R² groups.
(1f) The group of (1a), wherein A is unsubstituted phenyl.
(1 g) Any of groups of (1a)-(1e), wherein each R² is independently halogen, —$C_1$-$C_6$alkyl, —$C_1$-$C_6$ haloalkyl, —$C_1$-$C_6$alkoxy, —$NO_2$ or —CN.
(1 h) Any of groups of (1a)-(1e), wherein each R² is independently halogen, —$C_1$-$C_6$alkyl, —$C_1$-$C_6$ haloalkyl or —$C_1$-$C_6$alkoxy.
(1i) Any of groups of (1a)-(1e), wherein each R² is independently —$NO_2$ or —CN.
(1j) Any of groups of (1a)-(1e), wherein each R² is independently halogen, —$C_1$-$C_6$alkyl or —$C_1$-$C_6$alkoxy.
(1k) Any of groups of (1a)-(1e), wherein each R² is independently halogen or —$C_1$-$C_6$alkyl.
(1l) Any of groups of (1a)-(1e), wherein each R² is independently halogen.
(1m) Any of groups of (1a)-(1e), wherein each R² is independently fluoro or chloro.
(1n) Any of groups of (1a)-(1e), wherein each R² is fluoro.
(1o) Any of groups of (1a)-(1e), wherein each R² is chloro.
(1p) Any of groups of (1a)-(1e), wherein each R² is independently —$C_1$-$C_6$alkyl.
(1q) Any of groups of (1a)-(1e), wherein each R² is independently methyl, ethyl n-propyl or i-propyl.
(1r) Any of groups of (1a)-(1e), wherein each R² is independently methyl or ethyl.
(1s) Any of groups of (1a)-(1e), wherein each R² is methyl.
(1t) Any of groups of (1a)-(1e), wherein each R² is ethyl.
(1u) Any of groups of (1a)-(1e), wherein each R² is independently —$C_1$-$C_6$alkoxy.
(1v) Any of groups of (1a)-(1e), wherein each R² is independently methoxy or ethoxy.
(1w) Any of groups of (1a)-(1e), wherein each R² is methoxy.
(1x) Any of groups of (1a)-(1e), wherein each R² is ethoxy.
(1y) Any of groups of (1b), wherein each R² is independently halogen, —$C_1$-$C_6$alkyl, —$C_1$-$C_6$ haloalkyl, —$C_1$-$C_6$alkoxy, —$NO_2$ or —CN.
(1z) Any of groups of (1b), wherein each R² is independently halogen, —$C_1$-$C_6$alkyl, —$C_1$-$C_6$ haloalkyl or —$C_1$-$C_6$alkoxy.
(1aa) Any of groups of (1b), wherein each R² is independently —$NO_2$ or —CN.
(1bb) Any of groups of (1b), wherein each R² is independently halogen, —$C_1$-$C_6$alkyl or —$C_1$-$C_6$alkoxy.
(1cc) Any of groups of (1b), wherein each R² is independently halogen or —$C_1$-$C_6$alkyl.
(1dd) Any of groups of (1b), wherein each R² is independently halogen.
(1ee) Any of groups of (1b), wherein each R² is independently —$C_1$-$C_6$alkyl.
(1ff) Any of groups of (1b), wherein each R² is independently —$C_1$-$C_6$alkoxy.
(1 gg) Any of groups of (1c), wherein each R² is independently halogen, —$C_1$-$C_6$alkyl, —$C_1$-$C_6$ haloalkyl, —$C_1$-$C_6$alkoxy, —$NO_2$ or —CN.
(1 hh) Any of groups of (1c), wherein each R² is independently halogen, —$C_1$-$C_6$alkyl, —$C_1$-$C_6$ haloalkyl or —$C_1$-$C_6$alkoxy.
(1ii) Any of groups of (1c), wherein each R² is independently —$NO_2$ or —CN.
(1jj) Any of groups of (1c), wherein each R² is independently halogen, —$C_1$-$C_6$alkyl or —$C_1$-$C_6$alkoxy.
(1kk) Any of groups of (1c), wherein each R² is independently halogen or —$C_1$-$C_6$alkyl.
(1ll) Any of groups of (1c), wherein each R² is independently halogen.
(1mm) Any of groups of (1c), wherein each R² is independently —$C_1$-$C_6$alkyl.
(1nn) Any of groups of (1c), wherein each R² is independently —$C_1$-$C_6$alkoxy.
(1oo) Any of groups of (1d), wherein each R² is independently halogen, —$C_1$-$C_6$alkyl, —$C_1$-$C_6$ haloalkyl, —$C_1$-$C_6$alkoxy, —$NO_2$ or —CN.
(1pp) Any of groups of (1d), wherein each R² is independently halogen, —$C_1$-$C_6$alkyl, —$C_1$-$C_6$ haloalkyl or —$C_1$-$C_6$alkoxy.
(1qq) Any of groups of (1d), wherein each R² is independently —$NO_2$ or —CN.

(1rr) Any of groups of (1d), wherein each $R^2$ is independently halogen, —$C_1$-$C_6$alkyl or —$C_1$-$C_6$alkoxy.
(1ss) Any of groups of (1d), wherein each $R^2$ is independently halogen or —$C_1$-$C_6$alkyl.
(1tt) Any of groups of (1d), wherein each $R^2$ is independently halogen.
(1uu) Any of groups of (1d), wherein each $R^2$ is independently —$C_1$-$C_6$alkyl.
(1vy) Any of groups of (1d), wherein each $R^2$ is independently —$C_1$-$C_6$alkoxy.
(1ww) Any of groups of (1e), wherein each $R^2$ is independently halogen, —$C_1$-$C_6$alkyl, —$C_1$-$C_6$ haloalkyl, —$C_1$-$C_6$alkoxy, —$NO_2$ or —CN.
(1xx) Any of groups of (1e), wherein each $R^2$ is independently halogen, —$C_1$-$C_6$alkyl, —$C_1$-$C_6$ haloalkyl or —$C_1$-$C_6$alkoxy.
(1yy) Any of groups of (1e), wherein each $R^2$ is independently —$NO_2$ or —CN.
(1zz) Any of groups of (1e), wherein each $R^2$ is independently halogen, —$C_1$-$C_6$alkyl or —$C_1$-$C_6$alkoxy.
(1aaa) Any of groups of (1e), wherein each $R^2$ is independently halogen or —$C_1$-$C_6$alkyl.
(1bbb) Any of groups of (1e), wherein each $R^2$ is independently halogen.
(1ccc) Any of groups of (1e), wherein each $R^2$ is independently —$C_1$-$C_6$alkyl.
(1ddd) Any of groups of (1e), wherein each $R^2$ is independently —$C_1$-$C_6$alkoxy.

Z is selected from one of the following groups (2a)-(2ccc):

(2a) Z is
a fused bicyclic ring of the formula,

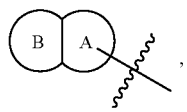

wherein
ring A is Ar or 5- or 6-membered Het,
ring B is 5- or 6-membered Het,
wherein
Z is optionally substituted by one or two —$R^Z$ groups that are each independently halogen, cyano, $C_{1-6}$alkyl, $C_{1-6}$ haloalkyl, —$C_1$-$C_6$alkoxy, —$OR^{S3}$, —$SR^{S3}$, —$NR^{S3}_2$, —$C(O)R^{S3}$, —$C(O)OR^{S3}$, —$C(O)NR^{S3}_2$, —$S(O)_2N^{S3}_2$, —$S(O)_2R^{S3}$, —$OC(O)R^{S3}$, —$N(R^{S3})C(O)R^{S3}$, —$OC(O)OR^{S3}$, —$OC(O)NR^{S3}_2$, —$N(R^{S3})C(O)OR^{S3}$, —$N(R^{S3})C(O)NR^{S3}_2$, —$N(R^{S3})S(O)_2R^{S3}$, —$OP(O)(OR^{S3})_2$ or —$CH_2$—$OP(O)(OR^{S3})$, wherein each alkyl, haloalkyl and alkoxy is optionally substituted by one or two —$R^{Z2}$ groups;
wherein each $R^{S3}$ is independently hydrogen, $C_1$-$C_6$alkyl, $C_1$-$C_6$ haloalkyl, —($C_0$-$C_6$alkyl)-Ar, —($C_0$-$C_6$alkyl)-Het, —($C_0$-$C_6$alkyl)-Cak, or —($C_0$-$C_6$alkyl)-Hca, wherein Ar, Het, Cak, Hca, alkyl, and haloalkyl are optionally substituted with $C_1$-$C_6$alkyl, halogen, $C_1$-$C_6$ haloalkyl or cyano; and
each —$R^{Z2}$ is independently halogen, cyano, $C_{1-6}$alkyl, $C_{1-6}$ haloalkyl, —$C_1$-$C_6$alkoxy, —$OR^{S4}$, —$SR^{S4}$, —$NR^{S4}_2$, —$C(O)R^{S4}$, —$C(O)OR^{S4}$, —$C(O)NR^{S4}_2$, —$S(O)_2NR^{S4}_2$, —$S(O)_2R^{S4}$, —$OC(O)R^{S4}$, —$N(R^{S4})C(O)R^{S4}$, —$OC(O)OR^{S4}$, —$OC(O)_{NR}{}^{S4}_2$, —$N(R^{S4})C(O)OR^{S4}$, —$N(R^{S4})C(O)NR^{S4}_2$, —$N(R^{S4})S(O)_2R^{S4}$, —$OP(O)(OR^{S4})_2$ or —$CH_2$—$OP(O)(OR^{S4})$;
wherein each $R^{S4}$ is independently hydrogen, $C_1$-$C_6$alkyl, $C_1$-$C_6$ haloalkyl, —($C_0$-$C_6$alkyl)-Ar, —($C_0$-$C_6$alkyl)-Het, —($C_0$-$C_6$alkyl)-Cak, or —($C_0$-$C_6$alkyl)-Hca, wherein Ar, Het, Cak, Hca, alkyl, and haloalkyl are optionally substituted with $C_1$-$C_6$alkyl, halogen, $C_1$-$C_6$ haloalkyl or cyano.

(2b) Z is as described in (2a), provided that Z is not

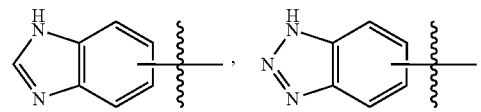

or a substituted analog thereof.

(2c) Z is as described in (2a), provided that Z is not

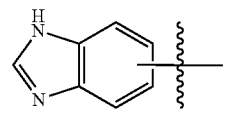

or a substituted analog thereof.

(2d) Z is as described in (2a), provided that Z is not

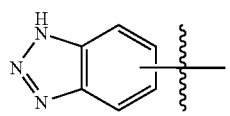

or a substituted analog thereof.

(2e) Z is as described in (2a), provided that Z is not

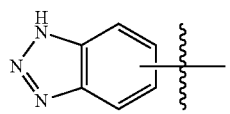

or a substituted analog thereof, or

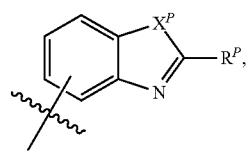

wherein $X^P$ is —N(H)—, —S—, or —N[S(O)$_2$$^i$Pr]—, and $R^P$ is —$NH_2$, —N(H)$CH_2$Ph, —N(H)$^i$Pr or —N(H)C(Me)Et.

(2f) Z is as described in (2a), provided that Z is not

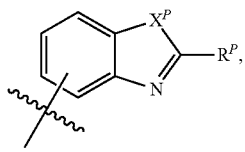

wherein $X^P$ is —N(H)—, —S—, or —N[S(O)$_2$$^i$Pr]—, and $R^P$ is —NH$_2$, —N(H)CH$_2$Ph, —N(H)$^i$Pr or —N(H)C(Me)Et.

(2 g) Z is a fused bicyclic ring of the formula,

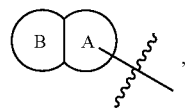

wherein
ring A is Ar or 5- or 6-membered Het; and
ring B is 5- or 6-membered Het; wherein
optionally substituted as described in (2a) above.

(2 h) Z is a fused bicyclic ring of the formula,

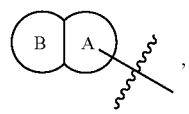

wherein
ring A is Ar; and
ring B is 5- or 6-membered Het; wherein
optionally substituted as described in (2a) above.

(2i) Z is a fused bicyclic ring of the formula,

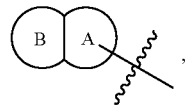

wherein
ring A is Ar; and
ring B is 5-membered Het; wherein
optionally substituted as described in (2a) above.

(2j) Z is a fused bicyclic ring of the formula,

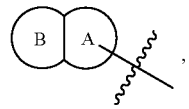

wherein
ring A is Ar; and
ring B is 6-membered Het; wherein
optionally substituted as described in (2a) above.

(2k) Z is a fused bicyclic ring of the formula,

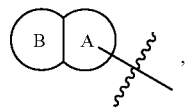

wherein
ring A is 5-membered Het; and
ring B is 5- or 6-membered Het; wherein
optionally substituted as described in (2a) above.

(2l) Z is a fused bicyclic ring of the formula,

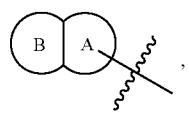

wherein
ring A is 5-membered Het; and
ring B is 5-membered Het; wherein
optionally substituted as described in (2a) above.

(2m) Z is a fused bicyclic ring of the formula,

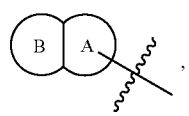

wherein
ring A is 5-membered Het; and
ring B is 6-membered Het; wherein
optionally substituted as described in (2a) above.

(2n) Z is a fused bicyclic ring of the formula,

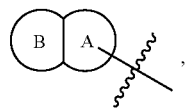

wherein
ring A is 6-membered Het; and
ring B is 5- or 6-membered Het; wherein
optionally substituted as described in (2a) above.

(2o) Z is a fused bicyclic ring of the formula,

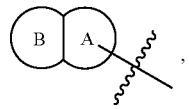

wherein
ring A is 6-membered Het; and
ring B is 5-membered Het; wherein
optionally substituted as described in (2a) above.

(2p) Z is a fused bicyclic ring of the formula,

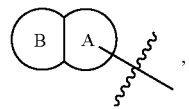

wherein
 ring A is 6-membered Het; and
 ring B is 6-membered Het; wherein
optionally substituted as described in (2a) above.
(2q) Z is

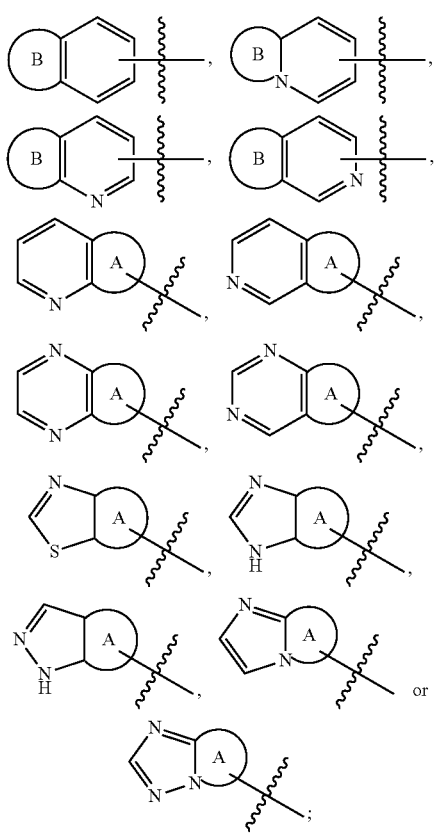

wherein ring A and B are as described in (2a), and Z is optionally substituted as described in (2a) above.
(2r) Z is

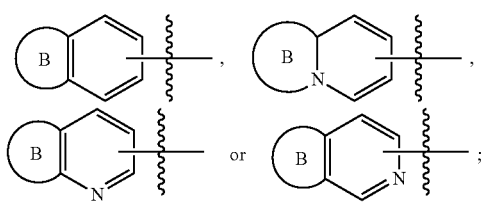

wherein ring B is as described in (2a), and Z is optionally substituted as described in (2a) above.

(2s) Z is

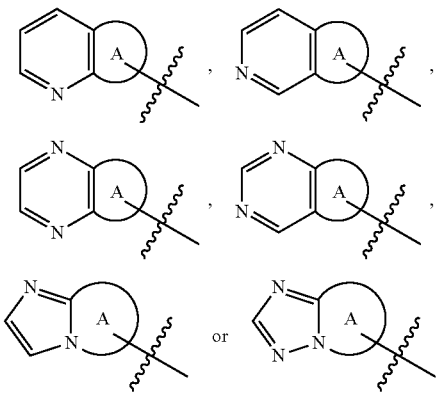

wherein ring A is as described in (2a), and Z is optionally substituted as described in (2a) above.
(2t) Z is

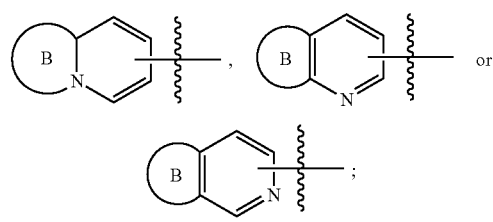

wherein ring B is as described in (2a), and Z is optionally substituted as described in (2a) above.
(2u) Z is

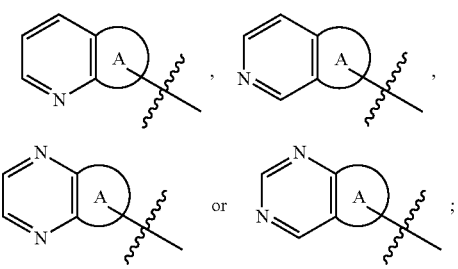

wherein ring A is as described in (2a), and Z is optionally substituted as described in (2a) above.
(2v) Z is

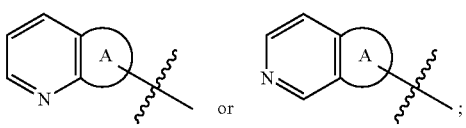

wherein ring A is as described in (2a), and Z is optionally substituted as described in (2a) above.

(2w) Z is

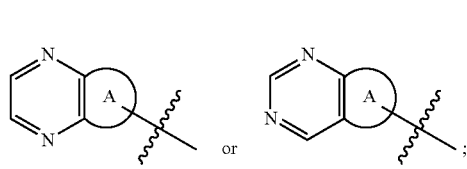
or ;

wherein ring A is as described in (2a), and Z is optionally substituted as described in (2a) above.

(2x) Z is

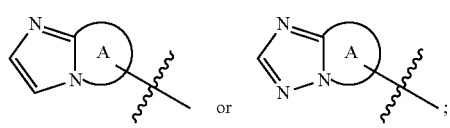
or ;

wherein ring A is as described in (2a), and Z is optionally substituted as described in (2a) above.

(2y) Z is

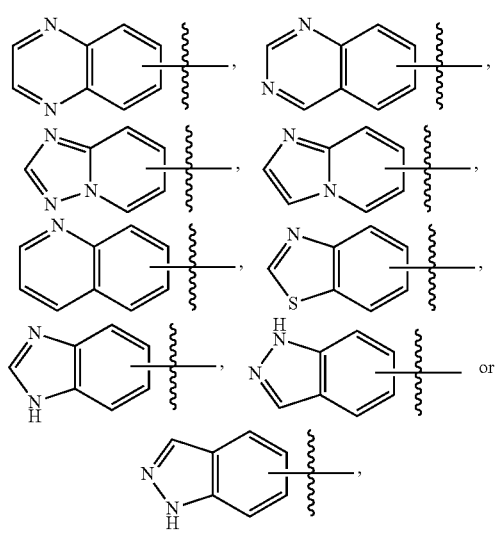
, , , , , , or

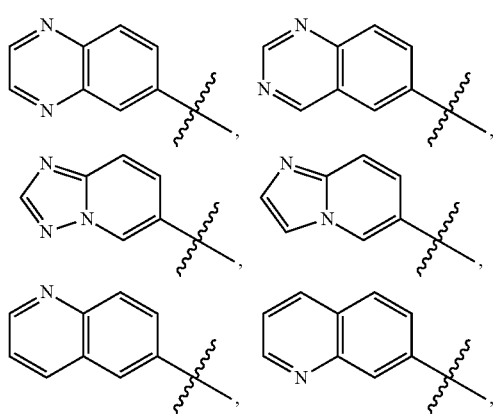
, each optionally substituted as described in (2a) above.

(2z) Z is each optionally substituted as described in (2a) above.

(2aa) Z is

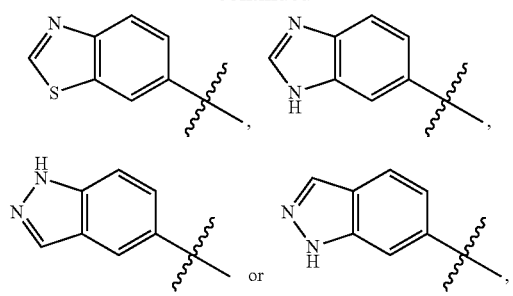

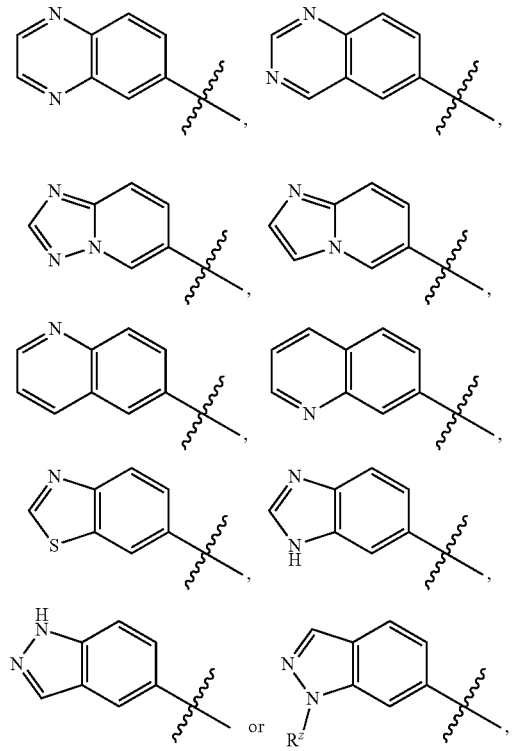
, , , , , , or each optionally substituted as described in (2a) above.

wherein each R$^Z$ is independently hydrogen or —C$_1$-C$_6$alkyl.

(2bb) Z is

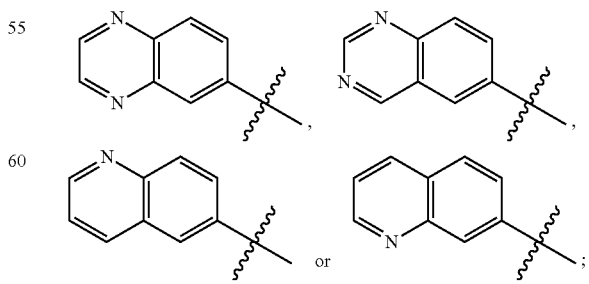
, , or ;

each optionally substituted as described in (2a) above.

(2cc) Z is

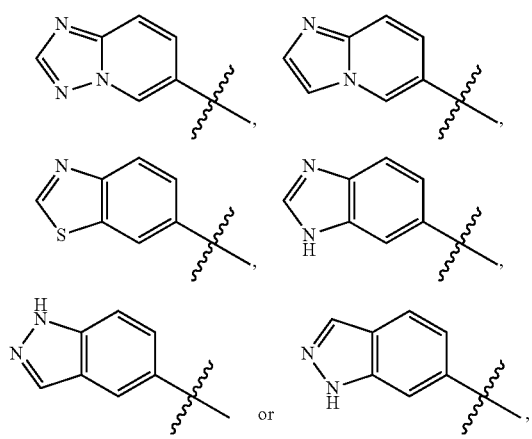

or each optionally substituted as described in (2a) above.

(2dd) Z is

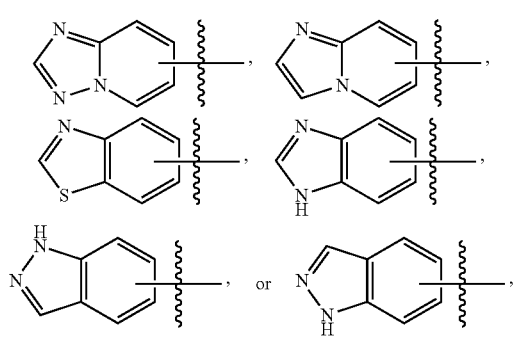

or each optionally substituted as described in (2a) above.

(2ee) Z is

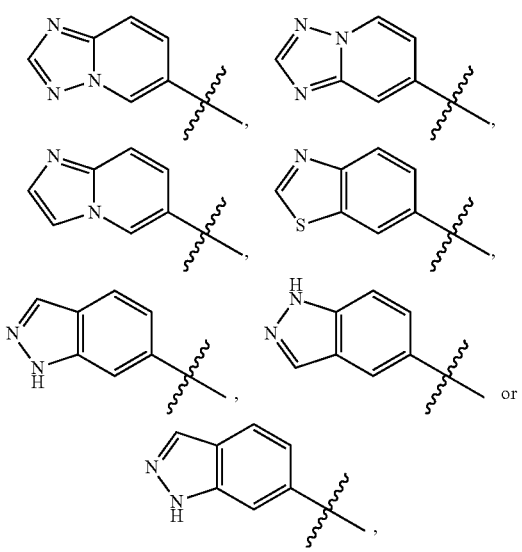

or each optionally substituted as described in (2a) above.

(2ff) Z is

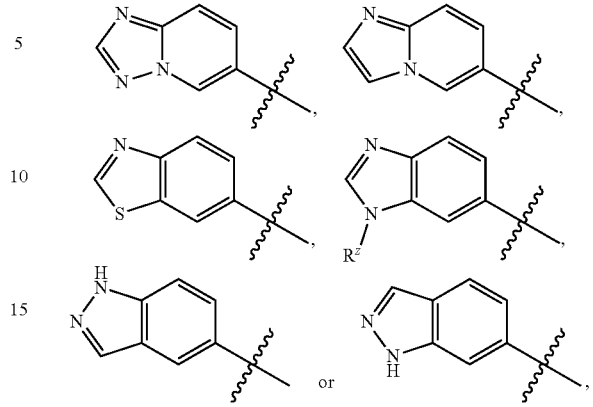

or wherein each $R^Z$ is independently hydrogen or —$C_1$-$C_6$alkyl.

(2 gg) Z is

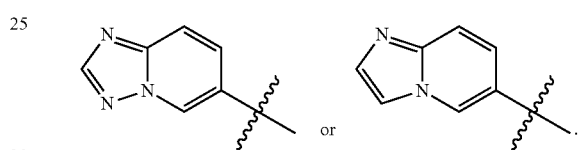

or (2 hh) Z is

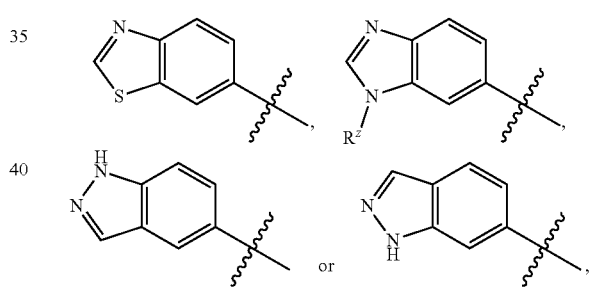

or wherein each $R^Z$ is independently hydrogen or —$C_1$-$C_6$alkyl.

(2ii) Z is

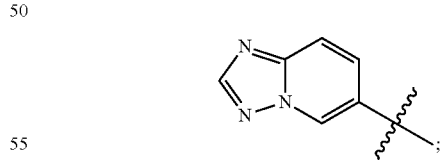

optionally substituted as described in (2a).

(2jj) Z is

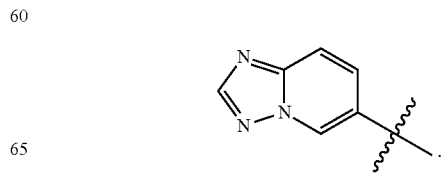

(2kk) Z is

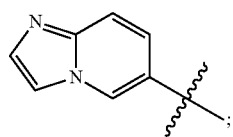 [SMILES: *c1ccc2nccn2c1]

optionally substituted as described in (2a) above.

(2ll) Z is

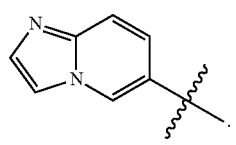 [SMILES: *c1ccc2nccn2c1]

(2mm) Z is

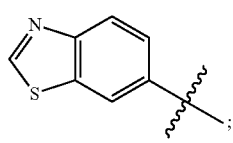 [SMILES: *c1ccc2ncsc2c1]

optionally substituted as described in (2a) above.

(2nn) Z is

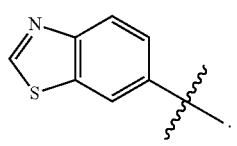 [SMILES: *c1ccc2ncsc2c1]

(2oo) Z is

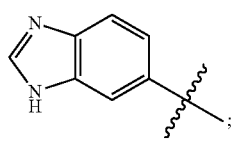 [SMILES: *c1ccc2nc[nH]c2c1]

optionally substituted as described in (2a) above.

(2pp) Z is

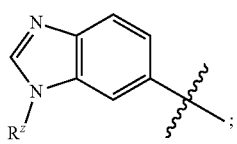

wherein each $R^Z$ is independently hydrogen or —$C_1$-$C_6$alkyl.

(2qq) Z is

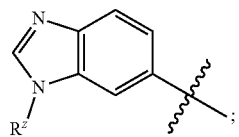

wherein each $R^Z$ is methyl.

(2rr) Z is

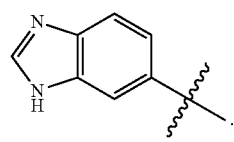 [SMILES: *c1ccc2nc[nH]c2c1]

(2ss) Z is

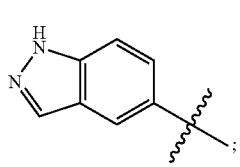 [SMILES: *c1ccc2[nH]ncc2c1]

optionally substituted as described in (2a) above.

(2tt) Z is

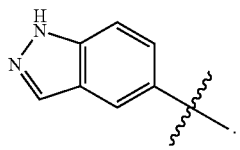 [SMILES: *c1ccc2[nH]ncc2c1]

(2uu) Z is

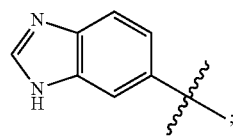

wherein $R^Z$ is as described in (2a).

(2vv) Z is

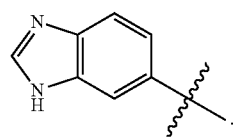 [SMILES: *c1ccc2nc[nH]c2c1]

(2ww) Z is

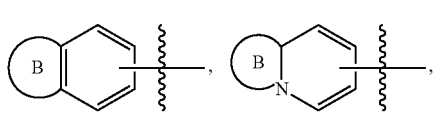

-continued

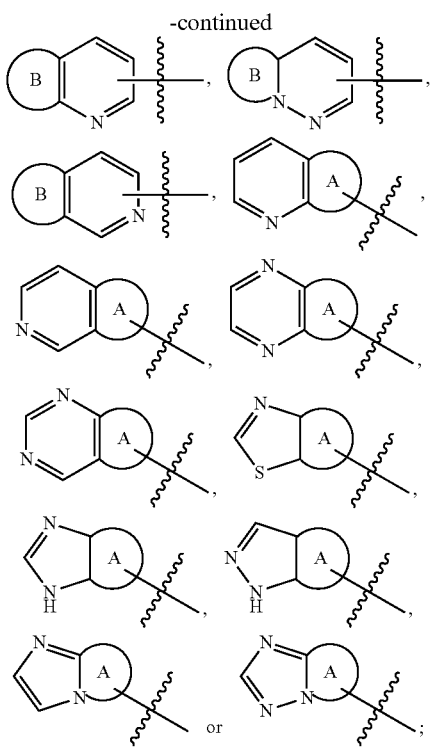

wherein ring A and B are as described in (2a), and Z is optionally substituted as described in (2a) above.

(2xx) Z is

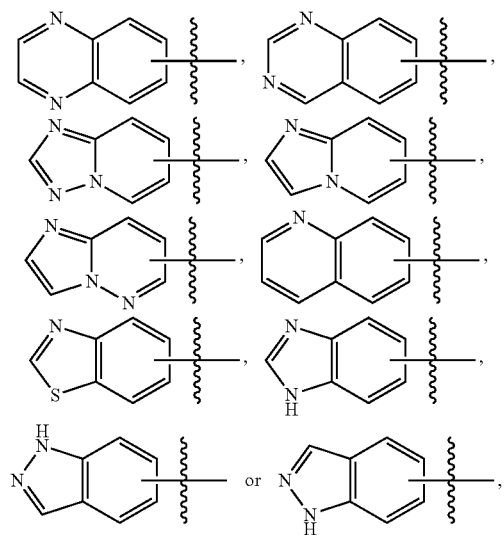

wherein ring B is as described in (2a), and Z is optionally substituted as described in (2a) above.

(2yy) Z is

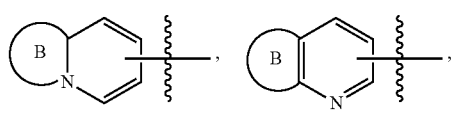

-continued

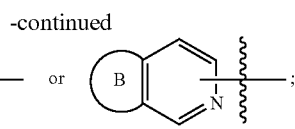

each optionally substituted as described in (2a) above.

(2zz) Z is

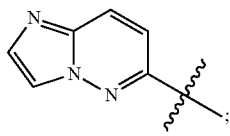 [SMILES: *c1ccc2nccn2n1]

optionally substituted as described in (2a) above.

(2aaa) Z is

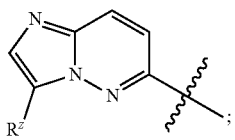

wherein $R^Z$ is hydrogen, —$C_1$-$C_6$alkyl, cyano, —C(O)NR$^{S3}_2$ or $C_{1-6}$alkyl-OR$^{S3}$.

(2bbb) Z is

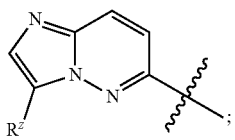

wherein $R^Z$ is cyano, —C(O)NR$^{S3}_2$ or $C_{1-6}$alkyl-OR$^{S3}$.

(2ccc) Z is

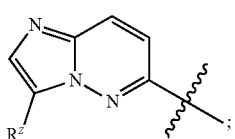

wherein $R^Z$ is cyano, —C(O)NH$_2$ or $C_{1-6}$alkyl-OH.

R' is Selected from One of the Following Groups (3a)-(3kk):

(3a) R' is hydrogen, $C_1$-$C_6$alkyl, $C_1$-$C_6$ haloalkyl, $C_1$-$C_6$alkyloxy, each optionally substituted with 1 to 3 moieties that are each independently $C_1$-$C_6$alkyl, halogen, $C_1$-$C_6$ haloalkyl or cyano.

(3b) R' is hydrogen, $C_1$-$C_6$alkyl, $C_1$-$C_6$ haloalkyl, $C_1$-$C_6$alkyloxy, each optionally substituted with 1 or 2 moieties that are each independently $C_1$-$C_6$alkyl, halogen, $C_1$-$C_6$ haloalkyl or cyano.

(3c) R' is hydrogen, $C_1$-$C_6$alkyl, $C_1$-$C_6$ haloalkyl, $C_1$-$C_6$alkyloxy, each optionally substituted with $C_1$-$C_6$alkyl, halogen, $C_1$-$C_6$ haloalkyl or cyano.

(3d) R' is hydrogen, $C_1$-$C_6$alkyl, $C_1$-$C_6$ haloalkyl, $C_1$-$C_6$alkyloxy, each optionally substituted with 1 to 3 moieties that are each independently halogen or cyano.

(3e) R' is hydrogen, $C_1$-$C_6$alkyl, $C_1$-$C_6$ haloalkyl, $C_1$-$C_6$alkyloxy, each optionally substituted with 1 to 3 moieties that are each halogen.

(3f) R' is hydrogen, $C_1$-$C_6$alkyl, $C_1$-$C_6$ haloalkyl or $C_1$-$C_6$alkyloxy.

(3 g) R' is hydrogen, $C_1$-$C_6$alkyl or $C_1$-$C_6$ haloalkyl.

(3 h) R' is hydrogen, $C_1$-$C_6$alkyl or $C_1$-$C_6$alkyloxy.

(3i) R' is hydrogen or $C_1$-$C_6$alkyl.

(3j) R' is hydrogen.

(3k) R' is $C_1$-$C_6$alkyl.

(3l) R' is hydrogen, methyl, ethyl, n-propyl, i-propyl.

(3m) R' is hydrogen or methyl.

(3n) R' is hydrogen or ethyl.

(3o) R' is methyl.

(3p) R' is ethyl.

(3q) R' is hydrogen, $C_1$-$C_6$alkyl, $C_1$-$C_6$ haloalkyl, $C_1$-$C_6$alkyloxy, —($C_0$-$C_{12}$alkyl)-Cak or —($C_0$-$C_6$alkyl)-Hca, each optionally substituted with 1 to 3 moieties that are each independently $C_1$-$C_6$alkyl, halogen, $C_1$-$C_6$ haloalkyl, —$OR^{SO}$, $C_1$-$C_6$alkyl-$OR^{SO'}$, —$C(O)OR^{SO}$, —$C(O)R^{SO}$, —$C(O)NR^{SO}_2$, —$R^{SO}$ or cyano;

wherein each $R^{SO}$ is independently hydrogen, $C_1$-$C_6$alkyl, $C_1$-$C_6$ haloalkyl, —($C_0$-$C_6$alkyl)-Ar, —($C_0$-$C_6$alkyl)-Het, —($C_0$-$C_6$alkyl)-Cak, or —($C_0$-$C_6$alkyl)-Hca, wherein Ar, Het, Cak, Hca, alkyl, and haloalkyl are optionally substituted with $C_1$-$C_6$alkyl, halogen, $C_1$-$C_6$ haloalkyl or cyano.

(3r) R' is $C_1$-$C_6$alkyl, $C_1$-$C_6$ haloalkyl, $C_1$-$C_6$alkyloxy, —($C_0$-$C_{12}$alkyl)-Cak or —($C_0$-$C_6$alkyl)-Hca, each optionally substituted with 1 to 3 moieties that are each independently $C_1$-$C_6$alkyl, halogen, $C_1$-$C_6$ haloalkyl, —$OR^{SO}$, $C_1$-$C_6$alkyl-$OR^{SO'}$, —$C(O)OR^{SO}$, —$C(O)R^{SO}$, —$C(O)NR^{SO}_2$, —$R^{SO}$ or cyano;

wherein each $R^{SO}$ is as described in (3q) above.

(3s) R' is hydrogen, $C_1$-$C_6$ haloalkyl, $C_1$-$C_6$alkyloxy, —($C_0$-$C_{12}$alkyl)-Cak or —($C_0$-$C_6$alkyl)-Hca, each optionally substituted with 1 to 3 moieties that are each independently $C_1$-$C_6$alkyl, halogen, $C_1$-$C_6$ haloalkyl, —$OR^{SO}$, $C_1$-$C_6$alkyl-$OR^{SO'}$, —$C(O)OR^{SO}$, —$C(O)R^{SO}$, —$C(O)NR^{SO}_2$, —$R^{SO}$ or cyano;

wherein each $R^{SO}$ is as described in (3q) above.

(3t) R' is hydrogen, $C_1$-$C_6$alkyl, $C_1$-$C_6$alkyloxy, —($C_0$-$C_{12}$alkyl)-Cak or —($C_0$-$C_6$alkyl)-Hca, each optionally substituted with 1 to 3 moieties that are each independently $C_1$-$C_6$alkyl, halogen, $C_1$-$C_6$ haloalkyl, —$OR^{SO}$, $C_1$-$C_6$alkyl-$OR^{SO'}$, —$C(O)OR^{SO}$, —$C(O)R^{SO}$, —$C(O)NR^{SO}_2$ or cyano;

wherein each $R^{SO}$ is as described in (3q) above.

(3u) R' is hydrogen, —($C_0$-$C_{12}$alkyl)-Cak or —($C_0$-$C_6$alkyl)-Hca, each optionally substituted with 1 to 3 moieties that are each independently $C_1$-$C_6$alkyl, halogen, $C_1$-$C_6$ haloalkyl, —$OR^{SO}$, $C_1$-$C_6$alkyl-$OR^{SO'}$, —$C(O)OR^{SO}$, —$C(O)R^{SO}$, —$C(O)NR^{SO}_2$, —$R^{SO}$ or cyano;

wherein each $R^{SO}$ is as described in (3q) above.

(3v) R' is hydrogen, $C_1$-$C_6$alkyl, $C_1$-$C_6$ haloalkyl, $C_1$-$C_6$alkyloxy, —($C_0$-$C_{12}$alkyl)-Cak or —($C_0$-$C_6$alkyl)-Hca, each optionally substituted with 1 to 3 moieties that are each independently $C_1$-$C_6$alkyl, halogen, $C_1$-$C_6$ haloalkyl, —$OR^{SO}$, $C_1$-$C_6$alkyl-$OR^{SO'}$, —$C(O)OR^{SO}$, —$C(O)R^{SO}$, —$C(O)NR^{SO}_2$, —$R^{SO}$ or cyano;

wherein each $R^{SO}$ is as described in (3q) above.

(3w) R' is hydrogen, $C_1$-$C_6$alkyl or $C_1$-$C_6$ haloalkyl, each optionally substituted with 1 to 3 moieties that are each independently $C_1$-$C_6$alkyl, halogen, $C_1$-$C_6$ haloalkyl, —$OR^{SO}$, $C_1$-$C_6$alkyl-$OR^{SO'}$, —$C(O)OR^{SO}$, —$C(O)R^{SO}$, —$C(O)NR^{SO}_2$, —$R^{SO}$ or cyano;

wherein each $R^{SO}$ is as described in (3q) above.

(3x) Any of groups (3q)-(3w), wherein each $R^{SO}$ is independently $C_1$-$C_6$alkyl, $C_1$-$C_6$ haloalkyl, —($C_0$-$C_6$alkyl)-Ar, —($C_0$-$C_6$alkyl)-Het, —($C_0$-$C_6$alkyl)-Cak or —($C_0$-$C_6$alkyl)-Hca, wherein Ar, Het, Cak, Hca, alkyl, and haloalkyl are unsubstituted.

(3y) Any of groups (3q)-(3w), wherein each $R^{SO}$ is independently $C_1$-$C_6$alkyl, $C_1$-$C_6$ haloalkyl, —($C_0$-$C_6$alkyl)-Ar, —($C_0$-$C_6$alkyl)-Het, —($C_0$-$C_6$alkyl)-Cak, or —($C_0$-$C_6$alkyl)-Hca, wherein Ar, Het, Cak, Hca, alkyl, and haloalkyl are optionally substituted with $C_1$-$C_6$alkyl, halogen, $C_1$-$C_6$ haloalkyl or cyano.

(3z) Any of groups (3q)-(3w), wherein each $R^{SO}$ is independently hydrogen, $C_1$-$C_6$alkyl, $C_1$—($C_0$-$C_6$alkyl)-Cak, or —($C_0$-$C_6$alkyl)-Hca, wherein Cak, Hca and alkyl are optionally substituted with $C_1$-$C_6$alkyl, halogen, $C_1$-$C_6$ haloalkyl or cyano.

(3aa) Any of groups (3q)-(3w), wherein each $R^{SO}$ is independently hydrogen, $C_1$-$C_6$alkyl, $C_1$—($C_0$-$C_6$alkyl)-Cak, or —($C_0$-$C_6$alkyl)-Hca, wherein Cak, Hca and alkyl are unsubstituted.

(3bb) Any of groups (3q)-(3w), wherein each $R^{SO}$ is independently hydrogen, $C_1$-$C_6$alkyl or $C_1$-$C_6$ haloalkyl.

(3cc) R' and $R^1$ combined with the atoms to which they are attached form a five- to eight-membered ring.

(3dd) R' and $R^1$ combined with the atoms to which they are attached form a five- to eight-membered Hca, each optionally substituted with 1 to 3 moieties that are each independently $C_1$-$C_6$alkyl, halogen, $C_1$-$C_6$ haloalkyl, —$OR^{SO}$, $C_1$-$C_6$alkyl-$OR^{SO'}$, —$C(O)OR^{SO}$, —$C(O)R^{SO}$, —$C(O)NR^{SO}_2$ or cyano.

(3ee) R' and $R^1$ combined with the atoms to which they are attached form a five- to eight-membered Hca, each optionally substituted with 1 or 2 moieties that are each independently $C_1$-$C_6$alkyl, halogen, $C_1$-$C_6$ haloalkyl, —$OR^{SO}$, $C_1$-$C_6$alkyl-$OR^{SO'}$, —$C(O)OR^{SO}$, —$C(O)R^{SO}$, —$C(O)NR^{SO}_2$ or cyano.

(3ff) R' and $R^1$ combined with the atoms to which they are attached form a five- to eight-membered Hca, each optionally substituted with $C_1$-$C_6$alkyl, halogen, $C_1$-$C_6$ haloalkyl, —$OR^{SO}$, $C_1$-$C_6$alkyl-$OR^{SO'}$, —$C(O)OR^{SO}$, —$C(O)R^{SO}$, —$C(O)NR^{SO}_2$ or cyano.

(3 gg) R' and $R^1$ combined with the atoms to which they are attached form a five- to eight-membered Hca, each optionally substituted with 1 to 3 moieties that are each independently $C_1$-$C_6$alkyl, $C_1$-$C_6$ haloalkyl, —$C(O)OR^{SO}$, —$C(O)R^{SO}$, —$C(O)NR^{SO}_2$ or cyano.

(3 hh) R' and $R^1$ combined with the atoms to which they are attached form a five- to eight-membered Hca, each optionally substituted with 1 to 3 moieties that are each independently $C_1$-$C_6$alkyl, $C_1$-$C_6$ haloalkyl, —$C(O)OR^{SO}$, —$C(O)R^{SO}$ or —$C(O)NR^{SO}_2$.

(3ii) R' and $R^1$ combined with the atoms to which they are attached form a five- to eight-membered Hca, each optionally substituted with $C_1$-$C_6$alkyl, $C_1$-$C_6$ haloalkyl, —$C(O)OR^{SO}$, —$C(O)R^{SO}$, —$C(O)NR^{SO}_2$ or cyano.

(3jj) R' and $R^1$ combined with the atoms to which they are attached form a five- to eight-membered Hca, each optionally substituted with $C_1$-$C_6$alkyl, $C_1$-$C_6$ haloalkyl, —$C(O)OR^{SO}$, —$C(O)R^{SO}$ or —$C(O)NR^{SO}_2$.

(3kk) R' and $R^1$ combined with the atoms to which they are attached form an unsubstituted five- to eight-membered Hca.

$R^1$ is Selected from One of the Following Groups (4a)-(4 gg):

(4a) $R^1$ is hydrogen, $C_1$-$C_6$alkyl, $C_1$-$C_6$ haloalkyl, $C_1$-$C_6$alkyloxy, —$OR^{S1}$, —$NR^{S1}{}_2$, —$SR^{S1}$, each optionally substituted with 1 to 3 moieties that are each independently $C_1$-$C_6$alkyl, halogen, $C_1$-$C_6$ haloalkyl or cyano.

(4b) $R^1$ is hydrogen, $C_1$-$C_6$alkyl, $C_1$-$C_6$ haloalkyl, $C_1$-$C_6$alkyloxy, —$OR^{S1}$, —$NR^{S1}{}_2$, —$SR^{S1}$, each optionally substituted with 1 or 2 moieties that are each independently $C_1$-$C_6$alkyl, halogen, $C_1$-$C_6$ haloalkyl or cyano.

(4c) $R^1$ is hydrogen, $C_1$-$C_6$alkyl, $C_1$-$C_6$ haloalkyl, $C_1$-$C_6$alkyloxy, —$OR^{S1}$, —$NR^{S1}{}_2$, —$SR^{S1}$, each optionally substituted with $C_1$-$C_6$alkyl, halogen, $C_1$-$C_6$ haloalkyl or cyano.

(4d) $R^1$ is hydrogen, $C_1$-$C_6$alkyl, $C_1$-$C_6$ haloalkyl, $C_1$-$C_6$alkyloxy, —$OR^{S1}$, —$NR^{S1}{}_2$, —$SR^{S1}$, each optionally substituted with 1 to 3 moieties that are each independently $C_1$-$C_6$alkyl or halogen.

(4e) $R^1$ is hydrogen, $C_1$-$C_6$alkyl, $C_1$-$C_6$ haloalkyl, $C_1$-$C_6$alkyloxy, —$OR^{S1}$, —$NR^{S1}{}_2$, —$SR^{S1}$ each optionally substituted with cyano.

(4f) $R^1$ is hydrogen, $C_1$-$C_6$alkyl, $C_1$-$C_6$ haloalkyl, $C_1$-$C_6$alkyloxy, —$OR^{S1}$, —$NR^{S1}{}_2$, or —$SR^{S1}$.

(4 g) $R^1$ is $C_1$-$C_6$alkyl, $C_1$-$C_6$ haloalkyl, $C_1$-$C_6$alkyloxy, —$OR^{S1}$, —$NR^{S1}{}_2$ or —$SR^{S1}$.

(4 h) $R^1$ is hydrogen, $C_1$-$C_6$alkyl, $C_1$-$C_6$ haloalkyl or $C_1$-$C_6$alkyloxy.

(4i) $R^1$ is $C_1$-$C_6$alkyl, $C_1$-$C_6$ haloalkyl or $C_1$-$C_6$alkyloxy.

(4j) $R^1$ is hydrogen, —$OR^{S1}$, —$NR^{S1}{}_2$ or —$SR^{S1}$.

(4k) $R^1$ is —$OR^{S1}$, —$NR^{S1}{}_2$ or —$SR^{S1}$.

(4l) $R^1$ is hydrogen, $C_1$-$C_6$alkyl or —$NR^{S1}{}_2$.

(4m) $R^1$ is $C_1$-$C_6$alkyl or —$NR^{S1}{}_2$.

(4n) $R^1$ is hydrogen, $C_1$-$C_6$alkyl or —$OR^{S1}$.

(4o) $R^1$ is $C_1$-$C_6$alkyl or —$OR^{S1}$.

(4p) $R^1$ is hydrogen, $C_1$-$C_6$alkyl or —$SR^{S1}$.

(4q) $R^1$ is $C_1$-$C_6$alkyl or —$SR^{S1}$.

(4r) $R^1$ is hydrogen or $C_1$-$C_6$alkyl.

(4s) $R^1$ is hydrogen or —$NR^{S1}{}_2$.

(4t) $R^1$ is —$NR^{S1}{}_2$.

(4u) $R^1$ is hydrogen.

(4v) $R^1$ is $C_1$-$C_6$alkyl.

(4w) $R^1$ is hydrogen, methyl, ethyl, n-propyl, i-propyl.

(4x) $R^1$ is hydrogen or methyl.

(4y) $R^1$ is hydrogen or ethyl.

(4z) $R^1$ is methyl.

(4aa) $R^1$ is ethyl.

(4bb) $R^1$ is hydrogen, $C_1$-$C_6$alkyl, $C_1$-$C_6$ haloalkyl, $C_1$-$C_6$alkyloxy, —$OR^{S1}$, —$NR^{S1}{}_2$, —$SR^{S1}$ or —$N(R^{S1})C(O)R^{S1'}$, each optionally substituted with 1 to 3 moieties that are each independently $C_1$-$C_6$alkyl, halogen, $C_1$-$C_6$ haloalkyl or cyano.

(4cc) Any of groups (4a)-(4q), wherein each $R^{S1}$ is independently hydrogen, $C_1$-$C_6$alkyl, $C_1$-$C_6$ haloalkyl, —($C_0$-$C_6$alkyl)-Ar, —($C_0$-$C_6$alkyl)-Het, —($C_0$-$C_6$alkyl)-Cak, or —($C_0$-$C_6$alkyl)-Hca, wherein Ar, Het, Cak, Hca, alkyl, and haloalkyl are optionally substituted with $C_1$-$C_6$alkyl, halogen, $C_1$-$C_6$ haloalkyl or cyano.

(4dd) Any of groups (4a)-(4q), wherein each $R^{S1}$ is independently hydrogen or $C_1$-$C_6$alkyl.

(4ee) Any of groups (4a)-(4q), wherein each $R^{S1}$ is independently hydrogen, $C_1$-$C_6$alkyl, $C_1$-$C_6$ haloalkyl, —($C_0$-$C_6$alkyl)-Ar, —($C_0$-$C_6$alkyl)-Het, —($C_0$-$C_6$alkyl)-Cak, or —($C_0$-$C_6$alkyl)-Hca, wherein Ar, Het, Cak, Hca, alkyl, and haloalkyl are unsubstituted.

(4ff) Any of groups (4a)-(4q), wherein each $R^{S1}$ is independently hydrogen, $C_1$-$C_6$alkyl, or $C_1$-$C_6$ haloalkyl, wherein alkyl, and haloalkyl are optionally substituted with $C_1$-$C_6$alkyl, halogen, $C_1$-$C_6$ haloalkyl or cyano.

(4 gg) Any of groups (4a)-(4q), wherein each $R^{S1}$ is independently hydrogen, —($C_0$-$C_6$alkyl)-Ar, —($C_0$-$C_6$alkyl)-Het, —($C_0$-$C_6$alkyl)-Cak, or —($C_0$-$C_6$alkyl)-Hca, wherein Ar, Het, Cak, Hca and alkyl are optionally substituted with $C_1$-$C_6$alkyl, halogen, $C_1$-$C_6$ haloalkyl or cyano.

Particular embodiments of this aspect of the invention comprise compounds of any one of the formulae (I), (I') and (Ia)-(Ix), each as defined in each of the following rows (or a pharmaceutically acceptable salt, prodrug, or N-oxide thereof, or a solvate or hydrate thereof), wherein each entry is a group number as defined above (e.g., (4z) refers to $R^1$ is methyl), and a dash "-" indicates that the variable is as defined in embodiment $I_1$ or defined according to any one of the applicable variable definitions (1a)-(1ddd), (2a)-(2ccc), (3a)-(3kk) and (4a)-(4 gg) [e.g., when $R^1$ is a dash, it can be either as defined in any of embodiments $I_1$-$I_7$ or any one of definitions (4a)-(4 gg)]:

| | (I) | A | Z | R' | $R^1$ |
|---|---|---|---|---|---|
| (1)-1 | (Ia) | (1a) | (2a) | (3a) | (4a) |
| (1)-2 | (Io) | (1c) | (2b) | (3i) | (4f) |
| (1)-3 | (Ic) | (1d) | (2g) | (3j) | (4j) |
| (1)-4 | (Id) | (1e) | (2i) | (3k) | (4l) |
| (1)-5 | (Ie) | (1h) | (2a) | (3l) | (4r) |
| (1)-6 | (If) | (1k) | (2q) | (3m) | (4u) |
| (1)-7 | (Ig) | (1l) | (2r) | (3n) | (4v) |
| (1)-8 | (Ih) | (1n) | (2t) | (3o) | (4x) |
| (1)-9 | (Ii) | (1s) | (2x) | (3p) | (4y) |
| (1)-10 | (Ij) | (1gg) | (2y) | (3i) | (4z) |
| (1)-11 | (Ib) | (1jj) | (2aa) | (3j) | (4r) |
| (1)-12 | (Ic) | (1kk) | (2ff) | (3k) | (4u) |
| (1)-13 | (Id) | (1ll) | (2qq) | (3l) | (4v) |
| (1)-14 | (Il) | (1mm) | (2tt) | (3j) | (4v) |
| (1)-15 | (Ic) | (1ss) | (2vv) | (3k) | (4a) |
| (1)-16 | (Ia) | (1tt) | (2g) | (3l) | (4f) |
| (1)-17 | (Ib) | (1uu) | (2i) | (3m) | (4j) |
| (1)-18 | (Im) | (1xx) | (2a) | (3n) | (4l) |
| (1)-19 | (Id) | (1aaa) | (2q) | (3o) | (4r) |
| (1)-20 | (Ie) | (1bbb) | (2ff) | (3p) | (4u) |
| (1)-21 | (If) | (1ccc) | (2qq) | (3n) | (4v) |
| (1)-22 | (Is) | (1aaa) | (2qq) | (3o) | (4x) |
| (1)-23 | (Ih) | (1bbb) | (2ff) | (3p) | (4y) |
| (1)-24 | (Ii) | (1ccc) | (2qq) | (3n) | (4z) |
| (1)-25 | (Ij) | (1uu) | (2i) | (3o) | (4r) |
| (1)-26 | (Ih) | (1xx) | (2a) | (3p) | (4u) |
| (1)-27 | (Ii) | (1s) | (2q) | (3j) | (4v) |
| (1)-28 | (Iv) | (1gg) | (2ff) | (3k) | (4j) |
| (1)-29 | (Ic) | (1d) | (2qq) | (3l) | (4l) |
| (1)-30 | (Id) | (1a) | (2b) | (3m) | (4j) |
| (1)-31 | (Ie) | (1c) | (2g) | (3n) | (4l) |
| (1)-32 | (Ir) | (1d) | (2i) | (3o) | (4r) |
| (1)-33 | (Ig) | (1s) | (2a) | (3p) | (4r) |
| (1)-34 | (Ih) | (1bbb) | (2q) | (3n) | (4j) |
| (1)-35 | (Ii) | (1ccc) | (2r) | (3o) | (4l) |
| (1)-36 | (Ij) | (1d) | (2t) | (3p) | (4r) |
| (1)-37 | (If) | (1e) | (2x) | (3j) | (4f) |
| (1)-38 | (Ik) | (1h) | (2y) | (3k) | (4j) |
| (1)-39 | (Ib) | (1k) | (2aa) | (3l) | (4l) |
| (1)-40 | (Ic) | (1l) | (2ff) | (3a) | (4l) |
| (1)-41 | (Ip) | (1n) | (2vv) | (3i) | (4r) |
| (1)-42 | (Ic) | (1s) | (2g) | (3j) | (4f) |
| (1)-43 | (Id) | (1gg) | (2i) | (3k) | (4j) |
| (1)-44 | (Ie) | (1jj) | (2a) | (3l) | (4l) |
| (1)-45 | (If) | (1kk) | (2q) | (3m) | (4r) |
| (1)-46 | (Ig) | (1ll) | (2a) | (3n) | (4a) |
| (1)-47 | (Ih) | (1mm) | (2b) | (3o) | (4f) |
| (1)-48 | (Ii) | (1ss) | (2g) | (3p) | (4j) |
| (1)-49 | (Ij) | (1tt) | (2i) | (3n) | (4l) |
| (1)-50 | (It) | (1uu) | (2a) | (3j) | (4r) |

-continued

|  | (I) | A | Z | R' | R¹ |
|---|---|---|---|---|---|
| (1)-51 | (Ii) | (1xx) | (2q) | (3k) | (4u) |
| (1)-52 | (Ij) | (1aaa) | (2r) | (3l) | (4v) |
| (1)-53 | (Ic) | (1bbb) | (2t) | (3m) | (4x) |
| (1)-54 | (Id) | (1ccc) | (2x) | (3i) | (4y) |
| (1)-55 | (Iq) | (1l) | (2y) | (3j) | (4z) |
| (1)-56 | (If) | (1n) | (2aa) | (3k) | (4r) |
| (1)-57 | (Ig) | (1s) | (2ff) | (3l) | (4u) |
| (1)-58 | (Ih) | (1a) | (2qq) | (3m) | (4v) |
| (1)-59 | (Ii) | (1c) | (2tt) | (3n) | (4r) |
| (1)-60 | (Ij) | (1d) | (2vv) | (3o) | (4u) |
| (1)-61 | (It) | (1e) | (2r) | (3p) | (4v) |
| (1)-62 | (Ii) | (1h) | (2t) | (3j) | (4j) |
| (1)-63 | (Ij) | (1k) | (2x) | (3k) | (4l) |
| (1)-64 | (Ia) | (1l) | (2y) | (3l) | (4r) |
| (1)-65 | (Ib) | (1n) | (2aa) | (3m) | (4f) |
| (1)-66 | (Ic) | (1s) | (2ff) | (3l) | (4j) |
| (1)-67 | (Ik) | (1gg) | (2qq) | (3a) | (4l) |
| (1)-68 | (Ib) | (1jj) | (2tt) | (3i) | (4v) |
| (1)-69 | (Ic) | (1kk) | (2vv) | (3j) | (4a) |
| (1)-70 | (Id) | (1ll) | (2ff) | (3i) | (4f) |
| (1)-71 | (Iq) | (1mm) | (2qq) | (3j) | (4j) |
| (1)-72 | (If) | (1ss) | (2i) | (3k) | (4l) |
| (1)-73 | (Is) | (1tt) | (2a) | (3l) | (4r) |
| (1)-74 | (Ih) | (1uu) | (2q) | (3m) | (4a) |
| (1)-75 | (Ii) | (1xx) | (2b) | (3n) | (4f) |
| (1)-76 | (Iv) | (1aaa) | (2g) | (3o) | (4j) |
| (1)-77 | (If) | (1bbb) | (2i) | (3p) | (4l) |
| (1)-78 | (Ia) | (1ccc) | (2a) | (3i) | (4a) |
| (1)-79 | (Ib) | (1n) | (2q) | (3j) | (4f) |
| (1)-80 | (In) | (1s) | (2r) | (3k) | (4j) |
| (1)-81 | (Ic) | (1gg) | (2t) | (3j) | (4l) |
| (1)-82 | (Id) | (1aaa) | (2x) | (3k) | (4r) |
| (1)-83 | (Ie) | (1bbb) | (2y) | (3l) | (4u) |
| (1)-84 | (If) | (1ccc) | (2aa) | (3m) | (4v) |
| (1)-85 | (Ig) | (1l) | (2ff) | (3k) | (4x) |
| (1)-86 | (Ih) | (1n) | (2qq) | (3l) | (4y) |
| (1)-87 | (Iu) | (1s) | (2tt) | (3a) | (4z) |
| (1)-88 | (Ij) | (1d) | (2vv) | (3i) | (4r) |
| (1)-89 | (Il) | (1e) | (2vv) | (3j) | (4u) |
| (1)-90 | (Ic) | (1h) | (2g) | (3k) | (4v) |
| (1)-91 | (Id) | (1k) | (2i) | (3l) | (4j) |
| (1)-92 | (Ib) | (1l) | (2a) | (3m) | (4l) |
| (1)-93 | (Im) | (1n) | (2q) | (3n) | (4a) |
| (1)-94 | (Id) | (1s) | (2i) | (3o) | (4f) |
| (1)-95 | (Ie) | (1gg) | (2a) | (3p) | (4l) |
| (1)-96 | (Ir) | (1jj) | (2q) | (3a) | (4r) |
| (1)-97 | (Ig) | (1kk) | (2r) | (3i) | (4u) |
| (1)-98 | (Ih) | (1ll) | (2t) | (3j) | (4v) |
| (1)-99 | (Ii) | (1mm) | (2x) | (3i) | (4x) |
| (1)-100 | (Ij) | (1ss) | (2y) | (3j) | (4y) |
| (1)-101 | (Ih) | (1tt) | (2aa) | (3i) | (4z) |
| (1)-102 | (Iu) | (1uu) | (2ff) | (3j) | (4r) |
| (1)-103 | (Ij) | (1xx) | (2qq) | (3k) | (4a) |
| (1)-104 | (Ic) | (1aaa) | (2tt) | (3l) | (4f) |
| (1)-105 | (Id) | (1bbb) | (2vv) | (3a) | (4j) |
| (1)-106 | (Ie) | (1ccc) | (2r) | (3i) | (4l) |
| (1)-107 | (If) | (1h) | (2vv) | (3j) | (4r) |
| (1)-108 | (Ik) | (1k) | (2g) | (3j) | (4u) |
| (1)-109 | (Ib) | (1l) | (2i) | (3k) | (4v) |
| (1)-110 | (Ic) | (1n) | (2a) | (3l) | (4x) |
| (1)-111 | (Id) | (1s) | (2q) | (3a) | (4y) |
| (1)-112 | (Ie) | (1gg) | (2qq) | (3i) | (4z) |
| (1)-113 | (If) | (1jj) | (2tt) | (3j) | (4j) |
| (1)-114 | (Ig) | (1kk) | (2vv) | (3j) | (4l) |
| (1)-115 | (It) | (1ll) | (2ff) | (3k) | (4a) |
| (1)-116 | (Ii) | (1mm) | (2qq) | (3l) | (4f) |
| (1)-117 | (Ij) | (1ss) | (2i) | (3m) | (4v) |
| (1)-118 | (Io) | (1tt) | (2a) | (3k) | (4j) |
| (1)-119 | (Ic) | (1uu) | (2q) | (3l) | (4l) |
| (1)-120 | (Id) | (1xx) | (2ff) | (3m) | (4a) |
| (1)-121 | (Ig) | (1aaa) | (2qq) | (3n) | (4f) |
| (1)-122 | (Ih) | (1bbb) | (2b) | (3o) | (4l) |
| (1)-123 | (Iq) | (1ccc) | (2g) | (3p) | (4r) |
| (1)-124 | (If) | (1l) | (2i) | (3i) | (4u) |
| (1)-125 | (Ig) | (1n) | (2a) | (3j) | (4v) |
| (1)-126 | (Ih) | (1s) | (2q) | (3k) | (4x) |
| (1)-127 | (Ib) | (1d) | (2r) | (3l) | (4y) |
| (1)-128 | (Ic) | (1e) | (2t) | (3a) | (4z) |
| (1)-129 | (Id) | (1h) | (2x) | (3i) | (4j) |
| (1)-130 | (Ie) | (1k) | (2y) | (3j) | (4l) |
| (1)-131 | (Ir) | (1n) | (2aa) | (3k) | (4a) |
| (1)-132 | (Ig) | (1s) | (2ff) | (3l) | (4f) |
| (1)-133 | (Ih) | (1gg) | (2qq) | (3m) | (4v) |
| (1)-134 | (Ii) | (1gg) | (2tt) | (3n) | (4j) |
| (1)-135 | (Ij) | (1jj) | (2vv) | (3o) | (4l) |
| (1)-136 | (Ih) | (1kk) | (2g) | (3p) | (4a) |
| (1)-137 | (Ii) | (1ll) | (2i) | (3a) | (4f) |
| (1)-138 | (Iv) | (1mm) | (2a) | (3i) | (4j) |
| (1)-139 | (Ic) | (1ss) | (2q) | (3j) | (4l) |
| (1)-140 | (Id) | (1tt) | (2b) | (3a) | (4r) |
| (1)-141 | (Iq) | (1uu) | (2g) | (3i) | (4u) |
| (1)-142 | (If) | (1xx) | (2i) | (3j) | (4v) |
| (1)-143 | (Ig) | (1aaa) | (2a) | (3i) | (4x) |
| (1)-144 | (Ih) | (1bbb) | (2q) | (3j) | (4y) |
| (1)-145 | (Ii) | (1ccc) | (2r) | (3k) | (4z) |
| (1)-146 | (Ij) | (1l) | (2t) | (3l) | (4j) |
| (1)-147 | (It) | (1n) | (2x) | (3m) | (4l) |
| (1)-148 | (Ii) | (1s) | (2y) | (3n) | (4a) |
| (1)-149 | (Iv) | (1n) | (2aa) | (3o) | (4f) |
| (1)-150 | (Id) | (1s) | (2ff) | (3p) | (4a) |
| (1)-151 | (Ia) | (1n) | (2qq) | (3i) | (4f) |
| (1)-152 | (Ib) | (1s) | (2tt) | (3j) | (4u) |
| (1)-153 | (Im) | (1gg) | (2vv) | (3k) | (4v) |
| (1)-154 | (Id) | (1c) | (2vv) | (3l) | (4j) |
| (1)-155 | (Ie) | (1d) | (2g) | (3i) | (4l) |
| (1)-156 | (If) | (1e) | (2i) | (3j) | (4a) |
| (1)-157 | (Is) | (1h) | (2a) | (3k) | (4f) |
| (1)-158 | (Ih) | (1k) | (2q) | (3l) | (4u) |
| (1)-159 | (Ii) | (1l) | (2g) | (3m) | (4v) |
| (1)-160 | (Ij) | (1n) | (2i) | (3n) | (4j) |
| (1)-161 | (Ih) | (1s) | (2a) | (3o) | (4l) |
| (1)-162 | (Iu) | (1gg) | (2q) | (3p) | (4a) |
| (1)-163 | (Ij) | (1jj) | (2g) | (3a) | (4f) |
| (1)-164 | (Ic) | (1kk) | (2i) | (3i) | (4j) |
| (1)-165 | (Id) | (1ll) | (2a) | (3j) | (4l) |
| (1)-166 | (Ie) | (1mm) | (2q) | (3a) | (4r) |
| (1)-167 | (If) | (1ss) | (2r) | (3i) | (4u) |
| (1)-168 | (Ig) | (1tt) | (2t) | (3j) | (4v) |
| (1)-169 | (Ih) | (1uu) | (2x) | (3k) | (4x) |
| (1)-170 | (Iu) | (1xx) | (2y) | (3l) | (4y) |
| (1)-171 | (Ij) | (1aaa) | (2aa) | (3m) | (4z) |
| (1)-172 | (Ie) | (1bbb) | (2ff) | (3n) | (4j) |
| (1)-173 | (If) | (1ccc) | (2qq) | (3o) | (4l) |
| (1)-174 | (Is) | (1n) | (2tt) | (3p) | (4a) |
| (1)-175 | (Ih) | (1s) | (2vv) | (3a) | (4f) |
| (1)-176 | (Ih) | (1gg) | (2g) | (3i) | (4r) |
| (1)-177 | (Ii) | (1e) | (2i) | (3j) | (4u) |
| (1)-178 | (Iv) | (1h) | (2a) | (3k) | (4j) |
| (1)-179 | (Ic) | (1k) | (2q) | (3l) | (4l) |
| (1)-180 | (Id) | (1l) | (2a) | (3a) | (4r) |
| (1)-181 | (Ie) | (1n) | (2b) | (3i) | (4f) |
| (1)-182 | (Ir) | (1s) | (2g) | (3j) | (4r) |
| (1)-183 | (Ig) | (1gg) | (2i) | (3k) | (4u) |
| (1)-184 | (Ih) | (1jj) | (2a) | (3l) | (4v) |
| (1)-185 | (Ii) | (1kk) | (2q) | (3m) | (4u) |
| (1)-186 | (Ij) | (1ll) | (2r) | (3n) | (4v) |
| (1)-187 | (It) | (1mm) | (2t) | (3o) | (4x) |
| (1)-188 | (Ii) | (1ss) | (2x) | (3p) | (4y) |
| (1)-189 | (Ij) | (1tt) | (2y) | (3i) | (4z) |
| (1)-190 | (Ig) | (1uu) | (2aa) | (3j) | (4r) |
| (1)-191 | (Ih) | (1xx) | (2ff) | (3k) | (4u) |
| (1)-192 | (Ih) | (1aaa) | (2qq) | (3l) | (4v) |
| (1)-193 | (Iu) | (1tt) | (2tt) | (3i) | (4j) |
| (1)-194 | (Ij) | (1uu) | (2vv) | (3j) | (4l) |
| (1)-195 | (Ig) | (1xx) | (2vv) | (3k) | (4a) |
| (1)-196 | (It) | (1l) | (2y) | (3l) | (4f) |
| (1)-197 | (Ic) | (1n) | (2aa) | (3m) | (4f) |
| (1)-198 | (Id) | (1s) | (2ff) | (3n) | (4j) |
| (1)-199 | (Ie) | (1n) | (2g) | (3o) | (4l) |
| (1)-200 | (If) | (1s) | (2i) | (3p) | (4r) |
| (1)-201 | (Ig) | (1gg) | (2a) | (3a) | (4u) |
| (1)-202 | (Ih) | (1d) | (2q) | (3i) | (4v) |
| (1)-203 | (Ii) | (1a) | (2a) | (3j) | (4x) |
| (1)-204 | (Ij) | (1c) | (2b) | (3n) | (4y) |

| (I) | A | Z | R' | R¹ |
|---|---|---|---|---|
| (1)-205 | (Iq) | (1d) | (2g) | (3o) | (4z) |
| (1)-206 | (If) | (1e) | (2i) | (3p) | (4j) |
| (1)-207 | (Ig) | (1h) | (2a) | (3k) | (4l) |
| (1)-208 | (Ih) | (1k) | (2q) | (3l) | (4r) |
| (1)-209 | (In) | (1l) | (2r) | (3a) | (4u) |
| (1)-210 | (Id) | (1n) | (2t) | (3i) | (4v) |
| (1)-211 | (Ie) | (1n) | (2x) | (3j) | (4x) |
| (1)-212 | (If) | (1s) | (2y) | (3k) | (4y) |
| (1)-213 | (Is) | (1gg) | (2aa) | (3l) | (4z) |
| (1)-214 | (Ih) | (1kk) | (2ff) | (3m) | (4j) |
| (1)-215 | (Ii) | (1ll) | (2qq) | (3n) | (4l) |
| (1)-216 | (Ij) | (1mm) | (2tt) | (3o) | (4a) |
| (1)-217 | (Ih) | (1ss) | (2vv) | (3p) | (4f) |
| (1)-218 | (Ii) | (1tt) | (2ff) | (3n) | (4v) |
| (1)-219 | (Ij) | (1uu) | (2qq) | (3o) | (4a) |
| (1)-220 | (Ig) | (1xx) | (2i) | (3p) | (4f) |
| (1)-221 | (Ih) | (1aaa) | (2a) | (3a) | (4j) |
| (1)-222 | (It) | (1bbb) | (2q) | (3i) | (4l) |
| (1)-223 | (Ii) | (1ccc) | (2ff) | (3j) | (4r) |
| (1)-224 | (Iv) | (1tt) | (2qq) | (3k) | (4u) |
| (1)-225 | (Id) | (1uu) | (2vv) | (3l) | (4v) |
| (1)-226 | (Ie) | (1xx) | (2g) | (3m) | (4x) |
| (1)-227 | (If) | (1gg) | (2i) | (3a) | (4y) |
| (1)-228 | (Is) | (1c) | (2a) | (3i) | (4z) |
| (1)-229 | (Ih) | (1d) | (2q) | (3j) | (4j) |
| (1)-230 | (Ib) | (1e) | (2i) | (3k) | (4l) |
| (1)-231 | (Ic) | (1n) | (2a) | (3l) | (4r) |
| (1)-232 | (Id) | (1s) | (2q) | (3m) | (4j) |
| (1)-233 | (Ik) | (1gg) | (2r) | (3n) | (4l) |
| (1)-234 | (Ib) | (1d) | (2vv) | (3o) | (4r) |
| (1)-235 | (Ic) | (1s) | (2g) | (3p) | (4u) |
| (1)-236 | (Id) | (1gg) | (2i) | (3a) | (4v) |
| (1)-237 | (Iq) | (1jj) | (2a) | (3i) | (4x) |
| (1)-238 | (If) | (1kk) | (2q) | (3j) | (4y) |
| (1)-239 | (Ig) | (1n) | (2qq) | (3k) | (4z) |
| (1)-240 | (Ih) | (1s) | (2tt) | (3l) | (4j) |
| (1)-241 | (Ii) | (1gg) | (2vv) | (3m) | (4l) |
| (1)-242 | (Ij) | (1tt) | (2vv) | (3n) | (4r) |
| (1)-243 | (Im) | (1uu) | (2y) | (3o) | (4u) |
| (1)-244 | (Id) | (1xx) | (2aa) | (3j) | (4v) |
| (1)-245 | (Ia) | (1aaa) | (2ff) | (3k) | (4x) |
| (1)-246 | (Im) | (1bbb) | (2i) | (3l) | (4y) |
| (1)-247 | (Id) | (1ccc) | (2a) | (3m) | (4z) |
| (1)-248 | (Ic) | (1tt) | (2q) | (3p) | (4a) |
| (1)-249 | (Id) | (1uu) | (2r) | (3n) | (4f) |
| (1)-250 | (Ik) | (1xx) | (2vv) | (3o) | (4j) |
| (1)-251 | (If) | (1n) | (2g) | (3j) | (4l) |
| (1)-252 | (Ig) | (1s) | (2i) | (3k) | (4r) |
| (1)-253 | (Ih) | (1gg) | (2a) | (3l) | (4u) |
| (1)-254 | (Ih) | (1c) | (2q) | (3m) | (4v) |
| (1)-255 | (Iu) | (1d) | (2qq) | (3p) | (4x) |
| (1)-256 | (Ij) | (1e) | (2tt) | (3j) | (4y) |
| (1)-257 | (Ic) | (1h) | (2vv) | (3k) | (4z) |
| (1)-258 | (Id) | (1k) | (2y) | (3l) | (4l) |
| (1)-259 | (Ic) | (1l) | (2aa) | (3m) | (4r) |
| (1)-260 | (Id) | (1n) | (2ff) | (3l) | (4u) |
| (1)-261 | (Ia) | (1s) | (2qq) | (3i) | (4v) |
| (1)-262 | (Ip) | (1n) | (2tt) | (3j) | (4x) |
| (1)-263 | (Ic) | (1s) | (2vv) | (3k) | (4y) |
| (1)-264 | (Id) | (1gg) | (2vv) | (3l) | (4z) |
| (1)-265 | (Ie) | (1ll) | (2y) | (3m) | (4l) |
| (1)-266 | (If) | (1mm) | (2aa) | (3n) | (4r) |
| (1)-267 | (Ig) | (1ss) | (2ff) | (3o) | (4u) |
| (1)-268 | (Ih) | (1tt) | (2a) | (3p) | (4v) |
| (1)-269 | (Ii) | (1n) | (2b) | (3n) | (4x) |
| (1)-270 | (Iv) | (1s) | (2g) | (3o) | (4y) |
| (1)-271 | (Ic) | (1gg) | (2i) | (3p) | (4z) |
| (1)-272 | (Id) | (1bbb) | (2a) | (3j) | (4j) |
| (1)-273 | (Ik) | (1ccc) | (2q) | (3k) | (4l) |
| (1)-274 | (Ic) | (1n) | (2r) | (3l) | (4a) |
| (1)-275 | (Id) | (1s) | (2t) | (3m) | (4f) |
| (1)-276 | (Ie) | (1gg) | (2x) | (3k) | (4j) |
| (1)-277 | (If) | (1d) | (2a) | (3l) | (4l) |
| (1)-278 | (Is) | (1xx) | (2b) | (3m) | (4r) |
| (1)-279 | (Ih) | (1n) | (2g) | (3n) | (4j) |
| (1)-280 | (Ii) | (1s) | (2i) | (3o) | (4l) |
| (1)-281 | (Ij) | (1gg) | (2a) | (3p) | (4r) |
| (1)-282 | (Ih) | (1d) | (2q) | (3n) | (4u) |
| (1)-283 | (Iu) | (1e) | (2r) | (3o) | (4v) |
| (1)-284 | (Ij) | (1h) | (2t) | (3p) | (4x) |
| (1)-285 | (Ig) | (1k) | (2x) | (3n) | (4y) |
| (1)-286 | (It) | (1l) | (2y) | (3o) | (4z) |
| (1)-287 | (Ih) | (1n) | (2aa) | (3p) | (4j) |
| (1)-288 | (Ii) | (1s) | (2ff) | (3j) | (4l) |
| (1)-289 | (Ij) | (1gg) | (2qq) | (3k) | (4r) |
| (1)-290 | (In) | (1jj) | (2tt) | (3l) | (4j) |
| (1)-291 | (Id) | (1kk) | (2vv) | (3m) | (4l) |
| (1)-292 | (Iq) | (1ll) | (2g) | (3l) | (4r) |
| (1)-293 | (If) | (1mm) | (2i) | (3m) | (4j) |
| (1)-294 | (Ig) | (1ss) | (2a) | (3j) | (4l) |
| (1)-295 | (Ih) | (1n) | (2q) | (3k) | (4r) |
| (1)-296 | (Ii) | (1s) | (2r) | (3l) | (4u) |
| (1)-297 | (Iv) | (1gg) | (2t) | (3m) | (4v) |
| (1)-298 | (Ie) | (1aaa) | (2x) | (3n) | (4x) |
| (1)-299 | (Ir) | (1bbb) | (2y) | (3o) | (4y) |
| (1)-300 | (Ig) | (1ccc) | (2aa) | (3p) | (4z) |
| (1)-301 | (Iw) | (1e) | (2ww) | (3q) | (4u) |
| (1)-302 | (Ix) | (1h) | (2xx) | (3r) | (4bb) |
| (1)-303 | (Iw) | (1k) | (2yy) | (3s) | (4cc) |
| (1)-304 | (Ix) | (1l) | (2zz) | (3t) | (4dd) |
| (1)-305 | (Iw) | (1n) | (2aaa) | (3u) | (4ee) |
| (1)-306 | (Ix) | (1s) | (2bbb) | (3v) | (4ff) |
| (1)-307 | (Iw) | (1gg) | (2ccc) | (3w) | (4gg) |
| (1)-308 | (Ix) | (1jj) | (2ww) | (3x) | (4u) |
| (1)-309 | (Iw) | (1kk) | (2xx) | (3y) | (4bb) |
| (1)-310 | (Ix) | (1ll) | (2yy) | (3z) | (4cc) |
| (1)-311 | (Iw) | (1mm) | (2zz) | (3aa) | (4dd) |
| (1)-312 | (Ix) | (1ss) | (2aaa) | (3bb) | (4ee) |
| (1)-313 | (Iw) | (1n) | (2bbb) | (3cc) | (4ff) |
| (1)-314 | (Ix) | (1s) | (2ccc) | (3dd) | (4gg) |
| (1)-315 | (Iw) | (1gg) | (2ww) | (3ee) | (4u) |
| (1)-316 | (Ix) | (1aaa) | (2xx) | (3ff) | (4bb) |
| (1)-317 | (Iw) | (1bbb) | (2yy) | (3gg) | (4cc) |
| (1)-318 | (Ix) | (1s) | (2zz) | (3hh) | (4dd) |
| (1)-319 | (Iw) | (1a) | (2aaa) | (3ii) | (4ee) |
| (1)-320 | (Ix) | (1c) | (2bbb) | (3jj) | (4ff) |
| (1)-321 | (Iw) | (1d) | (2ccc) | (3kk) | (4gg) |
| (1)-322 | (Ix) | (1e) | (2aaa) | (3cc) | (4u) |
| (1)-323 | (Iw) | (1h) | (2bbb) | (3ff) | (4bb) |
| (1)-324 | (Ix) | (1k) | (2ccc) | (3cc) | (4cc) |
| (1)-325 | (Iw) | (1l) | (2yy) | (3aa) | (4u) |
| (1)-326 | (Ix) | (1n) | (2zz) | (3pp) | (4bb) |
| (1)-327 | (Iw) | (1s) | (2aaa) | (3kk) | (4cc) |
| (1)-328 | (Ix) | (1gg) | (2bbb) | (3q) | (4bb) |
| (1)-329 | (Iw) | (1jj) | (2ccc) | (3r) | (4cc) |
| (1)-330 | (Ix) | (1kk) | (2ww) | (3s) | (4dd) |
| (1)-331 | (Iw) | (1ll) | (2xx) | (3t) | (4ee) |
| (1)-332 | (Ix) | (1mm) | (2yy) | (3u) | (4ff) |
| (1)-333 | (Iw) | (1ss) | (2zz) | (3v) | (4gg) |
| (1)-334 | (Ix) | (1tt) | (2aaa) | (3dd) | (4u) |
| (1)-335 | (Iw) | (1uu) | (2ww) | (3ee) | (4bb) |
| (1)-336 | (Ix) | (1xx) | (2xx) | (3ff) | (4cc) |
| (1)-337 | (Iw) | (1aaa) | (2yy) | (3gg) | (4bb) |
| (1)-338 | (Ix) | (1bbb) | (2zz) | (3hh) | (4cc) |
| (1)-339 | (Iw) | (1d) | (2aaa) | (3ii) | (4dd) |
| (1)-340 | (Ix) | (1e) | (2bbb) | (3dd) | (4ee) |

In some embodiments, the compound of formulae (I), (I') or (Ia)-(Ix) is one of the following compounds (or a pharmaceutically acceptable salt, prodrug, or N-oxide thereof, or a solvate or hydrate thereof):

TABLE A

| No. | Structure | Name |
|---|---|---|
| 1 | 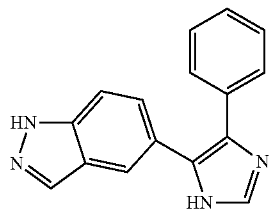 [SMILES: c1ccc(-c2nc[nH]c2-c2ccc3[nH]ncc3c2)cc1] | 5-(4-Phenyl-1H-imidazol-5-yl)-1H-indazole |
| 2 | 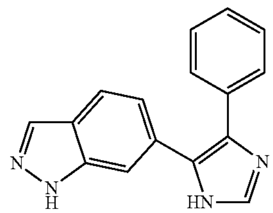 [SMILES: c1ccc(-c2nc[nH]c2-c2ccc3cn[nH]c3c2)cc1] | 6-(4-Phenyl-1H-imidazol-5-yl)-1H-indazole |
| 3 | 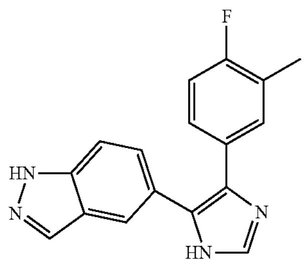 [SMILES: Cc1cc(-c2nc[nH]c2-c2ccc3[nH]ncc3c2)ccc1F] | 5-(4-(4-Fluoro-3-methylphenyl)-1H-imidazol-5-yl)-1H-indazole |
| 4 | 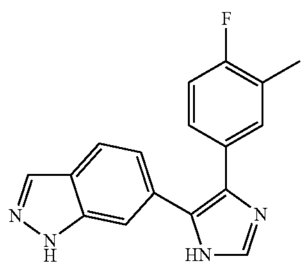 [SMILES: Cc1cc(-c2nc[nH]c2-c2ccc3cn[nH]c3c2)ccc1F] | 6-(4-(4-Fluoro-3-methylphenyl)-1H-imidazol-5-yl)-1H-indazole |
| 5 | 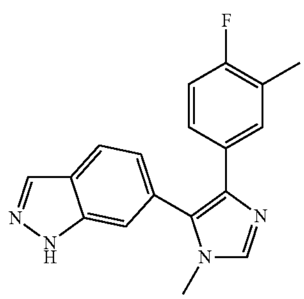 [SMILES: Cc1cc(-c2ncn(C)c2-c2ccc3cn[nH]c3c2)ccc1F] | 6-(4-(4-Fluoro-3-methylphenyl)-1-methyl-1H-imidazol-5-yl)-1H-indazole |
| 6 | 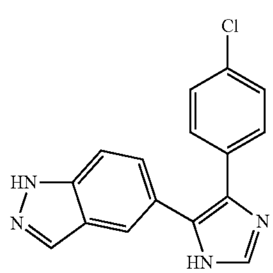 | 5-(4-(4-Chlorophenyl)-1H-imidazol-5-yl)-1H-indazole |

TABLE A-continued

| No. | Structure | Name |
|---|---|---|
| 7 | 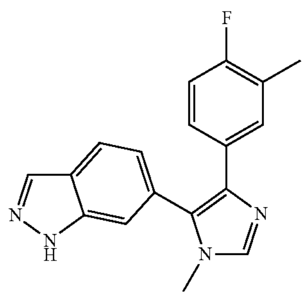 [SMILES: Cc1cc(-c2ncn(C)c2-c2ccc3cn[nH]c3c2)ccc1F] | 6-(4-(4-Fluoro-3-methylphenyl)-1-methyl-1H-imidazol-5-yl)-1H-indazole |
| 8 | 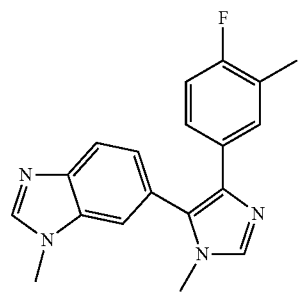 [SMILES: Cc1cc(-c2ncn(C)c2-c2ccc3ncn(C)c3c2)ccc1F] | 6-(4-(4-Fluoro-3-methylphenyl)-1-methyl-1H-imidazol-5-yl)-1-methyl-1H-benzo[d]imidazole |
| 9 | 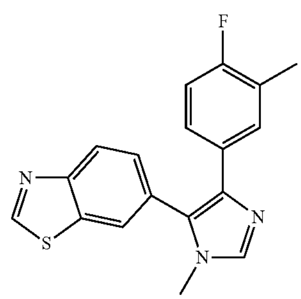 [SMILES: Cc1cc(-c2ncn(C)c2-c2ccc3ncsc3c2)ccc1F] | 6-(4-(4-Fluoro-3-methylphenyl)-1-methyl-1H-imidazol-5-yl)benzo[d]thiazole |
| 10 | 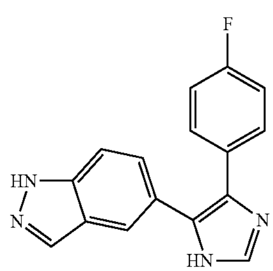 [SMILES: Fc1ccc(-c2nc[nH]c2-c2ccc3[nH]ncc3c2)cc1] | 5-(4-(4-Fluorophenyl)-1H-imidazol-5-yl)-1H-indazole |
| 11 | 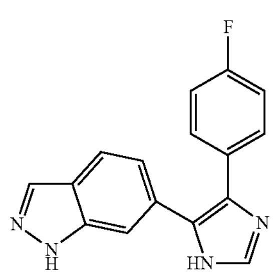 [SMILES: Fc1ccc(-c2nc[nH]c2-c2ccc3cn[nH]c3c2)cc1] | 6-(4-(4-Fluorophenyl)-1H-imidazol-5-yl)-1H-indazole |

TABLE A-continued

| No. | Structure | Name |
| --- | --- | --- |
| 12 | 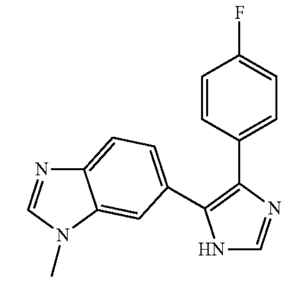 [SMILES: Cn1cnc2ccc(-c3[nH]cnc3-c3ccc(F)cc3)cc21] | 6-(4-(4-Fluorophenyl)-1H-imidazol-5-yl)-1-methyl-1H-benzo[d]imidazole |
| 13 | 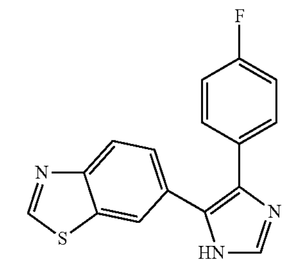 [SMILES: Fc1ccc(-c2nc[nH]c2-c2ccc3ncsc3c2)cc1] | 6-(4-(4-Fluorophenyl)-1H-imidazol-5-yl)benzo[d]thiazole |
| 14 | 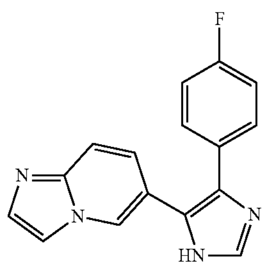 [SMILES: Fc1ccc(-c2nc[nH]c2-c2ccc3nccn3c2)cc1] | 6-(4-(4-Fluorophenyl)-1H-imidazol-5-yl)imidazo[1,2-a]pyridine |
| 15 | 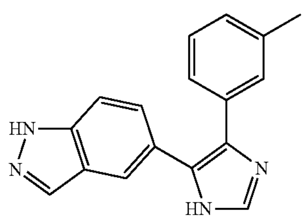 [SMILES: Cc1cccc(-c2nc[nH]c2-c2ccc3[nH]ncc3c2)c1] | 5-(4-(m-Tolyl)-1H-imidazol-5-yl)-1H-indazole |
| 16 | 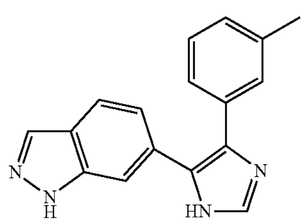 [SMILES: Cc1cccc(-c2nc[nH]c2-c2ccc3cn[nH]c3c2)c1] | -(4-(m-Tolyl)-1H-imidazol-5-yl)-1H-indazole |
| 17 | 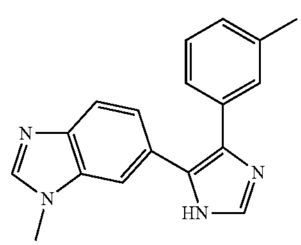 [SMILES: Cc1cccc(-c2nc[nH]c2-c2ccc3ncn(C)c3c2)c1] | 1-Methyl-6-(4-(m-tolyl)-1H-imidazol-5-yl)-1H-benzo[d]imidazole |

TABLE A-continued

| No. | Structure | Name |
|---|---|---|
| 18 | 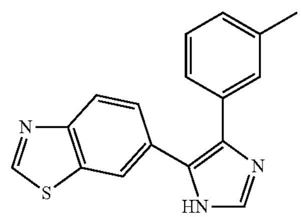 [SMILES: Cc1cccc(-c2nc[nH]c2-c2ccc3ncsc3c2)c1] | 6-(4-(m-Tolyl)-1H-imidazol-5-yl)benzo[d]thiazole |
| 19 | 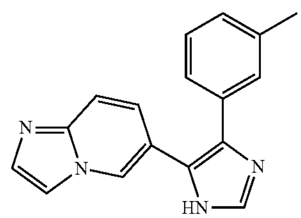 [SMILES: Cc1cccc(-c2nc[nH]c2-c2ccc3nccn3c2)c1] | 6-(4-(m-Tolyl)-1H-imidazol-5-yl)imidazo[1,2-a]pyridine |
| 20 | 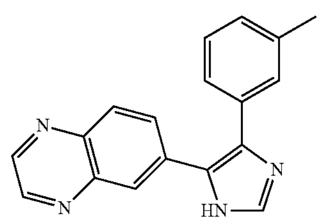 [SMILES: Cc1cccc(-c2nc[nH]c2-c2ccc3nccnc3c2)c1] | 6-(4-(m-Tolyl)-1H-imidazol-5-yl)quinoxaline |
| 21 | 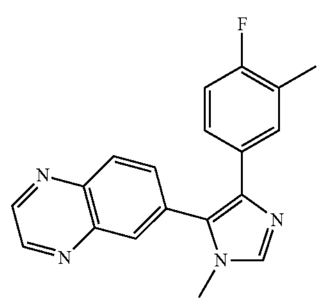 [SMILES: Cc1cc(-c2ncn(C)c2-c2ccc3nccnc3c2)ccc1F] | 6-(4-(4-Fluoro-3-methylphenyl)-1-methyl-1H-imidazol-5-yl)quinoxaline |
| 22 | 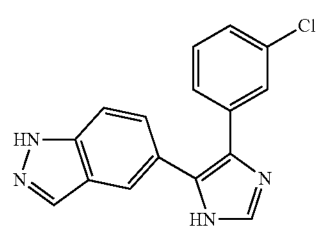 [SMILES: Clc1cccc(-c2nc[nH]c2-c2ccc3[nH]ncc3c2)c1] | 5-(4-(3-Chlorophenyl)-1H-imidazol-5-yl)-1H-indazole |
| 23 | 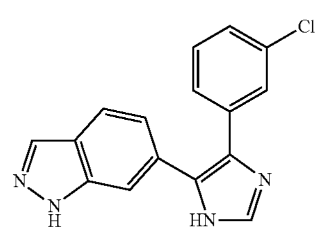 [SMILES: Clc1cccc(-c2nc[nH]c2-c2ccc3cn[nH]c3c2)c1] | 6-(4-(3-Chlorophenyl)-1H-imidazol-5-yl)-1H-indazole |

TABLE A-continued
| No. | Structure | Name |
|---|---|---|
| 24 | 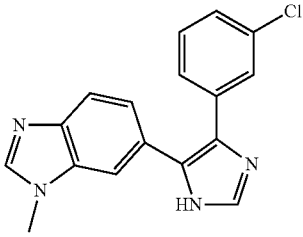 [SMILES: Cn1cnc2ccc(-c3[nH]cnc3-c3cccc(Cl)c3)cc21] | 6-(4-(3-Chlorophenyl)-1H-imidazol-5-yl)-1-methyl-1H-benzo[d]imidazole |
| 25 | 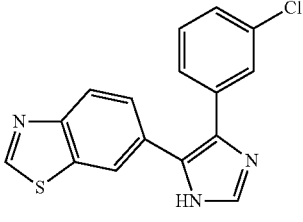 [SMILES: Clc1cccc(-c2nc[nH]c2-c2ccc3ncsc3c2)c1] | 6-(4-(3-Chlorophenyl)-1H-imidazol-5-yl)benzo[d]thiazole |
| 26 | 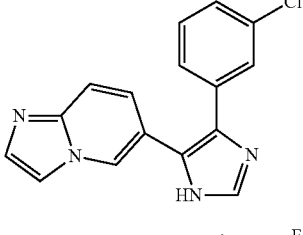 | 6-(4-(3-Chlorophenyl)-1H-imidazol-5-yl)imidazo[1,2-a]pyridine |
| 27 | 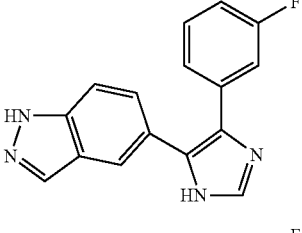 | 5-(4-(3-Fluorophenyl)-1H-imidazol-5-yl)-1H-indazole |
| 28 | 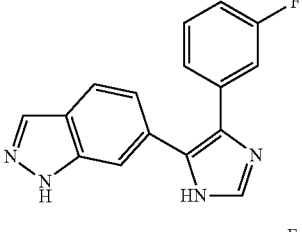 | 6-(4-(3-Fluorophenyl)-1H-imidazol-5-yl)-1H-indazole |
| 29 | 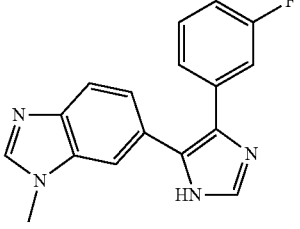 | 6-(4-(3-Fluorophenyl)-1H-imidazol-5-yl)-1-methyl-1H-benzo[d]imidazole |
| 30 | 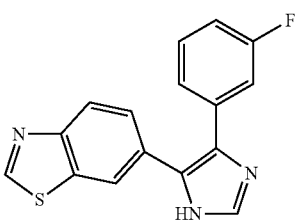 [SMILES: Fc1cccc(-c2nc[nH]c2-c2ccc3ncsc3c2)c1] | 6-(4-(3-Fluorophenyl)-1H-imidazol-5-yl)benzo[d]thiazole |

TABLE A-continued

| No. | Structure | Name |
|---|---|---|
| 31 | 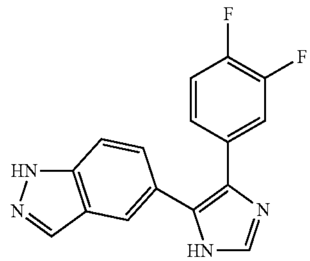 [SMILES: Fc1ccc(-c2nc[nH]c2-c2ccc3[nH]ncc3c2)cc1F] | 5-(4-(3,4-Difluorophenyl)-1H-imidazol-5-yl)-1H-indazole |
| 32 | 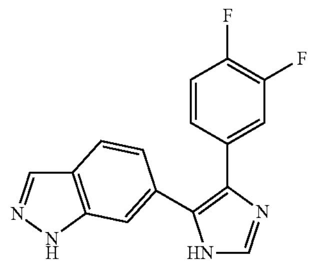 [SMILES: Fc1ccc(-c2nc[nH]c2-c2ccc3cn[nH]c3c2)cc1F] | 6-(4-(3,4-Difluorophenyl)-1H-imidazol-5-yl)-1H-indazole |
| 33 | 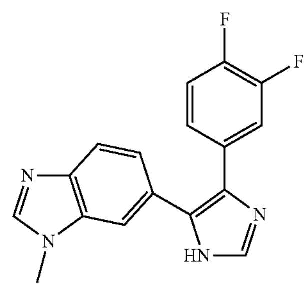 [SMILES: Cn1cnc2ccc(-c3[nH]cnc3-c3ccc(F)c(F)c3)cc21] | 6-(4-(3,4-Difluorophenyl)-1H-imidazol-5-yl)-1-methyl-1H-benzo[d]imidazole |
| 34 | 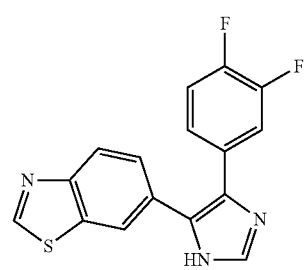 [SMILES: Fc1ccc(-c2nc[nH]c2-c2ccc3ncsc3c2)cc1F] | 6-(4-(3,4-Difluorophenyl)-1H-imidazol-5-yl)benzo[d]thiazole |
| 35 | 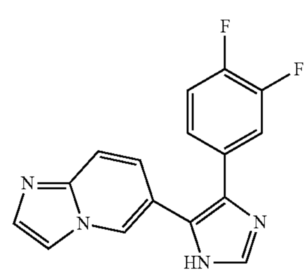 [SMILES: Fc1ccc(-c2nc[nH]c2-c2ccc3nccn3c2)cc1F] | 6-(4-(3,4-Difluorophenyl)-1H-imidazol-5-yl)imidazo[1,2-a]pyridine |

TABLE A-continued

| No. | Structure | Name |
|---|---|---|
| 36 | 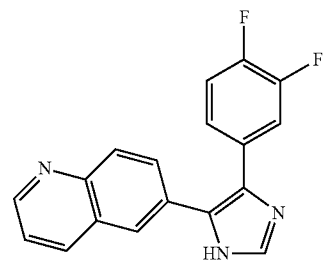 [SMILES: Fc1ccc(-c2nc[nH]c2-c2ccc3ncccc3c2)cc1F] | 6-(4-(3,4-Difluorophenyl)-1H-imidazol-5-yl)quinoline |
| 37 | 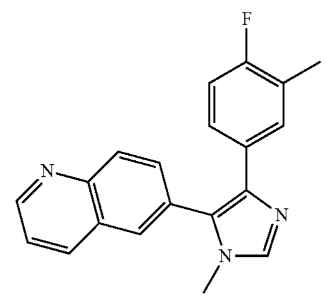 [SMILES: Cc1cc(-c2ncn(C)c2-c2ccc3ncccc3c2)ccc1F] | 6-(4-(4-Fluoro-3-methylphenyl)-1-methyl-1H-imidazol-5-yl)quinoline |
| 38 | 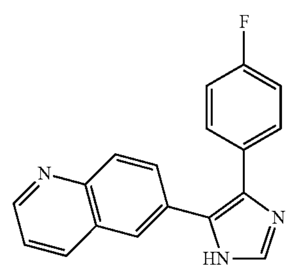 [SMILES: Fc1ccc(-c2nc[nH]c2-c2ccc3ncccc3c2)cc1] | 6-(4-(4-Fluorophenyl)-1H-imidazol-5-yl)quinoline |
| 39 | 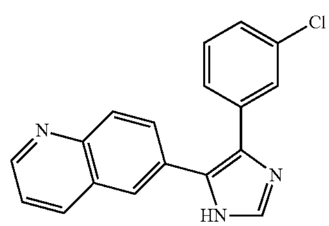 [SMILES: Clc1cccc(-c2nc[nH]c2-c2ccc3ncccc3c2)c1] | 6-(4-(3-Chlorophenyl)-1H-imidazol-5-yl)quinoline |
| 40 | 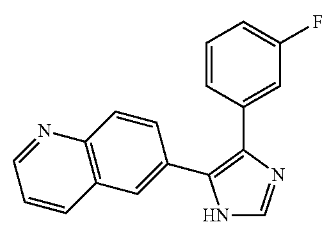 [SMILES: Fc1cccc(-c2nc[nH]c2-c2ccc3ncccc3c2)c1] | 6-(4-(3-Fluorophenyl)-1H-imidazol-5-yl)quinoline |
| 41 | 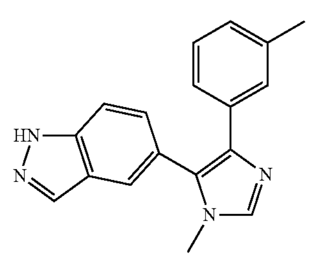 [SMILES: Cc1cccc(-c2ncn(C)c2-c2ccc3[nH]ncc3c2)c1] | 5-(1-Methyl-4-(m-tolyl)-1H-imidazol-5-yl)-1H-indazole |

TABLE A-continued

| No. | Structure | Name |
|---|---|---|
| 42 | 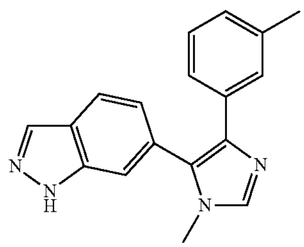 [SMILES: Cc1cccc(-c2ncn(C)c2-c2ccc3cn[nH]c3c2)c1] | 6-(1-Methyl-4-(m-tolyl)-1H-imidazol-5-yl)-1H-indazole |
| 43 | 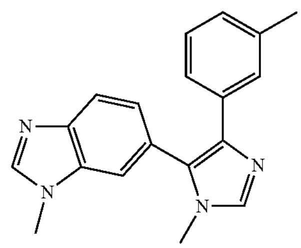 [SMILES: Cc1cccc(-c2ncn(C)c2-c2ccc3ncn(C)c3c2)c1] | 1-Methyl-6-(1-methyl-4-(m-tolyl)-1H-imidazol-5-yl)-1H-benzo[d]imidazole |
| 44 | 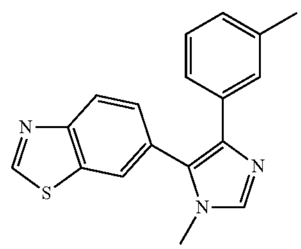 [SMILES: Cc1cccc(-c2ncn(C)c2-c2ccc3ncsc3c2)c1] | 6-(1-Methyl-4-(m-tolyl)-1H-imidazol-5-yl)benzo[d]thiazole |
| 45 | 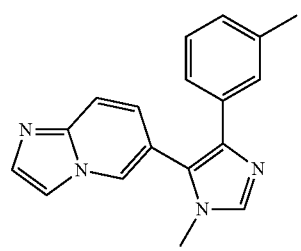 [SMILES: Cc1cccc(-c2ncn(C)c2-c2ccc3nccn3c2)c1] | 6-(1-Methyl-4-(m-tolyl)-1H-imidazol-5-yl)imidazo[1,2-a]pyridine |
| 46 | 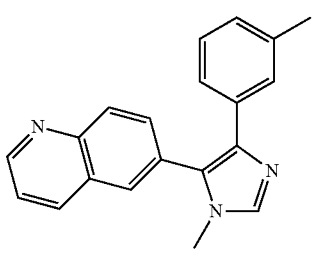 [SMILES: Cc1cccc(-c2ncn(C)c2-c2ccc3ncccc3c2)c1] | 6-(1-Methyl-4-(m-tolyl)-1H-imidazol-5-yl)quinoline |
| 47 | 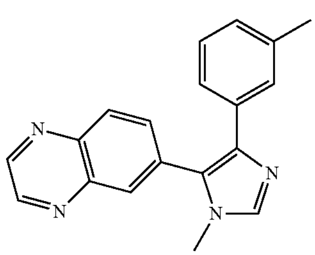 [SMILES: Cc1cccc(-c2ncn(C)c2-c2ccc3nccnc3c2)c1] | 6-(1-Methyl-4-(m-tolyl)-1H-imidazol-5-yl)quinoxaline |

TABLE A-continued

| No. | Structure | Name |
|---|---|---|
| 48 | 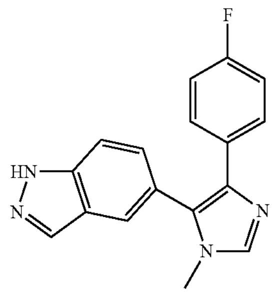 [SMILES: Cn1cnc(-c2ccc(F)cc2)c1-c1ccc2[nH]ncc2c1] | -(4-(4-Fluorophenyl)-1-methyl-1H-imidazol-5-yl)-1H-indazole |
| 49 | 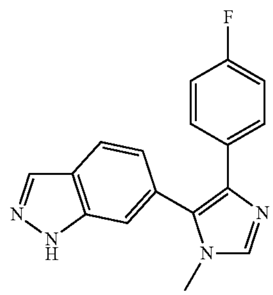 [SMILES: Cn1cnc(-c2ccc(F)cc2)c1-c1ccc2cn[nH]c2c1] | 6-(4-(4-Fluorophenyl)-1-methyl-1H-imidazol-5-yl)-1H-indazole |
| 50 | 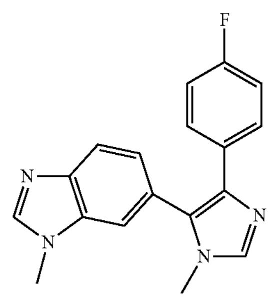 [SMILES: Cn1cnc(-c2ccc(F)cc2)c1-c1ccc2ncn(C)c2c1] | 6-(4-(4-Fluorophenyl)-1-methyl-1H-imidazol-5-yl)-1-methyl-1H-benzo[d]imidazole |
| 51 | 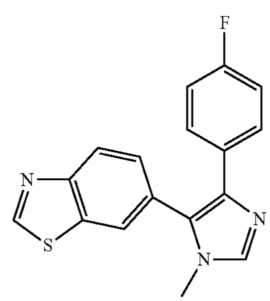 [SMILES: Cn1cnc(-c2ccc(F)cc2)c1-c1ccc2ncsc2c1] | 6-(4-(4-Fluorophenyl)-1-methyl-1H-imidazol-5-yl)benzo[d]thiazole |
| 52 | 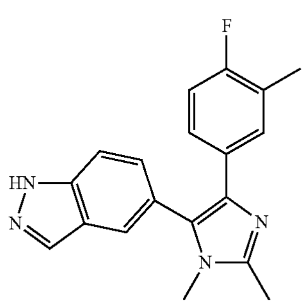 [SMILES: Cc1cc(-c2nc(C)n(C)c2-c2ccc3[nH]ncc3c2)ccc1F] | 5-(4-(4-Fluoro-3-methylphenyl)-1,2-dimethyl-1H-imidazol-5-yl)-1H-indazole |

TABLE A-continued

| No. | Structure | Name |
|-----|-----------|------|
| 53 | 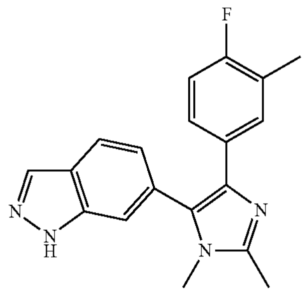 [SMILES: Cc1cc(-c2nc(C)n(C)c2-c2ccc3cn[nH]c3c2)ccc1F] | 6-(4-(4-Fluoro-3-methylphenyl)-1,2-dimethyl-1H-imidazol-5-yl)-1H-indazole |
| 54 | 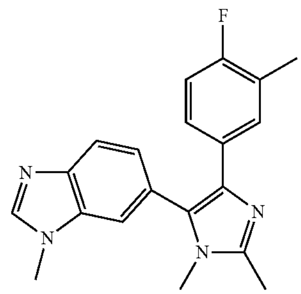 [SMILES: Cc1cc(-c2nc(C)n(C)c2-c2ccc3ncn(C)c3c2)ccc1F] | 6-(4-(4-Fluoro-3-methylphenyl)-1,2-dimethyl-1H-imidazol-5-yl)-1-methyl-1H-benzo[d]imidazole |
| 55 | 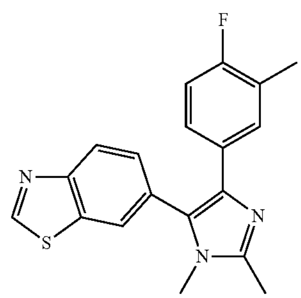 [SMILES: Cc1cc(-c2nc(C)n(C)c2-c2ccc3ncsc3c2)ccc1F] | 6-(4-(4-Fluoro-3-methylphenyl)-1,2-dimethyl-1H-imidazol-5-yl)benzo[d]thiazole |
| 56 | 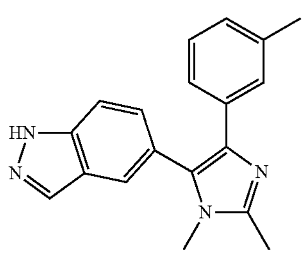 [SMILES: Cc1cccc(-c2nc(C)n(C)c2-c2ccc3[nH]ncc3c2)c1] | 5-(1,2-Dimethyl-4-(m-tolyl)-1H-imidazol-5-yl)-1H-indazole |
| 57 | 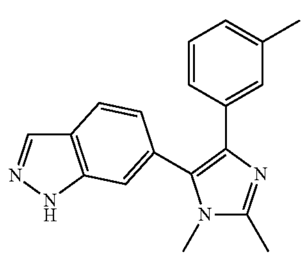 [SMILES: Cc1cccc(-c2nc(C)n(C)c2-c2ccc3cn[nH]c3c2)c1] | 6-(1,2-Dimethyl-4-(m-tolyl)-1H-imidazol-5-yl)-1H-indazole |

TABLE A-continued

| No. | Structure | Name |
|---|---|---|
| 58 | 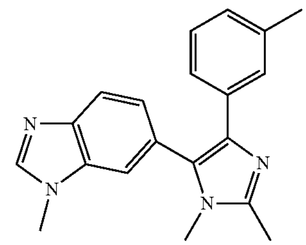 [SMILES: Cc1cccc(-c2nc(C)n(C)c2-c2ccc3ncn(C)c3c2)c1] | 6-(1,2-Dimethyl-4-(m-tolyl)-1H-imidazol-5-yl)-1-methyl-1H-benzo[d]imidazole |
| 59 | 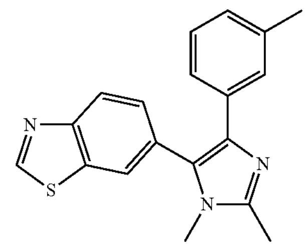 [SMILES: Cc1cccc(-c2nc(C)n(C)c2-c2ccc3ncsc3c2)c1] | 6-(1,2-Dimethyl-4-(m-tolyl)-1H-imidazol-5-yl)benzo[d]thiazole |
| 60 | 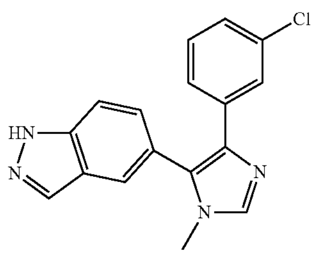 [SMILES: Cn1cnc(-c2cccc(Cl)c2)c1-c1ccc2[nH]ncc2c1] | 5-(4-(3-Chlorophenyl)-1-methyl-1H-imidazol-5-yl)-1H-indazole |
| 61 | 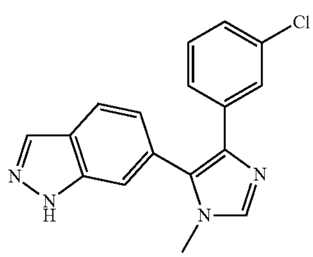 [SMILES: Cn1cnc(-c2cccc(Cl)c2)c1-c1ccc2cn[nH]c2c1] | 6-(4-(3-Chlorophenyl)-1-methyl-1H-imidazol-5-yl)-1H-indazole |
| 62 | 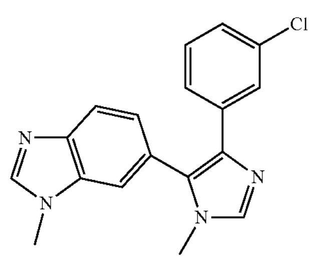 [SMILES: Cn1cnc(-c2cccc(Cl)c2)c1-c1ccc2ncn(C)c2c1] | 6-(4-(3-Chlorophenyl)-1-methyl-1H-imidazol-5-yl)-1-methyl-1H-benzo[d]imidazole |
| 63 | 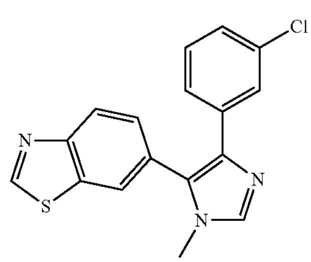 [SMILES: Cn1cnc(-c2cccc(Cl)c2)c1-c1ccc2ncsc2c1] | 6-(4-(3-Chlorophenyl)-1-methyl-1H-imidazol-5-yl)benzo[d]thiazole |

TABLE A-continued

| No. | Structure | Name |
|---|---|---|
| 64 | 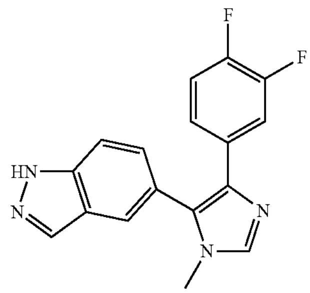 [SMILES: Cn1cnc(-c2ccc(F)c(F)c2)c1-c1ccc2[nH]ncc2c1] | 5-(4-(3,4-Difluorophenyl)-1-methyl-1H-imidazol-5-yl)-1H-indazole |
| 65 | 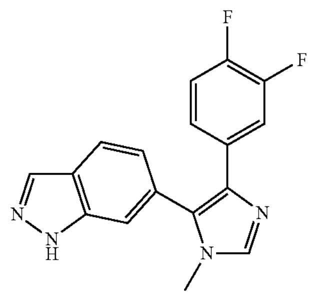 [SMILES: Cn1cnc(-c2ccc(F)c(F)c2)c1-c1ccc2cn[nH]c2c1] | 6-(4-(3,4-Difluorophenyl)-1-methyl-1H-imidazol-5-yl)-1H-indazole |
| 66 | 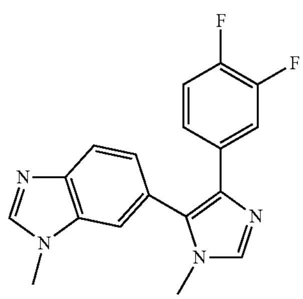 [SMILES: Cn1cnc(-c2ccc(F)c(F)c2)c1-c1ccc2ncn(C)c2c1] | 6-(4-(3,4-Difluorophenyl)-1-methyl-1H-imidazol-5-yl)-1-methyl-1H-benzo[d]imidazole |
| 67 | 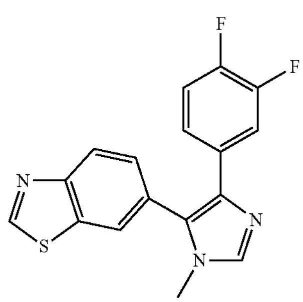 [SMILES: Cn1cnc(-c2ccc(F)c(F)c2)c1-c1ccc2ncsc2c1] | 6-(4-(3,4-Difluorophenyl)-1-methyl-1H-imidazol-5-yl)benzo[d]thiazole |
| 68 | 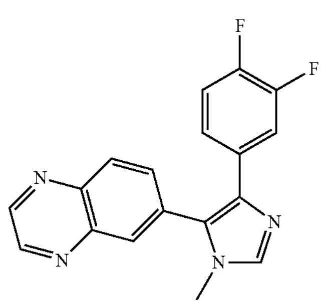 [SMILES: Cn1cnc(-c2ccc(F)c(F)c2)c1-c1ccc2nccnc2c1] | 6-(4-(3,4-Difluorophenyl)-1-methyl-1H-imidazol-5-yl)quinoxaline |

TABLE A-continued

| No. | Structure | Name |
|---|---|---|
| 69 | 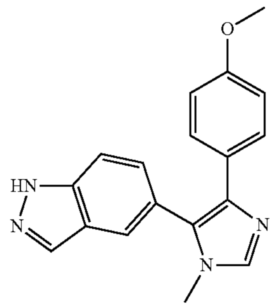 [SMILES: COc1ccc(-c2ncn(C)c2-c2ccc3[nH]ncc3c2)cc1] | 5-(4-(4-Methoxyphenyl)-1-methyl-1H-imidazol-5-yl)-1H-indazole |
| 70 | 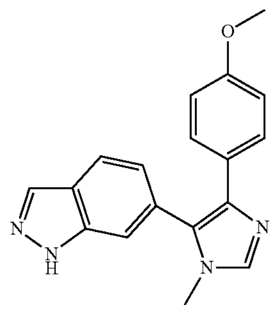 [SMILES: COc1ccc(-c2ncn(C)c2-c2ccc3cn[nH]c3c2)cc1] | 6-(4-(4-Methoxyphenyl)-1-methyl-1H-imidazol-5-yl)-1H-indazole |
| 71 | 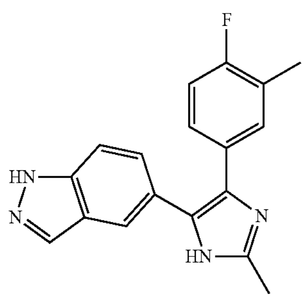 [SMILES: Cc1nc(-c2ccc(F)c(C)c2)c(-c2ccc3[nH]ncc3c2)[nH]1] | 5-(4-(4-Fluoro-3-methylphenyl)-2-methyl-1H-imidazol-5-yl)-1H-indazole |
| 72 | 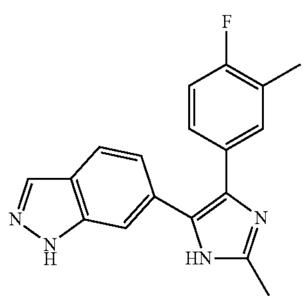 [SMILES: Cc1nc(-c2ccc(F)c(C)c2)c(-c2ccc3cn[nH]c3c2)[nH]1] | 6-(4-(4-Fluoro-3-methylphenyl)-2-methyl-1H-imidazol-5-yl)-1H-indazole |
| 73 | 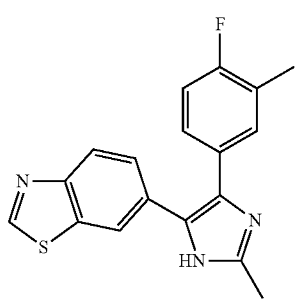 [SMILES: Cc1nc(-c2ccc(F)c(C)c2)c(-c2ccc3ncsc3c2)[nH]1] | 6-(4-(4-Fluoro-3-methylphenyl)-2-methyl-1H-imidazol-5-yl)benzo[d]thiazole |

TABLE A-continued
| No. | Structure | Name |
|---|---|---|
| 74 | 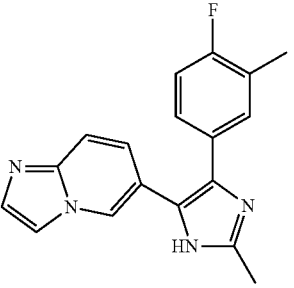 [SMILES: Cc1nc(-c2ccc(F)c(C)c2)c(-c2ccc3nccn3c2)[nH]1] | 6-(4-(4-Fluoro-3-methylphenyl)-2-methyl-1H-imidazol-5-yl)imidazo[1,2-a]pyridine |
| 75 | 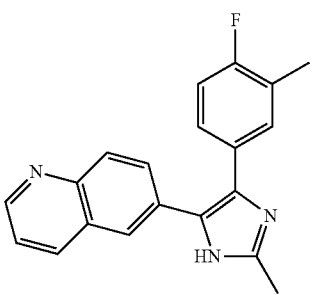 [SMILES: Cc1nc(-c2ccc(F)c(C)c2)c(-c2ccc3ncccc3c2)[nH]1] | 6-(4-(4-Fluoro-3-methylphenyl)-2-methyl-1H-imidazol-5-yl)quinoline |
| 76 | 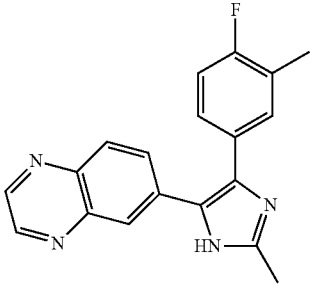 [SMILES: Cc1nc(-c2ccc(F)c(C)c2)c(-c2ccc3nccnc3c2)[nH]1] | 6-(4-(4-Fluoro-3-methylphenyl)-2-methyl-1H-imidazol-5-yl)quinoxaline |
| 77 | 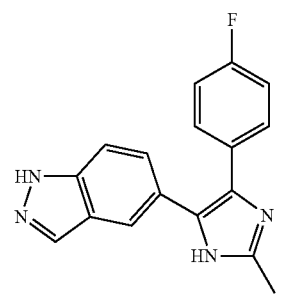 [SMILES: Cc1nc(-c2ccc(F)cc2)c(-c2ccc3[nH]ncc3c2)[nH]1] | 5-(4-(4-Fluorophenyl)-2-methyl-1H-imidazol-5-yl)-1H-indazole |
| 78 | 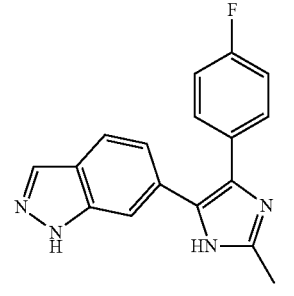 [SMILES: Cc1nc(-c2ccc(F)cc2)c(-c2ccc3cn[nH]c3c2)[nH]1] | 6-(4-(4-Fluorophenyl)-2-methyl-1H-imidazol-5-yl)-1H-indazole |

TABLE A-continued
| No. | Structure | Name |
|---|---|---|
| 79 | 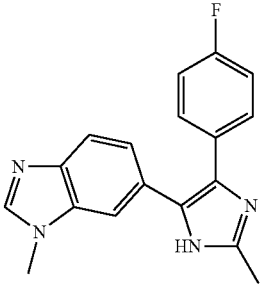 [SMILES: Cc1nc(-c2ccc(F)cc2)c(-c2ccc3ncn(C)c3c2)[nH]1] | 6-(4-(4-Fluorophenyl)-2-methyl-1H-imidazol-5-yl)-1-methyl-1H-benzo[d]imidazole |
| 80 | 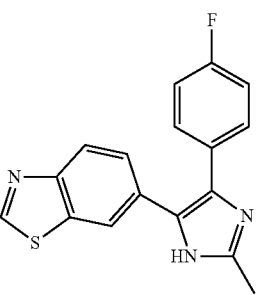 [SMILES: Cc1nc(-c2ccc(F)cc2)c(-c2ccc3ncsc3c2)[nH]1] | 6-(4-(4-Fluorophenyl)-2-methyl-1H-imidazol-5-yl)benzo[d]thiazole |
| 81 | 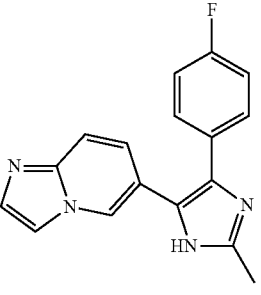 [SMILES: Cc1nc(-c2ccc(F)cc2)c(-c2ccc3nccn3c2)[nH]1] | 6-(4-(4-Fluorophenyl)-2-methyl-1H-imidazol-5-yl)imidazo[1,2-a]pyridine |
| 82 | 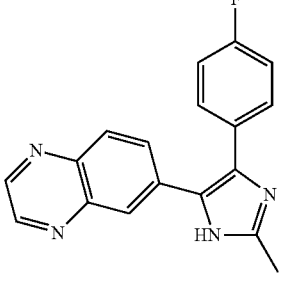 | 6-(4-(4-Fluorophenyl)-2-methyl-1H-imidazol-5-yl)quinoxaline |
| 83 | 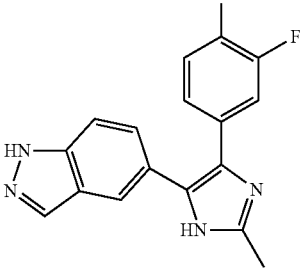 | 5-(4-(3,4-Difluorophenyl)-2-methyl-1H-imidazol-5-yl)-1H-indazole |

TABLE A-continued

| No. | Structure | Name |
|---|---|---|
| 84 | 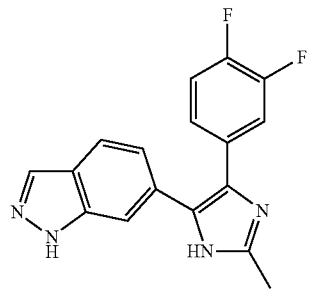 [SMILES: Cc1nc(-c2ccc(F)c(F)c2)c(-c2ccc3cn[nH]c3c2)[nH]1] | 6-(4-(3,4-Difluorophenyl)-2-methyl-1H-imidazol-5-yl)-1H-indazole |
| 85 | 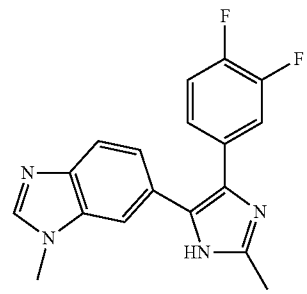 [SMILES: Cc1nc(-c2ccc(F)c(F)c2)c(-c2ccc3ncn(C)c3c2)[nH]1] | 6-(4-(3,4-Difluorophenyl)-2-methyl-1H-imidazol-5-yl)-1-methyl-1H-benzo[d]imidazole |
| 86 | 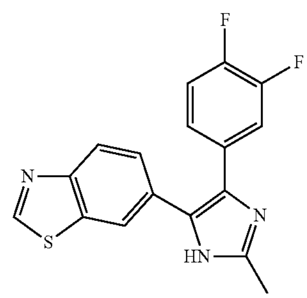 [SMILES: Cc1nc(-c2ccc(F)c(F)c2)c(-c2ccc3ncsc3c2)[nH]1] | 6-(4-(3,4-Difluorophenyl)-2-methyl-1H-imidazol-5-yl)benzo[d]thiazole |
| 87 | 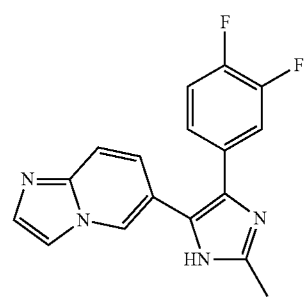 [SMILES: Cc1nc(-c2ccc(F)c(F)c2)c(-c2ccc3nccn3c2)[nH]1] | 6-(4-(3,4-Difluorophenyl)-2-methyl-1H-imidazol-5-yl)imidazo[1,2-a]pyridine |
| 88 | 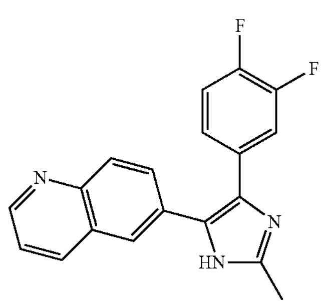 [SMILES: Cc1nc(-c2ccc(F)c(F)c2)c(-c2ccc3ncccc3c2)[nH]1] | 6-(4-(3,4-Difluorophenyl)-2-methyl-1H-imidazol-5-yl)quinoline |

TABLE A-continued

| No. | Structure | Name |
|---|---|---|
| 89 | 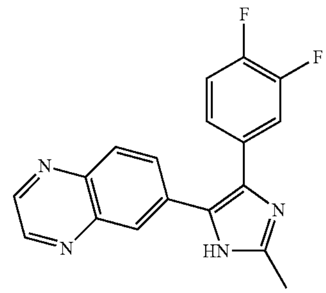 [SMILES: Cc1nc(-c2ccc(F)c(F)c2)c(-c2ccc3nccnc3c2)[nH]1] | 6-(4-(3,4-Difluorophenyl)-2-methyl-1H-imidazol-5-yl)quinoxaline |
| 90 | 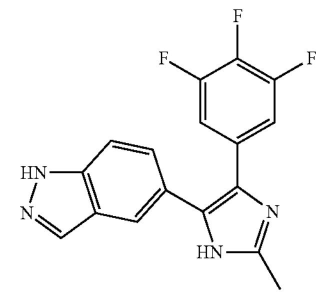 [SMILES: Cc1nc(-c2cc(F)c(F)c(F)c2)c(-c2ccc3[nH]ncc3c2)[nH]1] | 5-(2-Methyl-4-(3,4,5-trifluorophenyl)-1H-imidazol-5-yl)-1H-indazole |
| 91 | 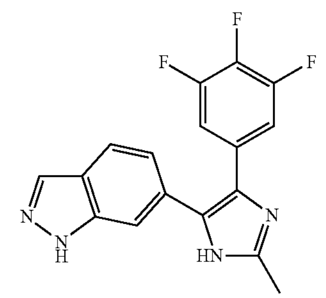 [SMILES: Cc1nc(-c2cc(F)c(F)c(F)c2)c(-c2ccc3cn[nH]c3c2)[nH]1] | 6-(2-Methyl-4-(3,4,5-trifluorophenyl)-1H-imidazol-5-yl)-1H-indazole |
| 92 | 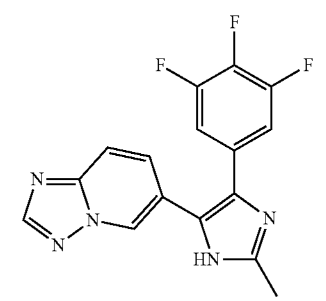 [SMILES: Cc1nc(-c2cc(F)c(F)c(F)c2)c(-c2ccc3ncnn3c2)[nH]1] | 6-(2-Methyl-4-(3,4,5-trifluorophenyl)-1H-imidazol-5-yl)-[1,2,4]triazolo[1,5-a]pyridine |
| 93 | 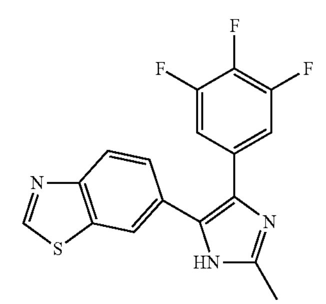 [SMILES: Cc1nc(-c2cc(F)c(F)c(F)c2)c(-c2ccc3ncsc3c2)[nH]1] | 6-(2-Methyl-4-(3,4,5-trifluorophenyl)-1H-imidazol-5-yl)benzo[d]thiazole |

TABLE A-continued

| No. | Structure | Name |
|---|---|---|
| 94 | 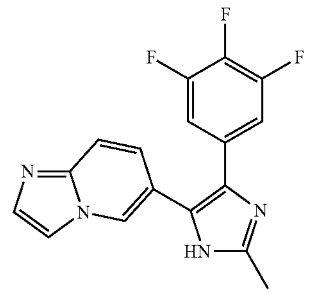 [SMILES: Cc1nc(-c2cc(F)c(F)c(F)c2)c(-c2ccc3nccn3c2)[nH]1] | 6-(2-Methyl-4-(3,4,5-trifluorophenyl)-1H-imidazol-5-yl)imidazo[1,2-a]pyridine |
| 95 | 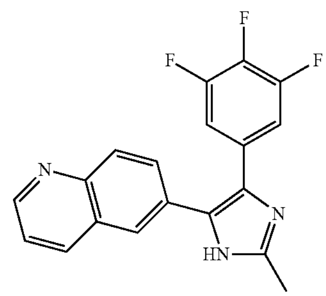 [SMILES: Cc1nc(-c2cc(F)c(F)c(F)c2)c(-c2ccc3ncccc3c2)[nH]1] | 6-(2-Methyl-4-(3,4,5-trifluorophenyl)-1H-imidazol-5-yl)quinoline |
| 96 | 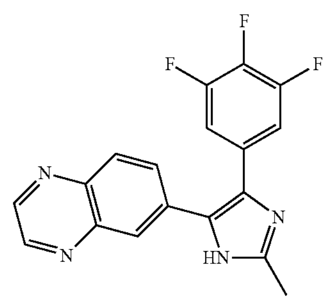 [SMILES: Cc1nc(-c2cc(F)c(F)c(F)c2)c(-c2ccc3nccnc3c2)[nH]1] | 6-(2-Methyl-4-(3,4,5-trifluorophenyl)-1H-imidazol-5-yl)quinoxaline |
| 97 | 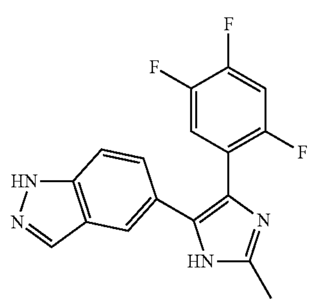 [SMILES: Cc1nc(-c2cc(F)c(F)cc2F)c(-c2ccc3[nH]ncc3c2)[nH]1] | 5-(2-Methyl-4-(2,4,5-trifluorophenyl)-1H-imidazol-5-yl)-1H-indazole |
| 98 | 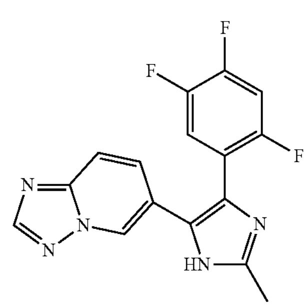 [SMILES: Cc1nc(-c2cc(F)c(F)cc2F)c(-c2ccc3ncnn3c2)[nH]1] | 6-(2-Methyl-4-(2,4,5-trifluorophenyl)-1H-imidazol-5-yl)-[1,2,4]triazolo[1,5-a]pyridine |

TABLE A-continued

| No. | Structure | Name |
|---|---|---|
| 99 | 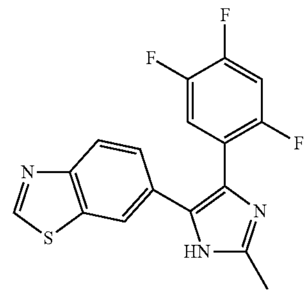 [SMILES: Cc1nc(-c2cc(F)c(F)cc2F)c(-c2ccc3ncsc3c2)[nH]1] | 6-(2-Methyl-4-(2,4,5-trifluorophenyl)-1H-imidazol-5-yl)benzo[d]thiazole |
| 100 | 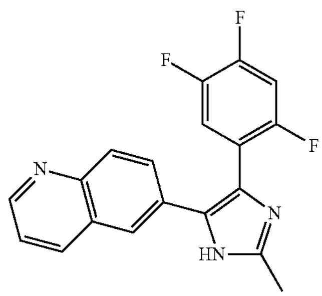 [SMILES: Cc1nc(-c2cc(F)c(F)cc2F)c(-c2ccc3ncccc3c2)[nH]1] | 6-(2-Methyl-4-(2,4,5-trifluorophenyl)-1H-imidazol-5-yl)quinoline |
| 101 | 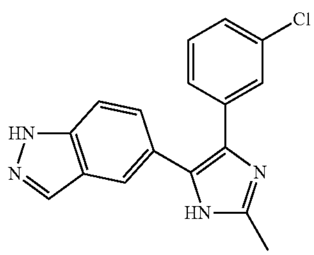 [SMILES: Cc1nc(-c2cccc(Cl)c2)c(-c2ccc3[nH]ncc3c2)[nH]1] | 5-(4-(3-Chlorophenyl)-2-methyl-1H-imidazol-5-yl)-1H-indazole |
| 102 | 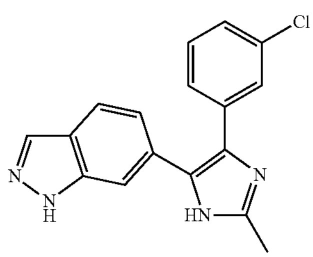 [SMILES: Cc1nc(-c2cccc(Cl)c2)c(-c2ccc3cn[nH]c3c2)[nH]1] | 6-(4-(3-Chlorophenyl)-2-methyl-1H-imidazol-5-yl)-1H-indazole |
| 103 | 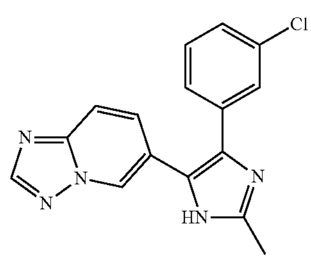 [SMILES: Cc1nc(-c2cccc(Cl)c2)c(-c2ccc3ncnn3c2)[nH]1] | 6-(4-(3-Chlorophenyl)-2-methyl-1H-imidazol-5-yl)-[1,2,4]triazolo[1,5-a]pyridine |
| 104 | 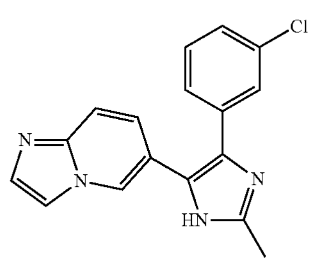 [SMILES: Cc1nc(-c2cccc(Cl)c2)c(-c2ccc3nccn3c2)[nH]1] | 6-(4-(3-Chlorophenyl)-2-methyl-1H-imidazol-5-yl)imidazo[1,2-a]pyridine |

TABLE A-continued

| No. | Structure | Name |
| --- | --- | --- |
| 105 | 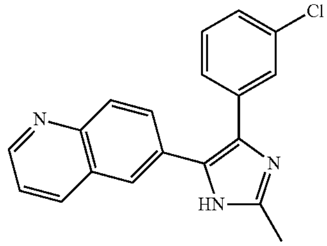 [SMILES: Cc1nc(-c2cccc(Cl)c2)c(-c2ccc3ncccc3c2)[nH]1] | 6-(4-(3-Chlorophenyl)-2-methyl-1H-imidazol-5-yl)quinoline |
| 106 | 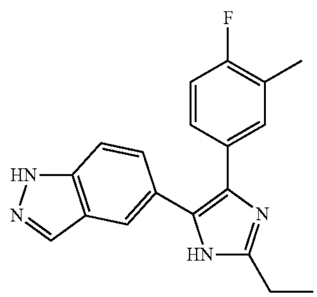 [SMILES: CCc1nc(-c2ccc(F)c(C)c2)c(-c2ccc3[nH]ncc3c2)[nH]1] | 5-(2-Ethyl-4-(4-fluoro-3-methylphenyl)-1H-imidazol-5-yl)-1H-indazole |
| 107 | 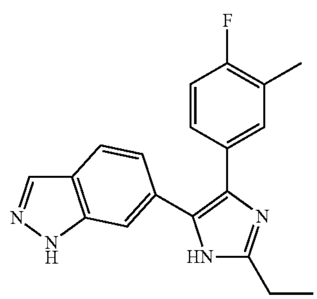 [SMILES: CCc1nc(-c2ccc(F)c(C)c2)c(-c2ccc3cn[nH]c3c2)[nH]1] | 6-(2-Ethyl-4-(4-fluoro-3-methylphenyl)-1H-imidazol-5-yl)-1H-indazole |
| 108 | 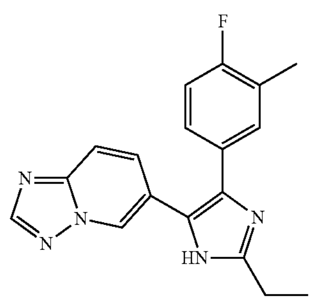 [SMILES: CCc1nc(-c2ccc(F)c(C)c2)c(-c2ccc3ncnn3c2)[nH]1] | 6-(2-Ethyl-4-(4-fluoro-3-methylphenyl)-1H-imidazol-5-yl)-[1,2,4]triazolo[1,5-a]pyridine |
| 109 | 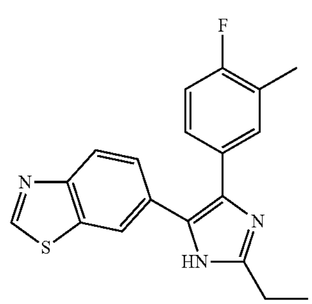 [SMILES: CCc1nc(-c2ccc(F)c(C)c2)c(-c2ccc3ncsc3c2)[nH]1] | 6-(2-Ethyl-4-(4-fluoro-3-methylphenyl)-1H-imidazol-5-yl)benzo[d]thiazole |

TABLE A-continued

| No. | Structure | Name |
|---|---|---|
| 110 | 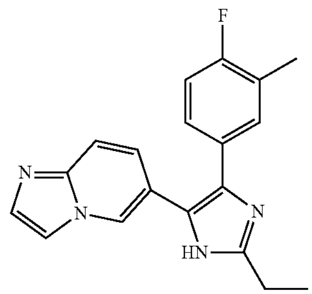 [SMILES: CCc1nc(-c2ccc(F)c(C)c2)c(-c2ccc3nccn3c2)[nH]1] | 6-(2-Ethyl-4-(4-fluoro-3-methylphenyl)-1H-imidazol-5-yl)imidazo[1,2-a]pyridine |
| 111 | 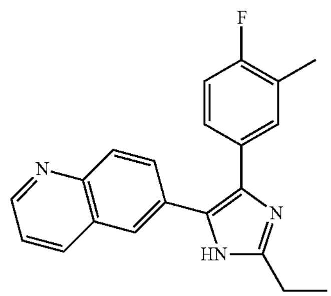 [SMILES: CCc1nc(-c2ccc(F)c(C)c2)c(-c2ccc3ncccc3c2)[nH]1] | 6-(2-Ethyl-4-(4-fluoro-3-methylphenyl)-1H-imidazol-5-yl)quinoline |
| 112 | 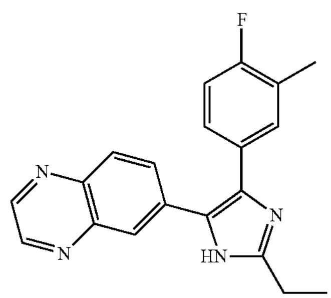 [SMILES: CCc1nc(-c2ccc(F)c(C)c2)c(-c2ccc3nccnc3c2)[nH]1] | 6-(2-Ethyl-4-(4-fluoro-3-methylphenyl)-1H-imidazol-5-yl)quinoxaline |
| 113 | 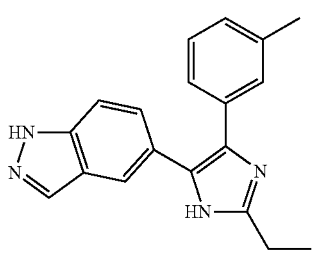 [SMILES: CCc1nc(-c2cccc(C)c2)c(-c2ccc3[nH]ncc3c2)[nH]1] | 5-(2-Ethyl-4-(m-tolyl)-1H-imidazol-5-yl)-1H-indazole |
| 114 | 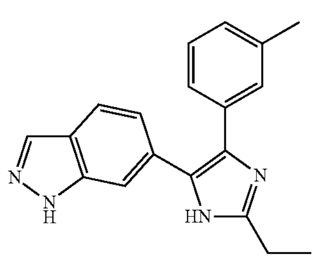 [SMILES: CCc1nc(-c2cccc(C)c2)c(-c2ccc3cn[nH]c3c2)[nH]1] | 6-(2-Ethyl-4-(m-tolyl)-1H-imidazol-5-yl)-1H-indazole |

TABLE A-continued

| No. | Structure | Name |
|---|---|---|
| 115 | 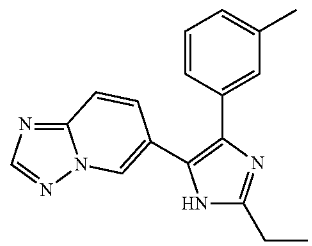 [SMILES: CCc1nc(-c2cccc(C)c2)c(-c2ccc3ncnn3c2)[nH]1] | 6-(2-Ethyl-4-(m-tolyl)-1H-imidazol-5-yl)-[1,2,4]triazolo[1,5-a]pyridine |
| 116 | 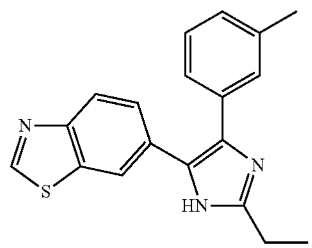 [SMILES: CCc1nc(-c2cccc(C)c2)c(-c2ccc3ncsc3c2)[nH]1] | 6-(2-Ethyl-4-(m-tolyl)-1H-imidazol-5-yl)benzo[d]thiazole |
| 117 | 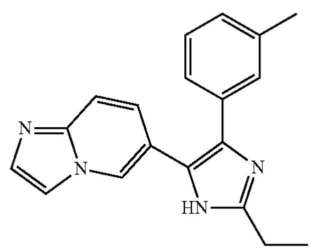 [SMILES: CCc1nc(-c2cccc(C)c2)c(-c2ccc3nccn3c2)[nH]1] | 6-(2-Ethyl-4-(m-tolyl)-1H-imidazol-5-yl)imidazo[1,2-a]pyridine |
| 118 | 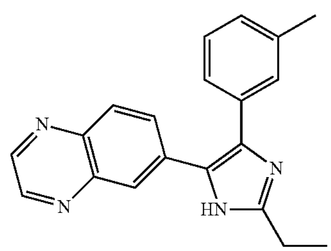 [SMILES: CCc1nc(-c2cccc(C)c2)c(-c2ccc3nccnc3c2)[nH]1] | 6-(2-Ethyl-4-(m-tolyl)-1H-imidazol-5-yl)quinoxaline |
| 119 | 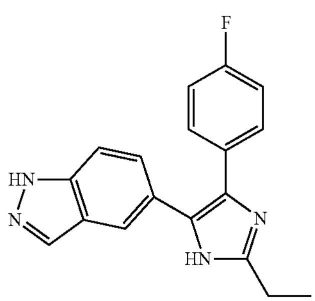 [SMILES: CCc1nc(-c2ccc(F)cc2)c(-c2ccc3[nH]ncc3c2)[nH]1] | 5-(2-Ethyl-4-(4-fluorophenyl)-1H-imidazol-5-yl)-1H-indazole |
| 120 | 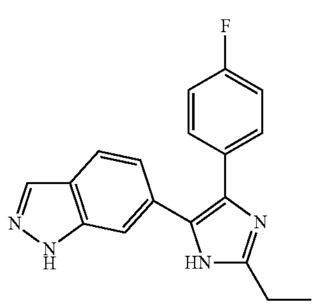 [SMILES: CCc1nc(-c2ccc(F)cc2)c(-c2ccc3cn[nH]c3c2)[nH]1] | 6-(2-Ethyl-4-(4-fluorophenyl)-1H-imidazol-5-yl)-1H-indazole |

TABLE A-continued

| No. | Structure | Name |
|---|---|---|
| 121 | 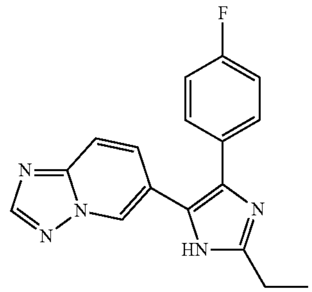 [SMILES: CCc1nc(-c2ccc(F)cc2)c(-c2ccc3ncnn3c2)[nH]1] | 6-(2-Ethyl-4-(4-fluorophenyl)-1H-imidazol-5-yl)-[1,2,4]triazolo[1,5-a]pyridine |
| 122 | 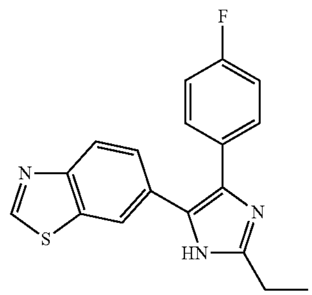 [SMILES: CCc1nc(-c2ccc(F)cc2)c(-c2ccc3ncsc3c2)[nH]1] | 6-(2-Ethyl-4-(4-fluorophenyl)-1H-imidazol-5-yl)benzo[d]thiazole |
| 123 | 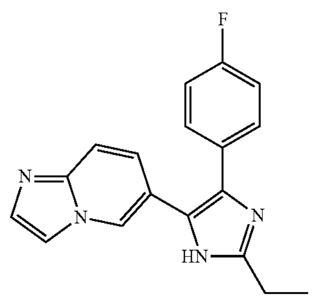 [SMILES: CCc1nc(-c2ccc(F)cc2)c(-c2ccc3nccn3c2)[nH]1] | 6-(2-Ethyl-4-(4-fluorophenyl)-1H-imidazol-5-yl)imidazo[1,2-a]pyridine |
| 124 | 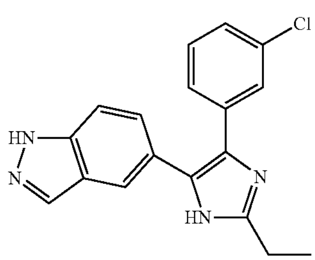 [SMILES: CCc1nc(-c2cccc(Cl)c2)c(-c2ccc3[nH]ncc3c2)[nH]1] | 5-(4-(3-Chlorophenyl)-2-ethyl-1H-imidazol-5-yl)-1H-indazole |
| 125 | 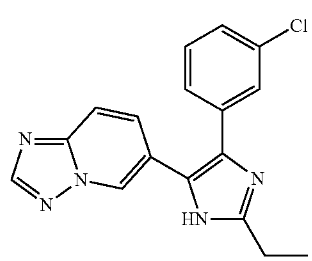 [SMILES: CCc1nc(-c2cccc(Cl)c2)c(-c2ccc3ncnn3c2)[nH]1] | 6-(4-(3-Chlorophenyl)-2-ethyl-1H-imidazol-5-yl)-[1,2,4]triazolo[1,5-a]pyridine |

TABLE A-continued

| No. | Structure | Name |
|---|---|---|
| 126 | 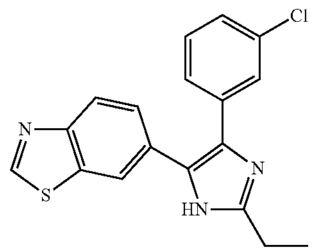 [SMILES: CCc1nc(-c2cccc(Cl)c2)c(-c2ccc3ncsc3c2)[nH]1] | 6-(4-(3-Chlorophenyl)-2-ethyl-1H-imidazol-5-yl)benzo[d]thiazole |
| 127 | 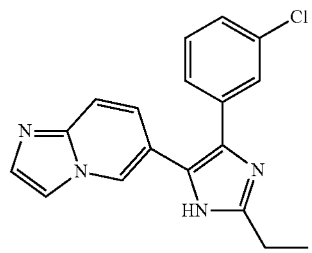 [SMILES: CCc1nc(-c2cccc(Cl)c2)c(-c2ccc3nccn3c2)[nH]1] | 6-(4-(3-Chlorophenyl)-2-ethyl-1H-imidazol-5-yl)imidazo[1,2-a]pyridine |
| 128 | 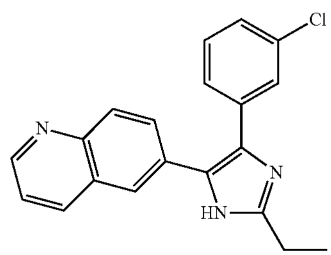 [SMILES: CCc1nc(-c2cccc(Cl)c2)c(-c2ccc3ncccc3c2)[nH]1] | 6-(4-(3-Chlorophenyl)-2-ethyl-1H-imidazol-5-yl)quinoline |
| 129 | 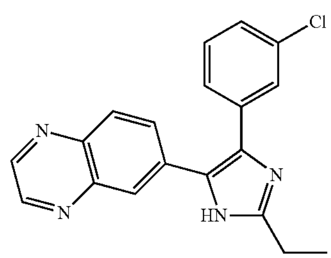 [SMILES: CCc1nc(-c2cccc(Cl)c2)c(-c2ccc3nccnc3c2)[nH]1] | 6-(4-(3-Chlorophenyl)-2-ethyl-1H-imidazol-5-yl)quinoxaline |
| 130 | 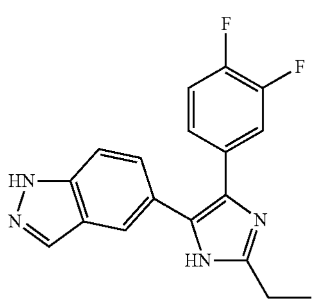 [SMILES: CCc1nc(-c2ccc(F)c(F)c2)c(-c2ccc3[nH]ncc3c2)[nH]1] | 5-(4-(3,4-Difluorophenyl)-2-ethyl-1H-imidazol-5-yl)-1H-indazole |
| 131 | 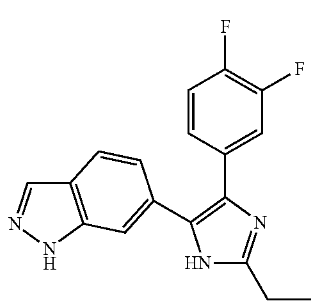 [SMILES: CCc1nc(-c2ccc(F)c(F)c2)c(-c2ccc3cn[nH]c3c2)[nH]1] | 6-(4-(3,4-Difluorophenyl)-2-ethyl-1H-imidazol-5-yl)-1H-indazole |

TABLE A-continued

| No. | Structure | Name |
|-----|-----------|------|
| 132 | 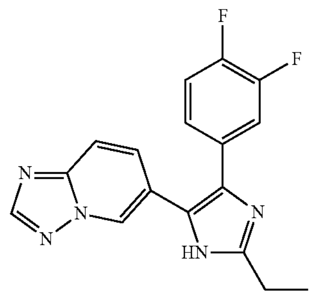 | 6-(4-(3,4-Difluorophenyl)-2-ethyl-1H-imidazol-5-yl)-[1,2,4]triazolo[1,5-a]pyridine |
| 133 | 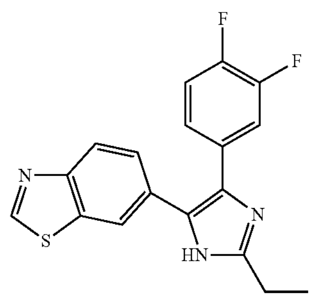 [SMILES: CCc1nc(-c2ccc(F)c(F)c2)c(-c2ccc3ncsc3c2)[nH]1] | 6-(4-(3,4-Difluorophenyl)-2-ethyl-1H-imidazol-5-yl)benzo[d]thiazole |
| 134 | 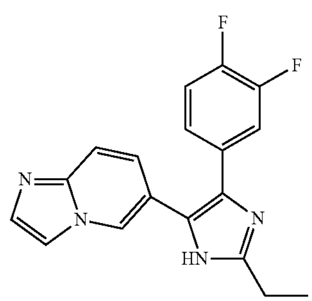 [SMILES: CCc1nc(-c2ccc(F)c(F)c2)c(-c2ccc3nccn3c2)[nH]1] | 6-(4-(3,4-Difluorophenyl)-2-ethyl-1H-imidazol-5-yl)imidazo[1,2-a]pyridine |
| 135 | 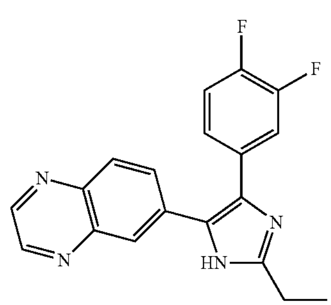 [SMILES: CCc1nc(-c2ccc(F)c(F)c2)c(-c2ccc3nccnc3c2)[nH]1] | 6-(4-(3,4-Difluorophenyl)-2-ethyl-1H-imidazol-5-yl)quinoxaline |
| 136 | 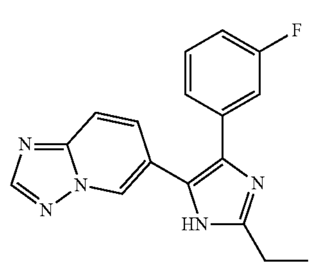 [SMILES: CCc1nc(-c2cccc(F)c2)c(-c2ccc3ncnn3c2)[nH]1] | 6-(2-Ethyl-4-(3-fluorophenyl)-1H-imidazol-5-yl)-[1,2,4]triazolo[1,5-a]pyridine |

TABLE A-continued

| No. | Structure | Name |
|---|---|---|
| 137 | 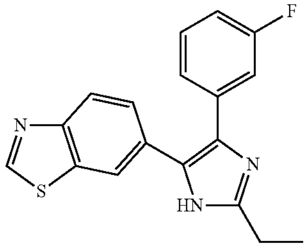 [SMILES: CCc1nc(-c2cccc(F)c2)c(-c2ccc3ncsc3c2)[nH]1] | 6-(2-Ethyl-4-(3-fluorophenyl)-1H-imidazol-5-yl)benzo[d]thiazole |
| 138 | 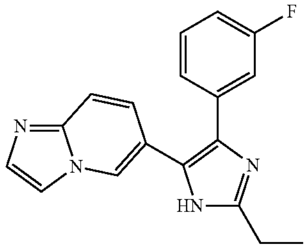 [SMILES: CCc1nc(-c2cccc(F)c2)c(-c2ccc3nccn3c2)[nH]1] | 6-(2-Ethyl-4-(3-fluorophenyl)-1H-imidazol-5-yl)imidazo[1,2-a]pyridine |
| 139 | 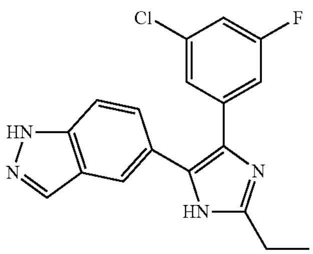 [SMILES: CCc1nc(-c2cc(F)cc(Cl)c2)c(-c2ccc3[nH]ncc3c2)[nH]1] | 5-(4-(3-Chloro-5-fluorophenyl)-2-ethyl-1H-imidazol-5-yl)-1H-indazole |
| 140 | 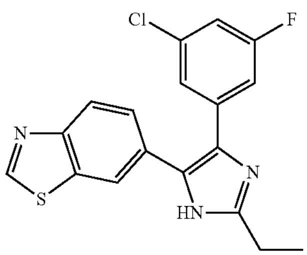 [SMILES: CCc1nc(-c2cc(F)cc(Cl)c2)c(-c2ccc3ncsc3c2)[nH]1] | 6-(4-(3-Chloro-5-fluorophenyl)-2-ethyl-1H-imidazol-5-yl)benzo[d]thiazole |
| 141 | 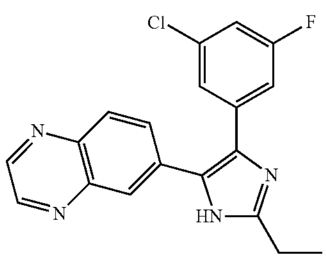 [SMILES: CCc1nc(-c2cc(F)cc(Cl)c2)c(-c2ccc3nccnc3c2)[nH]1] | 6-(4-(3-Chloro-5-fluorophenyl)-2-ethyl-1H-imidazol-5-yl)quinoxaline |
| 142 | 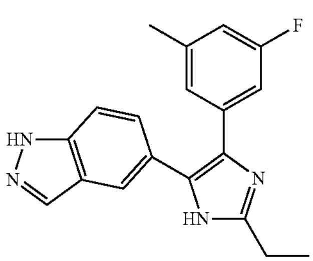 [SMILES: CCc1nc(-c2cc(C)cc(F)c2)c(-c2ccc3[nH]ncc3c2)[nH]1] | 5-(2-Ethyl-4-(3-fluoro-5-methylphenyl)-1H-imidazol-5-yl)-1H-indazole |

TABLE A-continued

| No. | Structure | Name |
|---|---|---|
| 143 | 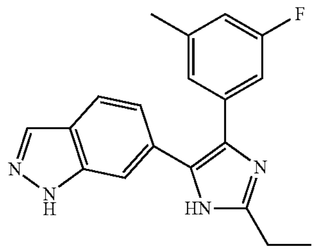 [SMILES: CCc1nc(-c2cc(C)cc(F)c2)c(-c2ccc3cn[nH]c3c2)[nH]1] | 6-(2-Ethyl-4-(3-fluoro-5-methylphenyl)-1H-imidazol-5-yl)-1H-indazole |
| 144 | 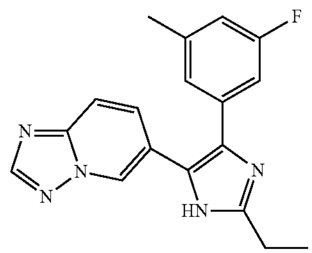 [SMILES: CCc1nc(-c2cc(C)cc(F)c2)c(-c2ccc3ncnn3c2)[nH]1] | 6-(2-Ethyl-4-(3-fluoro-5-methylphenyl)-1H-imidazol-5-yl)-[1,2,4]triazolo[1,5-a]pyridine |
| 145 | 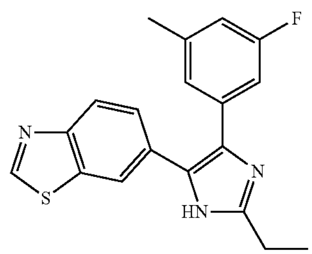 [SMILES: CCc1nc(-c2cc(C)cc(F)c2)c(-c2ccc3ncsc3c2)[nH]1] | 6-(2-Ethyl-4-(3-fluoro-5-methylphenyl)-1H-imidazol-5-yl)benzo[d]thiazole |
| 146 | 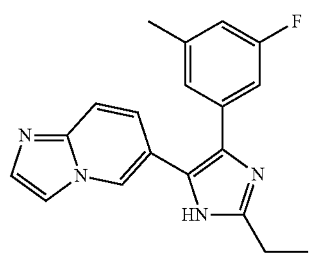 [SMILES: CCc1nc(-c2cc(C)cc(F)c2)c(-c2ccc3nccn3c2)[nH]1] | 6-(2-Ethyl-4-(3-fluoro-5-methylphenyl)-1H-imidazol-5-yl)imidazo[1,2-a]pyridine |
| 147 | 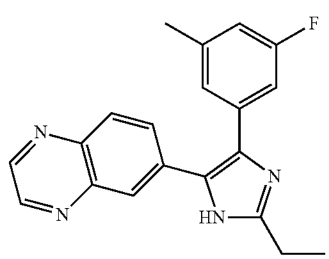 [SMILES: CCc1nc(-c2cc(C)cc(F)c2)c(-c2ccc3nccnc3c2)[nH]1] | 6-(2-Ethyl-4-(3-fluoro-5-methylphenyl)-1H-imidazol-5-yl)quinoxaline |
| 148 | 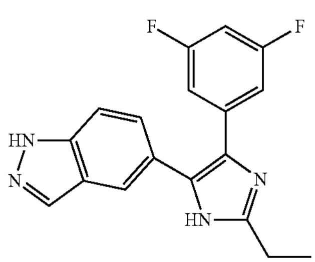 [SMILES: CCc1nc(-c2cc(F)cc(F)c2)c(-c2ccc3[nH]ncc3c2)[nH]1] | 5-(4-(3,5-Difluorophenyl)-2-methyl-1H-imidazol-5-yl)-1H-indazole |

TABLE A-continued

| No. | Structure | Name |
|---|---|---|
| 149 | 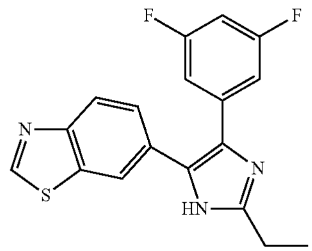 [SMILES: CCc1nc(-c2cc(F)cc(F)c2)c(-c2ccc3ncsc3c2)[nH]1] | 6-(4-(3,5-Difluorophenyl)-2-ethyl-1H-imidazol-5-yl)benzo[d]thiazole |
| 150 | 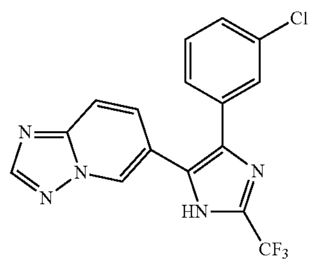 [SMILES: FC(F)(F)c1nc(-c2cccc(Cl)c2)c(-c2ccc3ncnn3c2)[nH]1] | 6-(4-(3-Chlorophenyl)-2-(trifluoromethyl)-1H-imidazol-5-yl)-[1,2,4]triazolo[1,5-a]pyridine |
| 151 | 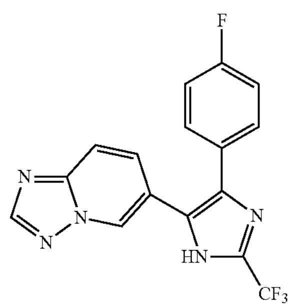 [SMILES: Fc1ccc(-c2nc(C(F)(F)F)[nH]c2-c2ccc3ncnn3c2)cc1] | 6-(4-(4-Fluorophenyl)-2-(trifluoromethyl)-1H-imidazol-5-yl)-[1,2,4]triazolo[1,5-a]pyridine |
| 152 | 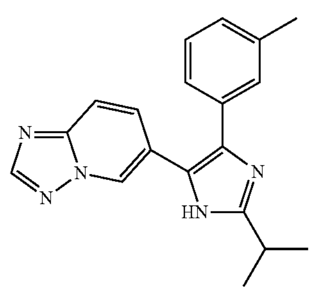 [SMILES: Cc1cccc(-c2nc(C(C)C)[nH]c2-c2ccc3ncnn3c2)c1] | 6-(2-Isopropyl-4-(m-tolyl)-1H-imidazol-5-yl)-[1,2,4]triazolo[1,5-a]pyridine |
| 153 | 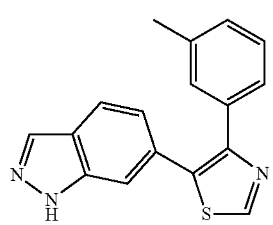 [SMILES: Cc1cccc(-c2ncsc2-c2ccc3cn[nH]c3c2)c1] | 5-(1H-indazol-6-yl)-4-(m-tolyl)thiazole |
| 154 | 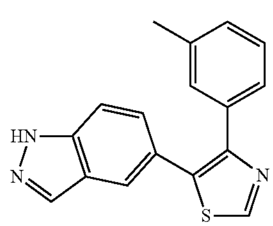 [SMILES: Cc1cccc(-c2ncsc2-c2ccc3[nH]ncc3c2)c1] | 5-(1H-indazol-5-yl)-4-(m-tolyl)thiazole |

TABLE A-continued

| No. | Structure | Name |
| --- | --- | --- |
| 155 | 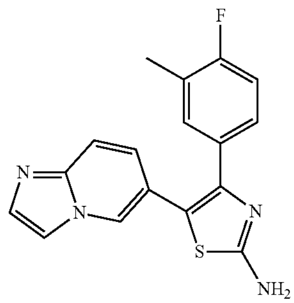 [SMILES: Cc1cc(-c2nc(N)sc2-c2ccc3nccn3c2)ccc1F] | 4-(4-fluoro-3-methylphenyl)-5-(imidazo[1,2-a]pyridin-6-yl)thiazol-2-amine |
| 156 | 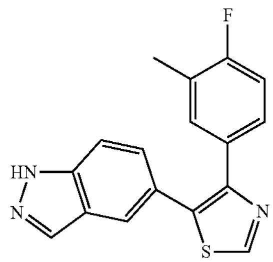 [SMILES: Cc1cc(-c2ncsc2-c2ccc3[nH]ncc3c2)ccc1F] | 4-(4-fluoro-3-methylphenyl)-5-(1H-indazol-5-yl)thiazole |
| 157 | 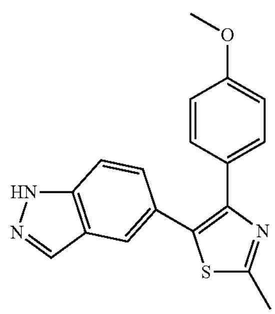 [SMILES: COc1ccc(-c2nc(C)sc2-c2ccc3[nH]ncc3c2)cc1] | 5-(1H-indazol-5-yl)-4-(4-methoxyphenyl)thiazol-2-amine |
| 158 | 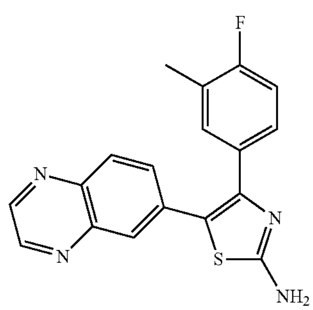 [SMILES: Cc1cc(-c2nc(N)sc2-c2ccc3nccnc3c2)ccc1F] | 4-(4-fluoro-3-methylphenyl)-5-(quinoxalin-6-yl)thiazol-2-amine |
| 159 | 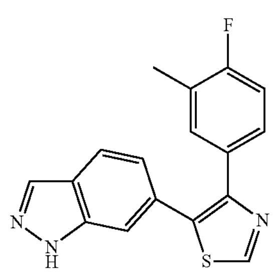 [SMILES: Cc1cc(-c2ncsc2-c2ccc3cn[nH]c3c2)ccc1F] | 4-(4-fluoro-3-methylphenyl)-5-(1H-indazol-6-yl)thiazole |

TABLE A-continued
| No. | Structure | Name |
| --- | --- | --- |
| 160 | 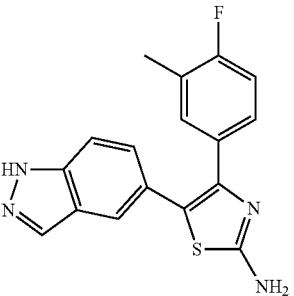 [SMILES: Cc1cc(-c2nc(N)sc2-c2ccc3[nH]ncc3c2)ccc1F] | 4-(4-fluoro-3-methylphenyl)-5-(1H-indazol-5-yl)thiazol-2-amine |
| 161 | 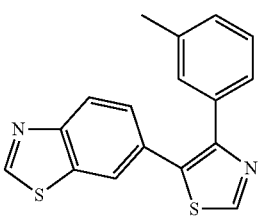 [SMILES: Cc1cccc(-c2ncsc2-c2ccc3ncsc3c2)c1] | 6-(4-(m-tolyl)thiazol-5-yl)benzo[d]thiazole |
| 162 | 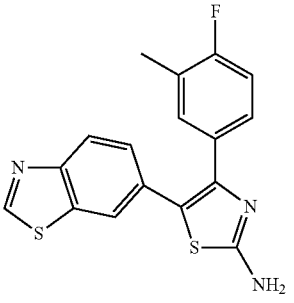 [SMILES: Cc1cc(-c2nc(N)sc2-c2ccc3ncsc3c2)ccc1F] | 5-(benzo[d]thiazol-6-yl)-4-(4-fluoro-3-methylphenyl)thiazol-2-amine |
| 163 | 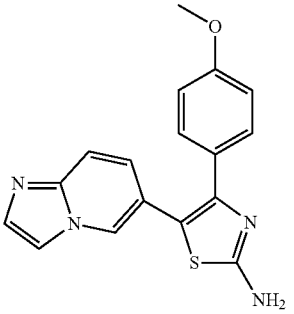 [SMILES: COc1ccc(-c2nc(N)sc2-c2ccc3nccn3c2)cc1] | 5-(imidazo[1,2-a]pyridin-6-yl)-4-(4-methoxyphenyl)thiazol-2-amine |
| 164 | 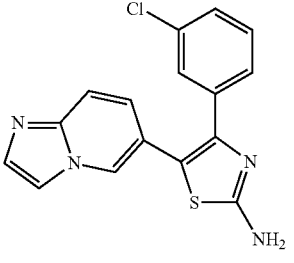 [SMILES: Nc1nc(-c2cccc(Cl)c2)c(-c2ccc3nccn3c2)s1] | 4-(3-chlorophenyl)-5-(imidazo[1,2-a]pyridin-6-yl)thiazol-2-amine |

TABLE A-continued

| No. | Structure | Name |
|---|---|---|
| 165 | 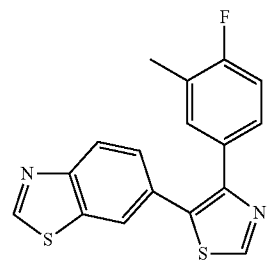 [SMILES: Cc1cc(-c2ncsc2-c2ccc3ncsc3c2)ccc1F] | 6-(4-(4-fluoro-3-methylphenyl)thiazol-5-yl)benzo[d]thiazole |
| 166 | 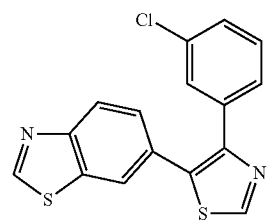 [SMILES: Clc1cccc(-c2ncsc2-c2ccc3ncsc3c2)c1] | 6-(4-(3-chlorophenyl)thiazol-5-yl)benzo[d]thiazole |
| 167 | 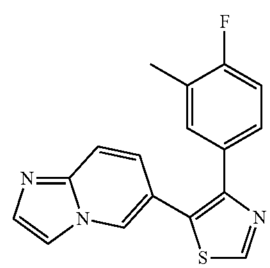 [SMILES: Cc1cc(-c2ncsc2-c2ccc3nccn3c2)ccc1F] | 4-(4-fluoro-3-methylphenyl)-5-(imidazo[1,2-a]pyridin-6-yl)thiazole |
| 168 | 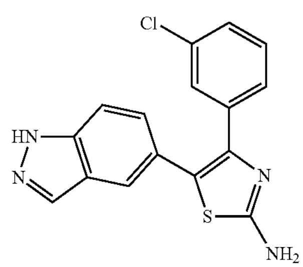 [SMILES: Nc1nc(-c2cccc(Cl)c2)c(-c2ccc3[nH]ncc3c2)s1] | 4-(3-chlorophenyl)-5-(1H-indazol-5-yl)thiazol-2-amine |
| 169 | 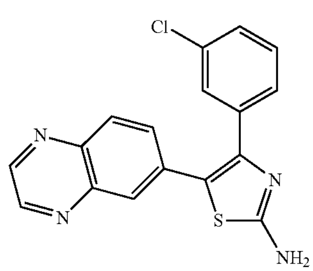 [SMILES: Nc1nc(-c2cccc(Cl)c2)c(-c2ccc3nccnc3c2)s1] | 4-(3-chlorophenyl)-5-(quinoxalin-6-yl)thiazol-2-amine |
| 170 | 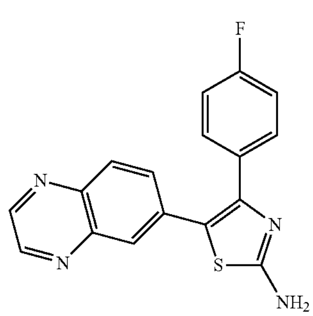 [SMILES: Nc1nc(-c2ccc(F)cc2)c(-c2ccc3nccnc3c2)s1] | 4-(4-fluorophenyl)-5-(quinoxalin-6-yl)thiazol-2-amine |

TABLE A-continued

| No. | Structure | Name |
|---|---|---|
| 171 | 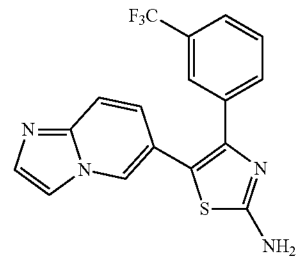 [SMILES: Nc1nc(-c2cccc(C(F)(F)F)c2)c(-c2ccc3nccn3c2)s1] | 5-(imidazo[1,2-a]pyridin-6-yl)-4-(3-(trifluoromethyl)phenyl)thiazol-2-amine |
| 172 | 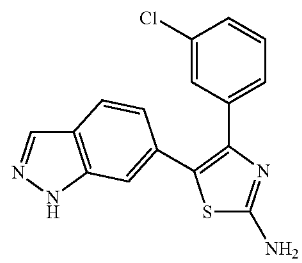 [SMILES: Nc1nc(-c2cccc(Cl)c2)c(-c2ccc3cn[nH]c3c2)s1] | 4-(3-chlorophenyl)-5-(1H-indazol-6-yl)thiazol-2-amine |
| 173 | 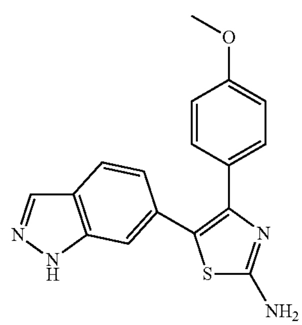 [SMILES: COc1ccc(-c2nc(N)sc2-c2ccc3cn[nH]c3c2)cc1] | 5-(1H-indazol-6-yl)-4-(4-methoxyphenyl)thiazol-2-amine |
| 174 | 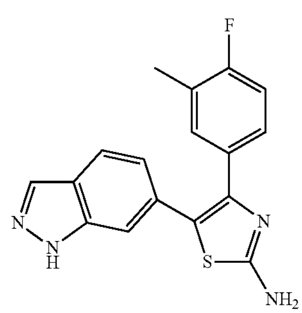 [SMILES: Cc1cc(-c2nc(N)sc2-c2ccc3cn[nH]c3c2)ccc1F] | 4-(4-fluoro-3-methylphenyl)-5-(1H-indazol-6-yl)thiazol-2-amine |
| 175 | 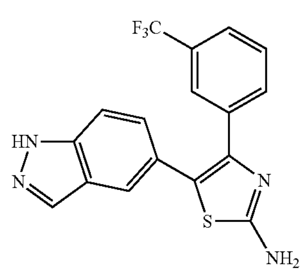 | 5-(1H-indazol-5-yl)-4-(3-(trifluoromethyl)phenyl)thiazol-2-amine |

TABLE A-continued

| No. | Structure | Name |
|---|---|---|
| 176 | 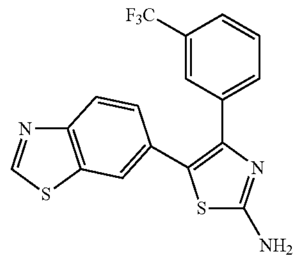 | 5-(benzo[d]thiazol-6-yl)-4-(3-(trifluoromethyl)phenyl)thiazol-2-amine |
| 177 | 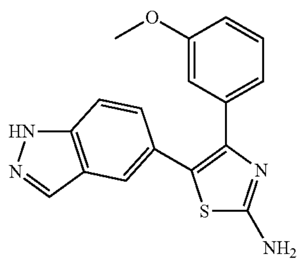 [SMILES: COc1cccc(-c2nc(N)sc2-c2ccc3[nH]ncc3c2)c1] | 5-(1H-indazol-5-yl)-4-(3-methoxyphenyl)thiazol-2-amine |
| 178 | 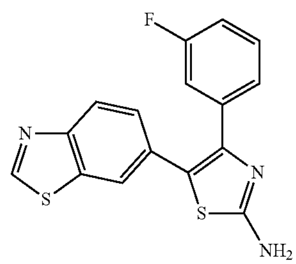 [SMILES: Nc1nc(-c2cccc(F)c2)c(-c2ccc3ncsc3c2)s1] | 5-(benzo[d]thiazol-6-yl)-4-(3-fluorophenyl)thiazol-2-amine |
| 179 | 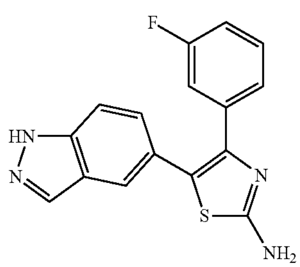 [SMILES: Nc1nc(-c2cccc(F)c2)c(-c2ccc3[nH]ncc3c2)s1] | 4-(3-fluorophenyl)-5-(1H-indazol-5-yl)thiazol-2-amine |
| 180 | 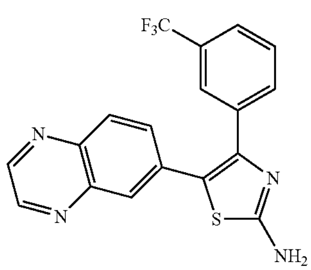 | 5-(quinoxalin-6-yl)-4-(3-(trifluoromethyl)phenyl)thiazol-2-amine |
| 181 | 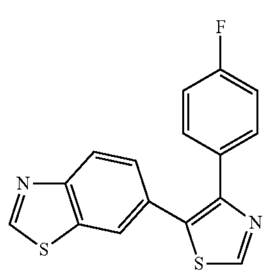 [SMILES: Fc1ccc(-c2ncsc2-c2ccc3ncsc3c2)cc1] | 6-(4-(4-fluorophenyl)thiazol-5-yl)benzo[d]thiazole |

TABLE A-continued
| No. | Structure | Name |
|---|---|---|
| 182 | 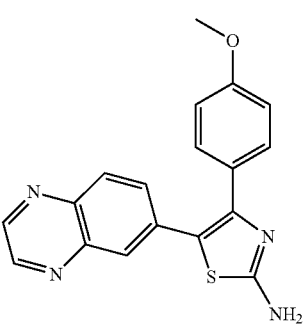 [SMILES: COc1ccc(-c2nc(N)sc2-c2ccc3nccnc3c2)cc1] | 4-(4-methoxyphenyl)-5-(quinoxalin-6-yl)thiazol-2-amine |
| 183 | 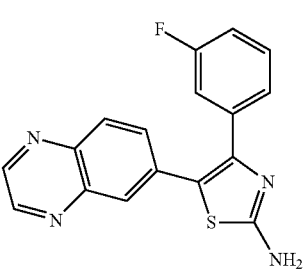 [SMILES: Nc1nc(-c2cccc(F)c2)c(-c2ccc3nccnc3c2)s1] | 4-(3-fluorophenyl)-5-(quinoxalin-6-yl)thiazol-2-amine |
| 184 | 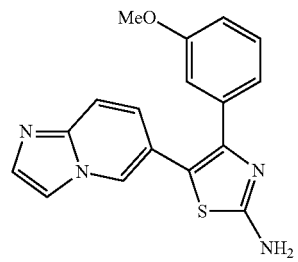 [SMILES: COc1cccc(-c2nc(N)sc2-c2ccc3nccn3c2)c1] | 5-(imidazo[1,2-a]pyridin-6-yl)-4-(3-methoxyphenyl)thiazol-2-amine |
| 185 | 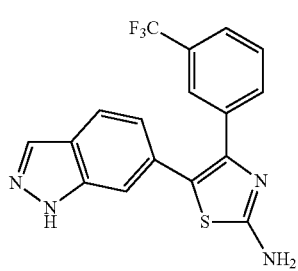 | 5-(1H-indazol-6-yl)-4-(3-(trifluoromethyl)phenyl)thiazol-2-amine |
| 186 | 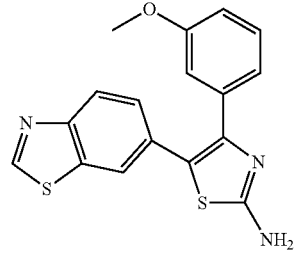 [SMILES: COc1cccc(-c2nc(N)sc2-c2ccc3ncsc3c2)c1] | 5-(benzo[d]thiazol-6-yl)-4-(3-methoxyphenyl)thiazol-2-amine |

TABLE A-continued

| No. | Structure | Name |
|---|---|---|
| 187 | 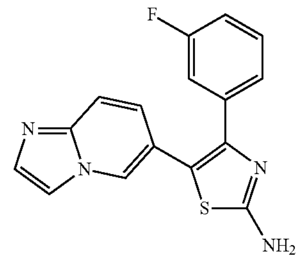 [SMILES: Nc1nc(-c2cccc(F)c2)c(-c2ccc3nccn3c2)s1] | 4-(3-fluorophenyl)-5-(imidazo[1,2-a]pyridin-6-yl)thiazol-2-amine |
| 188 | 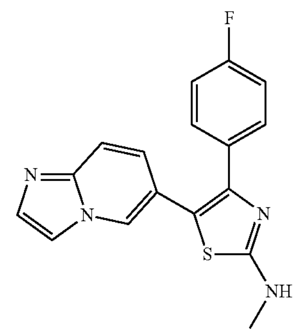 [SMILES: CNc1nc(-c2ccc(F)cc2)c(-c2ccc3nccn3c2)s1] | 4-(4-fluorophenyl)-5-(imidazo[1,2-a]pyridin-6-yl)-N-methylthiazol-2-amine |
| 1' | 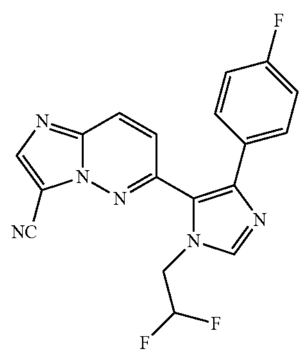 [SMILES: N#Cc1cnc2ccc(-c3c(-c4ccc(F)cc4)ncn3CC(F)F)nn12] | 6-(1-(2,2-difluoroethyl)-4-(4-fluorophenyl)-1H-imidazol-5-yl)imidazo[1,2-b]pyridazine-3-carbonitrile |
| 2' | 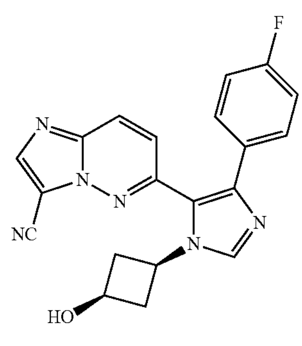 [SMILES: N#Cc1cnc2ccc(-c3c(-c4ccc(F)cc4)ncn3[C@H]3C[C@@H](O)C3)nn12] | 6-(4-(4-fluorophenyl)-1-cis-3-hydroxycyclobutyl)-1H-imidazol-5-yl)imidazo[1,2-b]pyridazine-3-carbonitrile |
| 3' | 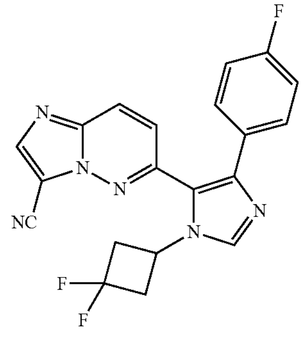 [SMILES: N#Cc1cnc2ccc(-c3c(-c4ccc(F)cc4)ncn3C3CC(F)(F)C3)nn12] | 6-(1-(3,3-difluorocyclobutyl)-4-(4-fluorophenyl)-1H-imidazol-5-yl)imidazo[1,2-b]pyridazine-3-carbonitrile |

TABLE A-continued

| No. | Structure | Name |
|---|---|---|
| 4' | 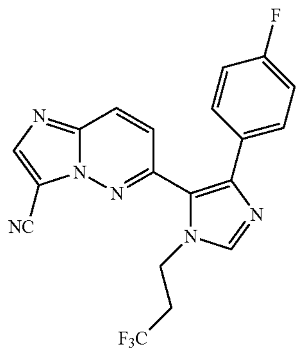 [SMILES: N#Cc1cnc2ccc(-c3c(-c4ccc(F)cc4)ncn3CCC(F)(F)F)nn12] | 6-(4-(4-fluorophenyl)-1-(3,3,3-trifluoropropyl)-1H-imidazol-5-yl)imidazo[1,2-b]pyridazine-3-carbonitrile |
| 5' | 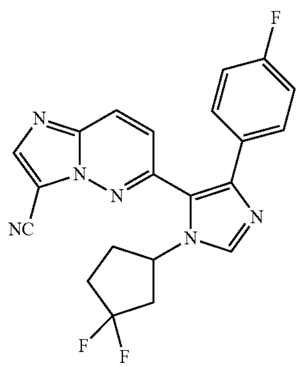 [SMILES: N#Cc1cnc2ccc(-c3c(-c4ccc(F)cc4)ncn3C3CCC(F)(F)C3)nn12] | 6-(1-(3,3-difluorocyclopentyl)-4-(4-fluorophenyl)-1H-imidazol-5-yl)imidazo[1,2-b]pyridazine-3-carbonitrile |
| 6' | 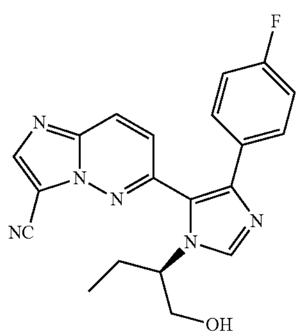 [SMILES: CC[C@H](CO)n1cnc(-c2ccc(F)cc2)c1-c1ccc2ncc(C#N)n2n1] | (S)-6-(4-(4-fluorophenyl)-1-(1-hydroxybutan-2-yl)-1H-imidazol-5-yl)imidazo[1,2-b]pyridazine-3-carbonitrile |
| 7' | 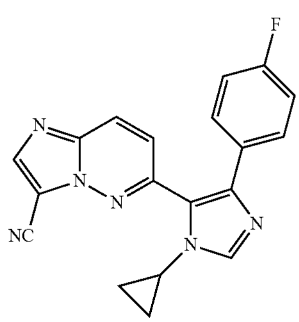 [SMILES: N#Cc1cnc2ccc(-c3c(-c4ccc(F)cc4)ncn3C3CC3)nn12] | 6-(1-cyclopropyl-4-(4-fluorophenyl)-1H-imidazol-5-yl)imidazo[1,2-b]pyridazine-3-carbonitrile |

TABLE A-continued

| No. | Structure | Name |
|---|---|---|
| 8' | 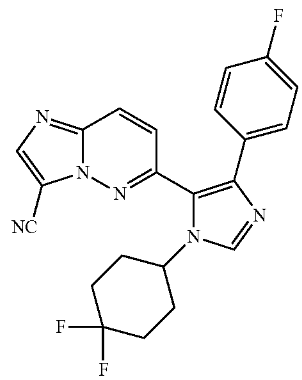 [SMILES: N#Cc1cnc2ccc(-c3c(-c4ccc(F)cc4)ncn3C3CCC(F)(F)CC3)nn12] | 6-(1-(4,4-difluorocyclohexyl)-4-(4-fluorophenyl)-1H-imidazol-5-yl)imidazo[1,2-b]pyridazine-3-carbonitrile |
| 9' | 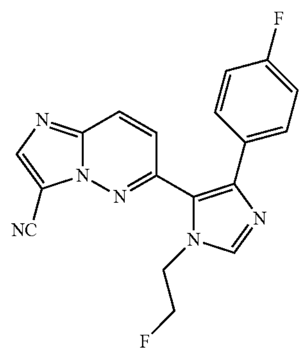 [SMILES: N#Cc1cnc2ccc(-c3c(-c4ccc(F)cc4)ncn3CCF)nn12] | 6-(1-(2-fluoroethyl)-4-(4-fluorophenyl)-1H-imidazol-5-yl)imidazo[1,2-b]pyridazine-3-carbonitrile |
| 10' | 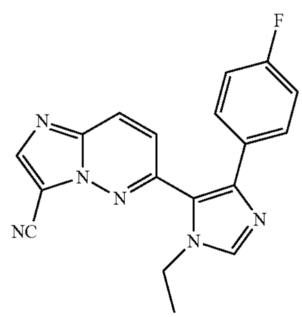 [SMILES: CCn1cnc(-c2ccc(F)cc2)c1-c1ccc2ncc(C#N)n2n1] | 6-(1-ethyl-4-(4-fluorophenyl)-1H-imidazol-5-yl)imidazo[1,2-b]pyridazine-3-carbonitrile |
| 11' | 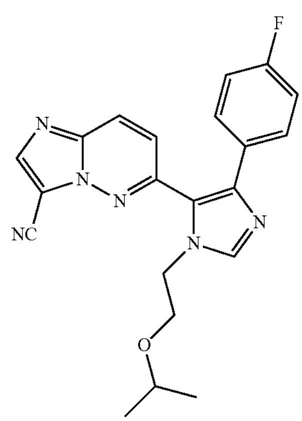 [SMILES: CC(C)OCCn1cnc(-c2ccc(F)cc2)c1-c1ccc2ncc(C#N)n2n1] | 6-(4-(4-fluorophenyl)-1-(2-isopropoxyethyl)-1H-imidazol-5-yl)imidazo[1,2-b]pyridazine-3-carbonitrile |

TABLE A-continued
| No. | Structure | Name |
|---|---|---|
| 12' | 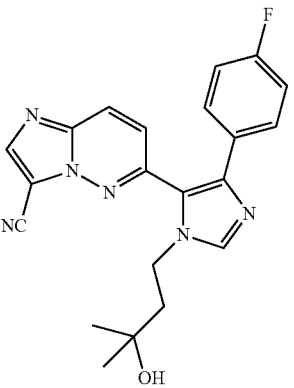 [SMILES: CC(C)(O)CCn1cnc(-c2ccc(F)cc2)c1-c1ccc2ncc(C#N)n2n1] | 6-(4-(4-fluorophenyl)-1-(3-hydroxy-3-methylbutyl)-1H-imidazol-5-yl)imidazo[1,2-b]pyridazine-3-carbonitrile |
| 13' | 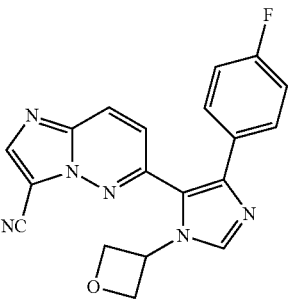 [SMILES: N#Cc1cnc2ccc(-c3c(-c4ccc(F)cc4)ncn3C3COC3)nn12] | 6-(4-(4-fluorophenyl)-1-(oxetan-3-yl)-1H-imidazol-5-yl)imidazo[1,2-b]pyridazine-3-carbonitrile |
| 14' | 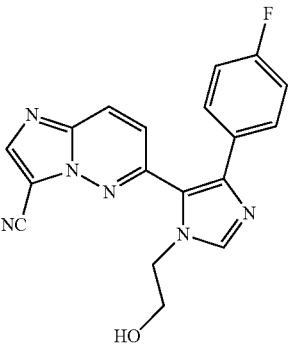 [SMILES: N#Cc1cnc2ccc(-c3c(-c4ccc(F)cc4)ncn3CCO)nn12] | 6-(4-(4-fluorophenyl)-1-(2-hydroxyethyl)-1H-imidazol-5-yl)imidazo[1,2-b]pyridazine-3-carbonitrile |
| 15' | 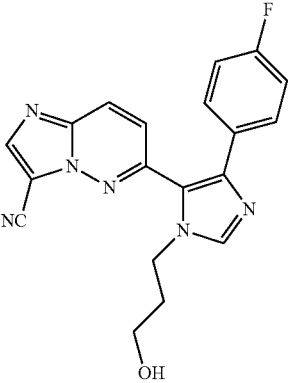 [SMILES: N#Cc1cnc2ccc(-c3c(-c4ccc(F)cc4)ncn3CCCO)nn12] | 6-(4-(4-fluorophenyl)-1-(3-hydroxypropyl)-1H-imidazol-5-yl)imidazo[1,2-b]pyridazine-3-carbonitrile |

TABLE A-continued

| No. | Structure | Name |
|---|---|---|
| 16' | 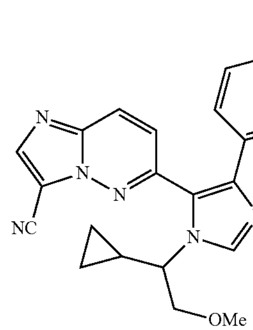 | 6-(1-(1-cyclopropyl-2-methoxyethyl)-4-(4-fluorophenyl)-1H-imidazol-5-yl)imidazo[1,2-b]pyridazine-3-carbonitrile |
| 17' | 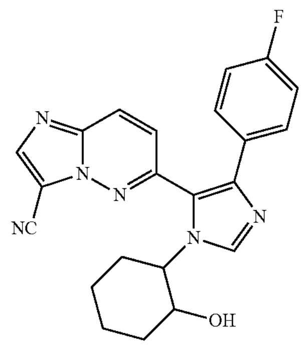 [SMILES: N#Cc1cnc2ccc(-c3c(-c4ccc(F)cc4)ncn3C3CCCCC3O)nn12] | 6-(4-(4-fluorophenyl)-1-(2-hydroxycyclohexyl)-1H-imidazol-5-yl)imidazo[1,2-b]pyridazine-3-carbonitrile |
| 18' | 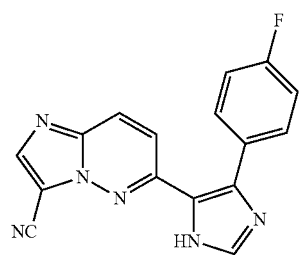 [SMILES: N#Cc1cnc2ccc(-c3[nH]cnc3-c3ccc(F)cc3)nn12] | 6-(4-(4-fluorophenyl)-1H-imidazol-5-yl)imidazo[1,2-b]pyridazine-3-carbonitrile |
| 19' | 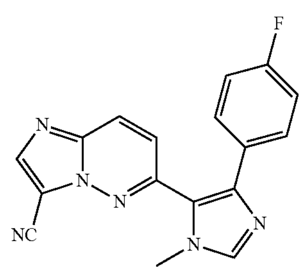 [SMILES: Cn1cnc(-c2ccc(F)cc2)c1-c1ccc2ncc(C#N)n2n1] | 6-(4-(4-fluorophenyl)-1-methyl-1H-imidazol-5-yl)imidazo[1,2-b]pyridazine-3-carbonitrile |
| 20' | 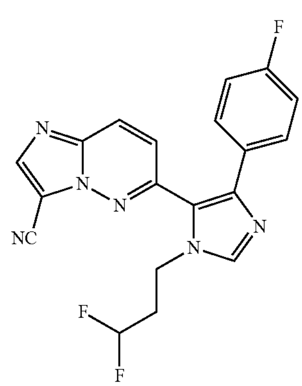 [SMILES: N#Cc1cnc2ccc(-c3c(-c4ccc(F)cc4)ncn3CCC(F)F)nn12] | 6-(1-(3,3-difluoropropyl)-4-(4-fluorophenyl)-1H-imidazol-5-yl)imidazo[1,2-b]pyridazine-3-carbonitrile |

TABLE A-continued

| No. | Structure | Name |
|---|---|---|
| 21' | 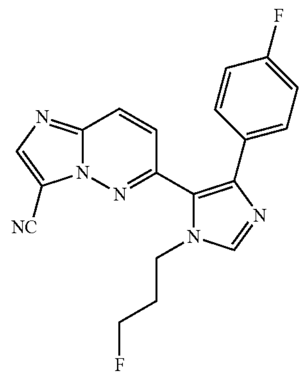 [SMILES: N#Cc1cnc2ccc(-c3c(-c4ccc(F)cc4)ncn3CCCF)nn12] | 6-(4-(4-fluorophenyl)-1-(3-fluoropropyl)-1H-imidazol-5-yl)imidazo[1,2-b]pyridazine-3-carbonitrile |
| 22' | 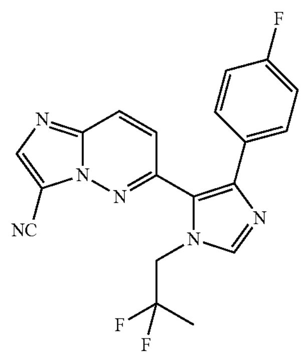 [SMILES: CC(F)(F)Cn1cnc(-c2ccc(F)cc2)c1-c1ccc2ncc(C#N)n2n1] | 6-(1-(2,2-difluoropropyl)-4-(4-fluorophenyl)-1H-imidazol-5-yl)imidazo[1,2-b]pyridazine-3-carbonitrile |
| 23' | 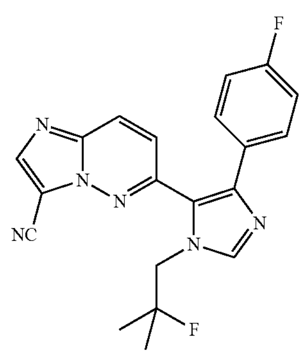 [SMILES: CC(C)(F)Cn1cnc(-c2ccc(F)cc2)c1-c1ccc2ncc(C#N)n2n1] | 6-(1-(2-fluoro-2-methylpropyl)-4-(4-fluorophenyl)-1H-imidazol-5-yl)imidazo[1,2-b]pyridazine-3-carbonitrile |
| 24' | 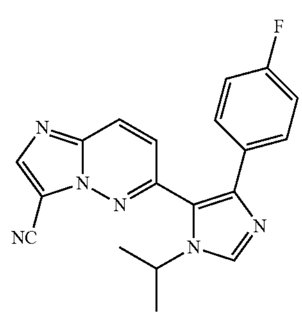 [SMILES: CC(C)n1cnc(-c2ccc(F)cc2)c1-c1ccc2ncc(C#N)n2n1] | 6-(4-(4-fluorophenyl)-1-isopropyl-1H-imidazol-5-yl)imidazo[1,2-b]pyridazine-3-carbonitrile |

TABLE A-continued

| No. | Structure | Name |
|---|---|---|
| 25' | 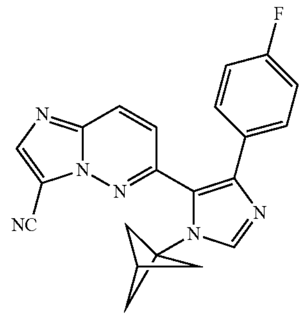 [SMILES: N#Cc1cnc2ccc(-c3c(-c4ccc(F)cc4)ncn3C34CC(C3)C4)nn12] | 6-(1-(bicyclo[1.1.1]pentan-1-yl)-4-(4-fluorophenyl)-1H-imidazol-5-yl)imidazo[1,2-b]pyridazine-3-carbonitrile |
| 26' | 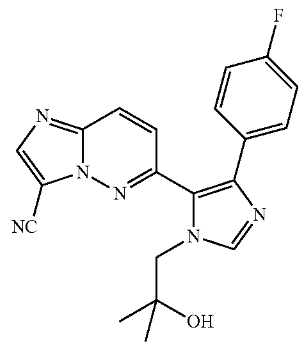 [SMILES: CC(C)(O)Cn1cnc(-c2ccc(F)cc2)c1-c1ccc2ncc(C#N)n2n1] | 6-(4-(4-fluorophenyl)-1-(2-hydroxy-2-methylpropyl)-1H-imidazol-5-yl)imidazo[1,2-b]pyridazine-3-carbonitrile |
| 27' | 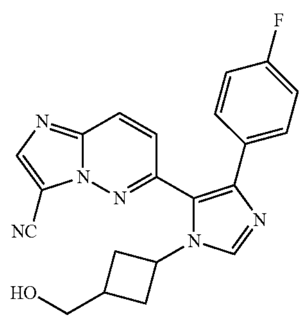 [SMILES: N#Cc1cnc2ccc(-c3c(-c4ccc(F)cc4)ncn3C3CC(CO)C3)nn12] | 6-(4-(4-fluorophenyl)-1-(3-(hydroxymethyl)cyclobutyl)-1H-imidazol-5-yl)imidazo[1,2-b]pyridazine-3-carbonitrile |
| 28' | 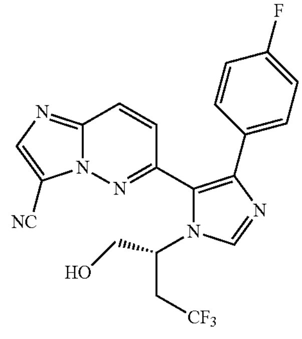 [SMILES: N#Cc1cnc2ccc(-c3c(-c4ccc(F)cc4)ncn3[C@@H](CO)CC(F)(F)F)nn12] | (R)-6-(4-(4-fluorophenyl)-1-(4,4,4-trifluoro-1-hydroxybutan-2-yl)-1H-imidazol-5-yl)imidazo[1,2-b]pyridazine-3-carbonitrile |

TABLE A-continued

| No. | Structure | Name |
|---|---|---|
| 29' | 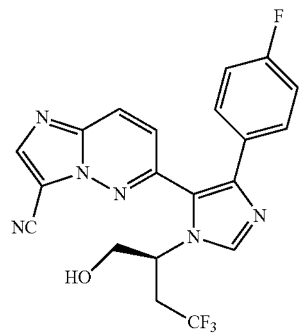 [SMILES: N#Cc1cnc2ccc(-c3c(-c4ccc(F)cc4)ncn3[C@H](CO)CC(F)(F)F)nn12] | (S)-6-(4-(4-fluorophenyl)-1-(4,4,4-trifluoro-1-hydroxybutan-2-yl)-1H-imidazol-5-yl)imidazo[1,2-b]pyridazine-3-carbonitrile |
| 30' | 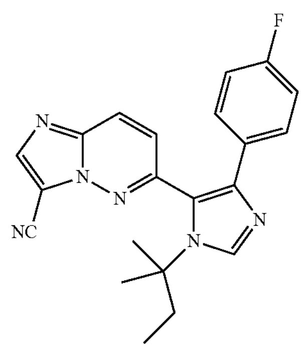 [SMILES: CCC(C)(C)n1cnc(-c2ccc(F)cc2)c1-c1ccc2ncc(C#N)n2n1] | 6-(4-(4-fluorophenyl)-1-(tert-pentyl)-1H-imidazol-5-yl)imidazo[1,2-b]pyridazine-3-carbonitrile |
| 31' | 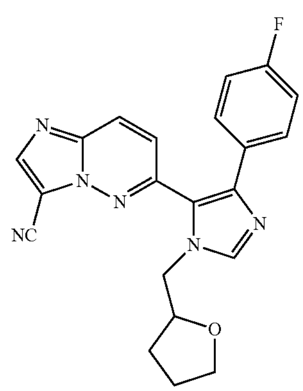 [SMILES: N#Cc1cnc2ccc(-c3c(-c4ccc(F)cc4)ncn3CC3CCCO3)nn12] | 6-(4-(4-fluorophenyl)-1-((tetrahydrofuran-2-yl)methyl)-1H-imidazol-5-yl)imidazo[1,2-b]pyridazine-3-carbonitrile |
| 32' | 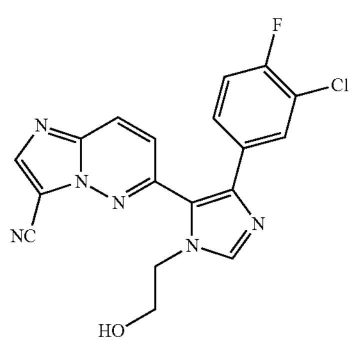 [SMILES: N#Cc1cnc2ccc(-c3c(-c4ccc(F)c(Cl)c4)ncn3CCO)nn12] | 6-(4-(3-chloro-4-fluorophenyl)-1-(2-hydroxyethyl)-1H-imidazol-5-yl)imidazo[1,2-b]pyridazine-3-carbonitrile |

TABLE A-continued

| No. | Structure | Name |
|---|---|---|
| 33' | 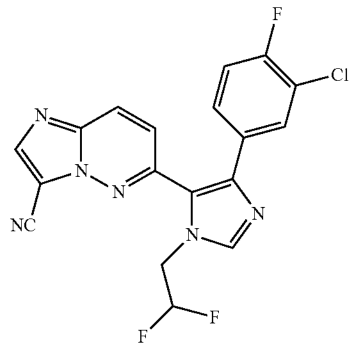 [SMILES: N#Cc1cnc2ccc(-c3c(-c4ccc(F)c(Cl)c4)ncn3CC(F)F)nn12] | 6-(4-(3-chloro-4-fluorophenyl)-1-(2,2-difluoroethyl)-1H-imidazol-5-yl)imidazo[1,2-b]pyridazine-3-carbonitrile |
| 34' | 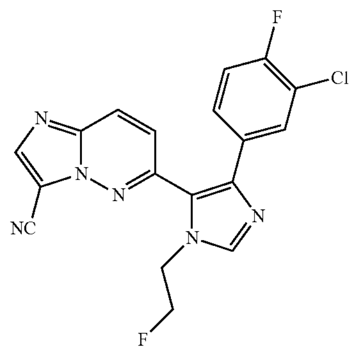 [SMILES: N#Cc1cnc2ccc(-c3c(-c4ccc(F)c(Cl)c4)ncn3CCF)nn12] | 6-(4-(3-chloro-4-fluorophenyl)-1-(2-fluoroethyl)-1H-imidazol-5-yl)imidazo[1,2-b]pyridazine-3-carbonitrile |
| 35' | 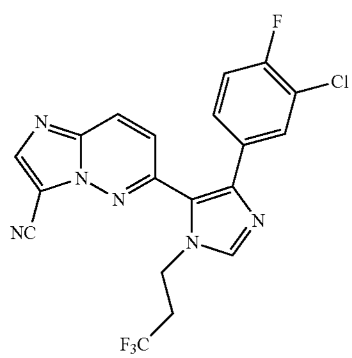 [SMILES: N#Cc1cnc2ccc(-c3c(-c4ccc(F)c(Cl)c4)ncn3CCC(F)(F)F)nn12] | 6-(4-(3-chloro-4-fluorophenyl)-1-(3,3,3-trifluoropropyl)-1H-imidazol-5-yl)imidazo[1,2-b]pyridazine-3-carbonitrile |
| 36' | 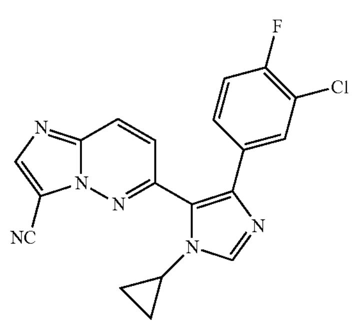 [SMILES: N#Cc1cnc2ccc(-c3c(-c4ccc(F)c(Cl)c4)ncn3C3CC3)nn12] | 6-(4-(3-chloro-4-fluorophenyl)-1-cyclopropyl-1H-imidazol-5-yl)imidazo[1,2-b]pyridazine-3-carbonitrile |

TABLE A-continued

| No. | Structure | Name |
| --- | --- | --- |
| 37' | 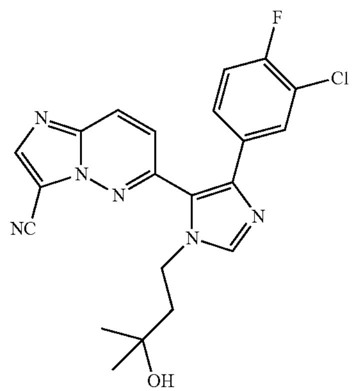 [SMILES: CC(C)(O)CCn1cnc(-c2ccc(F)c(Cl)c2)c1-c1ccc2ncc(C#N)n2n1] | 6-(4-(3-chloro-4-fluorophenyl)-1-(3-hydroxy-3-methylbutyl)-1H-imidazol-5-yl)imidazo[1,2-b]pyridazine-3-carbonitrile |
| 38' | 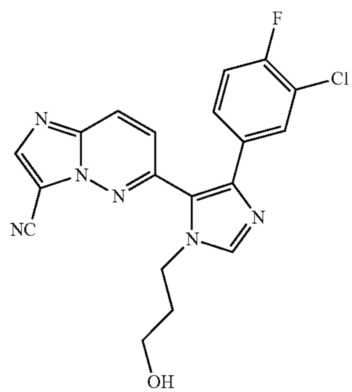 [SMILES: N#Cc1cnc2ccc(-c3c(-c4ccc(F)c(Cl)c4)ncn3CCCO)nn12] | 6-(4-(3-chloro-4-fluorophenyl)-1-(3-hydroxypropyl)-1H-imidazol-5-yl)imidazo[1,2-b]pyridazine-3-carbonitrile |
| 39' | 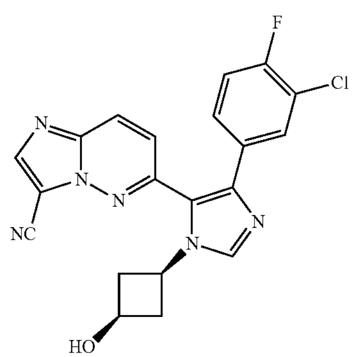 [SMILES: N#Cc1cnc2ccc(-c3c(-c4ccc(F)c(Cl)c4)ncn3[C@H]3C[C@@H](O)C3)nn12] | 6-(4-(3-chloro-4-fluorophenyl)-1-((cis)-3-hydroxycyclobutyl)-1H-imidazol-5-yl)imidazo[1,2-b]pyridazine-3-carbonitrile |
| 40' | 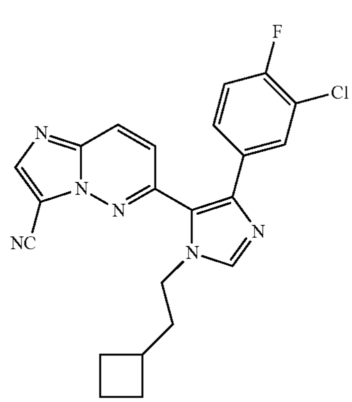 [SMILES: N#Cc1cnc2ccc(-c3c(-c4ccc(F)c(Cl)c4)ncn3CCC3CCC3)nn12] | 6-(4-(3-chloro-4-fluorophenyl)-1-(2-cyclobutylethyl)-1H-imidazol-5-yl)imidazo[1,2-b]pyridazine-3-carbonitrile |

TABLE A-continued

| No. | Structure | Name |
|---|---|---|
| 41' | 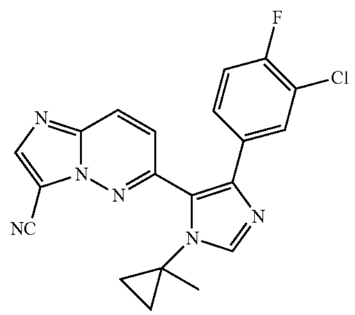 [SMILES: CC1(n2cnc(-c3ccc(F)c(Cl)c3)c2-c2ccc3ncc(C#N)n3n2)CC1] | 6-(4-(3-chloro-4-fluorophenyl)-1-(1-methylcyclopropyl)-1H-imidazol-5-yl)imidazo[1,2-b]pyridazine-3-carbonitrile |
| 42' | 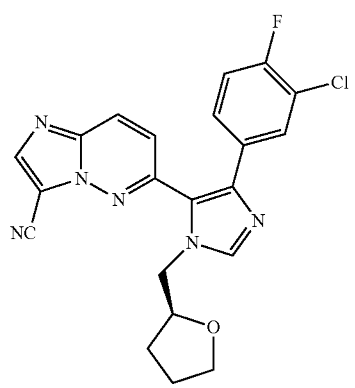 [SMILES: N#Cc1cnc2ccc(-c3c(-c4ccc(F)c(Cl)c4)ncn3C[C@@H]3CCCO3)nn12] | (S)-6-(4-(3-chloro-4-fluorophenyl)-1-((tetrahydrofuran-2-yl)methyl)-1H-imidazol-5-yl)imidazo[1,2-b]pyridazine-3-carbonitrile |
| 43' | 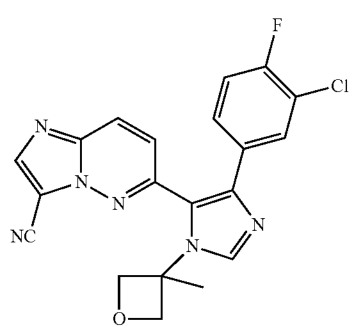 [SMILES: CC1(n2cnc(-c3ccc(F)c(Cl)c3)c2-c2ccc3ncc(C#N)n3n2)COC1] | 6-(4-(3-chloro-4-fluorophenyl)-1-(3-methyloxetan-3-yl)-1H-imidazol-5-yl)imidazo[1,2-b]pyridazine-3-carbonitrile |
| 44' | 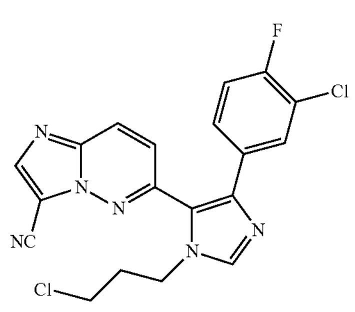 [SMILES: N#Cc1cnc2ccc(-c3c(-c4ccc(F)c(Cl)c4)ncn3CCCCl)nn12] | 6-(4-(3-chloro-4-fluorophenyl)-1-(3-chloropropyl)-1H-imidazol-5-yl)imidazo[1,2-b]pyridazine-3-carbonitrile |

TABLE A-continued

| No. | Structure | Name |
| --- | --- | --- |
| 45' | 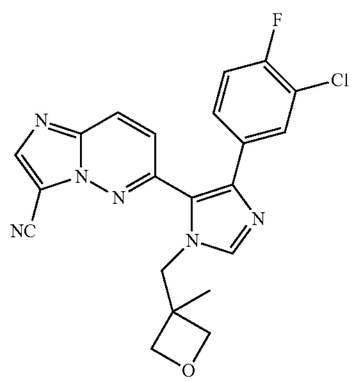 [SMILES: CC1(Cn2cnc(-c3ccc(F)c(Cl)c3)c2-c2ccc3ncc(C#N)n3n2)COC1] | 6-(4-(3-chloro-4-fluorophenyl)-1-((3-methyloxetan-3-yl)methyl)-1H-imidazol-5-yl)imidazo[1,2-b]pyridazine-3-carbonitrile |
| 46' | 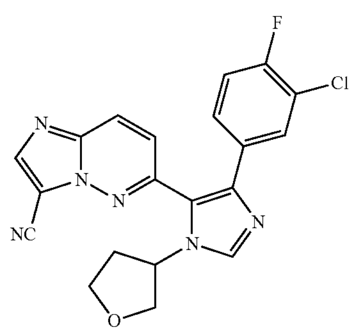 [SMILES: N#Cc1cnc2ccc(-c3c(-c4ccc(F)c(Cl)c4)ncn3C3CCOC3)nn12] | 6-(4-(3-chloro-4-fluorophenyl)-1-(tetrahydrofuran-3-yl)-1H-imidazol-5-yl)imidazo[1,2-b]pyridazine-3-carbonitrile |
| 47' | 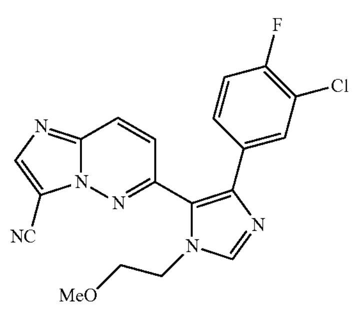 [SMILES: COCCn1cnc(-c2ccc(F)c(Cl)c2)c1-c1ccc2ncc(C#N)n2n1] | 6-(4-(3-chloro-4-fluorophenyl)-1-(2-methoxyethyl)-1H-imidazol-5-yl)imidazo[1,2-b]pyridazine-3-carbonitrile |
| 48' | 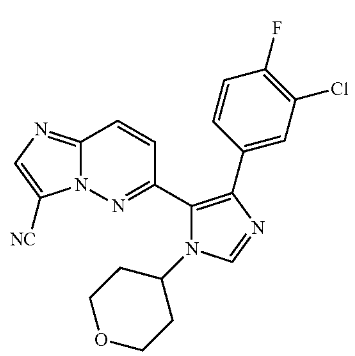 [SMILES: N#Cc1cnc2ccc(-c3c(-c4ccc(F)c(Cl)c4)ncn3C3CCOCC3)nn12] | 6-(4-(3-chloro-4-fluorophenyl)-1-(tetrahydro-2H-pyran-4-yl)-1H-imidazol-5-yl)imidazo[1,2-b]pyridazine-3-carbonitrile |

TABLE A-continued

| No. | Structure | Name |
|---|---|---|
| 49' | 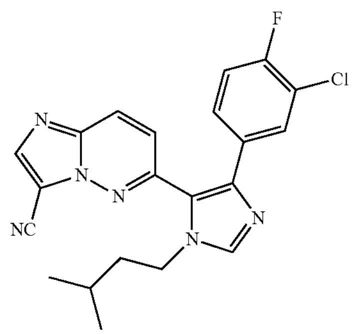 [SMILES: CC(C)CCn1cnc(-c2ccc(F)c(Cl)c2)c1-c1ccc2ncc(C#N)n2n1] | 6-(4-(3-chloro-4-fluorophenyl)-1-isopentyl-1H-imidazol-5-yl)imidazo[1,2-b]pyridazine-3-carbonitrile |
| 50' | 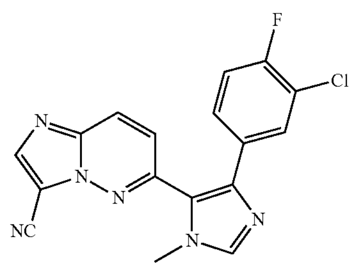 [SMILES: Cn1cnc(-c2ccc(F)c(Cl)c2)c1-c1ccc2ncc(C#N)n2n1] | 6-(4-(3-chloro-4-fluorophenyl)-1-methyl-1H-imidazol-5-yl)imidazo[1,2-b]pyridazine-3-carbonitrile |
| 51' | 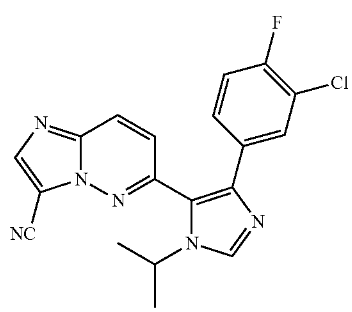 [SMILES: CC(C)n1cnc(-c2ccc(F)c(Cl)c2)c1-c1ccc2ncc(C#N)n2n1] | 6-(4-(3-chloro-4-fluorophenyl)-1-isopropyl-1H-imidazol-5-yl)imidazo[1,2-b]pyridazine-3-carbonitrile |
| 52' | 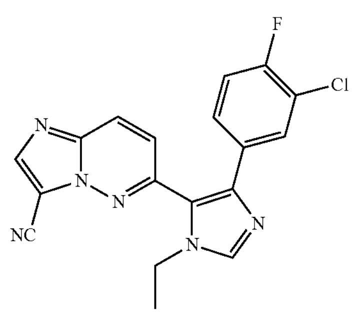 [SMILES: CCn1cnc(-c2ccc(F)c(Cl)c2)c1-c1ccc2ncc(C#N)n2n1] | 6-(4-(3-chloro-4-fluorophenyl)-1-ethyl-1H-imidazol-5-yl)imidazo[1,2-b]pyridazine-3-carbonitrile |
| 53' | 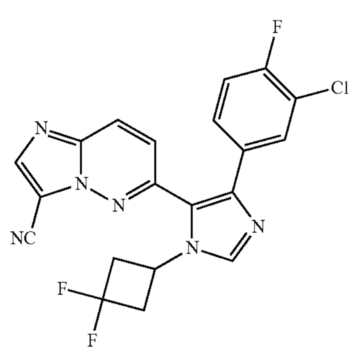 [SMILES: N#Cc1cnc2ccc(-c3c(-c4ccc(F)c(Cl)c4)ncn3C3CC(F)(F)C3)nn12] | 6-(4-(3-chloro-4-fluorophenyl)-1-(3,3-difluorocyclobutyl)-1H-imidazol-5-yl)imidazo[1,2-b]pyridazine-3-carbonitrile |

TABLE A-continued

| No. | Structure | Name |
|---|---|---|
| 54' | 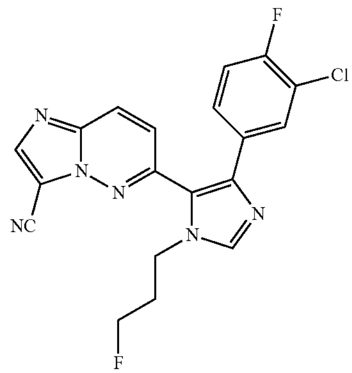 [SMILES: N#Cc1cnc2ccc(-c3c(-c4ccc(F)c(Cl)c4)ncn3CCCF)nn12] | 6-(4-(3-chloro-4-fluorophenyl)-1-(3-fluoropropyl)-1H-imidazol-5-yl)imidazo[1,2-b]pyridazine-3-carbonitrile |
| 55' | 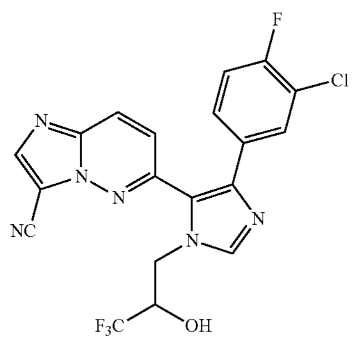 [SMILES: N#Cc1cnc2ccc(-c3c(-c4ccc(F)c(Cl)c4)ncn3CC(O)C(F)(F)F)nn12] | 6-(4-(3-chloro-4-fluorophenyl)-1-(3,3,3-trifluoro-2-hydroxypropyl)-1H-imidazol-5-yl)imidazo[1,2-b]pyridazine-3-carbonitrile |
| 56' | 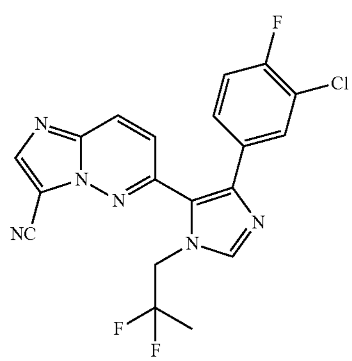 [SMILES: CC(F)(F)Cn1cnc(-c2ccc(F)c(Cl)c2)c1-c1ccc2ncc(C#N)n2n1] | 6-(4-(3-chloro-4-fluorophenyl)-1-(2,2-difluoropropyl)-1H-imidazol-5-yl)imidazo[1,2-b]pyridazine-3-carbonitrile |
| 57' | 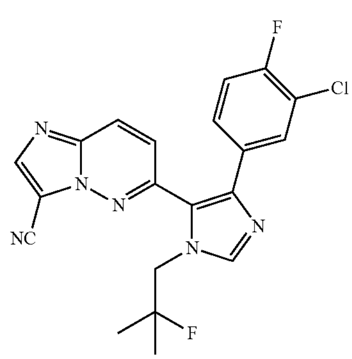 [SMILES: CC(C)(F)Cn1cnc(-c2ccc(F)c(Cl)c2)c1-c1ccc2ncc(C#N)n2n1] | 6-(4-(3-chloro-4-fluorophenyl)-1-(2-fluoro-2-methylpropyl)-1H-imidazol-5-yl)imidazo[1,2-b]pyridazine-3-carbonitrile |

TABLE A-continued

| No. | Structure | Name |
|---|---|---|
| 58' | 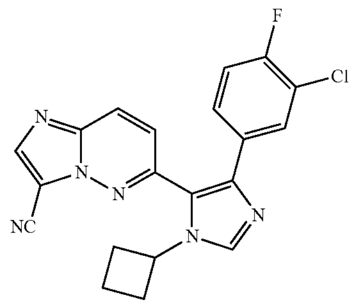 [SMILES: N#Cc1cnc2ccc(-c3c(-c4ccc(F)c(Cl)c4)ncn3C3CCC3)nn12] | 6-(4-(3-chloro-4-fluorophenyl)-1-cyclobutyl-1H-imidazol-5-yl)imidazo[1,2-b]pyridazine-3-carbonitrile |
| 59' | 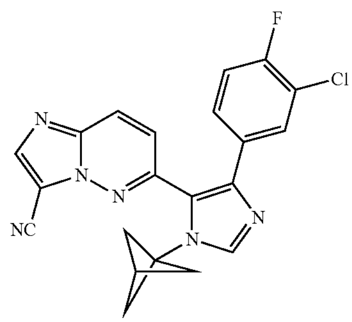 [SMILES: N#Cc1cnc2ccc(-c3c(-c4ccc(F)c(Cl)c4)ncn3C34CC(C3)C4)nn12] | 6-(1-(bicyclo[1.1.1]pentan-1-yl)-4-(3-chloro-4-fluorophenyl)-1H-imidazol-5-yl)imidazo[1,2-b]pyridazine-3-carbonitrile |
| 60' | 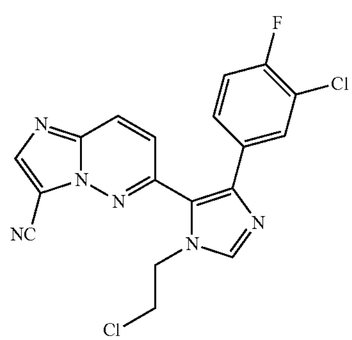 [SMILES: N#Cc1cnc2ccc(-c3c(-c4ccc(F)c(Cl)c4)ncn3CCCl)nn12] | 6-(4-(3-chloro-4-fluorophenyl)-1-(2-chloroethyl)-1H-imidazol-5-yl)imidazo[1,2-b]pyridazine-3-carbonitrile |
| 61' | 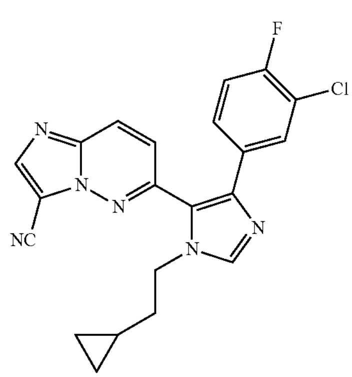 [SMILES: N#Cc1cnc2ccc(-c3c(-c4ccc(F)c(Cl)c4)ncn3CCC3CC3)nn12] | 6-(4-(3-chloro-4-fluorophenyl)-1-(2-cyclopropylethyl)-1H-imidazol-5-yl)imidazo[1,2-b]pyridazine-3-carbonitrile |

TABLE A-continued

| No. | Structure | Name |
|---|---|---|
| 62' | 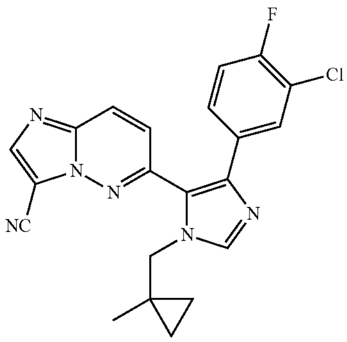 [SMILES: CC1(Cn2cnc(-c3ccc(F)c(Cl)c3)c2-c2ccc3ncc(C#N)n3n2)CC1] | 6-(4-(3-chloro-4-fluorophenyl)-1-((1-methylcyclopropyl)methyl)-1H-imidazol-5-yl)imidazo[1,2-b]pyridazine-3-carbonitrile |
| 63' | 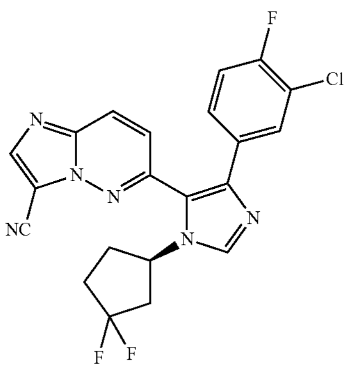 [SMILES: N#Cc1cnc2ccc(-c3c(-c4ccc(F)c(Cl)c4)ncn3[C@@H]3CCC(F)(F)C3)nn12] | (R)-6-(4-(3-chloro-4-fluorophenyl)-1-(3,3-difluorocyclopentyl)-1H-imidazol-5-yl)imidazo[1,2-b]pyridazine-3-carbonitrile |
| 64' | 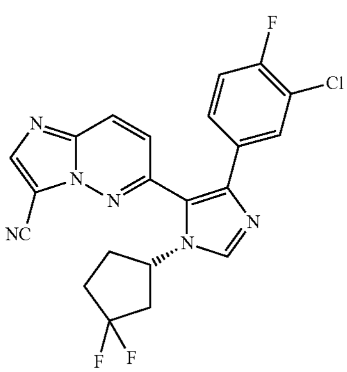 | (S)-6-(4-(3-chloro-4-fluorophenyl)-1-(3,3-difluorocyclopentyl)-1H-imidazol-5-yl)imidazo[1,2-b]pyridazine-3-carbonitrile |
| 65 | 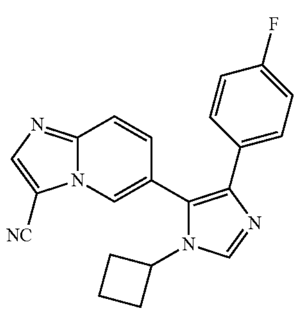 [SMILES: N#Cc1cnc2ccc(-c3c(-c4ccc(F)cc4)ncn3C3CCC3)cn12] | 6-(1-cyclobutyl-4-(4-fluorophenyl)-1H-imidazol-5-yl)imidazo[1,2-a]pyridine-3-carbonitrile |

TABLE A-continued

| No. | Structure | Name |
|---|---|---|
| 66' | 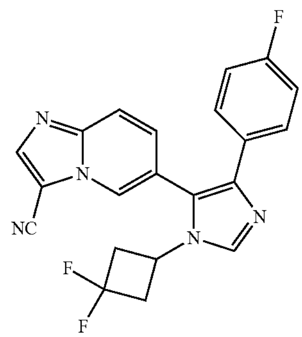 [SMILES: N#Cc1cnc2ccc(-c3c(-c4ccc(F)cc4)ncn3C3CC(F)(F)C3)cn12] | 6-(1-(3,3-difluorocyclobutyl)-4-(4-fluorophenyl)-1H-imidazol-5-yl)imidazo[1,2-a]pyridine-3-carbonitrile |
| 67' | 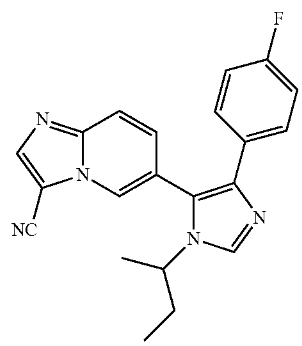 [SMILES: CCC(C)n1cnc(-c2ccc(F)cc2)c1-c1ccc2ncc(C#N)n2c1] | 6-(1-(sec-butyl)-4-(4-fluorophenyl)-1H-imidazol-5-yl)imidazo[1,2-a]pyridine-3-carbonitrile |
| 68' | 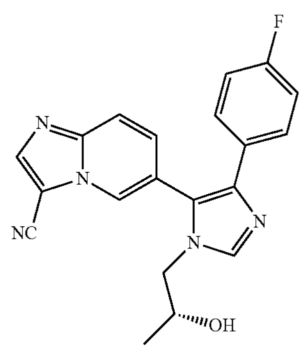 [SMILES: C[C@@H](O)Cn1cnc(-c2ccc(F)cc2)c1-c1ccc2ncc(C#N)n2c1] | (R)-6-(4-(4-fluorophenyl)-1-(2-hydroxypropyl)-1H-imidazol-5-yl)imidazo[1,2-a]pyridine-3-carbonitrile |
| 69' | 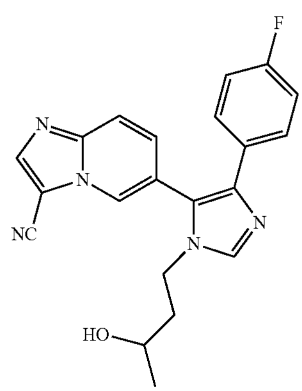 [SMILES: CC(O)CCn1cnc(-c2ccc(F)cc2)c1-c1ccc2ncc(C#N)n2c1] | 6-(4-(4-fluorophenyl)-1-(3-hydroxybutyl)-1H-imidazol-5-yl)imidazo[1,2-a]pyridine-3-carbonitrile |

TABLE A-continued
| No. | Structure | Name |
|---|---|---|
| 70' | 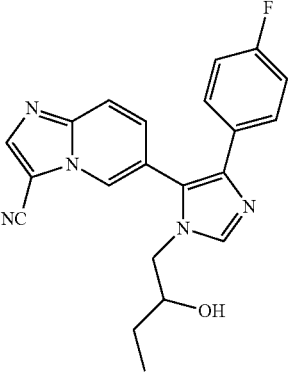 [SMILES: CCC(O)Cn1cnc(-c2ccc(F)cc2)c1-c1ccc2ncc(C#N)n2c1] | 6-(4-(4-fluorophenyl)-1-(2-hydroxybutyl)-1H-imidazol-5-yl)imidazo[1,2-a]pyridine-3-carbonitrile |
| 71' | 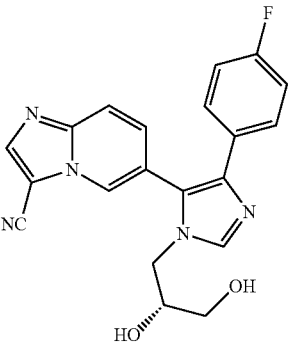 [SMILES: N#Cc1cnc2ccc(-c3c(-c4ccc(F)cc4)ncn3C[C@@H](O)CO)cn12] | (R)-6-(1-(2,3-dihydroxypropyl)-4-(4-fluorophenyl)-1H-imidazol-5-yl)imidazo[1,2-a]pyridine-3-carbonitrile |
| 72' | 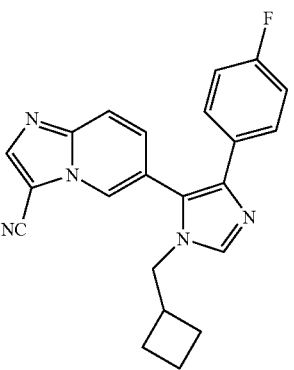 [SMILES: N#Cc1cnc2ccc(-c3c(-c4ccc(F)cc4)ncn3CC3CCC3)cn12] | 6-(1-(cyclobutylmethyl)-4-(4-fluorophenyl)-1H-imidazol-5-yl)imidazo[1,2-a]pyridine-3-carbonitrile |
| 73' | 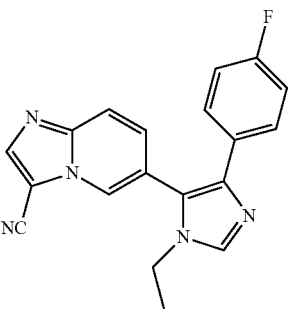 [SMILES: CCn1cnc(-c2ccc(F)cc2)c1-c1ccc2ncc(C#N)n2c1] | 6-(1-ethyl-4-(4-fluorophenyl)-1H-imidazol-5-yl)imidazo[1,2-a]pyridine-3-carbonitrile |

TABLE A-continued

| No. | Structure | Name |
| --- | --- | --- |
| 74' | 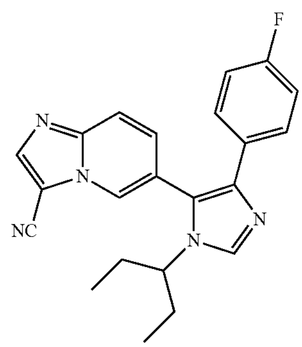 [SMILES: CCC(CC)n1cnc(-c2ccc(F)cc2)c1-c1ccc2ncc(C#N)n2c1] | 6-(4-(4-fluorophenyl)-1-(pentan-3-yl)-1H-imidazol-5-yl)imidazo[1,2-a]pyridine-3-carbonitrile |
| 75' | 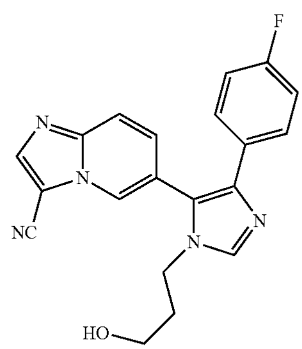 [SMILES: N#Cc1cnc2ccc(-c3c(-c4ccc(F)cc4)ncn3CCCO)cn12] | 6-(4-(4-fluorophenyl)-1-(3-hydroxypropyl)-1H-imidazol-5-yl)imidazo[1,2-a]pyridine-3-carbonitrile |
| 76' | 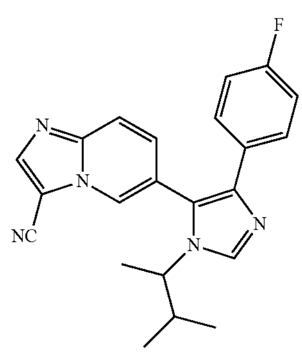 [SMILES: CC(C)C(C)n1cnc(-c2ccc(F)cc2)c1-c1ccc2ncc(C#N)n2c1] | 6-(4-(4-fluorophenyl)-1-(3-methylbutan-2-yl)-1H-imidazol-5-yl)imidazo[1,2-a]pyridine-3-carbonitrile |
| 77' | 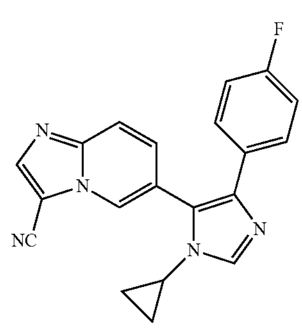 [SMILES: N#Cc1cnc2ccc(-c3c(-c4ccc(F)cc4)ncn3C3CC3)cn12] | 6-(1-cyclopropyl-4-(4-fluorophenyl)-1H-imidazol-5-yl)imidazo[1,2-a]pyridine-3-carbonitrile |

TABLE A-continued

| No. | Structure | Name |
|---|---|---|
| 78' | 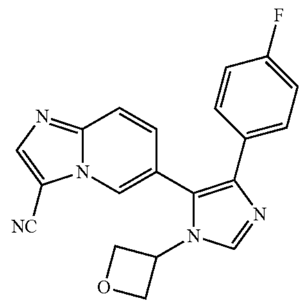 | 6-(4-(4-fluorophenyl)-1-(oxetan-3-yl)-1H-imidazol-5-yl)imidazo[1,2-a]pyridine-3-carbonitrile |
| 79' | 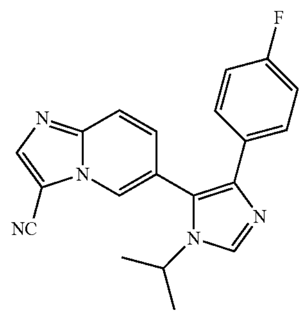 [SMILES: CC(C)n1cnc(-c2ccc(F)cc2)c1-c1ccc2ncc(C#N)n2c1] | 6-(4-(4-fluorophenyl)-1-isopropyl-1H-imidazol-5-yl)imidazo[1,2-a]pyridine-3-carbonitrile |
| 80' | 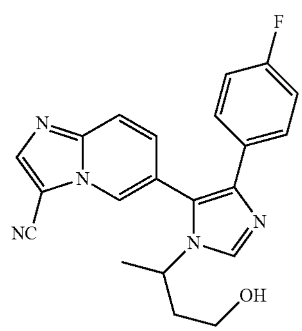 [SMILES: CC(CCO)n1cnc(-c2ccc(F)cc2)c1-c1ccc2ncc(C#N)n2c1] | 6-(4-(4-fluorophenyl)-1-(4-hydroxybutan-2-yl)-1H-imidazol-5-yl)imidazo[1,2-a]pyridine-3-carbonitrile |
| 81' | 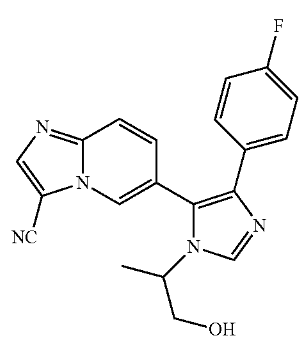 [SMILES: CC(CO)n1cnc(-c2ccc(F)cc2)c1-c1ccc2ncc(C#N)n2c1] | 6-(4-(4-fluorophenyl)-1-(1-hydroxypropan-2-yl)-1H-imidazol-5-yl)imidazo[1,2-a]pyridine-3-carbonitrile |

TABLE A-continued
| No. | Structure | Name |
|---|---|---|
| 82' | 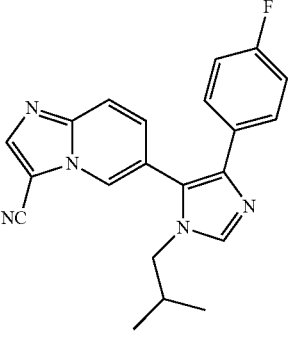 [SMILES: CC(C)Cn1cnc(-c2ccc(F)cc2)c1-c1ccc2ncc(C#N)n2c1] | 6-(4-(4-fluorophenyl)-1-isobutyl-1H-imidazol-5-yl)imidazo[1,2-a]pyridine-3-carbonitrile |
| 83' | 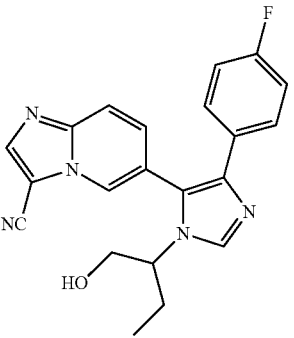 [SMILES: CCC(CO)n1cnc(-c2ccc(F)cc2)c1-c1ccc2ncc(C#N)n2c1] | 6-(4-(4-fluorophenyl)-1-(1-hydroxybutan-2-yl)-1H-imidazol-5-yl)imidazo[1,2-a]pyridine-3-carbonitrile |
| 84' | 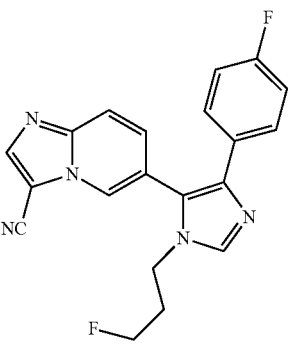 [SMILES: N#Cc1cnc2ccc(-c3c(-c4ccc(F)cc4)ncn3CCCF)cn12] | 6-(4-(4-fluorophenyl)-1-(3-fluoropropyl)-1H-imidazol-5-yl)imidazo[1,2-a]pyridine-3-carbonitrile |
| 85' | 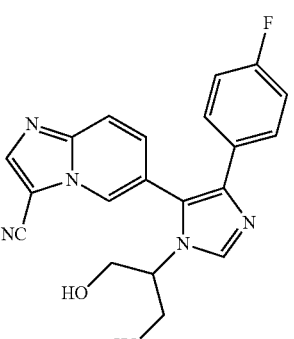 | 6-(1-(1,3-dihydroxypropan-2-yl)-4-(4-fluorophenyl)-1H-imidazol-5-yl)imidazo[1,2-a]pyridine-3-carbonitrile |

TABLE A-continued

| No. | Structure | Name |
|---|---|---|
| 86' | 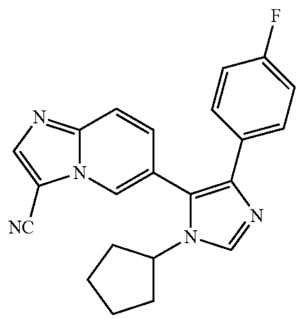 [SMILES: N#Cc1cnc2ccc(-c3c(-c4ccc(F)cc4)ncn3C3CCCC3)cn12] | 6-(1-cyclopentyl-4-(4-fluorophenyl)-1H-imidazol-5-yl)imidazo[1,2-a]pyridine-3-carbonitrile |
| 87' | 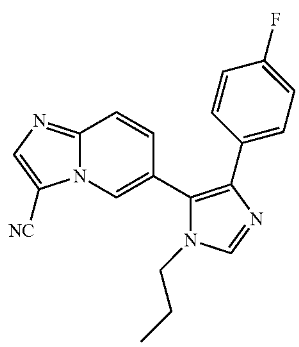 [SMILES: CCCn1cnc(-c2ccc(F)cc2)c1-c1ccc2ncc(C#N)n2c1] | 6-(4-(4-fluorophenyl)-1-propyl-1H-imidazol-5-yl)imidazo[1,2-a]pyridine-3-carbonitrile |
| 88' | 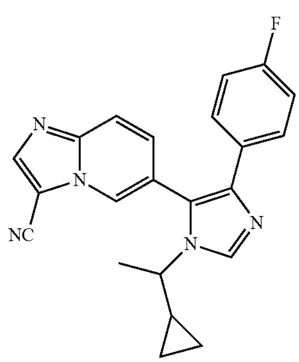 [SMILES: CC(C1CC1)n1cnc(-c2ccc(F)cc2)c1-c1ccc2ncc(C#N)n2c1] | 6-(1-(1-cyclopropylethyl)-4-(4-fluorophenyl)-1H-imidazol-5-yl)imidazo[1,2-a]pyridine-3-carbonitrile |
| 89' | 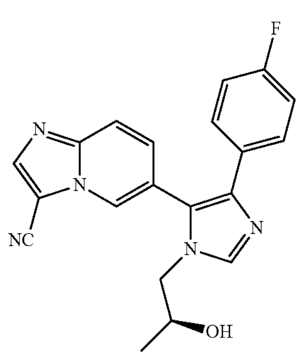 [SMILES: C[C@H](O)Cn1cnc(-c2ccc(F)cc2)c1-c1ccc2ncc(C#N)n2c1] | (S)-6-(4-(4-fluorophenyl)-1-(2-hydroxypropyl)-1H-imidazol-5-yl)imidazo[1,2-a]pyridine-3-carbonitrile |

TABLE A-continued

| No. | Structure | Name |
|---|---|---|
| 90' | 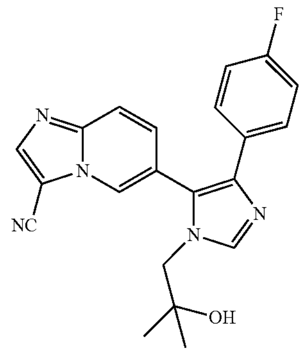 [SMILES: CC(C)(O)Cn1cnc(-c2ccc(F)cc2)c1-c1ccc2ncc(C#N)n2c1] | 6-(4-(4-fluorophenyl)-1-(2-hydroxy-2-methylpropyl)-1H-imidazol-5-yl)imidazo[1,2-a]pyridine-3-carbonitrile |
| 91' | 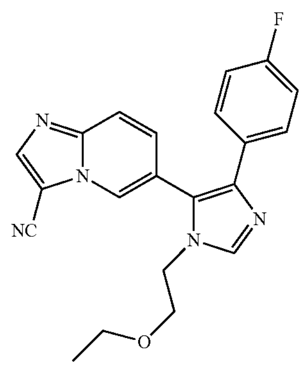 [SMILES: CCOCCn1cnc(-c2ccc(F)cc2)c1-c1ccc2ncc(C#N)n2c1] | 6-(1-(2-ethoxyethyl)-4-(4-fluorophenyl)-1H-imidazol-5-yl)imidazo[1,2-a]pyridine-3-carbonitrile |
| 92' | 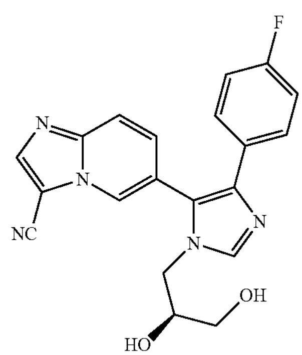 [SMILES: N#Cc1cnc2ccc(-c3c(-c4ccc(F)cc4)ncn3C[C@H](O)CO)cn12] | (S)-6-(1-(2,3-dihydroxypropyl)-4-(4-fluorophenyl)-1H-imidazol-5-yl)imidazo[1,2-a]pyridine-3-carbonitrile |
| 93' | 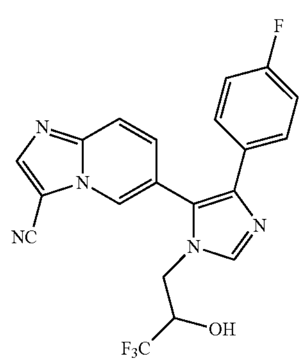 [SMILES: N#Cc1cnc2ccc(-c3c(-c4ccc(F)cc4)ncn3CC(O)C(F)(F)F)cn12] | 6-(4-(4-fluorophenyl)-1-(3,3,3-trifluoro-2-hydroxypropyl)-1H-imidazol-5-yl)imidazo[1,2-a]pyridine-3-carbonitrile |

US 11,352,360 B2

TABLE A-continued

| No. | Structure | Name |
|---|---|---|
| 94' | 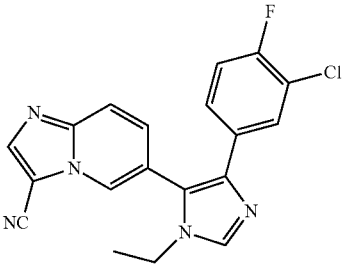 [SMILES: CCn1cnc(-c2ccc(F)c(Cl)c2)c1-c1ccc2ncc(C#N)n2c1] | 6-(4-(3-chloro-4-fluorophenyl)-1-ethyl-1H-imidazol-5-yl)imidazo[1,2-a]pyridine-3-carbonitrile |
| 95' | 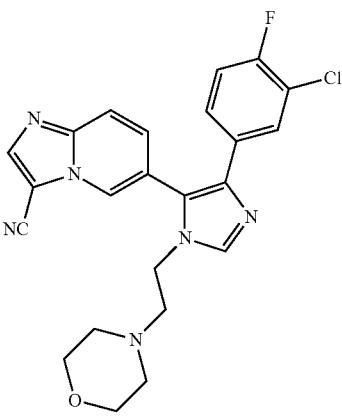 [SMILES: N#Cc1cnc2ccc(-c3c(-c4ccc(F)c(Cl)c4)ncn3CCN3CCOCC3)cn12] | 6-(4-(3-chloro-4-fluorophenyl)-2-(2-morpholinoethyl)-1H-imidazol-5-yl)imidazo[1,2-a]pyridine-3-carbonitrile |
| 96' | 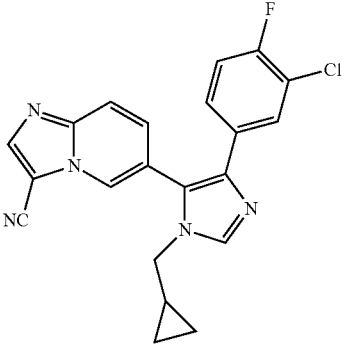 [SMILES: N#Cc1cnc2ccc(-c3c(-c4ccc(F)c(Cl)c4)ncn3CC3CC3)cn12] | 6-(4-(3-chloro-4-fluorophenyl)-1-(cyclopropylmethyl)-1H-imidazol-5-yl)imidazo[1,2-a]pyridine-3-carbonitrile |
| 97' | 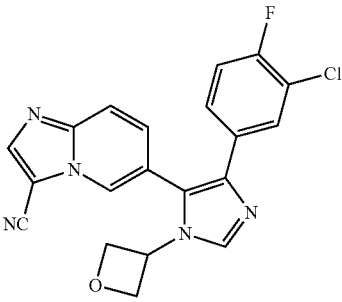 [SMILES: N#Cc1cnc2ccc(-c3c(-c4ccc(F)c(Cl)c4)ncn3C3COC3)cn12] | 6-(4-(3-chloro-4-fluorophenyl)-1-(oxetan-3-yl)-1H-imidazol-5-yl)imidazo[1,2-a]pyridine-3-carbonitrile |
| 98' | 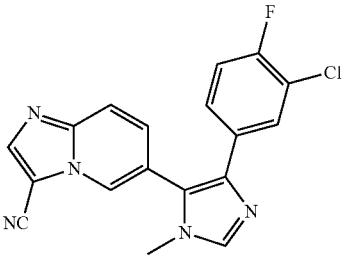 [SMILES: Cn1cnc(-c2ccc(F)c(Cl)c2)c1-c1ccc2ncc(C#N)n2c1] | 6-(4-(3-chloro-4-fluorophenyl)-1-methyl-1H-imidazol-5-yl)imidazo[1,2-a]pyridine-3-carbonitrile |

TABLE A-continued

| No. | Structure | Name |
|---|---|---|
| 99' | 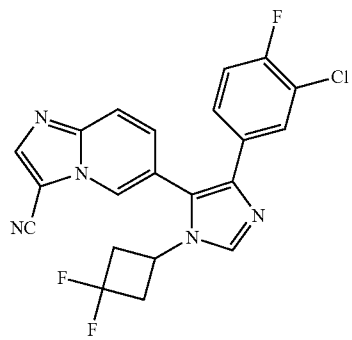 [SMILES: N#Cc1cnc2ccc(-c3c(-c4ccc(F)c(Cl)c4)ncn3C3CC(F)(F)C3)cn12] | 6-(4-(3-chloro-4-fluorophenyl)-1-(3,3-difluorocyclobutyl)-1H-imidazol-5-yl)imidazo[1,2-a]pyridine-3-carbonitrile |
| 100' | 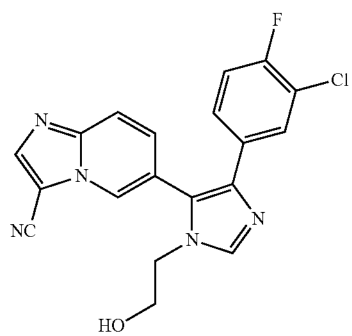 [SMILES: N#Cc1cnc2ccc(-c3c(-c4ccc(F)c(Cl)c4)ncn3CCO)cn12] | 6-(4-(3-chloro-4-fluorophenyl)-1-(2-hydroxyethyl)-1H-imidazol-5-yl)imidazo[1,2-a]pyridine-3-carbonitrile |
| 101' | 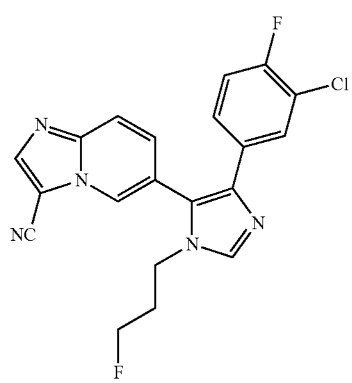 [SMILES: N#Cc1cnc2ccc(-c3c(-c4ccc(F)c(Cl)c4)ncn3CCCF)cn12] | 6-(4-(3-chloro-4-fluorophenyl)-1-(3-fluoropropyl)-1H-imidazol-5-yl)imidazo[1,2-a]pyridine-3-carbonitrile |
| 102 | 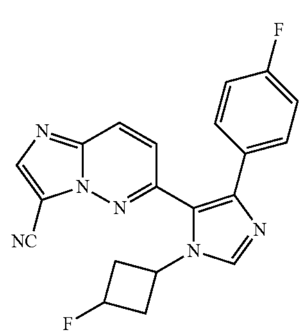 [SMILES: N#Cc1cnc2ccc(-c3c(-c4ccc(F)cc4)ncn3C3CC(F)C3)nn12] | 6-(1-(3-fluorocyclobutyl)-4-(4-fluorophenyl)-1H-imidazol-5-yl)imidazo[1,2-b]pyridazine-3-carbonitrile |

TABLE A-continued

| No. | Structure | Name |
|---|---|---|
| 103' | 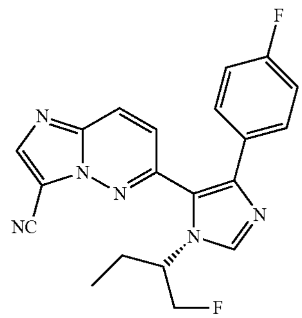 | (S)-6-(1-(1-fluorobutan-2-yl)-4-(4-fluorophenyl)-1H-imidazol-5-yl)imidazo[1,2-b]pyridazine-3-carbonitrile |
| 104' | 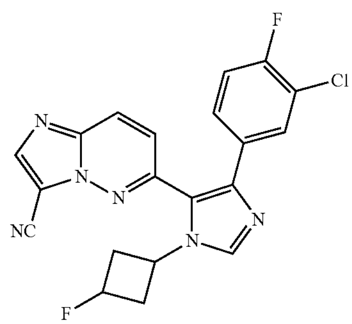 [SMILES: N#Cc1cnc2ccc(-c3c(-c4ccc(F)c(Cl)c4)ncn3C3CC(F)C3)nn12] | 6-(4-(3-chloro-4-fluorophenyl)-1-(3-fluorocyclobutyl)-1H-imidazol-5-yl)imidazo[1,2-b]pyridazine-3-carbonitrile |
| 105 | 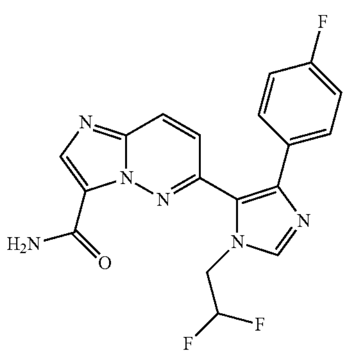 [SMILES: NC(=O)c1cnc2ccc(-c3c(-c4ccc(F)cc4)ncn3CC(F)F)nn12] | 6-(1-(2,2-difluoroethyl)-4-(4-fluorophenyl)-1H-imidazol-5-yl)imidazo[1,2-b]pyridazine-3-carboxamide |
| 106' | 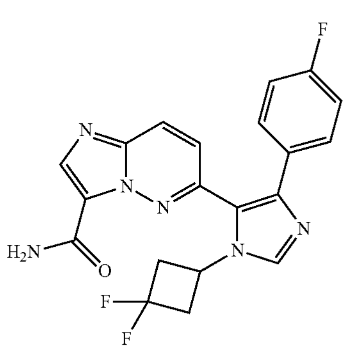 [SMILES: NC(=O)c1cnc2ccc(-c3c(-c4ccc(F)cc4)ncn3C3CC(F)(F)C3)nn12] | 6-(1-(3,3-difluorocyclobutyl)-4-(4-fluorophenyl)-1H-imidazol-5-yl)imidazo[1,2-b]pyridazine-3-carboxamide |

TABLE A-continued

| No. | Structure | Name |
|---|---|---|
| 107' | 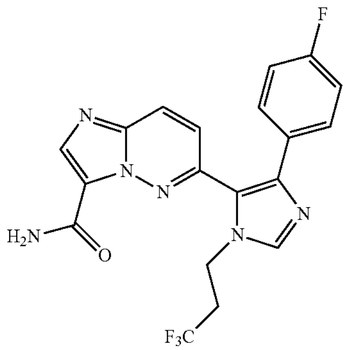 [SMILES: NC(=O)c1cnc2ccc(-c3c(-c4ccc(F)cc4)ncn3CCC(F)(F)F)nn12] | 6-(4-(4-fluorophenyl)-1-(3,3,3-trifluoropropyl)-1H-imidazol-5-yl)imidazo[1,2-b]pyridazine-3-carboxamide |
| 108' | 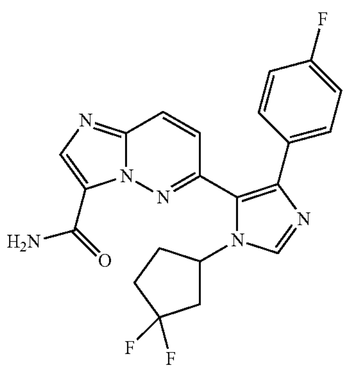 [SMILES: NC(=O)c1cnc2ccc(-c3c(-c4ccc(F)cc4)ncn3C3CCC(F)(F)C3)nn12] | 6-(1-(3,3-difluorocyclopentyl)-4-(4-fluorophenyl)-1H-imidazol-5-yl)imidazo[1,2-b]pyridazine-3-carboxamide |
| 109' | 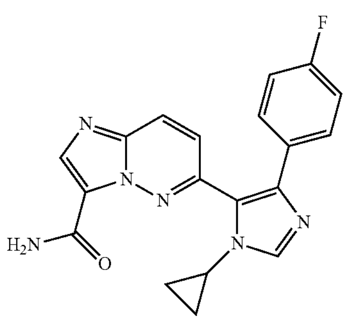 [SMILES: NC(=O)c1cnc2ccc(-c3c(-c4ccc(F)cc4)ncn3C3CC3)nn12] | 6-(1-cyclopropyl-4-(4-fluorophenyl)-1H-imidazol-5-yl)imidazo[1,2-b]pyridazine-3-carboxamide |
| 110' | 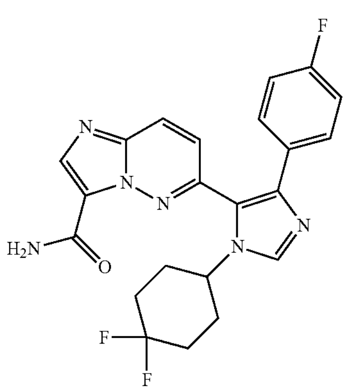 [SMILES: NC(=O)c1cnc2ccc(-c3c(-c4ccc(F)cc4)ncn3C3CCC(F)(F)CC3)nn12] | 6-(1-(4,4-difluorocyclohexyl)-4-(4-fluorophenyl)-1H-imidazol-5-yl)imidazo[1,2-b]pyridazine-3-carboxamide |

TABLE A-continued

| No. | Structure | Name |
|---|---|---|
| 111' | 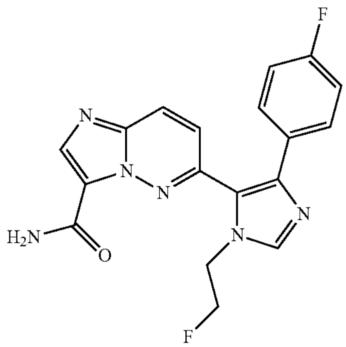 [SMILES: NC(=O)c1cnc2ccc(-c3c(-c4ccc(F)cc4)ncn3CCF)nn12] | 6-(1-(2-fluoroethyl)-4-(4-fluorophenyl)-1H-imidazol-5-yl)imidazo[1,2-b]pyridazine-3-carboxamide |
| 112' | 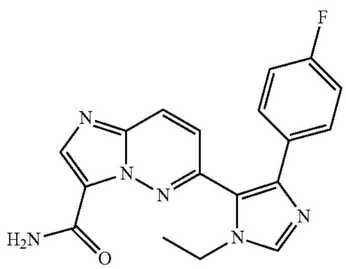 [SMILES: CCn1cnc(-c2ccc(F)cc2)c1-c1ccc2ncc(C(N)=O)n2n1] | 6-(1-ethyl-4-(4-fluorophenyl)-1H-imidazol-5-yl)imidazo[1,2-b]pyridazine-3-carboxamide |
| 113' | 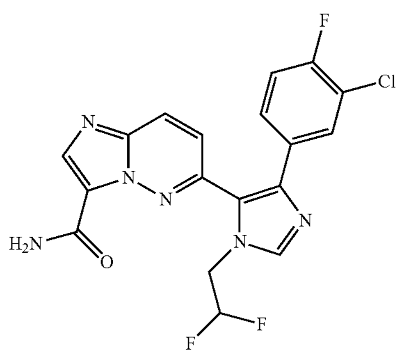 [SMILES: NC(=O)c1cnc2ccc(-c3c(-c4ccc(F)c(Cl)c4)ncn3CC(F)F)nn12] | 6-(4-(3-chloro-4-fluorophenyl)-1-(2,2-difluoroethyl)-1H-imidazol-5-yl)imidazo[1,2-b]pyridazine-3-carboxamide |
| 114' | 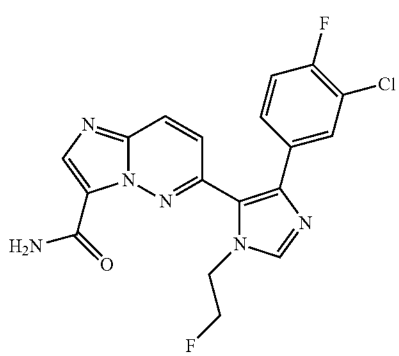 [SMILES: NC(=O)c1cnc2ccc(-c3c(-c4ccc(F)c(Cl)c4)ncn3CCF)nn12] | 6-(4-(3-chloro-4-fluorophenyl)-1-(2-fluoroethyl)-1H-imidazol-5-yl)imidazo[1,2-b]pyridazine-3-carboxamide |

TABLE A-continued

| No. | Structure | Name |
|---|---|---|
| 115' | 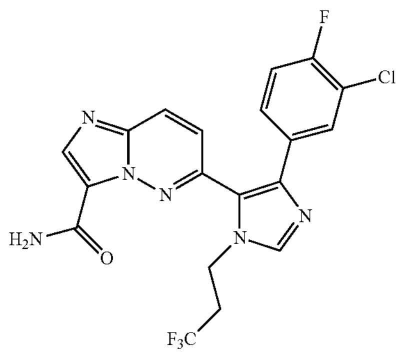 [SMILES: NC(=O)c1cnc2ccc(-c3c(-c4ccc(F)c(Cl)c4)ncn3CCC(F)(F)F)nn12] | 6-(4-(3-chloro-4-fluorophenyl)-1-(3,3,3-trifluoropropyl)-1H-imidazol-5-yl)imidazo[1,2-b]pyridazine-3-carboxamide |
| 116' | 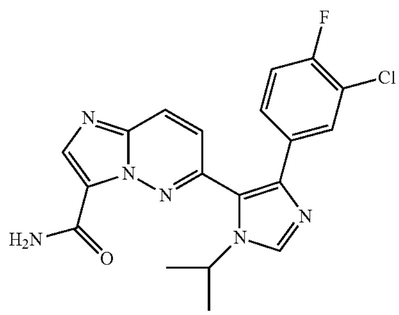 [SMILES: CC(C)n1cnc(-c2ccc(F)c(Cl)c2)c1-c1ccc2ncc(C(N)=O)n2n1] | 6-(4-(3-chloro-4-fluorophenyl)-1-isopropyl-1H-imidazol-5-yl)imidazo[1,2-b]pyridazine-3-carboxamide |
| 117' | 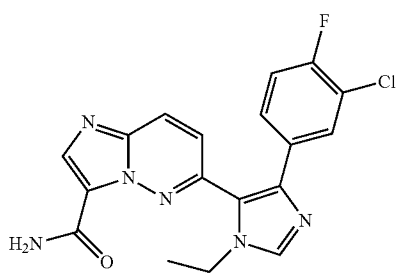 [SMILES: CCn1cnc(-c2ccc(F)c(Cl)c2)c1-c1ccc2ncc(C(N)=O)n2n1] | 6-(4-(3-chloro-4-fluorophenyl)-1-ethyl-1H-imidazol-5-yl)imidazo[1,2-b]pyridazine-3-carboxamide |
| 118' | 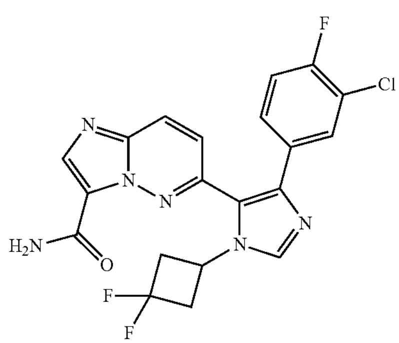 [SMILES: NC(=O)c1cnc2ccc(-c3c(-c4ccc(F)c(Cl)c4)ncn3C3CC(F)(F)C3)nn12] | 6-(4-(3-chloro-4-fluorophenyl)-1-(3,3-difluorocyclobutyl)-1H-imidazol-5-yl)imidazo[1,2-b]pyridazine-3-carboxamide |
| 119' | 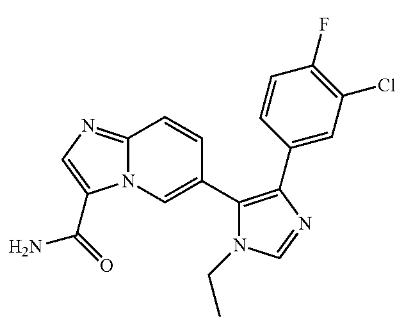 [SMILES: CCn1cnc(-c2ccc(F)c(Cl)c2)c1-c1ccc2ncc(C(N)=O)n2c1] | 6-(4-(3-chloro-4-fluorophenyl)-1-ethyl-1H-imidazol-5-yl)imidazo[1,2-a]pyridine-3-carboxamide |

TABLE A-continued

| No. | Structure | Name |
|---|---|---|
| 120' | 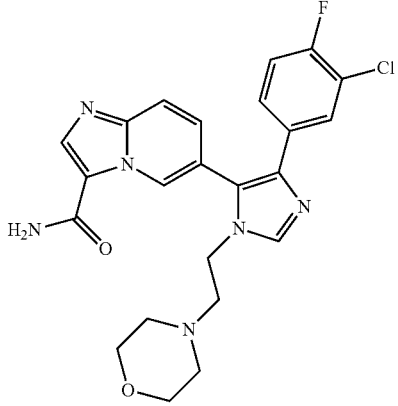 [SMILES: NC(=O)c1cnc2ccc(-c3c(-c4ccc(F)c(Cl)c4)ncn3CCN3CCOCC3)cn12] | 6-(4-(3-chloro-4-fluorophenyl)-1-(2-morpholinoethyl)-1H-imidazol-5-yl)imidazo[1,2-a]pyridine-3-carboxamide |
| 121' | 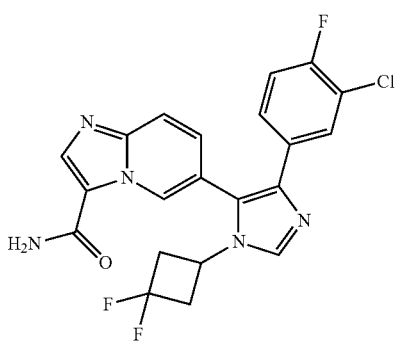 [SMILES: NC(=O)c1cnc2ccc(-c3c(-c4ccc(F)c(Cl)c4)ncn3C3CC(F)(F)C3)cn12] | 6-(4-(3-chloro-4-fluorophenyl)-1-(3,3-difluorocyclobutyl)-1H-imidazol-5-yl)imidazo[1,2-a]pyridine-3-carboxamide |
| 122' | 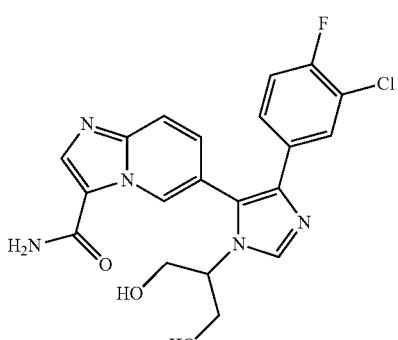 | 6-(4-(3-chloro-4-fluorophenyl)-1-(1,3-dihydroxypropan-2-yl)-1H-imidazol-5-yl)imidazo[1,2-a]pyridine-3-carboxamide |
| 123' | 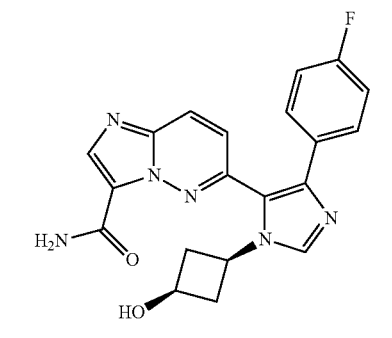 [SMILES: NC(=O)c1cnc2ccc(-c3c(-c4ccc(F)cc4)ncn3[C@H]3C[C@@H](O)C3)nn12] | 6-(4-(4-fluorophenyl)-1-cis-3-hydroxy-cyclobutyl)-1H-imidazol-5-yl)imidazo[1,2-b]pyridazine-3-carboxamide |

TABLE A-continued

| No. | Structure | Name |
|---|---|---|
| 124' | 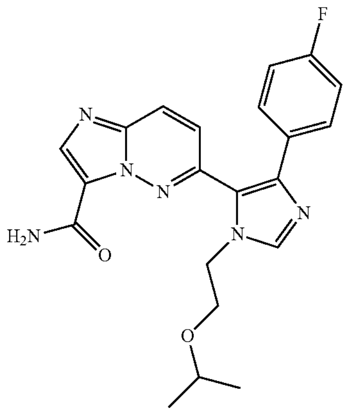 [SMILES: CC(C)OCCn1cnc(-c2ccc(F)cc2)c1-c1ccc2ncc(C(N)=O)n2n1] | 6-(4-(4-fluorophenyl)-1-(2-isopropoxy-ethyl)-1H-imidazol-5-yl)imidazo[1,2-b]pyridazine-3-carboxamide |
| 125' | 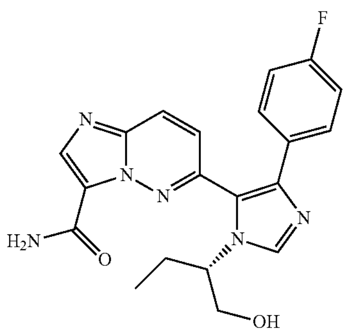 [SMILES: CC[C@@H](CO)n1cnc(-c2ccc(F)cc2)c1-c1ccc2ncc(C(N)=O)n2n1] | (S)-6-(4-(4-fluorophenyl)-1-(1-hydroxy-butan-2-yl)-1H-imidazol-5-yl)imidazo[1,2-b]pyridazine-3-carboxamide |
| 126' | 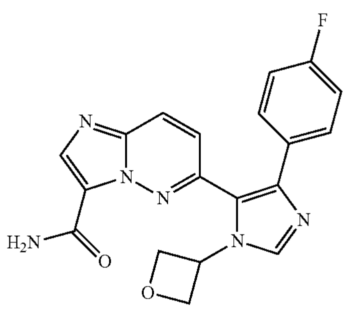 | 6-(4-(4-fluorophenyl)-1-(oxetan-3-yl)-1H-imidazol-5-yl)imidazo[1,2-b]pyridazine-3-carboxamide |
| 127' | 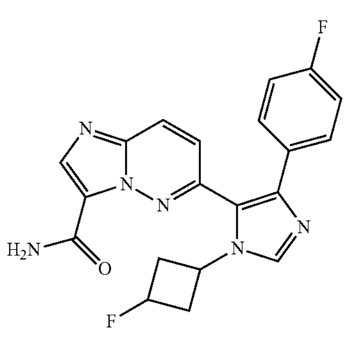 [SMILES: NC(=O)c1cnc2ccc(-c3c(-c4ccc(F)cc4)ncn3C3CC(F)C3)nn12] | 6-(1-(3-fluorocyclobutyl)-4-(4-fluorophenyl)-1H-imidazol-5-yl)imidazo[1,2-b]pyridazine-3-carboxamide |

TABLE A-continued

| No. | Structure | Name |
|---|---|---|
| 128' | 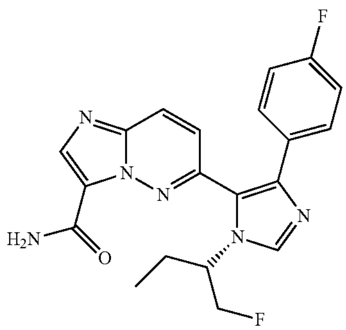 | (S)-6-(1-(1-fluorobutan-2-yl)-4-(4-fluorophenyl)-1H-imidazol-5-yl)imidazo[1,2-b]pyridazine-3-carboxamide |
| 129' | 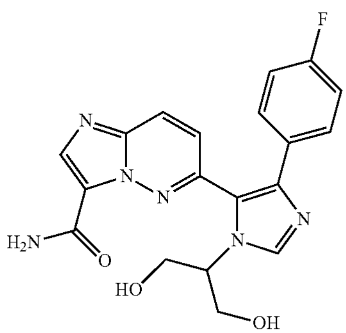 [SMILES: NC(=O)c1cnc2ccc(-c3c(-c4ccc(F)cc4)ncn3C(CO)CO)nn12] | 6-(1-(1,3-dihydroxypropan-2-yl)-4-(4-fluorophenyl)-1H-imidazol-5-yl)imidazo[1,2-b]pyridazine-3-carboxamide |
| 130' | 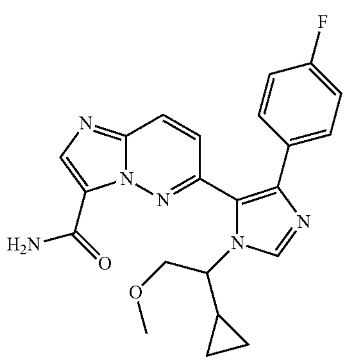 [SMILES: COCC(C1CC1)n1cnc(-c2ccc(F)cc2)c1-c1ccc2ncc(C(N)=O)n2n1] | 6-(1-(1-cyclopropyl-2-methoxyethyl)-4-(4-fluorophenyl)-1H-imidazol-5-yl)imidazo[1,2-b]pyridazine-3-carboxamide |
| 131' | 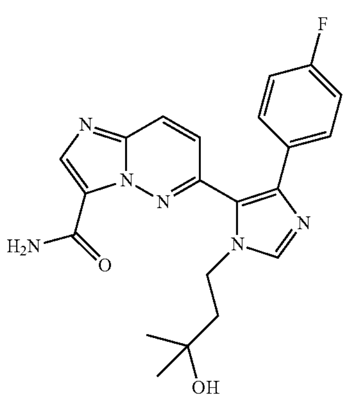 [SMILES: CC(C)(O)CCn1cnc(-c2ccc(F)cc2)c1-c1ccc2ncc(C(N)=O)n2n1] | 6-(4-(4-fluorophenyl)-1-(3-hydroxy-3-methylbutyl)-1H-imidazol-5-yl)imidazo[1,2-b]pyridazine-3-carboxamide |

TABLE A-continued

| No. | Structure | Name |
|---|---|---|
| 132' | 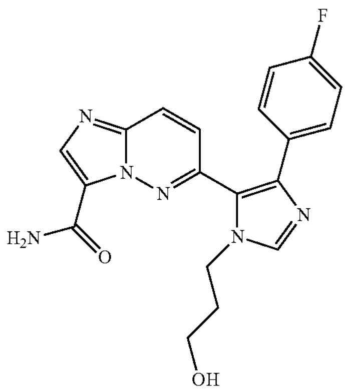 [SMILES: NC(=O)c1cnc2ccc(-c3c(-c4ccc(F)cc4)ncn3CCCO)nn12] | 6-(4-(4-fluorophenyl)-1-(3-hydroxypropyl)-1H-imidazol-5-yl)imidazo[1,2-b]pyridazine-3-carboxamide |
| 133' | 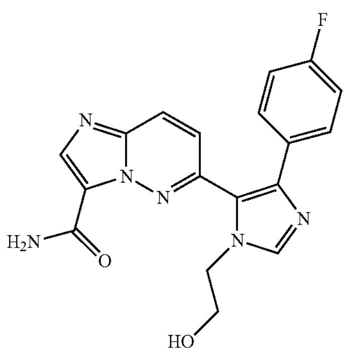 [SMILES: NC(=O)c1cnc2ccc(-c3c(-c4ccc(F)cc4)ncn3CCO)nn12] | 6-(4-(4-fluorophenyl)-1-(2-hydroxyethyl)-1H-imidazol-5-yl)imidazo[1,2-b]pyridazine-3-carboxamide |
| 134' | 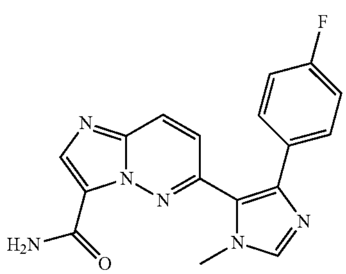 [SMILES: Cn1cnc(-c2ccc(F)cc2)c1-c1ccc2ncc(C(N)=O)n2n1] | 6-(4-(4-fluorophenyl)-1-methyl-1H-imidazol-5-yl)imidazo[1,2-b]pyridazine-3-carboxamide |
| 135' | 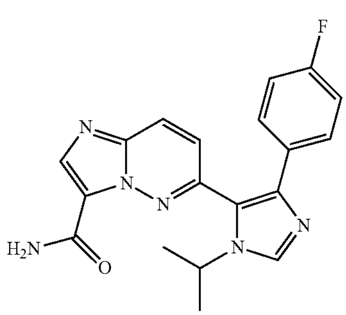 [SMILES: CC(C)n1cnc(-c2ccc(F)cc2)c1-c1ccc2ncc(C(N)=O)n2n1] | 6-(4-(4-fluorophenyl)-1-isopropyl-1H-imidazol-5-yl)imidazo[1,2-b]pyridazine-3-carboxamide |

TABLE A-continued

| No. | Structure | Name |
|---|---|---|
| 136' | 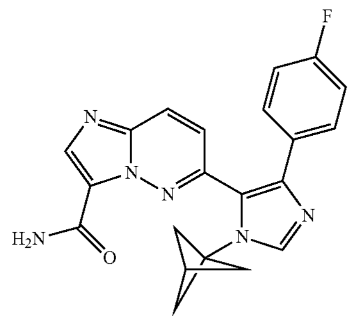 [SMILES: NC(=O)c1cnc2ccc(-c3c(-c4ccc(F)cc4)ncn3C34CC(C3)C4)nn12] | 6-(1-(bicyclo[1.1.1]pentan-1-yl)-4-(4-fluorophenyl)-1H-imidazol-5-yl)imidazo[1,2-b]pyridazine-3-carboxamide |
| 137' | 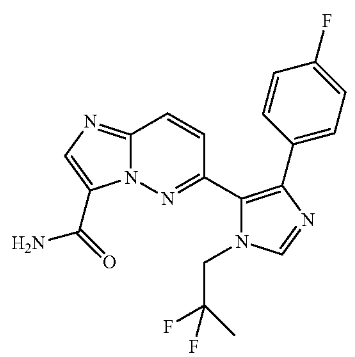 [SMILES: CC(F)(F)Cn1cnc(-c2ccc(F)cc2)c1-c1ccc2ncc(C(N)=O)n2n1] | 6-(1-(2,2-difluoropropyl)-4-(4-fluorophenyl)-1H-imidazol-5-yl)imidazo[1,2-b]pyridazine-3-carboxamide |
| 138' | 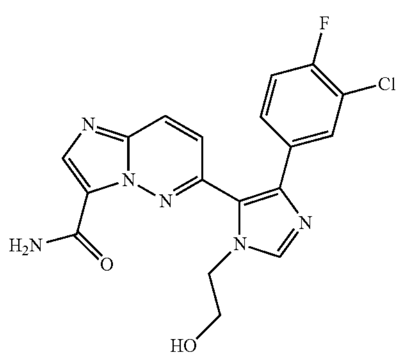 [SMILES: NC(=O)c1cnc2ccc(-c3c(-c4ccc(F)c(Cl)c4)ncn3CCO)nn12] | 6-(4-(3-chloro-4-fluorophenyl)-1-(2-hydroxyethyl)-1H-imidazol-5-yl)imidazo[1,2-b]pyridazine-3-carboxamide |
| 139' | 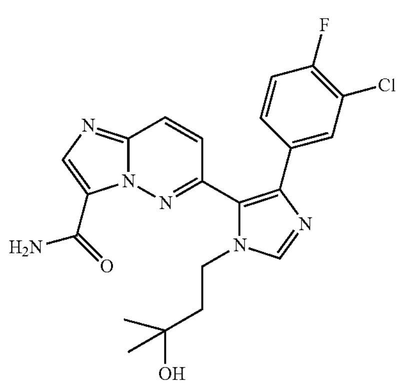 [SMILES: CC(C)(O)CCn1cnc(-c2ccc(F)c(Cl)c2)c1-c1ccc2ncc(C(N)=O)n2n1] | 6-(4-(3-chloro-4-fluorophenyl)-1-(3-hydroxy-3-methylbutyl)-1H-imidazol-5-yl)imidazo[1,2-b]pyridazine-3-carboxamide |

TABLE A-continued

| No. | Structure | Name |
|---|---|---|
| 140' | 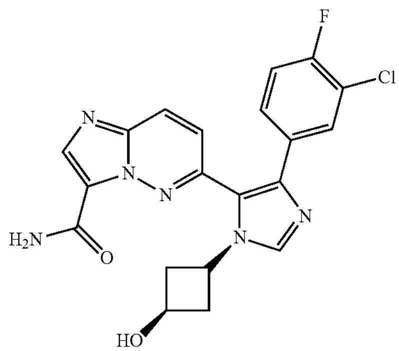 | 6-(4-(3-chloro-4-fluorophenyl)-1-((1s,3s)-3-hydroxycyclobutyl)-1H-imidazol-5-yl)imidazo[1,2-b]pyridazine-3-carboxamide |
| 141' | 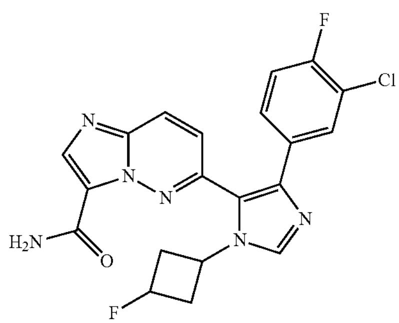 [SMILES: NC(=O)c1cnc2ccc(-c3c(-c4ccc(F)c(Cl)c4)ncn3C3CC(F)C3)nn12] | 6-(4-(3-chloro-4-fluorophenyl)-1-(3-fluorocyclobutyl)-1H-imidazol-5-yl)imidazo[1,2-b]pyridazine-3-carboxamide |
| 142' | 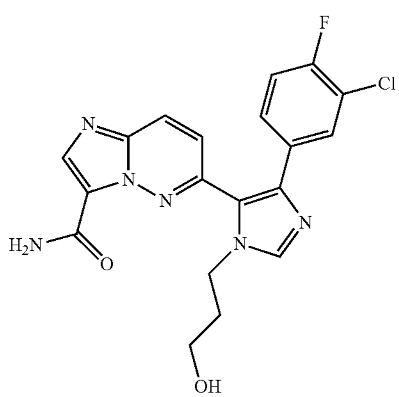 [SMILES: NC(=O)c1cnc2ccc(-c3c(-c4ccc(F)c(Cl)c4)ncn3CCCO)nn12] | 6-(4-(3-chloro-4-fluorophenyl)-1-(3-hydroxypropyl)-1H-imidazol-5-yl)imidazo[1,2-b]pyridazine-3-carboxamide |
| 143' | 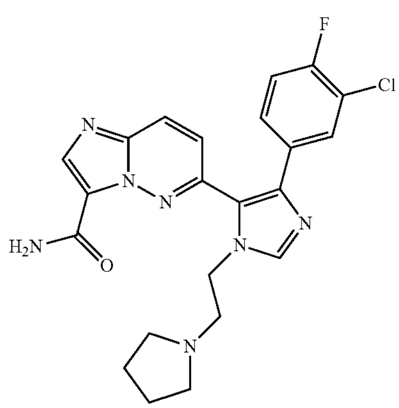 [SMILES: NC(=O)c1cnc2ccc(-c3c(-c4ccc(F)c(Cl)c4)ncn3CCN3CCCC3)nn12] | 6-(4-(3-chloro-4-fluorophenyl)-1-(2-(pyrrolidin-1-yl)ethyl)-1H-imidazol-5-yl)imidazo[1,2-b]pyridazine-3-carboxamide |

TABLE A-continued

| No. | Structure | Name |
|---|---|---|
| 144' | 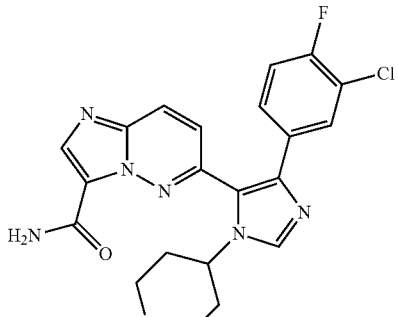 | 6-(4-(3-chloro-4-fluorophenyl)-1-(tetrahydro-2H-pyran-4-yl)-1H-imidazol-5-yl)imidazo[1,2-b]pyridazine-3-carboxamide |
| 145' | 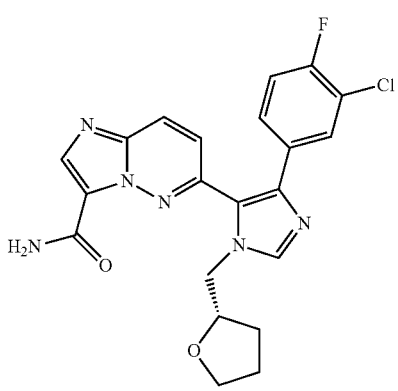 [SMILES: NC(=O)c1cnc2ccc(-c3c(-c4ccc(F)c(Cl)c4)ncn3C[C@@H]3CCCO3)nn12] | (S)-6-(4-(3-chloro-4-fluorophenyl)-1-((tetrahydrofuran-2-yl)methyl)-1H-imidazol-5-yl)imidazo[1,2-b]pyridazine-3-carboxamide |
| 146' | 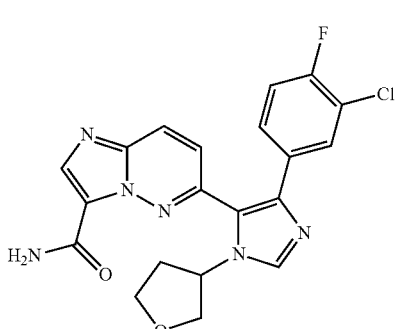 | 6-(4-(3-chloro-4-fluorophenyl)-1-(tetra-hydrofuran-3-yl)-1H-imidazol-5-yl)imidazo[1,2-b]pyridazine-3-carboxamide |
| 147' | 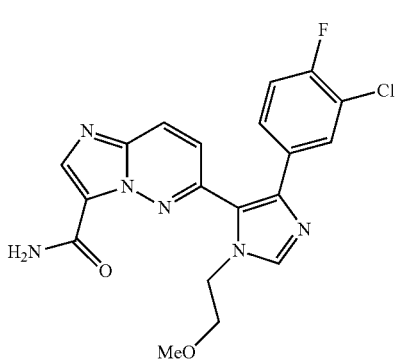 [SMILES: COCCn1cnc(-c2ccc(F)c(Cl)c2)c1-c1ccc2ncc(C(N)=O)n2n1] | 6-(4-(3-chloro-4-fluorophenyl)-1-(2-methoxyethyl)-1H-imidazol-5-yl)imidazo[1,2-b]pyridazine-3-carboxamide |

TABLE A-continued

| No. | Structure | Name |
|---|---|---|
| 148' | 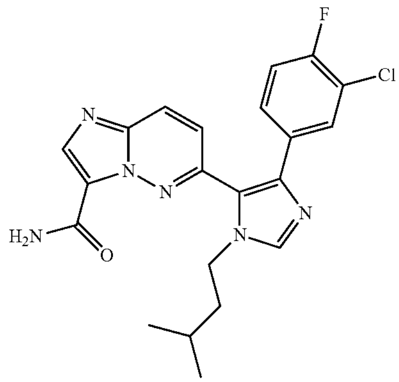 [SMILES: CC(C)CCn1cnc(-c2ccc(F)c(Cl)c2)c1-c1ccc2ncc(C(N)=O)n2n1] | 6-(4-(3-chloro-4-fluorophenyl)-1-isopentyl-1H-imidazol-5-yl)imidazo[1,2-b]pyridazine-3-carboxamide |
| 149' | 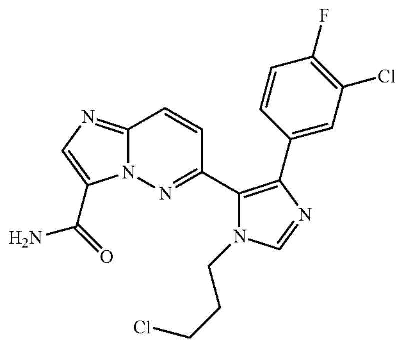 [SMILES: NC(=O)c1cnc2ccc(-c3c(-c4ccc(F)c(Cl)c4)ncn3CCCCl)nn12] | 6-(4-(3-chloro-4-fluorophenyl)-1-(3-chloropropyl)-1H-imidazol-5-yl)imidazo[1,2-b]pyridazine-3-carboxamide |
| 150' | 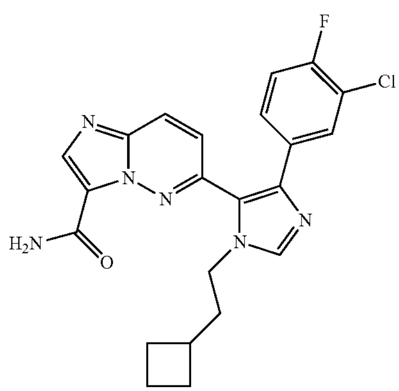 [SMILES: NC(=O)c1cnc2ccc(-c3c(-c4ccc(F)c(Cl)c4)ncn3CCC3CCC3)nn12] | 6-(4-(3-chloro-4-fluorophenyl)-1-(2-cyclobutylethyl)-1H-imidazol-5-yl)imidazo[1,2-b]pyridazine-3-carboxamide |
| 151' | 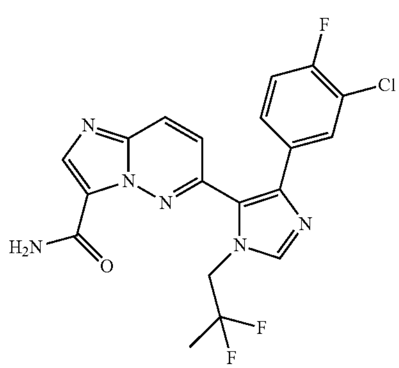 [SMILES: CC(F)(F)Cn1cnc(-c2ccc(F)c(Cl)c2)c1-c1ccc2ncc(C(N)=O)n2n1] | 6-(4-(3-chloro-4-fluorophenyl)-1-(2,2-difluoropropyl)-1H-imidazol-5-yl)imidazo[1,2-b]pyridazine-3-carboxamide |

TABLE A-continued

| No. | Structure | Name |
|---|---|---|
| 152' | 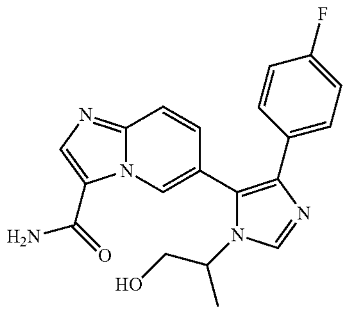 [SMILES: CC(CO)n1cnc(-c2ccc(F)cc2)c1-c1ccc2ncc(C(N)=O)n2c1] | 6-(4-(4-fluorophenyl)-1-(1-hydroxypropan-2-yl)-1H-imidazol-5-yl)imidazo[1,2-a]pyridine-3-carboxamide |
| 153' | 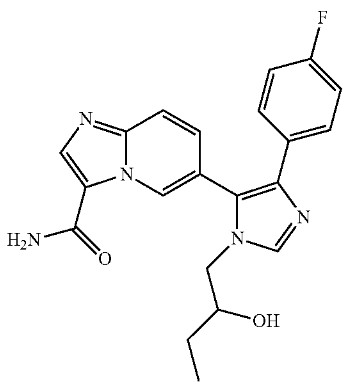 [SMILES: CCC(O)Cn1cnc(-c2ccc(F)cc2)c1-c1ccc2ncc(C(N)=O)n2c1] | 6-(4-(4-fluorophenyl)-1-(2-hydroxybutyl)-1H-imidazol-5-yl)imidazo[1,2-a]pyridine-3-carboxamide |
| 154' | 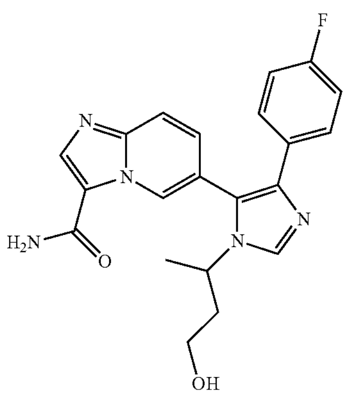 [SMILES: CC(CCO)n1cnc(-c2ccc(F)cc2)c1-c1ccc2ncc(C(N)=O)n2c1] | 6-(4-(4-fluorophenyl)-1-(4-hydroxybutan-2-yl)-1H-imidazol-5-yl)imidazo[1,2-a]pyridine-3-carboxamide |
| 155' | 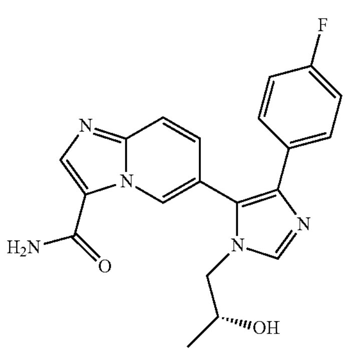 [SMILES: C[C@@H](O)Cn1cnc(-c2ccc(F)cc2)c1-c1ccc2ncc(C(N)=O)n2c1] | (R)-6-(4-(4-fluorophenyl)-1-(2-hydroxypropyl)-1H-imidazol-5-yl)imidazo[1,2-a]pyridine-3-carboxamide |

TABLE A-continued

| No. | Structure | Name |
|---|---|---|
| 156' | 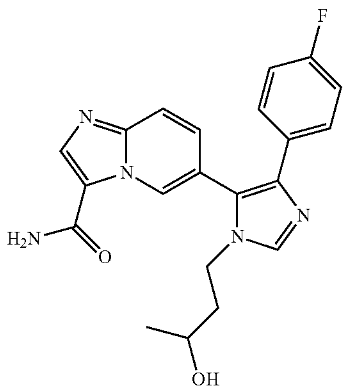 [SMILES: CC(O)CCn1cnc(-c2ccc(F)cc2)c1-c1ccc2ncc(C(N)=O)n2c1] | 6-(4-(4-fluorophenyl)-1-(3-hydroxybutyl)-1H-imidazol-5-yl)imidazo[1,2-a]pyridine-3-carboxamide |
| 157' | 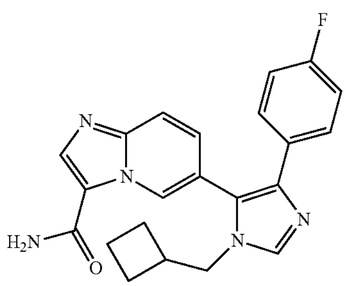 [SMILES: NC(=O)c1cnc2ccc(-c3c(-c4ccc(F)cc4)ncn3CC3CCC3)cn12] | 6-(1-(cyclobutylmethyl)-4-(4-fluorophenyl)-1H-imidazol-5-yl)imidazo[1,2-a]pyridine-3-carboxamide |
| 158' | 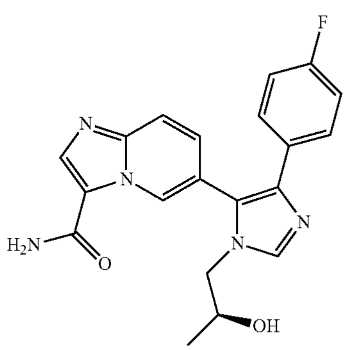 [SMILES: C[C@H](O)Cn1cnc(-c2ccc(F)cc2)c1-c1ccc2ncc(C(N)=O)n2c1] | (S)-6-(4-(4-fluorophenyl)-1-(2-hydroxypropyl)-1H-imidazol-5-yl)imidazo[1,2-a]pyridine-3-carboxamide |
| 159' | 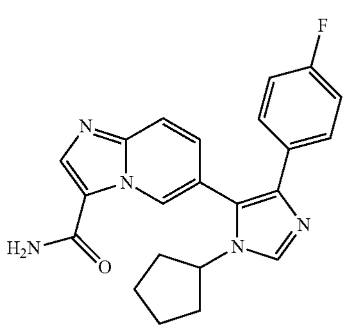 [SMILES: NC(=O)c1cnc2ccc(-c3c(-c4ccc(F)cc4)ncn3C3CCCC3)cn12] | 6-(1-cyclopentyl-4-(4-fluorophenyl)-1H-imidazol-5-yl)imidazo[1,2-a]pyridine-3-carboxamide |

TABLE A-continued

| No. | Structure | Name |
|---|---|---|
| 160' | 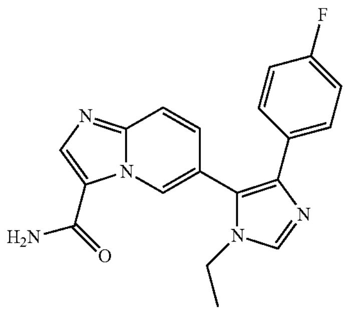 [SMILES: CCn1cnc(-c2ccc(F)cc2)c1-c1ccc2ncc(C(N)=O)n2c1] | 6-(1-ethyl-4-(4-fluorophenyl)-1H-imidazol-5-yl)imidazo[1,2-a]pyridine-3-carboxamide |
| 161' | 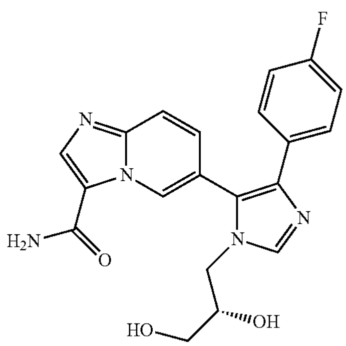 [SMILES: NC(=O)c1cnc2ccc(-c3c(-c4ccc(F)cc4)ncn3C[C@H](O)CO)cn12] | (S)-6-(1-(2,3-dihydroxypropyl)-4-(4-fluorophenyl)-1H-imidazol-5-yl)imidazo[1,2-a]pyridine-3-carboxamide |
| 162' | 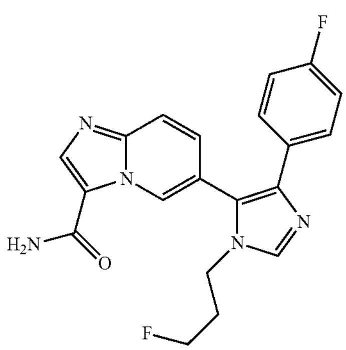 [SMILES: NC(=O)c1cnc2ccc(-c3c(-c4ccc(F)cc4)ncn3CCCF)cn12] | 6-(4-(4-fluorophenyl)-1-(3-fluoropropyl)-1H-imidazol-5-yl)imidazo[1,2-a]pyridine-3-carboxamide |
| 163' | 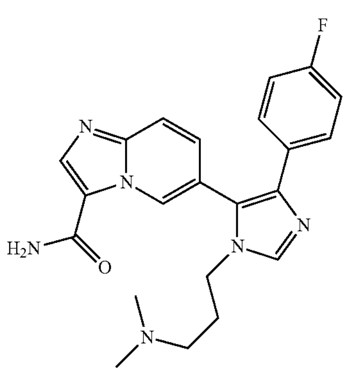 [SMILES: CN(C)CCCn1cnc(-c2ccc(F)cc2)c1-c1ccc2ncc(C(N)=O)n2c1] | 6-(1-(3-(dimethylamino)propyl)-4-(4-fluorophenyl)-1H-imidazol-5-yl)imidazo[1,2-a]pyridine-3-carboxamide |

TABLE A-continued
| No. | Structure | Name |
|---|---|---|
| 164' | 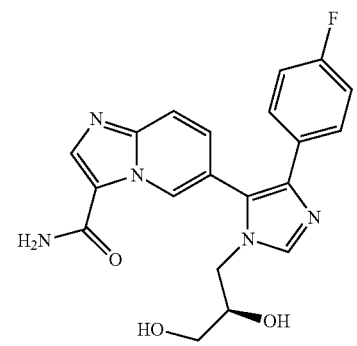 [SMILES: NC(=O)c1cnc2ccc(-c3c(-c4ccc(F)cc4)ncn3C[C@@H](O)CO)cn12] | (R)-6-(1-(2,3-dihydroxypropyl)-4-(4-fluorophenyl)-1H-imidazol-5-yl)imidazo[1,2-a]pyridine-3-carboxamide |
| 165' | 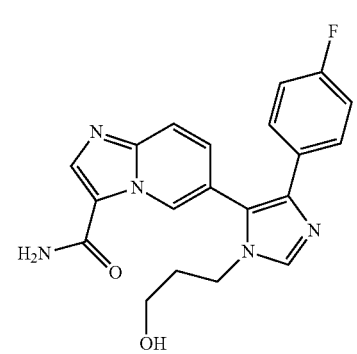 [SMILES: NC(=O)c1cnc2ccc(-c3c(-c4ccc(F)cc4)ncn3CCCO)cn12] | 6-(4-(4-fluorophenyl)-1-(3-hydroxypropyl)-1H-imidazol-5-yl)imidazo[1,2-a]pyridine-3-carboxamide |
| 166' | 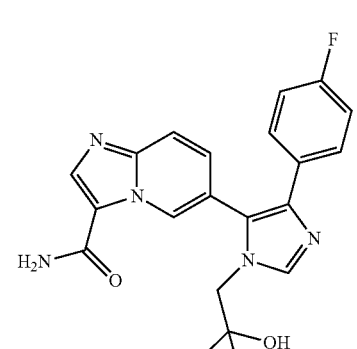 | 6-(4-(4-fluorophenyl)-1-(2-hydroxy-2-methylpropyl)-1H-imidazol-5-yl)imidazo[1,2-a]pyridine-3-carboxamide |
| 167' | 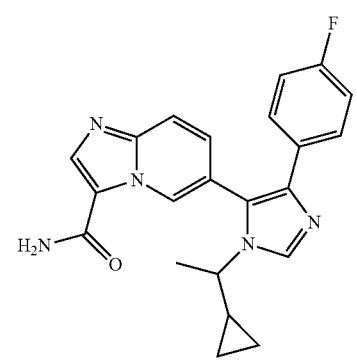 [SMILES: CC(C1CC1)n1cnc(-c2ccc(F)cc2)c1-c1ccc2ncc(C(N)=O)n2c1] | 6-(1-(1-cyclopropylethyl)-4-(4-fluorophenyl)-1H-imidazol-5-yl)imidazo[1,2-a]pyridine-3-carboxamide |

TABLE A-continued

| No. | Structure | Name |
| --- | --- | --- |
| 168' | 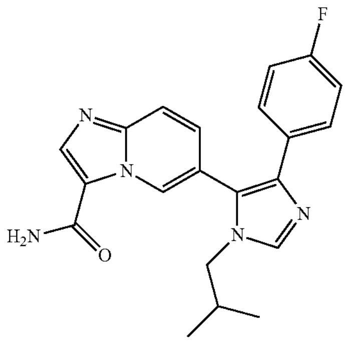 [SMILES: CC(C)Cn1cnc(-c2ccc(F)cc2)c1-c1ccc2ncc(C(N)=O)n2c1] | 6-(4-(4-fluorophenyl)-1-isobutyl-1H-imidazol-5-yl)imidazo[1,2-a]pyridine-3-carboxamide |
| 169' | 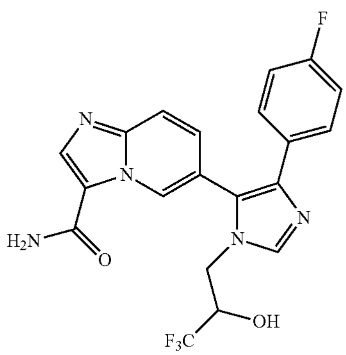 [SMILES: NC(=O)c1cnc2ccc(-c3c(-c4ccc(F)cc4)ncn3CC(O)C(F)(F)F)cn12] | 6-(4-(4-fluorophenyl)-1-(3,3,3-trifluoro-2-hydroxypropyl)-1H-imidazol-5-yl)imidazo[1,2-a]pyridine-3-carboxamide |
| 170' | 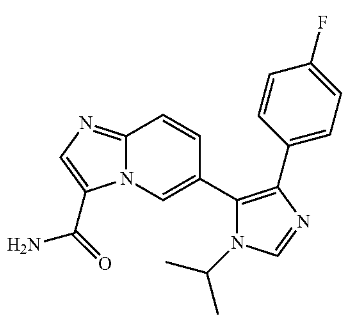 [SMILES: CC(C)n1cnc(-c2ccc(F)cc2)c1-c1ccc2ncc(C(N)=O)n2c1] | 6-(4-(4-fluorophenyl)-1-isopropyl-1H-imidazol-5-yl)imidazo[1,2-a]pyridine-3-carboxamide |
| 171' | 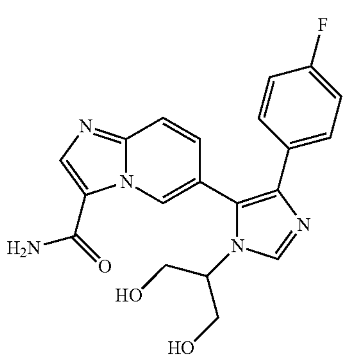 [SMILES: NC(=O)c1cnc2ccc(-c3c(-c4ccc(F)cc4)ncn3C(CO)CO)cn12] | 6-(1-(1,3-dihydroxypropan-2-yl)-4-(4-fluorophenyl)-1H-imidazol-5-yl)imidazo[1,2-a]pyridine-3-carboxamide |

TABLE A-continued

| No. | Structure | Name |
|---|---|---|
| 172' | 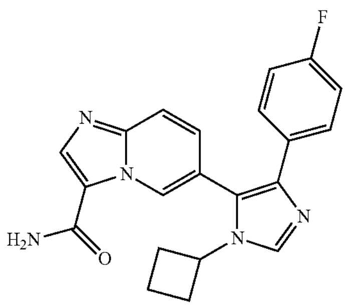 [SMILES: NC(=O)c1cnc2ccc(-c3c(-c4ccc(F)cc4)ncn3C3CCC3)cn12] | 6-(1-cyclobutyl-4-(4-fluorophenyl)-1H-imidazol-5-yl)imidazo[1,2-a]pyridine-3-carboxamide |
| 173' | 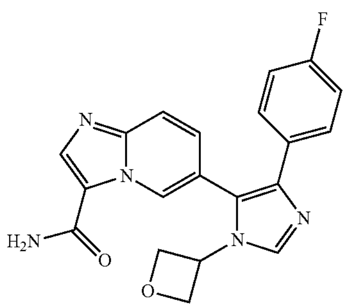 | 6-(4-(4-fluorophenyl)-1-(oxetan-3-yl)-1H-imidazol-5-yl)imidazo[1,2-a]pyridine-3-carboxamide |
| 174' | 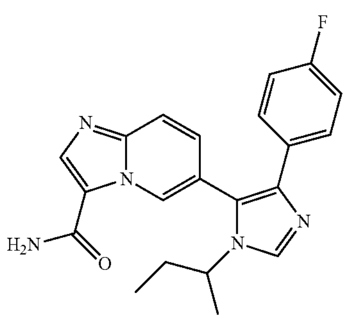 [SMILES: CCC(C)n1cnc(-c2ccc(F)cc2)c1-c1ccc2ncc(C(N)=O)n2c1] | 6-(1-(sec-butyl)-4-(4-fluorophenyl)-1H-imidazol-5-yl)imidazo[1,2-a]pyridine-3-carboxamide |
| 175' | 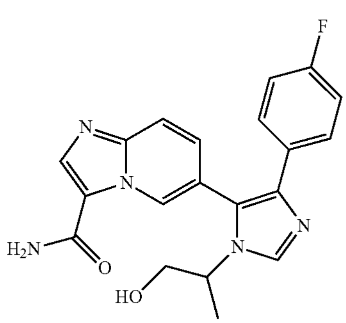 [SMILES: CC(CO)n1cnc(-c2ccc(F)cc2)c1-c1ccc2ncc(C(N)=O)n2c1] | 6-(4-(4-fluorophenyl)-1-(1-hydroxypropan-2-yl)-1H-imidazol-5-yl)imidazo[1,2-a]pyridine-3-carboxamide |
| 176' | 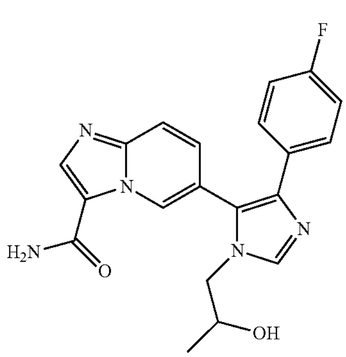 [SMILES: CC(O)Cn1cnc(-c2ccc(F)cc2)c1-c1ccc2ncc(C(N)=O)n2c1] | 6-(4-(4-fluorophenyl)-1-(2-hydroxypropyl)-1H-imidazol-5-yl)imidazo[1,2-a]pyridine-3-carboxamide |

TABLE A-continued

| No. | Structure | Name |
|---|---|---|
| 177' | 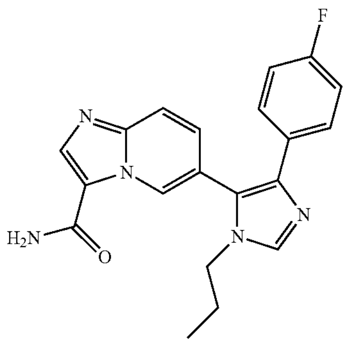 [SMILES: CCCn1cnc(-c2ccc(F)cc2)c1-c1ccc2ncc(C(N)=O)n2c1] | 6-(4-(4-fluorophenyl)-1-propyl-1H-imidazol-5-yl)imidazo[1,2-a]pyridine-3-carboxamide |
| 178' | 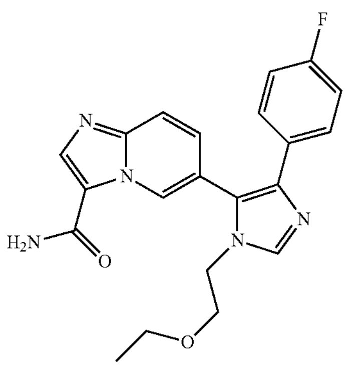 [SMILES: CCOCCn1cnc(-c2ccc(F)cc2)c1-c1ccc2ncc(C(N)=O)n2c1] | 6-(1-(2-ethoxyethyl)-4-(4-fluorophenyl)-1H-imidazol-5-yl)imidazo[1,2-a]pyridine-3-carboxamide |
| 179' | 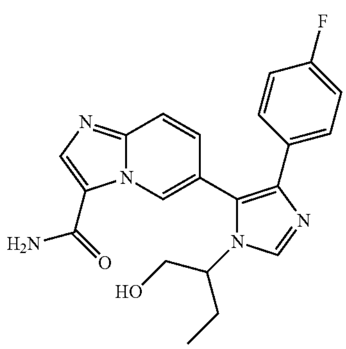 [SMILES: CCC(CO)n1cnc(-c2ccc(F)cc2)c1-c1ccc2ncc(C(N)=O)n2c1] | 6-(4-(4-fluorophenyl)-1-(1-hydroxybutan-2-yl)-1H-imidazol-5-yl)imidazo[1,2-a]pyridine-3-carboxamide |
| 180' | 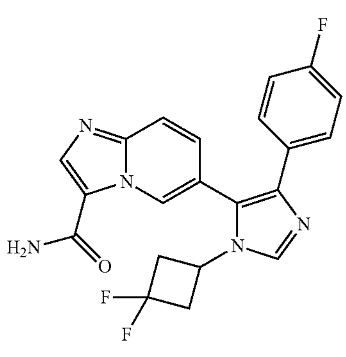 [SMILES: NC(=O)c1cnc2ccc(-c3c(-c4ccc(F)cc4)ncn3C3CC(F)(F)C3)cn12] | 6-(1-(3,3-difluorocyclobutyl)-4-(4-fluorophenyl)-1H-imidazol-5-yl)imidazo[1,2-a]pyridine-3-carboxamide |

TABLE A-continued

| No. | Structure | Name |
|---|---|---|
| 181' | 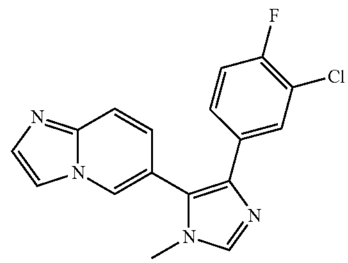 [SMILES: Cn1cnc(-c2ccc(F)c(Cl)c2)c1-c1ccc2nccn2c1] | 6-(4-(3-chloro-4-fluorophenyl)-1-methyl-1H-imidazol-5-yl)imidazo[1,2-a]pyridine |
| 182' | 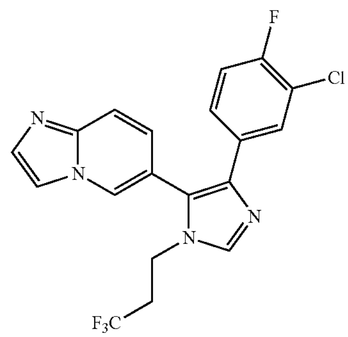 [SMILES: Fc1ccc(-c2ncn(CCC(F)(F)F)c2-c2ccc3nccn3c2)cc1Cl] | 6-(4-(3-chloro-4-fluorophenyl)-1-(3,3,3-trifluoropropyl)-1H-imidazol-5-yl)imidazo[1,2-a]pyridine |
| 183' | 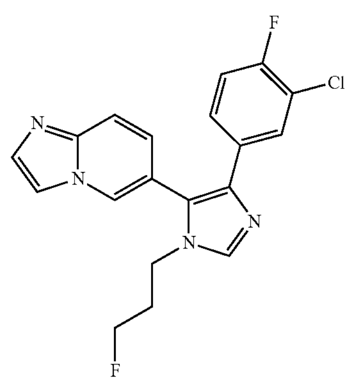 [SMILES: FCCCn1cnc(-c2ccc(F)c(Cl)c2)c1-c1ccc2nccn2c1] | 6-(4-(3-chloro-4-fluorophenyl)-1-(3-fluoropropyl)-1H-imidazol-5-yl)imidazo[1,2-a]pyridine |
| 184' | 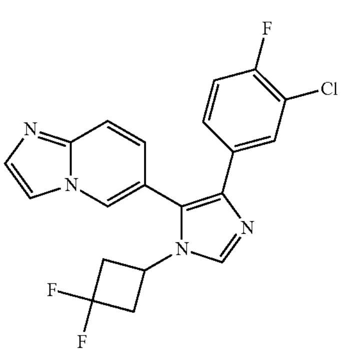 [SMILES: Fc1ccc(-c2ncn(C3CC(F)(F)C3)c2-c2ccc3nccn3c2)cc1Cl] | 6-(4-(3-chloro-4-fluorophenyl)-1-(3,3-difluorocyclobutyl)-1H-imidazol-5-yl)imidazo[1,2-a]pyridine |

TABLE A-continued

| No. | Structure | Name |
|---|---|---|
| 185' | 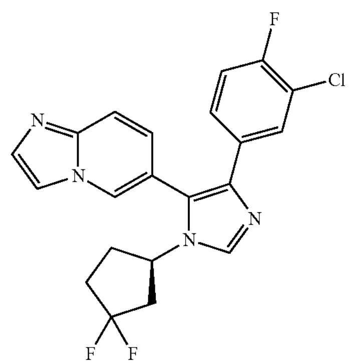 [SMILES: Fc1ccc(-c2ncn([C@@H]3CCC(F)(F)C3)c2-c2ccc3nccn3c2)cc1Cl] | (R)-6-(4-(3-chloro-4-fluorophenyl)-1-(3,3-difluorocyclopentyl)-1H-imidazol-5-yl)imidazo[1,2-a]pyridine |
| 186' | 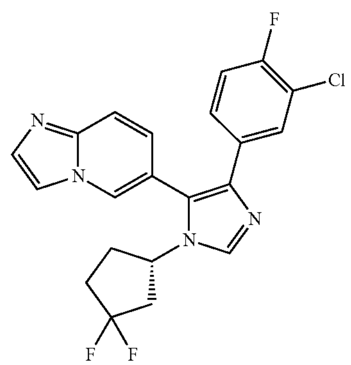 [SMILES: Fc1ccc(-c2ncn([C@H]3CCC(F)(F)C3)c2-c2ccc3nccn3c2)cc1Cl] | (S)-6-(4-(3-chloro-4-fluorophenyl)-1-(3,3-difluorocyclopentyl)-1H-imidazol-5-yl)imidazo[1,2-a]pyridine |
| 187' | 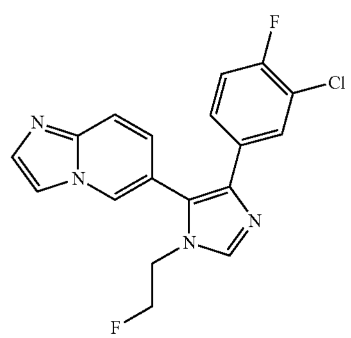 [SMILES: FCCn1cnc(-c2ccc(F)c(Cl)c2)c1-c1ccc2nccn2c1] | 6-(4-(3-chloro-4-fluorophenyl)-1-(2-fluoroethyl)-1H-imidazol-5-yl)imidazo[1,2-a]pyridine |
| 188' | 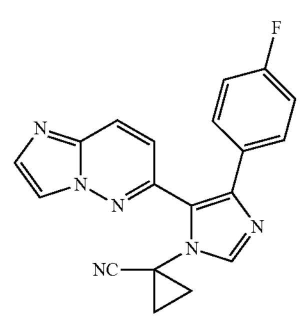 [SMILES: N#CC1(n2cnc(-c3ccc(F)cc3)c2-c2ccc3nccn3n2)CC1] | 1-(4-(4-fluorophenyl)-5-(imidazo[1,2-b]pyridazin-6-yl)-1H-imidazol-1-yl)cyclopropanecarbonitrile |

TABLE A-continued

| No. | Structure | Name |
|---|---|---|
| 189' | 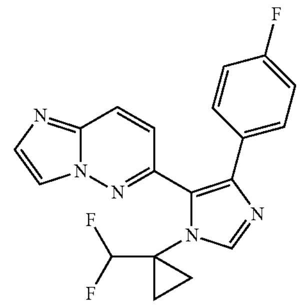 [SMILES: Fc1ccc(-c2ncn(C3(C(F)F)CC3)c2-c2ccc3nccn3n2)cc1] | 6-(1-(1-(difluoromethyl)cyclopropyl)-4-(4-fluorophenyl)-1H-imidazol-5-yl)imidazo[1,2-b]pyridazine |
| 190' | 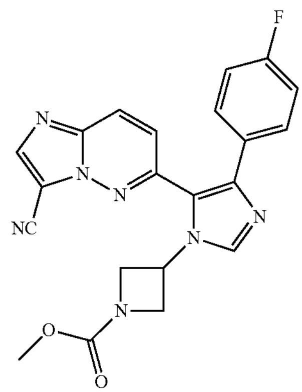 [SMILES: COC(=O)N1CC(n2cnc(-c3ccc(F)cc3)c2-c2ccc3ncc(C#N)n3n2)C1] | methyl 3-(5-(3-cyanoimidazo[1,2-b]pyridazin-6-yl)-4-(4-fluorophenyl)-1H-imidazol-1-yl)azetidine-1-carboxylate |
| 191' | 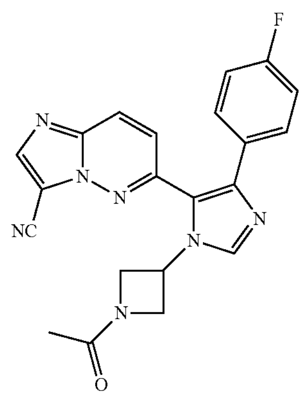 [SMILES: CC(=O)N1CC(n2cnc(-c3ccc(F)cc3)c2-c2ccc3ncc(C#N)n3n2)C1] | 6-(1-(1-acetylazetidin-3-yl)-4-(4-fluorophenyl)-1H-imidazol-5-yl)imidazo[1,2-b]pyridazine-3-carbonitrile |
| 192' | 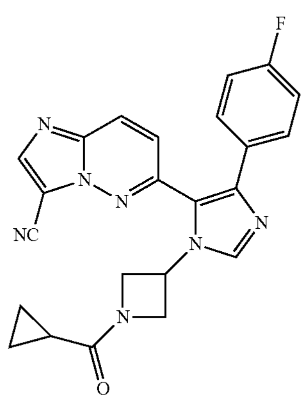 [SMILES: N#Cc1cnc2ccc(-c3c(-c4ccc(F)cc4)ncn3C3CN(C(=O)C4CC4)C3)nn12] | 6-(1-(1-(cyclopropanecarbonyl)azetidin-3-yl)-4-(4-fluorophenyl)-1H-imidazol-5-yl)imidazo[1,2-b]pyridazine-3-carbonitrile |

TABLE A-continued

| No. | Structure | Name |
|---|---|---|
| 193' | 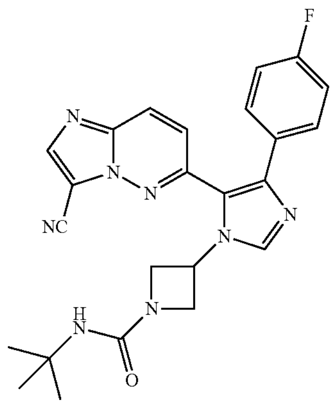 [SMILES: CC(C)(C)NC(=O)N1CC(n2cnc(-c3ccc(F)cc3)c2-c2ccc3ncc(C#N)n3n2)C1] | N-(tert-butyl)-3-(5-(3-cyanoimidazo[1,2-b]pyridazin-6-yl)-4-(4-fluorophenyl)-1H-imidazol-1-yl)azetidine-1-carboxamide |
| 194' | 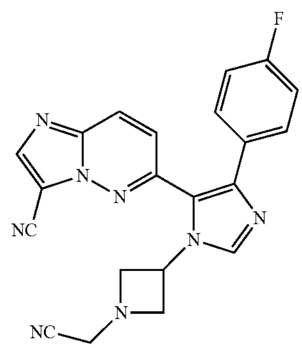 [SMILES: N#CCN1CC(n2cnc(-c3ccc(F)cc3)c2-c2ccc3ncc(C#N)n3n2)C1] | 6-(1-(1-(cyanomethyl)azetidin-3-yl)-4-(4-fluorophenyl)-1H-imidazol-5-yl)imidazo[1,2-b]pyridazine-3-carbonitrile |
| 195' | 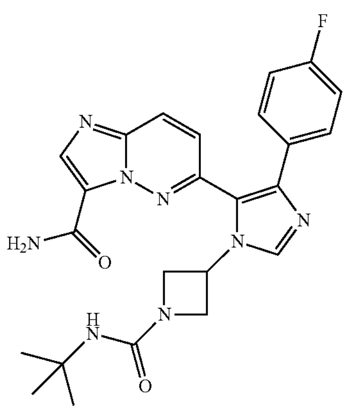 [SMILES: CC(C)(C)NC(=O)N1CC(n2cnc(-c3ccc(F)cc3)c2-c2ccc3ncc(C(N)=O)n3n2)C1] | 6-(1-(1-(tert-butylcarbamoyl)azetidin-3-yl)-4-(4-fluorophenyl)-1H-imidazol-5-yl)imidazo[1,2-b]pyridazine-3-carboxamide |
| 196' | 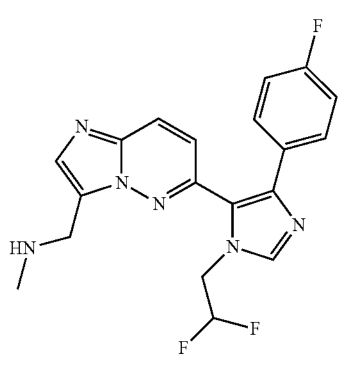 [SMILES: CNCc1cnc2ccc(-c3c(-c4ccc(F)cc4)ncn3CC(F)F)nn12] | (6-(1-(2,2-difluoroethyl)-4-(4-fluorophenyl)-1H-imidazol-5-yl)imidazo[1,2-b]pyridazin-3-yl)methanamine |

TABLE A-continued

| No. | Structure | Name |
|---|---|---|
| 197' | 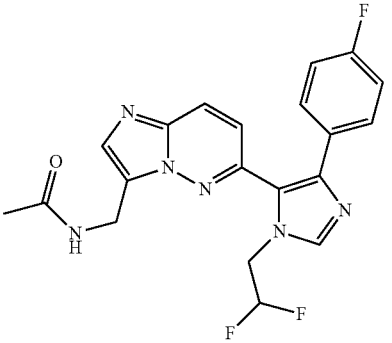 [SMILES: CC(=O)NCc1cnc2ccc(-c3c(-c4ccc(F)cc4)ncn3CC(F)F)nn12] | N-((6-(1-(2,2-difluoroethyl)-4-(4-fluorophenyl)-1H-imidazol-5-yl)imidazo[1,2-b]pyridazin-3-yl)methyl)acetamide |
| 198' | 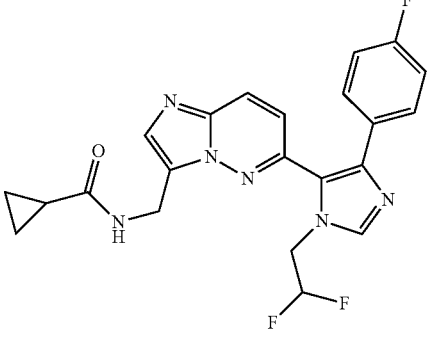 | N-((6-(1-(2,2-difluoroethyl)-4-(4-fluorophenyl)-1H-imidazol-5-yl)imidazo[1,2-b]pyridazin-3-yl)methyl)cyclopropanecarboxamide |
| 199' | 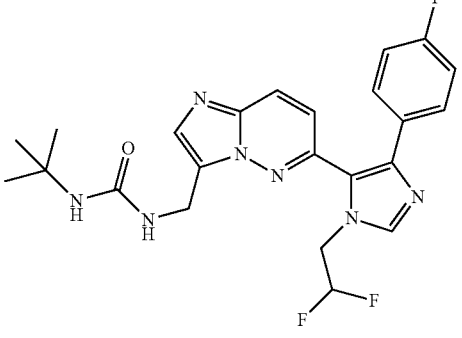 | 1-(tert-butyl)-3-((6-(1-(2,2-difluoroethyl)-4-(4-fluorophenyl)-1H-imidazol-5-yl)imidazo[1,2-b]pyridazin-3-yl)methyl)urea |
| 200' | 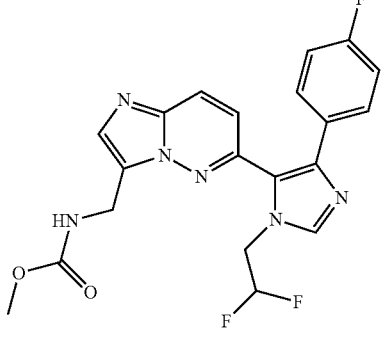 | methyl ((6-(1-(2,2-difluoroethyl)-4-(4-fluorophenyl)-1H-imidazol-5-yl)imidazo[1,2-b]pyridazin-3-yl)methyl)carbamate |

TABLE A-continued

| No. | Structure | Name |
|---|---|---|
| 201' | 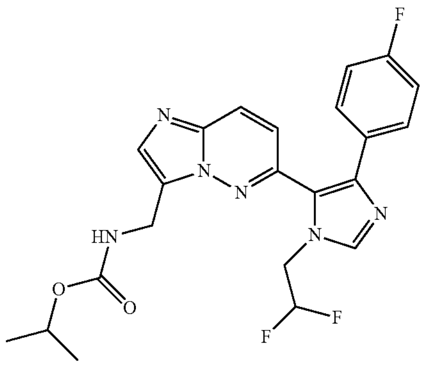 [SMILES: CC(C)OC(=O)NCc1cnc2ccc(-c3c(-c4ccc(F)cc4)ncn3CC(F)F)nn12] | isopropyl ((6-(1-(2,2-difluoroethyl)-4-(4-fluorophenyl)-1H-imidazol-5-yl)imidazo[1,2-b]pyridazin-3-yl)methyl)carbamate |
| 202' | 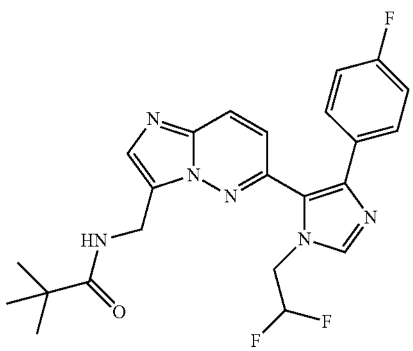 [SMILES: CC(C)(C)C(=O)NCc1cnc2ccc(-c3c(-c4ccc(F)cc4)ncn3CC(F)F)nn12] | N-((6-(1-(2,2-difluoroethyl)-4-(4-fluorophenyl)-1H-imidazol-5-yl)imidazo[1,2-b]pyridazin-3-yl)methyl)pivalamide |
| 203' | 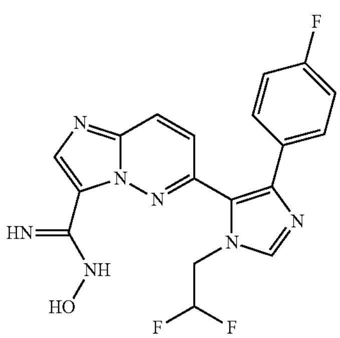 [SMILES: N=C(NO)c1cnc2ccc(-c3c(-c4ccc(F)cc4)ncn3CC(F)F)nn12] | 6-(1-(2,2-difluoroethyl)-4-(4-fluorophenyl)-1H-imidazol-5-yl)-N-hydroxyimidazo[1,2-b]pyridazine-3-carboximidamide |
| 204' | 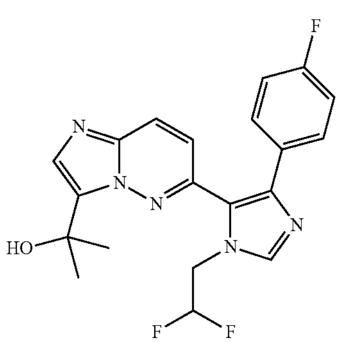 [SMILES: CC(C)(O)c1cnc2ccc(-c3c(-c4ccc(F)cc4)ncn3CC(F)F)nn12] | 2-(6-(1-(2,2-difluoroethyl)-4-(4-fluorophenyl)-1H-imidazol-5-yl)imidazo[1,2-b]pyridazin-3-yl)propan-2-ol |

TABLE A-continued

| No. | Structure | Name |
|---|---|---|
| 205' | 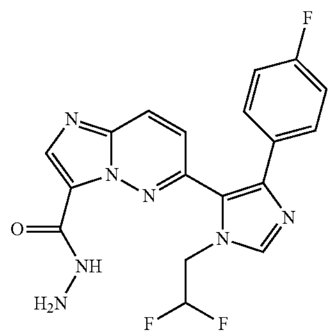 [SMILES: NNC(=O)c1cnc2ccc(-c3c(-c4ccc(F)cc4)ncn3CC(F)F)nn12] | 6-(1-(2,2-difluoroethyl)-4-(4-fluorophenyl)-1H-imidazol-5-yl)imidazo[1,2-b]pyridazine-3-carbohydrazide |
| 206' | 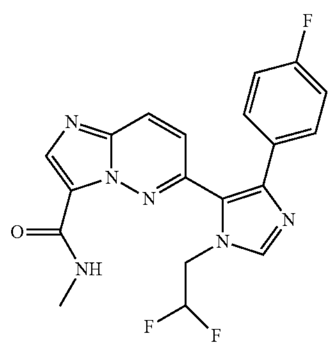 [SMILES: CNC(=O)c1cnc2ccc(-c3c(-c4ccc(F)cc4)ncn3CC(F)F)nn12] | 6-(1-(2,2-difluoroethyl)-4-(4-fluorophenyl)-1H-imidazol-5-yl)-N-methyl-imidazo[1,2-b]pyridazine-3-carboxamide |
| 207' | 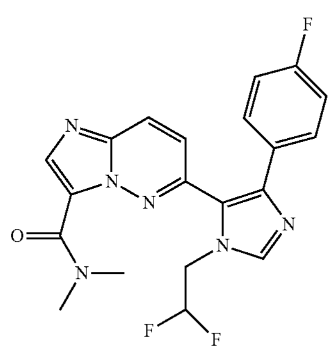 [SMILES: CN(C)C(=O)c1cnc2ccc(-c3c(-c4ccc(F)cc4)ncn3CC(F)F)nn12] | 6-(1-(2,2-difluoroethyl)-4-(4-fluorophenyl)-1H-imidazol-5-yl)-N,N-dimethylimidazo[1,2-b]pyridazine-3-carboxamide |
| 208' | 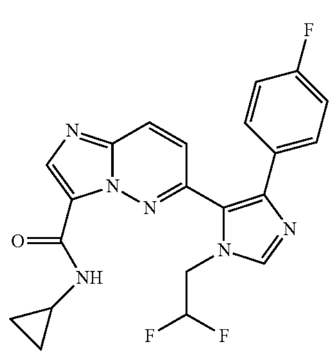 [SMILES: O=C(NC1CC1)c1cnc2ccc(-c3c(-c4ccc(F)cc4)ncn3CC(F)F)nn12] | N-cyclopropyl-6-(1-(2,2-difluoroethyl)-4-(4-fluorophenyl)-1H-imidazol-5-yl)imidazo[1,2-b]pyridazine-3-carboxamide |

TABLE A-continued

| No. | Structure | Name |
|---|---|---|
| 209' | 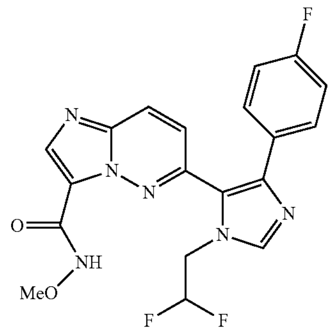 [SMILES: CONC(=O)c1cnc2ccc(-c3c(-c4ccc(F)cc4)ncn3CC(F)F)nn12] | 6-(1-(2,2-difluoroethyl)-4-(4-fluorophenyl)-1H-imidazol-5-yl)-N-methoxyimidazo[1,2-b]pyridazine-3-carboxamide |
| 210' | 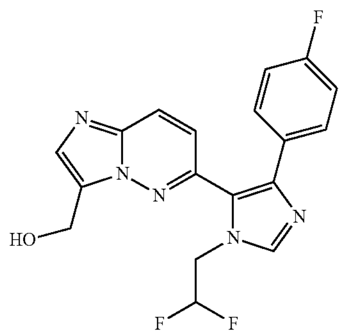 [SMILES: OCc1cnc2ccc(-c3c(-c4ccc(F)cc4)ncn3CC(F)F)nn12] | (6-(1-(2,2-difluoroethyl)-4-(4-fluorophenyl)-1H-imidazol-5-yl)imidazo[1,2-b]pyridazin-3-yl)methanol |
| 211' | 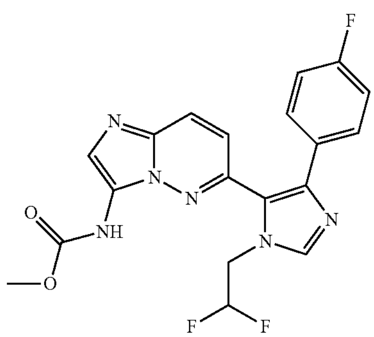 [SMILES: COC(=O)Nc1cnc2ccc(-c3c(-c4ccc(F)cc4)ncn3CC(F)F)nn12] | methyl (6-(1-(2,2-difluoroethyl)-4-(4-fluorophenyl)-1H-imidazol-5-yl)imidazo[1,2-b]pyridazin-3-yl)carbamate |
| 212' | 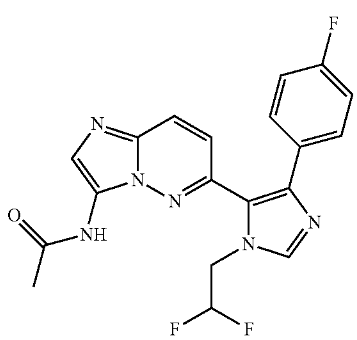 [SMILES: CC(=O)Nc1cnc2ccc(-c3c(-c4ccc(F)cc4)ncn3CC(F)F)nn12] | N-(6-(1-(2,2-difluoroethyl)-4-(4-fluorophenyl)-1H-imidazol-5-yl)imidazo[1,2-b]pyridazin-3-yl)acetamide |

TABLE A-continued
| No. | Structure | Name |
|---|---|---|
| 213' | 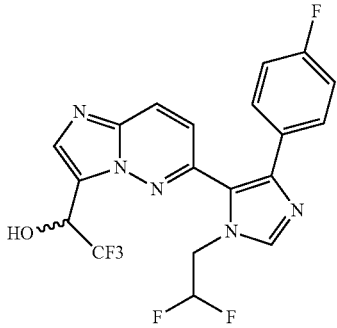 [SMILES: OC(c1cnc2ccc(-c3c(-c4ccc(F)cc4)ncn3CC(F)F)nn12)C(F)(F)F] | 1-(6-(1-(2,2-difluoroethyl)-4-(4-fluorophenyl)-1H-imidazol-5-yl)imidazo[1,2-b]pyridazin-3-yl)-2,2,2-trifluoroethanol |
| 214' | 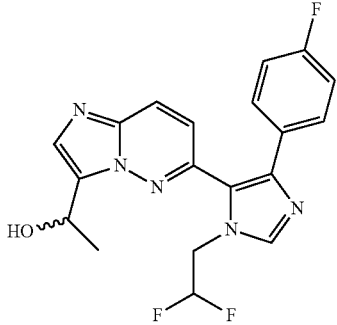 [SMILES: CC(O)c1cnc2ccc(-c3c(-c4ccc(F)cc4)ncn3CC(F)F)nn12] | 1-(6-(1-(2,2-difluoroethyl)-4-(4-fluorophenyl)-1H-imidazol-5-yl)imidazo[1,2-b]pyridazin-3-yl)ethanol |
| 215' | 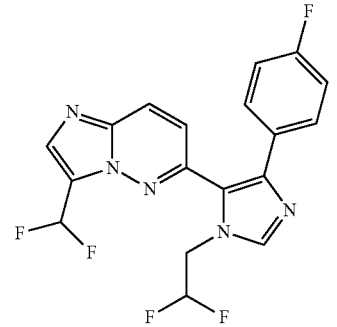 [SMILES: Fc1ccc(-c2ncn(CC(F)F)c2-c2ccc3ncc(C(F)F)n3n2)cc1] | 6-(1-(2,2-difluoroethyl)-4-(4-fluorophenyl)-1H-imidazol-5-yl)-3-(difluoromethyl)imidazo[1,2-b]pyridazine |
| 216' | 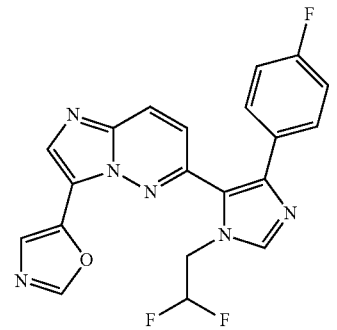 [SMILES: Fc1ccc(-c2ncn(CC(F)F)c2-c2ccc3ncc(-c4cnco4)n3n2)cc1] | 5-(6-(1-(2,2-difluoroethyl)-4-(4-fluorophenyl)-1H-imidazol-5-yl)imidazo[1,2-b]pyridazin-3-yl)oxazole |

TABLE A-continued

| No. | Structure | Name |
|---|---|---|
| 217' | 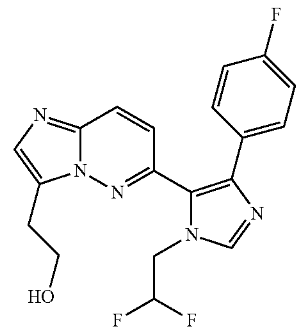 [SMILES: OCCc1cnc2ccc(-c3c(-c4ccc(F)cc4)ncn3CC(F)F)nn12] | 2-(6-(1-(2,2-difluoroethyl)-4-(4-fluorophenyl)-1H-imidazol-5-yl)imidazo[1,2-b]pyridazin-3-yl)ethanol |
| 218' | 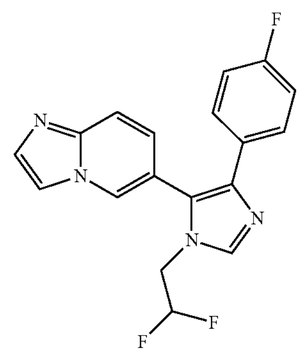 [SMILES: Fc1ccc(-c2ncn(CC(F)F)c2-c2ccc3nccn3c2)cc1] | 6-(1-(2,2-difluoroethyl)-4-(4-fluorophenyl)-1H-imidazol-5-yl)imidazo[1,2-a]pyridine |
| 219' | 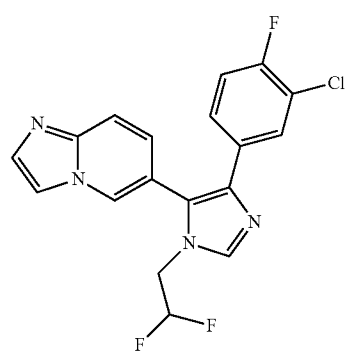 [SMILES: Fc1ccc(-c2ncn(CC(F)F)c2-c2ccc3nccn3c2)cc1Cl] | 6-(4-(3-chloro-4-fluorophenyl)-1-(2,2-difluoroethyl)-1H-imidazol-5-yl)imidazo[1,2-a]pyridine |
| 220' | 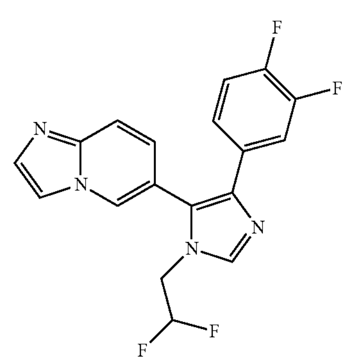 [SMILES: Fc1ccc(-c2ncn(CC(F)F)c2-c2ccc3nccn3c2)cc1F] | 6-(1-(2,2-difluoroethyl)-4-(3,4-difluorophenyl)-1H-imidazol-5-yl)imidazo[1,2-a]pyridine |

TABLE A-continued

| No. | Structure | Name |
|---|---|---|
| 221' | 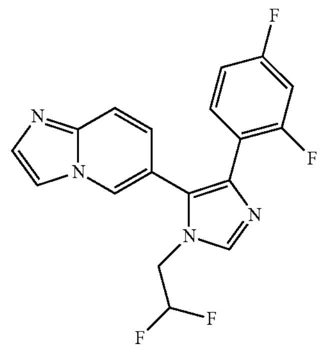 [SMILES: Fc1ccc(-c2ncn(CC(F)F)c2-c2ccc3nccn3c2)c(F)c1] | 6-(1-(2,2-difluoroethyl)-4-(2,4-difluorophenyl)-1H-imidazol-5-yl)imidazo[1,2-a]pyridine |
| 222' | 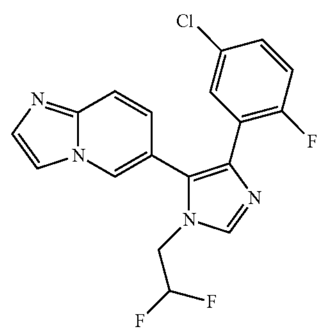 [SMILES: Fc1ccc(Cl)cc1-c1ncn(CC(F)F)c1-c1ccc2nccn2c1] | 6-(4-(5-chloro-2-fluorophenyl)-1-(2,2-difluoroethyl)-1H-imidazol-5-yl)imidazo[1,2-a]pyridine |
| 223' | 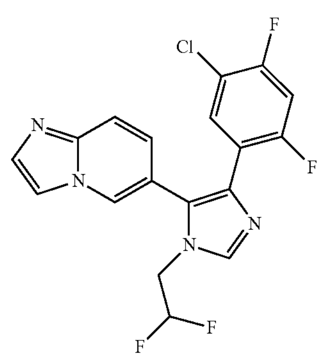 [SMILES: Fc1cc(F)c(-c2ncn(CC(F)F)c2-c2ccc3nccn3c2)cc1Cl] | 6-(4-(5-chloro-2,4-difluorophenyl)-1-(2,2-difluoroethyl)-1H-imidazol-5-yl)imidazo[1,2-a]pyridine |
| 224' | 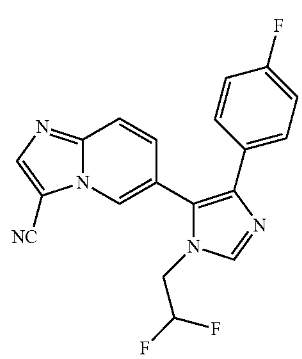 [SMILES: N#Cc1cnc2ccc(-c3c(-c4ccc(F)cc4)ncn3CC(F)F)cn12] | 6-(1-(2,2-difluoroethyl)-4-(4-fluorophenyl)-1H-imidazol-5-yl)imidazo[1,2-a]pyridine-3-carbonitrile |

TABLE A-continued

| No. | Structure | Name |
|---|---|---|
| 225' | 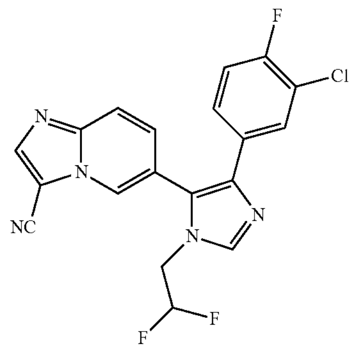 [SMILES: N#Cc1cnc2ccc(-c3c(-c4ccc(F)c(Cl)c4)ncn3CC(F)F)cn12] | 6-(4-(3-chloro-4-fluorophenyl)-1-(2,2-difluoroethyl)-1H-imidazol-5-yl)imidazo[1,2-a]pyridine-3-carbonitrile |
| 226' | 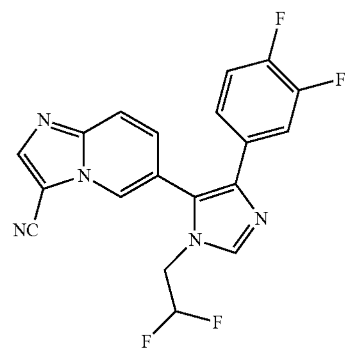 [SMILES: N#Cc1cnc2ccc(-c3c(-c4ccc(F)c(F)c4)ncn3CC(F)F)cn12] | 6-(1-(2,2-difluoroethyl)-4-(3,4-difluorophenyl)-1H-imidazol-5-yl)imidazo[1,2-a]pyridine-3-carbonitrile |
| 227' | 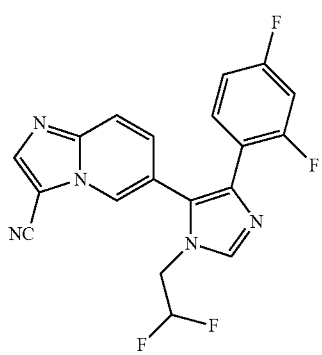 [SMILES: N#Cc1cnc2ccc(-c3c(-c4ccc(F)cc4F)ncn3CC(F)F)cn12] | 6-(1-(2,2-difluoroethyl)-4-(2,4-difluorophenyl)-1H-imidazol-5-yl)imidazo[1,2-a]pyridine-3-carbonitrile |
| 228' | 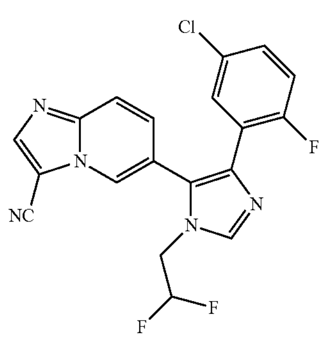 [SMILES: N#Cc1cnc2ccc(-c3c(-c4cc(Cl)ccc4F)ncn3CC(F)F)cn12] | 6-(4-(5-chloro-2-fluorophenyl)-1-(2,2-difluoroethyl)-1H-imidazol-5-yl)imidazo[1,2-a]pyridine-3-carbonitrile |

TABLE A-continued

| No. | Structure | Name |
|---|---|---|
| 229' | 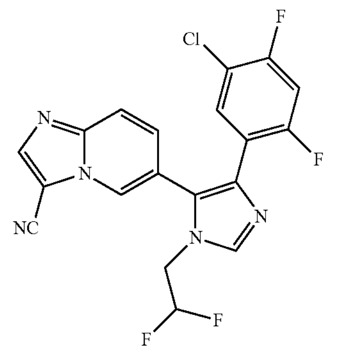 [SMILES: N#Cc1cnc2ccc(-c3c(-c4cc(Cl)c(F)cc4F)ncn3CC(F)F)cn12] | 6-(4-(5-chloro-2,4-difluorophenyl)-1-(2,2-difluoroethyl)-1H-imidazol-5-yl)imidazo[1,2-a]pyridine-3-carbonitrile |
| 230' | 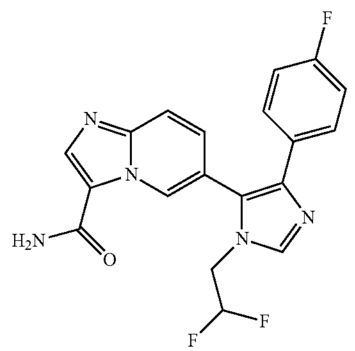 [SMILES: NC(=O)c1cnc2ccc(-c3c(-c4ccc(F)cc4)ncn3CC(F)F)cn12] | 6-(1-(2,2-difluoroethyl)-4-(4-fluorophenyl)-1H-imidazol-5-yl)imidazo[1,2-a]pyridine-3-carboxamide |
| 231' | 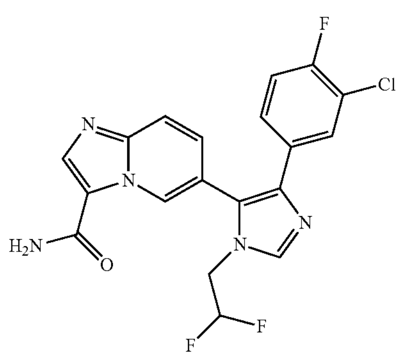 [SMILES: NC(=O)c1cnc2ccc(-c3c(-c4ccc(F)c(Cl)c4)ncn3CC(F)F)cn12] | 6-(4-(3-chloro-4-fluorophenyl)-1-(2,2-difluoroethyl)-1H-imidazol-5-yl)imidazo[1,2-a]pyridine-3-carboxamide |
| 232' | 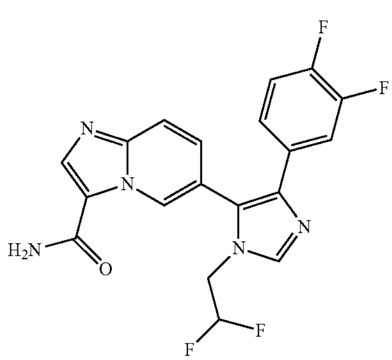 [SMILES: NC(=O)c1cnc2ccc(-c3c(-c4ccc(F)c(F)c4)ncn3CC(F)F)cn12] | 6-(1-(2,2-difluoroethyl)-4-(3,4-difluorophenyl)-1H-imidazol-5-yl)imidazo[1,2-a]pyridine-3-carboxamide |

TABLE A-continued

| No. | Structure | Name |
|---|---|---|
| 233' | 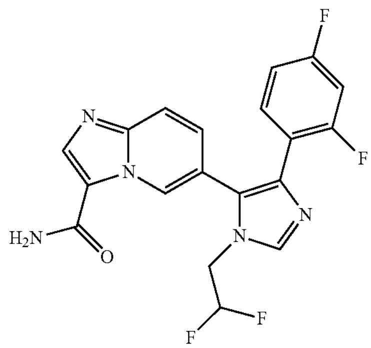 [SMILES: NC(=O)c1cnc2ccc(-c3c(-c4ccc(F)cc4F)ncn3CC(F)F)cn12] | 6-(1-(2,2-difluoroethyl)-4-(2,4-difluorophenyl)-1H-imidazol-5-yl)imidazo[1,2-a]pyridine-3-carboxamide |
| 234' | 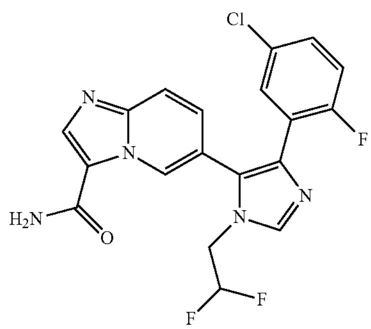 [SMILES: NC(=O)c1cnc2ccc(-c3c(-c4cc(Cl)ccc4F)ncn3CC(F)F)cn12] | 6-(4-(5-chloro-2-fluorophenyl)-1-(2,2-difluoroethyl)-1H-imidazol-5-yl)imidazo[1,2-a]pyridine-3-carboxamide |
| 235' | 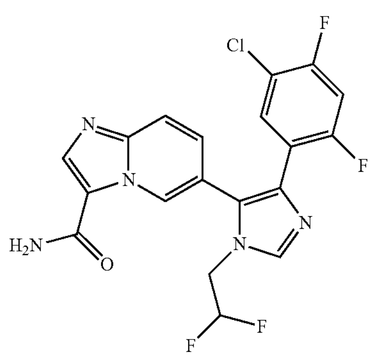 [SMILES: NC(=O)c1cnc2ccc(-c3c(-c4cc(Cl)c(F)cc4F)ncn3CC(F)F)cn12] | 6-(4-(5-chloro-2,4-difluorophenyl)-1-(2,2-difluoroethyl)-1H-imidazol-5-yl)imidazo[1,2-a]pyridine-3-carboxamide |
| 236 | 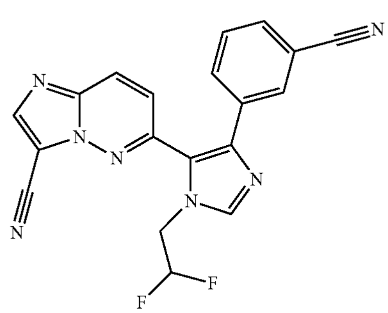 [SMILES: N#Cc1cccc(-c2ncn(CC(F)F)c2-c2ccc3ncc(C#N)n3n2)c1] | 6-(4-(3-cyanophenyl)-1-(2,2-difluoroethyl)-1H-imidazol-5-yl)imidazo[1,2-b]pyridazine-3-carbonitrile |
| 237' | 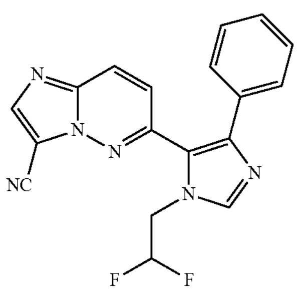 [SMILES: N#Cc1cnc2ccc(-c3c(-c4ccccc4)ncn3CC(F)F)nn12] | 6-(1-(2,2-difluoroethyl)-4-phenyl-1H-imidazol-5-yl)imidazo[1,2-b]pyridazine-3-carbonitrile |

TABLE A-continued

| No. | Structure | Name |
|---|---|---|
| 238' | 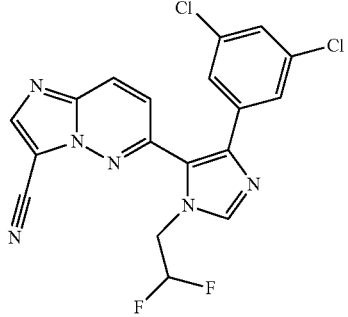 [SMILES: N#Cc1cnc2ccc(-c3c(-c4cc(Cl)cc(Cl)c4)ncn3CC(F)F)nn12] | 6-(4-(3,5-dichlorophenyl)-1-(2,2-difluoro-ethyl)-1H-imidazol-5-yl)imidazo[1,2-b]pyridazine-3-carbonitrile |
| 239' | 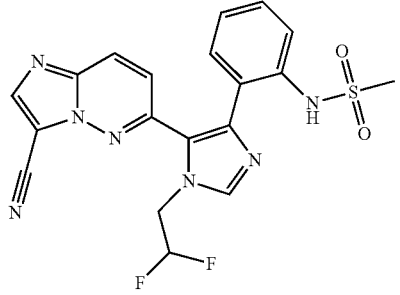 [SMILES: CS(=O)(=O)Nc1ccccc1-c1ncn(CC(F)F)c1-c1ccc2ncc(C#N)n2n1] | N-(2-(5-(3-cyanoimidazo[1,2-b]pyridazin-6-yl)-1-(2,2-difluoroethyl)-1H-imidazol-4-yl)phenyl)methanesulfonamide |
| 240' | 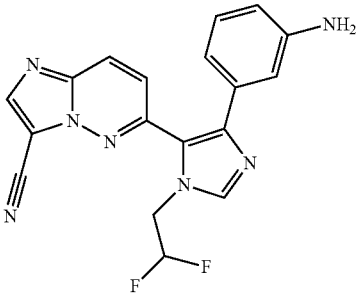 | 6-(4-(3-aminophenyl)-1-(2,2-difluoroethyl)-1H-imidazol-5-yl)imidazo[1,2-b]pyridazine-3-carbonitrile |
| 241' | 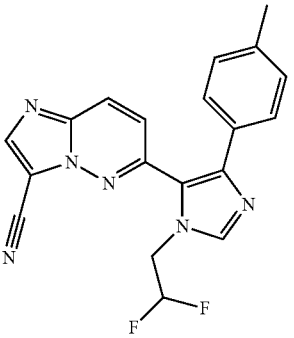 [SMILES: Cc1ccc(-c2ncn(CC(F)F)c2-c2ccc3ncc(C#N)n3n2)cc1] | 6-(1-(2,2-difluoroethyl)-4-(p-tolyl)-1H-imidazol-5-yl)imidazo[1,2-b]pyridazine-3-carbonitrile |

TABLE A-continued

| No. | Structure | Name |
|---|---|---|
| 242' | 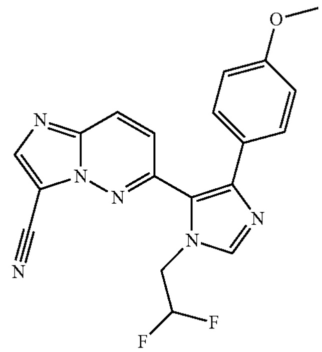 [SMILES: COc1ccc(-c2ncn(CC(F)F)c2-c2ccc3ncc(C#N)n3n2)cc1] | 6-(1-(2,2-difluoroethyl)-4-(4-methoxyphenyl)-1H-imidazol-5-yl)imidazo[1,2-b]pyridazine-3-carbonitrile |
| 243' | 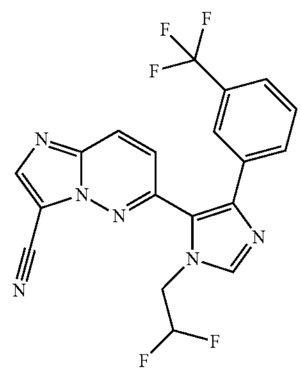 [SMILES: N#Cc1cnc2ccc(-c3c(-c4cccc(C(F)(F)F)c4)ncn3CC(F)F)nn12] | 6-(1-(2,2-difluoroethyl)-4-(3-(trifluoromethyl)phenyl)-1H-imidazol-5-yl)imidazo[1,2-b]pyridazine-3-carbonitrile |
| 244' | 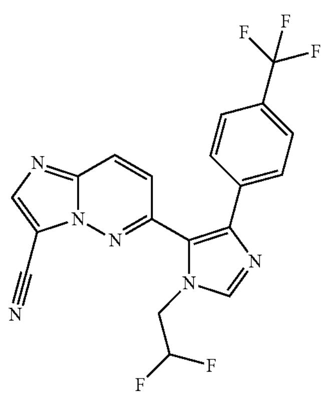 [SMILES: N#Cc1cnc2ccc(-c3c(-c4ccc(C(F)(F)F)cc4)ncn3CC(F)F)nn12] | 6-(1-(2,2-difluoroethyl)-4-(4-(trifluoromethyl)phenyl)-1H-imidazol-5-yl)imidazo[1,2-b]pyridazine-3-carbonitrile |
| 245' | 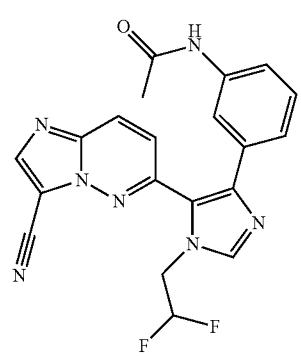 [SMILES: CC(=O)Nc1cccc(-c2ncn(CC(F)F)c2-c2ccc3ncc(C#N)n3n2)c1] | N-(3-(5-(3-cyanoimidazo[1,2-b]pyridazin-6-yl)-1-(2,2-difluoroethyl)-1H-imidazol-4-yl)phenyl)acetamide |

TABLE A-continued

| No. | Structure | Name |
|---|---|---|
| 246' | 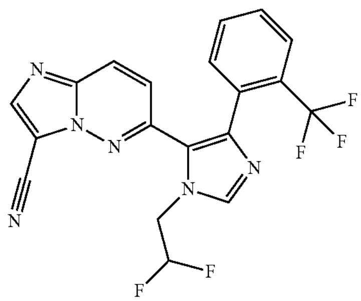 [SMILES: N#Cc1cnc2ccc(-c3c(-c4ccccc4C(F)(F)F)ncn3CC(F)F)nn12] | 6-(1-(2,2-difluoroethyl)-4-(2-(trifluoromethyl)phenyl)-1H-imidazol-5-yl)imidazo[1,2-b]pyridazine-3-carbonitrile |
| 247' | 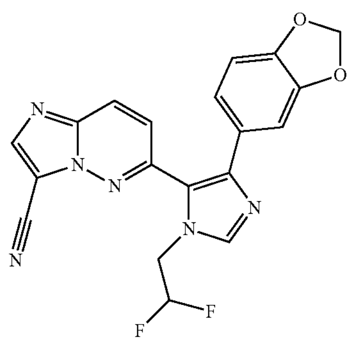 [SMILES: N#Cc1cnc2ccc(-c3c(-c4ccc5c(c4)OCO5)ncn3CC(F)F)nn12] | 6-(4-(benzo[d][1,3]dioxol-5-yl)-1-(2,2-difluoroethyl)-1H-imidazol-5-yl)imidazo[1,2-b]pyridazine-3-carbonitrile |
| 248' | 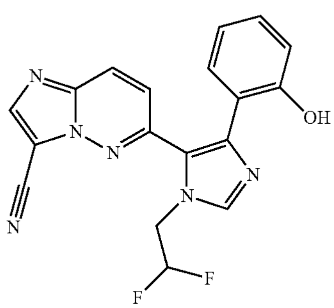 [SMILES: N#Cc1cnc2ccc(-c3c(-c4ccccc4O)ncn3CC(F)F)nn12] | 6-(1-(2,2-difluoroethyl)-4-(2-hydroxyphenyl)-1H-imidazol-5-yl)imidazo[1,2-b]pyridazine-3-carbonitrile |
| 249' | 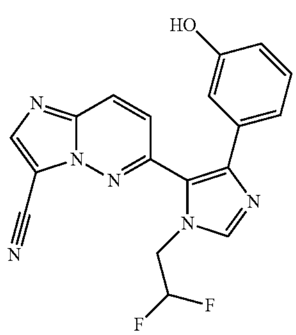 [SMILES: N#Cc1cnc2ccc(-c3c(-c4cccc(O)c4)ncn3CC(F)F)nn12] | 6-(1-(2,2-difluoroethyl)-4-(3-hydroxyphenyl)-1H-imidazol-5-yl)imidazo[1,2-b]pyridazine-3-carbonitrile |

TABLE A-continued

| No. | Structure | Name |
|---|---|---|
| 250' | 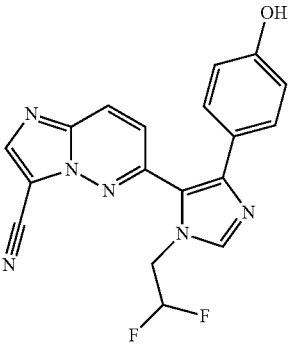 [SMILES: N#Cc1cnc2ccc(-c3c(-c4ccc(O)cc4)ncn3CC(F)F)nn12] | 6-(1-(2,2-difluoroethyl)-4-(4-hydroxyphenyl)-1H-imidazol-5-yl)imidazo[1,2-b]pyridazine-3-carbonitrile |
| 251' | 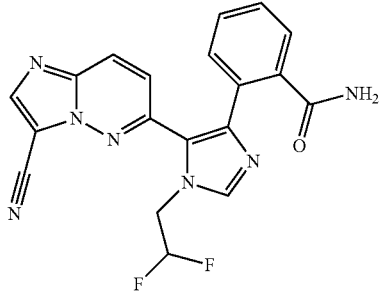 [SMILES: N#Cc1cnc2ccc(-c3c(-c4ccccc4C(N)=O)ncn3CC(F)F)nn12] | 2-(5-(3-cyanoimidazo[1,2-b]pyridazin-6-yl)-1-(2,2-difluoroethyl)-1H-imidazol-4-yl)benzamide |
| 252' | 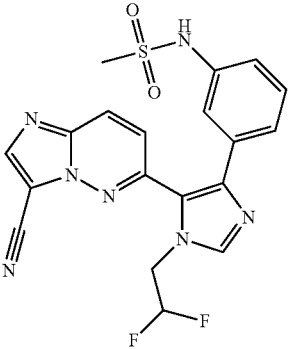 [SMILES: CS(=O)(=O)Nc1cccc(-c2ncn(CC(F)F)c2-c2ccc3ncc(C#N)n3n2)c1] | N-(3-(5-(3-cyanoimidazo[1,2-b]pyridazin-6-yl)-1-(2,2-difluoroethyl)-1H-imidazol-4-yl)phenyl)methanesulfonamide |
| 253' | 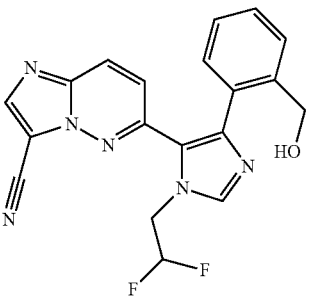 [SMILES: N#Cc1cnc2ccc(-c3c(-c4ccccc4CO)ncn3CC(F)F)nn12] | 6-(1-(2,2-difluoroethyl)-4-(2-(hydroxymethyl)phenyl)-1H-imidazol-5-yl)imidazo[1,2-b]pyridazine-3-carbonitrile |

TABLE A-continued

| No. | Structure | Name |
|---|---|---|
| 254' | 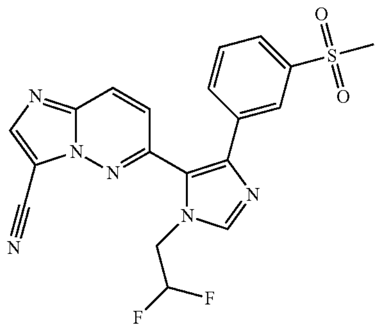 [SMILES: CS(=O)(=O)c1cccc(-c2ncn(CC(F)F)c2-c2ccc3ncc(C#N)n3n2)c1] | 6-(1-(2,2-difluoroethyl)-4-(3-(methyl-sulfonyl)phenyl)-1H-imidazol-5-yl)imidazo[1,2-b]pyridazine-3-carbonitrile |
| 255' | 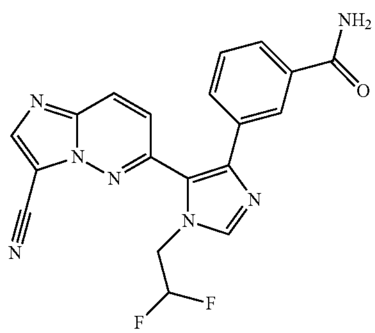 [SMILES: N#Cc1cnc2ccc(-c3c(-c4cccc(C(N)=O)c4)ncn3CC(F)F)nn12] | 3-(5-(3-cyanoimidazo[1,2-b]pyridazin-6-yl)-1-(2,2-difluoroethyl)-1H-imidazol-4-yl)benzamide |
| 256' | 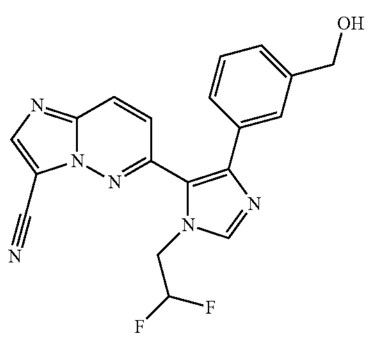 [SMILES: N#Cc1cnc2ccc(-c3c(-c4cccc(CO)c4)ncn3CC(F)F)nn12] | 6-(1-(2,2-difluoroethyl)-4-(3-(hydroxy-methyl)phenyl)-1H-imidazol-5-yl)imidazo[1,2-b]pyridazine-3-carbonitrile |
| 257' | 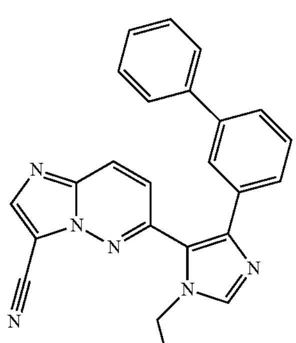 | 6-(4-([1,1'-biphenyl]-3-yl)-1-(2,2-difluoro-ethyl)-1H-imidazol-5-yl)imidazo[1,2-b]pyridazine-3-carbonitrile |

TABLE A-continued

| No. | Structure | Name |
|---|---|---|
| 258' | 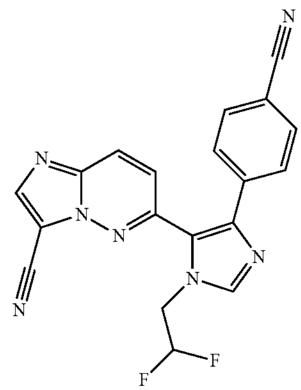 [SMILES: N#Cc1ccc(-c2ncn(CC(F)F)c2-c2ccc3ncc(C#N)n3n2)cc1] | 6-(4-(4-cyanophenyl)-1-(2,2-difluoro-ethyl)-1H-imidazol-5-yl)imidazo[1,2-b]pyridazine-3-carbonitrile |
| 259' | 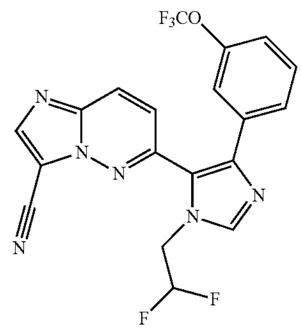 [SMILES: N#Cc1cnc2ccc(-c3c(-c4cccc(OC(F)(F)F)c4)ncn3CC(F)F)nn12] | 6-(1-(2,2-difluoroethyl)-4-(3-(trifluoro-methoxy)phenyl)-1H-imidazol-5-yl)imidazo[1,2-b]pyridazine-3-carbonitrile |
| 260' | 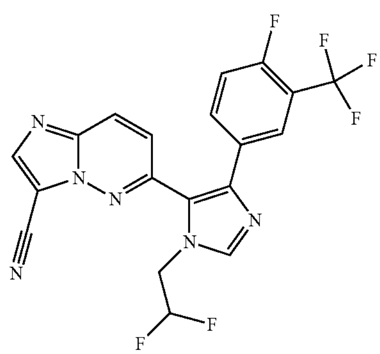 [SMILES: N#Cc1cnc2ccc(-c3c(-c4ccc(F)c(C(F)(F)F)c4)ncn3CC(F)F)nn12] | 6-(1-(2,2-difluoroethyl)-4-(4-fluoro-3-(trifluoromethyl)phenyl)-1H-imidazol-5-yl)imidazo[1,2-b]pyridazine-3-carbonitrile |
| 261' | 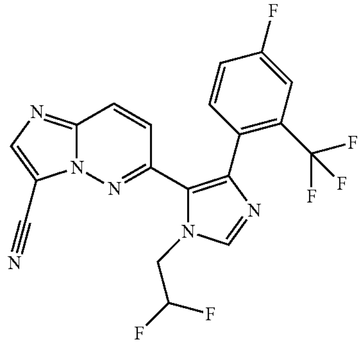 [SMILES: N#Cc1cnc2ccc(-c3c(-c4ccc(F)cc4C(F)(F)F)ncn3CC(F)F)nn12] | 6-(1-(2,2-difluoroethyl)-4-(4-fluoro-2-(trifluoromethyl)phenyl)-1H-imidazol-5-yl)imidazo[1,2-b]pyridazine-3-carbonitrile |

TABLE A-continued

| No. | Structure | Name |
|---|---|---|
| 262' | 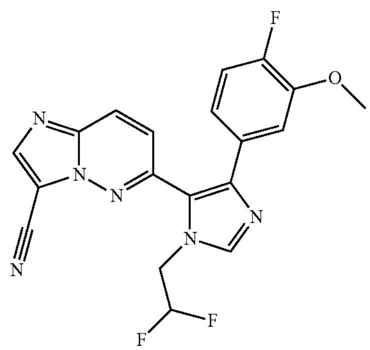 [SMILES: COc1cc(-c2ncn(CC(F)F)c2-c2ccc3ncc(C#N)n3n2)ccc1F] | 6-(1-(2,2-difluoroethyl)-4-(4-fluoro-3-methoxyphenyl)-1H-imidazol-5-yl)imidazo[1,2-b]pyridazine-3-carbonitrile |
| 263' | 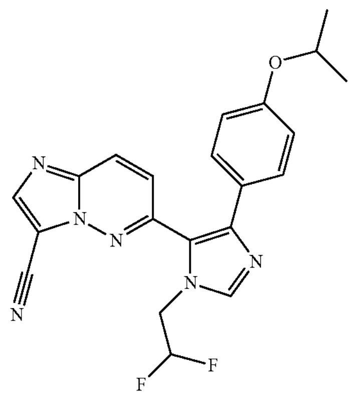 [SMILES: CC(C)Oc1ccc(-c2ncn(CC(F)F)c2-c2ccc3ncc(C#N)n3n2)cc1] | 6-(1-(2,2-difluoroethyl)-4-(4-isopropoxyphenyl)-1H-imidazol-5-yl)imidazo[1,2-b]pyridazine-3-carbonitrile |
| 264' | 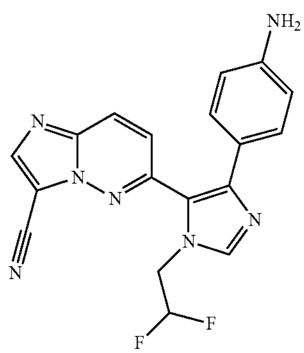 [SMILES: N#Cc1cnc2ccc(-c3c(-c4ccc(N)cc4)ncn3CC(F)F)nn12] | 6-(4-(4-aminophenyl)-1-(2,2-difluoroethyl)-1H-imidazol-5-yl)imidazo[1,2-b]pyridazine-3-carbonitrile |
| 265' | 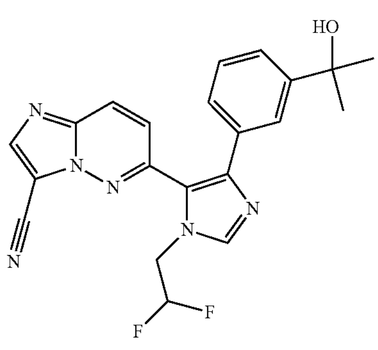 [SMILES: CC(C)(O)c1cccc(-c2ncn(CC(F)F)c2-c2ccc3ncc(C#N)n3n2)c1] | 6-(1-(2,2-difluoroethyl)-4-(3-(2-hydroxypropan-2-yl)phenyl)-1H-imidazol-5-yl)imidazo[1,2-b]pyridazine-3-carbonitrile |

TABLE A-continued

| No. | Structure | Name |
|---|---|---|
| 266' | 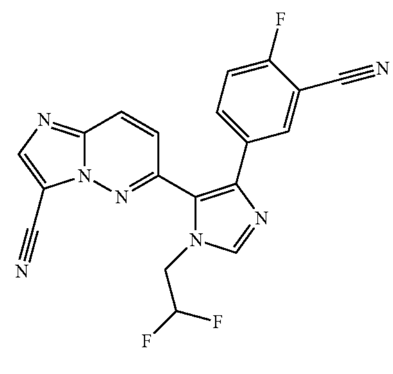 [SMILES: N#Cc1cc(-c2ncn(CC(F)F)c2-c2ccc3ncc(C#N)n3n2)ccc1F] | 6-(4-(3-cyano-4-fluorophenyl)-1-(2,2-difluoroethyl)-1H-imidazol-5-yl)imidazo[1,2-b]pyridazine-3-carbonitrile |
| 267' | 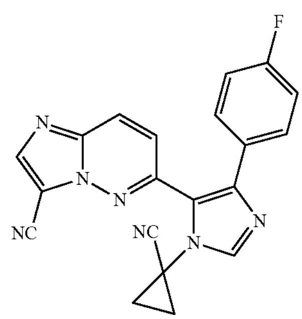 [SMILES: N#Cc1cnc2ccc(-c3c(-c4ccc(F)cc4)ncn3C3(C#N)CC3)nn12] | 6-(1-(1-cyanocyclopropyl)-4-(4-fluorophenyl)-1H-imidazol-5-yl)imidazo[1,2-b]pyridazine-3-carbonitrile |
| 268' | 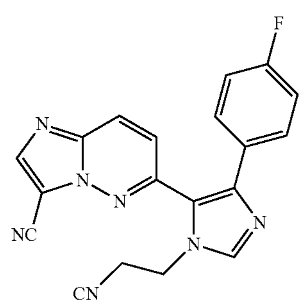 | 6-(1-(2-cyanoethyl)-4-(4-fluorophenyl)-1H-imidazol-5-yl)imidazo[1,2-b]pyridazine-3-carbonitrile |
| 269' | 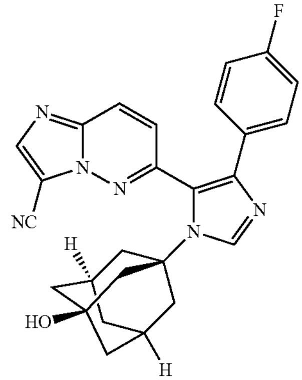 [SMILES: N#Cc1cnc2ccc(-c3c(-c4ccc(F)cc4)ncn3[C@@]34CC5C[C@@H](C[C@@](O)(C5)C3)C4)nn12] | 6-(4-(4-fluorophenyl)-1-((1r,3s,5R,7S)-3-hydroxyadamantan-1-yl)-1H-imidazol-5-yl)imidazo[1,2-b]pyridazine-3-carbonitrile |

TABLE A-continued

| No. | Structure | Name |
| --- | --- | --- |
| 270' | 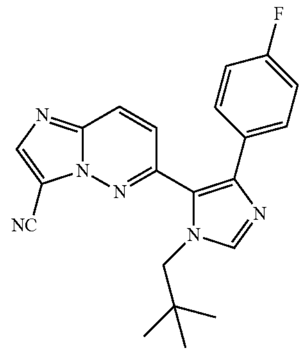 [SMILES: CC(C)(C)Cn1cnc(-c2ccc(F)cc2)c1-c1ccc2ncc(C#N)n2n1] | 6-(4-(4-fluorophenyl)-1-neopentyl-1H-imidazol-5-yl)imidazo[1,2-b]pyridazine-3-carbonitrile |
| 271' | 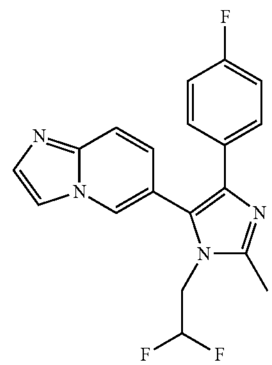 [SMILES: Cc1nc(-c2ccc(F)cc2)c(-c2ccc3nccn3c2)n1CC(F)F] | 6-(1-(2,2-difluoroethyl)-4-(4-fluorophenyl)-2-methyl-1H-imidazol-5-yl)imidazo[1,2-a]pyridine |
| 272' | 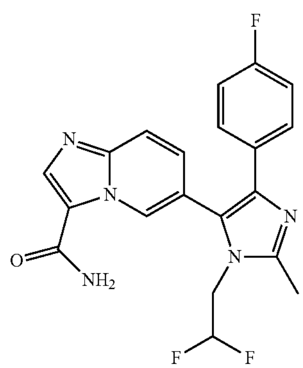 [SMILES: Cc1nc(-c2ccc(F)cc2)c(-c2ccc3ncc(C(N)=O)n3c2)n1CC(F)F] | 6-(1-(2,2-difluoroethyl)-4-(4-fluorophenyl)-2-methyl-1H-imidazol-5-yl)imidazo[1,2-a]pyridine-3-carboxamide |
| 273' | 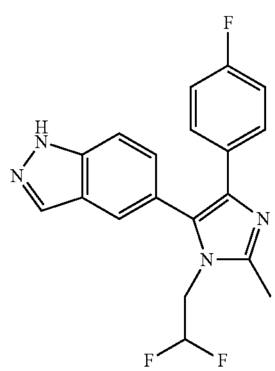 [SMILES: Cc1nc(-c2ccc(F)cc2)c(-c2ccc3[nH]ncc3c2)n1CC(F)F] | 5-(1-(2,2-difluoroethyl)-4-(4-fluorophenyl)-2-methyl-1H-imidazol-5-yl)-1H-indazole |

TABLE A-continued

| No. | Structure | Name |
|---|---|---|
| 274' | 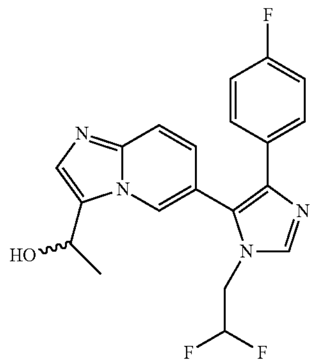 [SMILES: CC(O)c1cnc2ccc(-c3c(-c4ccc(F)cc4)ncn3CC(F)F)cn12] | 1-(6-(1-(2,2-difluoroethyl)-4-(4-fluorophenyl)-1H-imidazol-5-yl)imidazo[1,2-b]pyridin-3-yl)ethanol |
| 275' | 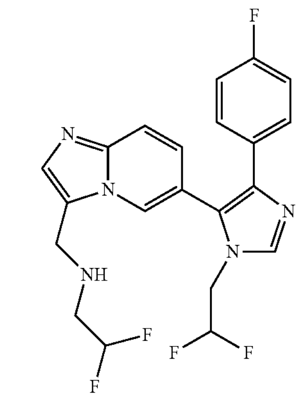 [SMILES: Fc1ccc(-c2ncn(CC(F)F)c2-c2ccc3ncc(CNCC(F)F)n3c2)cc1] | N-((6-(1-(2,2-difluoroethyl)-4-(4-fluorophenyl)-1H-imidazol-5-yl)imidazo[1,2-a]pyridin-3-yl)methyl)-2,2-difluoroethanamine |
| 276' | 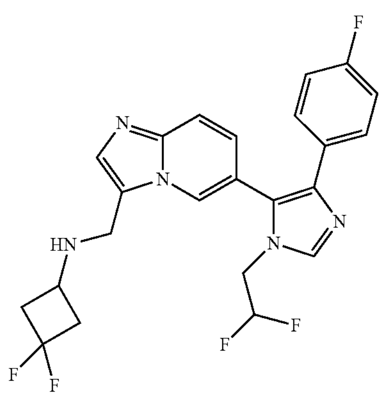 [SMILES: Fc1ccc(-c2ncn(CC(F)F)c2-c2ccc3ncc(CNC4CC(F)(F)C4)n3c2)cc1] | N-((6-(1-(2,2-difluoroethyl)-4-(4-fluorophenyl)-1H-imidazol-5-yl)imidazo[1,2-a]pyridin-3-yl)methyl)-3,3-difluorocyclobutanamine |
| 277' | 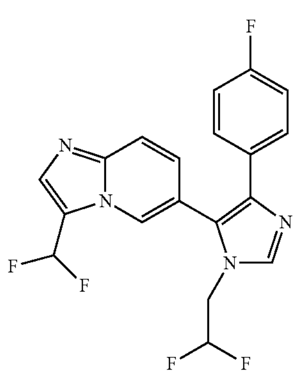 [SMILES: Fc1ccc(-c2ncn(CC(F)F)c2-c2ccc3ncc(C(F)F)n3c2)cc1] | 6-(1-(2,2-difluoroethyl)-4-(4-fluorophenyl)-1H-imidazol-5-yl)-3-(difluoromethyl)imidazo[1,2-a]pyridine |

TABLE A-continued

| No. | Structure | Name |
|---|---|---|
| 278' | 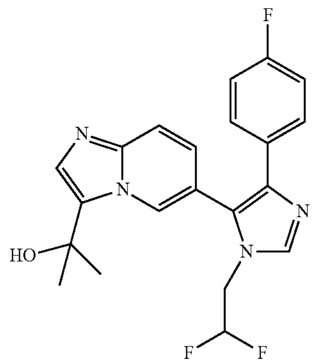 [SMILES: CC(C)(O)c1cnc2ccc(-c3c(-c4ccc(F)cc4)ncn3CC(F)F)cn12] | 1-(6-(1-(2,2-difluoroethyl)-4-(4-fluorophenyl)-1H-imidazol-5-yl)imidazo[1,2-a]pyridin-3-yl)ethanol |
| 279' | 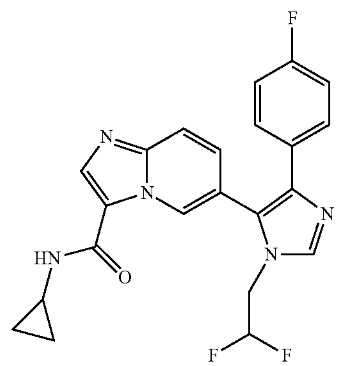 [SMILES: O=C(NC1CC1)c1cnc2ccc(-c3c(-c4ccc(F)cc4)ncn3CC(F)F)cn12] | N-cyclopropyl-6-(1-(2,2-difluoroethyl)-4-(4-fluorophenyl)-1H-imidazol-5-yl)imidazo[1,2-a]pyridine-3-carboxamide |
| 280' | 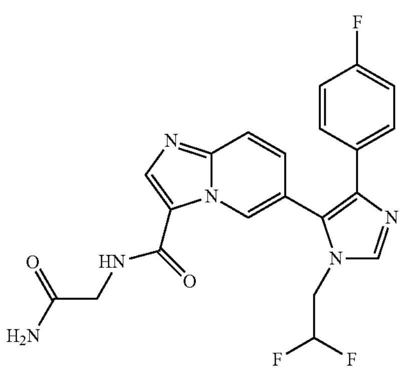 [SMILES: NC(=O)CNC(=O)c1cnc2ccc(-c3c(-c4ccc(F)cc4)ncn3CC(F)F)cn12] | N-(2-amino-2-oxoethyl)-6-(1-(2,2-difluoroethyl)-4-(4-fluorophenyl)-1H-imidazol-5-yl)imidazo[1,2-a]pyridine-3-carboxamide |
| 281' | 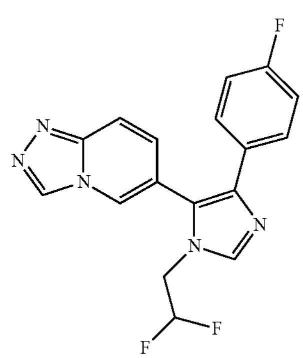 [SMILES: Fc1ccc(-c2ncn(CC(F)F)c2-c2ccc3nncn3c2)cc1] | 6-(1-(2,2-difluoroethyl)-4-(4-fluorophenyl)-1H-imidazol-5-yl)-[1,2,4]triazolo[4,3-a]pyridine |

TABLE A-continued

| No. | Structure | Name |
| --- | --- | --- |
| 282' | 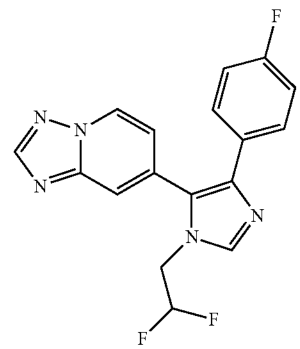 [SMILES: Fc1ccc(-c2ncn(CC(F)F)c2-c2ccn3ncnc3c2)cc1] | 7-(1-(2,2-difluoroethyl)-4-(4-fluorophenyl)-1H-imidazol-5-yl)-[1,2,4]triazolo[1,5-a]pyridine |
| 283' | 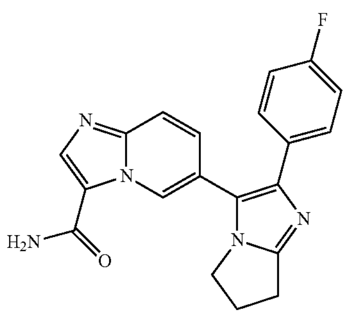 [SMILES: NC(=O)c1cnc2ccc(-c3c(-c4ccc(F)cc4)nc4n3CCC4)cn12] | 6-(2-(4-fluorophenyl)-6,7-dihydro-5H-pyrrolo[1,2-a]imidazol-3-yl)imidazo[1,2-a]pyridine-3-carboxamide |
| 284' | 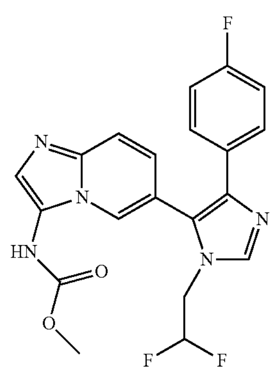 [SMILES: COC(=O)Nc1cnc2ccc(-c3c(-c4ccc(F)cc4)ncn3CC(F)F)cn12] | methyl (6-(1-(2,2-difluoroethyl)-4-(4-fluorophenyl)-1H-imidazol-5-yl)imidazo[1,2-a]pyridin-3-yl)carbamate |
| 285' | 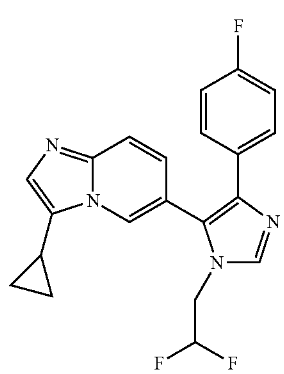 [SMILES: Fc1ccc(-c2ncn(CC(F)F)c2-c2ccc3ncc(C4CC4)n3c2)cc1] | 3-cyclopropyl-6-(1-(2,2-difluoroethyl)-4-(4-fluorophenyl)-1H-imidazol-5-yl)imidazo[1,2-a]pyridine |

TABLE A-continued

| No. | Structure | Name |
|---|---|---|
| 286' | 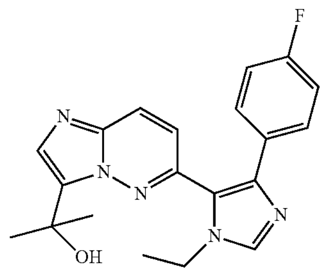 [SMILES: CCn1cnc(-c2ccc(F)cc2)c1-c1ccc2ncc(C(C)(C)O)n2n1] | 2-(6-(1-ethyl-4-(4-fluorophenyl)-1H-imidazol-5-yl)imidazo[1,2-b]pyridazin-3-yl)propan-2-ol |
| 287' | 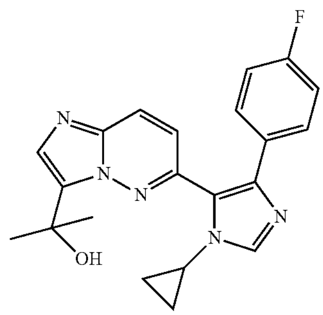 [SMILES: CC(C)(O)c1cnc2ccc(-c3c(-c4ccc(F)cc4)ncn3C3CC3)nn12] | 2-(6-(1-cyclopropyl-4-(4-fluorophenyl)-1H-imidazol-5-yl)imidazo[1,2-b]pyridazin-3-yl)propan-2-ol |
| 288' | 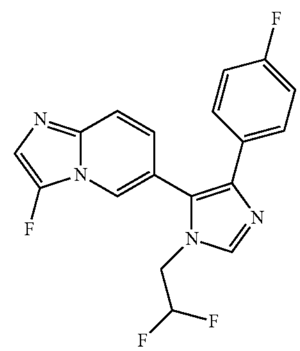 [SMILES: Fc1ccc(-c2ncn(CC(F)F)c2-c2ccc3ncc(F)n3c2)cc1] | 6-(1-(2,2-difluoroethyl)-4-(4-fluorophenyl)-1H-imidazol-5-yl)-3-fluoro-imidazo[1,2-a]pyridine |
| 289' | 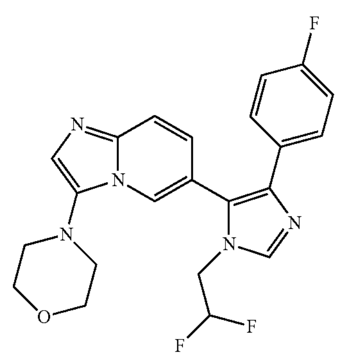 [SMILES: Fc1ccc(-c2ncn(CC(F)F)c2-c2ccc3ncc(N4CCOCC4)n3c2)cc1] | 4-(6-(1-(2,2-difluoroethyl)-4-(4-fluorophenyl)-1H-imidazol-5-yl)imidazo[1,2-a]pyridin-3-yl)morpholine |
| 290' | 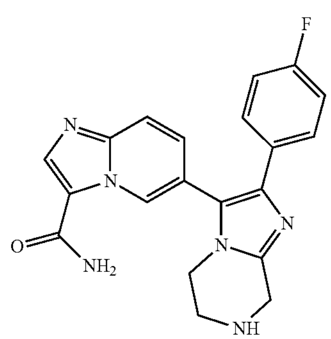 [SMILES: NC(=O)c1cnc2ccc(-c3c(-c4ccc(F)cc4)nc4n3CCNC4)cn12] | 6-(2-(4-fluorophenyl)-5,6,7,8-tetrahydro-imidazo[1,2-a]pyrazin-3-yl)imidazo[1,2-a]pyridine-3-carboxamide |

TABLE A-continued

| No. | Structure | Name |
|---|---|---|
| 291' | 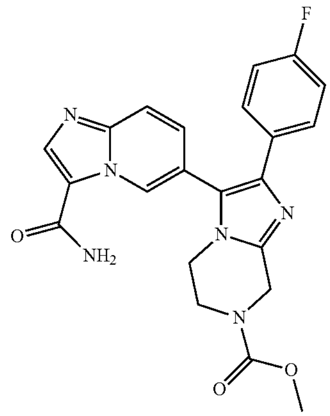 [SMILES: COC(=O)N1CCn2c(nc(-c3ccc(F)cc3)c2-c2ccc3ncc(C(N)=O)n3c2)C1] | methyl 3-(3-carbamoylimidazo[1,2-a]pyridin-6-yl)-2-(4-fluorophenyl)-5,6-dihydroimidazo[1,2-a]pyrazine-7(8H)-carboxylate |
| 292' | 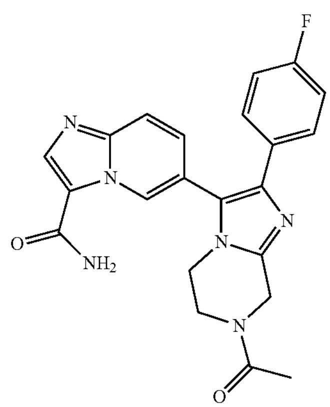 [SMILES: CC(=O)N1CCn2c(nc(-c3ccc(F)cc3)c2-c2ccc3ncc(C(N)=O)n3c2)C1] | 6-(7-acetyl-2-(4-fluorophenyl)-5,6,7,8-tetrahydroimidazo[1,2-a]pyrazin-3-yl)imidazo[1,2-a]pyridine-3-carboxamide |
| 293' | 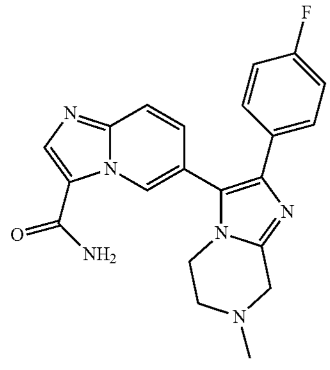 [SMILES: CN1CCn2c(nc(-c3ccc(F)cc3)c2-c2ccc3ncc(C(N)=O)n3c2)C1] | 6-(2-(4-fluorophenyl)-7-methyl-5,6,7,8-tetrahydroimidazo[1,2-a]pyrazin-3-yl)imidazo[1,2-a]pyridine-3-carboxamide |

TABLE A-continued

| No. | Structure | Name |
|---|---|---|
| 294' | 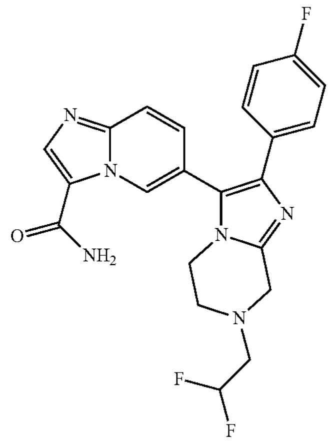 [SMILES: NC(=O)c1cnc2ccc(-c3c(-c4ccc(F)cc4)nc4n3CCN(CC(F)F)C4)cn12] | 6-(7-(2,2-difluoroethyl)-2-(4-fluorophenyl)-5,6,7,8-tetrahydroimidazo[1,2-a]pyrazin-3-yl)imidazo[1,2-a]pyridine-3-carboxamide |
| 295' | 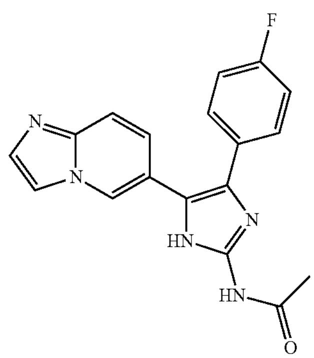 [SMILES: CC(=O)Nc1nc(-c2ccc(F)cc2)c(-c2ccc3nccn3c2)[nH]1] | N-(4-(4-fluorophenyl)-5-(imidazo[1,2-a]pyridin-6-yl)-1H-imidazol-2-yl)acetamide |
| 296' | 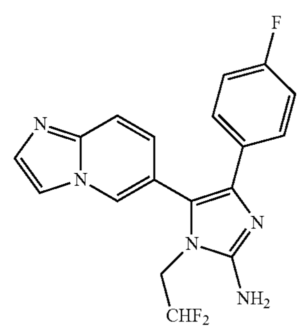 [SMILES: Nc1nc(-c2ccc(F)cc2)c(-c2ccc3nccn3c2)n1CC(F)F] | 1-(2,2-difluoroethyl)-4-(4-fluorophenyl)-5-(imidazo[1,2-a]pyridin-6-yl)-1H-imidazol-2-amine |
| 297' | 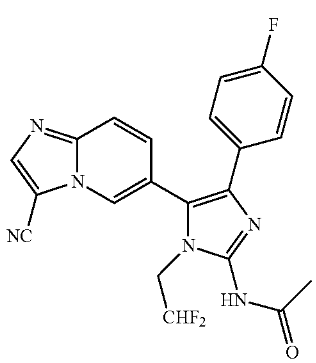 [SMILES: CC(=O)Nc1nc(-c2ccc(F)cc2)c(-c2ccc3ncc(C#N)n3c2)n1CC(F)F] | N-(5-(3-cyanoimidazo[1,2-a]pyridin-6-yl)-1-(2,2-difluoroethyl)-4-(4-fluorophenyl)-1H-imidazol-2-yl)acetamide |

TABLE A-continued

| No. | Structure | Name |
|---|---|---|
| 298' | 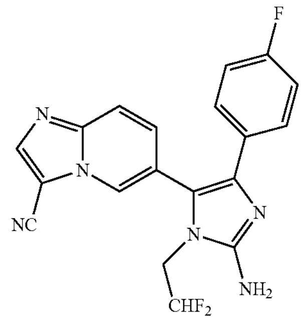 [SMILES: N#Cc1cnc2ccc(-c3c(-c4ccc(F)cc4)nc(N)n3CC(F)F)cn12] | 6-(2-amino-1-(2,2-difluoroethyl)-4-(4-fluorophenyl)-1H-imidazol-5-yl)imidazo[1,2-a]pyridine-3-carbonitrile |
| 190C' | 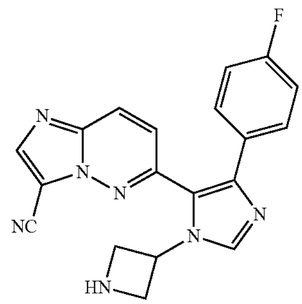 [SMILES: N#Cc1cnc2ccc(-c3c(-c4ccc(F)cc4)ncn3C3CNC3)nn12] | 6-(1-(azetidin-3-yl)-4-(4-fluorophenyl)-1H-imidazol-5-yl)imidazo[1,2-b]pyridazine-3-carbonitrile |
| 195A' | 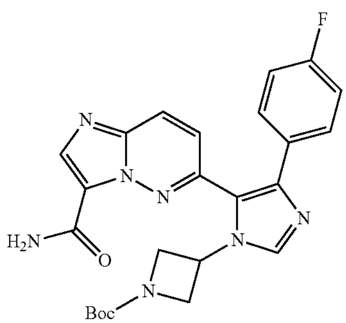 [SMILES: CC(C)(C)OC(=O)N1CC(n2cnc(-c3ccc(F)cc3)c2-c2ccc3ncc(C(N)=O)n3n2)C1] | tert-butyl 3-(5-(3-carbamoylimidazo[1,2-b]pyridazin-6-yl)-4-(4-fluorophenyl)-1H-imidazol-1-yl)azetidine-1-carboxylate |
| 195B' | 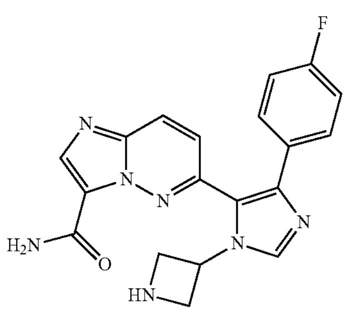 [SMILES: NC(=O)c1cnc2ccc(-c3c(-c4ccc(F)cc4)ncn3C3CNC3)nn12] | 6-(1-(azetidin-3-yl)-4-(4-fluorophenyl)-1H-imidazol-5-yl)imidazo[1,2-b]pyridazine-3-carboxamide |
| 196A' | 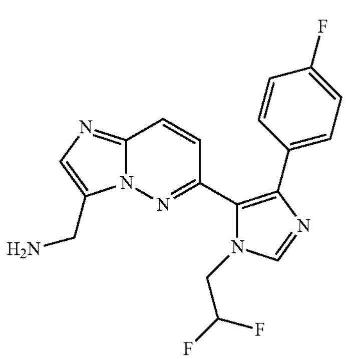 [SMILES: NCc1cnc2ccc(-c3c(-c4ccc(F)cc4)ncn3CC(F)F)nn12] | (6-(1-(2,2-difluoroethyl)-4-(4-fluorophenyl)-1H-imidazol-5-yl)imidazo[1,2-b]pyridazin-3-yl)methanamine |

TABLE A-continued

| No. | Structure | Name |
|---|---|---|
| 213E' | 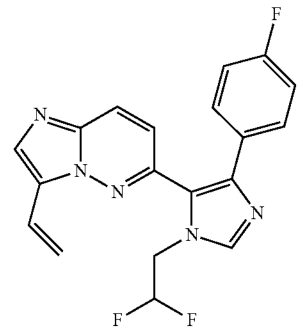 [SMILES: C=Cc1cnc2ccc(-c3c(-c4ccc(F)cc4)ncn3CC(F)F)nn12] | 6-(1-(2,2-difluoroethyl)-4-(4-fluorophenyl)-1H-imidazol-5-yl)-3-vinyl-imidazo[1,2-b]pyridazine |
| 272A' | 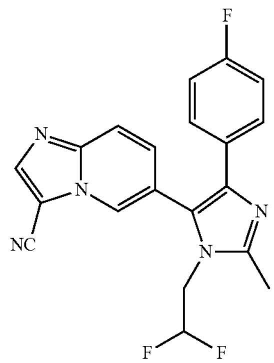 [SMILES: Cc1nc(-c2ccc(F)cc2)c(-c2ccc3ncc(C#N)n3c2)n1CC(F)F] | 6-(1-(2,2-difluoroethyl)-4-(4-fluorophenyl)-2-methyl-1H-imidazol-5-yl)imidazo[1,2-a]pyridine-3-carbonitrile |
| 274C' | 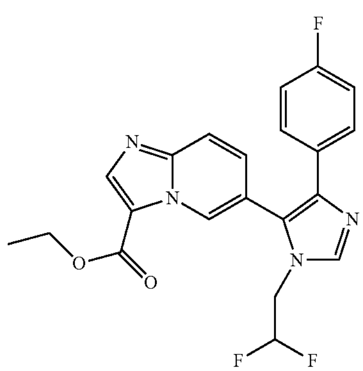 [SMILES: CCOC(=O)c1cnc2ccc(-c3c(-c4ccc(F)cc4)ncn3CC(F)F)cn12] | ethyl 6-(1-(2,2-difluoroethyl)-4-(4-fluorophenyl)-1H-imidazol-5-yl)imidazo[1,2-a]pyridine-3-carboxylate |
| 274D' | 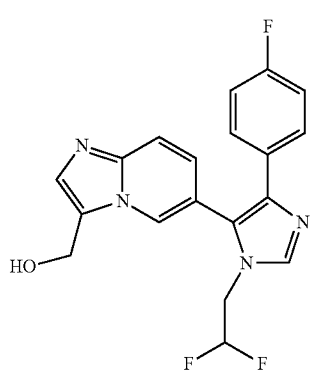 [SMILES: OCc1cnc2ccc(-c3c(-c4ccc(F)cc4)ncn3CC(F)F)cn12] | (6-(1-(2,2-difluoroethyl)-4-(4-fluorophenyl)-1H-imidazol-5-yl)imidazo[1,2-a]pyridin-3-yl)methanol |

TABLE A-continued

| No. | Structure | Name |
|---|---|---|
| 283B' | 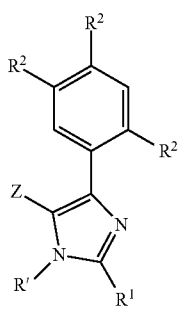 | 6-(2-(4-fluorophenyl)-6,7-dihydro-5H-pyrrolo[1,2-a]imidazol-3-yl)imidazo[1,2-a]pyridine-3-carbonitrile |
| 284D' | 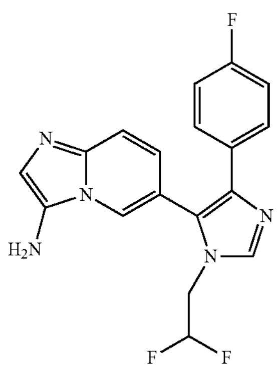 [SMILES: Nc1cnc2ccc(-c3c(-c4ccc(F)cc4)ncn3CC(F)F)cn12] | 6-(1-(2,2-difluoroethyl)-4-(4-fluorophenyl)-1H-imidazol-5-yl)imidazo[1,2-a]pyridin-3-amine |

In embodiment II° of this aspect, the invention comprises compounds having the structure of formula (II°):

$$(II°)$$

or a pharmaceutically acceptable salt, prodrug or N-oxide thereof, or solvate or hydrate thereof, wherein R' is hydrogen, $C_1$-$C_6$alkyl, $C_1$-$C_6$ haloalkyl, —($C_0$-$C_{12}$alkyl)-Cak or —($C_0$-$C_6$alkyl)-Hca, each optionally substituted with 1 to 3 moieties that are each independently $C_1$-$C_6$alkyl, halogen, $C_1$-$C_6$ haloalkyl, $C_1$-$C_6$alkyl-$OR^{S0}$, —$OR^{S0}$, —$R^{S0}$ or cyano;

wherein each $R^{S0}$ is independently hydrogen, $C_1$-$C_6$alkyl, $C_1$-$C_6$ haloalkyl, —($C_0$-$C_6$alkyl)-Ar, —($C_0$-$C_6$alkyl)-Het, —($C_0$-$C_6$alkyl)-Cak, or —($C_0$-$C_6$alkyl)-Hca, wherein Ar, Het, Cak, Hca, alkyl, and haloalkyl are optionally substituted with $C_1$-$C_6$alkyl, halogen, $C_1$-$C_6$ haloalkyl or cyano;

$R^1$ is hydrogen or $C_1$-$C_6$alkyl;

or R' and $R^1$ combined with the atoms to which they are attached form a five- to eight-membered Hca;

each $R^2$ is independently hydrogen, halogen, —$C_1$-$C_6$alkyl, —$C_1$-$C_6$alkyl-$OR^{S2}$ or —$OR^{S2}$;

Z is a fused bicyclic ring of the formula,

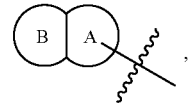

wherein
ring A is 6-membered Het, and
ring B is a 5-membered Het; and

Z is optionally substituted by one or two —$R^Z$ groups that are each independently halogen, cyano, $C_{1-6}$alkyl, $C_{1-6}$alkenyl, $C_{1-6}$ haloalkyl, —$C_1$-$C_6$alkoxy, —($C_0$-$C_6$alkyl)-Het, —($C_0$-$C_6$alkyl)-Hca, —$OR^{S3}$, —$SR^{S3}$, —$NR^{S3}_2$, —$C(O)R^{S3}$, —$C(O)OR^{S3}$, —$C(O)NR^{S3}_2$, —$C(NR^{S3})NR^{S3}OR^{S3}$, —$S(O)_2NR^{S3}_2$, —$S(O)_2R^{S3}$, —$OC(O)R^{S3}$, —$N(R^{S3})C(O)R^{S3}$, —$OC(O)OR^{S3}$, —$OC(O)NR^{S3}_2$, —$N(R^{S3})C(O)OR^{S3}$, —$N(R^{S3})C(O)NR^{S3}_2$, —$N(R^{S3})S(O)_2R^{S3}$, —$OP(O)(OR^{S3})_2$ or —$CH_2$—$OP(O)(OR^{S3})$, wherein each alkyl, haloalkyl and alkoxy is optionally substituted by one or two —$R^{Z2}$ groups;

wherein each $R^{S3}$ is independently hydrogen, —$NR^{S3}_2$, —$OR^{S3}$, $C_1$-$C_6$alkyl, $C_1$-$C_6$ haloalkyl, —($C_0$-$C_6$alkyl)-Ar, —($C_0$-$C_6$alkyl)-Het, —($C_0$-$C_6$alkyl)-Cak, or —($C_0$-$C_6$alkyl)-Hca, wherein Ar, Het, Cak, Hca, alkyl, and haloalkyl are optionally substituted with $C_1$-$C_6$alkyl, halogen, $C_1$-$C_6$ haloalkyl, —C(O)$NR^{S4}_2$ or cyano; and each —$R^{Z2}$ is independently halogen, cyano, $C_1$-$C_6$alkyl, $C_1$-$C_6$ haloalkyl, —$C_1$-$C_6$alkoxy, —$OR^{S4}$, —$SR^{S4}$, —$NR^{S4}_2$, —$C(O)R^{S4}$, —$C(O)OR^{S4}$, —$C(O)NR^{S4}_2$, —$S(O)_2NR^{S4}_2$, —$S(O)_2R^{S4}$, —OC(O)R$^{S4}$, —N(R$^{S4}$)C(O)R$^{S4}$, —OC(O)OR$^{S4}$, —OC(O)NR$^{S4}_2$, —N(R$^{S4}$)C(O)OR$^{S4}$, —N(R$^{S4}$)C(O)NR$^{S4}_2$, —N(R$^{S4}$)S(O)$_2$R$^{S4}$, —OP(O)(OR$^{S4}$)$_2$ or —CH$_2$—OP(O)(OR$^{S4}$); and wherein each R$^{S4}$ is independently hydrogen, $C_1$-$C_6$alkyl, $C_1$-$C_6$ haloalkyl, —($C_0$-$C_6$alkyl)-Ar, —($C_0$-$C_6$alkyl)-Het, —($C_0$-$C_6$alkyl)-Cak, or —($C_0$-$C_6$alkyl)-Hca, wherein Ar, Het, Cak, Hca, alkyl, and haloalkyl are optionally substituted with one or two $C_1$-$C_6$alkyl, halogen, $C_1$-$C_6$ haloalkyl or cyano.

In embodiment Ih of this aspect, the invention comprises compounds having the structure of formula (II):

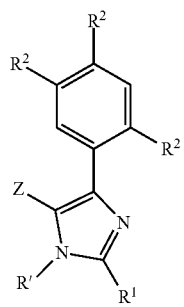

(II)

or a pharmaceutically acceptable salt, prodrug or N-oxide thereof, or solvate or hydrate thereof, wherein
R' is hydrogen or $C_1$-$C_6$alkyl;
R$^1$ is hydrogen or $C_1$-$C_6$alkyl;
each R$^2$ is independently hydrogen, halogen or —$C_1$-$C_6$alkyl;
Z is
(a) a fused bicyclic ring of the formula,

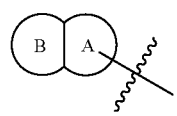

wherein
ring A is 6-membered Het, and
ring B is a 5-membered Het; or
(b)

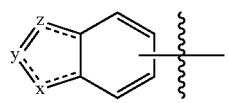

wherein
z is CH, O, S or N;
y is CH, CH$_2$, or N; and
x is CH, O, S, N(R$^a$);
provided that when z is N and x is N(R$^a$), y is not N;
wherein R$^a$ is hydrogen or —$C_1$-$C_6$alkyl.

In embodiment II$_2$ of this aspect, the invention comprises compounds of embodiment II$_1$, wherein Z is a fused bicyclic ring of the formula,

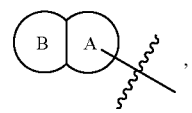

wherein
ring A is 6-membered Het, and
ring B is a 5-membered Het.

In embodiment II$_3$ of this aspect, the invention comprises compounds of embodiment II$_1$, wherein
Z is a

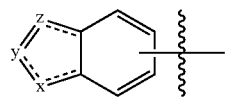

wherein
z is CH, O, S or N;
y is CH, CH$_2$, or N; and
x is CH, O, S, N(R$^a$);
wherein R$^a$ is hydrogen or —$C_1$-$C_6$alkyl;
provided that when z is N and x is N(R$^a$), y is not N.

In embodiment II$_4$, the compounds of the invention are one of formulae (IIa)-(IIj);

(IIa)
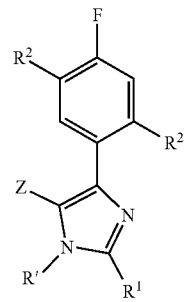

(IIb)
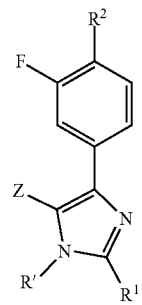

(IIc)
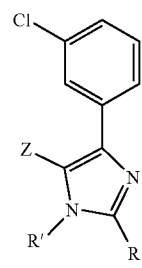

-continued

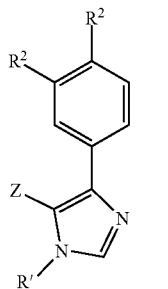

(IId)

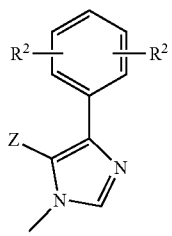

(IIe)

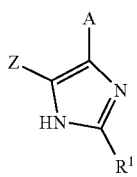

(IIf)

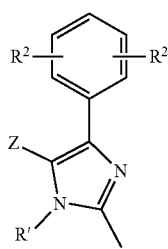

(IIg)

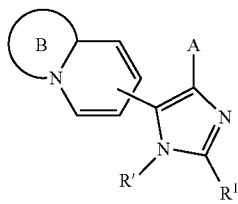

(IIh)

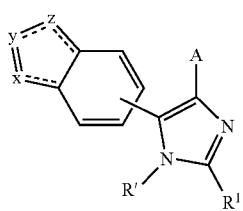

(IIi)

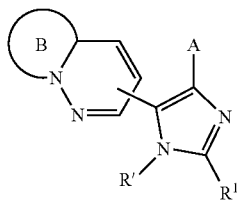

(IIj)

wherein A, $R^1$, $R^2$, R' and Z are as defined in embodiments II° and $II_1$-$II_3$ above.

Particular embodiments of this aspect of the invention comprise compounds of any one of the formulae (II°), (II), and (IIa)-(IIj), each as defined in each of the following rows (or a pharmaceutically acceptable salt, prodrug, or N-oxide thereof, or a solvate or hydrate thereof), wherein each entry is a group number as defined above (e.g., (4z) refers to $R^1$ is methyl), and a dash "-" indicates that the variable is as defined in embodiment $I_1$ or defined according to any one of the applicable variable definitions (1a)-(1ddd), (2a)-(2ccc), (3a)-(3kk) and (4a)-(4 gg) [e.g., when $R^1$ is a dash, it can be either as defined in any of embodiments $II_1$-$II_4$ or any one of the applicable definitions (4a)-(4 gg)]:

|        | (II)  | A      | Z      | R'    | $R^1$ |
|--------|-------|--------|--------|-------|-------|
| (2)-1  | (IIa) | (1a)   | (2a)   | (3a)  | (4a)  |
| (2)-2  | (IIb) | (1c)   | (2b)   | (3i)  | (4f)  |
| (2)-3  | (IIc) | (1d)   | (2g)   | (3j)  | (4j)  |
| (2)-4  | (IId) | (1e)   | (2i)   | (3k)  | (4l)  |
| (2)-5  | (IIe) | (1h)   | (2a)   | (3l)  | (4r)  |
| (2)-6  | (IIf) | (1k)   | (2q)   | (3m)  | (4u)  |
| (2)-7  | (IIg) | (1l)   | (2r)   | (3n)  | (4v)  |
| (2)-8  | (IIh) | (1n)   | (2t)   | (3o)  | (4x)  |
| (2)-9  | (IIi) | (1s)   | (2x)   | (3p)  | (4y)  |
| (2)-10 | (IIf) | (1gg)  | (2y)   | (3i)  | (4z)  |
| (2)-11 | (IIb) | (1jj)  | (2aa)  | (3j)  | (4r)  |
| (2)-12 | (IIc) | (1kk)  | (2ff)  | (3k)  | (4u)  |
| (2)-13 | (IId) | (1ll)  | (2qq)  | (3l)  | (4v)  |
| (2)-14 | (IIf) | (1mm)  | (2tt)  | (3j)  | (4v)  |
| (2)-15 | (IIb) | (1ss)  | (2vv)  | (3k)  | (4a)  |
| (2)-16 | (IIc) | (1tt)  | (2g)   | (3l)  | (4f)  |
| (2)-17 | (IId) | (1uu)  | (2i)   | (3m)  | (4j)  |
| (2)-18 | (IIc) | (1xx)  | (2a)   | (3n)  | (4l)  |
| (2)-19 | (IId) | (1aaa) | (2q)   | (3o)  | (4r)  |
| (2)-20 | (IIe) | (1bbb) | (2ff)  | (3p)  | (4u)  |
| (2)-21 | (IIf) | (1ccc) | (2qq)  | (3n)  | (4v)  |
| (2)-22 | (IIg) | (1aaa) | (2qq)  | (3o)  | (4x)  |
| (2)-23 | (IIh) | (1bbb) | (2ff)  | (3p)  | (4y)  |
| (2)-24 | (IIi) | (1ccc) | (2qq)  | (3n)  | (4z)  |
| (2)-25 | (IIf) | (1uu)  | (2i)   | (3o)  | (4r)  |
| (2)-26 | (IIb) | (1xx)  | (2a)   | (3p)  | (4u)  |
| (2)-27 | (IIc) | (1s)   | (2q)   | (3j)  | (4v)  |
| (2)-28 | (IId) | (1gg)  | (2ff)  | (3k)  | (4j)  |
| (2)-29 | (IIc) | (1d)   | (2qq)  | (3l)  | (4l)  |
| (2)-30 | (IId) | (1a)   | (2b)   | (3m)  | (4j)  |
| (2)-31 | (IIb) | (1c)   | (2g)   | (3n)  | (4l)  |
| (2)-32 | (IIc) | (1d)   | (2i)   | (3o)  | (4r)  |
| (2)-33 | (IId) | (1s)   | (2a)   | (3p)  | (4r)  |
| (2)-34 | (IIe) | (1bbb) | (2q)   | (3n)  | (4j)  |
| (2)-35 | (IIf) | (1ccc) | (2r)   | (3o)  | (4l)  |
| (2)-36 | (IIg) | (1d)   | (2t)   | (3p)  | (4r)  |
| (2)-37 | (IIh) | (1e)   | (2x)   | (3j)  | (4f)  |
| (2)-38 | (IIi) | (1h)   | (2y)   | (3k)  | (4j)  |
| (2)-39 | (IIc) | (1k)   | (2aa)  | (3l)  | (4l)  |
| (2)-40 | (IId) | (1l)   | (2ff)  | (3a)  | (4l)  |
| (2)-41 | (IIb) | (1n)   | (2vv)  | (3i)  | (4r)  |
| (2)-42 | (IIc) | (1s)   | (2g)   | (3j)  | (4f)  |
| (2)-43 | (IId) | (1gg)  | (2i)   | (3k)  | (4j)  |
| (2)-44 | (IIc) | (1jj)  | (2a)   | (3l)  | (4l)  |
| (2)-45 | (IId) | (1kk)  | (2q)   | (3m)  | (4r)  |
| (2)-46 | (IIb) | (1ll)  | (2a)   | (3n)  | (4a)  |
| (2)-47 | (IIc) | (1mm)  | (2b)   | (3o)  | (4f)  |
| (2)-48 | (IId) | (1ss)  | (2g)   | (3p)  | (4j)  |
| (2)-49 | (IIe) | (1tt)  | (2i)   | (3n)  | (4l)  |
| (2)-50 | (IIf) | (1uu)  | (2a)   | (3j)  | (4r)  |
| (2)-51 | (IIg) | (1xx)  | (2q)   | (3k)  | (4u)  |
| (2)-52 | (IIh) | (1aaa) | (2r)   | (3l)  | (4v)  |
| (2)-53 | (IIi) | (1bbb) | (2t)   | (3m)  | (4x)  |
| (2)-54 | (IIf) | (1ccc) | (2x)   | (3i)  | (4y)  |
| (2)-55 | (IIb) | (1l)   | (2y)   | (3j)  | (4z)  |
| (2)-56 | (IIc) | (1n)   | (2aa)  | (3k)  | (4r)  |
| (2)-57 | (IId) | (1s)   | (2ff)  | (3l)  | (4u)  |
| (2)-58 | (IIc) | (1a)   | (2qq)  | (3m)  | (4v)  |
| (2)-59 | (IId) | (1c)   | (2tt)  | (3n)  | (4r)  |
| (2)-60 | (IIb) | (1d)   | (2vv)  | (3o)  | (4u)  |

| | (II) | A | Z | R' | R¹ |
|---|---|---|---|---|---|
| (2)-61 | (IIc) | (1e) | (2r) | (3p) | (4v) |
| (2)-62 | (IId) | (1h) | (2t) | (3j) | (4j) |
| (2)-63 | (IIe) | (1k) | (2x) | (3k) | (4l) |
| (2)-64 | (IIf) | (1l) | (2y) | (3l) | (4r) |
| (2)-65 | (IIg) | (1n) | (2aa) | (3m) | (4f) |
| (2)-66 | (IIh) | (1s) | (2ff) | (3l) | (4j) |
| (2)-67 | (IIi) | (1gg) | (2qq) | (3a) | (4l) |
| (2)-68 | (IIf) | (1jj) | (2tt) | (3i) | (4v) |
| (2)-69 | (IIb) | (1kk) | (2vv) | (3j) | (4a) |
| (2)-70 | (IIc) | (1ll) | (2ff) | (3i) | (4f) |
| (2)-71 | (IId) | (1mm) | (2qq) | (3j) | (4j) |
| (2)-72 | (IIg) | (1ss) | (2i) | (3k) | (4l) |
| (2)-73 | (IIh) | (1tt) | (2a) | (3l) | (4r) |
| (2)-74 | (IIi) | (1uu) | (2q) | (3m) | (4a) |
| (2)-75 | (IIc) | (1xx) | (2b) | (3n) | (4f) |
| (2)-76 | (IId) | (1aaa) | (2g) | (3o) | (4j) |
| (2)-77 | (IIe) | (1bbb) | (2i) | (3p) | (4l) |
| (2)-78 | (IIf) | (1ccc) | (2a) | (3i) | (4a) |
| (2)-79 | (IIg) | (1n) | (2q) | (3j) | (4f) |
| (2)-80 | (IIh) | (1s) | (2r) | (3k) | (4j) |
| (2)-81 | (IIi) | (1gg) | (2t) | (3j) | (4l) |
| (2)-82 | (IIf) | (1aaa) | (2x) | (3k) | (4r) |
| (2)-83 | (IIb) | (1bbb) | (2y) | (3l) | (4u) |
| (2)-84 | (IIc) | (1ccc) | (2aa) | (3m) | (4v) |
| (2)-85 | (IId) | (1l) | (2ff) | (3k) | (4x) |
| (2)-86 | (IIf) | (1n) | (2qq) | (3l) | (4y) |
| (2)-87 | (IIb) | (1s) | (2tt) | (3a) | (4z) |
| (2)-88 | (IIc) | (1d) | (2vv) | (3i) | (4r) |
| (2)-89 | (IId) | (1e) | (2vv) | (3j) | (4u) |
| (2)-90 | (IId) | (1h) | (2g) | (3k) | (4v) |
| (2)-91 | (IIe) | (1k) | (2i) | (3l) | (4j) |
| (2)-92 | (IIf) | (1l) | (2a) | (3m) | (4l) |
| (2)-93 | (IIg) | (1n) | (2q) | (3n) | (4a) |
| (2)-94 | (IIh) | (1s) | (2i) | (3o) | (4f) |
| (2)-95 | (IIi) | (1gg) | (2a) | (3p) | (4l) |
| (2)-96 | (IIf) | (1jj) | (2q) | (3a) | (4r) |
| (2)-97 | (IIb) | (1kk) | (2r) | (3i) | (4u) |
| (2)-98 | (IIc) | (1ll) | (2t) | (3j) | (4v) |
| (2)-99 | (IId) | (1mm) | (2x) | (3i) | (4x) |
| (2)-100 | (IIf) | (1ss) | (2y) | (3j) | (4y) |
| (2)-101 | (IIb) | (1tt) | (2aa) | (3i) | (4z) |
| (2)-102 | (IIc) | (1uu) | (2ff) | (3j) | (4r) |
| (2)-103 | (IId) | (1xx) | (2qq) | (3k) | (4a) |
| (2)-104 | (IId) | (1aaa) | (2tt) | (3l) | (4f) |
| (2)-105 | (IIe) | (1bbb) | (2vv) | (3a) | (4j) |
| (2)-106 | (IIf) | (1ccc) | (2r) | (3i) | (4l) |
| (2)-107 | (IIg) | (1h) | (2vv) | (3j) | (4r) |
| (2)-108 | (IIh) | (1k) | (2g) | (3j) | (4u) |
| (2)-109 | (IIi) | (1l) | (2i) | (3k) | (4v) |
| (2)-110 | (IIi) | (1n) | (2a) | (3l) | (4x) |
| (2)-111 | (IIf) | (1s) | (2q) | (3a) | (4y) |
| (2)-112 | (IIb) | (1gg) | (2qq) | (3i) | (4z) |
| (2)-113 | (IIc) | (1jj) | (2tt) | (3j) | (4j) |
| (2)-114 | (IId) | (1kk) | (2vv) | (3j) | (4l) |
| (2)-115 | (IId) | (1ll) | (2ff) | (3k) | (4a) |
| (2)-116 | (IIe) | (1mm) | (2qq) | (3l) | (4f) |
| (2)-117 | (IIf) | (1ss) | (2i) | (3m) | (4v) |
| (2)-118 | (IIg) | (1tt) | (2a) | (3k) | (4j) |
| (2)-119 | (IIh) | (1uu) | (2q) | (3l) | (4l) |
| (2)-120 | (IIi) | (1xx) | (2ff) | (3m) | (4a) |
| (2)-121 | (IIf) | (1aaa) | (2qq) | (3n) | (4f) |
| (2)-122 | (IIb) | (1bbb) | (2b) | (3o) | (4l) |
| (2)-123 | (IIc) | (1ccc) | (2g) | (3p) | (4r) |
| (2)-124 | (IId) | (1l) | (2i) | (3i) | (4u) |
| (2)-125 | (IIb) | (1n) | (2a) | (3j) | (4v) |
| (2)-126 | (IIc) | (1s) | (2q) | (3k) | (4x) |
| (2)-127 | (IId) | (1d) | (2r) | (3l) | (4y) |
| (2)-128 | (IIe) | (1e) | (2t) | (3a) | (4z) |
| (2)-129 | (IIf) | (1h) | (2x) | (3i) | (4j) |
| (2)-130 | (IIg) | (1k) | (2y) | (3j) | (4l) |
| (2)-131 | (IIh) | (1n) | (2aa) | (3k) | (4a) |
| (2)-132 | (IIi) | (1s) | (2ff) | (3l) | (4f) |
| (2)-133 | (IIf) | (1gg) | (2qq) | (3m) | (4v) |
| (2)-134 | (IIb) | (1gg) | (2tt) | (3n) | (4j) |
| (2)-135 | (IIc) | (1jj) | (2vv) | (3o) | (4l) |
| (2)-136 | (IId) | (1kk) | (2g) | (3p) | (4a) |
| (2)-137 | (IIf) | (1ll) | (2i) | (3a) | (4f) |
| (2)-138 | (IIb) | (1mm) | (2a) | (3i) | (4j) |
| (2)-139 | (IIc) | (1ss) | (2q) | (3j) | (4l) |
| (2)-140 | (IId) | (1tt) | (2b) | (3a) | (4r) |
| (2)-141 | (IId) | (1uu) | (2g) | (3i) | (4u) |
| (2)-142 | (IIe) | (1xx) | (2i) | (3j) | (4v) |
| (2)-143 | (IIf) | (1aaa) | (2a) | (3i) | (4x) |
| (2)-144 | (IIg) | (1bbb) | (2q) | (3j) | (4y) |
| (2)-145 | (IIh) | (1ccc) | (2r) | (3k) | (4z) |
| (2)-146 | (IIi) | (1l) | (2t) | (3l) | (4j) |
| (2)-147 | (IIf) | (1n) | (2x) | (3m) | (4l) |
| (2)-148 | (IIb) | (1s) | (2y) | (3n) | (4a) |
| (2)-149 | (IIc) | (1n) | (2aa) | (3o) | (4f) |
| (2)-150 | (IId) | (1s) | (2ff) | (3p) | (4a) |
| (2)-151 | (IIb) | (1n) | (2qq) | (3i) | (4f) |
| (2)-152 | (IIc) | (1s) | (2tt) | (3j) | (4u) |
| (2)-153 | (IId) | (1gg) | (2vv) | (3k) | (4v) |
| (2)-154 | (IIe) | (1c) | (2vv) | (3l) | (4j) |
| (2)-155 | (IIf) | (1d) | (2g) | (3i) | (4l) |
| (2)-156 | (IIg) | (1e) | (2i) | (3j) | (4a) |
| (2)-157 | (IIh) | (1h) | (2a) | (3k) | (4f) |
| (2)-158 | (IIi) | (1k) | (2q) | (3l) | (4u) |
| (2)-159 | (IId) | (1l) | (2g) | (3m) | (4v) |
| (2)-160 | (IIe) | (1n) | (2i) | (3n) | (4j) |
| (2)-161 | (IIf) | (1s) | (2a) | (3o) | (4l) |
| (2)-162 | (IIg) | (1gg) | (2q) | (3p) | (4a) |
| (2)-163 | (IIh) | (1jj) | (2g) | (3a) | (4f) |
| (2)-164 | (IIi) | (1kk) | (2i) | (3i) | (4j) |
| (2)-165 | (IIb) | (1ll) | (2a) | (3j) | (4l) |
| (2)-166 | (IIb) | (1mm) | (2q) | (3a) | (4r) |
| (2)-167 | (IIc) | (1ss) | (2r) | (3i) | (4u) |
| (2)-168 | (IId) | (1tt) | (2t) | (3j) | (4v) |
| (2)-169 | (IIc) | (1uu) | (2x) | (3k) | (4x) |
| (2)-170 | (IIc) | (1xx) | (2y) | (3l) | (4y) |
| (2)-171 | (IId) | (1aaa) | (2aa) | (3m) | (4z) |
| (2)-172 | (IIe) | (1bbb) | (2ff) | (3n) | (4j) |
| (2)-173 | (IIf) | (1ccc) | (2qq) | (3o) | (4l) |
| (2)-174 | (IIg) | (1n) | (2tt) | (3p) | (4a) |
| (2)-175 | (IIh) | (1s) | (2vv) | (3a) | (4f) |
| (2)-176 | (IIi) | (1gg) | (2g) | (3i) | (4r) |
| (2)-177 | (IId) | (1e) | (2i) | (3j) | (4u) |
| (2)-178 | (IIh) | (1h) | (2a) | (3k) | (4j) |
| (2)-179 | (IIf) | (1k) | (2q) | (3l) | (4l) |
| (2)-180 | (IIb) | (1l) | (2a) | (3a) | (4r) |
| (2)-181 | (IIc) | (1n) | (2b) | (3i) | (4f) |
| (2)-182 | (IId) | (1s) | (2g) | (3j) | (4r) |
| (2)-183 | (IIe) | (1gg) | (2i) | (3k) | (4u) |
| (2)-184 | (IIf) | (1jj) | (2a) | (3l) | (4v) |
| (2)-185 | (IIg) | (1kk) | (2q) | (3m) | (4u) |
| (2)-186 | (IIh) | (1ll) | (2r) | (3n) | (4v) |
| (2)-187 | (IIi) | (1mm) | (2t) | (3o) | (4x) |
| (2)-188 | (IIf) | (1ss) | (2x) | (3p) | (4y) |
| (2)-189 | (IIb) | (1tt) | (2y) | (3i) | (4z) |
| (2)-190 | (IIc) | (1uu) | (2aa) | (3j) | (4r) |
| (2)-191 | (IId) | (1xx) | (2ff) | (3k) | (4u) |
| (2)-192 | (IIg) | (1aaa) | (2qq) | (3l) | (4v) |
| (2)-193 | (IIh) | (1tt) | (2tt) | (3i) | (4j) |
| (2)-194 | (IIi) | (1uu) | (2vv) | (3j) | (4l) |
| (2)-195 | (IIb) | (1xx) | (2vv) | (3k) | (4a) |
| (2)-196 | (IIc) | (1l) | (2y) | (3l) | (4f) |
| (2)-197 | (IId) | (1n) | (2aa) | (3m) | (4f) |
| (2)-198 | (IIe) | (1s) | (2ff) | (3n) | (4j) |
| (2)-199 | (IIf) | (1n) | (2g) | (3o) | (4l) |
| (2)-200 | (IIg) | (1s) | (2i) | (3p) | (4r) |
| (2)-201 | (IIh) | (1gg) | (2a) | (3a) | (4u) |
| (2)-202 | (IIi) | (1d) | (2q) | (3i) | (4v) |
| (2)-203 | (IId) | (1a) | (2a) | (3j) | (4x) |
| (2)-204 | (IIe) | (1c) | (2b) | (3n) | (4y) |
| (2)-205 | (IIf) | (1d) | (2g) | (3o) | (4z) |
| (2)-206 | (IIb) | (1e) | (2i) | (3p) | (4j) |
| (2)-207 | (IIc) | (1h) | (2a) | (3k) | (4l) |
| (2)-208 | (IId) | (1k) | (2q) | (3l) | (4r) |
| (2)-209 | (IIe) | (1l) | (2r) | (3a) | (4u) |
| (2)-210 | (IIf) | (1n) | (2t) | (3i) | (4v) |
| (2)-211 | (IIg) | (1n) | (2x) | (3j) | (4x) |
| (2)-212 | (IIh) | (1s) | (2y) | (3k) | (4y) |
| (2)-213 | (IIi) | (1gg) | (2aa) | (3l) | (4z) |
| (2)-214 | (IId) | (1kk) | (2ff) | (3m) | (4j) |

| (II) | A | Z | R' | R¹ |
|---|---|---|---|---|
| (2)-215 | (IIe) | (1ll) | (2qq) | (3n) | (4l) |
| (2)-216 | (IIf) | (1mm) | (2tt) | (3o) | (4a) |
| (2)-217 | (IIa) | (1ss) | (2vv) | (3p) | (4f) |
| (2)-218 | (IIb) | (1tt) | (2ff) | (3n) | (4v) |
| (2)-219 | (IIc) | (1uu) | (2qq) | (3o) | (4a) |
| (2)-220 | (IId) | (1xx) | (2i) | (3p) | (4f) |
| (2)-221 | (IIa) | (1aaa) | (2a) | (3a) | (4j) |
| (2)-222 | (IIb) | (1bbb) | (2q) | (3i) | (4l) |
| (2)-223 | (IIc) | (1ccc) | (2ff) | (3j) | (4r) |
| (2)-224 | (IId) | (1tt) | (2qq) | (3k) | (4u) |
| (2)-225 | (IIe) | (1uu) | (2vv) | (3l) | (4v) |
| (2)-226 | (IIf) | (1xx) | (2g) | (3m) | (4x) |
| (2)-227 | (IIg) | (1gg) | (2i) | (3a) | (4y) |
| (2)-228 | (IIh) | (1c) | (2a) | (3i) | (4z) |
| (2)-229 | (IIi) | (1d) | (2q) | (3j) | (4j) |
| (2)-230 | (IIg) | (1e) | (2i) | (3k) | (4l) |
| (2)-231 | (IIh) | (1n) | (2a) | (3l) | (4r) |
| (2)-232 | (IIi) | (1s) | (2q) | (3m) | (4j) |
| (2)-233 | (IIf) | (1gg) | (2r) | (3n) | (4l) |
| (2)-234 | (IIa) | (1d) | (2vv) | (3o) | (4r) |
| (2)-235 | (IIb) | (1s) | (2g) | (3p) | (4u) |
| (2)-236 | (IIc) | (1gg) | (2i) | (3a) | (4v) |
| (2)-237 | (IId) | (1jj) | (2a) | (3i) | (4x) |
| (2)-238 | (IIe) | (1kk) | (2q) | (3j) | (4y) |
| (2)-239 | (IIf) | (1n) | (2qq) | (3k) | (4z) |
| (2)-240 | (IIg) | (1s) | (2tt) | (3l) | (4j) |
| (2)-241 | (IIg) | (1gg) | (2vv) | (3m) | (4l) |
| (2)-242 | (IIh) | (1tt) | (2vv) | (3n) | (4r) |
| (2)-243 | (IIi) | (1uu) | (2y) | (3o) | (4u) |
| (2)-244 | (IId) | (1xx) | (2aa) | (3j) | (4v) |
| (2)-245 | (IIe) | (1aaa) | (2ff) | (3k) | (4x) |
| (2)-246 | (IIf) | (1bbb) | (2i) | (3l) | (4y) |
| (2)-247 | (IIg) | (1ccc) | (2a) | (3m) | (4z) |
| (2)-248 | (IIh) | (1tt) | (2q) | (3p) | (4a) |
| (2)-249 | (IIi) | (1uu) | (2r) | (3n) | (4f) |
| (2)-250 | (IIg) | (1xx) | (2vv) | (3o) | (4j) |
| (2)-251 | (IIh) | (1n) | (2g) | (3j) | (4l) |
| (2)-252 | (IIi) | (1s) | (2i) | (3k) | (4r) |
| (2)-253 | (IId) | (1gg) | (2a) | (3l) | (4u) |
| (2)-254 | (IIe) | (1c) | (2q) | (3m) | (4v) |
| (2)-255 | (IIf) | (1d) | (2qq) | (3p) | (4x) |
| (2)-256 | (IId) | (1e) | (2tt) | (3j) | (4y) |
| (2)-257 | (IIe) | (1h) | (2vv) | (3k) | (4z) |
| (2)-258 | (IIf) | (1k) | (2y) | (3l) | (4l) |
| (2)-259 | (IIa) | (1l) | (2aa) | (3m) | (4r) |
| (2)-260 | (IIb) | (1n) | (2ff) | (3l) | (4u) |
| (2)-261 | (IIc) | (1s) | (2qq) | (3i) | (4v) |
| (2)-262 | (IId) | (1n) | (2tt) | (3j) | (4x) |
| (2)-263 | (IIe) | (1s) | (2vv) | (3k) | (4y) |
| (2)-264 | (IIf) | (1gg) | (2vv) | (3l) | (4z) |
| (2)-265 | (IIg) | (1ll) | (2y) | (3m) | (4l) |
| (2)-266 | (IIh) | (1mm) | (2aa) | (3n) | (4r) |
| (2)-267 | (IIi) | (1ss) | (2ff) | (3o) | (4u) |
| (2)-268 | (IId) | (1tt) | (2a) | (3p) | (4v) |
| (2)-269 | (IIe) | (1n) | (2b) | (3n) | (4x) |
| (2)-270 | (IIf) | (1s) | (2g) | (3o) | (4y) |
| (2)-271 | (IIe) | (1gg) | (2i) | (3p) | (4z) |
| (2)-272 | (IIf) | (1bbb) | (2a) | (3j) | (4j) |
| (2)-273 | (IIg) | (1ccc) | (2q) | (3k) | (4l) |
| (2)-274 | (IIh) | (1n) | (2r) | (3l) | (4a) |
| (2)-275 | (IIi) | (1s) | (2t) | (3m) | (4f) |
| (2)-276 | (IIe) | (1gg) | (2x) | (3k) | (4j) |
| (2)-277 | (IIf) | (1d) | (2a) | (3l) | (4l) |
| (2)-278 | (IIg) | (1xx) | (2b) | (3m) | (4r) |
| (2)-279 | (IIh) | (1n) | (2g) | (3n) | (4j) |
| (2)-280 | (IIi) | (1s) | (2i) | (3o) | (4l) |
| (2)-281 | (IIe) | (1gg) | (2a) | (3p) | (4r) |
| (2)-282 | (IIf) | (1d) | (2q) | (3n) | (4u) |
| (2)-283 | (IIb) | (1e) | (2r) | (3o) | (4v) |
| (2)-284 | (IIc) | (1h) | (2t) | (3p) | (4x) |
| (2)-285 | (IId) | (1k) | (2x) | (3n) | (4y) |
| (2)-286 | (IIe) | (1l) | (2y) | (3o) | (4z) |
| (2)-287 | (IIf) | (1n) | (2aa) | (3p) | (4j) |
| (2)-288 | (IIg) | (1s) | (2ff) | (3j) | (4l) |
| (2)-289 | (IIh) | (1gg) | (2qq) | (3k) | (4r) |
| (2)-290 | (IIi) | (1jj) | (2tt) | (3l) | (4j) |
| (2)-291 | (IIc) | (1kk) | (2vv) | (3m) | (4l) |
| (2)-292 | (IId) | (1ll) | (2g) | (3l) | (4r) |
| (2)-293 | (IIe) | (1mm) | (2i) | (3m) | (4j) |
| (2)-294 | (IIf) | (1ss) | (2a) | (3j) | (4l) |
| (2)-295 | (IIg) | (1n) | (2q) | (3k) | (4r) |
| (2)-296 | (IIh) | (1s) | (2r) | (3l) | (4u) |
| (2)-297 | (IIi) | (1gg) | (2t) | (3m) | (4v) |
| (2)-298 | (IId) | (1aaa) | (2x) | (3n) | (4x) |
| (2)-299 | (IIe) | (1bbb) | (2y) | (3o) | (4y) |
| (2)-300 | (IIf) | (1ccc) | (2aa) | (3p) | (4z) |
| (2)-301 | (IIj) | (1e) | (2ww) | (3q) | (4u) |
| (2)-302 | (IIj) | (1h) | (2xx) | (3r) | (4bb) |
| (2)-303 | (IIj) | (1k) | (2yy) | (3s) | (4cc) |
| (2)-304 | (IIj) | (1l) | (2zz) | (3t) | (4dd) |
| (2)-305 | (IIj) | (1n) | (2aaa) | (3u) | (4ee) |
| (2)-306 | (IIj) | (1s) | (2bbb) | (3v) | (4ff) |
| (2)-307 | (IIj) | (1gg) | (2ccc) | (3w) | (4gg) |
| (2)-308 | (IIj) | (1jj) | (2ww) | (3x) | (4u) |
| (2)-309 | (IIj) | (1kk) | (2xx) | (3y) | (4bb) |
| (2)-310 | (IIj) | (1ll) | (2yy) | (3z) | (4cc) |
| (2)-311 | (IIj) | (1mm) | (2zz) | (3aa) | (4dd) |
| (2)-312 | (IIj) | (1ss) | (2aaa) | (3bb) | (4ee) |
| (2)-313 | (IIj) | (1n) | (2bbb) | (3cc) | (4ff) |
| (2)-314 | (IIj) | (1s) | (2ccc) | (3dd) | (4gg) |
| (2)-315 | (IIj) | (1gg) | (2ww) | (3ee) | (4u) |
| (2)-316 | (IIj) | (1aaa) | (2xx) | (3ff) | (4bb) |
| (2)-317 | (IIj) | (1bbb) | (2yy) | (3gg) | (4cc) |
| (2)-318 | (IIj) | (1s) | (2zz) | (3hh) | (4dd) |
| (2)-319 | (IIj) | (1a) | (2aaa) | (3ii) | (4ee) |
| (2)-320 | (IIj) | (1c) | (2bbb) | (3jj) | (4ff) |

In some embodiments, the compound of formulae (II) or (IIa)-(IIj) is one of the following compounds (or a pharmaceutically acceptable salt, prodrug, or N-oxide thereof, or a solvate or hydrate thereof): 1, 2, 3, 4, 5, 6, 7, 8, 9, 10, 11, 15, 16, 17, 18, 22, 23, 24, 25, 27, 28, 31, 32, 33, 34, 41, 42, 48, 60, 61, 62, 63, 64, 71, 98, 99, 102, 104, 108, 125, 126.

In embodiment III° of this aspect, the invention comprises compounds having the structure of formula (III°):

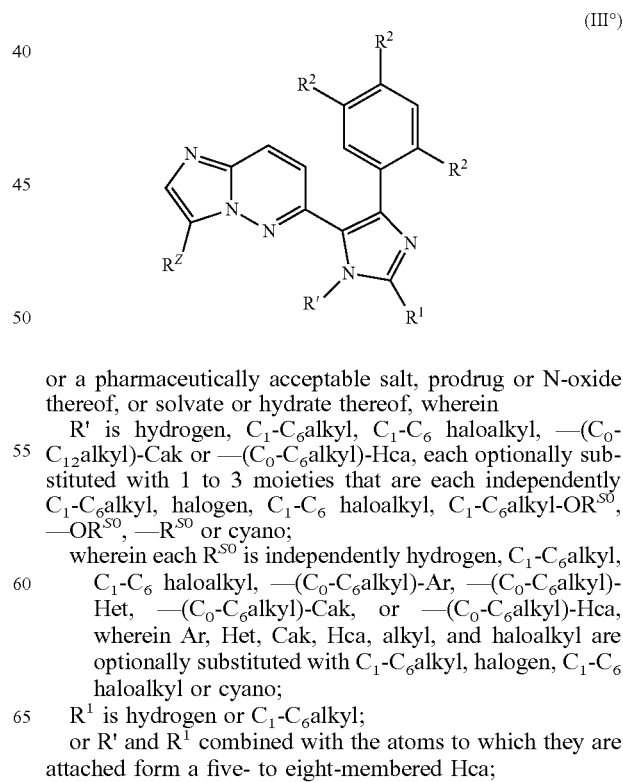

(III°)

or a pharmaceutically acceptable salt, prodrug or N-oxide thereof, or solvate or hydrate thereof, wherein R' is hydrogen, $C_1$-$C_6$alkyl, $C_1$-$C_6$ haloalkyl, —($C_0$-$C_{12}$alkyl)-Cak or —($C_0$-$C_6$alkyl)-Hca, each optionally substituted with 1 to 3 moieties that are each independently $C_1$-$C_6$alkyl, halogen, $C_1$-$C_6$ haloalkyl, $C_1$-$C_6$alkyl-$OR^{SO}$, —$OR^{SO}$, —$R^{SO}$ or cyano;

wherein each $R^{SO}$ is independently hydrogen, $C_1$-$C_6$alkyl, $C_1$-$C_6$ haloalkyl, —($C_0$-$C_6$alkyl)-Ar, —($C_0$-$C_6$alkyl)-Het, —($C_0$-$C_6$alkyl)-Cak, or —($C_0$-$C_6$alkyl)-Hca, wherein Ar, Het, Cak, Hca, alkyl, and haloalkyl are optionally substituted with $C_1$-$C_6$alkyl, halogen, $C_1$-$C_6$ haloalkyl or cyano;

$R^1$ is hydrogen or $C_1$-$C_6$alkyl;

or R' and $R^1$ combined with the atoms to which they are attached form a five- to eight-membered Hca;

each R² is independently hydrogen, halogen, —C₁-C₆alkyl, —C₁-C₆alkyl-OR^S2 or —OR^S2; and R^Z is halogen, cyano, C₁₋₆alkyl, C₁₋₆alkenyl, C₁₋₆ haloalkyl, —C₁-C₆alkoxy, —(C₀-C₆alkyl)-Het, —(C₀-C₆alkyl)-Hca, —OR^S3, —SR^S3, —NR^S3₂, —C(O)R^S3, —C(O)OR^S3, —C(O)NR^S3₂, —C(NR^S3)NR^S3OR^S3, —S(O)₂NR^S3₂, —S(O)₂R^S3, —OC(O)R^S3, —N(R^S3)C(O)R^S3, —OC(O)OR^S3, —OC(O)_NR^S3₂, —N(R^S3)C(O)OR^S3, —N(R^S3)C(O)NR^S3₂, —N(R^S3)S(O)₂R^S3, —OP(O)(OR^S3)₂ or —CH₂—OP(O)(OR^S3), wherein each alkyl, haloalkyl and alkoxy is optionally substituted by one or two —R^Z2 groups;

wherein each R^S3 is independently hydrogen, —NR^S3₂, —OR^S3, C₁-C₆alkyl, C₁-C₆ haloalkyl, —(C₀-C₆alkyl)-Ar, —(C₀-C₆alkyl)-Het, —(C₀-C₆alkyl)-Cak, or —(C₀-C₆alkyl)-Hca, wherein Ar, Het, Cak, Hca, alkyl, and haloalkyl are optionally substituted with C₁-C₆alkyl, halogen, C₁-C₆ haloalkyl, —C(O)NR^S4₂ or cyano; and each —R^Z2 is independently halogen, cyano, C₁₋₆alkyl, C₁₋₆ haloalkyl, —C₁-C₆alkoxy, —OR^S4, —SR^S4, —NR^S4₂, —C(O)R^S4, —C(O)R^S4, —C(O)NR^S4₂, —S(O)₂NR^S4₂, —S(O)₂R^S4, —OC(O)R^S4, —N(R^S4)C(O)R^S4, —OC(O)OR^S4, —OC(O)NR^S4₂, —N(R^S4)C(O)OR^S4, —N(R^S4)C(O)NR^S4₂, —N(R^S4)S(O)₂R^S4, —OP(O)(OR^S4)₂ or —CH₂—OP(O)(OR^S4); and wherein each R^S4 is independently hydrogen, C₁-C₆alkyl, C₁-C₆ haloalkyl, —(C₀-C₆alkyl)-Ar, —(C₀-C₆alkyl)-Het, —(C₀-C₆alkyl)-Cak, or —(C₀-C₆alkyl)-Hca, wherein Ar, Het, Cak, Hca, alkyl, and haloalkyl are optionally substituted with one or two C₁-C₆alkyl, halogen, C₁-C₆ haloalkyl or cyano.

In embodiment III₁ of this aspect, the invention comprises compounds having the structure of formula (III):

(III)

or a pharmaceutically acceptable salt, prodrug or N-oxide thereof, or solvate or hydrate thereof, wherein R' is hydrogen or C₁-C₆alkyl;

each R² is independently hydrogen, halogen or —C₁-C₆alkyl;

z is CH, O, S or N;

y is CH, CH₂, or N; and x is CH, O, S, N(R^a);

wherein R^a is hydrogen or —C₁-C₆alkyl.

provided that when z is N and x is N(R^a), y is not N.

In embodiment III₂, the compounds of the invention are of one of formulae (IIIa)-(IIIj):

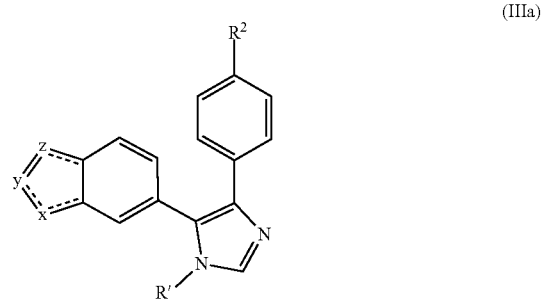

(IIIa)

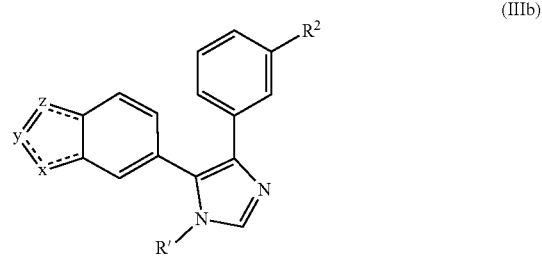

(IIIb)

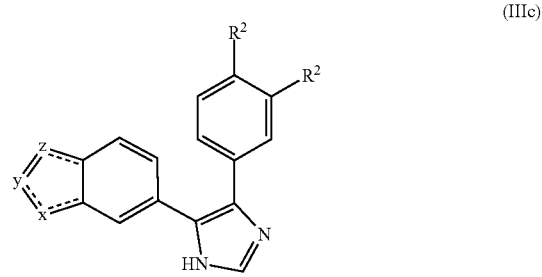

(IIIc)

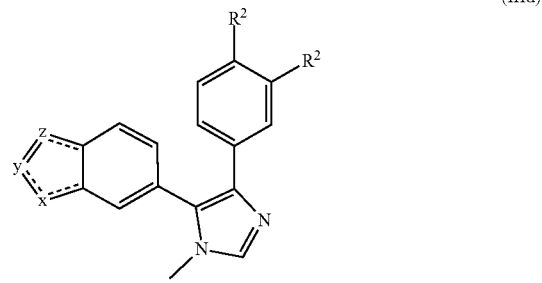

(IIId)

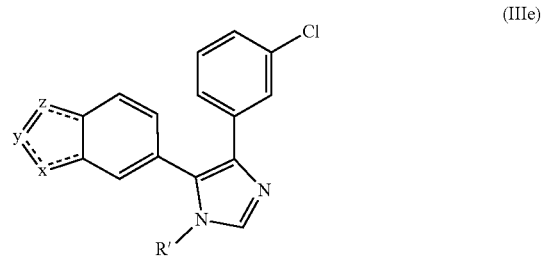

(IIIe)

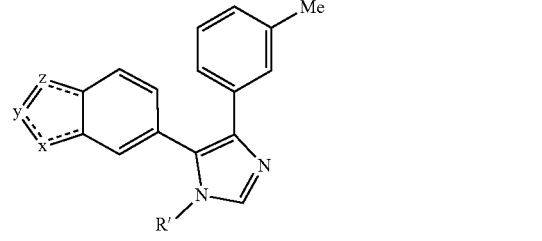

(IIIf)

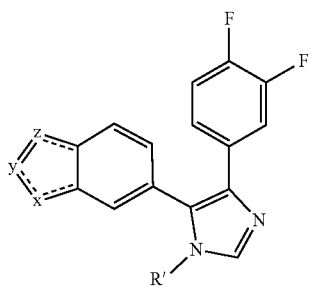
(IIIg)

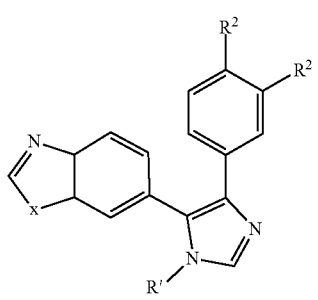
(IIIh)

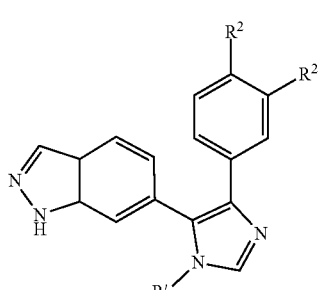
(IIIi)

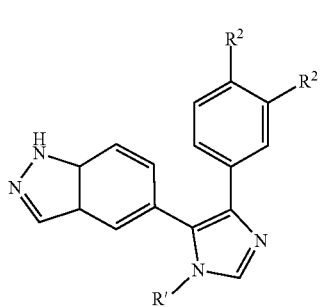
(IIIj)

wherein $R^2$, R', x, y, z and $R^a$ are as defined in embodiment $III_1$ above.

Particular embodiments of this aspect of the invention comprise compounds of any one of the formulae (III°), (III), and (IIIa)-(IIIj), each as defined in each of the following rows (or a pharmaceutically acceptable salt, prodrug, or N-oxide thereof, or a solvate or hydrate thereof), wherein each entry is a group number as defined above (e.g., (3o) refers to R' is methyl), an "X" indicates that the variable is defined by another group in the embodiment (e.g., in embodiment (3)-9 below, Z is defined in (IIIi)) and a dash "-" indicates that the variable is as defined in embodiment $I_1$ or defined according to any one of the applicable variable definitions (1a)-(1ddd), (2a)-(2ccc), (3a)-(3kk) and (4a)-(4gg) [e.g., when R' is a dash, it can be either as defined in embodiment $III_1$ or $III_2$, or any one of the applicable definitions (3a)-(3kk)]:

| (III) | A | Z | R' |
|---|---|---|---|
| (3)-1 | (IIIa) | (1a) | (2i) | (3a) |
| (3)-2 | (IIIb) | (1c) | (2cc) | (3i) |
| (3)-3 | (IIIc) | (1d) | — | X |
| (3)-4 | (IIId) | (1e) | (2i) | X |
| (3)-5 | (IIIe) | X | (2cc) | (3l) |
| (3)-6 | (IIIf) | X | (2i) | (3m) |
| (3)-7 | (IIIg) | (1l) | (2cc) | (3n) |
| (3)-8 | (IIIh) | (1n) | (2mm) | (3o) |
| (3)-9 | (IIIi) | (1s) | X | (3p) |
| (3)-10 | (IIIj) | (1gg) | X | (3j) |
| (3)-11 | (IIIa) | (1xx) | — | (3k) |
| (3)-12 | (IIIb) | (1kk) | (2i) | (3l) |
| (3)-13 | (IIIc) | (1d) | (2cc) | X |
| (3)-14 | (IIId) | (1mm) | — | X |
| (3)-15 | (IIIa) | (1aaa) | (2i) | (3a) |
| (3)-16 | (IIIb) | (1tt) | (2cc) | (3i) |
| (3)-17 | (IIIc) | (1uu) | — | X |
| (3)-18 | (IIId) | (1xx) | — | X |
| (3)-19 | (IIIe) | X | (2i) | — |
| (3)-20 | (IIIf) | X | (2cc) | (3j) |
| (3)-21 | (IIIg) | (1ccc) | — | (3k) |
| (3)-22 | (IIIh) | (1k) | (2mm) | (3l) |
| (3)-23 | (IIIi) | (1ss) | X | (3a) |
| (3)-24 | (IIIj) | (1tt) | X | (3i) |
| (3)-25 | (IIIa) | (1xx) | — | (3j) |
| (3)-26 | (IIIb) | (1aaa) | — | (3k) |
| (3)-27 | (IIIc) | (1h) | (2i) | X |
| (3)-28 | (IIId) | — | (2cc) | X |
| (3)-29 | (IIIc) | — | — | X |
| (3)-30 | (IIIe) | X | (2i) | — |
| (3)-31 | (IIIf) | X | — | (3n) |
| (3)-32 | (IIIa) | (1aaa) | — | (3o) |
| (3)-33 | (IIId) | — | (2cc) | X |
| (3)-34 | (IIIe) | X | (2i) | — |
| (3)-35 | (IIIf) | X | (2cc) | (3j) |
| (3)-36 | (IIIg) | (1ss) | — | (3k) |
| (3)-37 | (IIIh) | (1tt) | (2mm) | (3l) |
| (3)-38 | (IIIi) | (1k) | X | (3a) |
| (3)-39 | (IIIj) | (1uu) | X | (3i) |
| (3)-40 | (IIIa) | (1bbb) | — | (3j) |
| (3)-41 | (IIIb) | (1aaa) | (2i) | (3k) |
| (3)-42 | (IIIc) | (1n) | (2cc) | X |
| (3)-43 | (IIId) | (1k) | — | X |
| (3)-44 | (IIId) | (1uu) | (2i) | X |
| (3)-45 | (IIIe) | X | (2cc) | — |
| (3)-46 | (IIIf) | X | (2i) | (3a) |
| (3)-47 | (IIIg) | (1ss) | (2cc) | (3j) |
| (3)-48 | (IIIh) | (1ss) | (2mm) | (3k) |
| (3)-49 | (IIIi) | (1tt) | X | (3l) |
| (3)-50 | (IIIj) | (1k) | X | (3i) |
| (3)-51 | (IIId) | (1uu) | — | X |
| (3)-52 | (IIIe) | X | (2i) | — |
| (3)-53 | (IIIf) | X | (2cc) | (3n) |
| (3)-54 | (IIIg) | (1k) | — | (3o) |
| (3)-55 | (IIIh) | (1uu) | (2mm) | (3p) |
| (3)-56 | (IIIi) | (1ss) | X | (3i) |
| (3)-57 | (IIIa) | (1xx) | (2i) | (3j) |
| (3)-58 | (IIIb) | (1e) | (2cc) | (3i) |
| (3)-59 | (IIIc) | (1l) | — | X |
| (3)-60 | (IIId) | (1k) | — | X |
| (3)-61 | (IIIc) | (1n) | — | X |
| (3)-62 | (IIId) | (1uu) | — | X |
| (3)-63 | (IIIe) | X | (2i) | — |
| (3)-64 | (IIIf) | X | (2cc) | (3i) |
| (3)-65 | (IIIg) | (1uu) | — | (3j) |
| (3)-66 | (IIIh) | (1tt) | (2mm) | (3j) |
| (3)-67 | (IIIi) | (1k) | X | (3k) |
| (3)-68 | (IIIj) | (1k) | X | (3l) |
| (3)-69 | (IIIc) | (1uu) | — | (3k) |
| (3)-70 | (IIIe) | X | — | — |
| (3)-71 | (IIIf) | X | (2i) | (3a) |
| (3)-72 | (IIIa) | (1ccc) | (2cc) | (3i) |
| (3)-73 | (IIIc) | (1k) | — | X |
| (3)-74 | (IIId) | (1uu) | — | — |
| (3)-75 | (IIIe) | X | (2i) | — |
| (3)-76 | (IIIf) | X | (2cc) | (3j) |
| (3)-77 | (IIIg) | (1ss) | — | (3k) |
| (3)-78 | (IIIh) | (1tt) | (2rr) | (3l) |
| (3)-79 | (IIIi) | (1k) | X | (3a) |

|  | (III) | A | Z | R' |
|---|---|---|---|---|
| (3)-80 | (IIIj) | (1uu) | X | (3i) |
| (3)-81 | (IIIb) | (1bbb) | (2cc) | (3j) |
| (3)-82 | (IIIc) | (1m) | — | X |
| (3)-83 | (IIIe) | X | (2i) | — |
| (3)-84 | (IIIf) | X | (2cc) | (3i) |
| (3)-85 | (IIIg) | (1ss) | (2i) | (3k) |
| (3)-86 | (IIIg) | (1tt) | (2cc) | (3a) |
| (3)-87 | (IIIh) | (1k) | (2mm) | (3k) |
| (3)-88 | (IIIe) | X | — | — |
| (3)-89 | (IIIf) | X | (2i) | (3i) |
| (3)-90 | (IIIg) | (1ss) | (2cc) | (3j) |
| (3)-91 | (IIIh) | (1tt) | (2mm) | (3k) |
| (3)-92 | (IIIi) | (1k) | X | (3l) |
| (3)-93 | (IIIj) | (1uu) | X | (3n) |
| (3)-94 | (IIIb) | (1aaa) | — | (3o) |
| (3)-95 | (IIIc) | (1k) | (2i) | X |
| (3)-96 | (IIIe) | X | (2cc) | — |
| (3)-97 | (IIIf) | X | — | (3n) |
| (3)-98 | (IIIg) | (1n) | — | (3o) |
| (3)-99 | (IIIg) | (1k) | — | (3p) |
| (3)-100 | (IIIh) | (1ss) | (2qq) | (3k) |
| (3)-101 | (IIIg) | (1tt) | — | (3l) |
| (3)-102 | (IIIh) | (1k) | (2mm) | (3a) |
| (3)-103 | (IIIi) | (1uu) | X | (3a) |
| (3)-104 | (IIIj) | (1k) | X | (3i) |
| (3)-105 | (IIIb) | (1ccc) | — | (3j) |
| (3)-106 | (IIIc) | (1k) | — | X |
| (3)-107 | (IIIe) | X | (2i) | — |
| (3)-108 | (IIIf) | X | (2cc) | (3i) |
| (3)-109 | (IIIg) | (1k) | — | (3j) |
| (3)-110 | (IIIg) | (1tt) | — | (3i) |
| (3)-111 | (IIIh) | (1ss) | (2mm) | (3a) |
| (3)-112 | (IIIf) | X | — | (3i) |
| (3)-113 | (IIIg) | (1k) | (2i) | (3j) |
| (3)-114 | (IIIh) | (1n) | (2cc) | (3j) |
| (3)-115 | (IIIi) | (1x) | X | (3k) |
| (3)-116 | (IIIj) | (1k) | X | (3n) |
| (3)-117 | (IIIb) | (1bbb) | — | (3o) |
| (3)-118 | (IIIc) | (1uu) | — | X |
| (3)-119 | (IIIe) | X | (2i) | — |
| (3)-120 | (IIIf) | X | (2cc) | (3k) |
| (3)-121 | (IIIg) | (1ss) | (2i) | (3a) |
| (3)-122 | (IIIg) | (1tt) | (2cc) | (3i) |
| (3)-123 | (IIIh) | (1k) | (2mm) | (3j) |
| (3)-124 | (IIIf) | X | (2i) | (3a) |
| (3)-125 | (IIIg) | (1uu) | (2i) | (3j) |
| (3)-126 | (IIIa) | (1aaa) | (2cc) | (3k) |
| (3)-127 | (IIIb) | (1xx) | — | (3l) |
| (3)-128 | (IIIc) | (1k) | — | X |
| (3)-129 | (IIId) | (1n) | (2i) | X |
| (3)-130 | (IIIe) | X | (2cc) | — |
| (3)-131 | (IIIf) | X | — | (3a) |
| (3)-132 | (IIIg) | (1k) | — | (3j) |
| (3)-133 | (IIIh) | (1n) | (2mm) | (3k) |
| (3)-134 | (IIIi) | (1l) | X | (3l) |
| (3)-135 | (IIIj) | (1uu) | X | (3k) |
| (3)-136 | (IIIa) | (1xx) | (2i) | (3a) |
| (3)-137 | (IIIb) | (1aaa) | (2cc) | (3i) |
| (3)-138 | (IIIc) | (1ss) | — | X |
| (3)-139 | (IIId) | (1tt) | — | X |
| (3)-140 | (IIIc) | (1k) | (2i) | X |
| (3)-141 | (IIIe) | X | (2cc) | — |
| (3)-142 | (IIIf) | X | — | (3i) |
| (3)-143 | (IIIa) | (1bbb) | (2i) | (3j) |
| (3)-144 | (IIIb) | (1aaa) | (2cc) | (3k) |
| (3)-145 | (IIIc) | (1uu) | — | X |
| (3)-146 | (IIId) | (1c) | — | X |
| (3)-147 | (IIIe) | X | (2i) | — |
| (3)-148 | (IIIf) | X | (2cc) | (3a) |
| (3)-149 | (IIIb) | (1xx) | — | (3i) |
| (3)-150 | (IIIc) | (1uu) | (2i) | X |
| (3)-151 | (IIIe) | X | (2cc) | — |
| (3)-152 | (IIIf) | X | (2i) | (3n) |
| (3)-153 | (IIIg) | (1d) | (2cc) | (3o) |
| (3)-154 | (IIIg) | (1k) | — | (3p) |
| (3)-155 | (IIIh) | (1d) | (2pp) | (3a) |
| (3)-156 | (IIIg) | (1n) | (2i) | (3i) |
| (3)-157 | (IIIh) | (1k) | (2cc) | (3j) |
| (3)-158 | (IIIi) | (1d) | X | (3k) |
| (3)-159 | (IIIj) | (1n) | X | (3n) |
| (3)-160 | (IIIb) | (1ccc) | — | (3o) |
| (3)-161 | (IIIc) | (1uu) | (2i) | X |
| (3)-162 | (IIIe) | X | (2i) | — |
| (3)-163 | (IIIf) | X | (2cc) | (3i) |
| (3)-164 | (IIIa) | (1aaa) | (2i) | (3j) |
| (3)-165 | (IIIb) | (1xx) | (2cc) | (3k) |
| (3)-166 | (IIIc) | (1d) | — | X |
| (3)-167 | (IIId) | (1k) | (2i) | X |
| (3)-168 | (IIIa) | (1ccc) | (2i) | (3k) |
| (3)-169 | (IIIb) | (1e) | (2cc) | (3a) |
| (3)-170 | (IIIa) | (1aaa) | (2i) | (3j) |
| (3)-171 | (IIIb) | (1e) | (2cc) | (3k) |
| (3)-172 | (IIIc) | (1uu) | — | (3l) |
| (3)-173 | (IIIa) | (1xx) | — | (3a) |
| (3)-174 | (IIIb) | (1ccc) | (2i) | (3i) |
| (3)-175 | (IIIc) | (1k) | (2cc) | X |
| (3)-176 | (IIId) | (1d) | (2i) | — |
| (3)-177 | (IIIc) | (1n) | (2cc) | X |
| (3)-178 | (IIIe) | X | — | — |
| (3)-179 | (IIIf) | X | (2i) | (3n) |
| (3)-180 | (IIIg) | (1ss) | (2cc) | (3o) |
| (3)-181 | (IIIg) | (1tt) | — | (3p) |
| (3)-182 | (IIIh) | (1k) | (2oo) | (3k) |
| (3)-183 | (IIIi) | (1uu) | X | (3l) |
| (3)-184 | (IIIj) | (1k) | X | (3i) |
| (3)-185 | (IIIa) | (1e) | (2i) | (3j) |
| (3)-186 | (IIIb) | (1aaa) | (2cc) | (3k) |
| (3)-187 | (IIIc) | (1ss) | — | (3l) |
| (3)-188 | (IIId) | (1tt) | (2i) | X |
| (3)-189 | (IIId) | (1k) | (2i) | X |
| (3)-190 | (IIIe) | X | (2cc) | — |
| (3)-191 | (IIIf) | X | (2i) | (3j) |
| (3)-192 | (IIIg) | (1ss) | (2cc) | (3k) |
| (3)-193 | (IIIb) | (1xx) | (2i) | (3n) |
| (3)-194 | (IIIb) | (1bbb) | (2cc) | (3o) |
| (3)-195 | (IIIc) | (1ss) | (2i) | (3p) |
| (3)-196 | (IIIe) | X | (2cc) | — |
| (3)-197 | (IIIf) | X | (2i) | (3a) |
| (3)-198 | (IIIg) | (1ss) | (2cc) | (3j) |
| (3)-199 | (IIIg) | (1tt) | — | (3k) |
| (3)-200 | (IIIh) | (1k) | (2nn) | (3l) |
| (3)-201 | (III°) | (1f) | (2zz) | (3q) |
| (3)-202 | (III°) | (1jj) | (2aaa) | (3r) |
| (3)-203 | (III°) | (1kk) | (2bbb) | (3s) |
| (3)-204 | (III°) | (1ll) | (2ccc) | (3t) |
| (3)-205 | (III°) | (1mm) | (2zz) | (3u) |
| (3)-206 | (III°) | (1nn) | (2aaa) | (3v) |
| (3)-207 | (III°) | (1rr) | (2bbb) | (3w) |
| (3)-208 | (III°) | (1ss) | (2ccc) | (3x) |
| (3)-209 | (III°) | (1tt) | (2zz) | (3y) |
| (3)-210 | (III°) | (1uu) | (2aaa) | (3z) |
| (3)-211 | (III°) | (1vv) | (2bbb) | (3aa) |
| (3)-212 | (III°) | (1zz) | (2ccc) | (3bb) |
| (3)-213 | (III°) | (1aaa) | (2zz) | (3q) |
| (3)-214 | (III°) | (1bbb) | (2aaa) | (3r) |
| (3)-215 | (III°) | (1ccc) | (2bbb) | (3s) |
| (3)-216 | (III°) | (1ddd) | (2ccc) | (3t) |
| (3)-217 | (III°) | (1f) | (2zz) | (3u) |
| (3)-218 | (III°) | (1jj) | (2aaa) | (3v) |
| (3)-219 | (III°) | (1rr) | (2bbb) | (3w) |
| (3)-220 | (III°) | (1zz) | (2ccc) | (3x) |

In some embodiments, the compound of formulae (I), (Ia)-(Iv), (II), (IIa)-(IIi), (III) and (IIIa)-(IIIj) is one of the following compounds (or a pharmaceutically acceptable salt, prodrug, or N-oxide thereof, or a solvate or hydrate thereof): 3, 4, 5, 7, 10, 11, 15, 16, 18, 22, 23, 24, 25, 27, 28, 31, 41, 42, 60, 61, 153, 154, 155, 156, 157, 158, 159, 160, 161.

In some embodiments, the compound of formulae (III) or (IIIa)-(IIIj) is one of the following compounds (or a pharmaceutically acceptable salt, prodrug, or N-oxide thereof, or a solvate or hydrate thereof): 3, 4, 5, 7, 10, 11, 15, 16, 18, 22, 23, 24, 25, 27, 28, 31, 41, 42, 60, 61.

In some embodiments, the compound of formulae (III) or (IIIa)-(IIIj) is one of the following compounds (or a pharmaceutically acceptable salt, prodrug, or N-oxide thereof, or a solvate or hydrate thereof): 3, 4, 5, 22, 23, 24.

In some embodiments, the compound of formula (I°), (Iw)-(Ix), (II°), (IIj) and (III°) is one of the following compounds (or a pharmaceutically acceptable salt, prodrug, or N-oxide thereof, or a solvate or hydrate thereof): 2', 12', 14', 24', 32', 105' and 204'.

In another aspect, the present invention comprises pharmaceutical compositions comprising a compound according to any one of the preceding aspects of the invention or any embodiment thereof, together with a pharmaceutically acceptable excipient, diluent, or carrier.

In another aspect, the invention comprises the use of a compound described by any one of the preceding aspects of the invention or any embodiment thereof, for the preparation of a medicament for the treatment of medical diseases or conditions that benefit from the inhibition of cytokine signaling. Medical conditions contemplated in this aspect include all diseases and conditions described herein.

The compounds of formulae (I°), (I), (Ia)-(Ix), (II°), (II), (IIa)-(IIj), (III°), (III) and (IIIa)-(IIIj) described above are useful as kinase inhibitors and/or inhibitors of cytokine signaling. Exemplary kinases inhibited by the presently disclosed compounds include, without limitation, ACVR1; ACVR1B (ALK-4); ACVR1C; ACVR2A; ACVR2B; ACVRL1; BMPR1A; BMPR1B; BMPR2; TGFBR1 (ALK-5), PI3K and MAP4K4 (HGK). Exemplary cytokines, the signaling of which is inhibited by the present compounds include, without limitation, TGF-β superfamily, including Activin, Nodal, TGF-β1, and GDF-8. In one aspect the present compounds are selective for one or more kinase and/or cytokine signaling pathway. For example, exemplary compounds inhibit TGF-β1 signaling, GDF-8 signaling, or both. In one aspect the present compounds inhibit GDF-8 signaling preferentially to TGF-β1 signaling, such that GDF8 signaling is inhibited at least about 1.5-fold more potently or from about 1.1-fold to about 25-fold more potently. In one embodiment certain compounds inhibit GDF8 signaling at least about 5-fold more potently, such as from about 8-fold to about 50-fold, or at least about 10-fold more potently, such as from about 15-fold to about 300-fold more potently.

In particular, the present compounds can be use to treat disorders, such as pulmonary hypertension, chronic renal disease, acute renal disease, wound healing, arthritis, osteoporosis, kidney disease, congestive heart failure, ulcers, ocular disorders, corneal wounds, diabetic nephropathy, impaired neurological function, Alzheimer's disease, atherosclerosis, peritoneal and sub-dermal adhesion, kidney fibrosis, lung fibrosis, including idiopathic pulmonary fibrosis, and liver fibrosis, hepatitis B, hepatitis C, alcohol-induced hepatitis, cancer, haemochromatosis, primary biliary cirrhosis, restenosis, retroperitoneal fibrosis, mesenteric fibrosis, endometriosis, keloids, cancer, abnormal bone function, inflammatory disorders, scarring and photoaging of the skin.

Particular proliferative diseases that can be treated with the present compounds include those selected from a benign or malignant tumor, carcinoma of the brain, kidney, liver, adrenal gland, bladder, breast, stomach, gastric tumors, ovaries, colon, rectum, prostate, pancreas, lung, vagina or thyroid, sarcoma, glioblastomas, multiple myeloma or gastrointestinal cancer, especially colon carcinoma or colorectal adenoma or a tumor of the neck and head, an epidermal hyperproliferation, melanoma, psoriasis, prostate hyperplasia, a neoplasia, a neoplasia of epithelial character, leukemias and lymphomas, a mammary carcinoma or a leukemia. Other diseases include Cowden syndrome, Lhermitte-Dudos disease and Bannayan-Zonana syndrome, or diseases in which the PI3K/PKB pathway is aberrantly activated.

The compounds described herein also include isotopically labeled compounds where one or more atoms have an atomic mass different from the atomic mass conventionally found in nature. Examples of isotopes that may be incorporated into the compounds disclosed herein include, but are not limited to, $^{2}H$, $^{3}H$, $^{11}C$, $^{13}C$, $^{14}C$, $^{15}N$, $^{18}O$, $^{17}O$, $^{18}F$ etc. Thus, the disclosed compounds may be enriched in one or more of these isotopes relative to the natural abundance of such isotope. As is known to those of skill in the art, such isotopically enriched compounds are useful for a variety of purposes. For example, substitution with heavier isotopes such as deuterium ($^{2}H$) may afford certain therapeutic advantages that result from greater metabolic stability. Substitution with positron emitting isotopes, such as 18F can be useful in Positron Emission Tomography (PET) studies. By way of example, deuterium ($^{2}H$) has a natural abundance of about 0.015%. Accordingly, for approximately every 6,500 hydrogen atoms occurring in nature, there is one deuterium atom. Specifically contemplated herein are compounds enriched in deuterium at one or more positions. Thus, deuterium containing compounds of the disclosure have deuterium at one or more positions (as the case may be) in an abundance of greater than 0.015%.

In another aspect, the invention comprises combination therapies for the treatment of cancer, including both pre-malignant and malignant neoplasms. In this aspect, the invention comprises a method of treating cancer comprising administering to a subject a compound disclosed herein in conjunction with a therapeutic treatment of cancer. In some embodiments of the invention, the compounds disclosed herein are used in combination of standard of care antiproliferative treatments of cancer. The amount of a compound disclosed herein for use in the combination therapy is an amount sufficient to inhibit signaling by members of the TGF-β superfamily, such as Nodal and Activin, which promote the survival and/or differentiation of cancer stem cells and thereby enhance the efficacy of the therapeutic treatment. Treatment with the present compounds thus blocks the ability of cancer stem cells to recapitulate a tumor destroyed by treatment with standard of care. Efficacy of treatment can be determined by any art recognized method generally employed for the particular cancer being treated and includes, for example, retardation, inhibition, or regression of tumor growth.

Reference to "combination therapy" and treatment with a compound disclosed herein "in conjunction with" another therapeutic treatment means that the compound and other therapeutic treatment can be administered simultaneously or sequentially such that the resultant treatment is more efficacious than either treatment alone.

One embodiment of treating cancer in a subject comprises administering to a subject in need thereof an amount described above of a compound disclosed herein in combination with the administration of a therapeutically effective amount of one or more chemotherapeutic agents, wherein the one or more chemotherapeutic agents is selected from the group consisting of antimetabolites, alkylating agents, coordination compounds, platinum complexes, DNA cross-linking compounds, inhibitors of transcription enzymes, tyrosine kinase inhibitors, protein kinase inhibitors, topoisomerase inhibitors, DNA minor-groove binding compounds, vinca alkyloids, taxanes, antitumor antibiotics, hormones, aromatase inhibitors, enzymes, growth factor receptors antibodies, cytokines, cell surface markers antibodies, HDAC inhibitors, HSP 90 inhibitors, BCL-2 inhibitors, B-raf inhibitors, MEK inhibitors, mTOR inhibitors, proteasome inhibitors and monoclonal antibodies.

Among the BCL-2 inhibitors useful in the invention is ABT-199.

Another embodiment of methods for treating a subject comprises administering to the subject an amount (as described above) of a compound disclosed herein in combination with the administration of a therapeutically effective amount of one or more chemotherapeutic agents, the one or more chemotherapeutic agents being independently selected from the group consisting of mechlorothamine, cyclophosphamide, ifosfamide, melphalan, chlorambucil, ethyleneimines, methylmelamines, procarbazine, dacarbazine, temozolomide, busulfan, carmustine, lomustine, methotrexate, fluorouracil, capecitabine, cytarabine, gemcitabine, cytosine arabinoside, mecaptopurine, fludarabine, cladribine, thioguanine, azathioprine, vinblastine, vincristine, paclitaxel, docetaxel, colchicine, actinomycin D, daunorubicin, bleomycin, L-asparaginase, cisplatin, carboplatin, oxaliplatin, prednisone, dexamethasone, amino glutethimide, formestane, anastrozole, hydroxyprogesterone caproate, medroxyprogesterone, tamoxifen, amsacrine, mitoxantrone, topotecan, irinotecan, camptothecin, afatinib, axitinib, bosutinib, bortezomib, carfilzomib, cabozantinib, cediranib, crizotinib, dasatinib, dabrafenib, evorolimus, ibrutinib, LDK378, LGX818, MEK162, regorafenib, ruxolitinib, selumetinib, sorafenib, trametinib, vemurafenib, erlotinib, gefitinib, imatinib, lapatinib, lestaurtinib, nilotinib, palbociclib, pazopanib, pomatinib, semaxanib, sirolimus, sunitinib, temsirolimus, vatalanib, vandetanib, anti Her2 antibodies, interferon-α, interferon-γ, interleukin 2, GM CSF, anti CTLA 4 antibodies, rituximab, anti CD33 antibodies, MGCD0103, vorinostat, 17-AAG, thalidomide, lenalidomide, rapamycin, CCI-779, doxorubicine, gemcitabine, melphalan, NPI052, gemtuzumab, alemtuzumab, cetuximab, ibritumomab tiuxaetan, tositumomab, iodine-131 tositumomab, trastuzumab, ado-trastuzumab emtansine, obinutuzumab, bevacizumab, rituximab, and anti-TRAIL death receptor antibodies.

Among the CTLA 4 antibodies that can be used in the present invention is ipilimumab, marketed as YERVOY® by Bristol-Myers Squibb.

Other chemotherapeutic agents include checkpoint pathway inhibitors, e.g., PD-1 inhibitors, such as nivolumab and lambrolizumab, and PD-L1 inhibitors, such as pembrolizumab, MEDI-4736 and MPDL3280A/RG7446. Additional checkpoint inhibitors for combination with the compounds disclosed herein include, Anti-LAG-3 agents, such as BMS-986016 (MDX-1408).

Further chemotherapeutic agents for combination with the presently disclosed TGF-β signalling inhibitors include Anti-SLAMF7 agents, such as the humanized monoclonal antibody elotuzumab (BMS-901608), anti-KIR agents, such as the anti-KIR monoclonal antibody lirilumab (BMS-986015), and anti-CD137 agents, such as the fully human monoclonal antibody urelumab (BMS-663513).

The following table displays exemplary cancers treatable in the combination therapies of the invention and the therapeutic drug and/or other treatment for use with the compounds disclosed herein:

| Cancer | Drug or Treatment |
|---|---|
| Glioma | lomustine, temozolide and/or radiation |
| hepatocellular carcinoma | sorafenib, regorafenib |
| myelodysplastic syndromes | decitabine or azacytidine |
| pancreatic cancer | Gemcitabine |
| ovarian cancer, such as epithelial ovarian carcinoma | carboplatin, cisplatin, doxorubicin, gemcitabine, paclitaxel |
| breast cancer | Trastuzumab |
| basal and squamous skin carcinomas | 5-fluorouracil, imiquimod, photodynamic therapy (e.g. with 5-aminolevulinic acid), |
| head and neck carcinoma | bleomycin, cisplatin, cetuximab, docetaxel, fluorouracil, methotrexate |
| triple negative breast cancer | Paclitaxel |
| Prostate | abiraterone, enzalutamide |

Further provided herein are methods of treatment wherein compounds of the invention are administered with one or more immuno-oncology agents. The immuno-oncology agents used herein, also known as cancer immunotherapies, are effective to enhance, stimulate, and/or up-regulate immune responses in a subject. In one aspect, the administration of a compound of the invention with an immuno-oncology agent has a synergic effect in inhibiting tumor growth.

In one aspect, the compound(s) of the invention are sequentially administered prior to administration of the immuno-oncology agent. In another aspect, compound(s) of the invention are administered concurrently with the immunology-oncology agent. In yet another aspect, compound(s) of the invention are sequentially administered after administration of the immuno-oncology agent.

In another aspect, compounds of the invention may be co-formulated with an immuno-oncology agent.

Immuno-oncology agents include, for example, a small molecule drug, antibody, or other biologic or small molecule. Examples of biologic immuno-oncology agents include, but are not limited to, cancer vaccines, antibodies, and cytokines. In one aspect, the antibody is a monoclonal antibody. In another aspect, the monoclonal antibody is humanized or human.

In one aspect, the immuno-oncology agent is (i) an agonist of a stimulatory (including a co-stimulatory) receptor or (ii) an antagonist of an inhibitory (including a co-inhibitory) signal on T cells, both of which result in amplifying antigen-specific T cell responses (often referred to as immune checkpoint regulators).

Certain of the stimulatory and inhibitory molecules are members of the immunoglobulin super family (IgSF). One important family of membrane-bound ligands that bind to co-stimulatory or co-inhibitory receptors is the B7 family, which includes B7-1, B7-2, B7-H1 (PD-L1), B7-DC (PD-L2), B7-H2 (ICOS-L), B7-H3, B7-H4, B7-H5 (VISTA), and B7-H6. Another family of membrane bound ligands that bind to co-stimulatory or co-inhibitory receptors is the TNF family of molecules that bind to cognate TNF receptor family members, which includes CD40 and CD40L, OX-40, OX-40L, CD70, CD27L, CD30, CD30L, 4-1BBL, CD137 (4-1BB), TRAIL/Apo2-L, TRAILR1/DR4, TRAILR2/DR5, TRAILR3, TRAILR4, OPG, RANK, RANKL, TWEAKR/Fn14, TWEAK, BAFFR, EDAR, XEDAR, TACI, APRIL, BCMA, LTβR, LIGHT, DcR3, HVEM, VEGI/TL1A, TRAMP/DR3, EDAR, EDA1, XEDAR, EDA2, TNFR1, Lymphotoxin α/TNFβ, TNFR2, TNFα, LTβR, Lymphotoxin α 1β2, FAS, FASL, RELT, DR6, TROY, NGFR.

In another aspect, the immuno-oncology agent is a cytokine that inhibits T cell activation (e.g., IL-6, IL-10, TGF-β, VEGF, and other immunosuppressive cytokines) or a cytokine that stimulates T cell activation, for stimulating an immune response.

In one aspect, T cell responses can be stimulated by a combination of a compound of the invention and one or more of (i) an antagonist of a protein that inhibits T cell activation (e.g., immune checkpoint inhibitors) such as CTLA-4, PD-1, PD-L1, PD-L2, LAG-3, TIM-3, Galectin 9, CEACAM-1, BTLA, CD69, Galectin-1, TIGIT, CD113, GPR56, VISTA, 2B4, CD48, GARP, PD1H, LAIR1, TIM-1, and TIM-4, and (ii) an agonist of a protein that stimulates T cell activation such as B7-1, B7-2, CD28, 4-1BB (CD137), 4-1BBL, ICOS, ICOS-L, OX40, OX40L, GITR, GITRL, CD70, CD27, CD40, DR3 and CD28H.

Other agents that can be combined with compounds of the invention for the treatment of cancer include antagonists of inhibitory receptors on NK cells or agonists of activating receptors on NK cells. For example, compounds of the invention can be combined with antagonists of KIR, such as lirilumab.

Yet other agents for combination therapies include agents that inhibit or deplete macrophages or monocytes, including but not limited to CSF-1R antagonists such as CSF-1R antagonist antibodies including RG7155 (WO11/70024, WO11/107553, WO11/131407, WO13/87699, WO13/119716, WO13/132044) or FPA-008 (WO11/140249; WO13169264; WO14/036357).

In another aspect, compounds of the invention can be used with one or more of agonistic agents that ligate positive costimulatory receptors, blocking agents that attenuate signaling through inhibitory receptors, antagonists, and one or more agents that increase systemically the frequency of anti-tumor T cells, agents that overcome distinct immune suppressive pathways within the tumor microenvironment (e.g., block inhibitory receptor engagement (e.g., PD-L1/PD-1 interactions), deplete or inhibit Tregs (e.g., using an anti-CD25 monoclonal antibody (e.g., daclizumab) or by ex vivo anti-CD25 bead depletion), inhibit metabolic enzymes such as IDO, or reverse/prevent T cell anergy or exhaustion) and agents that trigger innate immune activation and/or inflammation at tumor sites.

In one aspect, the immuno-oncology agent is a CTLA-4 antagonist, such as an antagonistic CTLA-4 antibody. Suitable CTLA-4 antibodies include, for example, YERVOY (ipilimumab) or tremelimumab.

In another aspect, the immuno-oncology agent is a PD-1 antagonist, such as an antagonistic PD-1 antibody. Suitable PD-1 antibodies include, for example, OPDIVO (nivolumab), KEYTRUDA (pembrolizumab), or MEDI-0680 (AMP-514; WO2012/145493). The immuno-oncology agent may also include pidilizumab (CT-011), though its specificity for PD-1 binding has been questioned. Another approach to target the PD-1 receptor is the recombinant protein composed of the extracellular domain of PD-L2 (B7-DC) fused to the Fc portion of IgG1, called AMP-224

In another aspect, the immuno-oncology agent is a PD-L1 antagonist, such as an antagonistic PD-L1 antibody. Suitable PD-L1 antibodies include, for example, MPDL3280A (RG7446; WO2010/077634), durvalumab (MEDI4736), BMS-936559 (WO2007/005874), and MSB0010718C (WO2013/79174).

In another aspect, the immuno-oncology agent is a LAG-3 antagonist, such as an antagonistic LAG-3 antibody. Suitable LAG3 antibodies include, for example, BMS-986016 (WO10/19570, WO14/08218), or IMP-731 or IMP-321 (WO08/132601, WO09/44273).

In another aspect, the immuno-oncology agent is a CD137 (4-1BB) agonist, such as an agonistic CD137 antibody. Suitable CD137 antibodies include, for example, urelumab and PF-05082566 (WO12/32433).

In another aspect, the immuno-oncology agent is a GITR agonist, such as an agonistic GITR antibody. Suitable GITR antibodies include, for example, BMS-986153, BMS-986156, TRX-518 (WO06/105021, WO09/009116) and MK-4166 (WO11/028683).

In another aspect, the immuno-oncology agent is an IDO antagonist. Suitable IDO antagonists include, for example, INCB-024360 (WO2006/122150, WO07/75598, WO08/36653, WO08/36642), indoximod, or NLG-919 (WO09/73620, WO09/1156652, WO11/56652, WO12/142237).

In another aspect, the immuno-oncology agent is an OX40 agonist, such as an agonistic OX40 antibody. Suitable OX40 antibodies include, for example, MEDI-6383 or MEDI-6469.

In another aspect, the immuno-oncology agent is an OX40L antagonist, such as an antagonistic OX40 antibody. Suitable OX40L antagonists include, for example, RG-7888 (WO06/029879).

In another aspect, the immuno-oncology agent is a CD40 agonist, such as an agonistic CD40 antibody. In yet another embodiment, the immuno-oncology agent is a CD40 antagonist, such as an antagonistic CD40 antibody. Suitable CD40 antibodies include, for example, lucatumumab or dacetuzumab.

In another aspect, the immuno-oncology agent is a CD27 agonist, such as an agonistic CD27 antibody. Suitable CD27 antibodies include, for example, varlilumab.

In another aspect, the immuno-oncology agent is MGA271 (to B7H3) (WO11/109400).

In another aspect, the invention comprises a method for treating a subject afflicted with cancer comprising administering to the subject a therapeutically effective amount of:
  a) a TGF-Beta inhibitor; and
  b) an anti-cancer agent which is an antibody or an antigen-binding portion thereof that binds specifically to a Programmed Death-1 (PD-1) receptor and inhibits PD-1 activity.

In some embodiments, the PD-1 inhibitor is administered by infusion.

In some embodiments, the anti-PD-1 antibody is nivolumab.

In another aspect, the invention comprises a method of determining and measuring the ability of the compounds disclosed herein to inhibit signaling by members of the TGF-β superfamily, such as Nodal and Activin, in order to identify cancers and, more specifically, tumors. In one embodiment, neoplasms susceptible to such combination therapy can be identified by testing for Nodal and Activin signaling activity using techniques known to those skilled in the art, including, for example, assays described in Lonardo, E. et al. (2011) Cell Stem Cell 9, 433-446 (which is hereby incorporated by reference in its entirety). Optionally in this embodiment, where the tested compound is found to inhibit signalling of a member of the TGF-β superfamily, such as Nodal and Activin, in the tested neoplasm, the compound is subsequently used in a combination therapy for treatment of the neoplasm, as described herein.

Definitions

Terms used herein may be preceded and/or followed by a single dash, "-", or a double dash, "=", to indicate the bond order of the bond between the named substituent and its parent moiety; a single dash indicates a single bond and a double dash indicates a double bond or a pair of single bonds in the case of a spiro-substituent. In the absence of a single or double dash it is understood that a single bond is formed between the substituent and its parent moiety; further, substituents are intended to be read "left to right" unless a dash indicates otherwise. For example, arylalkyl, arylalkyl-, and -alkylaryl indicate the same functionality.

For simplicity, chemical moieties are defined and referred to throughout primarily as univalent chemical moieties (e.g., alkyl, aryl, etc.). Nevertheless, such terms are also used to convey corresponding multivalent moieties under the appropriate structural circumstances clear to those skilled in the art. For example, while an "alkyl" moiety can refer to a monovalent radical (e.g. $CH_3$—$CH_2$—), in some circumstances a bivalent linking moiety can be "alkyl," in which case those skilled in the art will understand the alkyl to be a divalent radical (e.g., —$CH_2$—$CH_2$—), which is equivalent to the term "alkylene." (Similarly, in circumstances in which a divalent moiety is required and is stated as being "aryl," those skilled in the art will understand that the term "aryl" refers to the corresponding divalent moiety, arylene). All atoms are understood to have their normal number of valences for bond formation (i.e., 4 for carbon, 3 for N, 2 for O, and 2, 4, or 6 for S, depending on the oxidation state of the S). Nitrogens in the presently disclosed compounds can be hypervalent, e.g., an N-oxide or tetrasubstituted ammonium salt. On occasion a moiety may be defined, for example, as $(A)_a$-B—, wherein a is 0 or 1. In such instances, when a is 0 the moiety is B— and when a is 1 the moiety is A-B—.

As used herein, the term "alkyl" includes alkyl, alkenyl and alkynyl groups of a designed number of carbon atoms, such as 1 to 6 carbons (i.e., inclusive of 1 and 6), 1 to 6 carbons, 1 to 3 carbons, or 1, 2, 3, 4, 5 or 6. The term "$C_m$-$C_n$alkyl" means an alkyl group having from m to n carbon atoms (i.e., inclusive of m and n). The term "$C_m$-$C_n$alkyl" means an alkyl group having from m to n carbon atoms. For example, "$C_1$-$C_6$alkyl" is an alkyl group having from one to six carbon atoms. Alkyl and alkyl groups may be straight or branched and depending on context, may be a monovalent radical or a divalent radical (i.e., an alkylene group). In the case of an alkyl or alkyl group having zero carbon atoms (i.e., "$C_0$alkyl"), the group is simply a single covalent bond if it is a divalent radical or is a hydrogen atom if it is a monovalent radical. For example, the moiety "—($C_0$-$C_6$alkyl)-Ar" signifies connection of an optionally substituted aryl through a single bond or an alkylene bridge having from 1 to 6 carbons. Examples of "alkyl" include, for example, methyl, ethyl, propyl, isopropyl, butyl, iso-, sec- and tert-butyl, pentyl, hexyl, heptyl, 3-ethylbutyl, 3-hexenyl and propargyl. If the number of carbon atoms is not specified, the subject "alkyl" or "alkyl" moiety has from 1 to 6 carbons.

The term "haloalkyl" is an alkyl group substituted with one or more halogen atoms, e.g. F, Cl, Br and I. A more specific term, e.g., "fluoroalkyl" is an alkyl group substituted with one or more fluorine atoms. Examples of "fluoroalkyl" include fluoromethyl, difluoromethyl, trifluoromethyl, pentafluoroethyl, hexafluoroisopropyl and the like. In certain embodiments of the compounds disclosed herein, each haloalkyl is a fluoroalkyl.

The term "aryl" or "Ar" represents an aromatic ring system having a single ring (e.g., phenyl) which is optionally fused to other aromatic hydrocarbon rings or non-aromatic hydrocarbon rings. "Aryl" includes ring systems having multiple condensed rings and in which at least one is carbocyclic and aromatic, (e.g., 1,2,3,4-tetrahydronaphthyl, naphthyl). Examples of aryl groups include phenyl, 1-naphthyl, 2-naphthyl, indanyl, indenyl, dihydronaphthyl, fluorenyl, tetralinyl, and 6,7,8,9-tetrahydro-5H-benzo[a]cycloheptenyl. In certain examples, aryl groups include those having a first carbocyclic, aromatic ring fused to an aromatic or aliphatic heterocycle, for example, 2,3-dihydrobenzofuranyl. The aryl groups herein are unsubstituted or, when specified as "optionally substituted", can unless stated otherwise be substituted in one or more substitutable positions with various groups, as described below.

The term "heteroaryl" or "Het" refers to an aromatic ring system containing at least one heteroatom selected from nitrogen, oxygen and sulfur in an aromatic ring. Most commonly, the heteroaryl groups will have 1, 2, 3, or 4 heteroatoms. The heteroaryl may be fused to one or more non-aromatic ring, for example, cycloalkyl or heterocycloalkyl rings, wherein the cycloalkyl (Cak) and heterocycloalkyl (Hca) rings are described herein. In one embodiment of the present compounds the heteroaryl group is bonded to the remainder of the structure through an atom in a heteroaryl group aromatic ring. In another embodiment, the heteroaryl group is bonded to the remainder of the structure through a non-aromatic ring atom. Examples of heteroaryl groups include, for example, pyridyl, pyrimidinyl, quinolinyl, benzothienyl, indolyl, indolinyl, pyridazinyl, pyrazinyl, isoindolyl, isoquinolyl, quinazolinyl, quinoxalinyl, phthalazinyl, imidazolyl, isoxazolyl, pyrazolyl, oxazolyl, thiazolyl, indolizinyl, indazolyl, benzothiazolyl, benzimidazolyl, benzofuranyl, furanyl, thienyl, pyrrolyl, oxadiazolyl, thiadiazolyl, benzo[1,4]oxazinyl, triazolyl, tetrazolyl, isothiazolyl, naphthyridinyl, isochromanyl, chromanyl, tetrahydroisoquinolinyl, isoindolinyl, isobenzotetrahydrofuranyl, isobenzotetrahydrothienyl, isobenzothienyl, benzoxazolyl, pyridopyridinyl, benzotetrahydrofuranyl, benzotetrahydrothienyl, purinyl, benzodioxolyl, triazinyl, pteridinyl, benzothiazolyl, imidazopyridinyl, imidazothiazolyl, dihydrobenzisoxazinyl, benzisoxazinyl, benzoxazinyl, dihydrobenzisothiazinyl, benzopyranyl, benzothiopyranyl, chromonyl, chromanonyl, pyridinyl-N-oxide, tetrahydroquinolinyl, dihydroquinolinyl, dihydroquinolinonyl, dihydroisoquinolinonyl, dihydrocoumarinyl, dihydroisocoumarinyl, isoindolinonyl, benzodioxanyl, benzoxazolinonyl, pyrrolyl N-oxide, pyrimidinyl N-oxide, pyridazinyl N-oxide, pyrazinyl N-oxide, quinolinyl N-oxide, indolyl N-oxide, indolinyl N-oxide, isoquinolyl N-oxide, quinazolinyl N-oxide, quinoxalinyl N-oxide, phthalazinyl N-oxide, imidazolyl N-oxide, isoxazolyl N-oxide, oxazolyl N-oxide, thiazolyl N-oxide, indolizinyl N-oxide, indazolyl N-oxide, benzothiazolyl N-oxide, benzimidazolyl N-oxide, pyrrolyl N-oxide, oxadiazolyl N-oxide, thiadiazolyl N-oxide, triazolyl N-oxide, tetrazolyl N-oxide, benzothiopyranyl S-oxide, benzothiopyranyl S,S-dioxide. Preferred heteroaryl groups include pyridyl, pyrimidyl, quinolinyl, indolyl, pyrrolyl, furanyl, thienyl and imidazolyl, pyrazolyl, indazolyl, thiazolyl and benzothiazolyl. In certain embodiments, each heteroaryl is selected from pyridyl, pyrimidinyl, pyridazinyl, pyrazinyl, imidazolyl, isoxazolyl, pyrazolyl, oxazolyl, thiazolyl, furanyl, thienyl, pyrrolyl, oxadiazolyl, thiadiazolyl, triazolyl, tetrazolyl, isothiazolyl, pyridinyl-N-oxide, pyrrolyl N-oxide, pyrimidinyl N-oxide, pyridazinyl N-oxide, pyrazinyl N-oxide, imidazolyl N-oxide, isoxazolyl N-oxide, oxazolyl N-oxide, thiazolyl N-oxide, pyrrolyl N-oxide, oxadiazolyl N-oxide, thiadiazolyl N-oxide, triazolyl N-oxide, and tetrazolyl N-oxide. Preferred heteroaryl groups include pyridyl, pyrimidyl, quinolinyl, indolyl, pyrrolyl, furanyl, thienyl, imidazolyl, pyrazolyl, indazolyl, thiazolyl and benzothiazolyl. The heteroaryl groups herein are unsubstituted or, when specified as "optionally substituted", can unless stated otherwise be substituted in one or more substitutable positions with various groups, as described below.

The term "heterocycloalkyl" or "Hca" refers to a non-aromatic ring or ring system containing at least one heteroatom that is preferably selected from nitrogen, oxygen and sulfur, wherein said heteroatom is in a non-aromatic ring. The heterocycloalkyl may have 1, 2, 3 or 4 heteroatoms. The heterocycloalkyl may be saturated (i.e., a heterocycloalkyl) or partially unsaturated (i.e., a heterocycloalkenyl). Heterocycloalkyl includes monocyclic groups of three to eight annular atoms as well as bicyclic and polycyclic ring systems, including bridged and fused systems, wherein each ring includes three to eight annular atoms. The heterocycloalkyl ring is optionally fused to other heterocycloalkyl rings and/or non-aromatic hydrocarbon rings and/or phenyl rings. In certain embodiments, the heterocycloalkyl groups have from 3 to 7 members in a single ring. In other embodiments, heterocycloalkyl groups have 5 or 6 members in a single ring. In some embodiments, the heterocycloalkyl groups have 3, 4, 5, 6 or 7 members in a single ring. Examples of heterocycloalkyl groups include, for example, azabicyclo[2.2.2]octyl (in each case also "quinuclidinyl" or a quinuclidine derivative), azabicyclo[3.2.1]octyl, 2,5-diazabicyclo[2.2.1]heptyl, morpholinyl, thiomorpholinyl, thiomorpholinyl S-oxide, thiomorpholinyl S,S-dioxide, 2-oxazolidonyl, piperazinyl, homopiperazinyl, piperazinonyl, pyrrolidinyl, azepanyl, azetidinyl, pyrrolinyl, tetrahydropyranyl, piperidinyl, tetrahydrofuranyl, tetrahydrothienyl, 3,4-dihydroisoquinolin-2(1H)-yl, isoindolindionyl, homopiperidinyl, homomorpholinyl, homothiomorpholinyl, homothiomorpholinyl S,S-dioxide, oxazolidinonyl, dihydropyrazolyl, dihydropyrrolyl, dihydropyrazinyl, dihydropyridinyl, dihydropyrimidinyl, dihydrofuryl, dihydropyranyl, imidazolidonyl, tetrahydrothienyl S-oxide, tetrahydrothienyl S,S-dioxide and homothiomorpholinyl S-oxide. Especially desirable heterocycloalkyl groups include morpholinyl, 3,4-dihydroisoquinolin-2(1H)-yl, tetrahydropyranyl, piperidinyl, aza-bicyclo[2.2.2]octyl, γ-butyrolactonyl (i.e., an oxo-substituted tetrahydrofuranyl), γ-butryolactamyl (i.e., an oxo-substituted pyrrolidine), pyrrolidinyl, piperazinyl, azepanyl, azetidinyl, thiomorpholinyl, thiomorpholinyl S,S-dioxide, 2-oxazolidonyl, imidazolidonyl, isoindolindionyl, piperazinonyl. The heterocycloalkyl groups herein are unsubstituted or, when specified as "optionally substituted", can unless stated otherwise be substituted in one or more substitutable positions with various groups, as described below.

The term "cycloalkyl" or "Cak" refers to a non-aromatic carbocyclic ring or ring system, which may be saturated (i.e., a cycloalkyl) or partially unsaturated (i.e., a cycloalkenyl). The cycloalkyl ring optionally fused to or otherwise attached (e.g., bridged systems) to other cycloalkyl rings. Certain examples of cycloalkyl groups present in the disclosed compounds have from 3 to 7 members in a single ring, such as having 5 or 6 members in a single ring. In some embodiments, the cycloalkyl groups have 3, 4, 5, 6 or 7 members in a single ring. Examples of cycloalkyl groups include, for example, cyclohexyl, cyclopentyl, cyclobutyl, cyclopropyl, tetrahydronaphthyl and bicyclo[2.2.1]heptane. The cycloalkyl groups herein are unsubstituted or, when specified as "optionally substituted", may be substituted in one or more substitutable positions with various groups.

The term "ring system" encompasses monocycles, as well as fused and/or bridged polycycles.

The term "oxa" means a divalent oxygen radical in a chain, sometimes designated as —O—.

The term "oxo" means a doubly bonded oxygen, sometimes designated as =O or for example in describing a carbonyl "C(O)" may be used to show an oxo substituted carbon.

The term "electron withdrawing group" means a group that withdraws electron density from the structure to which it is attached than would a similarly-attached hydrogen atom. For example, electron withdrawing groups can be selected from the group consisting of halo (e.g., fluoro, chloro, bromo, and iodo), cyano, —($C_1$-$C_4$ fluoroalkyl), —O—($C_1$-$C_4$ fluoroalkyl), —C(O)—($C_0$-$C_4$alkyl), —C(O)O—($C_0$-$C_4$alkyl), —C(O)N($C_0$-$C_4$alkyl)($C_0$-$C_4$alkyl), —S(O)$_2$O—($C_0$-$C_4$alkyl), NO$_2$ and —C(O)-Hca in which the Hca includes a nitrogen atom to which the —C(O)— is bound, in which no alkyl, fluoroalkyl or heterocycloalkyl is substituted with an aryl, heteroaryl, cycloalkyl or heterocycloalkyl-containing group.

The term "substituted," when used to modify a specified group or radical, means that one or more hydrogen atoms of the specified group or radical are each, independently of one another, replaced with the same or different substituent groups as defined below, unless specified otherwise.

Substituent groups for substituting for hydrogens on saturated carbon atoms in the specified group or radical are, unless otherwise specified, —$R^{60}$, halo, —O$^-$M$^+$, =O, —O$R^{70}$, —S$R^{70}$, —S$^-$M$^+$, =S, —N$R^{80}R^{80}$, =N$R^{70}$, =N—O$R^{70}$, trihalomethyl, —CF$_3$, —CN, —OCN, —SCN, —NO, —NO$_2$, =N$_2$, —N$_3$, —SO$_2R^{70}$, —SO$_2$O$^-$M$^+$, —SO$_2$O$R^{70}$, —OSO$_2R^{70}$, —OSO$_2$O$^-$M$^+$, —OSO$_2$O$R^{70}$, —P(O)(O$^-$)$_2$(M$^+$)$_2$, —P(O)(O$R^{70}$)O$^-$M$^+$, —P(O)(O$R^{70}$)$_2$, —C(O)$R^{70}$, —C(S)$R^{70}$, —C(N$R^{70}$)$R^{70}$, —C(O)O$^-$M$^+$, —C(O)O$R^{70}$, —C(S)O$R^{70}$, —C(O)N$R^{80}R^{80}$, —C(N$R^{70}$)N$R^{80}R^{80}$, —OC(O)$R^{70}$, —OC(S)$R^{70}$, —OC(O)O$^-$M$^+$, —OC(O)O$R^{70}$, —OC(S)O$R^{70}$, —N$R^{70}$C(O)$R^{70}$, —N$R^{70}$, —C(S)$R^{70}$, —N$R^{70}$CO$_2$$^-$M$^+$, —N$R^{70}$CO$_2R^{70}$, —N$R^{70}$C(S)O$R^{70}$, —N$R^{70}$C(O)N$R^{80}R^{80}$, —N$R^{70}$C(N$R^{70}$)$R^{70}$ and —N$R^{70}$C(N$R^{70}$)N$R^{80}R^{80}$. Each $R^{60}$ is independently selected from the group consisting of alkyl, heteroalkyl, cycloalkyl, heterocycloalkyl, heterocycloalkylalkyl, cycloalkylalkyl, aryl, arylalkyl, heteroaryl and heteroarylalkyl, each of which is optionally substituted with 1, 2, 3, 4 or 5 groups selected from the group consisting of halo, —O$^-$M$^+$, =O, —O$R^{71}$, —S$R^{71}$, —S$^-$M$^+$, =S, —N$R^{81}R^{81}$, =N$R^{71}$, =N—O$R^{71}$, trihalomethyl, —CF$_3$, —CN, —OCN, —SCN, —NO, —NO$_2$, =N$_2$, —N$_3$, —SO$_2R^{71}$, —SO$_2$O$^-$M$^+$, —SO$_2$O$R^{71}$, —OSO$_2R^{71}$, —OSO$_2$O$^-$M$^+$, —OSO$_2$O$R^{71}$, —P(O)(O$^-$)$_2$(M$^+$)$_2$, —P(O)(O$R^{71}$)O$^-$M$^+$, —P(O)(O$R^{71}$)$_2$, —C(O)$R^{71}$, —C(S)$R^{71}$, —C(N$R^{71}$)$R^{71}$, —C(O)O$^-$M$^+$, —C(O)O$R^{71}$, —C(S)O$R^{71}$, —C(O)N$R^{81}R^{81}$, —C(N$R^{71}$)N$R^{81}R^{81}$, —OC(O)$R^{71}$, —OC(S)$R^{71}$, —OC(O)O$^-$M$^+$, —OC(O)O$R^{71}$, —OC(S)O$R^{71}$, —N$R^{71}$C(O)$R^{71}$, —N$R^{71}$C(S)$R^{71}$, —N$R^{71}$CO$_2$$^-$M$^+$, —N$R^{71}$CO$_2R^{71}$, —N$R^{71}$C(S)O$R^{71}$, —N$R^{71}$C(O)N$R^{81}R^{81}$, —N$R^{71}$C(N$R^{71}$)$R^{71}$ and —N$R^{71}$C(N$R^{71}$)N$R^{81}R^{81}$. Each $R^{70}$ is independently hydrogen or $R^{60}$; each $R^{80}$ is independently $R^{70}$ or alternatively, two $R^{80}$'s, taken together with the nitrogen atom to which they are bonded, form a 5-, 6- or 7-membered heterocycloalkyl which may optionally include from 1 to 4 of the same or different additional heteroatoms selected from the group consisting of O, N and S, of which N may have —H or $C_1$-$C_3$alkyl substitution; and each M$^+$ is a counter ion with a net single positive charge. Each $R^{71}$ is independently hydrogen or $R^{61}$, in which $R^{61}$ is alkyl, heteroalkyl, cycloalkyl, heterocycloalkyl, heterocycloalkylalkyl, cycloalkylalkyl, aryl, arylalkyl, heteroaryl and heteroarylalkyl, each of which is optionally substituted with 1, 2, 3, 4 or 5 groups selected from the group consisting of halo, —O$^-$M$^+$, =O, —OR$^{72}$, —S$^{72}$, —S$^-$M$^+$, =S, —NR$^{82}$R$^{82}$, =NR$^{72}$, =N—OR$^{72}$, trihalomethyl, —CF$_3$, —CN, —OCN, —SCN, —NO, —NO$_2$, =N$_2$, —N$_3$, —SO$_2$R$^{71}$, —SO$_2$O$^-$M$^+$, —SO$_2$OR$^{72}$, —OSO$_2$R$^{72}$, —OSO$_2$O$^-$M$^+$, —OSO$_2$OR$^{72}$, —P(O)(O$^-$)$_2$(M$^+$)$_2$, —P(O)(OR$^{72}$)O$^-$M$^+$, —P(O)(OR$^{72}$)$_2$, —C(O)R$^{72}$, —C(S)R$^{72}$, —C(NR$^{72}$)R$^{72}$, —C(O)O$^-$M$^+$, —C(O)OR$^{72}$, —C(S)OR$^{72}$, —C(O)NR$^{82}$R$^{82}$, —C(NR$^{72}$)NR$^{82}$R$^{82}$, —OC(O)R$^{72}$, —OC(S)R$^{72}$, —OC(O)O$^-$M$^+$, —OC(O)OR$^{72}$, —OC(S)OR$^{72}$, —NR$^{72}$C(O)R$^{72}$, —NR$^{72}$C(S)R$^{72}$, —NR$^{72}$CO$_2^-$M$^+$, —NR$^{72}$CO$_2$R$^{72}$, —NR$^{72}$C(S)OR$^{72}$, —NR$^{72}$C(O)NR$^{82}$R$^{82}$, —NR$^{72}$C(NR$^{72}$)R$^{72}$ and —NR$^{72}$C(NR$^{72}$)NR$^{82}$R$^{82}$; and each R$^{81}$ is independently R$^{71}$ or alternatively, two R$^{81}$s, taken together with the nitrogen atom to which they are bonded, form a 5-, 6- or 7-membered heterocycloalkyl which may optionally include from 1 to 4 of the same or different additional heteroatoms selected from the group consisting of O, N and S, of which N may have —H or C$_1$-C$_3$ alkyl substitution. Each R$^{72}$ is independently hydrogen, (C$_1$-C$_6$alkyl) or (C$_1$-C$_6$fluoroalkyl); each R$^{82}$ is independently R$^{72}$ or alternatively, two R$^{82}$s, taken together with the nitrogen atom to which they are bonded, form a 5-, 6- or 7-membered heterocycloalkyl which may optionally include 1, 2, 3 or 4 of the same or different additional heteroatoms selected from the group consisting of O, N and S, of which N may have —H or C$_1$-C$_3$alkyl substitution. Each M$^+$ may independently be, for example, an alkali ion, such as K$^+$, Na$^+$, Li$^+$; an ammonium ion, such as $^+$N(R$^{60}$)$_4$; or an alkaline earth ion, such as [Ca$^{2+}$]$_{0.5}$, [Mg$^{2+}$]$_{0.5}$, or [Ba$^{2+}$]$_{0.5}$ ("subscript 0.5 means e.g. that one of the counter ions for such divalent alkali earth ions can be an ionized form of a presently disclosed compound and the other a typical counter ion such as chloride, or two ionized presently disclosed molecules can serve as counter ions for such divalent alkali earth ions, or a doubly ionized compound can serve as the counter ion for such divalent alkali earth ions). As specific examples, —NR$^{80}$R$^{80}$ is meant to include —NH$_2$, —NH-alkyl, N-pyrrolidinyl, N-piperazinyl, 4-methyl-piperazin-1-yl and N-morpholinyl.

Substituent groups for hydrogens on unsaturated carbon atoms in "substituted" alkene, alkyne, aryl and heteroaryl groups are, unless otherwise specified, —R$^{60}$, halo, —O$^-$M$^+$, —OR$^{70}$, —SR$^{70}$, —S$^-$M$^+$, —NR$^{80}$R$^{80}$, trihalomethyl, —CF$_3$, —CN, —OCN, —SCN, —NO, —NO$_2$, —N$_3$, —SO$_2$R$^{70}$, —SO$_3^-$M$^+$, —SO$_3$R$^{70}$, —OSO$_2$R$^{70}$, —OSO$_3^-$M$^+$, —OSO$_3$R$^{70}$, —PO$_3^{-2}$(M$^+$)$_2$, —P(O)(OR$^{70}$)O$^-$M$^+$, —P(O)(OR$^{70}$)$_2$, —C(O)R$^{70}$, —C(S)R$^{70}$, —C(NR$^{70}$)R$^{70}$, —CO$_2^-$M$^+$, —CO$_2$R$^{70}$, —C(S)OR$^{70}$, —C(O)NR$^{80}$R$^{80}$, —C(NR$^{70}$)NR$^{80}$R$^{80}$, —OC(O)R$^{70}$, —OC(S)R$^{70}$, —OCO$_2^-$M$^+$, —OCO$_2$R$^{70}$, —OC(S)OR$^{70}$, —NR$^{70}$C(O)R$^{70}$, —NR$^{70}$C(S)R$^{70}$, —NR$^{70}$CO$_2^-$M$^+$, —NR$^{70}$CO$_2$R$^{70}$, —NR$^{70}$C(S)OR$^{70}$, —NR$^{70}$C(O)NR$^{80}$R$^{80}$, —NR$^{70}$C(NR$^{70}$)R$^{70}$ and —NR$^{70}$C(NR$^{70}$)NR$^{80}$R$^{80}$, where R$^{60}$, R$^{70}$, R$^{80}$ and M$^+$ are as previously defined.

Substituent groups for hydrogens on nitrogen atoms in "substituted" heteroalkyl and heterocycloalkyl groups are, unless otherwise specified, —R$^{60}$, —O$^-$M$^+$, —OR$^{70}$, —SR$^{70}$, —S$^-$M$^+$, —NR$^{80}$R$^{80}$, trihalomethyl, —CF$_3$, —CN, —NO, —NO$_2$, —S(O)$_2$R$^{70}$, —S(O)$_2$O$^-$M$^+$, —S(O)$_2$OR$^{70}$, —OS(O)$_2$R$^{70}$, —OS(O)$_2$O$^-$M$^+$, —OS(O)$_2$OR$^{70}$, —P(O)(O$^-$)$_2$(M$^+$)$_2$, —P(O)(OR$^{70}$)O$^-$M$^+$, —P(O)(OR$^{70}$)(OR$^{70}$), —C(O)R$^{70}$, —C(S)R$^{70}$, —C(NR$^{70}$)R$^{70}$, —C(O)OR$^{70}$, —C(S)OR$^{70}$, —C(O)NR$^{80}$R$^{80}$, —C(NR$^{70}$)NR$^{80}$R$^{80}$, —OC(O)—R$^{70}$, —OC(S)R$^{70}$, —OC(O)OR$^{70}$, —OC(S)OR$^{70}$, —NR$^{70}$C(O)R$^{70}$, —NR$^{70}$C(S)R$^{70}$, —NR$^{70}$C(O)OR$^{70}$, —NR$^{70}$C(S)OR$^{70}$, —NR$^{70}$C(O)NR$^{80}$R$^{80}$, —NR$^{70}$C(NR$^{70}$)R$^{70}$ and —NR$^{70}$C(NR$^{70}$)NR$^{80}$R$^{80}$, where R$^{60}$, R$^{70}$, R$^{80}$ and M$^+$ are as previously defined.

In certain embodiments of the compounds disclosed herein, a group that is substituted has 1, 2, 3, or 4 substituents, 1, 2, or 3 substituents, 1 or 2 substituents, or 1 substituent.

In certain embodiments, substituent groups on "substituted" alkyl, cycloalkyl, heterocycloalkyl, aryl and heteroaryl groups are -halo, —OH, —O—(C$_1$-C$_4$alkyl), —O—(C$_1$-C$_4$ haloalkyl), —N(C$_0$-C$_4$ alkyl)(C$_0$-C$_4$alkyl), —SH, —S(O)$_{0-2}$—(C$_1$-C$_4$alkyl), —(C$_1$-C$_4$alkyl), —(C$_1$-C$_4$ haloalkyl), —C(O)—(C$_0$-C$_4$alkyl), —C(O)N(C$_0$-C$_4$alkyl)(C$_0$-C$_4$alkyl), —N(C$_0$-C$_4$alkyl)C(O)(C$_0$-C$_4$alkyl)(C$_0$-C$_4$alkyl), —C(O)O—(C$_0$-C$_4$alkyl), —OC(O)—(C$_0$-C$_4$alkyl), S(O)$_2$—O(C$_0$-C$_4$alkyl), and —NO$_2$, in which no alkyl is further substituted.

The compounds disclosed herein can also be provided as pharmaceutically acceptable salts. The term "pharmaceutically acceptable salts" or "a pharmaceutically acceptable salt thereof" refer to salts prepared from pharmaceutically acceptable non-toxic acids or bases including inorganic acids and bases and organic acids and bases. If the compound is basic, salts may be prepared from pharmaceutically acceptable non-toxic acids. Such salts may be, for example, acid addition salts of at least one of the following acids: benzenesulfonic acid, citric acid, α-glucoheptonic acid, D-gluconic acid, glycolic acid, lactic acid, malic acid, malonic acid, mandelic acid, phosphoric acid, propanoic acid, succinic acid, sulfuric acid, tartaric acid (d, l, or dl), tosic acid (toluenesulfonic acid), valeric acid, palmitic acid, pamoic acid, sebacic acid, stearic acid, lauric acid, acetic acid, adipic acid, carbonic acid, 4-chlorobenzenesulfonic acid, ethanedisulfonic acid, ethylsuccinic acid, fumaric acid, galactaric acid (mucic acid), D-glucuronic acid, 2-oxoglutaric acid, glycerophosphoric acid, hippuric acid, isethionic acid (ethanolsulfonic acid), lactobionic acid, maleic acid, 1,5-naphthalene-disulfonic acid, 2-naphthalene-sulfonic acid, pivalic acid, terephthalic acid, thiocyanic acid, cholic acid, n-dodecyl sulfate, 3-hydroxy-2-naphthoic acid, 1-hydroxy-2-naphthoic acid, oleic acid, undecylenic acid, ascorbic acid, (+)-camphoric acid, d-camphorsulfonic acid, dichloroacetic acid, ethanesulfonic acid, formic acid, hydriodic acid, hydrobromic acid, hydrochloric acid, methanesulfonic acid, nicotinic acid, nitric acid, orotic acid, oxalic acid, picric acid, L-pyroglutamic acid, saccharine, salicylic acid, gentisic acid, and/or 4-acetamidobenzoic acid.

The compounds described herein can also be provided in prodrug form. "Prodrug" refers to a derivative of an active compound (drug) that undergoes a transformation under the conditions of use, such as within the body, to release the active drug. Prodrugs are frequently, but not necessarily, pharmacologically inactive until converted into the active drug. Prodrugs are typically obtained by masking a functional group in the drug believed to be in part required for activity with a progroup (defined below) to form a promoiety which undergoes a transformation, such as cleavage, under the specified conditions of use to release the functional group, and hence the active drug. The cleavage of the promoiety can proceed spontaneously, such as by way of a hydrolysis reaction, or it can be catalyzed or induced by another agent, such as by an enzyme, by light, by acid, or by a change of or exposure to a physical or environmental parameter, such as a change of temperature. The agent can be endogenous to the conditions of use, such as an enzyme present in the cells to which the prodrug is administered or the acidic conditions of the stomach, or it can be supplied exogenously. A wide variety of progroups, as well as the resultant promoieties, suitable for masking functional groups in the active drugs to yield prodrugs are well-known in the art. For example, a hydroxyl functional group can be masked as a sulfonate, ester or carbonate promoiety, which can be hydrolyzed in vivo to provide the hydroxyl group. An amino functional group can be masked as an amide, carbamate, imine, urea, phosphenyl, phosphoryl or sulfenyl promoiety, which can be hydrolyzed in vivo to provide the amino group. A carboxyl group can be masked as an ester (including silyl esters and thioesters), amide or hydrazide promoiety, which can be hydrolyzed in vivo to provide the carboxyl group. Specific examples of suitable progroups and their respective promoieties will be apparent to those of skill in the art.

The compounds disclosed herein can also be provided as N-oxides.

The presently disclosed compounds, salts, prodrugs and N-oxides can be provided, for example, in solvate or hydrate form.

One of ordinary skill in the art of medicinal chemistry also will appreciate that the disclosed structures are intended to include isotopically enriched forms of the present compounds. As used herein "isotopes" includes those atoms having the same atomic number but different mass numbers. As is known to those of skill in the art, certain atoms, such as hydrogen occur in different isotopic forms. For example, hydrogen includes three isotopic forms, protium, deuterium and tritium. As will be apparent to those of skill in the art upon consideration of the present compounds, certain compounds can be enriched at a given position with a particular isotope of the atom at that position. For example, compounds having a fluorine atom, may be synthesized in a form enriched in the radioactive fluorine isotope $^{18}$F. Similarly, compounds may be enriched in the heavy isotopes of hydrogen: deuterium and tritium; and similarly can be enriched in a radioactive isotope of carbon, such as $^{13}$C. Such isotopic variant compounds undergo different metabolic pathways and can be useful, for example, in studying the ubiquitination pathway and its role in disease.

As used herein, the term "cell" is meant to refer to a cell that is in vitro, ex vivo or in vivo. In some embodiments, an ex vivo cell can be part of a tissue sample excised from an organism such as a mammal. In some embodiments, an in vitro cell can be a cell in a cell culture. In some embodiments, an in vivo cell is a cell living in an organism such as a mammal.

As used herein, the term "contacting" refers to the bringing together of indicated moieties in an in vitro system or an in vivo system. For example, "contacting" an enzyme with a compound includes the administration of a compound described herein to an individual or patient, such as a human, as well as, for example, introducing a compound into a sample containing a cellular or purified preparation containing the enzyme.

As used herein, the terms "individual," "patient," or "subject" are used interchangeably, refers to any animal, including mammals, preferably mice, rats, other rodents, rabbits, dogs, cats, swine, cattle, sheep, horses, or primates, and most preferably humans.

As used herein, the phrase "therapeutically effective amount" refers to the amount of active compound or pharmaceutical agent that elicits the biological or medicinal response that is being sought in a tissue, system, animal, individual or human by a researcher, veterinarian, medical doctor or other clinician.

In certain embodiments, a therapeutically effective amount can be an amount suitable for (1) preventing the disease; for example, preventing a disease, condition or disorder in an individual who may be predisposed or otherwise susceptible to the disease, condition or disorder but does not yet experience or display the pathology or symptomatology of the disease;

(2) inhibiting the disease; for example, inhibiting a disease, condition or disorder in an individual who is experiencing or displaying the pathology or symptomatology of the disease, condition or disorder; or (3) ameliorating the disease (including a symptom thereof); for example, ameliorating a disease, condition or disorder in an individual who is experiencing or displaying the pathology or symptomatology of the disease, condition or disorder (i.e., reversing the pathology and/or symptomatology) such as decreasing the severity of disease.

As used here, the terms "treatment" and "treating" means (i) ameliorating the referenced disease state, condition, or disorder (or a symptom thereof), such as, for example, ameliorating a disease, condition or disorder in an individual who is experiencing or displaying the pathology or symptomatology of the disease, condition or disorder (i.e., reversing or improving the pathology and/or symptomatology) such as decreasing the severity of disease or symptom thereof; or (ii) eliciting the referenced biological effect (e.g., modulation or inhibition of GDF-8 or TGF-β1).

Manifestation of amelioration of a disease condition by inhibiting GDF-8 or TGF-β1 may require the concomitant or sequential administration of additional therapeutic agents, such as antineoplastic agents in the case of cancer, or antiretroviral agents in the case of viral diseases. For example, administration of GDF-8 and TGF-β1 inhibitors for the treatment of cancer does not always produce a direct antitumor effect when used as a single agent. However, when combined with chemotherapeutic drugs (antineoplastic) the antitumor effect observed is higher than the sum of effects of each agent alone.

As used herein, the terms "catalytic pocket", "catalytic site", "active site" collectively and indistinctly refer to a region of the enzyme that contains amino acid residues responsible for the substrate binding (charge, hydrophobicity, steric hindrance) and catalytic amino acid residues which act as proton donors or acceptors or are responsible for binding a cofactor and participate in the catalysis of a chemical reaction.

As used herein, the phrase "pharmaceutically acceptable salt" refers to both pharmaceutically acceptable acid and base addition salts and solvates. Such pharmaceutically acceptable salts include salts of acids such as hydrochloric, phosphoric, hydrobromic, sulfuric, sulfinic, formic, toluenesulfonic, methanesulfonic, nitric, benzoic, citric, tartaric, maleic, hydroiodic, alkanoic such as acetic, HOOC—$(CH_2)_n$—COOH where n is 0-4, and the like. Non-toxic pharmaceutical base addition salts include salts of bases such as sodium, potassium, calcium, ammonium, and the like. Those skilled in the art will recognize a wide variety of non-toxic pharmaceutically acceptable addition salts.

Pharmaceutical Formulations and Dosage Forms

The compounds of structural formulae (I)-(III) can be administered, for example, orally, topically, parenterally, by inhalation or spray or rectally in dosage unit formulations containing one or more pharmaceutically acceptable carriers, diluents or excipients. The term parenteral as used herein includes percutaneous, subcutaneous, intravascular (e.g., intravenous), intramuscular, or intrathecal injection or infusion techniques and the like.

Pharmaceutical compositions can be made using the presently disclosed compounds. For example, in one embodiment, a pharmaceutical composition includes a pharmaceutically acceptable carrier, diluent or excipient, and compound as described above with reference to structural formulae (I)-(III).

In the pharmaceutical compositions disclosed herein, one or more compounds of structural formulae (I)-(III) may be present in association with one or more pharmaceutically acceptable carriers, diluents or excipients, and, if desired, other active ingredients. The pharmaceutical compositions containing compounds of structural formulae (I)-(III) may be in a form suitable for oral use, for example, as tablets, troches, lozenges, aqueous or oily suspensions, dispersible powders or granules, emulsion, hard or soft capsules, or syrups or elixirs.

Compositions intended for oral use can be prepared according to any suitable method for the manufacture of pharmaceutical compositions and such compositions may contain one or more agents selected from the group consisting of sweetening agents, flavoring agents, coloring agents and preservative agents in order to provide pharmaceutically elegant and palatable preparations. Tablets contain the active ingredient in admixture with non-toxic pharmaceutically acceptable excipients that are suitable for the manufacture of tablets. These excipients can be for example, inert diluents, such as calcium carbonate, sodium carbonate, lactose, calcium phosphate or sodium phosphate; granulating and disintegrating agents, for example, corn starch, or alginic acid; binding agents, for example starch, gelatin or acacia, and lubricating agents, for example magnesium stearate, stearic acid or talc. The tablets can be uncoated or they can be coated by known techniques. In some cases such coatings can be prepared by suitable techniques to delay disintegration and absorption in the gastrointestinal tract and thereby provide a sustained action over a longer period. For example, a time delay material such as glyceryl monostearate or glyceryl distearate can be employed.

Formulations for oral use can also be presented as hard gelatin capsules, wherein the active ingredient is mixed with an inert solid diluent, for example, calcium carbonate, calcium phosphate or kaolin, or as soft gelatin capsules wherein the active ingredient is mixed with water or an oil medium, for example peanut oil, liquid paraffin or olive oil.

Formulations for oral use can also be presented as lozenges.

Aqueous suspensions contain the active materials in admixture with excipients suitable for the manufacture of aqueous suspensions. Such excipients can be suspending agents, for example sodium carboxymethylcellulose, methylcellulose, hydropropylmethylcellulose, sodium alginate, polyvinylpyrrolidone, gum tragacanth and gum acacia; dispersing or wetting agents such as a naturally-occurring phosphatide, for example, lecithin, or condensation products of an alkylene oxide with fatty acids, for example polyoxyethylene stearate, or condensation products of ethylene oxide with long chain aliphatic alcohols, for example heptadecaethyleneoxycetanol, or condensation products of ethylene oxide with partial esters derived from fatty acids and a hexitol such as polyoxyethylene sorbitol monooleate, or condensation products of ethylene oxide with partial esters derived from fatty acids and hexitol anhydrides, for example polyethylene sorbitan monooleate. The aqueous suspensions may also contain one or more preservatives, for example ethyl, or n-propyl p-hydroxybenzoate, one or more coloring agents, one or more flavoring agents, and one or more sweetening agents, such as sucrose or saccharin.

Oily suspensions can be formulated by suspending the active ingredients in a vegetable oil, for example arachis oil, olive oil, sesame oil or coconut oil, or in a mineral oil such as liquid paraffin. The oily suspensions may contain a thickening agent, for example beeswax, hard paraffin or cetyl alcohol. Sweetening agents and flavoring agents may be added to provide palatable oral preparations. These compositions may be preserved by the addition of an antioxidant such as ascorbic acid.

Dispersible powders and granules suitable for preparation of an aqueous suspension by the addition of water provide the active ingredient in admixture with a dispersing or wetting agent, suspending agent and one or more preservatives. Suitable dispersing or wetting agents or suspending agents are exemplified by those already mentioned above. Additional excipients, for example sweetening, flavoring and coloring agents, can also be present.

Pharmaceutical compositions can also be in the form of oil-in-water emulsions. The oily phase can be a vegetable oil or a mineral oil or mixtures of these. Suitable emulsifying agents can be naturally-occurring gums, for example gum acacia or gum tragacanth, naturally-occurring phosphatides, for example soy bean, lecithin, and esters or partial esters derived from fatty acids and hexitol, anhydrides, for example sorbitan monooleate, and condensation products of the said partial esters with ethylene oxide, for example polyoxyethylene sorbitan monooleate. The emulsions can also contain sweetening and flavoring agents.

In some embodiments, the pharmaceutically acceptable carrier, diluent, or excipient is not water. In other embodiments, the water comprises less than 50% of the composition. In some embodiments, compositions comprising less than 50% water have at least 1%, 2%, 3%, 4% or 5% water. In other embodiments, the water content is present in the composition in a trace amount.

In some embodiments, the pharmaceutically acceptable carrier, diluent, or excipient is not alcohol. In other embodiments, the alcohol comprises less than 50% of the composition. In some embodiments, composiitons comprising less than 50% alcohol have at least 1%, 2%, 3%, 4% or 5% alcohol. In other embodiments, the alcohol content is present in the composition in a trace amount.

Syrups and elixirs can be formulated with sweetening agents, for example glycerol, propylene glycol, sorbitol, glucose or sucrose. Such formulations can also contain a demulcent, a preservative, flavoring, and coloring agents. The pharmaceutical compositions can be in the form of a sterile injectable aqueous or oleaginous suspension. This suspension can be formulated according to the known art using those suitable dispersing or wetting agents and suspending agents that have been mentioned above. The sterile injectable preparation can also be a sterile injectable solution or suspension in a non-toxic parentally acceptable diluent or solvent, for example as a solution in 1,3-butanediol. Among the acceptable vehicles and solvents that can be employed are water, Ringer's solution and isotonic sodium chloride solution. In addition, sterile, fixed oils can be employed as a solvent or suspending medium. For this purpose any bland fixed oil can be employed including synthetic mono- or diglycerides. In addition, fatty acids such as oleic acid find use in the preparation of injectables.

Compounds of structural formulae (I)-(III) can also be administered in the form of suppositories, e.g., for rectal administration of the drug. These compositions can be prepared by mixing the compound with a suitable non-irritating excipient that is solid at ordinary temperatures but liquid at the rectal temperature and will therefore melt in the rectum to release the drug. Such materials include cocoa butter and polyethylene glycols.

Compounds of structural formula (I)-(III) can also be administered parenterally in a sterile medium. The drug, depending on the vehicle and concentration used, can either be suspended or dissolved in the vehicle. Advantageously, adjuvants such as local anesthetics, preservatives and buffering agents can be dissolved in the vehicle.

The compositions can be formulated in a unit dosage form, each dosage containing from about 5 to about 100 mg, more usually about 10 to about 30 mg, of the active ingredient. The term "unit dosage forms" refers to physically discrete units suitable as unitary dosages for human subjects and other mammals, each unit containing a predetermined quantity of active material calculated to produce the desired therapeutic effect, in association with a suitable pharmaceutical excipient.

The active compound can be effective over a wide dosage range and is generally administered in a pharmaceutically effective amount. It will be understood, however, that the amount of the compound actually administered will usually be determined by a physician, according to the relevant circumstances, including the condition to be treated, the chosen route of administration, the actual compound administered, the age, weight, and response of the individual patient, the severity of the patient's symptoms, and the like.

For preparing solid compositions such as tablets, the principal active ingredient is mixed with a pharmaceutical excipient to form a solid preformulation composition containing a homogeneous mixture of a compound described herein. When referring to these preformulation compositions as homogeneous, the active ingredient is typically dispersed evenly throughout the composition so that the composition can be readily subdivided into equally effective unit dosage forms such as tablets, pills and capsules. This solid preformulation is then subdivided into unit dosage forms of the type described above containing from, for example, 0.1 to about 500 mg of the active ingredient of a compound described herein.

The tablets or pills can be coated or otherwise compounded to provide a dosage form affording the advantage of prolonged action. For example, the tablet or pill can comprise an inner dosage and an outer dosage component, the latter being in the form of an envelope over the former. The two components can be separated by an enteric layer which serves to resist disintegration in the stomach and permit the inner component to pass intact into the duodenum or to be delayed in release. A variety of materials can be used for such enteric layers or coatings, such materials including a number of polymeric acids and mixtures of polymeric acids with such materials as shellac, cetyl alcohol, and cellulose acetate.

The amount of compound or composition administered to a patient will vary depending upon what is being administered, the purpose of the administration, such as prophylaxis or therapy, the state of the patient, the manner of administration, and the like. In therapeutic applications, compositions can be administered to a patient already suffering from a disease in an amount sufficient to cure or at least partially arrest the symptoms of the disease and its complications. Effective doses will depend on the disease condition being treated as well as by the judgment of the attending clinician depending upon factors such as the severity of the disease, the age, weight and general condition of the patient, and the like.

The compositions administered to a patient can be in the form of pharmaceutical compositions described above. These compositions can be sterilized by conventional sterilization techniques, or may be sterile filtered. Aqueous solutions can be packaged for use as is, or lyophilized, the lyophilized preparation being combined with a sterile aqueous carrier prior to administration. The pH of the compound preparations typically will be between 3 and 11, more preferably from 5 to 9 and most preferably from 7 to 8. It will be understood that use of certain of the foregoing excipients, carriers, or stabilizers will result in the formation of pharmaceutical salts.

The therapeutic dosage of the compounds can vary according to, for example, the particular use for which the treatment is made, the manner of administration of the compound, the health and condition of the patient, and the judgment of the prescribing physician. The proportion or concentration of a compound described herein in a pharmaceutical composition can vary depending upon a number of factors including dosage, chemical characteristics (e.g., hydrophobicity), and the route of administration. For example, the compounds described herein can be provided in an aqueous physiological buffer solution containing about 0.1 to about 10% w/v of the compound for parenteral administration. Some typical dose ranges are from about 1 µg/kg to about 1 g/kg of body weight per day. In some embodiments, the dose range is from about 0.01 mg/kg to about 100 mg/kg of body weight per day. The dosage is likely to depend on such variables as the type and extent of progression of the disease or disorder, the overall health status of the particular patient, the relative biological efficacy of the compound selected, formulation of the excipient, and its route of administration. Effective doses can be extrapolated from dose-response curves derived from in vitro or animal model test systems.

The compounds described herein can also be formulated in combination with one or more additional active ingredients which can include any pharmaceutical agent such as anti-viral agents, vaccines, antibodies, immune enhancers, immune suppressants, anti-inflammatory agents and the like.

EXAMPLES

General Synthetic Methodologies

Many general references providing commonly known chemical synthetic schemes and conditions useful for synthesizing the disclosed compounds are available (see, e.g., Smith and March, March's Advanced Organic Chemistry: Reactions, Mechanisms, and Structure, Fifth Edition, Wiley-Interscience, 2001; or Vogel, A Textbook of Practical Organic Chemistry, Including Qualitative Organic Analysis, Fourth Edition, New York: Longman, 1978).

Compounds as described herein can be purified by any of the means known in the art, including chromatographic means, such as HPLC, preparative thin layer chromatography, flash column chromatography and ion exchange chromatography. Any suitable stationary phase can be used, including normal and reversed phases as well as ionic resins. Most typically the disclosed compounds are purified via silica gel and/or alumina chromatography. See, e.g., Introduction to Modern Liquid Chromatography, 2nd Edition, ed. L. R. Snyder and J. J. Kirkland, John Wiley and Sons, 1979; and Thin Layer Chromatography, ed E. Stahl, Springer-Verlag, New York, 1969.

During any of the processes for preparation of the subject compounds, it may be necessary and/or desirable to protect sensitive or reactive groups on any of the molecules concerned. This may be achieved by means of conventional protecting groups as described in standard works, such as J.

F. W. McOmie, "Protective Groups in Organic Chemistry," Plenum Press, London and New York 1973, in T. W. Greene and P. G. M. Wuts, "Protective Groups in Organic Synthesis," Third edition, Wiley, New York 1999, in "The Peptides"; Volume 3 (editors: E. Gross and J. Meienhofer), Academic Press, London and New York 1981, in "Methoden der organischen Chemie," Houben-Weyl, 4.sup.th edition, Vol. 15/1, Georg Thieme Verlag, Stuttgart 1974, in H.-D. Jakubke and H. Jescheit, "Aminosauren, Peptide, Proteine," Verlag Chemie, Weinheim, Deerfield Beach, and Basel 1982, and/or in Jochen Lehmann, "Chemie der Kohlenhydrate: Monosaccharide and Derivate," Georg Thieme Verlag, Stuttgart 1974. The protecting groups may be removed at a convenient subsequent stage using methods known from the art.

The compounds disclosed herein can be made using procedures familiar to the person of ordinary skill in the art and as described herein. For example, compounds of structural formula (I) can be prepared according to Schemes 1-3, or analogous synthetic schemes.

One of skill in the art can adapt the reaction sequences of Schemes 1 and 2 to fit the desired target molecule. Of course, in certain situations one of skill in the art will use different reagents to affect one or more of the individual steps or to use protected versions of certain of the substituents. Additionally, one skilled in the art would recognize that compounds of structural formulae (I)-(III) can be synthesized using different routes altogether.

Compounds suitable for use in the presently disclosed pharmaceutical compositions include compounds of Table A, above. These compounds can be made according to the general schemes described above, for example using a procedure similar to that described below in the Examples.

The following examples are intended to further illustrate certain embodiments and are not intended to limit the scope of the presently disclosed compounds.

EXAMPLES

Example 1

Synthesis and Characterization

Scheme 1: General Synthesis of 4,5-Diarylimidazoles

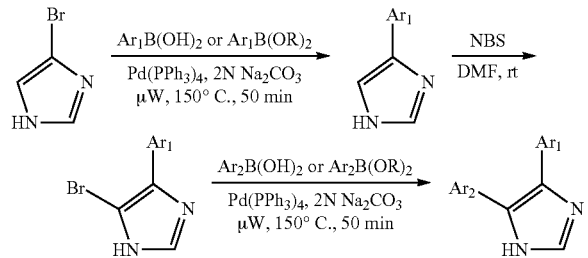

Step 1: A solution of 4-bromo-1H-imidazole (1.0 g, 6.8 mmol), (4-fluoro-3-methylphenyl)boronic acid (1.1 g, 7.1 mmol), tetrakis(triphenylphosphine)palladium(0) (0.63 g, 0.55 mmol) and aqueous $Na_2CO_3$ (2 M, 4 mL, 8.0 mmol) in a mixture of DME/EtOH/$H_2O$ (7:3:2, 10 mL) was evacuated and then refilled with nitrogen (three cycles). Resulting reaction mixture was then irradiated in the microwave at 150° C. for 50 min., dried ($MgSO_4$), filtered and concentrated under reduced pressure to give a black residue. The residue was purified by column chromatography eluting with MeOH/DCM to provide 4-(4-fluoro-3-methylphenyl)-1H-imidazole (1.1 g, 92%). MS m/e: 177 (M+H)⁺.

Step 2: To a solution of 4-(4-fluoro-3-methylphenyl)-1H-imidazole (1.1 g, 6.2 mmol) in DMF (10 mL), N-bromosuccinimide (1.2 g, 6.7 mmol) was added at room temperature. The resulting reaction mixture was allowed to stir at room temperature for 1 h, and then transferred dropwise into a stirred solution of ice-water (50 mL). The resulting yellow precipitate was filtered, washed with water and dried under vacuum overnight to give 5-bromo-4-(4-fluoro-3-methylphenyl)-1H-imidazole (1.2 g, 74%). MS m/e: 255 (M+H)⁺.

Step 3: A degassed solution of 5-bromo-4-(4-fluoro-3-methylphenyl)-1H-imidazole (50 mg, 0.2 mmol), indazole-5-boronic acid pinacol ester (60 mg, 0.25 mmol), tetrakis(triphenylphosphine)palladium(0) (25 mg, 0.02 mmol) and aqueous $Na_2CO_3$ (2 M, 0.3 mL) in a mixture of DME/EtOH/$H_2O$ (7:3:2, 1.0 mL) was irradiated in the microwave at 150° C. for 50 min. The reaction mixture was then dried ($MgSO_4$), filtered and concentrated under reduced pressure to give a black residue, which was purified by HPLC to provide 5-(4-(4-fluoro-3-methylphenyl)-1H-imidazol-5-yl)-1H-indazole. MS m/e: 293 (M+H)⁺.

Scheme 2: General Synthesis of 1-Methyl-4,5-diarylimidazoles

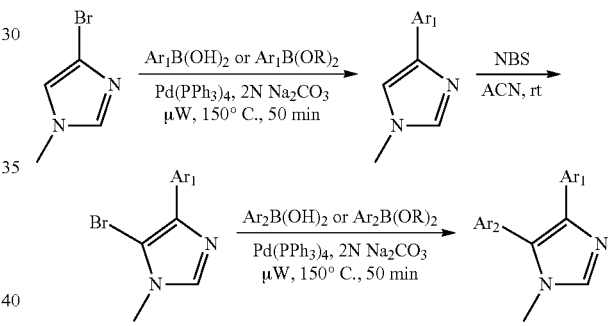

Step 1: A solution of 4-bromo-1-methyl-1H-imidazole (1.0 g, 6.2 mmol), (4-fluoro-3-methylphenyl)boronic acid (1.0 g, 6.5 mmol), tetrakis(triphenylphosphine)-palladium (0) (0.6 g, 0.52 mmol) and aqueous $Na_2CO_3$ (2 M, 4 mL, 8.0 mmol) in a mixture of DME/EtOH/$H_2O$ (7:3:2, 10 mL) was evacuated and then refilled with nitrogen (three cycles). Resulting reaction mixture was then irradiated in the microwave at 150° C. for 50 min., dried ($MgSO_4$), filtered and concentrated under reduced pressure to give a black residue, which was purified by column chromatography eluting with MeOH/DCM to provide 4-(4-fluoro-3-methylphenyl)-1-methyl-1H-imidazole (0.6 g, 51%). MS m/e: 191 (M+H)⁺.

Step 2: To a solution of 4-(4-fluoro-3-methylphenyl)-1-methyl-1H-imidazole (0.6 g, 3.2 mmol) in acetonitrile (10 mL), N-bromosuccinimide (0.62 g, 3.5 mmol) was added at room temperature. The resulting reaction mixture was allowed to stir at room temperature for 1 h, and then transferred dropwise into a stirred solution of ice-water (50 mL). The resulting yellow precipitate was filtered, washed with water and dried under vacuum overnight to give 5-bromo-4-(4-fluoro-3-methylphenyl)-1-methyl-1H-imidazole (0.6 g, 71%). MS m/e: 269 (M+H)⁺.

Step 3: A degassed solution of 5-bromo-4-(4-fluoro-3-methylphenyl)-1-methyl-1H-imidazole (50 mg, 0.2 mmol), indazole-5-boronic acid pinacol ester (60 mg, 0.25 mmol), tetrakis(triphenylphosphine)palladium(0) (25 mg, 0.02 mmol) and aqueous Na$_2$CO$_3$ (2 M, 0.3 mL) in a mixture of DME/EtOH/H$_2$O (7:3:2, 1.0 mL) was irradiated in the microwave at 150° C. for 50 min. The reaction mixture was then dried (MgSO$_4$), filtered and concentrated under reduced pressure to give a black residue, which was purified by HPLC to provide 5-(4-(4-fluoro-3-methylphenyl)-1-methyl-1H-imidazol-5-yl)-1H-indazole. MS m/e: 307 (M+H)$^+$.

Scheme 3: General Synthesis of 2-Methyl-4,5-diarylimidazoles

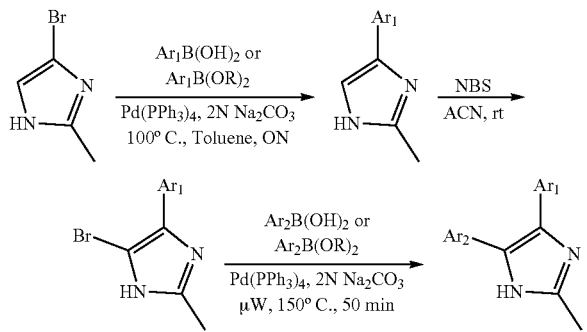

Step 1: A solution of 4-bromo-2-methyl-1H-imidazole (1.0 g, 6.2 mmol), (4-fluoro-3-methylphenyl)boronic acid (1.1 g, 7.1 mmol) and tetrakis(triphenylphosphine)palladium(0) (0.33 g, 0.3 mmol) in a mixture of aqueous Na$_2$CO$_3$ solution (2 M, 10 mL, 20 mmol) and toluene (10 mL) was evacuated and then refilled with nitrogen (three cycles). Resulting reaction mixture was then allowed to stir at 100° C. overnight, cooled down to room temperature, dried (MgSO$_4$), filtered and concentrated under reduced pressure to give a black residue. Purification by column chromatography eluting with MeOH/DCM provided 4-(4-fluoro-3-methylphenyl)-2-methyl-1H-imidazole (1.1 g, 93%). MS m/e: 191 (M+H)$^+$.

Step 2: To a solution of 4-(4-fluoro-3-methylphenyl)-2-methyl-1H-imidazole (1.1 g, 5.8 mmol) in acetonitrile (10 mL), N-bromosuccinimide (0.62 g, 3.5 mmol) was added. The resulting reaction mixture was allowed to stir at room temperature for 1 h, and then transferred dropwise into a stirred solution of ice-water (50 mL). The resulting yellow precipitate was filtered, washed with water and dried under vacuum overnight to give 5-bromo-4-(4-fluoro-3-methylphenyl)-2-methyl-1H-imidazole as a yellow solid (0.89 g, 57%). MS m/e: 269 (M+H)$^+$.

Step 3: A degassed solution of 5-bromo-4-(4-fluoro-3-methylphenyl)-2-methyl-1H-imidazole (50 mg, 0.2 mmol), indazole-5-boronic acid pinacol ester (60 mg, 0.25 mmol), tetrakis(triphenylphosphine)palladium(0) (25 mg, 0.02 mmol) and aqueous Na$_2$CO$_3$ (2 M, 0.3 mL) in a mixture of DME/EtOH/H$_2$O (7:3:2, 1.0 mL) was irradiated in the microwave at 150° C. for 50 min. The reaction mixture was then dried (MgSO$_4$), filtered and concentrated under reduced pressure to give a black residue, which was purified by HPLC to provide 5-(4-(4-fluoro-3-methylphenyl)-2-methyl-1H-imidazol-5-yl)-1H-indazole. MS m/e: 307 (M+H)$^+$.

Scheme 4: General Synthesis of 1,2-Dimethyl-4,5-diarylimidazoles

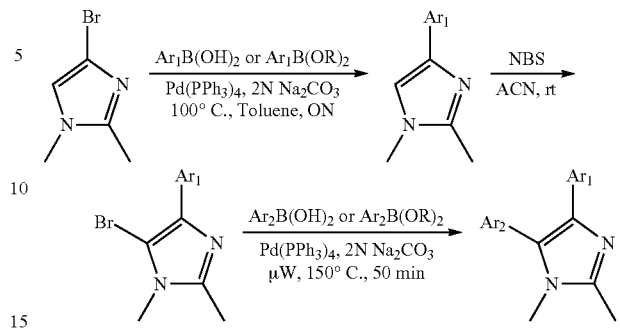

Step 1: A solution of 4-bromo-1,2-dimethyl-1H-imidazole (1.0 g, 5.7 mmol), (4-fluoro-3-methylphenyl)boronic acid (0.92 g, 6.0 mmol), tetrakis(triphenylphosphine)-palladium(0) (0.33 g, 0.3 mmol) and aqueous Na$_2$CO$_3$ (2 M, 10 mL, 20 mmol) in toluene (10 ml) was evacuated and then refilled with nitrogen (three cycles). Resulting reaction mixture was then allowed to stir at 100° C. overnight, cooled down to room temperature, dried (MgSO$_4$), filtered and concentrated under reduced pressure to give a black residue. Column chromatography on silica gel, eluting with MeOH/DCM provided 4-(4-fluoro-3-methylphenyl)-1,2-dimethyl-1H-imidazole (0.88 g, 75%). MS m/e: 205 (M+H)$^+$.

Step 2: To a solution of 4-(4-fluoro-3-methylphenyl)-1,2-dimethyl-1H-imidazole (0.88 g, 4.3 mmol) in acetonitrile (10 mL), N-bromosuccinimide (0.81 g, 4.5 mmol) was added. The resulting reaction mixture was allowed to stir at room temperature for 1 h, and then transferred dropwise into a stirred solution of ice-water (50 mL). The resulting white precipitate was filtered, washed with water and dried under vacuum overnight to give 5-bromo-4-(4-fluoro-3-methylphenyl)-1,2-dimethyl-1H-imidazole (0.94 g, 77%). MS m/e: 283 (M+H)$^+$.

Step 3: A degassed solution of 5-bromo-4-(4-fluoro-3-methylphenyl)-1,2-dimethyl-1H-imidazole (50 mg, 0.2 mmol), indazole-5-boronic acid pinacol ester (60 mg, 0.25 mmol), tetrakis(triphenylphosphine)palladium(0) (25 mg, 0.02 mmol) and aqueous Na$_2$CO$_3$ (2 M, 0.3 mL) in a mixture of DME/EtOH/H$_2$O (7:3:2, 1.0 mL) was irradiated in the microwave at 150° C. for 50 min. The reaction mixture was then dried (MgSO$_4$), filtered and concentrated under reduced pressure to give a black residue, which was purified by HPLC to provide 5-(4-(4-fluoro-3-methylphenyl)-1,2-dimethyl-1H-imidazol-5-yl)-1H-indazole. MS m/e: 321 (M+H)$^+$.

Scheme 5: General Synthesis of 2-Ethyl-4,5-diarylimidazoles

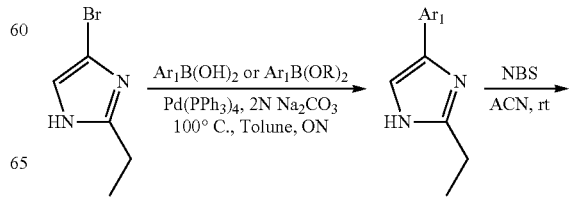

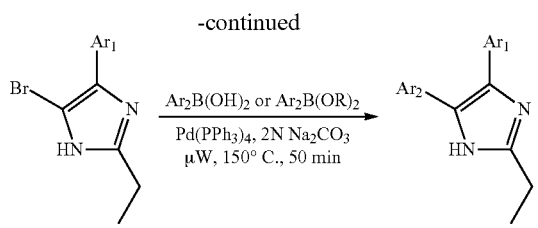

Step 1: A solution of 4-bromo-2-ethyl-1H-imidazole (1.0 g, 5.7 mmol), (4-fluoro-3-methylphenyl)boronic acid (0.97 g, 6.3 mmol), tetrakis(triphenylphosphine)palladium(0) (0.33 g, 0.3 mmol) and aqueous Na$_2$CO$_3$ (2 M, 10 mL, 20 mmol) in toluene (10 ml) was evacuated and then refilled with nitrogen (three cycles). Resulting reaction mixture was then allowed to stir at 100° C. overnight, cooled down to room temperature, dried (MgSO$_4$), filtered and concentrated under reduced pressure to give a black residue. Column chromatography on silica gel, eluting with MeOH/DCM provided 2-ethyl-4-(4-fluoro-3-methylphenyl)-1H-imidazole as a colorless oil (0.95 g, 81%). MS m/e: 205 (M+H)$^+$.

Step 2: To a solution of 4-(4-fluoro-3-methylphenyl)-2-ethyl-1H-imidazole (0.95 g, 4.7 mmol) in acetonitrile (10 mL), N-bromosuccinimide (0.87 g, 4.9 mmol) was added. The resulting reaction mixture was allowed to stir at room temperature for 1 h, concentrated and added water (30 mL) and dichloromethane (30 mL). The organic layer was then separated and the aqueous layer was extracted with dichloromethane (3×20 mL), dried (MgSO$_4$) and chromatographed on silica gel, eluting with MeOH/DCM, to give 5-bromo-2-ethyl-4-(4-fluoro-3-methylphenyl)-1H-imidazole (0.34 g, 26%). MS m/e: 283 (M+H)$^+$.

Step 3: A degassed solution of 5-bromo-4-(4-fluoro-3-methylphenyl)-2-ethyl-1H-imidazole (50 mg, 0.2 mmol), indazole-5-boronic acid pinacol ester (60 mg, 0.25 mmol), tetrakis(triphenylphosphine)palladium(0) (25 mg, 0.02 mmol) and aqueous Na$_2$CO$_3$ (2 M, 0.3 mL) in a mixture of DME/EtOH/H$_2$O (7:3:2, 1.0 mL) was irradiated in the microwave at 150° C. for 50 min. The reaction mixture was then dried (MgSO$_4$), filtered and concentrated under reduced pressure to give a black residue, which was purified by HPLC to provide 5-(2-ethyl-4-(4-fluoro-3-methylphenyl)-1H-imidazol-5-yl)-1H-indazole. MS m/e: 321 (M+H)$^+$.

Scheme 6: General Synthesis of 4,5-Diaryl-2-trifluoromethylimidazoles

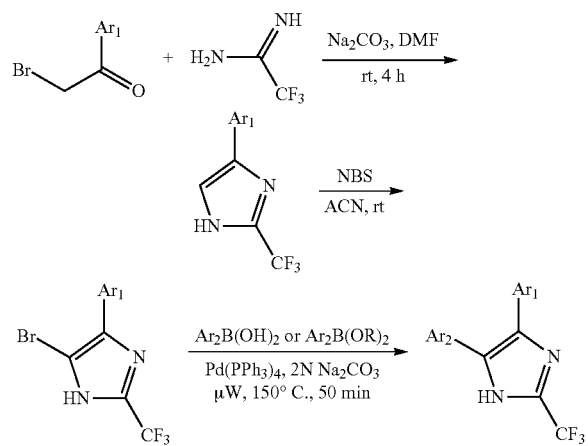

Step 1: To a solution of 2-bromo-3'-fluoroacetophenone (1.0 g, 4.3 mmol) in 10 mL of N,N-dimethylformamide was added the free base of 2,2,2-trifluoroacetimidamide (3 g, 26.8 mmol). The resulting solution was allowed to stir at room temperature for 4 h, after which time ethyl acetate (30 mL) was added. The resulting organic layer was then washed with saturated sodium bicarbonate solution and dried over sodium sulfate. The crude product was purified by silica gel chromatography to give 4-(3-chlorophenyl)-2-(trifluoromethyl)-1H-imidazole (0.38 g, 36%). MS m/e: 247 (M+H)$^+$.

Step 2: To a solution of 4-(3-chlorophenyl)-2-(trifluoromethyl)-1H-imidazole (0.38 g, 1.5 mmol) in acetonitrile (10 mL), N-bromosuccinimide (0.33 g, 1.9 mmol) was added. The resulting reaction mixture was allowed to stir at room temperature for 1 h, concentrated and added water (30 mL) and dichloromethane (30 mL). The organic layer was then separated and the aqueous layer was extracted with dichloromethane (3×20 mL), dried (MgSO$_4$) and chromatographed on silica gel, eluting with MeOH/DCM, to give 5-bromo-4-(3-chlorophenyl)-2-(trifluoromethyl)-1H-imidazole (0.25 g, 50%). MS m/e: 325 (M+H)$^+$.

Step 3: A degassed solution of 5-bromo-4-(3-chlorophenyl)-2-(trifluoromethyl)-1H-imidazole (35 mg, 0.1 mmol), 6-(4,4,5,5-tetramethyl-1,3,2-dioxaborolan-2-yl)-[1,2,4]triazolo-[1,5-a]pyridine (32 mg, 0.13 mmol), tetrakis(triphenylphosphine)palladium(0) (25 mg, 0.02 mmol) and aqueous Na$_2$CO$_3$ (2 M, 0.3 mL) in a mixture of DME/EtOH/H$_2$O (7:3:2, 1.0 mL) was irradiated in the microwave at 100° C. for 30 min. The reaction mixture was then dried (MgSO$_4$), filtered and concentrated under reduced pressure to give a black residue, which was purified by HPLC to provide 6-(4-(3-chlorophenyl)-2-(trifluoromethyl)-1H-imidazol-5-yl)-[1,2,4]triazolo[1,5-a]pyridine. MS m/e: 364 (M+H)$^+$.

Scheme 7: General Synthesis of 4,5-Diaryl-2-isopropylimidazoles

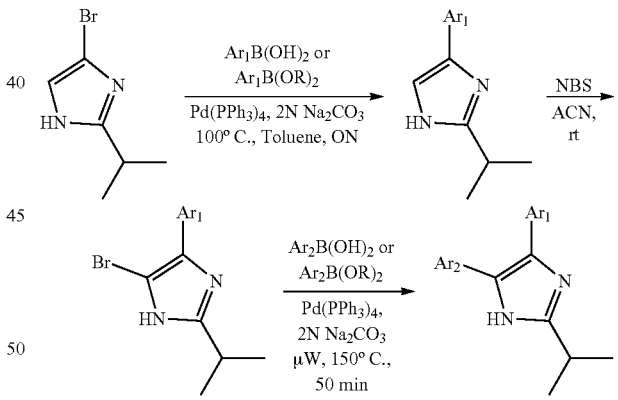

Step 1: A solution of 4-bromo-2-isopropyl-1H-imidazole (1.0 g, 5.3 mmol), m-tolylboronic acid (1.2 g, 8.8 mmol), tetrakis(triphenylphosphine)palladium(0) (0.33 g, 0.3 mmol) and aqueous Na$_2$CO$_3$ (4 M, 10 mL, 40 mmol) in toluene (20 ml) was evacuated and then refilled with nitrogen (three cycles). Resulting reaction mixture was then allowed to stir at 100° C. overnight, cooled down to room temperature, dried (MgSO$_4$), filtered and concentrated under reduced pressure to give a black residue. Column chromatography on silica gel, eluting with MeOH/DCM provided 2-isopropyl-4-(m-tolyl)-1H-imidazole as a yellow oil (0.43 g, 41%). MS m/e: 201 (M+H)$^+$.

Step 2: To a solution of 2-isopropyl-4-(m-tolyl)-1H-imidazole (0.43 g, 2.1 mmol) in acetonitrile (10 mL), N-bromosuccinimide (0.42 g, 2.4 mmol) was added. The resulting reaction mixture was allowed to stir at room temperature for 1 h, concentrated and added water (30 mL) and dichloromethane (30 mL). The organic layer was then separated and the aqueous layer was extracted with dichloromethane (3×20 mL), dried (MgSO₄) and chromatographed on silica gel, eluting with MeOH/DCM, to give 5-bromo-2-isopropyl-4-(m-tolyl)-1H-imidazole (0.45 g, 75%). MS m/e: 279 (M+H)⁺.

Step 3: A degassed solution of 5-bromo-2-isopropyl-4-(m-tolyl)-1H-imidazole (50 mg, 0.18 mmol), 6-(4,4,5,5-tetramethyl-1,3,2-dioxaborolan-2-yl)-[1,2,4]triazolo[1,5-a]pyridine (55 mg, 0.22 mmol), tetrakis(triphenylphosphine)palladium(0) (25 mg, 0.02 mmol) and aqueous Na₂CO₃ (2 M, 0.3 mL) in a mixture of DME/EtOH/H₂O (7:3:2, 1.0 mL) was irradiated in the microwave at 150° C. for 50 min. The reaction mixture was then dried (MgSO₄), filtered and concentrated under reduced pressure to give a black residue, which was purified by HPLC to provide 6-(2-isopropyl-4-(m-tolyl)-1H-imidazol-5-yl)-[1,2,4]triazolo[1,5-a]pyridine. MS m/e: 318 (M+H)⁺.

in anhydrous EtOH (5 mL) was heated at reflux for 1 h. After that, the solvent was removed in vacuo, and saturated aqueous NaHCO₃ was added. The mixture was then extracted with ethyl acetate. The combined organic phases were washed with brine, dried over sodium sulfate, filtered, and concentrated under reduced pressure to give 4-(3-chlorophenyl)thiazol-2-amine as a solid (0.4 g, 93%).

Step 3: To a solution of 4-(3-chlorophenyl)thiazol-2-amine (0.4 g, 2.0 mmol) in acetic acid (2 mL) was added bromine (0.1 g, 2.2 mmol) at room temperature. The mixture was stirred at room temperature for 2 min and solidified. The mixture was carefully basified with saturated aqueous NaHCO₃, and then extracted with dichloromethane. The combined organic layers were dried over sodium sulfate, filtered, and concentrated under reduced pressure to give a residue, which was purified by chromatography eluting with ethyl acetate/hexanes (1/4) to provide 5-bromo-4-(3-chlorophenyl)thiazol-2-amine as a white solid (0.5 g, 92%).

Step 4: A mixture of 5-bromo-4-(3-chlorophenyl)thiazol-2-amine (0.04 g, 0.14 mmol), 6-(4,4,5,5-tetramethyl-1,3,2-dioxaborolan-2-yl)benzo[d]thiazole (0.05 g, 0.18 mmol), Scheme 8: General Synthesis of Thiazoles

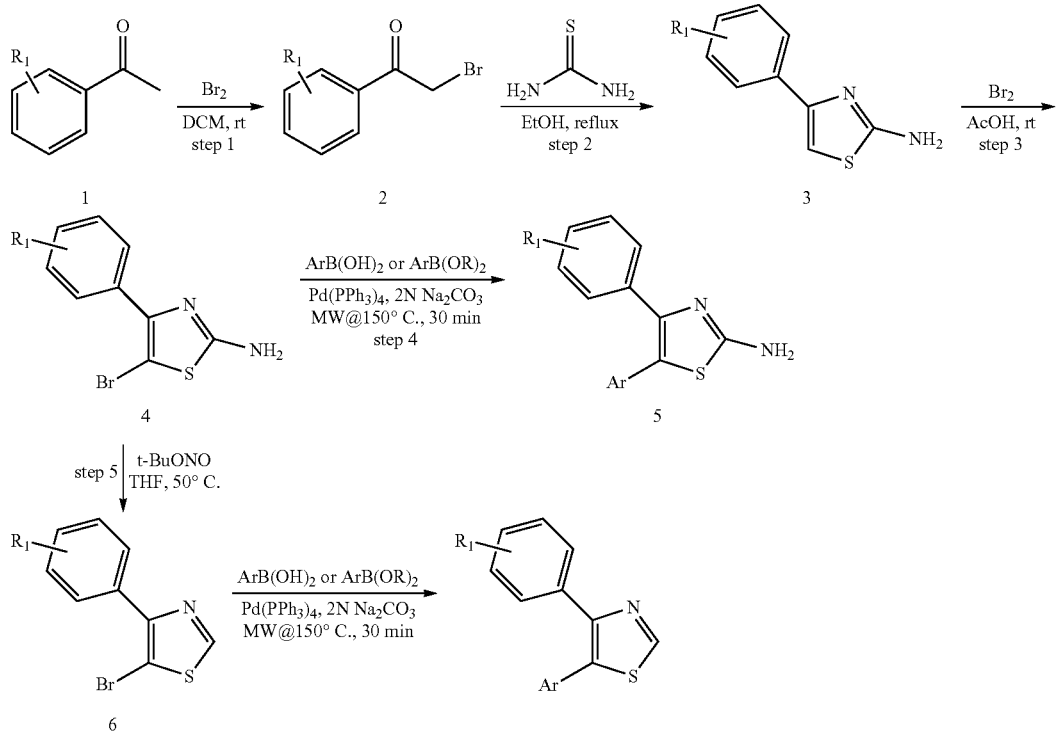

Step 1: To a solution of 2',4',5'-triifluoroacetophenone (2.4 g, 14 mmol) in dichloromethane (16 mL) at room temperature was added a solution of bromine (2.2 g, 13.9 mmol) in dichloromethane (7 mL) drop wise. Once the addition was complete, the resulting solution was stirred at room temperature for 1 h. Ice water was then added into reaction flask and the mixture was stirred for 15 min. The organic layer was separated, washed with water, dried over sodium sulfate, filtered, and concentrated under reduced pressure to give 2-bromo-1-(2,4,5-trifluorophenyl)ethan-1-one as a pale yellow oil (3.0 g, 85%).

Step 2: To a mixture of 2-bromo-1-(3-chlorophenyl)ethan-1-one (0.5 g, 2.1 mmol) and thiourea (0.2 g, 2.3 mmol)

tetrakis(triphenylphosphine)palladium(0) (0.02 g, 0.02 mmol), and 2.0 M of aqueous Na₂CO₃ (0.2 mL) in 1,2-dimethoxyethane (1.4 mL), EtOH (0.6 mL) and water (0.4 mL) was irradiated under microwave at 150° C. for 0.5 h. The mixture was then concentrated under reduced pressure to give a residue, which was purified by chromatography eluting with ethyl acetate to provide 5-(benzo[d]thiazol-6-yl)-4-(3-chlorophenyl)thiazol-2-amine as a pale white solid (0.03 g, 55%).

Step 5: A solution of 5-bromo-4-(m-tolyl)thiazol-2-amine (0.4 g, 1.6 mmol) and tert-butylnitrite (0.3 g, 2.4 mmol) in THF (15 mL) was heated at 50° C. for 4 h. The reaction mixture was diluted with ethyl acetate and washed with water. The organic layer was dried over sodium sulfate, filtered, and concentrated under reduced pressure to give a residue, which was purified by chromatography eluting with ethyl acetate/hexanes (1/9) to give 5-bromo-4-(m-tolyl)thiazole (0.13 g, 33%).

Compound 1: 5-(4-Phenyl-1H-imidazol-5-yl)-1H-indazole. $^1$H NMR (CD$_3$OD, 300 MHz) δ 8.01 (d, J=1.0 Hz, 1H), 7.88 (s, 1H), 7.85 (dd, J=1.6, 0.9 Hz, 1H), 7.51 (dt, J=8.7, 1.0 Hz, 1H), 7.47-7.40 (m, 3H), 7.34-7.26 (m, 3H). MS m/e: 261 (M+H)$^+$.

Compound 2: 6-(4-Phenyl-1H-imidazol-5-yl)-1H-indazole. $^1$H NMR (CD$_3$OD, 300 MHz) δ 8.02 (d, J=1.0 Hz, 1H), 7.83 (s, 1H), 7.71 (dd, J=8.5, 0.9 Hz, 1H), 7.62 (q, J=1.1 Hz, 1H), 7.49-7.41 (m, 2H), 7.37-7.27 (m, 3H), 7.23 (dd, J=8.4, 1.4 Hz, 1H). MS m/e: 261 (M+H)$^+$.

Compound 3: 5-(4-(4-Fluoro-3-methylphenyl)-1H-imidazol-5-yl)-1H-indazole. $^1$H NMR (CD$_3$OD, 300 MHz) δ 8.03 (d, J=1.0 Hz, 1H), 7.84 (dd, J=1.5, 0.9 Hz, 1H), 7.83 (s, 1H), 7.52 (dt, J=8.7, 1.0 Hz, 1H), 7.42 (dd, J=8.7, 1.5 Hz, 1H), 7.33 (dd, J=7.5, 1.6 Hz, 1H), 7.24-7.18 (m, 1H), 6.96 (dd, J=9.7, 8.5 Hz, 1H), 2.20 (d, J=1.9 Hz, 3H). MS m/e: 293 (M+H)$^+$.

Compound 4: 6-(4-(4-Fluoro-3-methylphenyl)-1H-imidazol-5-yl)-1H-indazole. $^1$H NMR (CD$_3$OD, 300 MHz) δ 8.02 (d, J=1.0 Hz, 1H), 7.80 (s, 1H), 7.72 (dd, J=8.5, 0.9 Hz, 1H), 7.60 (q, J=1.1 Hz, 1H), 7.34 (dd, J=7.5, 1.6 Hz, 1H), 7.28-7.18 (m, 2H), 6.99 (dd, J=9.7, 8.5 Hz, 1H), 2.21 (d, J=1.9 Hz, 3H). MS m/e: 293 (M+H)$^+$.

Compound 5: 6-(4-(4-Fluoro-3-methylphenyl)-1-methyl-1H-imidazol-5-yl)-1H-indazole. $^1$H NMR (CD$_3$OD, 300 MHz) δ 8.10 (d, J=1.0 Hz, 1H), 7.79 (dd, J=1.5, 0.9 Hz, 1H), 7.76 (s, 1H), 7.65 (dt, J=8.6, 1.0 Hz, 1H), 7.33-7.27 (m, 2H), 7.12-7.07 (m, 1H), 6.79 (dd, J=9.7, 8.6 Hz, 1H), 3.55 (s, 3H), 2.10 (d, J=1.9 Hz, 3H). MS m/e: 307 (M+H)$^+$.

Compound 6: 5-(4-(4-Chlorophenyl)-1H-imidazol-5-yl)-1H-indazole. $^1$H NMR (CD$_3$OD, 300 MHz) δ 8.04 (d, J=1.0 Hz, 1H), 7.84 (dd, J=1.6, 0.9 Hz, 1H), 7.80 (s, 1H), 7.54 (dt, J=8.7, 1.0 Hz, 1H), 7.44-7.40 (m, 3H), 7.29 (dt, J=8.8, 2.4, 2.1 Hz, 2H). MS m/e: 295 (M+H)$^+$.

Compound 7: 6-(4-(4-Fluoro-3-methylphenyl)-1-methyl-1H-imidazol-5-yl)-1H-indazole. $^1$H NMR (CD$_3$OD, 300 MHz) δ 8.50 (s, 1H), 8.16 (d, J=1.0 Hz, 1H), 7.94 (dd, J=8.3, 0.9 Hz, 1H), 7.61 (q, J=1.1 Hz, 1H), 7.29 (dd, J=7.3, 1.5 Hz, 1H), 7.15 (dd, J=8.4, 1.3 Hz, 1H), 7.15-7.09 (m, 1H), 6.91 (t, J=9.1 Hz, 1H), 3.69 (s, 3H), 2.14 (d, J=1.9 Hz, 3H). MS m/e: 295 (M+H)$^+$.

Compound 8: 6-(4-(4-Fluoro-3-methylphenyl)-1-methyl-1H-imidazol-5-yl)-1-methyl-1H-benzo[d]imidazole. $^1$H NMR (CD$_3$OD, 300 MHz) δ 8.23 (s, 1H), 7.89 (s, 1H), 7.78 (dd, J=8.3, 0.7 Hz, 1H), 7.60 (dd, J=1.5, 0.7 Hz, 1H), 7.30 (dd, J=7.3, 2.1 Hz, 1H), 7.26 (dd, J=8.3, 1.6 Hz, 1H), 7.13-7.03 (m, 1H), 6.80 (t, J=9.1 Hz, 1H), 3.89 (s, 3H), 3.57 (s, 3H), 2.11 (d, J=1.9 Hz, 3H). MS m/e: 321 (M+H)$^+$.

Compound 9: 6-(4-(4-Fluoro-3-methylphenyl)-1-methyl-1H-imidazol-5-yl)benzo[d]thiazole. $^1$H NMR (CD$_3$OD, 300 MHz) δ 9.33 (s, 1H), 8.17 (dd, J=8.5, 0.6 Hz, 1H), 8.11 (dd, J=1.7, 0.6 Hz, 1H), 7.82 (s, 1H), 7.52 (dd, J=8.4, 1.7 Hz, 1H), 7.28 (dd, J=7.6, 2.3 Hz, 1H), 7.10-7.05 (m, 1H), 6.82 (dd, J=9.7, 8.6 Hz, 1H), 3.59 (s, 3H), 2.12 (d, J=2.1 Hz, 3H). MS m/e: 324 (M+H)$^+$.

Compound 10: 5-(4-(4-Fluorophenyl)-1H-imidazol-5-yl)-1H-indazole. $^1$H NMR (CD$_3$OD, 300 MHz) δ 8.03 (d, J=1.0 Hz, 1H), 7.93 (s, 1H), 7.84 (dd, J=1.6, 0.9 Hz, 1H), 7.52 (dt, J=8.7, 1.0 Hz, 1H), 7.49-7.36 (m, 3H), 7.10-6.98 (m, 2H). MS m/e: 279 (M+H)$^+$.

Compound 11: 6-(4-(4-Fluorophenyl)-1H-imidazol-5-yl)-1H-indazole. $^1$H NMR (CD$_3$OD, 300 MHz) δ 8.02 (d, J=1.0 Hz, 1H), 7.88 (s, 1H), 7.72 (dd, J=8.4, 0.9 Hz, 1H), 7.60 (q, J=1.1 Hz, 1H), 7.50-7.40 (m, 2H), 7.20 (dd, J=8.4, 1.4 Hz, 1H), 7.13-7.00 (m, 2H). MS m/e: 279 (M+H)$^+$.

Compound 12: 6-(4-(4-Fluorophenyl)-1H-imidazol-5-yl)-1-methyl-1H-benzo[d]imidazole. $^1$H NMR (CD$_3$OD, 300 MHz) δ 8.12 (s, 1H), 7.81 (s, 1H), 7.62 (d, J=2.6 Hz, 1H), 7.60 (d, J=3.5 Hz, 1H), 7.53-7.37 (m, 2H), 7.32 (dd, J=8.5, 1.5 Hz, 1H), 7.16-6.91 (m, 2H), 3.83 (s, 3H). MS m/e: 293 (M+H)$^+$.

Compound 13: 6-(4-(4-Fluorophenyl)-1H-imidazol-5-yl)benzo[d]thiazole. $^1$H NMR (CD$_3$OD, 300 MHz) δ 9.22 (s, 1H), 8.12 (d, J=1.2 Hz, 1H), 8.00 (d, J=8.5 Hz, 1H), 7.85 (s, 1H), 7.58 (dd, J=8.5, 1.7 Hz, 1H), 7.51-7.37 (m, 2H), 7.13-7.04 (m, 2H). MS m/e: 296 (M+H)$^+$.

Compound 14: 6-(4-(4-Fluorophenyl)-1H-imidazol-5-yl)imidazo[1,2-a]pyridine. $^1$H NMR (CD$_3$OD, 300 MHz) δ 8.52 (dd, J=1.7, 1.0 Hz, 1H), 7.85 (s, 1H), 7.83 (d, J=0.9 Hz, 1H), 7.58 (d, J=1.4 Hz, 1H), 7.54-7.41 (m, 3H), 7.29 (dd, J=9.4, 1.7 Hz, 1H), 7.18-7.07 (m, 2H). MS m/e: 279 (M+H)$^+$.

Compound 15: 5-(4-(m-Tolyl)-1H-imidazol-5-yl)-1H-indazole. $^1$H NMR (CD$_3$OD, 300 MHz) δ 8.02 (d, J=1.0 Hz, 1H), 7.93 (s, 1H), 7.86 (dd, J=1.6, 0.9 Hz, 1H), 7.51 (dt, J=8.7, 0.9 Hz, 1H), 7.44 (dd, J=8.6, 1.6 Hz, 1H), 7.31-7.28 (m, 1H), 7.23-7.15 (m, 2H), 7.13-7.09 (m, 1H), 2.27 (s, 3H). MS m/e: 275 (M+H)$^+$.

Compound 16: 6-(4-(m-Tolyl)-1H-imidazol-5-yl)-1H-indazole. $^1$H NMR (CD$_3$OD, 300 MHz) δ 8.02 (d, J=1.0 Hz, 1H), 7.83 (s, 1H), 7.70 (dd, J=8.4, 0.9 Hz, 1H), 7.63 (q, J=1.1 Hz, 1H), 7.32-7.28 (m, 1H), 7.26-7.19 (m, 3H), 7.16-7.08 (m, 1H), 2.29 (s, 3H). MS m/e: 275 (M+H)$^+$.

Compound 17: 1-Methyl-6-(4-(m-tolyl)-1H-imidazol-5-yl)-1H-benzo[d]imidazole. $^1$H NMR (CD$_3$OD, 300 MHz) δ 8.11 (s, 1H), 7.85 (s, 1H), 7.63 (d, J=1.2 Hz, 1H), 7.58 (d, J=8.5 Hz, 1H), 7.34 (dd, J=8.5, 1.8 Hz, 1H), 7.30 (br s, 1H), 7.21-7.17 (m, 2H), 7.13-7.07 (m, 1H), 3.81 (s, 3H), 2.27 (s, 3H). MS m/e: 289 (M+H)$^+$.

Compound 18: 6-(4-(m-Tolyl)-1H-imidazol-5-yl)benzo[d]thiazole. MS m/e: 292 (M+H)$^+$.

Compound 19: 6-(4-(m-Tolyl)-1H-imidazol-5-yl)imidazo[1,2-a]pyridine. $^1$H NMR (CD$_3$OD, 300 MHz) δ 8.50 (dd, J=1.7, 1.0 Hz, 1H), 7.83 (s, 1H), 7.80 (d, J=0.6 Hz, 1H), 7.56 (d, J=1.4 Hz, 1H), 7.46 (d, J=9.4 Hz, 1H), 7.33-7.26 (m, 2H), 7.24-7.19 (m, 2H), 7.16-7.12 (m, 1H), 2.29 (s, 3H). MS m/e: 275 (M+H)$^+$.

Compound 20: 6-(4-(m-Tolyl)-1H-imidazol-5-yl)quinoxaline. $^1$H NMR (CD$_3$OD, 300 MHz) δ 8.82 (s, 2H), 8.19 (dd, J=1.8, 0.7 Hz, 1H), 8.00 (dd, J=8.8, 0.7 Hz, 1H), 7.95 (dd, J=8.9, 1.8 Hz, 1H), 7.87 (s, 1H), 7.36-7.15 (m, 4H), 2.32 (s, 3H). MS m/e: 287 (M+H)$^+$.

Compound 21: 6-(4-(4-Fluoro-3-methylphenyl)-1-methyl-1H-imidazol-5-yl)quinoxaline. $^1$H NMR (CD$_3$OD, 300 MHz) δ 8.93 (q, J=1.9 Hz, 2H), 8.17 (d, J=8.8 Hz, 1H), 8.12 (d, J=1.8 Hz, 1H), 7.86 (s, 1H), 7.78 (dd, J=8.7, 1.9 Hz, 1H), 7.30 (dd, J=7.3, 1.8 Hz, 1H), 7.09 (ddd, J=7.6, 4.9, 2.3 Hz, 1H), 6.84 (dd, J=9.5, 8.6 Hz, 1H), 3.68 (s, 3H), 2.13 (d, J=2.1 Hz, 3H). MS m/e: 319 (M+H)$^+$.

Compound 22: 5-(4-(3-Chlorophenyl)-1H-imidazol-5-yl)-1H-indazole. $^1$H NMR (CD$_3$OD, 300 MHz) δ 8.04 (d, J=1.0 Hz, 1H), 7.85 (dd, J=1.6, 0.9 Hz, 1H), 7.82 (s, 1H), 7.55 (dt, J=8.8, 1.0 Hz, 1H), 7.49-7.47 (m, 1H), 7.41 (dd, J=8.7, 1.6 Hz, 1H), 7.36-7.31 (m, 1H), 7.26-7.21 (m, 2H). MS m/e: 295 (M+H)$^+$.

Compound 23: 6-(4-(3-Chlorophenyl)-1H-imidazol-5-yl)-1H-indazole. $^1$H NMR (CD$_3$OD, 300 MHz) δ 8.05 (d, J=1.0 Hz, 1H), 7.83 (s, 1H), 7.77 (dd, J=8.4, 0.7 Hz, 1H), 7.61 (q, J=1.1 Hz, 1H), 7.51-7.47 (m, 1H), 7.38-7.33 (m, 1H), 7.29-7.26 (m, 2H), 7.21 (dd, J=8.4, 1.4 Hz, 1H). MS m/e: 295 (M+H)$^+$.

Compound 24: 6-(4-(3-Chlorophenyl)-1H-imidazol-5-yl)-1-methyl-1H-benzo[d]imidazole. $^1$H NMR (CD$_3$OD, 300 MHz) δ 8.15 (s, 1H), 7.84 (s, 1H), 7.65 (d, J=7.6 Hz, 1H), 7.63 (s, 1H), 7.51-7.48 (m, 1H), 7.37-7.30 (m, 2H), 7.28-7.24 (m, 2H), 3.85 (s, 3H). MS m/e: 309 (M+H)$^+$.

Compound 25: 6-(4-(3-Chlorophenyl)-1H-imidazol-5-yl)benzo[d]thiazole. $^1$H NMR (CD$_3$OD, 300 MHz) δ 9.23 (s, 1H), 8.13 (d, J=1.5 Hz, 1H), 8.07 (d, J=8.5 Hz, 1H), 7.85 (s, 1H), 7.58 (dd, J=8.5, 1.7 Hz, 1H), 7.50-7.44 (m, 1H), 7.36-7.25 (m, 3H). MS m/e: 312 (M+H)$^+$.

Compound 26: 6-(4-(3-Chlorophenyl)-1H-imidazol-5-yl)imidazo[1,2-a]pyridine. $^1$H NMR (CD$_3$OD, 300 MHz) δ 8.55 (br s, 1H), 7.87 (s, 1H), 7.86 (s, 1H), 7.60 (d, J=0.9 Hz, 1H), 7.55 (d, J=9.4 Hz, 1H), 7.51 (t, J=1.5 Hz, 1H), 7.38-7.27 (m, 4H). MS m/e: 295 (M+H)$^+$.

Compound 27: 5-(4-(3-Fluorophenyl)-1H-imidazol-5-yl)-1H-indazole. MS m/e: 279 (M+H)$^+$.

Compound 28: 6-(4-(3-Fluorophenyl)-1H-imidazol-5-yl)-1H-indazole. MS m/e: 279 (M+H)$^+$.

Compound 29: 6-(4-(3-Fluorophenyl)-1H-imidazol-5-yl)-1-methyl-1H-benzo[d]imidazole. $^1$H NMR (CD$_3$OD, 300 MHz) δ 8.13 (s, 1H), 7.81 (s, 1H), 7.65-7.63 (m, 2H), 7.35-7.13 (m, 4H), 7.02-6.91 (m, 1H), 3.83 (s, 3H). MS m/e: 293 (M+H)$^+$.

Compound 30: 6-(4-(3-Fluorophenyl)-1H-imidazol-5-yl)benzo[d]thiazole. $^1$H NMR (CD$_3$OD, 300 MHz) δ 9.28 (s, 1H), 8.17 (dd, J=1.7, 0.6 Hz, 1H), 8.07 (d, J=8.5 Hz, 1H), 7.88 (s, 1H), 7.63 (dd, J=8.6, 1.6 Hz, 1H), 7.32 (dd, J=8.1, 6.0 Hz, 1H), 7.26 (dt, J=7.8, 1.3 Hz, 1H), 7.24-7.19 (m, 1H), 7.09-7.02 (m, 1H). MS m/e: 296 (M+H)$^+$.

Compound 31: 5-(4-(3,4-Difluorophenyl)-1H-imidazol-5-yl)-1H-indazole. $^1$H NMR (CD$_3$OD, 300 MHz) δ 8.06 (d, J=1.0 Hz, 1H), 7.85 (dd, J=1.6, 0.9 Hz, 1H), 7.81 (s, 1H), 7.56 (dt, J=8.7, 1.0 Hz, 1H), 7.41 (dd, J=8.7, 1.6 Hz, 1H), 7.37-7.27 (m, 1H), 7.24-7.10 (m, 2H). MS m/e: 297 (M+H)$^+$.

Compound 32: 6-(4-(3,4-Difluorophenyl)-1H-imidazol-5-yl)-1H-indazole. $^1$H NMR (CD$_3$OD, 300 MHz) δ 8.05 (d, J=1.0 Hz, 1H), 7.84 (s, 1H), 7.77 (dd, J=8.5, 0.6 Hz, 1H), 7.60 (q, J=1.1 Hz, 1H), 7.39-7.30 (m, 1H), 7.24-7.16 (m, 3H). MS m/e: 297 (M+H)$^+$.

Compound 33: 6-(4-(3,4-Difluorophenyl)-1H-imidazol-5-yl)-1-methyl-1H-benzo[d]imidazole. $^1$H NMR (CD$_3$OD, 300 MHz) δ 8.15 (s, 1H), 7.82 (s, 1H), 7.66 (d, J=7.6 Hz, 1H), 7.63 (dd, J=1.7, 0.7 Hz, 1H), 7.38-7.29 (m, 2H), 7.25-7.10 (m, 2H), 3.86 (s, 3H). MS m/e: 311 (M+H)$^+$.

Compound 34: 6-(4-(3,4-Difluorophenyl)-1H-imidazol-5-yl)benzo[d]thiazole. $^1$H NMR (CD$_3$OD, 300 MHz) δ 9.25 (s, 1H), 8.13 (dd, J=1.7, 0.6 Hz, 1H), 8.05 (dd, J=8.6, 0.6 Hz, 1H), 7.84 (s, 1H), 7.58 (dd, J=8.5, 1.7 Hz, 1H), 7.39-7.28 (m, 1H), 7.25-7.16 (m, 2H). MS m/e: 314 (M+H)$^+$.

Compound 35: 6-(4-(3,4-Difluorophenyl)-1H-imidazol-5-yl)imidazo[1,2-a]pyridine. $^1$H NMR (CD$_3$OD, 300 MHz) δ 8.55 (dd, J=1.8, 1.0 Hz, 1H), 7.89-7.83 (m, 2H), 7.59 (d, J=1.4 Hz, 1H), 7.55 (dt, J=9.4, 0.9 Hz, 1H), 7.42-7.34 (m, 1H), 7.29 (dd, J=9.4, 1.6 Hz, 1H), 7.26-7.21 (m, 2H). MS m/e: 297 (M+H)$^+$.

Compound 36: 6-(4-(3,4-Difluorophenyl)-1H-imidazol-5-yl)quinoline. $^1$H NMR (CD$_3$OD, 300 MHz) δ 8.84 (dd, J=4.4, 1.7 Hz, 1H), 8.31 (dd, J=8.5, 0.9 Hz, 1H), 8.02 (s, 1H), 8.01 (d, J=12.0 Hz, 1H), 7.88 (s, 1H), 7.79 (dd, J=8.8, 2.0 Hz, 1H), 7.54 (dd, J=8.3, 4.3 Hz, 1H), 7.41-7.32 (m, 1H), 7.26-7.19 (m, 2H). MS m/e: 308 (M+H)$^+$.

Compound 37: 6-(4-(4-Fluoro-3-methylphenyl)-1-methyl-1H-imidazol-5-yl)quinoline. $^1$H NMR (CD$_3$OD, 300 MHz) δ 8.91 (dd, J=4.4, 1.7 Hz, 1H), 8.38 (dd, J=8.5, 0.9 Hz, 1H), 8.11 (d, J=8.8 Hz, 1H), 7.98 (d, J=1.9 Hz, 1H), 7.82 (s, 1H), 7.69 (dd, J=8.7, 2.0 Hz, 1H), 7.59 (dd, J=8.3, 4.3 Hz, 1H), 7.29 (ddd, J=7.6, 2.3, 0.9 Hz, 1H), 7.10-7.05 (m, 1H), 6.81 (dd, J=9.7, 8.6 Hz, 1H), 3.62 (s, 3H), 2.10 (d, J=1.9 Hz, 3H). MS m/e: 318 (M+H)$^+$.

Compound 38: 6-(4-(4-Fluorophenyl)-1H-imidazol-5-yl)quinoline. $^1$H NMR (CD$_3$OD, 300 MHz) δ 8.80 (dd, J=4.3, 1.7 Hz, 1H), 8.25 (dd, J=8.5, 0.9 Hz, 1H), 8.00 (d, J=1.9 Hz, 1H), 7.95 (d, J=8.8 Hz, 1H), 7.86 (s, 1H), 7.78 (dd, J=8.8, 2.0 Hz, 1H), 7.50 (dd, J=8.4, 4.4 Hz, 1H), 7.48-7.42 (m, 2H), 7.14-7.04 (m, 2H). MS m/e: 290 (M+H)$^+$.

Compound 39: 6-(4-(3-Chlorophenyl)-1H-imidazol-5-yl)quinoline. $^1$H NMR (CD$_3$OD, 300 MHz) δ 8.82 (dd, J=4.3, 1.7 Hz, 1H), 8.28 (d, J=7.6 Hz, 1H), 8.02 (d, J=2.0 Hz, 1H), 7.98 (d, J=9.1 Hz, 1H), 7.88 (s, 1H), 7.78 (dd, J=8.8, 2.0 Hz, 1H), 7.56-7.46 (m, 3H), 7.34-7.28 (m, 2H). MS m/e: 306 (M+H)$^+$.

Compound 40: 6-(4-(3-Fluorophenyl)-1H-imidazol-5-yl)quinoline. $^1$H NMR (CD$_3$OD, 300 MHz) δ 8.82 (dd, J=4.3, 1.7 Hz, 1H), 8.29 (d, J=8.5 Hz, 1H), 8.03 (d, J=2.0 Hz, 1H), 7.98 (d, J=8.8 Hz, 1H), 7.88 (s, 1H), 7.79 (dd, J=8.8, 2.0 Hz, 1H), 7.53 (dd, J=8.3, 4.3 Hz, 1H), 7.36-7.28 (m, 1H), 7.28-7.16 (m, 2H), 7.08-7.01 (m, 1H). MS m/e: 290 (M+H)$^+$.

Compound 41: 5-(1-Methyl-4-(m-tolyl)-1H-imidazol-5-yl)-1H-indazole. $^1$H NMR (CD$_3$OD, 300 MHz) δ 8.08 (d, J=1.0 Hz, 1H), 7.80-7.73 (m, 2H), 7.63 (dt, J=8.6, 1.0 Hz, 1H), 7.30 (dd, J=8.6, 1.5 Hz, 1H), 7.27-7.24 (m, 1H), 7.12-7.05 (m, 1H), 7.04 (dd, J=8.7, 7.6 Hz, 1H), 6.96-6.91 (m, 1H), 3.54 (s, 3H), 2.16 (s, 3H). MS m/e: 289 (M+H)$^+$.

Compound 42: 6-(1-Methyl-4-(m-tolyl)-1H-imidazol-5-yl)-1H-indazole. $^1$H NMR (CD$_3$OD, 300 MHz) δ 8.15 (d, J=1.0 Hz, 1H), 7.91 (dd, J=8.4, 0.9 Hz, 1H), 7.82 (s, 1H), 7.54 (q, J=1.1 Hz, 1H), 7.30-7.27 (m, 1H), 7.14 (dd, J=8.3, 1.3 Hz, 1H), 7.12-7.09 (m, 1H), 7.02 (t, J=7.5 Hz, 1H), 7.00-6.95 (m, 1H), 3.61 (s, 3H), 2.21 (s, 3H). MS m/e: 289 (M+H)$^+$.

Compound 43: 1-Methyl-6-(1-methyl-4-(m-tolyl)-1H-imidazol-5-yl)-1H-benzo[d]imidazole. $^1$H NMR (CD$_3$OD, 300 MHz) δ 8.23 (s, 1H), 7.81-7.78 (m, 2H), 7.59 (d, J=1.6, 0.7 Hz, 1H), 7.32-7.29 (m, 1H), 7.27 (dd, J=8.4, 1.6 Hz, 1H), 7.12-7.07 (m, 1H), 7.02 (t, J=7.5 Hz, 1H), 6.98-6.42 (m, 1H), 3.89 (s, 3H), 3.57 (s, 3H), 2.20 (s, 3H). MS m/e: 303 (M+H)$^+$.

Compound 44: 6-(1-Methyl-4-(m-tolyl)-1H-imidazol-5-yl)benzo[d]thiazole. $^1$H NMR (CD$_3$OD, 300 MHz) δ 9.33 (s, 1H), 8.17 (dd, J=8.4, 0.6 Hz, 1H), 8.08 (dd, J=1.7, 0.6 Hz, 1H), 7.82 (s, 1H), 7.52 (dd, J=8.4, 1.7 Hz, 1H), 7.29-7.26 (m, 1H), 7.10-6.97 (m, 3H), 3.60 (s, 3H), 2.20 (s, 3H). MS m/e: 306 (M+H)$^+$.

Compound 45: 6-(1-Methyl-4-(m-tolyl)-1H-imidazol-5-yl)imidazo[1,2-a]pyridine. MS m/e: 289 (M+H)$^+$.

Compound 46: 6-(1-Methyl-4-(m-tolyl)-1H-imidazol-5-yl)quinoline. MS m/e: 300 (M+H)$^+$.

Compound 47: 6-(1-Methyl-4-(m-tolyl)-1H-imidazol-5-yl)quinoxaline. MS m/e: 301 (M+H)$^+$.

Compound 48: -(4-(4-Fluorophenyl)-1-methyl-1H-imidazol-5-yl)-1H-indazole. MS m/e: 293 (M+H)$^+$.

Compound 49: 6-(4-(4-Fluorophenyl)-1-methyl-1H-imidazol-5-yl)-1H-indazole. MS m/e: 293 (M+H)$^+$.

Compound 50: 6-(4-(4-Fluorophenyl)-1-methyl-1H-imidazol-5-yl)-1-methyl-1H-benzo[d]imidazole. MS m/e: 307 (M+H)$^+$.

Compound 51: 6-(4-(4-Fluorophenyl)-1-methyl-1H-imidazol-5-yl)benzo[d]thiazole. MS m/e: 310 (M+H)$^+$.

Compound 52: 5-(4-(4-Fluoro-3-methylphenyl)-1,2-dimethyl-1H-imidazol-5-yl)-1H-indazole. MS m/e: 321 (M+H)$^+$.

Compound 53: 6-(4-(4-Fluoro-3-methylphenyl)-1,2-dimethyl-1H-imidazol-5-yl)-1H-indazole. MS m/e: 321 (M+H)$^+$.

Compound 54: 6-(4-(4-Fluoro-3-methylphenyl)-1,2-dimethyl-1H-imidazol-5-yl)-1-methyl-1H-benzo[d]imidazole. MS m/e: 335 (M+H)$^+$.

Compound 55: 6-(4-(4-Fluoro-3-methylphenyl)-1,2-dimethyl-1H-imidazol-5-yl)benzo[d]thiazole. MS m/e: 338 (M+H)$^+$.

Compound 56: 5-(1,2-Dimethyl-4-(m-tolyl)-1H-imidazol-5-yl)-1H-indazole. MS m/e: 303 (M+H)$^+$.

Compound 57: 6-(1,2-Dimethyl-4-(m-tolyl)-1H-imidazol-5-yl)-1H-indazole. MS m/e: 303 (M+H)$^+$.

Compound 58: 6-(1,2-Dimethyl-4-(m-tolyl)-1H-imidazol-5-yl)-1-methyl-1H-benzo[d]imidazole. MS m/e: 317 (M+H)$^+$.

Compound 59: 6-(1,2-Dimethyl-4-(m-tolyl)-1H-imidazol-5-yl)benzo[d]thiazole. MS m/e: 320 (M+H)$^+$.

Compound 60: 5-(4-(3-Chlorophenyl)-1-methyl-1H-imidazol-5-yl)-1H-indazole. MS m/e: 309 (M+H)$^+$.

Compound 61: 6-(4-(3-Chlorophenyl)-1-methyl-1H-imidazol-5-yl)-1H-indazole. MS m/e: 309 (M+H)$^+$.

Compound 62: 6-(4-(3-Chlorophenyl)-1-methyl-1H-imidazol-5-yl)-1-methyl-1H-benzo[d]imidazole. MS m/e: 323 (M+H)$^+$.

Compound 63: 6-(4-(3-Chlorophenyl)-1-methyl-1H-imidazol-5-yl)benzo[d]thiazole. MS m/e: 326 (M+H)$^+$.

Compound 64: 5-(4-(3,4-Difluorophenyl)-1-methyl-1H-imidazol-5-yl)-1H-indazole. MS m/e: 311 (M+H)$^+$.

Compound 65: 6-(4-(3,4-Difluorophenyl)-1-methyl-1H-imidazol-5-yl)-1H-indazole. MS m/e: 311 (M+H)$^+$.

Compound 66: 6-(4-(3,4-Difluorophenyl)-1-methyl-1H-imidazol-5-yl)-1-methyl-1H-benzo[d]imidazole. MS m/e: 325 (M+H)$^+$.

Compound 67: 6-(4-(3,4-Difluorophenyl)-1-methyl-1H-imidazol-5-yl)benzo[d]thiazole. MS m/e: 328 (M+H)$^+$.

Compound 68: 6-(4-(3,4-Difluorophenyl)-1-methyl-1H-imidazol-5-yl)quinoxaline. MS m/e: 323 (M+H)$^+$.

Compound 69: 5-(4-(4-Methoxyphenyl)-1-methyl-1H-imidazol-5-yl)-1H-indazole. MS m/e: 305 (M+H)$^+$.

Compound 70: 6-(4-(4-Methoxyphenyl)-1-methyl-1H-imidazol-5-yl)-1H-indazole. MS m/e: 305 (M+H)$^+$.

Compound 71: 5-(4-(4-Fluoro-3-methylphenyl)-2-methyl-1H-imidazol-5-yl)-1H-indazole. MS m/e: 307 (M+H)$^+$.

Compound 72: 6-(4-(4-Fluoro-3-methylphenyl)-2-methyl-1H-imidazol-5-yl)-1H-indazole. MS m/e: 307 (M+H)$^+$.

Compound 73: 6-(4-(4-Fluoro-3-methylphenyl)-2-methyl-1H-imidazol-5-yl)benzo[d]thiazole. MS m/e: 324 (M+H)$^+$.

Compound 74: 6-(4-(4-Fluoro-3-methylphenyl)-2-methyl-1H-imidazol-5-yl)imidazo[1,2-a]pyridine. MS m/e: 307 (M+H)$^+$.

Compound 75: 6-(4-(4-Fluoro-3-methylphenyl)-2-methyl-1H-imidazol-5-yl)quinoline. $^1$H NMR (CD$_3$OD, 300 MHz) δ 8.82 (dd, J=4.4, 1.7 Hz, 1H), 8.28 (d, J=7.6 Hz, 1H), 8.02 (d, J=1.9 Hz, 1H), 7.95 (d, J=8.8 Hz, 1H), 7.80 (dd, J=8.9, 2.0 Hz, 1H), 7.54 (dd, J=8.3, 4.3 Hz, 1H), 7.35 (dd, J=7.5, 2.1 Hz, 1H), 7.27-7.22 (m, 1H), 7.03 (dd, J=9.7, 8.5 Hz, 1H), 2.50 (s, 3H), 2.25 (d, J=1.5 Hz, 3H). MS m/e: 318 (M+H)$^+$.

Compound 76: 6-(4-(4-Fluoro-3-methylphenyl)-2-methyl-1H-imidazol-5-yl)quinoxaline. MS m/e: 319 (M+H)$^+$.

Compound 77: 5-(4-(4-Fluorophenyl)-2-methyl-1H-imidazol-5-yl)-1H-indazole. MS m/e: 293 (M+H)$^+$.

Compound 78: 6-(4-(4-Fluorophenyl)-2-methyl-1H-imidazol-5-yl)-1H-indazole. MS m/e: 293 (M+H)$^+$.

Compound 79: 6-(4-(4-Fluorophenyl)-2-methyl-1H-imidazol-5-yl)-1-methyl-1H-benzo[d]imidazole. MS m/e: 307 (M+H)$^+$.

Compound 80: 6-(4-(4-Fluorophenyl)-2-methyl-1H-imidazol-5-yl)benzo[d]thiazole. MS m/e: 310 (M+H)$^+$.

Compound 81: 6-(4-(4-Fluorophenyl)-2-methyl-1H-imidazol-5-yl)imidazo[1,2-a]pyridine. MS m/e: 293 (M+H)$^+$.

Compound 82: 6-(4-(4-Fluorophenyl)-2-methyl-1H-imidazol-5-yl)quinoxaline. MS m/e: 305 (M+H)$^+$.

Compound 83: 5-(4-(3,4-Difluorophenyl)-2-methyl-1H-imidazol-5-yl)-1H-indazole. MS m/e: 311 (M+H)$^+$.

Compound 84: 6-(4-(3,4-Difluorophenyl)-2-methyl-1H-imidazol-5-yl)-1H-indazole. MS m/e: 311 (M+H)$^+$.

Compound 85: 6-(4-(3,4-Difluorophenyl)-2-methyl-1H-imidazol-5-yl)-1-methyl-1H-benzo[d]imidazole. MS m/e: 325 (M+H)$^+$.

Compound 86: 6-(4-(3,4-Difluorophenyl)-2-methyl-1H-imidazol-5-yl)benzo[d]thiazole. MS m/e: 328 (M+H)$^+$.

Compound 87: 6-(4-(3,4-Difluorophenyl)-2-methyl-1H-imidazol-5-yl)imidazo[1,2-a]pyridine. MS m/e: 311 (M+H)$^+$.

Compound 88: 6-(4-(3,4-Difluorophenyl)-2-methyl-1H-imidazol-5-yl)quinoline. MS m/e: 322 (M+H)$^+$.

Compound 89: 6-(4-(3,4-Difluorophenyl)-2-methyl-1H-imidazol-5-yl)quinoxaline. MS m/e: 323 (M+H)$^+$.

Compound 90: 5-(2-Methyl-4-(3,4,5-trifluorophenyl)-1H-imidazol-5-yl)-1H-indazole. MS m/e: 329 (M+H)$^+$.

Compound 91: 6-(2-Methyl-4-(3,4,5-trifluorophenyl)-1H-imidazol-5-yl)-1H-indazole. MS m/e: 329 (M+H)$^+$.

Compound 92: 6-(2-Methyl-4-(3,4,5-trifluorophenyl)-1H-imidazol-5-yl)-[1,2,4]triazolo[1,5-a]pyridine. MS m/e: 330 (M+H)$^+$.

Compound 93: 6-(2-Methyl-4-(3,4,5-trifluorophenyl)-1H-imidazol-5-yl)benzo[d]thiazole. MS m/e: 346 (M+H)$^+$.

Compound 94: 6-(2-Methyl-4-(3,4,5-trifluorophenyl)-1H-imidazol-5-yl)imidazo[1,2-a]pyridine. MS m/e: 329 (M+H)$^+$.

Compound 95: 6-(2-Methyl-4-(3,4,5-trifluorophenyl)-1H-imidazol-5-yl)quinoline. MS m/e: 340 (M+H)$^+$.

Compound 96: 6-(2-Methyl-4-(3,4,5-trifluorophenyl)-1H-imidazol-5-yl)quinoxaline. MS m/e: 341 (M+H)$^+$.

Compound 97: 5-(2-Methyl-4-(2,4,5-trifluorophenyl)-1H-imidazol-5-yl)-1H-indazole. MS m/e: 329 (M+H)$^+$.

Compound 98: 6-(2-Methyl-4-(2,4,5-trifluorophenyl)-1H-imidazol-5-yl)-[1,2,4]triazolo[1,5-a]pyridine. MS m/e: 330 (M+H)$^+$.

Compound 99: 6-(2-Methyl-4-(2,4,5-trifluorophenyl)-1H-imidazol-5-yl)benzo[d]thiazole. MS m/e: 346 (M+H)$^+$.

Compound 100: 6-(2-Methyl-4-(2,4,5-trifluorophenyl)-1H-imidazol-5-yl)quinoline. MS m/e: 340 (M+H)$^+$.

Compound 101: 5-(4-(3-Chlorophenyl)-2-methyl-1H-imidazol-5-yl)-1H-indazole. MS m/e: 309 (M+H)$^+$.

Compound 102: 6-(4-(3-Chlorophenyl)-2-methyl-1H-imidazol-5-yl)-1H-indazole. MS m/e: 309 (M+H)$^+$.

Compound 103: 6-(4-(3-Chlorophenyl)-2-methyl-1H-imidazol-5-yl)-[1,2,4]triazolo[1,5-a]pyridine. MS m/e: 310 (M+H)$^+$.

Compound 104: 6-(4-(3-Chlorophenyl)-2-methyl-1H-imidazol-5-yl)imidazo[1,2-a]pyridine. MS m/e: 309 (M+H)$^+$.

Compound 105: 6-(4-(3-Chlorophenyl)-2-methyl-1H-imidazol-5-yl)quinoline. MS m/e: 320 (M+H)$^+$.

Compound 106: 5-(2-Ethyl-4-(4-fluoro-3-methylphenyl)-1H-imidazol-5-yl)-1H-indazole. MS m/e: 321 (M+H)$^+$.

Compound 107: 6-(2-Ethyl-4-(4-fluoro-3-methylphenyl)-1H-imidazol-5-yl)-1H-indazole. MS m/e: 321 (M+H)$^+$.

Compound 108: 6-(2-Ethyl-4-(4-fluoro-3-methylphenyl)-1H-imidazol-5-yl)-[1,2,4]triazolo[1,5-a]pyridine. MS m/e: 322 (M+H)$^+$.

Compound 109: 6-(2-Ethyl-4-(4-fluoro-3-methylphenyl)-1H-imidazol-5-yl)benzo[d]thiazole. MS m/e: 338 (M+H)$^+$.

Compound 110: 6-(2-Ethyl-4-(4-fluoro-3-methylphenyl)-1H-imidazol-5-yl)imidazo[1,2-a]pyridine. MS m/e: 321 (M+H)$^+$.

Compound 111: 6-(2-Ethyl-4-(4-fluoro-3-methylphenyl)-1H-imidazol-5-yl)quinoline. MS m/e: 332 (M+H)$^+$.

Compound 112: 6-(2-Ethyl-4-(4-fluoro-3-methylphenyl)-1H-imidazol-5-yl)quinoxaline. MS m/e: 333 (M+H)$^+$.

Compound 113: 5-(2-Ethyl-4-(m-tolyl)-1H-imidazol-5-yl)-1H-indazole. MS m/e: 303 (M+H)$^+$.

Compound 114: 6-(2-Ethyl-4-(m-tolyl)-1H-imidazol-5-yl)-1H-indazole. MS m/e: 303 (M+H)$^+$.

Compound 115: 6-(2-Ethyl-4-(m-tolyl)-1H-imidazol-5-yl)-[1,2,4]triazolo[1,5-a]pyridine. $^1$H NMR (CD$_3$OD, 300 MHz) δ 8.82 (dd, J=1.5, 1.1 Hz, 1H), 8.40 (s, 1H), 7.77-7.67 (m, 2H), 7.33-7.31 (m, 1H), 7.29 (d, J=7.0 Hz, 1H), 7.25-7.19 (m, 2H), 2.85 (q, J=7.7 Hz, 2H), 2.35 (s, 3H), 1.41 (t, J=7.7 Hz, 3H). MS m/e: 304 (M+H)$^+$.

Compound 116: 6-(2-Ethyl-4-(m-tolyl)-1H-imidazol-5-yl)benzo[d]thiazole. MS m/e: 320 (M+H)$^+$.

Compound 117: 6-(2-Ethyl-4-(m-tolyl)-1H-imidazol-5-yl)imidazo[1,2-a]pyridine. MS m/e: 303 (M+H)$^+$.

Compound 118: 6-(2-Ethyl-4-(m-tolyl)-1H-imidazol-5-yl)quinoxaline. MS m/e: 315 (M+H)$^+$.

Compound 119: 5-(2-Ethyl-4-(4-fluorophenyl)-1H-imidazol-5-yl)-1H-indazole. MS m/e: 307 (M+H)$^+$.

Compound 120: 6-(2-Ethyl-4-(4-fluorophenyl)-1H-imidazol-5-yl)-1H-indazole. MS m/e: 307 (M+H)$^+$.

Compound 121: 6-(2-Ethyl-4-(4-fluorophenyl)-1H-imidazol-5-yl)-[1,2,4]triazolo[1,5-a]pyridine. MS m/e: 308 (M+H)$^+$.

Compound 122: 6-(2-Ethyl-4-(4-fluorophenyl)-1H-imidazol-5-yl)benzo[d]thiazole. MS m/e: 324 (M+H)$^+$.

Compound 123: 6-(2-Ethyl-4-(4-fluorophenyl)-1H-imidazol-5-yl)imidazo[1,2-a]pyridine. MS m/e: 307 (M+H)$^+$.

Compound 124: 5-(4-(3-Chlorophenyl)-2-ethyl-1H-imidazol-5-yl)-1H-indazole. MS m/e: 323 (M+H)$^+$.

Compound 125: 6-(4-(3-Chlorophenyl)-2-ethyl-1H-imidazol-5-yl)-[1,2,4]triazolo[1,5-a]pyridine. MS m/e: 324 (M+H)$^+$.

Compound 126: 6-(4-(3-Chlorophenyl)-2-ethyl-1H-imidazol-5-yl)benzo[d]thiazole. MS m/e: 340 (M+H)$^+$.

Compound 127: 6-(4-(3-Chlorophenyl)-2-ethyl-1H-imidazol-5-yl)imidazo[1,2-a]pyridine. MS m/e: 323 (M+H)$^+$.

Compound 128: 6-(4-(3-Chlorophenyl)-2-ethyl-1H-imidazol-5-yl)quinoline. MS m/e: 334 (M+H)$^+$.

Compound 129: 6-(4-(3-Chlorophenyl)-2-ethyl-1H-imidazol-5-yl)quinoxaline. MS m/e: 335 (M+H)$^+$.

Compound 130: 5-(4-(3,4-Difluorophenyl)-2-ethyl-1H-imidazol-5-yl)-1H-indazole. MS m/e: 325 (M+H)$^+$.

Compound 131: 6-(4-(3,4-Difluorophenyl)-2-ethyl-1H-imidazol-5-yl)-1H-indazole. MS m/e: 325 (M+H)$^+$.

Compound 132: 6-(4-(3,4-Difluorophenyl)-2-ethyl-1H-imidazol-5-yl)-[1,2,4]triazolo[1,5-a]pyridine. MS m/e: 326 (M+H)$^+$.

Compound 133: 6-(4-(3,4-Difluorophenyl)-2-ethyl-1H-imidazol-5-yl)benzo[d]thiazole. MS m/e: 342 (M+H)$^+$.

Compound 134: 6-(4-(3,4-Difluorophenyl)-2-ethyl-1H-imidazol-5-yl)imidazo[1,2-a]pyridine. MS m/e: 325 (M+H)$^+$.

Compound 135: 6-(4-(3,4-Difluorophenyl)-2-ethyl-1H-imidazol-5-yl)quinoxaline. MS m/e: 337 (M+H)$^+$.

Compound 136: 6-(2-Ethyl-4-(3-fluorophenyl)-1H-imidazol-5-yl)-[1,2,4]triazolo[1,5-a]pyridine. MS m/e: 308 (M+H)$^+$.

Compound 137: 6-(2-Ethyl-4-(3-fluorophenyl)-1H-imidazol-5-yl)benzo[d]thiazole. MS m/e: 324 (M+H)$^+$.

Compound 138: 6-(2-Ethyl-4-(3-fluorophenyl)-1H-imidazol-5-yl)imidazo[1,2-a]pyridine. MS m/e: 307 (M+H)$^+$.

Compound 139: 5-(4-(3-Chloro-5-fluorophenyl)-2-ethyl-1H-imidazol-5-yl)-1H-indazole. MS m/e: 341 (M+H)$^+$.

Compound 140: 6-(4-(3-Chloro-5-fluorophenyl)-2-ethyl-1H-imidazol-5-yl)benzo[d]thiazole. MS m/e: 358 (M+H)$^+$.

Compound 141: 6-(4-(3-Chloro-5-fluorophenyl)-2-ethyl-1H-imidazol-5-yl)quinoxaline. MS m/e: 353 (M+H)$^+$.

Compound 142: 5-(2-Ethyl-4-(3-fluoro-5-methylphenyl)-1H-imidazol-5-yl)-1H-indazole. MS m/e: 321 (M+H)$^+$.

Compound 143: 6-(2-Ethyl-4-(3-fluoro-5-methylphenyl)-1H-imidazol-5-yl)-1H-indazole. MS m/e: 321 (M+H)$^+$.

Compound 144: 6-(2-Ethyl-4-(3-fluoro-5-methylphenyl)-1H-imidazol-5-yl)-[1,2,4]triazolo[1,5-a]pyridine. MS m/e: 322 (M+H)$^+$.

Compound 145: 6-(2-Ethyl-4-(3-fluoro-5-methylphenyl)-1H-imidazol-5-yl)benzo[d]thiazole. MS m/e: 338 (M+H)$^+$.

Compound 146: 6-(2-Ethyl-4-(3-fluoro-5-methylphenyl)-1H-imidazol-5-yl)imidazo[1,2-a]pyridine. MS m/e: 321 (M+H)$^+$.

Compound 147: 6-(2-Ethyl-4-(3-fluoro-5-methylphenyl)-1H-imidazol-5-yl)quinoxaline. MS m/e: 333 (M+H)$^+$.

Compound 148: 5-(4-(3,5-Difluorophenyl)-2-methyl-1H-imidazol-5-yl)-1H-indazole. MS m/e: 311 (M+H)$^+$.

Compound 149: 6-(4-(3,5-Difluorophenyl)-2-ethyl-1H-imidazol-5-yl)benzo[d]thiazole. MS m/e: 342 (M+H)$^+$.

Compound 150: 6-(4-(3-Chlorophenyl)-2-(trifluoromethyl)-1H-imidazol-5-yl)-[1,2,4]triazolo[1,5-a]pyridine. MS m/e: 364 (M+H)$^+$.

Compound 151: 6-(4-(4-Fluorophenyl)-2-(trifluoromethyl)-1H-imidazol-5-yl)-[1,2,4]triazolo[1,5-a]pyridine. MS m/e: 348 (M+H)$^+$.

Compound 152: 6-(2-Isopropyl-4-(m-tolyl)-1H-imidazol-5-yl)-[1,2,4]triazolo[1,5-a]pyridine. MS m/e: 318 (M+H)$^+$.

Compound 153: 5-(1H-indazol-6-yl)-4-(m-tolyl)thiazole $^1$H NMR (CD3OD, 300 MHz) 9.04 (m, 1H), 8.05 (m, 1H), 7.73 (m, 1H), 7.51 (m, 1H), 7.32 (m, 1H), 7.12 (m, 4H), 2.24 (s, 3H) ppm; MS m/e: 292 (M+H)$^+$ Compound 154: 5-(1H-indazol-5-yl)-4-(m-tolyl)thiazole. $^1$H NMR (CD3OD, 300 MHz) 8.98 (m, 1H), 8.03 (m, 1H), 7.79 (m, 1H), 7.50 (m, 1H), 7.29 (m, 2H), 7.15 (m, 3H), 2.23 (s, 3H) ppm; MS m/e: 292 (M+H)$^+$ Compound 155: 4-(4-fluoro-3-methylphenyl)-5-(imidazo[1,2-a]pyridin-6-yl)thiazol-2-amine. $^1$H NMR (DMSO-d$_6$, 300 MHz)) 8.54 (m, 1H), 7.89 (m, 1H), 7.55 (m, 1H), 7.42 (m, 2H), 7.18 (bs, 2H), 7.13 (m, 1H), 6.96 (m, 2H), 2.14 (s, 3H) ppm; MS m/e: 325 (M+H)$^+$ Compound 156: 4-(4-fluoro-3-methylphenyl)-5-(1H-indazol-5-yl)thiazole. $^1$H NMR (DMSO-d$_6$, 300 MHz) 9.14 (m, 1H), 8.08 (m, 1H), 7.81 (m, 1H), 7.53 (m, 1H), 7.47 (m, 1H), 7.23 (m, 1H), 7.15 (m, 1H), 7.00 (m, 1H), 2.13 (s, 3H) ppm; MS m/e: 310 (M+H)$^+$ Compound 157: 5-(1H-indazol-5-yl)-4-(4-methoxyphenyl)thiazol-2-amine
MS m/e: 323 (M+H)$^+$ Compound 158: 4-(4-fluoro-3-methylphenyl)-5-(quinoxalin-6-yl)thiazol-2-amine. $^1$H NMR (CD3OD, 300

MHz) 8.81 (m, 2H), 7.90 (m, 2H), 7.60 (m, 1H), 7.35 (m, 1H), 7.19 (m, 1H), 6.95 (m, 1H), 2.20 (s, 3H) ppm; MS m/e: 337 (M+H)+

Compound 159: 4-(4-fluoro-3-methylphenyl)-5-(1H-indazol-6-yl)thiazole. $^1$H NMR (CD3OD, 300 MHz) 9.26 (m, 1H), 9.06 (m, 1H), 8.06 (m, 1H), 8.01 (m, 1H), 7.47 (m, 1H), 7.37 (m, 1H), 7.20 (m, 1H), 6.93 (m, 1H), 2.17 (s, 3H) ppm; MS m/e: 310 (M+H)+

Compound 160: 4-(4-fluoro-3-methylphenyl)-5-(1H-indazol-5-yl)thiazol-2-amine $^1$H NMR (CD3OD, 300 MHz) 7.98 (m, 1H), 7.66 (m, 1H), 7.42 (m, 1H), 7.28 (m, 1H), 7.19 (m, 1H), 7.13 (m, 1H), 6.86 (m, 1H), 2.14 (s, 3H) ppm; MS m/e: 325 (M+H)+

Compound 161: 6-(4-(m-tolyl)thiazol-5-yl)benzo[d]thiazole. $^1$H NMR (CD3OD, 300 MHz) 9.03 (s, 1H), 8.05 (m, 1H), 7.74 (m, 1H), 7.51 (m, 1H), 7.37 (m, 1H), 7.22 (m, 1H), 7.08 (m, 1H), 6.93 (m, 1H), 2.16 (s, 3H) ppm; MS m/e: 309 (M+H)+

Compound 162: 5-(benzo[d]thiazol-6-yl)-4-(4-fluoro-3-methylphenyl)thiazol-2-amine. $^1$H NMR (DMSO-$d_6$, 300 MHz) 9.35 (m, 1H), 8.05 (m, 1H), 7.95 (m, 1H), 7.37 (m, 1H), 7.30 (m, 1H), 7.18 (bs, 2H), 7.08 (m, 1H), 6.96 (m, 1H), 2.13 (s, 3H) ppm; MS m/e: 342 (M+H)+

Compound 163: 5-(imidazo[1,2-a]pyridin-6-yl)-4-(4-methoxyphenyl)thiazol-2-amine. MS m/e: 323 (M+H+)

Compound 164: 4-(3-chlorophenyl)-5-(imidazo[1,2-a]pyridin-6-yl)thiazol-2-amine. MS m/e: 327 (M+H)+

Compound 165: 6-(4-(4-fluoro-3-methylphenyl)thiazol-5-yl)benzo[d]thiazole. $^1$H NMR (CD3OD, 300 MHz) 9.27 (m, 1H), 9.06 (m, 1H), 8.08 (m, 1H), 8.02 (m, 1H), 7.47 (m, 1H), 7.32 (m, 1H), 7.16 (m, 2H), 2.24 (s, 3H) ppm; MS m/e: 327 (M+H)+

Compound 166: 5-(benzo[d]thiazol-6-yl)-4-(3-chlorophenyl)thiazol-2-amine. $^1$H NMR (CD3OD, 300 MHz) 9.28 (m, 1H), 8.03 (m, 2H), 7.35 (m, 5H) ppm; MS m/e: 344 (M+H)+

Compound 167: 4-(4-fluoro-3-methylphenyl)-5-(imidazo[1,2-a]pyridin-6-yl)thiazole. MS m/e: 310 (M+H)+

Compound 168: 4-(3-chlorophenyl)-5-(1H-indazol-5-yl)thiazol-2-amine. $^1$H NMR (CD3OD, 300 MHz) 8.00 (m, 1H), 7.69 (m, 1H), 7.45 (m, 2H), 7.21 (m, 4H) ppm; MS m/e: 327 (M+H)+

Compound 169: 4-(3-chlorophenyl)-5-(quinoxalin-6-yl)thiazol-2-amine. $^1$H NMR (CD3OD, 300 MHz) 8.82 (m, 2H), 7.93 (m, 2H), 7.61 (m, 1H), 7.48 (m, 1H), 7.30 (m, 3H) ppm; MS m/e: 339 (M+H)+

Compound 170: 4-(4-fluorophenyl)-5-(quinoxalin-6-yl)thiazol-2-amine. $^1$H NMR (CD3OD, 300 MHz) 8.81 (m, 2H), 7.91 (m, 1H), 7.60 (m, 2H), 7.45 (m, 2H), 7.05 (m, 2H) ppm; MS m/e: 323 (M+H)+

Compound 171: 5-(imidazo[1,2-a]pyridin-6-yl)-4-(3-(trifluoromethyl)phenyl)thiazol-2-amine. $^1$H NMR (DMSO-$d_6$, 300 MHz) 8.61 (m, 1H), 7.90 (m, 1H), 7.82 (m, 1H), 7.57 (m, 3H), 7.47 (m, 2H), 7.31 (bs, 2H), 6.97 (m, 1H) ppm; MS m/e: 361 (M+H)+

Compound 172: 4-(3-chlorophenyl)-5-(1H-indazol-6-yl)thiazol-2-amine. $^1$H NMR (CD3OD, 300 MHz) 8.05 (m, 1H), 7.75 (m, 1H), 7.48 (m, 2H), 7.40 (m, 1H), 7.32 (m, 2H), 7.02 (m, 1H) ppm; MS m/e: 327 (M+H)+

Compound 173: 5-(1H-indazol-6-yl)-4-(4-methoxyphenyl)thiazol-2-amine. MS m/e: 323 (M+H)+

Compound 174: 4-(4-fluoro-3-methylphenyl)-5-(1H-indazol-6-yl)thiazol-2-amine. $^1$H NMR (CD3OD, 300 MHz) 7.99 (m, 1H), 7.71 (m, 2H), 7.56 (m, 1H), 7.48 (m, 2H), 7.36 (m, 1H), 7.22 (m, 1H) ppm; MS m/e: 325 (M+H)+

Compound 175: 5-(1H-indazol-5-yl)-4-(3-(trifluoromethyl)phenyl)thiazol-2-amine. $^1$H NMR (CD3OD, 300 MHz) 8.00 (m, 1H), 7.66 (m, 1H), 7.42 (m, 1H), 7.28 (m, 1H), 7.19 (m, 1H), 7.13 (m, 1H), 6.86 (m, 1H), 2.14 (s, 3H) ppm; MS m/e: 361 (M+H)+

Compound 176: 5-(benzo[d]thiazol-6-yl)-4-(3-(trifluoromethyl)phenyl)thiazol-2-amine. $^1$H NMR (CD3OD, 300 MHz) 9.23 (m, 1H), 7.97 (m, 2H), 7.72 (m, 1H), 7.56 (m, 2H), 7.41 (m, 2H) ppm; MS m/e: 378 (M+H)+

Compound 177: 5-(1H-indazol-5-yl)-4-(3-methoxyphenyl)thiazol-2-amine. $^1$H NMR (DMSO-$d_6$, 300 MHz) 13.1 (s, 1H), 8.02 (s, 1H), 7.66 (m, 1H), 7.45 (m, 1H), 7.15 (m, 1H), 7.08 (m, 3H), 6.93 (m, 2H), 6.74 (m, 1H) ppm; MS m/e: 323 (M+H)+

Compound 178: 5-(benzo[d]thiazol-6-yl)-4-(3-fluorophenyl)thiazol-2-amine $^1$H NMR (CD3OD, 300 MHz) 9.22 (m, 1H), 7.96 (m, 2H), 7.39 (m, 1H), 7.20 (m, 3H), 6.99 (m, 1H) ppm; MS m/e: 328 (M+H)+

Compound 179: 4-(3-fluorophenyl)-5-(1H-indazol-5-yl)thiazol-2-amine. $^1$H NMR (CD3OD, 300 MHz) 8.05 (m, 1H), 7.79 (m, 1H), 7.52 (m, 1H), 7.36 (m, 1H), 7.23 (m, 1H), 7.17 (m, 3H) ppm; MS m/e: 311 (M+H)+

Compound 180: 5-(quinoxalin-6-yl)-4-(3-(trifluoromethyl)phenyl)thiazol-2-amine. $^1$H NMR (DMSO-$d_6$, 300 MHz) 8.89 (m, 2H), 7.97 (m, 1H), 7.90 (m, 1H), 7.79 (m, 1H), 7.62 (m, 3H), 7.48 (m, 1H) ppm; MS m/e: 373 (M+H)+

Compound 181: 6-(4-(4-fluorophenyl)thiazol-5-yl)benzo[d]thiazole. MS m/e: 313 (M+H)

Compound 182: 4-(4-methoxyphenyl)-5-(quinoxalin-6-yl)thiazol-2-amine. $^1$H NMR (CD3OD, 300 MHz) 8.87 (s, 1H), 8.01 (m, 2H), 7.62 (m, 1H), 7.38 (m, 2H), 6.97 (m, 2H), 3.82 (s, 3H) ppm; MS m/e: 335 (M+H)+

Compound 183: 4-(3-fluorophenyl)-5-(quinoxalin-6-yl)thiazol-2-amine. $^1$H NMR (DMSO-$d_6$, 300 MHz) 8.88 (m, 2H), 7.97 (m, 1H), 7.87 (m, 1H), 7.58 (m, 1H), 7.30 (m, 1H), 7.19 (m, 3H) ppm; MS m/e: 323 (M+H)+

Compound 184: 5-(imidazo[1,2-a]pyridin-6-yl)-4-(3-methoxyphenyl)thiazol-2-amine. MS m/e: 323 (M+H)+

Compound 185: 5-(1H-indazol-6-yl)-4-(3-(trifluoromethyl)phenyl)thiazol-2-amine. $^1$H NMR (CD3OD, 300 MHz) 8.06 (m, 1H), 7.75 (m, 2H), 7.68 (m, 1H), 7.61 (m, 1H), 7.52 (m, 2H), 7.01 (m, 1H) ppm; MS m/e: 361 (M+H)+

Compound 186: 5-(benzo[d]thiazol-6-yl)-4-(3-methoxyphenyl)thiazol-2-amine. MS m/e: 340 (M+H)+

Compound 187: 4-(3-fluorophenyl)-5-(imidazo[1,2-a]pyridin-6-yl)thiazol-2-amine. MS m/e: 311 (M+H)+

Compound 188: 4-(4-fluorophenyl)-5-(imidazo[1,2-a]pyridin-6-yl)-N-methylthiazol-2-amine. MS m/e: 325 (M+H)+

Example 2

AlphaScreen® SureFire® SMAD3 (p-Ser423/425) Assay

The p-SMAD-3 (Ser423/425) SureFire® assay has been designed to measure the phosphorylation of endogenous cellular p-SMAD-3 (Ser423/425) in cell lysates and is a system for the screening of both modulators of receptor activation (e.g. agonists and antagonists) as well as agents acting intracellularly, such as small molecule inhibitors of upstream events. The assay will measure p-SMAD-3 (Ser423/425) activation by either cloned or endogenous receptors, and can be applied to primary cells.

P-SMAD-3 (Ser423/425) SureFire® Assay Protocols

Step A: Preparation of Buffers

1× Lysis buffer: 1 ml of 5× Lysis buffer was diluted with 4 ml of sterile water. After dilution, excess 1× Lysis buffer can be frozen and thawed up to 5 times without loss in activity.

Activation buffer: The buffer was warmed slowly to 37° C. and gently mixed to re-suspend. Activation buffer can be stored at room temperature with no loss in activity.

Reaction buffer: The buffer was kept at 4° C. while in use.

AlphaScreen® Protein A IgG Kit: The kit was stored at 4° C. in the dark.

Reaction buffer+Activation buffer+AlphaScreen® Acceptor beads: Reaction buffer (40 parts), Activation Buffer (10 parts) and Acceptor beads (1 part) were mixed and the mixture was stored at room temperature and used the same day. Mixture was added to 384-well plates; excess mixture was discarded.

Dilution buffer+AlphaScreen® Donor beads: Dilution buffer (20 parts) and Donor beads (1 part) were mixed and the mixture was stored at room temperature and used the same day. Excess mixture was discarded.

Assay control samples: After reconstitution in 250 µl of water, lysates were at −20° C. in single use aliquots.

Step B: Preparation of Samples and Cells 96-well Assay Protocol for 293FT and RMS13 adherent cells can be carried out manually or in high throughput with liquid handling robots.

The cells (80 µL of cells for 96 well plates) were plated in collagen coated tissue culture plates in RPMI or FreeStyle medium (Invitrogen) and incubated overnight. For manual analysis, 6 plates for GDF8, 6 plates for TGF-β, and optionally 6 plates for Alk5ca(ALK5 constitutively active) were used.

The compound dilution plates were prepared as follows: 12 µL of DMSO was transferred into first column of 96-well plate, and 16 µL of DMSO was transferred into columns 2-12 of the 96-well plate. 12 µL of compound solution was transferred into first column of the DMSO-containing 96-well plate. Three-fold dilution was performed up to column 10 of the DMSO-containing 96-well plate.

Step C: Treatment and Analysis

The plate containing cells were treated with compounds for about 10 minutes, and then ligand was added. GDF8 or TGFb was added to plates to stimulate. 293FL cells were stimulated for 90 minutes at 37° C.; and RMS13 cells were stimulated for 60 minutes at 37° C. The medium was then removed from the cells, and 1× Lysis Buffer (about 25 µL) was added and the plate was gently agitated on plate shaker for 5-10 minutes.

The lysate (5 µL) was then placed into 384-well shallow plates avoiding the generation of bubbles. To this, the Reaction Buffer+Activation Buffer+AlphaScreen® Acceptor beads mixture (5 µL) was added. The plate was sealed with adhesive cover and shielded from light (e.g., with metal foil), and agitated gently on plate shaker for 2 hours at room temperature.

Dilution buffer+AlphaScreen® Donor beads (2 µL) was then added, and the plate was intubated on the plate shaker for an additional 1½ hours. After completion, the plate was read on Synergy-4 or Enspire plate reader, using AlphaScreen® pSMAD3® settings.

Representative results for inhibition of GDF8 (data=GDF pSMAD (MPC11) (µM)) and TGF-β (data=TGF-β pSMAD (MPC-11) (µM)) signaling are shown in the following table:

| No. | GDF8 | TGF-β |
|---|---|---|
| 1 | 0.07 | 0.23 |
| 2 | 0.06 | 0.2 |
| 3 | 0.01 | 0.01 |
| 4 | 0.01 | 0.02 |
| 5 | 0.01 | 0.02 |
| 6 | 0.16 | 0.62 |
| 7 | 0.04 | 0.15 |
| 8 | 0.09 | 0.21 |
| 9 | 0.06 | 0.33 |
| 10 | 0.01 | 0.06 |
| 11 | 0.04 | 0.13 |
| 12 | 0.13 | 0.27 |
| 13 | 0.12 | 0.38 |
| 14 | 0.61 | 1.82 |
| 15 | 0.01 | 0.06 |
| 16 | 0.02 | 0.1 |
| 17 | 0.05 | 0.14 |
| 18 | 0.04 | 0.15 |
| 19 | 0.15 | 0.73 |
| 20 | 0.18 | 0.16 |
| 21 | 0.38 | 0.74 |
| 22 | 0.02 | 0.03 |
| 23 | 0.01 | 0.03 |
| 24 | 0.01 | 0.01 |
| 25 | 0.04 | 0.06 |
| 26 | 0.22 | 0.26 |
| 27 | 0.09 | 0.12 |
| 28 | 0.05 | 0.06 |
| 29 | 0.29 | — |
| 30 | 0.27 | 0.32 |
| 31 | 0.02 | 0.09 |
| 32 | 0.05 | 0.14 |
| 33 | 0.06 | 0.07 |
| 34 | 0.07 | 0.14 |
| 35 | 0.3 | 0.64 |
| 36 | 0.5 | 1.48 |
| 37 | 0.26 | 0.92 |
| 38 | 0.93 | 2.55 |
| 39 | 0.19 | 0.39 |
| 40 | 0.46 | 1.22 |
| 41 | 0.02 | 0.06 |
| 42 | 0.03 | 0.15 |
| 43 | 0.19 | 0.53 |
| 44 | 0.18 | 0.72 |
| 45 | 0.44 | 1.78 |
| 46 | 0.26 | 1.68 |
| 47 | 0.18 | 0.66 |
| 48 | 0.06 | 0.25 |
| 49 | 0.57 | 1.21 |
| 50 | 1.02 | 1.87 |
| 51 | 0.78 | 2.71 |
| 52 | 0.21 | 0.91 |
| 53 | 0.78 | 3.34 |
| 54 | 0.41 | 3.1 |
| 55 | 0.84 | 7.76 |
| 56 | 0.73 | 5.3 |
| 57 | 0.71 | 9.21 |
| 58 | 0.99 | 9.64 |
| 59 | 0.69 | 6.75 |
| 60 | 0.02 | 0.06 |
| 61 | 0.03 | 0.15 |
| 62 | 0.05 | 0.22 |
| 63 | 0.06 | 0.23 |
| 64 | 0.09 | 0.27 |
| 65 | 0.22 | 1.06 |
| 66 | 0.52 | 0.98 |
| 67 | 0.58 | 1.68 |
| 68 | 1.05 | 2.87 |
| 69 | 0.14 | 1.77 |
| 70 | 0.7 | 5.22 |
| 71 | 0.09 | 0.8 |
| 72 | 0.1 | 0.97 |
| 73 | 0.1 | 0.95 |
| 74 | 0.2 | 1.41 |
| 75 | 0.51 | 4.39 |
| 76 | 0.19 | 1.21 |
| 77 | 0.22 | 1.43 |
| 78 | 0.29 | 2.47 |
| 79 | 0.11 | 0.85 |

| No. | GDF8 | TGF-β |
|---|---|---|
| 80 | 0.22 | 1.63 |
| 81 | 0.39 | 2.62 |
| 82 | 0.48 | 3.27 |
| 83 | 0.13 | 1.33 |
| 84 | 0.32 | 2.9 |
| 85 | 0.18 | 0.67 |
| 86 | 0.22 | 1.28 |
| 87 | 0.33 | 3.46 |
| 88 | 1.02 | 11.48 |
| 89 | 0.43 | 4.19 |
| 90 | 0.63 | 3.56 |
| 91 | 0.39 | 2.23 |
| 92 | 0.47 | 2.27 |
| 93 | 0.3 | 2.34 |
| 94 | 0.58 | 2.91 |
| 95 | 0.3 | 1.88 |
| 96 | 0.44 | 2.43 |
| 97 | 0.1 | 0.54 |
| 98 | 0.05 | 0.19 |
| 99 | 0.04 | 0.24 |
| 100 | 0.17 | 1.37 |
| 101 | 0.14 | 0.5 |
| 102 | 0.06 | 0.44 |
| 103 | 0.13 | 0.69 |
| 104 | 0.08 | 0.51 |
| 105 | 0.27 | 2.04 |
| 106 | 0.15 | 0.92 |
| 107 | 0.34 | 1.85 |
| 108 | 0.08 | 0.4 |
| 109 | 0.15 | 0.87 |
| 110 | 0.25 | 1.05 |
| 111 | 0.79 | 4.48 |
| 112 | 0.28 | 1.37 |
| 113 | 0.46 | 3.11 |
| 114 | 0.18 | 1.13 |
| 115 | 0.16 | 0.75 |
| 116 | 0.28 | 1.52 |
| 117 | 0.33 | 2.18 |
| 118 | 0.23 | 1.39 |
| 119 | 0.41 | 4.74 |
| 120 | 0.47 | 8.16 |
| 121 | 0.46 | 2.07 |
| 122 | 0.58 | 4.53 |
| 123 | 0.74 | 9.37 |
| 124 | 0.54 | 1.34 |
| 125 | 0.05 | 0.12 |
| 126 | 0.09 | 0.34 |
| 127 | 0.19 | 0.57 |
| 128 | 0.46 | 1.48 |
| 129 | 0.29 | 1.34 |
| 130 | 0.65 | 2.32 |
| 131 | 0.92 | 3.91 |
| 132 | 0.55 | 1.39 |
| 133 | 0.36 | 2.21 |
| 134 | 0.87 | 2.54 |
| 135 | 0.77 | 3.42 |
| 136 | 0.75 | 2.3 |
| 137 | 0.57 | 2.54 |
| 138 | 0.73 | 3.26 |
| 139 | 0.65 | 2.03 |
| 140 | 0.62 | 2.22 |
| 141 | 0.66 | 2.91 |
| 142 | 0.67 | 4.39 |
| 143 | 0.45 | 3.14 |
| 144 | 0.31 | 1.53 |
| 145 | 0.53 | 2.95 |
| 146 | 1 | 5.96 |
| 147 | 0.55 | 2.21 |
| 148 | 0.73 | 2.84 |
| 149 | 0.72 | 3.22 |
| 150 | 0.35 | 0.85 |
| 151 | 0.59 | 1.4 |
| 152 | 0.19 | 0.38 |
| 153 | 0.0113 | 0.2073 |
| 154 | 0.0145 | 0.1161 |
| 155 | 0.0229 | 0.0724 |
| 156 | 0.0253 | 0.1335 |
| 157 | 0.0256 | 0.1595 |
| 158 | 0.036 | 0.2278 |
| 159 | 0.0367 | 0.1709 |
| 160 | 0.0385 | 0.0998 |
| 161 | 0.0468 | 0.4273 |
| 162 | 0.0523 | 0.1274 |
| 163 | 0.054 | 0.1685 |
| 164 | 0.0663 | 0.2183 |
| 165 | 0.0696 | 0.2621 |
| 166 | 0.0702 | 0.2204 |
| 167 | 0.078 | 0.215 |
| 168 | 0.08 | 0.3379 |
| 169 | 0.0951 | 0.2358 |
| 170 | 0.0986 | 0.6559 |
| 171 | 0.1088 | 0.4229 |
| 172 | 0.121 | 0.9089 |
| 173 | 0.1237 | 0.8982 |
| 174 | 0.1444 | 0.4309 |
| 175 | 0.1545 | 0.9379 |
| 176 | 0.1582 | 0.5998 |
| 177 | 0.2345 | 1.035 |
| 178 | 0.2516 | 1.1 |
| 179 | 0.2681 | 1.277 |
| 180 | 0.3011 | 0.6209 |
| 181 | 0.3363 | 4.552 |
| 182 | 0.3516 | 1.122 |
| 183 | 0.3646 | 1.485 |
| 184 | 0.4024 | 1.165 |
| 185 | 0.4252 | 2.357 |
| 186 | 0.4775 | 1.11 |
| 187 | 0.481 | 3.098 |
| 188 | 0.7845 | 0.3647 |

Analytical LC-MS/HPLC retention time reported for each example and intermediate uses one of the following general analytical LC-MS/HPLC conditions:

Method A: Column: Waters Acquity UPLC BEH C18, 2.1×50 mm, 1.7 μm particles; Mobile Phase A: 5:95 acetonitrile:water with 0.1% TFA; Mobile Phase B: 95:5 acetonitrile:water with 0.1% TFA; Temperature: 50° C.; Gradient: 0-100% B over 3 minutes, then a 0.75 minute hold at 100% B; Flow: 1.0 mL/min; Detection: UV at 220 nm.

Method B: Column Waters Acquity UPLC BEH C18, 2.1×50 mm, 1.7 μm particles; Mobile Phase A: 5:95 acetonitrile:water with 10 mM NH$_4$OAc; Mobile Phase B: 95:5 acetonitrile:water with 10 mM NH$_4$OAc; Temperature: 50° C.; Gradient: 0-100% B over 3 minutes, then a 0.75 minute hold at 100% B; Flow: 1.0 mL/min; Detection: UV at 220 nm.

Method C: Column: Waters Acquity UPLC BEH C18, 2.1×50 mm, 1.7 μm particles; Mobile Phase A: acetonitrile with 0.05% TFA; Mobile Phase B: water with 0.05% TFA; Temperature: 50° C.; Gradient: 2-98% B over 1.5 minutes, then a 0.1-minute hold at 100% B; Flow: 0.8 mL/min; Detection: UV at 220 nm.

Method D: Column: Phenomenex LUNA C18, 30×2, 3 μm particles; Mobile Phase A: 5:95 acetonitrile:water with 10 mM NH$_4$OAc; Mobile Phase B: 95:5 acetonitrile:water with 10 mM NH$_4$OAc; Temperature: 50° C.; Gradient: 0-100% B over 3 minutes, then a 0.75 minute hold at 100% B; Flow: 1.0 mL/min; Detection: UV at 220 nm.

Method E: Phenomenex Luna 2.0×50 mm 3 μm column; Mobile Phase A: 10:90 methanol:water with 0.1% TFA; Mobile Phase B: 90:10 methanol:water with 0.1% TFA; Temperature: 50° C.; Gradient: 0-100% B over 4 minutes, then a 1.0 minute hold at 100% B; flow rate 0.8 mL/min; Detection: UV at 220 nm.

Method F: Column: Waters Acquity UPLC BEH C18 (2.1×50 mm), 1.7μ; Mobile phase A: 0.1% TFA in water;

Mobile phase B: 0.1% TFA in acetonitrile; Gradient=20-90% B over 1.1 minute, then a 0.6 minute hold at 90% B; Temperature: 50° C.; Flow rate: 0.7 mL/min; Detection: UV at 220 nm.

Method G: Column: Waters Acquity UPLC BEH C18 (2.1×50 mm) 1.7μ; Mobile phase A: 10 mM NH₄OAc in water:acetonitrile (95:5); Mobile phase B: 10 mM NH₄OAc in water:acetonitrile (5:95), Gradient=20-90% B over 1.1 minute, then a 0.6 minute hold at 90% B; Temperature: 50° C.; Flow rate: 0.7 mL/min; Detection: UV at 220 nm Method H: Column: Ascentis Express C18 (2.1×50 mm), 2.7μ; Mobile phase A: 10 mM NH₄OAc in water:acetonitrile (95:5), Mobile phase B: 10 mM NH₄OAc in water:acetonitrile (5:95), Gradient=0-100% B over 3 minutes; Temperature: 50° C.; Flow rate: 1.1 mL/min; Detection: UV at 220 nm.

Method I: Column: Ascentis Express C18 (50×2.1) mm, 2.7μ; Mobile phase A: 0.1% TFA in water:acetonitrile (95:5), Mobile phase B: 0.1% TFA in water:acetonitrile (5:95), Gradient=0-100% B over 3 minutes; Temperature: 50° C.; Flow rate: 1.1 mL/min; Detection: UV at 220 nm.

Method J: Column: Kinetex XB-C18 (75×3 mm) 2.6μ; Mobile phase A: 10 mM HCO₂NH₄ in water:acetonitrile (98:2), Mobile phase B: 10 mM HCO₂NH₄ in water:acetonitrile (2:98), Gradient=20-100% B over 4 minutes, then a 0.6 minute hold at 100% B; Temperature: 27° C.; Flow rate: 1.0 mL/min; Detection: UV at 220 nm.

Method K: Column: ZORBAX-SBC18 (50×4.6 mm) 5μ; Mobile phase A: 10 mM HCO₂NH₄ in water:acetonitrile (98:2), Mobile phase B: 10 mM HCO₂NH₄ in water:acetonitrile (2:98), Gradient=20-100% B over 4 minutes, then a 0.6 minute hold at 100% B; Temperature: 27° C.; Flow rate: 1.5 mL/min; Detection: UV at 220 nm Method L: Column: Waters X-Bridge C18, 19×150 mm, 5μ; Mobile Phase A: 0.1% TFA in water; Mobile Phase B: acetonitrile; Gradient: 10-100% B over 25 minutes, then a 5 minute hold at 100% B; Flow: 15 mL/min.

Method M: Column: Inertsil ODS, 250×20 mm ID, 5μ; Mobile Phase A: 10 mM NH₄OAc in water; Mobile Phase B: methanol; Gradient: 10-100% B over 25 minutes, then a 5 minute hold at 100% B; Flow: 17 mL/min.

Method N: Column: Inertsil ODS, 150×4.6 mm, 5μ; Mobile Phase A: 10 mM NH₄OAc in water; Mobile Phase B: acetonitrile; Gradient: 0-100% B over 18 minutes, then a 5 minute hold at 100% B; Flow: 17 mL/min.

Method O: Column: Sunfire C18, 150×19 mm ID, 5μ; Mobile Phase A: 10 mM NH₄OAc in water; Mobile Phase B: acetonitrile; Gradient: 0-100% B over 18 minutes, then a 5 minute hold at 100% B; Flow: 17 mL/min.

Method P: Column: Waters X-Bridge C18, 19×150 mm, 5μ; Mobile Phase A: 10 mM NH₄OAc in water; Mobile Phase B: acetonitrile; Gradient: 0-100% B over 18 minutes, then a 5 minute hold at 100% B; Flow: 17 mL/min.

Method Q: Column: Inertsil ODS, 250×20 mm ID, 5μ; Mobile Phase A: 0.1% TFA in water; Mobile Phase B: acetonitrile; Gradient: 10-100% B over 25 minutes, then a 5 minute hold at 100% B; Flow: 17 mL/min.

Method R: Column: Symmetry C8, 300×19 mm ID, 7μ; Mobile Phase A: 10 mM NH₄OAc in water; Mobile Phase B: acetonitrile; Gradient: 0-100% B over 18 minutes, then a 5 minute hold at 100% B; Flow: 17 mL/min.

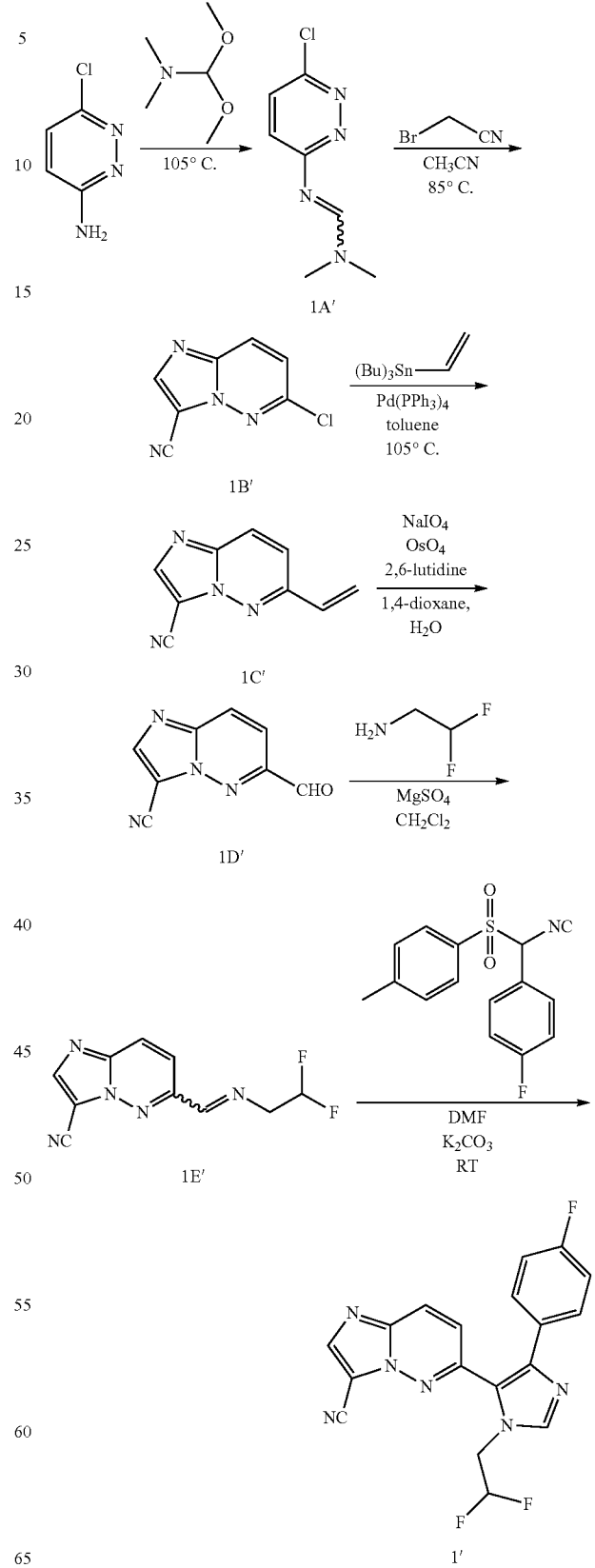

Scheme 1

Intermediate 1A': N-(6-chloropyridazin-3-yl)-N,N-dimethylformimidamide

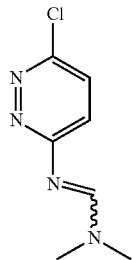

A suspension of 6-chloropyridazin-3-amine (7.3 g, 56 mmol) in 1,1-dimethoxy-N,N-dimethylmethanamine (7.9 g, 62 mmol) was heated at 105° C. for 2 h. The reaction mixture was cooled to RT and concentrated to give 1A' (10.3 g, 100%) as a tan solid. MS (ES): m/z=185/187 [M+H]$^+$; HPLC Ret. Time 0.38 min. (HPLC Method C).

Intermediate 1B': 6-chloroimidazo[1,2-b]pyridazine-3-carbonitrile

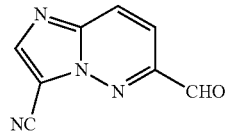

To a suspension of (10.3 g, 56 mmol) in acetonitrile (75 mL) was added bromoacetonitrile (10.2 g, 80.5 mmol). The reaction mixture was heated at 85° C. for 6 h. The suspension became a solution and then suspension again (HBr salt). The reaction mixture was cooled to RT and concentrated in vacuo. The residue was diluted with DCM, treated with Hunig's base (19.64 mL, 112 mmol) and the resulting solution was stirred at RT for 1 h and concentrated. The residue was purified by silica gel chromatography (220 g RediSep® column, eluting with a gradient from 0-55% EtOAc in hexanes). Fractions containing the product were combined and evaporated to afford intermediate 1B' (10.2 g, 50.8% yield) as a tan powder. MS (ES): m/z=179/181 [M+H]$^+$; HPLC Ret. Time 0.63 min. (HPLC Method C).

Intermediate 1C': 6-vinylimidazo[1,2-b]pyridazine-3-carbonitrile

To a pressure bottle were added tributyl(vinyl)stannane (11.63 g, 36.7 mmol), 1B' (2.2 g, 12.22 mmol) and toluene (15 mL). The solution was purged with nitrogen for 2 min. and Pd(Ph$_3$P)$_4$ (1.41 g, 1.222 mmol) was added. The reaction mixture was heated at 105° C. overnight, cooled to RT and concentrated in vacuo. The resulting residue was purified by silica gel chromatography (80 g RediSep® column, eluting with a gradient from 0-85% EtOAc in hexanes). Fractions containing the product were combined and evaporated to afford intermediate 1C' (1.34 g, 64.4% yield) as a tan powder. MS (ES): m/z=171 [M+H]$^+$; HPLC Ret. Time 0.66 min. (HPLC Method C); $^1$H NMR (400 MHz, CDCl$_3$) δ ppm 8.23 (s, 1H), 8.05 (d, J=9.5 Hz, 1H), 7.54 (d, J=9.5 Hz, 1H), 6.95 (dd, J=17.8, 11.0 Hz, 1H), 6.28 (d, J=17.8 Hz, 1H), 5.85 (d, J=11.0 Hz, 1H).

Intermediate 1D': 6-formylimidazo[1,2-b]pyridazine-3-carbonitrile

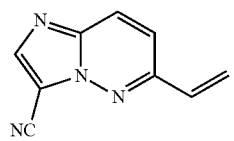

To a solution of intermediate 1C' (290 mg, 1.704 mmol) in 1,4-dioxane (12 mL) and water (4 mL) were added 2,6-lutidine (0.397 mL, 3.41 mmol), sodium periodate (1458 mg, 6.82 mmol), and 4% aq. solution of osmium tetroxide (0.401 mL, 0.051 mmol). The reaction mixture was stirred at RT for 4 h and diluted with water and DCM. The layers were separated. The aqueous layer was extracted with DCM. The combined organic layers were washed with brine, dried over Na$_2$SO$_4$, and filtered. The filtrate was concentrated and the residue was purified by silica gel chromatography (80 g RediSep® column, eluting with a gradient from 15-65% EtOAc in hexanes). Fractions containing the product were combined and evaporated to afford intermediate 1D' (210 mg, 71.6% yield). MS (ES): m/z=357.2; HPLC Ret. Time 2.711 (HPLC method E); $^1$H NMR (400 MHz, CDCl$_3$) δ ppm 10.18 (d, J=1.0 Hz, 1H), 8.44 (s, 1H), 8.27 (dd, J=9.4, 0.9 Hz, 1H), 7.92 (d, J=9.3 Hz, 1H).

Intermediate 1E': 6-(((2,2-difluoroethyl)imino)methyl)imidazo[1,2-b]pyridazine-3-carbonitrile

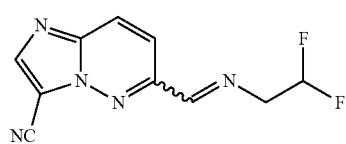 [SMILES: N#Cc1cnc2ccc(C=NCC(F)F)nn12]

To a solution of intermediate 1D' (210 mg, 1.22 mmol) in DCM (10 mL) were added anhydrous magnesium sulfate (1175 mg, 9.76 mmol) and 2,2-difluoroethanamine (109 mg, 1.342 mmol). The reaction mixture was stirred at RT for 4 h and filtered. The filtrate was concentrated and the crude product was used in the next step without purification. MS (ES): m/z=236 [M+H]$^+$; HPLC Ret. Time 1.43 min. (HPLC Method D); $^1$H NMR (400 MHz, CDCl$_3$) δ ppm 8.55 (s, 1H), 8.31 (s, 1H), 8.18-8.02 (m, 2H), 6.19 (t, J=4.3 Hz, 1H), 4.13 (ddd, J=14.9, 4.3, 1.5 Hz, 2H).

Example 1'

6-(1-(2,2-difluoroethyl)-4-(4-fluorophenyl)-1H-imidazol-5-yl)imidazo[1,2-b]pyridazine-3-carbonitrile

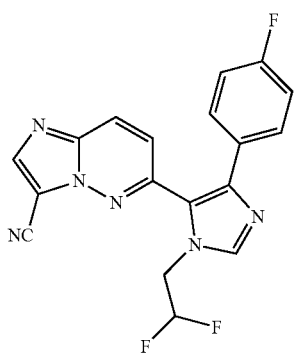

To a solution of intermediate 1E' (26 mg, 0.111 mmol) in DMF (1 mL) were added 1-fluoro-4-(isocyano(tosyl)methyl)benzene (32 mg, 0.111 mmol) and potassium carbonate (20 mg, 1.44 mmol). The reaction mixture was stirred at RT overnight, and diluted with EtOAc and water, The layers were separated and the aqueous layer was extracted with EtOAc. The combined organic layers were washed with brine, dried over $Na_2SO_4$, filtered, and the filtrate was concentrated. The crude product was dissolved in a mixture of DMF and methanol and purified via preparative HPLC. Fractions containing the desired product were combined and dried under vacuum to afford Example 1' (18.1 mg, 44% yield). MS (ES): m/z=369 [M+H]$^+$; HPLC Ret. Time 1.322 and 1.532 min. (HPLC Methods A and B, respectively); $^1$H NMR (400 MHz, CDCl$_3$) δ ppm 8.29 (s, 1H), 7.93 (d, J=9.5 Hz, 1H), 7.83 (s, 1H), 7.56-7.47 (m, 2H), 7.18-7.04 (m, 3H), 6.38 (t, J=3.8 Hz, 1H), 4.71 (dd, J=13.9, 3.6 Hz, 2H).

Scheme 2

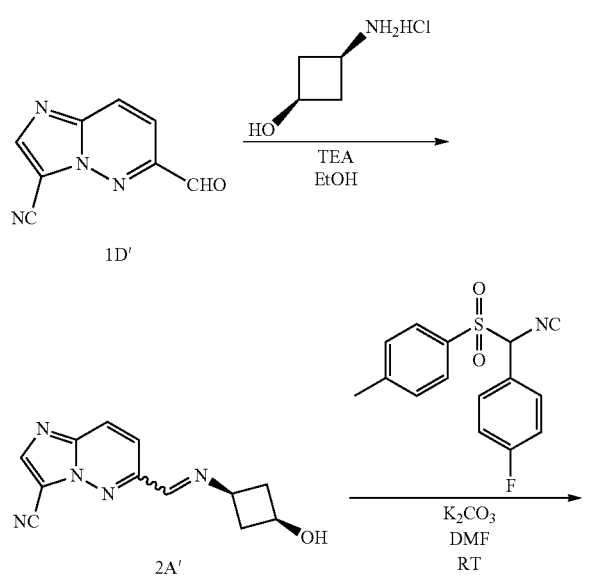

Intermediate 2A': 6-(((cis-3-hydroxycyclobutyl)imino)methyl)imidazo[1,2-b]pyridazine-3-carbonitrile

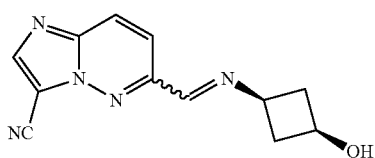 [SMILES: N#Cc1cnc2ccc(C=N[C@H]3C[C@@H](O)C3)nn12]

To a solution of intermediate 1D' (280 mg, 1.627 mmol) in ethanol (10 mL) were added cis-3-aminocyclobutanol hydrochloride (220 mg, 1.780 mmol) and TEA (340 μL, 2.440 mmol). The reaction mixture was stirred at RT for 6 h. It became a suspension after 2 h. The reaction mixture was concentrated to afford a residue that was used in the next step without further purification. MS (ES): m/z=242 [M+H]$^+$; HPLC Ret. Time 1.20 min. (HPLC Method D); $^1$H NMR (400 MHz, CDCl$_3$) δ ppm 8.38 (d, J=1.3 Hz, 1H), 8.28 (s, 1H), 8.16-8.02 (m, 2H), 4.29 (t, J=7.3 Hz, 1H), 4.00-3.84 (m, 1H), 2.96-2.78 (m, 2H), 2.28-2.14 (m, 2H).

Example 2'

6-(4-(4-fluorophenyl)-1-cis-3-hydroxycyclobutyl)-1H-imidazol-5-yl)imidazo[1,2-b]pyridazine-3-carbonitrile

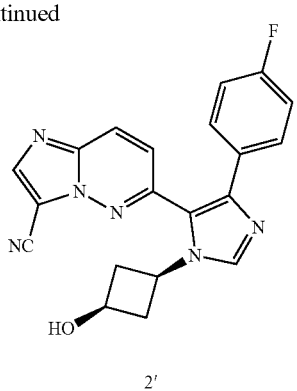

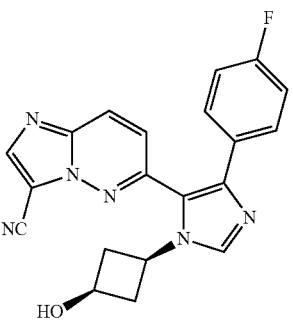 [SMILES: N#Cc1cnc2ccc(-c3c(-c4ccc(F)cc4)ncn3[C@H]3C[C@@H](O)C3)nn12]

To a solution of intermediate 2A' (200 mg, 0.829 mmol) in DMF (2 mL) were added 1-fluoro-4-(isocyano(tosyl)methyl)benzene (240 mg, 0.829 mmol) and potassium carbonate (115 mg, 0.829 mmol). The reaction mixture was stirred at RT overnight, and diluted with EtOAc and water. The layers were separated and the aqueous layer was extracted with EtOAc. The combined organic layers were washed with brine, dried over $Na_2SO_4$, and filtered. The filtrate was concentrated and the crude product was purified via preparative HPLC. Fractions containing the desired product were combined and dried under vacuum to afford Example 2' (152 mg, 49% yield). MS (ES): m/z=375.1 [M+H]$^+$; HPLC Ret. Time 0.997 and 1.218 min. (HPLC Methods A and B, respectively); $^1$H NMR (500 MHz, DMSO-$d_6$) δ ppm 8.64 (s, 1H), 8.32 (d, J=9.2 Hz, 1H), 8.25 (s, 1H), 7.52 (dd, J=8.8, 5.5 Hz, 2H), 7.30 (d, J=9.2 Hz, 1H), 7.14 (t, J=8.8 Hz, 2H), 4.30 (t, J=7.7 Hz, 1H), 3.90 (d, J=5.9 Hz, 1H), 2.85-2.73 (m, 2H), 2.38-2.18 (m, 3H).

Compounds shown in Table 1 have been prepared in a manner similar to Example 1', if the amine is a free base, or a manner similar to Example 2', if the amine is an HCl salt, using intermediate 1D' and 1-fluoro-4-(isocyano(tosyl)methyl)benzene.

TABLE 1

| Ex. | Structure | Name | [M + H]$^+$ | Ret Time (min.) | HPLC Method |
|-----|-----------|------|-------------|-----------------|-------------|
| 3' | 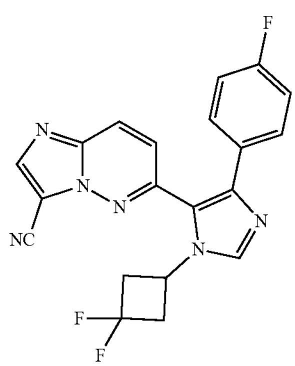 [SMILES: N#Cc1cnc2ccc(-c3c(-c4ccc(F)cc4)ncn3C3CC(F)(F)C3)nn12] | 6-(1-(3,3-difluorocyclobutyl)-4-(4-fluorophenyl)-1H-imidazol-5-yl)imidazo[1,2-b]pyridazine-3-carbonitrile | 395.0 | 1.307<br>1.619 | A<br>B |
| 4' | 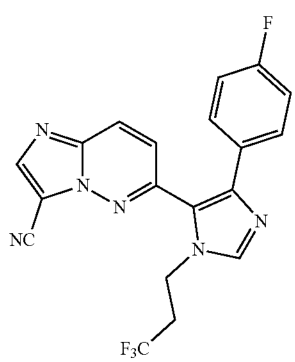 [SMILES: N#Cc1cnc2ccc(-c3c(-c4ccc(F)cc4)ncn3CCC(F)(F)F)nn12] | 6-(4-(4-fluorophenyl)-1-(3,3,3-trifluoropropyl)-1H-imidazol-5-yl)imidazo[1,2-b]pyridazine-3-carbonitrile | 400.9 | 1.389<br>1.668 | A<br>B |
| 5' | 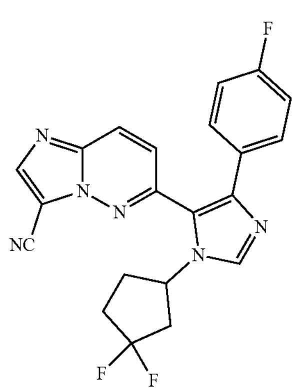 [SMILES: N#Cc1cnc2ccc(-c3c(-c4ccc(F)cc4)ncn3C3CCC(F)(F)C3)nn12] | 6-(1-(3,3-difluorocyclopentyl)-4-(4-fluorophenyl)-1H-imidazol-5-yl)imidazo[1,2-b]pyridazine-3-carbonitrile | 409.0 | 1.363<br>1.679 | A<br>B |

TABLE 1-continued

| Ex. | Structure | Name | [M + H]+ | Ret Time (min.) | HPLC Method |
|---|---|---|---|---|---|
| 6' | 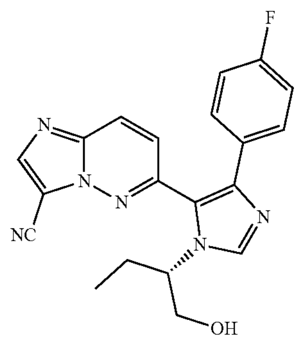 [SMILES: CC[C@@H](CO)n1cnc(-c2ccc(F)cc2)c1-c1ccc2ncc(C#N)n2n1] | (S)-6-(4-(4-fluorophenyl)-1-(1-hydroxybutan-2-yl)-1H-imidazol-5-yl)imidazo[1,2-b]pyridazine-3-carbonitrile | 377.1 | 1.222<br>1.423 | A<br>B |
| 7' | 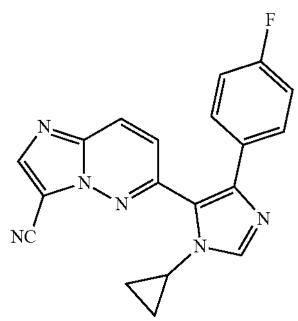 [SMILES: N#Cc1cnc2ccc(-c3c(-c4ccc(F)cc4)ncn3C3CC3)nn12] | 6-(1-cyclopropyl-4-(4-fluorophenyl)-1H-imidazol-5-yl)imidazo[1,2-b]pyridazine-3-carbonitrile | 345.0 | 1.175<br>1.606 | A<br>B |
| 8' | 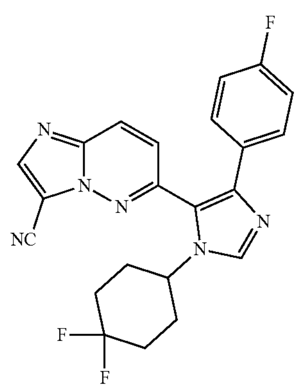 [SMILES: N#Cc1cnc2ccc(-c3c(-c4ccc(F)cc4)ncn3C3CCC(F)(F)CC3)nn12] | 6-(1-(4,4-difluorocyclohexyl)-4-(4-fluorophenyl)-1H-imidazol-5-yl)imidazo[1,2-b]pyridazine-3-carbonitrile | 423.0 | 1.355<br>1.731 | A<br>B |
| 9' | 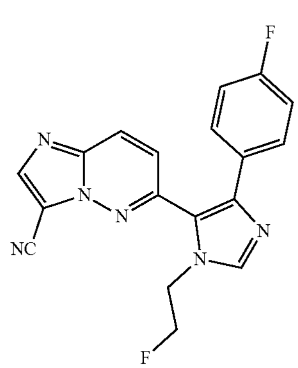 [SMILES: N#Cc1cnc2ccc(-c3c(-c4ccc(F)cc4)ncn3CCF)nn12] | 6-(1-(2-fluoroethyl)-4-(4-fluorophenyl)-1H-imidazol-5-yl)imidazo[1,2-b]pyridazine-3-carbonitrile | 351.0 | 1.287<br>1.423 | A<br>B |

TABLE 1-continued

| Ex. | Structure | Name | [M + H]⁺ | Ret Time (min.) | HPLC Method |
|---|---|---|---|---|---|
| 10' | 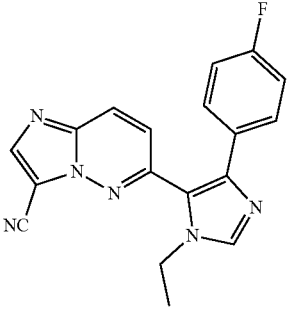 [SMILES: CCn1cnc(-c2ccc(F)cc2)c1-c1ccc2ncc(C#N)n2n1] | 6-(1-ethyl-4-(4-fluorophenyl)-1H-imidazol-5-yl)imidazo[1,2-b]pyridazine-3-carbonitrile | 333.1 | 1.195<br>1.571 | A<br>B |
| 11' | 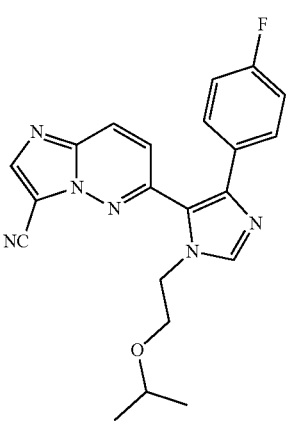 [SMILES: CC(C)OCCn1cnc(-c2ccc(F)cc2)c1-c1ccc2ncc(C#N)n2n1] | 6-(4-(4-fluorophenyl)-1-(2-isopropoxyethyl)-1H-imidazol-5-yl)imidazo[1,2-b]pyridazine-3-carbonitrile | 391.1 | 1.412<br>1.651 | A<br>B |
| 12' | 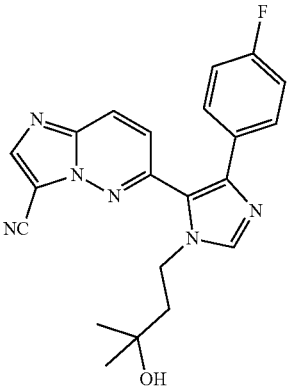 [SMILES: CC(C)(O)CCn1cnc(-c2ccc(F)cc2)c1-c1ccc2ncc(C#N)n2n1] | 6-(4-(4-fluorophenyl)-1-(3-hydroxy-3-methylbutyl)-1H-imidazol-5-yl)imidazo[1,2-b]pyridazine-3-carbonitrile | 391.1 | 1.150<br>1.540 | A<br>B |
| 13' | 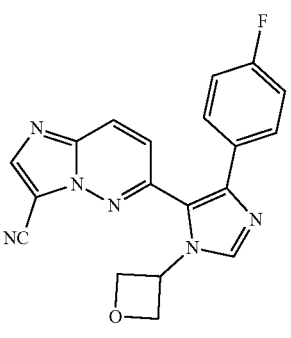 [SMILES: N#Cc1cnc2ccc(-c3c(-c4ccc(F)cc4)ncn3C3COC3)nn12] | 6-(4-(4-fluorophenyl)-1-(oxetan-3-yl)-1H-imidazol-5-yl)imidazo[1,2-b]pyridazine-3-carbonitrile | 361.0 | 1.056<br>1.263 | A<br>B |

TABLE 1-continued

| Ex. | Structure | Name | [M + H]+ | Ret Time (min.) | HPLC Method |
|---|---|---|---|---|---|
| 14' | 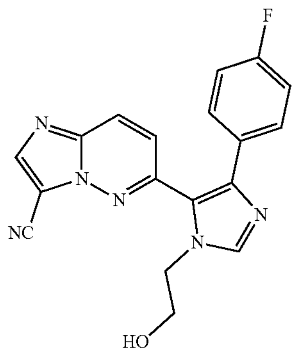 [SMILES: N#Cc1cnc2ccc(-c3c(-c4ccc(F)cc4)ncn3CCO)nn12] | 6-(4-(4-fluorophenyl)-1-(2-hydroxyethyl)-1H-imidazol-5-yl)imidazo[1,2-b]pyridazine-3-carbonitrile | 349.1 | 1.135<br>1.212 | A<br>B |
| 15' | 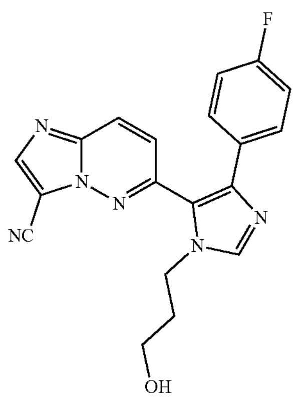 [SMILES: N#Cc1cnc2ccc(-c3c(-c4ccc(F)cc4)ncn3CCCO)nn12] | 6-(4-(4-fluorophenyl)-1-(3-hydroxypropyl)-1H-imidazol-5-yl)imidazo[1,2-b]pyridazine-3-carbonitrile | 363.1 | 1.054<br>1.274 | A<br>B |
| 16' | 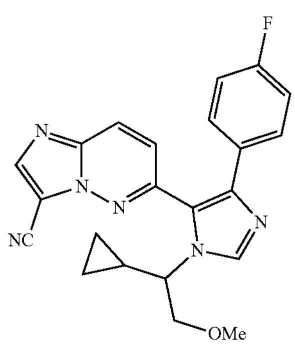 [SMILES: COCC(C1CC1)n1cnc(-c2ccc(F)cc2)c1-c1ccc2ncc(C#N)n2n1] | 6-(1-(1-cyclopropyl-2-methoxyethyl)-4-(4-fluorophenyl)-1H-imidazol-5-yl)imidazo[1,2-b]pyridazine-3-carbonitrile | 403.1 | 1.274<br>1.727 | A<br>B |
| 17' | 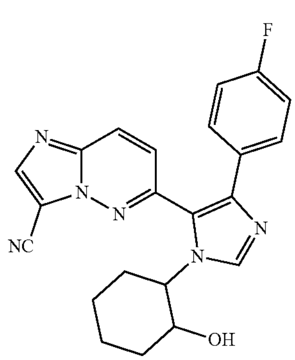 [SMILES: N#Cc1cnc2ccc(-c3c(-c4ccc(F)cc4)ncn3C3CCCCC3O)nn12] | 6-(4-(4-fluorophenyl)-1-(2-hydroxycyclohexyl)-1H-imidazol-5-yl)imidazo[1,2-b]pyridazine-3-carbonitrile | 403.4 | 1.274<br>1.670 | A<br>B |

TABLE 1-continued

| Ex. | Structure | Name | [M + H]+ | Ret Time (min.) | HPLC Method |
|---|---|---|---|---|---|
| 18' | 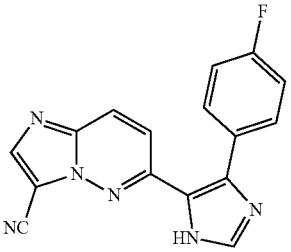 [SMILES: N#Cc1cnc2ccc(-c3[nH]cnc3-c3ccc(F)cc3)nn12] | 6-(4-(4-fluorophenyl)-1H-imidazol-5-yl)imidazo[1,2-b]pyridazine-3-carbonitrile | 305.1 | 1.151<br>1.323 | A<br>B |
| 19' | 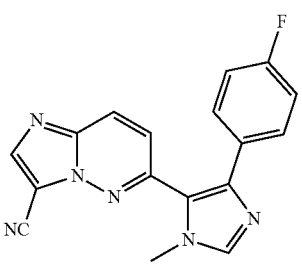 [SMILES: Cn1cnc(-c2ccc(F)cc2)c1-c1ccc2ncc(C#N)n2n1] | 6-(4-(4-fluorophenyl)-1-methyl-1H-imidazol-5-yl)imidazo[1,2-b]pyridazine-3-carbonitrile | 319.2 | 0.87<br>1.21 | A<br>B |
| 20' | 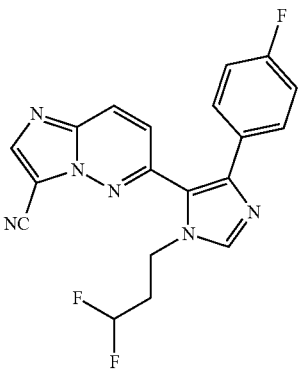 [SMILES: N#Cc1cnc2ccc(-c3c(-c4ccc(F)cc4)ncn3CCC(F)F)nn12] | 6-(1-(3,3-difluoropropyl)-4-(4-fluorophenyl)-1H-imidazol-5-yl)imidazo[1,2-b]pyridazine-3-carbonitrile | 383.3 | 1.22<br>1.54 | A<br>B |
| *21' | 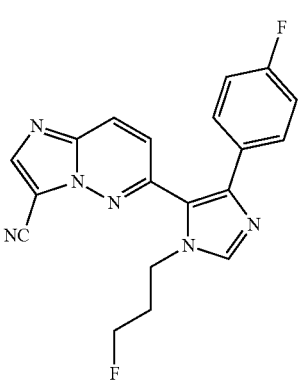 [SMILES: N#Cc1cnc2ccc(-c3c(-c4ccc(F)cc4)ncn3CCCF)nn12] | 6-(4-(4-fluorophenyl)-1-(3-fluoropropyl)-1H-imidazol-5-yl)imidazo[1,2-b]pyridazine-3-carbonitrile | 365.3 | 1.165<br>1.50 | A<br>B |

TABLE 1-continued

| Ex. | Structure | Name | [M + H]+ | Ret Time (min.) | HPLC Method |
|---|---|---|---|---|---|
| 22' | 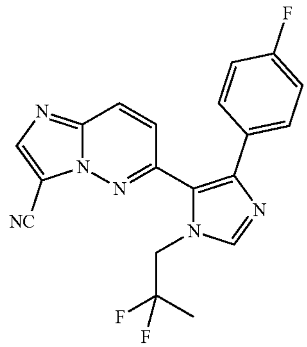 [SMILES: CC(F)(F)Cn1cnc(-c2ccc(F)cc2)c1-c1ccc2ncc(C#N)n2n1] | 6-(1-(2,2-difluoropropyl)-4-(4-fluorophenyl)-1H-imidazol-5-yl)imidazo[1,2-b]pyridazine-3-carbonitrile | 383.3 | 1.35<br>1.56 | A<br>B |
| 23' | 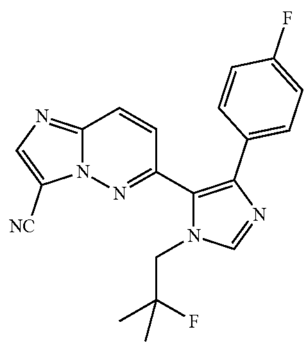 [SMILES: CC(C)(F)Cn1cnc(-c2ccc(F)cc2)c1-c1ccc2ncc(C#N)n2n1] | 6-(1-(2-fluoro-2-methylpropyl)-4-(4-fluorophenyl)-1H-imidazol-5-yl)imidazo[1,2-b]pyridazine-3-carbonitrile | 379.3 | 1.289<br>1.627 | A<br>B |
| 24' | 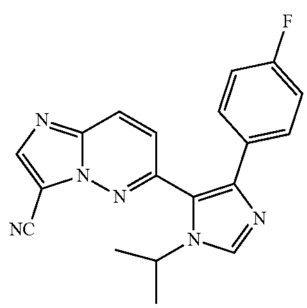 [SMILES: CC(C)n1cnc(-c2ccc(F)cc2)c1-c1ccc2ncc(C#N)n2n1] | 6-(4-(4-fluorophenyl)-1-isopropyl-1H-imidazol-5-yl)imidazo[1,2-b]pyridazine-3-carbonitrile | 347.2 | 2.129 | J |
| 25' | 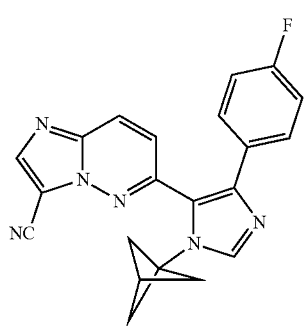 [SMILES: N#Cc1cnc2ccc(-c3c(-c4ccc(F)cc4)ncn3C34CC(C3)C4)nn12] | 6-(1-(bicyclo[1.1.1]pentan-1-yl)-4-(4-fluorophenyl)-1H-imidazol-5-yl)imidazo[1,2-b]pyridazine-3-carbonitrile | 371.2 | 1.182<br>1.60 | A<br>B |

TABLE 1-continued

| Ex. | Structure | Name | [M + H]+ | Ret Time (min.) | HPLC Method |
|---|---|---|---|---|---|
| 26' | 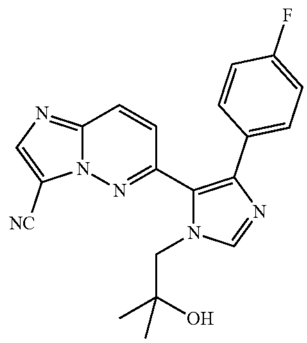 [SMILES: CC(C)(O)Cn1cnc(-c2ccc(F)cc2)c1-c1ccc2ncc(C#N)n2n1] | 6-(4-(4-fluorophenyl)-1-(2-hydroxy-2-methylpropyl)-1H-imidazol-5-yl)imidazo[1,2-b]pyridazine-3-carbonitrile | 377.3 | 1.123<br>1.36 | A<br>B |
| 27' | 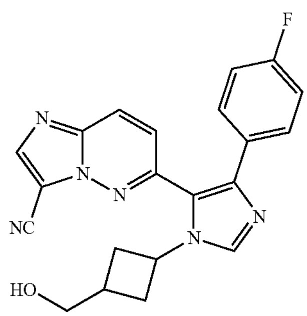 [SMILES: N#Cc1cnc2ccc(-c3c(-c4ccc(F)cc4)ncn3C3CC(CO)C3)nn12] | 6-(4-(4-fluorophenyl)-1-(3-(hydroxymethyl)cyclobutyl)-1H-imidazol-5-yl)imidazo[1,2-c]pyridazine-3-carbonitrile | 389.3 | 1.09<br>1.352 | A<br>B |
| 28' | 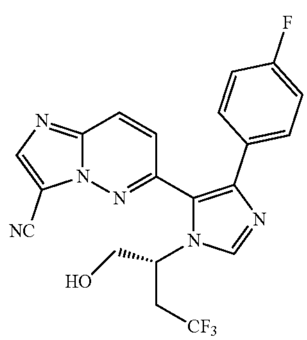 [SMILES: N#Cc1cnc2ccc(-c3c(-c4ccc(F)cc4)ncn3[C@@H](CO)CC(F)(F)F)nn12] | (R)-6-(4-(4-fluorophenyl)-1-(4,4,4-trifluoro-1-hydroxybutan-2-yl)-1H-imidazol-5-yl)imidazo[1,2-b]pyridazine-3-carbonitrile | 431.3 | 1.274<br>1.46 | A<br>B |
| 29' | 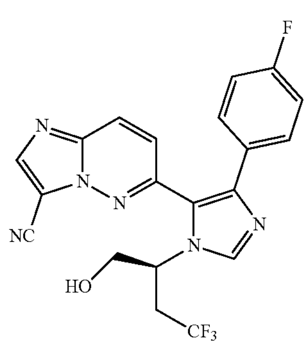 [SMILES: N#Cc1cnc2ccc(-c3c(-c4ccc(F)cc4)ncn3[C@H](CO)CC(F)(F)F)nn12] | (S)-6-(4-(4-fluorophenyl)-1-(4,4,4-trifluoro-1-hydroxybutan-2-yl)-1H-imidazol-5-yl)imidazo[1,2-b]pyridazine-3-carbonitrile | 431.3 | 1.274<br>1.46 | A<br>B |

TABLE 1-continued
| Ex. | Structure | Name | [M + H]+ | Ret Time (min.) | HPLC Method |
|---|---|---|---|---|---|
| 30' | 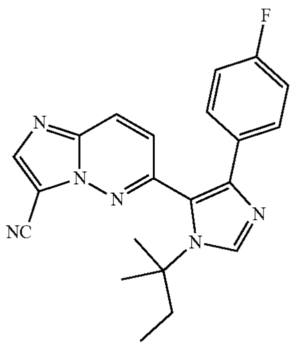 [SMILES: CCC(C)(C)n1cnc(-c2ccc(F)cc2)c1-c1ccc2ncc(C#N)n2n1] | 6-(4-(4-fluorophenyl)-1-(tert-pentyl)-1H-imidazol-5-yl)imidazo[1,2-b]pyridazine-3-carbonitrile | 375.0 | 1.30 | I |
| 31' | 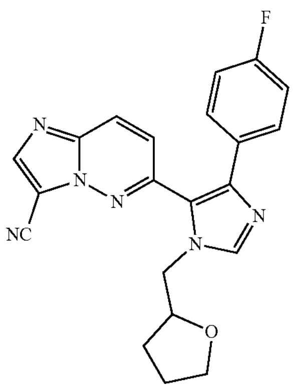 [SMILES: N#Cc1cnc2ccc(-c3c(-c4ccc(F)cc4)ncn3CC3CCCO3)nn12] | 6-(4-(4-fluorophenyl)-1-((tetrahydrofuran-2-yl)methyl)-1H-imidazol-5-yl)imidazo[1,2-b]pyridazine-3-carbonitrile | 389.0 | 1.633<br>1.265 | H<br>I |
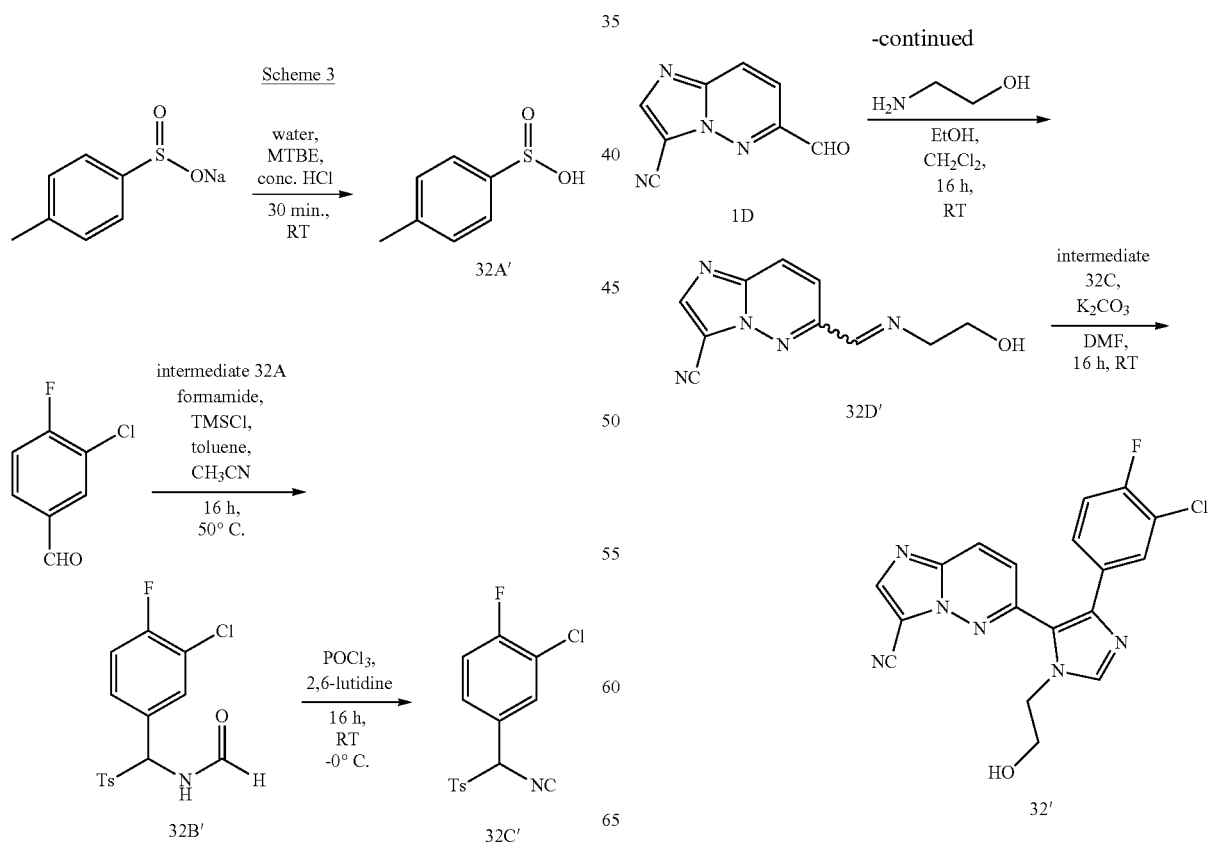

Intermediate 32A': 4-methylbenzenesulfinic acid

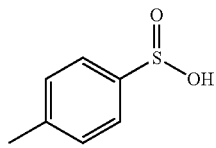

Sodium 4-methylbenzenesulfinate (25 g, 140 mmol) was dissolved in water (175 mL) and stirred for 20 min. The solution was diluted with MTBE (15 mL) and treated with conc. HCl (11.69 mL, 140 mmol). The resultant mixture was stirred for 20 min. and the two layers were separated. Toluene (~150 mL) was added to the organic layer and the organic layer was concentrated until most of the solvent was removed (water bath temperature <35° C.). Heptane (~100 mL) was then added to the residue to precipitate out a white solid. The solid was filtered off and the filter-cake was washed with some more heptane and dried under high vacuum to afford intermediate 32A' (12.9 g, 58.9% yield) as a white solid. $^1$H NMR (400 MHz, DMSO-$d_6$) δ ppm 12.38 (br. s, 1H), 7.63-7.51 (m, 2H), 7.45-7.32 (m, J=7.8 Hz, 2H), 2.38 (s, 3H).

Intermediate 32B': N-((3-chloro-4-fluorophenyl)(tosyl)methyl)formamide

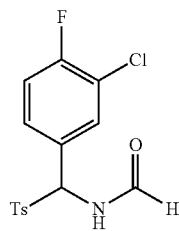 [SMILES: Cc1ccc(S(=O)(=O)C(NC=O)c2ccc(F)c(Cl)c2)cc1]

To a solution of 3-chloro-4-fluorobenzaldehyde (7.0 mL, 59.6 mmol) in toluene (27.4 mL) and acetonitrile (27.4 mL) were added formamide (5.93 mL, 149 mmol), TMS-Cl (8.38 mL, 65.6 mmol) and intermediate 32A' (12.66 g, 81 mmol). The reaction mixture was heated in an oil-bath at 50° C. for 16 h, cooled to RT and quenched by adding water (~20 mL) to generate a precipitate. To the mixture was then added MTBE (~15 mL) and the mixture was stirred for a few min. before being filtered off. The filter-cake was washed with water and then air-dried. It was purified by silica gel chromatography (220 g RediSep® column, eluting with a gradient of 5-90% EtOAc in hexanes). Fractions containing the product were combined and evaporated to afford intermediate 32B' (12.9 g, 63.3% yield) as a white solid. MS (ES): m/z=341.9 [M+H]$^+$; $^1$H NMR (400 MHz, DMSO-$d_6$) δ ppm 9.75 (d, J=10.8 Hz, 1H), 7.98 (d, J=1.0 Hz, 1H), 7.91-7.81 (m, 1H), 7.79-7.69 (m, 2H), 7.67-7.58 (m, 1H), 7.53-7.41 (m, 3H), 6.55 (d, J=10.5 Hz, 1H), 2.46-2.39 (m, 3H).

Intermediate 32C': 2-chloro-1-fluoro-4-(isocyano(tosyl)methyl)benzene

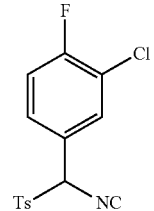

To a solution of intermediate 32B' (12.58 g, 36.8 mmol) in THF (184 mL) was added POCl$_3$ (8.58 mL, 92 mmol) at RT. The reaction mixture was stirred for 30 min, cooled to 0° C., and treated with 2,6-lutidine (27.9 mL, 239 mmol). The resultant mixture was stirred for 1 h at 0° C. and then at RT for 16 h. The reaction was poured into ice-cold aq. NaHCO$_3$ solution and extracted with EtOAc (3×125 mL). The combined organic layers were washed with 1N aq. HCl, followed by satd. aq. NaHCO$_3$, water and brine, dried over anhydrous MgSO$_4$, and filtered. The filtrate was concentrated under reduced pressure to give a solid, which was purified by silica gel chromatography (120 g RediSep® column, eluting with a gradient of 0-25% EtOAc in hexanes). Fractions containing the product were combined and evaporated to afford intermediate 32C' (8.5 g, 71.3% yield) as a pale yellow solid. MS (ES): m/z=322.2 [M–H]$^+$; HPLC Ret. Time 2.67 min. (HPLC Method D); $^1$H NMR (400 MHz, DMSO-$d_6$) δ ppm 7.71 (d, J=8.3 Hz, 3H), 7.66-7.55 (m, 3H), 7.51 (dd, J=6.9, 2.1 Hz, 1H), 7.40 (dt, J=4.3, 2.0 Hz, 1H), 2.48 (s, 3H).

Intermediate 32D': 6-(((2-hydroxyethyl)imino)methyl)imidazo[1,2-b]pyridazine-3-carbonitrile

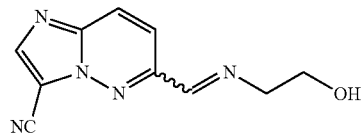 [SMILES: N#Cc1cnc2ccc(C=NCCO)nn12]

To a solution of 2-aminoethanol (0.257 mL, 4.25 mmol) in ethanol (19.3 mL) and DCM (19.3 mL) was added intermediate 1D' (0.665 g, 3.86 mmol). The reaction mixture was stirred at RT for 16 h and concentrated to dryness under reduced pressure (water-bath temp.<25° C.) to afford intermediate 32D' (0.84 g, crude). MS (ES): m/z=216.04 [M+H]$^+$; HPLC Ret. Time 1.46 min. (HPLC Method D). The intermediate was sufficiently pure to use directly in the next step without purification.

Example 32'

6-(4-(3-chloro-4-fluorophenyl)-1-(2-hydroxyethyl)-1H-imidazol-5-yl)imidazo[1,2-b]pyridazine-3-carbonitrile

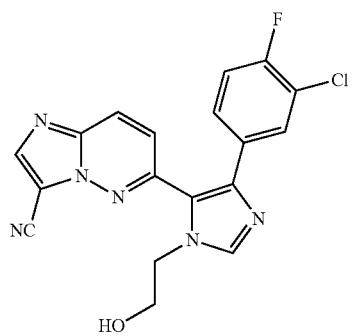

To intermediate 32D' (0.84 g, crude) was added potassium carbonate (0.694 g, 5.02 mmol) and a solution of intermediate 32C' (1.25 g, 3.86 mmol) in DMF (~10 mL). The resultant mixture was stirred at RT for 16 h. The resulting precipitate was then filtered off and filter-cake rinsed with DCM. The combined filtrates were concentrated under reduced pressure to afford a crude syrup, which was purified by silica gel chromatography (120 g RediSep® column, eluting with a gradient of 1-5% MeOH in EtOAc). Fractions containing the desired product were evaporated to afford Example 32' (1.4 g, 94% yield) as a pale yellow solid. MS (ES): m/z=383.2 [M+H]$^+$; HPLC Ret. Time 1.27 min. and 1.36 min. (HPLC Methods A and B, respectively); $^1$H NMR (400 MHz, DMSO-d$_6$) δ ppm 8.65 (s, 1H), 8.33 (d, J=9.3 Hz, 1H), 8.00 (s, 1H), 7.75 (dd, J=7.3, 2.3 Hz, 1H), 7.46-7.28 (m, 3H), 4.84 (t, J=5.4 Hz, 1H), 4.40-4.15 (m, 3H), 3.45 (dd, J=7.0, 5.3 Hz, 1H).

Compounds shown in Table 2 have been prepared in a manner similar to Example 1', if the amine is a free base or a manner similar to Example 2', if the amine is an HCl salt, using intermediates 1D' and 32C'.

TABLE 2

| Ex. | Structure | Name | [M + H]$^+$ | Ret Time (min.) | HPLC Method |
|---|---|---|---|---|---|
| 33' | 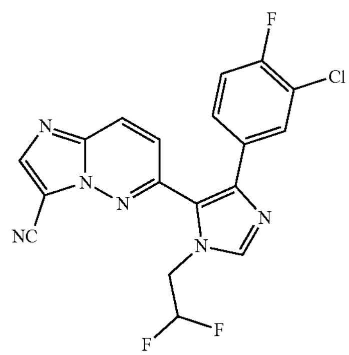 [SMILES: N#Cc1cnc2ccc(-c3c(-c4ccc(F)c(Cl)c4)ncn3CC(F)F)nn12] | 6-(4-(3-chloro-4-fluorophenyl)-1-(2,2-difluoroethyl)-1H-imidazol-5-yl)imidazo[1,2-b]pyridazine-3-carbonitrile | 403.0 | 1.544<br>1.658 | A<br>B |
| 34' | 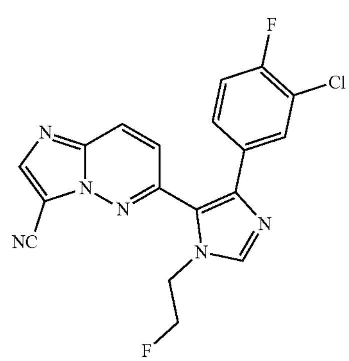 [SMILES: N#Cc1cnc2ccc(-c3c(-c4ccc(F)c(Cl)c4)ncn3CCF)nn12] | 6-(4-(3-chloro-4-fluorophenyl)-1-(2-fluoroethyl-1H-imidazol-5-yl)imidazo[1,2-b]pyridazine-3-carbonitrile | 358.0 | 1.511<br>1.603 | A<br>B |

TABLE 2-continued

| Ex. | Structure | Name | [M + H]+ | Ret Time (min.) | HPLC Method |
|---|---|---|---|---|---|
| 35' | 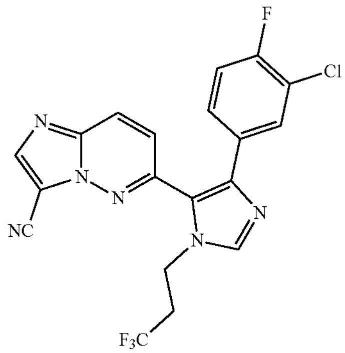 [SMILES: N#Cc1cnc2ccc(-c3c(-c4ccc(F)c(Cl)c4)ncn3CCC(F)(F)F)nn12] | 6-(4-(3-chloro-4-fluorophenyl)-1-(3,3,3-trifluoropropyl)-1H-imidazol-5-yl)imidazo[1,2-b]pyridazine-3-carbonitrile | 435.2 | 1.501<br>1.676 | A<br>B |
| 36' | 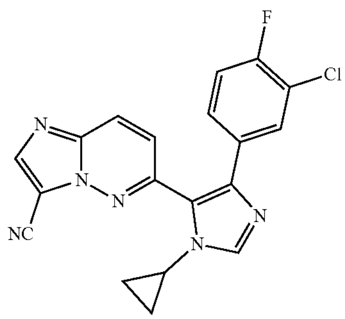 [SMILES: N#Cc1cnc2ccc(-c3c(-c4ccc(F)c(Cl)c4)ncn3C3CC3)nn12] | 6-(4-(3-chloro-4-fluorophenyl)-1-cyclopropyl-1H-imidazol-5-yl)imidazo[1,2-b]pyridazine-3-carbonitrile | 379.0 | 1.308<br>1.612 | A<br>B |
| 37' | 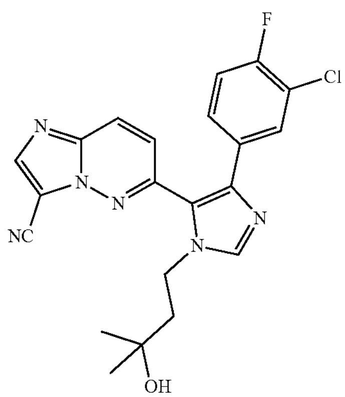 [SMILES: CC(C)(O)CCn1cnc(-c2ccc(F)c(Cl)c2)c1-c1ccc2ncc(C#N)n2n1] | 6-(4-(3-chloro-4-fluorophenyl)-1-(3-hydroxy-3-methylbutyl)-1H-imidazol-5-yl)imidazo[1,2-b]pyridazine-3-carbonitrile | 425.1 | 1.383<br>1.623 | A<br>B |
| 38' | 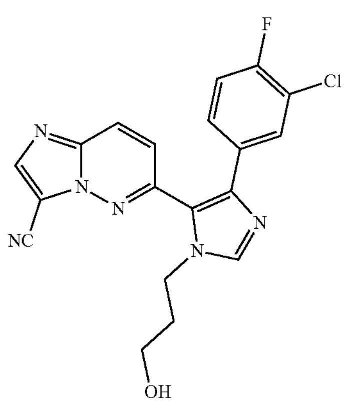 [SMILES: N#Cc1cnc2ccc(-c3c(-c4ccc(F)c(Cl)c4)ncn3CCCO)nn12] | 6-(4-(3-chloro-4-fluorophenyl)-1-(3-hydroxypropyl)-1H-imidazol-5-yl)imidazo[1,2-b]pyridazine-3-carbonitrile | 397.1 | 1.166<br>1.530 | A<br>B |

TABLE 2-continued

| Ex. | Structure | Name | [M + H]⁺ | Ret Time (min.) | HPLC Method |
|---|---|---|---|---|---|
| 39' | 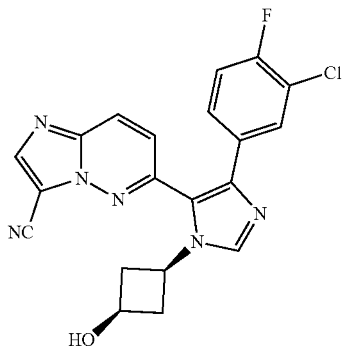 [SMILES: N#Cc1cnc2ccc(-c3c(-c4ccc(F)c(Cl)c4)ncn3[C@H]3C[C@@H](O)C3)nn12] | 6-(4-(3-chloro-4-fluorophenyl)-1-((cis)-3-hydroxycyclobutyl)-1H-imidazol-5-yl)imidazo[1,2-b]pyridazine-3-carbonitrile | 427.0 | 1.031<br>1.252 | A<br>B |
| 40' | 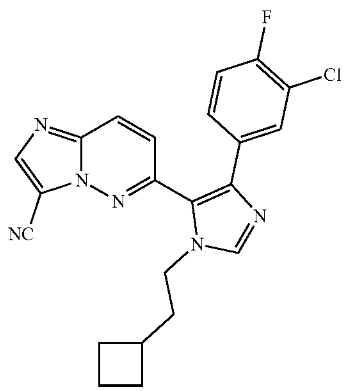 [SMILES: N#Cc1cnc2ccc(-c3c(-c4ccc(F)c(Cl)c4)ncn3CCC3CCC3)nn12] | 6-(4-(3-chloro-4-fluorophenyl)-1-(2-cyclobutylethyl)-1H-imidazol-5-yl)imidazo[1,2-b]pyridazine-3-carbonitrile | 421.3 | 1.612<br>1.916 | A<br>B |
| 41' | 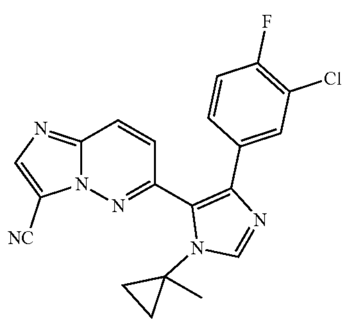 [SMILES: CC1(n2cnc(-c3ccc(F)c(Cl)c3)c2-c2ccc3ncc(C#N)n3n2)CC1] | 6-(4-(3-chloro-4-fluorophenyl)-1-(1-methylcyclopropyl)-1H-imidazol-5-yl)imidazo[1,2-b]pyridazine-3-carbonitrile | 393 | 1.453<br>1.776 | A<br>B |
| 42' | 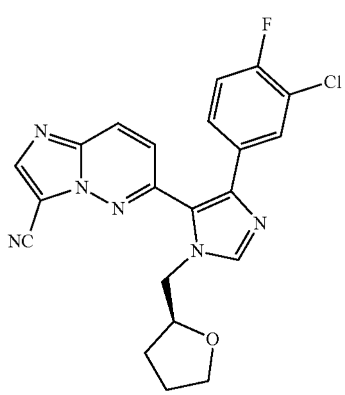 [SMILES: N#Cc1cnc2ccc(-c3c(-c4ccc(F)c(Cl)c4)ncn3C[C@@H]3CCCO3)nn12] | (S)-6-(4-(3-chloro-4-fluorophenyl)-1-((tetrahydrofuran-2-yl)methyl)-1H-imidazol-5-yl)imidazo[1,2-b]pyridazine-3-carbonitrile | 423.1 | 1.41<br>1.687 | A<br>B |

TABLE 2-continued

| Ex. | Structure | Name | [M + H]+ | Ret Time (min.) | HPLC Method |
|---|---|---|---|---|---|
| 43' | 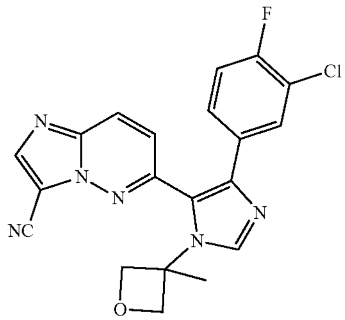 [SMILES: CC1(n2cnc(-c3ccc(F)c(Cl)c3)c2-c2ccc3ncc(C#N)n3n2)COC1] | 6-(4-(3-chloro-4-fluorophenyl)-1-(3-methyloxetan-3-yl)-1H-imidazol-5-yl)imidazo[1,2-b]pyridazine-3-carbonitrile | 409.0 | 1.389<br>1.448 | A<br>B |
| 44' | 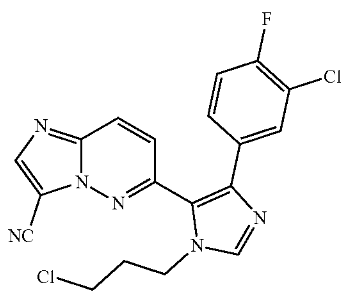 [SMILES: N#Cc1cnc2ccc(-c3c(-c4ccc(F)c(Cl)c4)ncn3CCCCl)nn12] | 6-(4-(3-chloro-4-fluorophenyl)-1-(3-chloropropyl)-1H-imidazol-5-yl)imidazo[1,2-b]pyridazine-3-carbonitrile | 415.0 | 1.48<br>1.787 | A<br>B |
| 45' | 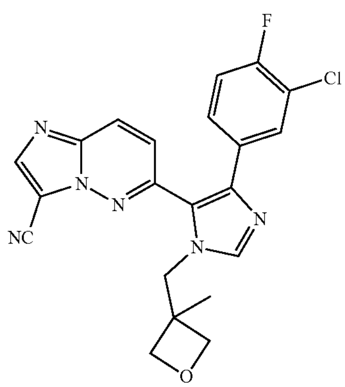 [SMILES: CC1(Cn2cnc(-c3ccc(F)c(Cl)c3)c2-c2ccc3ncc(C#N)n3n2)COC1] | 6-(4-(3-chloro-4-fluorophenyl)-1-((3-methyloxetan-3-yl)methyl)-1H-imidazol-5-yl)imidazo[1,2-b]pyridazine-3-carbonitrile | 423.1 | 1.379<br>1.568 | A<br>B |
| 46' | 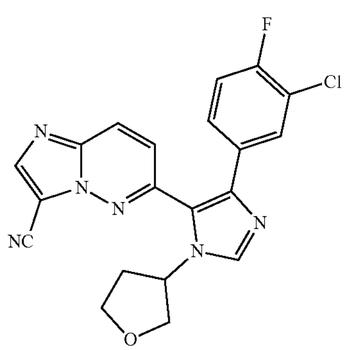 [SMILES: N#Cc1cnc2ccc(-c3c(-c4ccc(F)c(Cl)c4)ncn3C3CCOC3)nn12] | 6-(4-(3-chloro-4-fluorophenyl)-1-(tetrahydrofuran-3-yl)-1H-imidazol-5-yl)imidazo[1,2-b]pyridazine-3-carbonitrile | 409.0 | 1.307<br>1.449 | A<br>B |

TABLE 2-continued

| Ex. | Structure | Name | [M + H]+ | Ret Time (min.) | HPLC Method |
|---|---|---|---|---|---|
| 47' | 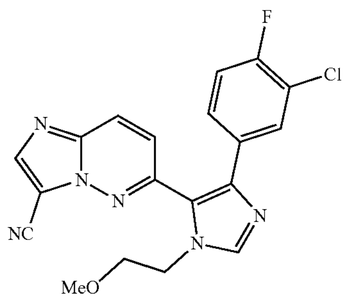 [SMILES: COCCn1cnc(-c2ccc(F)c(Cl)c2)c1-c1ccc2ncc(C#N)n2n1] | 6-(4-(3-chloro-4-fluorophenyl)-1-(2-methoxyethyl)-1H-imidazol-5-yl)imidazo[1,2-b]pyridazine-3-carbonitrile | 397.0 | 1.344<br>1.620 | A<br>B |
| 48' | 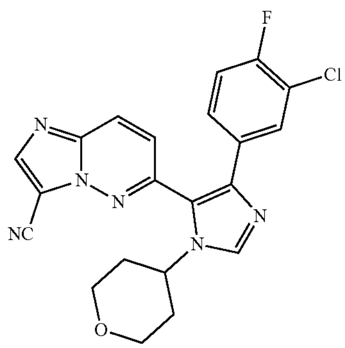 [SMILES: N#Cc1cnc2ccc(-c3c(-c4ccc(F)c(Cl)c4)ncn3C3CCOCC3)nn12] | 6-(4-(3-chloro-4-fluorophenyl)-1-(tetrahydro-2H-pyran-4-yl)-1H-imidazol-5-yl)imidazo[1,2-b]pyridazine-3-carbonitrile | 423.0 | 1.62<br>2.194 | A<br>B |
| 49' | 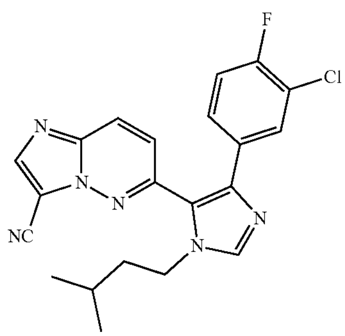 [SMILES: CC(C)CCn1cnc(-c2ccc(F)c(Cl)c2)c1-c1ccc2ncc(C#N)n2n1] | 6-(4-(3-chloro-4-fluorophenyl)-1-isopentyl-1H-imidazol-5-yl)imidazo[1,2-b]pyridazine-3-carbonitrile | 409.1 | 1.603<br>1.994 | A<br>B |
| 50' | 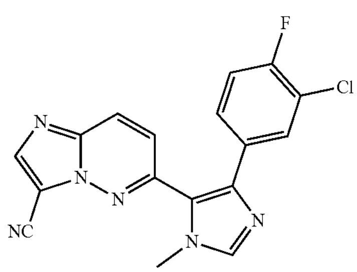 [SMILES: Cn1cnc(-c2ccc(F)c(Cl)c2)c1-c1ccc2ncc(C#N)n2n1] | 6-(4-(3-chloro-4-fluorophenyl)-1-methyl-1H-imidazol-5-yl)imidazo[1,2-b]pyridazine-3-carbonitrile | 353.1 | 1.55<br>1.49 | A<br>B |
| 51' | 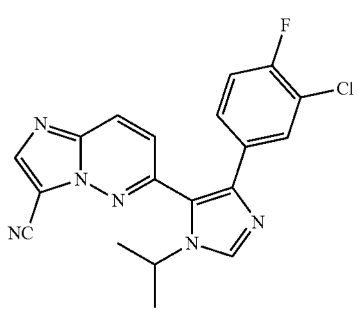 [SMILES: CC(C)n1cnc(-c2ccc(F)c(Cl)c2)c1-c1ccc2ncc(C#N)n2n1] | 6-(4-(3-chloro-4-fluorophenyl)-1-isopropyl-1H-imidazol-5-yl)imidazo[1,2-b]pyridazine-3-carbonitrile | 391.3 | 1.36<br>1.74 | A<br>B |

TABLE 2-continued

| Ex. | Structure | Name | [M + H]+ | Ret Time (min.) | HPLC Method |
|---|---|---|---|---|---|
| 52' | 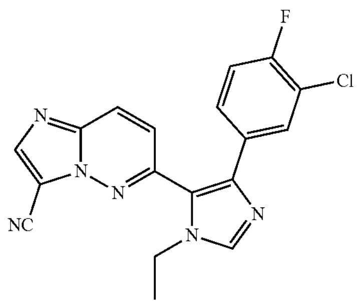 [SMILES: CCn1cnc(-c2ccc(F)c(Cl)c2)c1-c1ccc2ncc(C#N)n2n1] | 6-(4-(3-chloro-4-fluorophenyl)-1-ethyl-1H-imidazol-5-yl)imidazo[1,2-b]pyridazine-3-carbonitrile | 367.2 | 1.15<br>1.51 | A<br>B |
| 53' | 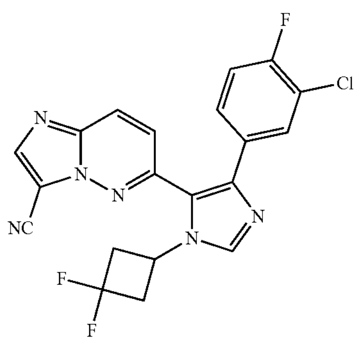 [SMILES: N#Cc1cnc2ccc(-c3c(-c4ccc(F)c(Cl)c4)ncn3C3CC(F)(F)C3)nn12] | 6-(4-(3-chloro-4-fluorophenyl)-1-(3,3-difluorocyclobutyl)-1H-imidazol-5-yl)imidazo[1,2-b]pyridazine-3-carbonitrile | 429.05 | 1.68<br>1.75 | A<br>B |
| 54' | 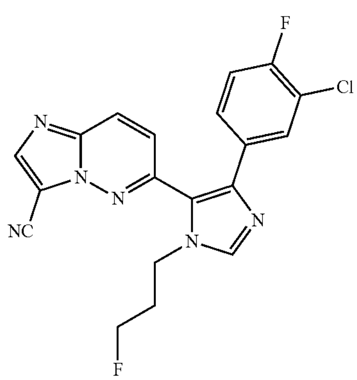 [SMILES: N#Cc1cnc2ccc(-c3c(-c4ccc(F)c(Cl)c4)ncn3CCCF)nn12] | 6-(4-(3-chloro-4-fluorophenyl)-1-(3-fluoropropyl)-1H-imidazol-5-yl)imidazo[1,2-b]pyridazine-3-carbonitrile | 399.2 | 1.50<br>1.63 | A<br>B |
| 55' | 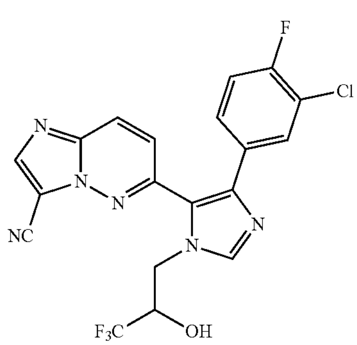 [SMILES: N#Cc1cnc2ccc(-c3c(-c4ccc(F)c(Cl)c4)ncn3CC(O)C(F)(F)F)nn12] | 6-(4-(3-chloro-4-fluorophenyl)-1-(3,3,3-trifluoro-2-hydroxypropyl)-1H-imidazol-5-yl)imidazo[1,2-b]pyridazine-3-carbonitrile | 451.2 | 1.47<br>1.64 | A<br>B |

TABLE 2-continued

| Ex. | Structure | Name | [M + H]+ | Ret Time (min.) | HPLC Method |
|---|---|---|---|---|---|
| 56' | 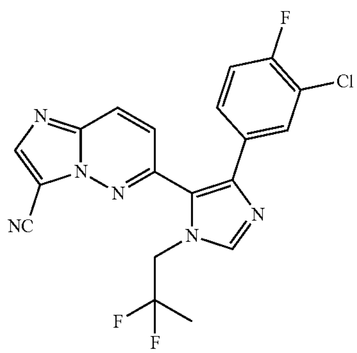 [SMILES: CC(F)(F)Cn1cnc(-c2ccc(F)c(Cl)c2)c1-c1ccc2ncc(C#N)n2n1] | 6-(4-(3-chloro-4-fluorophenyl)-1-(2,2-difluoropropyl)-1H-imidazol-5-yl)imidazo[1,2-b]pyridazine-3-carbonitrile | 417.2 | 1.62<br>1.77 | A<br>B |
| 57' | 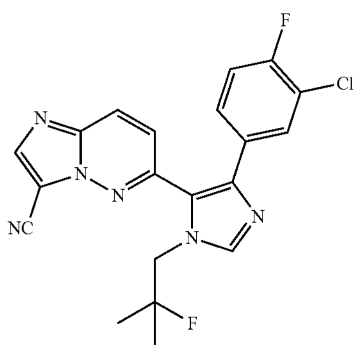 [SMILES: CC(C)(F)Cn1cnc(-c2ccc(F)c(Cl)c2)c1-c1ccc2ncc(C#N)n2n1] | 6-(4-(3-chloro-4-fluorophenyl)-1-(2-fluoro-2-methylpropyl)-1H-imidazol-5-yl)imidazo[1,2-b]pyridazine-3-carbonitrile | 413.3 | 1.56<br>1.81 | A<br>B |
| 58' | 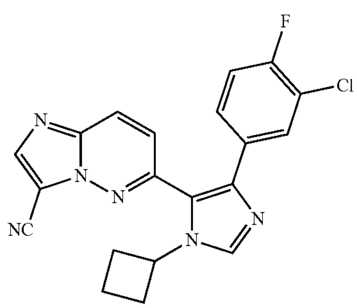 [SMILES: N#Cc1cnc2ccc(-c3c(-c4ccc(F)c(Cl)c4)ncn3C3CCC3)nn12] | 6-(4-(3-chloro-4-fluorophenyl)-1-cyclobutyl-1H-imidazol-5-yl)imidazo[1,2-b]pyridazine-3-carbonitrile | 393.3 | 1.38<br>1.66 | A<br>B |
| 59' | 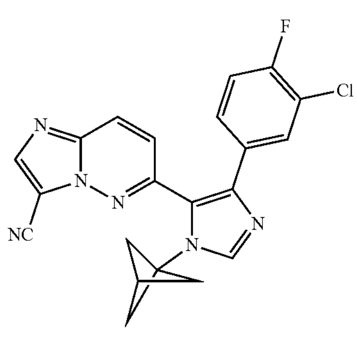 [SMILES: N#Cc1cnc2ccc(-c3c(-c4ccc(F)c(Cl)c4)ncn3C34CC(C3)C4)nn12] | 6-(1-(bicyclo[1.1.1]pentan-1-yl)-4-(3-chloro-4-fluorophenyl)-1H-imidazol-5-yl)imidazo[1,2-b]pyridazine-3-carbonitrile | 405.2 | 1.55<br>1.85 | A<br>B |

TABLE 2-continued

| Ex. | Structure | Name | [M + H]+ | Ret Time (min.) | HPLC Method |
|---|---|---|---|---|---|
| 60' | 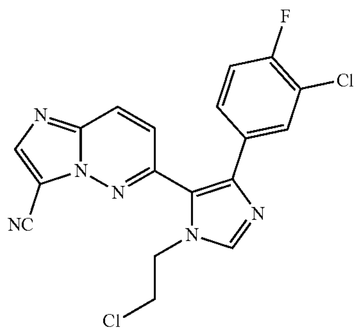 [SMILES: N#Cc1cnc2ccc(-c3c(-c4ccc(F)c(Cl)c4)ncn3CCCl)nn12] | 6-(4-(3-chloro-4-fluorophenyl)-1-(2-chloroethyl)-1H-imidazol-5-yl)imidazo[1,2-b]pyridazine-3-carbonitrile | 401.1 | 1.49<br>1.73 | A<br>B |
| 61' | 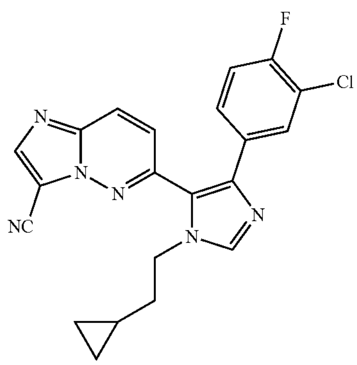 [SMILES: N#Cc1cnc2ccc(-c3c(-c4ccc(F)c(Cl)c4)ncn3CCC3CC3)nn12] | 6-(4-(3-chloro-4-fluorophenyl)-1-(2-cyclopropylethyl)-1H-imidazol-5-yl)imidazo[1,2-b]pyridazine-3-carbonitrile | 407.3 | 1.53<br>1.89 | A<br>B |
| 62' | 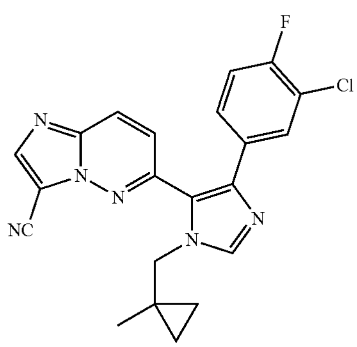 [SMILES: CC1(Cn2cnc(-c3ccc(F)c(Cl)c3)c2-c2ccc3ncc(C#N)n3n2)CC1] | 6-(4-(3-chloro-4-fluorophenyl)-1-((1-methylcyclopropyl)methyl)-1H-imidazol-5-yl)imidazo[1,2-b]pyridazine-3-carbonitrile | 407.3 | 1.40<br>1.75 | A<br>B |
| 63' | 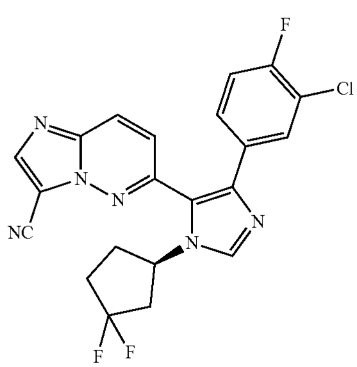 [SMILES: N#Cc1cnc2ccc(-c3c(-c4ccc(F)c(Cl)c4)ncn3[C@@H]3CCC(F)(F)C3)nn12] | (R)-6-(4-(3-chloro-4-fluorophenyl)-1-(3,3-difluorocyclopentyl)-1H-imidazol-5-yl)imidazo[1,2-b]pyridazine-3-carbonitrile | 443.0 | 1.580<br>1.848 | A<br>B |

TABLE 2-continued
| Ex. | Structure | Name | [M + H]+ | Ret Time (min.) | HPLC Method |
|---|---|---|---|---|---|
| 64' | 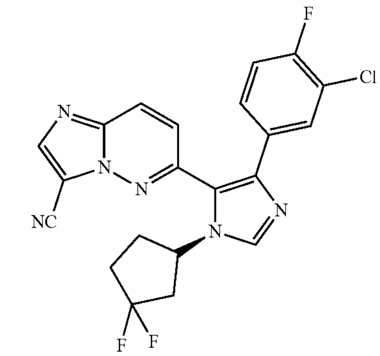 | (S)-6-(4-(3-chloro-4-fluorophenyl)-1-(3,3-difluorocyclopentyl)-1H-imidazol-5-yl)imidazo[1,2-b]pyridazine-3-carbonitrile | 443.0 | 1.576<br>1.847 | A<br>B |
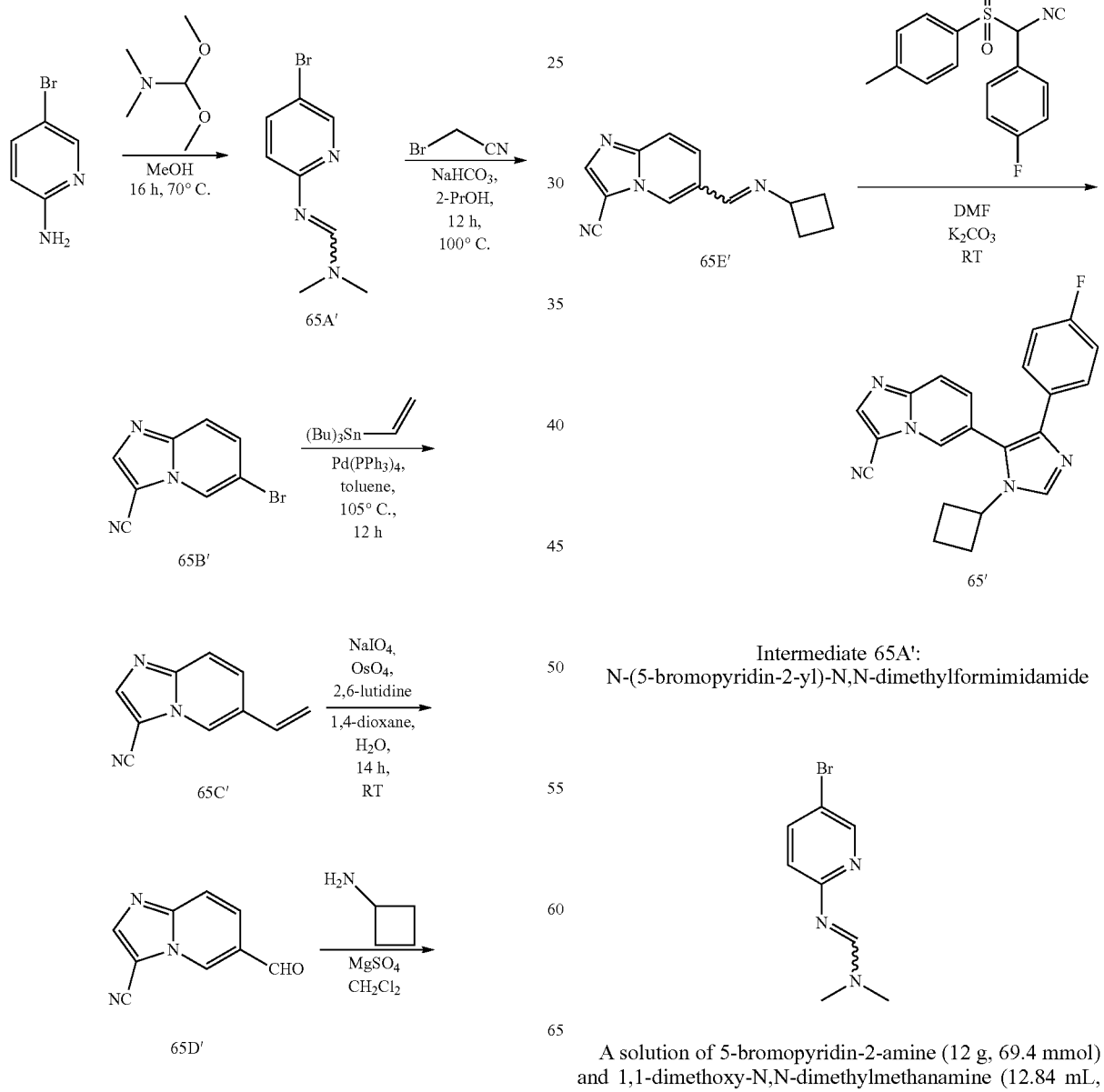
Intermediate 65A':
N-(5-bromopyridin-2-yl)-N,N-dimethylformimidamide
A solution of 5-bromopyridin-2-amine (12 g, 69.4 mmol) and 1,1-dimethoxy-N,N-dimethylmethanamine (12.84 mL, 90 mmol) in MeOH (72.2 mL) was heated in an oil-bath at 70° C. for 16 h. The reaction mixture was concentrated under reduced pressure to near dryness to give an oil. The oil was dissolved in hexanes the solution evaporated to dryness to afford intermediate 65A' (15.66 g, >99% yield) as a solid. MS (ES): m/z=228/230.0 [M+H]$^+$. The solid was used directly in cyclization step without further purification.

Intermediate 65B': 6-bromoimidazo[1,2-a]pyridine-3-carbonitrile

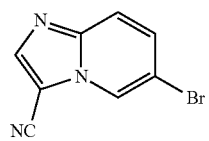 [SMILES: N#Cc1cnc2ccc(Br)cn12]

To a suspension of intermediate 65A' (12.0 g, 52.6 mmol) and sodium bicarbonate (13.26 g, 158 mmol) in 2-propanol (133 mL) was added 2-bromoacetonitrile (9.46 mL, 132 mmol). The reaction mixture was heated in an oil-bath at 100° C. for 12 h. The reaction was then poured into water (~250 mL) and the mixture was stirred at RT for 1 h. The solid was filtered off and the filter-cake was washed with water until the filtrate was light yellow in color. The solid was dried under high vacuum to afford intermediate 65B' (8.0 g, 68.5% yield) as a dark solid. MS (ES): m/z=222/224.0 [M+H]$^+$.

Intermediate 65C': 6-vinylimidazo[1,2-a]pyridine-3-carbonitrile

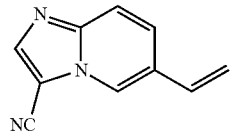

Intermediate 65C' was synthesized analogous to intermediate 1C' by coupling intermediate 65B' and tributyl(vinyl)stannane. The crude product was purified by silica gel chromatography (120 g RediSep® column, eluting with a gradient of 10-60% EtOAc in hexanes). Fractions containing the desired product were combined and evaporated to afford intermediate 65C' (1.625 g, 82% yield). MS (ES): m/z=170.1 [M+H]$^+$; $^1$H NMR (400 MHz, DMSO-d$_6$) δ ppm 8.74 (s, 1H), 8.44 (s, 1H), 7.93 (dd, J=9.4, 1.6 Hz, 1H), 7.84 (d, J=9.5 Hz, 1H), 6.92 (dd, J=17.8, 11.0 Hz, 1H), 6.05 (d, J=17.6 Hz, 1H), 5.45 (d, J=11.0 Hz, 1H).

Intermediate 65D': 6-formylimidazo[1,2-a]pyridine-3-carbonitrile

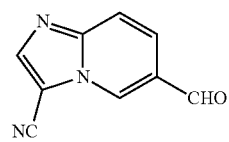

Intermediate 65D' was synthesized analogous to intermediate 1D' by treating intermediate 65C' with OsO$_4$/NaIO$_4$. The crude product was purified by silica gel chromatography (40 g RediSep® column, eluting with a gradient of 40-60% EtOAc in hexanes). Fractions containing the desired product were combined and evaporated to afford intermediate 65D' (0.24 g, 95% yield). MS (ES): m/z=172.1 [M+H]$^+$; $^1$H NMR (400 MHz, DMSO-d$_6$) δ ppm 10.14 (d, J=0.8 Hz, 1H), 9.52 (dd, J=1.6, 0.9 Hz, 1H), 8.63 (s, 1H), 8.01-7.92 (m, 1H), 7.91-7.82 (m, 1H).

Example 65'

6-(1-cyclobutyl-4-(4-fluorophenyl)-1H-imidazol-5-yl)imidazo[1,2-a]pyridine-3-carbonitrile

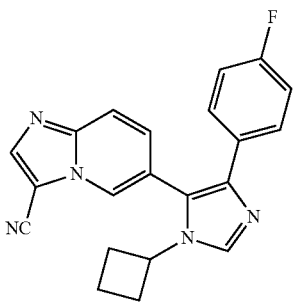

Example 65' was synthesized analogous to Example 1' (Scheme 1) by treating intermediate 65D' with cyclobutanamine to first form the imine intermediate 65E', followed by reacting intermediate 65E' with 1-fluoro-4-(isocyano(tosyl)methyl)benzene. The crude product was purified via preparative HPLC. Fractions containing the product were combined and evaporated to afford Example 65' (56.2 mg, 63.15% yield). MS (ES): m/z=358.1 [M+H]$^+$; HPLC Ret. Time 1.099 min. and 1.666 min. (HPLC Methods A and B, respectively); $^1$H NMR (500 MHz, DMSO-d$_6$) δ ppm 9.18 (s, 1H), 8.88 (s, 1H), 8.57 (s, 1H), 7.98 (d, J=9.5 Hz, 1H), 7.57-7.41 (m, 3H), 7.31-7.12 (m, 2H), 4.69 (t, J=8.3 Hz, 1H), 2.46 (d, J=9.9 Hz, 2H), 2.26-2.12 (m, 2H), 1.82-1.65 (m, 2H). C Compounds shown in Table 3 have been prepared in a manner similar to Example 1', if the amine is a free base, or in a manner similar to Example 2', if the amine is an HCl salt, using aldehyde intermediate 65D' and 1-fluoro-4-(isocyano(tosyl)methyl)benzene.

TABLE 3

| Ex. | Structure | Name | [M + H]+ | Ret Time (min.) | HPLC Method |
|---|---|---|---|---|---|
| 66' | 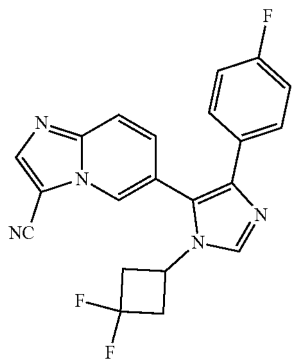 [SMILES: N#Cc1cnc2ccc(-c3c(-c4ccc(F)cc4)ncn3C3CC(F)(F)C3)cn12] | 6-(1-(3,3-difluorocyclobutyl)-4-(4-fluorophenyl)-1H-imidazol-5-yl)imidazo[1,2-a]pyridine-3-carbonitrile | 394.0 | 1.186<br>1.464 | A<br>B |
| 67' | 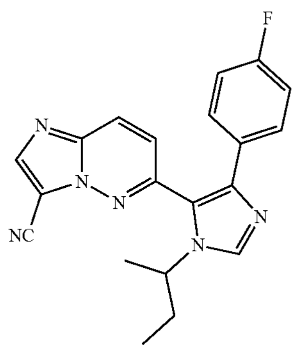 [SMILES: CCC(C)n1cnc(-c2ccc(F)cc2)c1-c1ccc2ncc(C#N)n2n1] | 6-(1-(sec-butyl)-4-(4-fluorophenyl)-1H-imidazol-5-yl)imidazo[1,2-a]pyridine-3-carbonitrile | 360.1 | 1.128<br>1.664 | A<br>B |
| 68' | 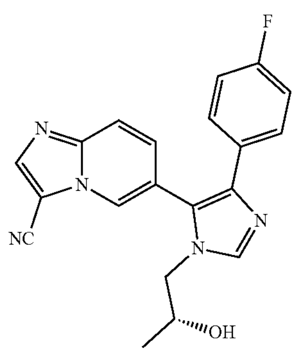 [SMILES: C[C@@H](O)Cn1cnc(-c2ccc(F)cc2)c1-c1ccc2ncc(C#N)n2c1] | (R)-6-(4-(4-fluorophenyl)-1-(2-hydroxypropyl)-1H-imidazol-5-yl)imidazo[1,2-a]pyridine-3-carbonitrile | 362.0 | 1.086<br>1.225 | A<br>B |
| 69' | 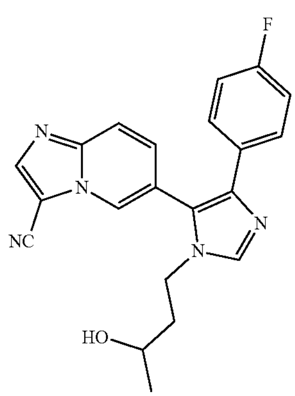 [SMILES: CC(O)CCn1cnc(-c2ccc(F)cc2)c1-c1ccc2ncc(C#N)n2c1] | 6-(4-(4-fluorophenyl)-1-(3-hydroxybutyl)-1H-imidazol-5-yl)imidazo[1,2-a]pyridine-3-carbonitrile | 376.1 | 1.065<br>1.247 | A<br>B |

TABLE 3-continued

| Ex. | Structure | Name | [M + H]+ | Ret Time (min.) | HPLC Method |
|---|---|---|---|---|---|
| 70' | 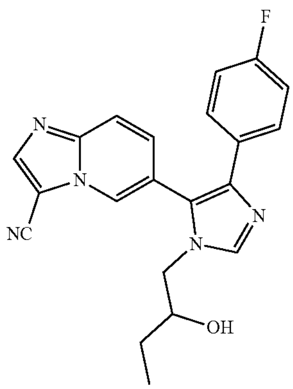 [SMILES: CCC(O)Cn1cnc(-c2ccc(F)cc2)c1-c1ccc2ncc(C#N)n2c1] | 6-(4-(4-fluorophenyl)-1-(2-hydroxybutyl)-1H-imidazol-5-yl)imidazo[1,2-a]pyridine-3-carbonitrile | 376.0 | 1.137<br>1.288 | A<br>B |
| 71' | 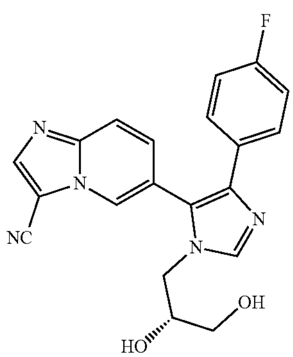 [SMILES: N#Cc1cnc2ccc(-c3c(-c4ccc(F)cc4)ncn3C[C@@H](O)CO)cn12] | (R)-6-(1-(2,3-dihydroxypropyl)-4-(4-fluorophenyl)-1H-imidazol-5-yl)imidazo[1,2-a]pyridine-3-carbonitrile | 378.1 | 0.962<br>1.175 | A<br>B |
| 72' | 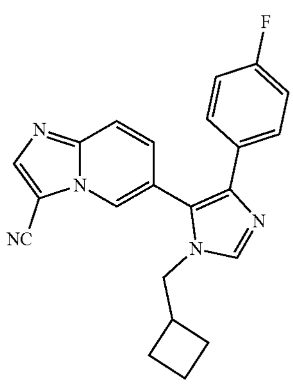 [SMILES: N#Cc1cnc2ccc(-c3c(-c4ccc(F)cc4)ncn3CC3CCC3)cn12] | 6-(1-(cyclobutylmethyl)-4-(4-fluorophenyl)-1H-imidazol-5-yl)imidazo[1,2-a]pyridine-3-carbonitrile | 372.1 | 1.198<br>1.680 | A<br>B |
| 73' | 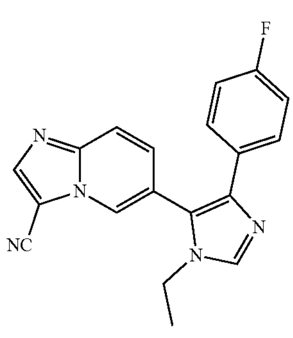 [SMILES: CCn1cnc(-c2ccc(F)cc2)c1-c1ccc2ncc(C#N)n2c1] | 6-(1-ethyl-4-(4-fluorophenyl)-1H-imidazol-5-yl)imidazo[1,2-a]pyridine-3-carbonitrile | 332.1 | 1.019<br>1.487 | A<br>B |

TABLE 3-continued

| Ex. | Structure | Name | [M + H]+ | Ret Time (min.) | HPLC Method |
|---|---|---|---|---|---|
| 74' | 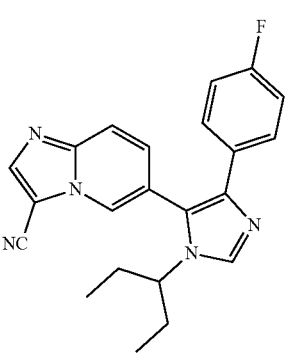 | 6-(4-(4-fluorophenyl)-1-(pentan-3-yl)-1H-imidazol-5-yl)imidazo[1,2-a]pyridine-3-carbonitrile | 374.1 | 1.210<br>1.711 | A<br>B |
| 75' | 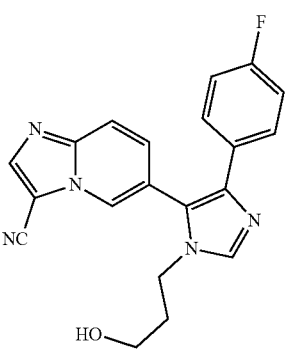 [SMILES: N#Cc1cnc2ccc(-c3c(-c4ccc(F)cc4)ncn3CCCO)cn12] | 6-(4-(4-fluorophenyl)-1-(3-hydroxypropyl)-1H-imidazol-5-yl)imidazo[1,2-a]pyridine-3-carbonitrile | 362.1 | 0.963<br>1.33 | A<br>B |
| 76' | 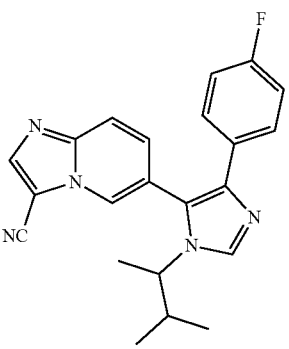 [SMILES: CC(C)C(C)n1cnc(-c2ccc(F)cc2)c1-c1ccc2ncc(C#N)n2c1] | 6-(4-(4-fluorophenyl)-1-(3-methylbutan-2-yl)-1H-imidazol-5-yl)imidazo[1,2-a]pyridine-3-carbonitrile | 374.1 | 1.364<br>1.72 | A<br>B |
| 77' | 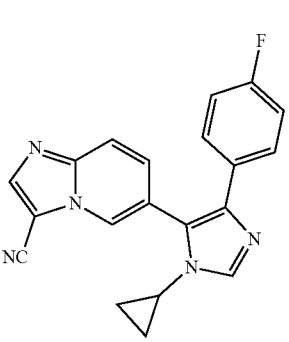 [SMILES: N#Cc1cnc2ccc(-c3c(-c4ccc(F)cc4)ncn3C3CC3)cn12] | 6-(1-cyclopropyl-4-(4-fluorophenyl)-1H-imidazol-5-yl)imidazo[1,2-a]pyridine-3-carbonitrile | 344.1 | 1.043<br>1.556 | A<br>B |

TABLE 3-continued

| Ex. | Structure | Name | [M + H]+ | Ret Time (min.) | HPLC Method |
|---|---|---|---|---|---|
| 78' | 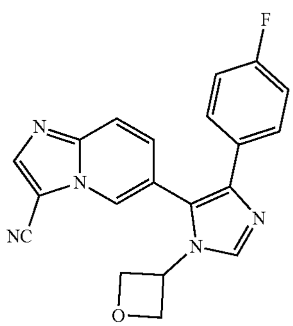 [SMILES: N#Cc1cnc2ccc(-c3c(-c4ccc(F)cc4)ncn3C3COC3)cn12] | 6-(4-(4-fluorophenyl)-1-(oxetan-3-yl)-1H-imidazol-5-yl)imidazo[1,2-a]pyridine-3-carbonitrile | 360.1 | 1.004<br>1.323 | A<br>B |
| 79' | 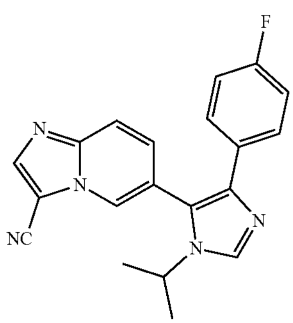 [SMILES: CC(C)n1cnc(-c2ccc(F)cc2)c1-c1ccc2ncc(C#N)n2c1] | 6-(4-(4-fluorophenyl)-1-isopropyl-1H-imidazol-5-yl)imidazo[1,2-a]pyridine-3-carbonitrile | 346.2 | 1.078<br>1.578 | A<br>B |
| 80' | 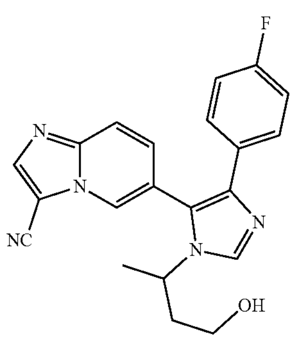 [SMILES: CC(CCO)n1cnc(-c2ccc(F)cc2)c1-c1ccc2ncc(C#N)n2c1] | 6-(4-(4-fluorophenyl)-1-(4-hydroxybutan-2-yl)-1H-imidazol-5-yl)imidazo[1,2-a]pyridine-3-carbonitrile | 376.1 | 0.96<br>1.303 | A<br>B |
| 81' | 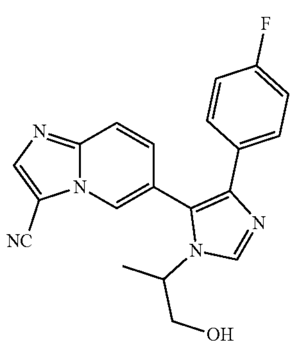 [SMILES: CC(CO)n1cnc(-c2ccc(F)cc2)c1-c1ccc2ncc(C#N)n2c1] | 6-(4-(4-fluorophenyl)-1-(1-hydroxypropan-2-yl)-1H-imidazol-5-yl)imidazo[1,2-a]pyridine-3-carbonitrile | 362.1 | 0.879<br>1.355 | A<br>B |

TABLE 3-continued

| Ex. | Structure | Name | [M + H]+ | Ret Time (min.) | HPLC Method |
|---|---|---|---|---|---|
| 82' | 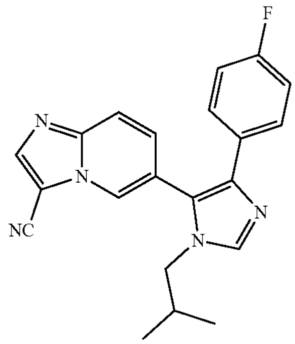 [SMILES: CC(C)Cn1cnc(-c2ccc(F)cc2)c1-c1ccc2ncc(C#N)n2c1] | 6-(4-(4-fluorophenyl)-1-isobutyl-1H-imidazol-5-yl)imidazo[1,2-a]pyridine-3-carbonitrile | 360.1 | 1.152<br>1.683 | A<br>B |
| 83' | 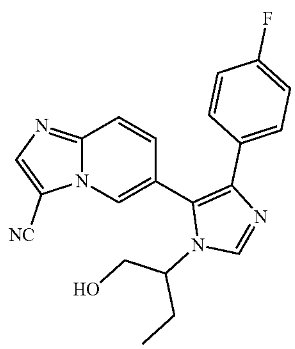 [SMILES: CCC(CO)n1cnc(-c2ccc(F)cc2)c1-c1ccc2ncc(C#N)n2c1] | 6-(4-(4-fluorophenyl)-1-(1-hydroxybutan-2-yl)-1H-imidazol-5-yl)imidazo[1,2-a]pyridine-3-carbonitrile | 376.0 | 1.119<br>1.293 | A<br>B |
| 84' | 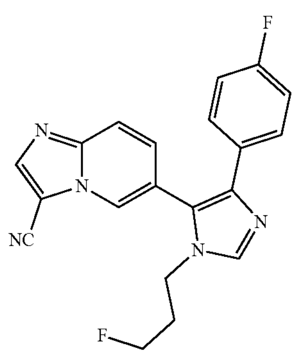 [SMILES: N#Cc1cnc2ccc(-c3c(-c4ccc(F)cc4)ncn3CCCF)cn12] | 6-(4-(4-fluorophenyl)-1-(3-fluoropropyl)-1H-imidazol-5-yl)imidazo[1,2-a]pyridine-3-carbonitrile | 364.2 | 1.129<br>1.357 | A<br>B |
| 85' | 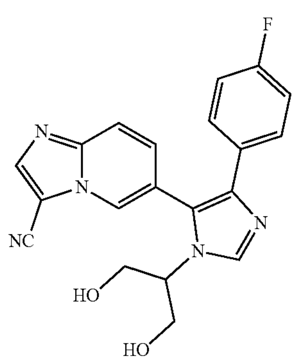 [SMILES: N#Cc1cnc2ccc(-c3c(-c4ccc(F)cc4)ncn3C(CO)CO)cn12] | 6-(1-(1,3-dihydroxypropan-2-yl)-4-(4-fluorophenyl)-1H-imidazol-5-yl)imidazo[1,2-a]pyridine-3-carbonitrile | 378.1 | 1.031<br>1.095 | A<br>B |

TABLE 3-continued

| Ex. | Structure | Name | [M + H]+ | Ret Time (min.) | HPLC Method |
|---|---|---|---|---|---|
| 86' | 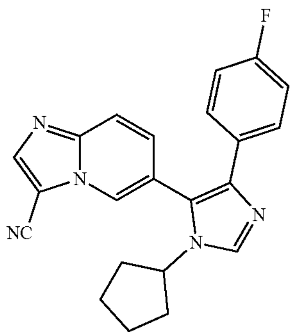 [SMILES: N#Cc1cnc2ccc(-c3c(-c4ccc(F)cc4)ncn3C3CCCC3)cn12] | 6-(1-cyclopentyl-4-(4-fluorophenyl)-1H-imidazol-5-yl)imidazo[1,2-a]pyridine-3-carbonitrile | 372.1 | 1.156<br>1.748 | A<br>B |
| 87' | 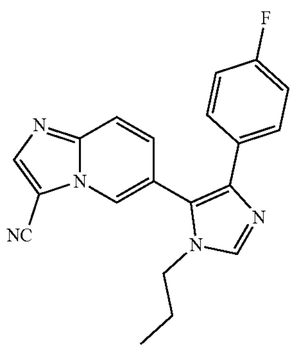 [SMILES: CCCn1cnc(-c2ccc(F)cc2)c1-c1ccc2ncc(C#N)n2c1] | 6-(4-(4-fluorophenyl)-1-propyl-1H-imidazol-5-yl)imidazo[1,2-a]pyridine-3-carbonitrile | 346.1 | 1.086<br>1.586 | A<br>B |
| 88' | 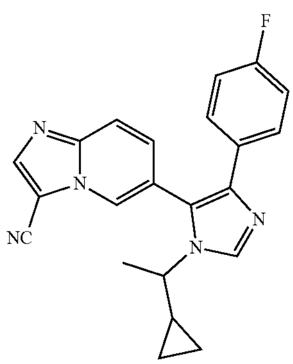 [SMILES: CC(C1CC1)n1cnc(-c2ccc(F)cc2)c1-c1ccc2ncc(C#N)n2c1] | 6-(1-(1-cyclopropylethyl)-4-(4-fluorophenyl)-1H-imidazol-5-yl)imidazo[1,2-a]pyridine-3-carbonitrile | 372.1 | 1.164<br>1.695 | A<br>B |
| 89' | 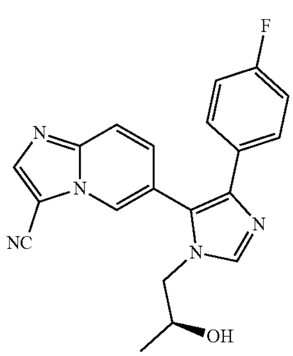 [SMILES: C[C@H](O)Cn1cnc(-c2ccc(F)cc2)c1-c1ccc2ncc(C#N)n2c1] | (S)-6-(4-(4-fluorophenyl)-1-(2-hydroxypropyl)-1H-imidazol-5-yl)imidazo[1,2-a]pyridine-3-carbonitrile | 362.0 | 1.095<br>1.224 | A<br>B |

TABLE 3-continued

| Ex. | Structure | Name | [M + H]+ | Ret Time (min.) | HPLC Method |
|---|---|---|---|---|---|
| 90' | 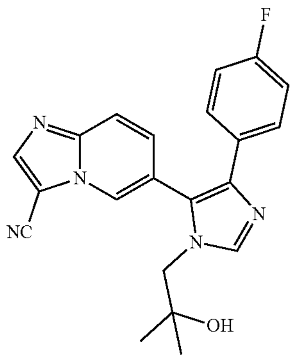 [SMILES: CC(C)(O)Cn1cnc(-c2ccc(F)cc2)c1-c1ccc2ncc(C#N)n2c1] | 6-(4-(4-fluorophenyl)-1-(2-hydroxy-2-methylpropyl)-1H-imidazol-5-yl)imidazo[1,2-a]pyridine-3-carbonitrile | 376.1 | 1.245<br>1.304 | A<br>B |
| 91' | 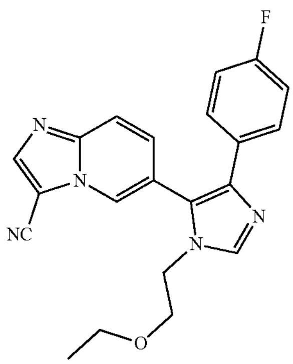 [SMILES: CCOCCn1cnc(-c2ccc(F)cc2)c1-c1ccc2ncc(C#N)n2c1] | 6-(1-(2-ethoxyethyl)-4-(4-fluorophenyl)-1H-imidazol-5-yl)imidazo[1,2-a]pyridine-3-carbonitrile | 376.0 | 1.209<br>1.432 | A<br>B |
| 92' | 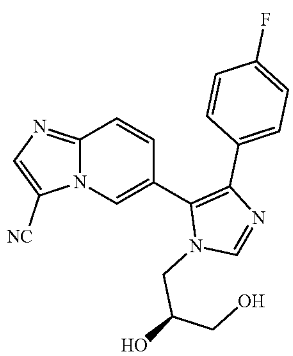 [SMILES: N#Cc1cnc2ccc(-c3c(-c4ccc(F)cc4)ncn3C[C@H](O)CO)cn12] | (S)-6-(1-(2,3-dihydroxypropyl)-4-(4-fluorophenyl)-1H-imidazol-5-yl)imidazo[1,2-a]pyridine-3-carbonitrile | 378.1 | 0.955<br>1.247 | A<br>B |
| 93' | 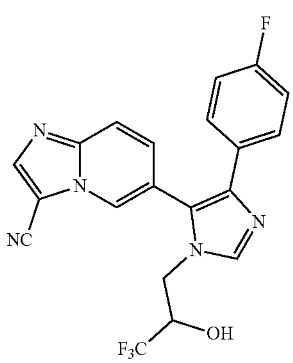 [SMILES: N#Cc1cnc2ccc(-c3c(-c4ccc(F)cc4)ncn3CC(O)C(F)(F)F)cn12] | 6-(4-(4-fluorophenyl)-1-(3,3,3-trifluoro-2-hydroxypropyl)-1H-imidazol-5-yl)imidazo[1,2-a]pyridine-3-carbonitrile | 416.0 | 1.157<br>1.369 | A<br>B |

Compounds shown in Table 4 have been prepared in a manner similar to Example 1', if the amine is a free base, or in a manner similar to Example 2', if the amine is an HCl salt, using intermediates aldehyde 65D' and 32C'.

TABLE 4

| Ex. | Structure | Name | [M + H]⁺ | Ret Time (min.) | HPLC Method |
|---|---|---|---|---|---|
| 94' | 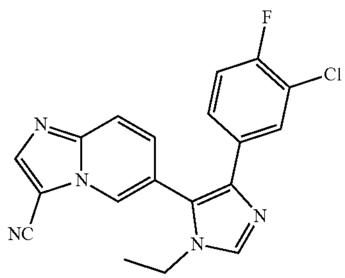 [SMILES: CCn1cnc(-c2ccc(F)c(Cl)c2)c1-c1ccc2ncc(C#N)n2c1] | 6-(4-(3-chloro-4-fluorophenyl)-1-ethyl-1H-imidazol-5-yl)imidazo[1,2-a]pyridine-3-carbonitrile | 366.0 | 1.211<br>1.561 | A<br>B |
| 95' | 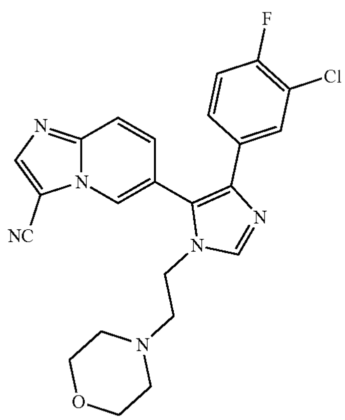 [SMILES: N#Cc1cnc2ccc(-c3c(-c4ccc(F)c(Cl)c4)ncn3CCN3CCOCC3)cn12] | 6-(4-(3-chloro-4-fluorophenyl)-1-(2-morpholinoethyl)-1H-imidazol-5-yl)imidazo[1,2-a]pyridine-3-carbonitrile | 451.3 | 1.139<br>1.501 | A<br>B |
| 96' | 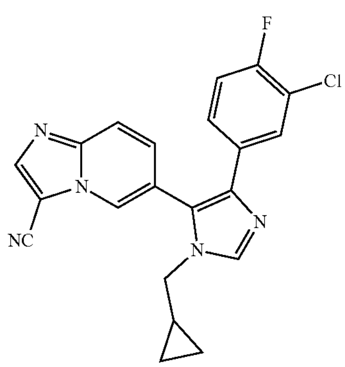 [SMILES: N#Cc1cnc2ccc(-c3c(-c4ccc(F)c(Cl)c4)ncn3CC3CC3)cn12] | 6-(4-(3-chloro-4-fluorophenyl)-1-(cyclopropylmethyl)-1H-imidazol-5-yl)imidazo[1,2-a]pyridine-3-carbonitrile | 392.0 | 1.277<br>1.686 | A<br>B |
| 97' | 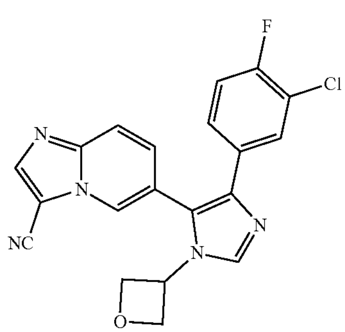 [SMILES: N#Cc1cnc2ccc(-c3c(-c4ccc(F)c(Cl)c4)ncn3C3COC3)cn12] | 6-(4-(3-chloro-4-fluorophenyl)-1-(oxetan-3-yl)-1H-imidazol-5-yl)imidazo[1,2-a]pyridine-3-carbonitrile | 394.0 | 1.167<br>1.467 | A<br>B |

TABLE 4-continued

| Ex. | Structure | Name | [M + H]+ | Ret Time (min.) | HPLC Method |
|---|---|---|---|---|---|
| 98' | 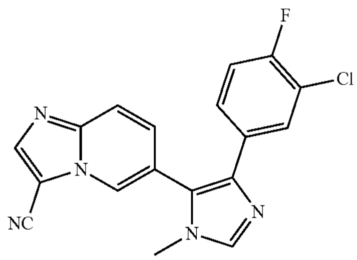 [SMILES: Cn1cnc(-c2ccc(F)c(Cl)c2)c1-c1ccc2ncc(C#N)n2c1] | 6-(4-(3-chloro-4-fluorophenyl)-1-methyl-1H-imidazol-5-yl)imidazo[1,2-a]pyridine-3-carbonitrile | 352.08 | 1.232<br>1.567 | A<br>B |
| 99' | 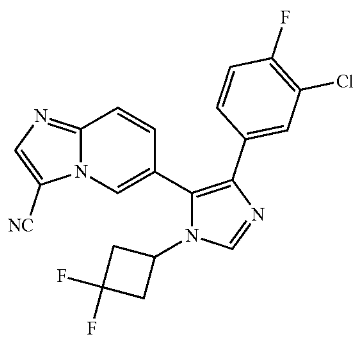 [SMILES: N#Cc1cnc2ccc(-c3c(-c4ccc(F)c(Cl)c4)ncn3C3CC(F)(F)C3)cn12] | 6-(4-(3-chloro-4-fluorophenyl)-1-(3,3-difluorocyclobutyl)-1H-imidazol-5-yl)imidazo[1,2-a]pyridine-3-carbonitrile | 428.12 | 1.400<br>1.803 | A<br>B |
| 100' | 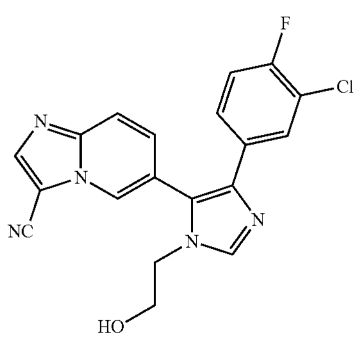 [SMILES: N#Cc1cnc2ccc(-c3c(-c4ccc(F)c(Cl)c4)ncn3CCO)cn12] | 6-(4-(3-chloro-4-fluorophenyl)-1-(2-hydroxyethyl)-1H-imidazol-5-yl)imidazo[1,2-a]pyridine-3-carbonitrile | 382.2 | 1.131<br>1.342 | A<br>B |
| 101' | 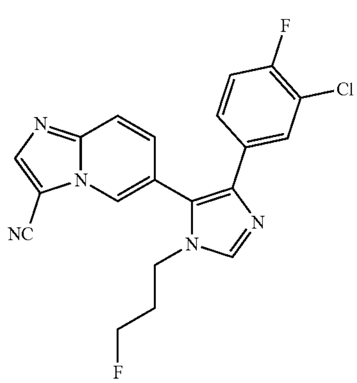 [SMILES: N#Cc1cnc2ccc(-c3c(-c4ccc(F)c(Cl)c4)ncn3CCCF)cn12] | 6-(4-(3-chloro-4-fluorophenyl)-1-(3-fluoropropyl)-1H-imidazol-5-yl)imidazo[1,2-a]pyridine-3-carbonitrile | 398.2 | 1.279<br>1.532 | A<br>B |

Scheme 5

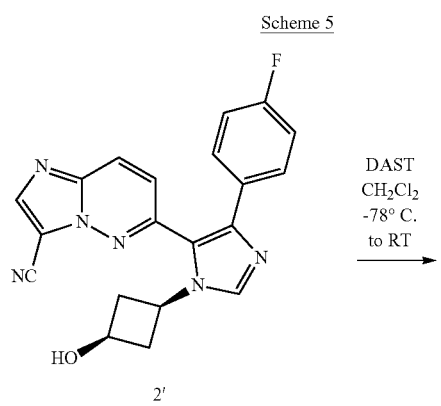

Example 102'

6-(1-(3-fluorocyclobutyl)-4-(4-fluorophenyl)-1H-imidazol-5-yl)imidazo[1,2-b]pyridazine-3-carbonitrile

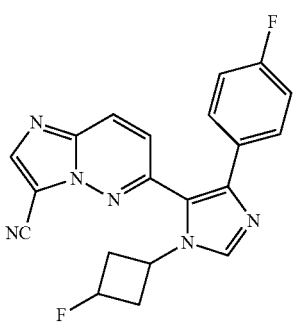 [SMILES: N#Cc1cnc2ccc(-c3c(-c4ccc(F)cc4)ncn3C3CC(F)C3)nn12]

To a solution of Example 2' (144 mg, 0.385 mmol) in DCM (10 mL) at −78° C. under nitrogen was added DAST (0.203 mL, 1.539 mmol). The reaction mixture was gradually warmed up to RT overnight and quenched slowly with sat'd aq. NaHCO$_3$ solution. The mixture was extracted with DCM. The combined organic layers were washed with brine, dried over Na$_2$SO$_4$, and filtered. The filtrate was concentrated and the crude product was dissolved in a mixture of DMF and methanol and purified via preparative HPLC. Fractions containing the desired product were combined and dried under vacuum to afford Example 102' (31.5 mg, 21% yield). MS (ES): m/z=377.1 [M+H]$^+$; HPLC Ret. Time 1.186 min. and 1.524 min. (HPLC Methods A and B, respectively); $^1$H NMR (500 MHz, DMSO-d$_6$) δ ppm 8.64 (s, 1H), 8.40-8.22 (m, 2H), 7.53 (dd, J=8.8, 5.5 Hz, 2H), 7.26 (d, J=9.2 Hz, 1H), 7.16 (t, J=8.8 Hz, 2H), 5.52-5.29 (m, 1H), 5.16 (t, J=7.7 Hz, 1H), 3.03-2.84 (m, 2H), 2.84-2.68 (m, 2H).

Compounds shown in Table 5 have been prepared in a manner similar to Example 102' using DAST. Example 103' was synthesized from Example 6' and Example 104' was synthesized from Example 39'.

TABLE 5

| Ex. | Structure | Name | [M + H]$^+$ | Ret Time (min.) | HPLC Method |
|---|---|---|---|---|---|
| 103' | 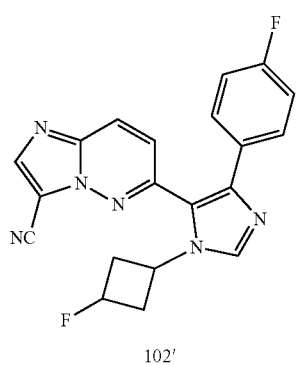 | (S)-6-(1-(1-fluorobutan-2-yl)-4-(4-fluorophenyl)-1H-imidazol-5-yl)imidazo[1,2-b]pyridazine-3-carbonitrile | 379.1 | 1.236<br>1.676 | A<br>B |

TABLE 5-continued

| Ex. | Structure | Name | [M + H]+ | Ret Time (min.) | HPLC Method |
|---|---|---|---|---|---|
| 104' | 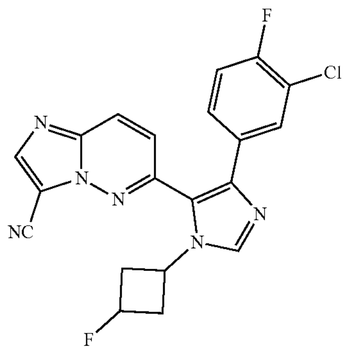 [SMILES: N#Cc1cnc2ccc(-c3c(-c4ccc(F)c(Cl)c4)ncn3C3CC(F)C3)nn12] | 6-(4-(3-chloro-4-fluorophenyl)-1-(3-fluorocyclobutyl)-1H-imidazol-5-yl)imidazo[1,2-b]pyridazine-3-carbonitrile | 411.0 | 1.392<br>1.715 | A<br>B |

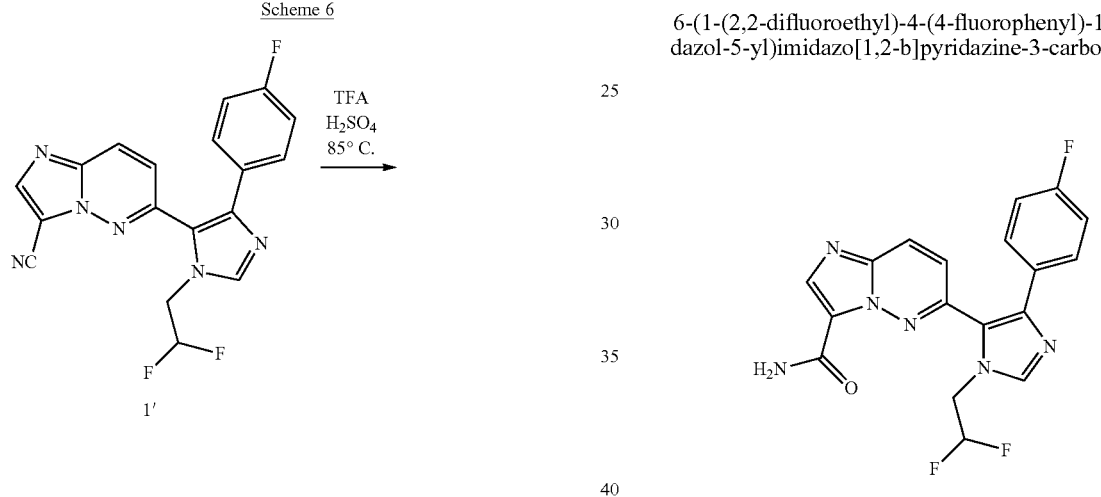

Scheme 6

Example 105'

6-(1-(2,2-difluoroethyl)-4-(4-fluorophenyl)-1H-imidazol-5-yl)imidazo[1,2-b]pyridazine-3-carboxamide To a vial were added TFA (0.063 mL, 0.815 mmol) and conc. sulfuric acid (0.014 mL, 0.272 mmol). The resulting mixture was allowed to stir for 5 min. prior to the addition of a solution of Example 1' (25 mg, 0.068 mmol) in TFA (0.5 mL). The reaction mixture was heated at 85° C. for 2 h. The reaction mixture was cooled to RT and concentrated. The residue was neutralized with sat'd aq. NaHCO$_3$ solution and diluted with DCM. The layers were separated and the aqueous layer was extracted with DCM. The combined organic layer was washed with brine, dried over Na$_2$SO$_4$, filtered, and the filtrate was concentrated. The crude product was dissolved in a mixture of DMF and methanol and purified by preparative HPLC. Fractions containing the desired product were combined and evaporated to Example 105' (9 mg, 34% yield). MS (ES): m/z=387.0 [M+H]+; HPLC Ret. Time 1.679 min. and 1.763 min. (HPLC Methods, A and B, respectively); $^1$H NMR (400 MHz, CDCl$_3$) δ ppm 8.58 (s, 1H), 8.06 (d, J=9.5 Hz, 1H), 7.84 (s, 1H), 7.56-7.42 (m, 2H), 7.18-6.89 (m, 3H), 6.07 (t, J=3.0 Hz, 1H), 5.93 (t, J=3.0 Hz, 1H), 4.61 (dd, J=14.8, 3.0 Hz, 2H).

Compounds shown in Table 6 have been prepared in a manner similar to Example 105' by heating the corresponding cyano compounds with TFA and sulfuric acid.

TABLE 6

| Ex. | Structure | Name | [M + H]+ | Ret Time (min.) | HPLC Method |
|---|---|---|---|---|---|
| 106' | 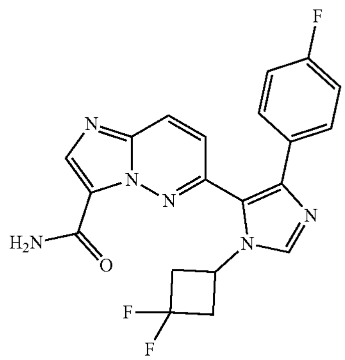 [SMILES: NC(=O)c1cnc2ccc(-c3c(-c4ccc(F)cc4)ncn3C3CC(F)(F)C3)nn12] | 6-(1-(3,3-difluorocyclobutyl)-4-(4-fluorophenyl)-1H-imidazol-5-yl)imidazo[1,2-b]pyridazine-3-carboxamide | 412.9 | 1.019<br>1.280 | A<br>B |
| 107' | 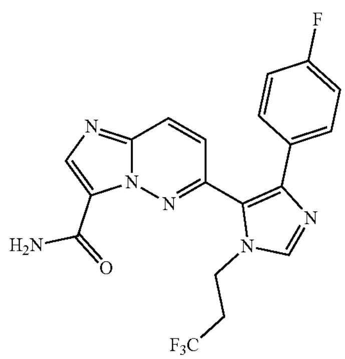 [SMILES: NC(=O)c1cnc2ccc(-c3c(-c4ccc(F)cc4)ncn3CCC(F)(F)F)nn12] | 6-(4-(4-fluorophenyl)-1-(3,3,3-trifluoropropyl)-1H-imidazol-5-yl)imidazo[1,2-b]pyridazine-3-carboxamide | 419.0 | 1.087<br>1.298 | A<br>B |
| 108' | 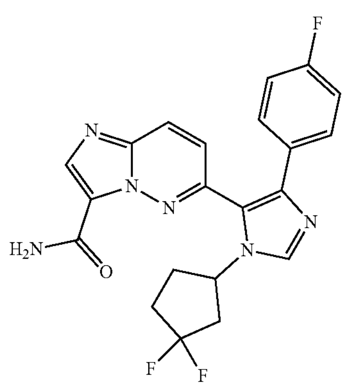 [SMILES: NC(=O)c1cnc2ccc(-c3c(-c4ccc(F)cc4)ncn3C3CCC(F)(F)C3)nn12] | 6-(1-(3,3-difluorocyclopentyl)-4-(4-fluorophenyl)-1H-imidazol-5-yl)imidazo[1,2-b]pyridazine-3-carboxamide | 427.0 | 1.036<br>1.335 | A<br>B |
| 109' | 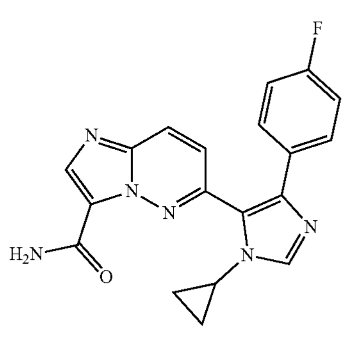 [SMILES: NC(=O)c1cnc2ccc(-c3c(-c4ccc(F)cc4)ncn3C3CC3)nn12] | 6-(1-cyclopropyl-4-(4-fluorophenyl)-1H-imidazol-5-yl)imidazo[1,2-b]pyridazine-3-carboxamide | 363.0 | 0.954<br>1.270 | A<br>B |

TABLE 6-continued

| Ex. | Structure | Name | [M + H]⁺ | Ret Time (min.) | HPLC Method |
|---|---|---|---|---|---|
| 110' | 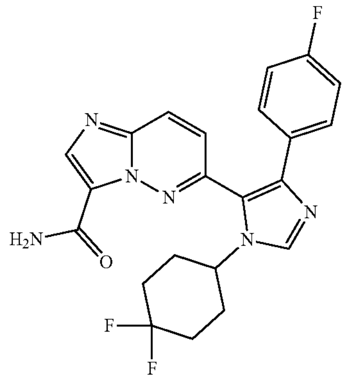 [SMILES: NC(=O)c1cnc2ccc(-c3c(-c4ccc(F)cc4)ncn3C3CCC(F)(F)CC3)nn12] | 6-(1-(4,4-difluorocyclohexyl)-4-(4-fluorophenyl)-1H-imidazol-5-yl)imidazo[1,2-b]pyridazine-3-carboxamide | 441.1 | 1.087<br>1.487 | A<br>B |
| 111' | 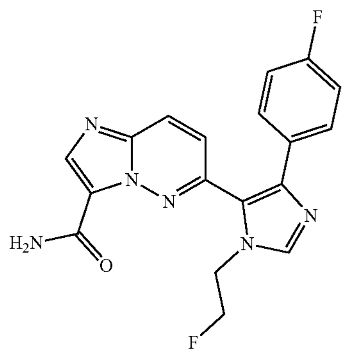 [SMILES: NC(=O)c1cnc2ccc(-c3c(-c4ccc(F)cc4)ncn3CCF)nn12] | 6-(1-(2-fluoroethyl)-4-(4-fluorophenyl)-1H-imidazol-5-yl)imidazo[1,2-b]pyridazine-3-carboxamide | 369.0 | 1.047<br>1.118 | A<br>B |
| 112' | 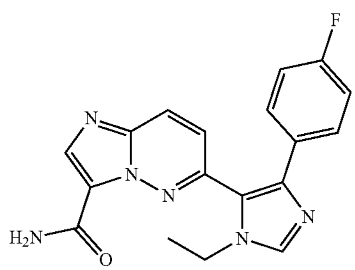 [SMILES: CCn1cnc(-c2ccc(F)cc2)c1-c1ccc2ncc(C(N)=O)n2n1] | 6-(1-ethyl-4-(4-fluorophenyl)-1H-imidazol-5-yl)imidazo[1,2-b]pyridazine-3-carboxamide | 351.1 | 0.85<br>1.191 | A<br>B |

Compounds shown in Table 7 have been prepared in a manner similar to Example 105' by heating the corresponding cyano compounds with TFA and sulfuric acid.

TABLE 7

| Ex. | Structure | Name | [M + H]⁺ | Ret Time (min.) | HPLC Method |
|---|---|---|---|---|---|
| 113' | 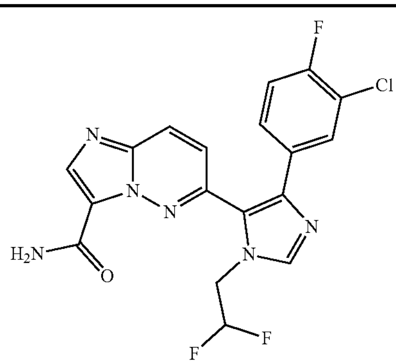 | 6-(4-(3-chloro-4-fluorophenyl)-1-(2,2-difluoroethyl)-1H-imidazol-5-yl)imidazo[1,2-b]pyridazine-3-carboxamide | 421.0 | 1.207<br>1.346 | A<br>B |

TABLE 7-continued

| Ex. | Structure | Name | [M + H]+ | Ret Time (min.) | HPLC Method |
|---|---|---|---|---|---|
| 114' | 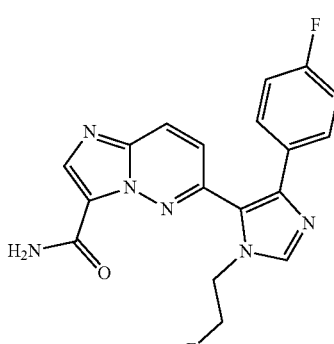 | 6-(4-(3-chloro-4-fluorophenyl)-1-(2-fluoroethyl)-1H-imidazol-5-yl)imidazo[1,2-b]pyridazine-3-carboxamide | 403.1 | 1.092<br>1.308 | A<br>B |
| 115' | 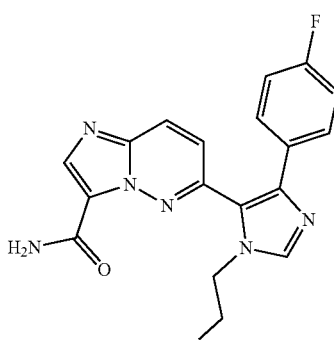 | 6-(4-(3-chloro-4-fluorophenyl)-1-(3,3,3-trifluoropropyl)-1H-imidazol-5-yl)imidazo[1,2-b]pyridazine-3-carboxamide | 452.9 | 1.308<br>1.612 | A<br>B |
| 116' | 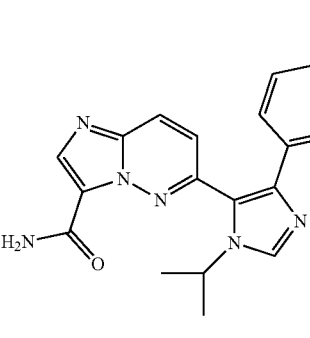 | 6-(4-(3-chloro-4-fluorophenyl)-1-isopropyl-1H-imidazol-5-yl)imidazo[1,2-b]pyridazine-3-carboxamide | 399.1 | 1.156<br>1.484 | A<br>B |
| 117' | 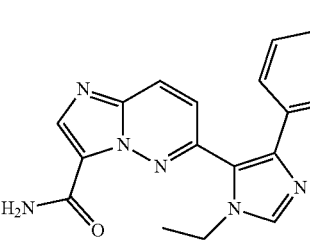 | 6-(4-(3-chloro-4-fluorophenyl)-1-ethyl-1H-imidazol-5-yl)imidazo[1,2-b]pyridazine-3-carboxamide | 385.0 | 1.098<br>1.271 | A<br>B |

TABLE 7-continued

| Ex. | Structure | Name | [M + H]+ | Ret Time (min.) | HPLC Method |
|---|---|---|---|---|---|
| 118' | 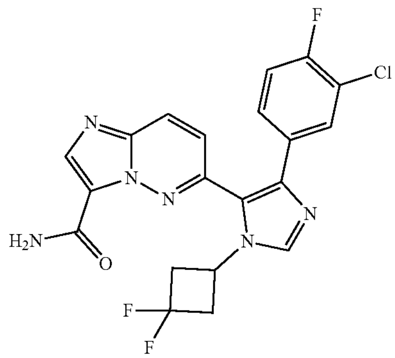 [SMILES: NC(=O)c1cnc2ccc(-c3c(-c4ccc(F)c(Cl)c4)ncn3C3CC(F)(F)C3)nn12] | 6-(4-(3-chloro-4-fluorophenyl)-1-(3,3-difluorocyclobutyl)-1H-imidazol-5-yl)imidazo[1,2-b]pyridazine-3-carboxamide | 447.0 | 1.296<br>1.531 | A<br>B |

Compounds shown in Table 8 have been prepared in a manner similar to Example 105' by heating the corresponding cyano compounds with TFA and sulfuric acid.

TABLE 8

| Ex. | Structure | Name | [M + H]+ | Ret Time (min.) | HPLC Method |
|---|---|---|---|---|---|
| 119' | 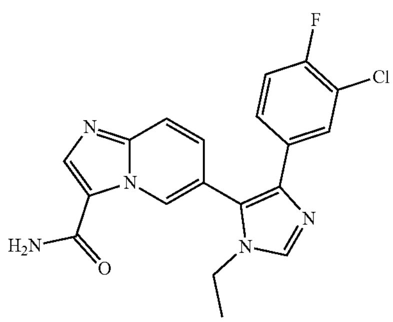 [SMILES: CCn1cnc(-c2ccc(F)c(Cl)c2)c1-c1ccc2ncc(C(N)=O)n2c1] | 6-(4-(3-chloro-4-fluorophenyl)-1-ethyl-1H-imidazol-5-yl)imidazo[1,2-a]pyridine-3-carboxamide | 384.0 | 1.091<br>1.396 | A<br>B |
| 120' | 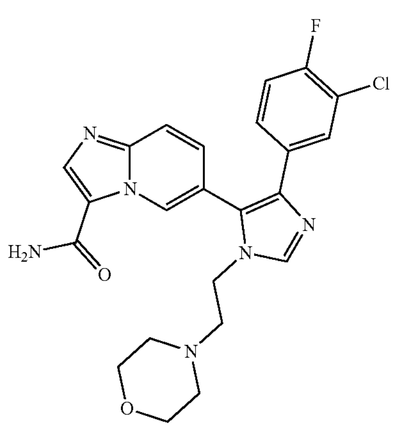 [SMILES: NC(=O)c1cnc2ccc(-c3c(-c4ccc(F)c(Cl)c4)ncn3CCN3CCOCC3)cn12] | 6-(4-(3-chloro-4-fluorophenyl)-1-(2-morpholinoethyl)-1H-imidazol-5-yl)imidazo[1,2-a]pyridine-3-carboxamide | 469.0 | 1.111<br>1.359 | A<br>B |

TABLE 8-continued

| Ex. | Structure | Name | [M + H]⁺ | Ret Time (min.) | HPLC Method |
|---|---|---|---|---|---|
| 121' | 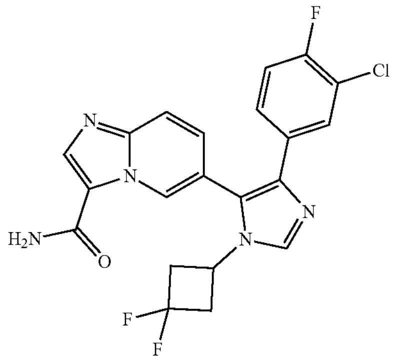 [SMILES: NC(=O)c1cnc2ccc(-c3c(-c4ccc(F)c(Cl)c4)ncn3C3CC(F)(F)C3)cn12] | 6-(4-(3-chloro-4-fluorophenyl)-1-(3,3-difluorocyclobutyl)-1H-imidazol-5-yl)imidazo[1,2-a]pyridine-3-carboxamide | 446.1 | 1.139<br>1.570 | A<br>B |
| 122' | 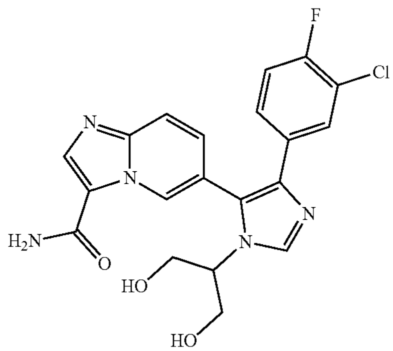 [SMILES: NC(=O)c1cnc2ccc(-c3c(-c4ccc(F)c(Cl)c4)ncn3C(CO)CO)cn12] | 6-(4-(3-chloro-4-fluorophenyl)-1-(1,3-dihydroxypropan-2-yl)-1H-imidazol-5-yl)imidazo[1,2-a]pyridine-3-carboxamide | 430.1 | 0.996<br>1.236 | A<br>B |

Example 123'

6-(4-(4-fluorophenyl)-1-cis-3-hydroxycyclobutyl)-1H-imidazol-5-yl)imidazo[1,2-b]pyridazine-3-carboxamide

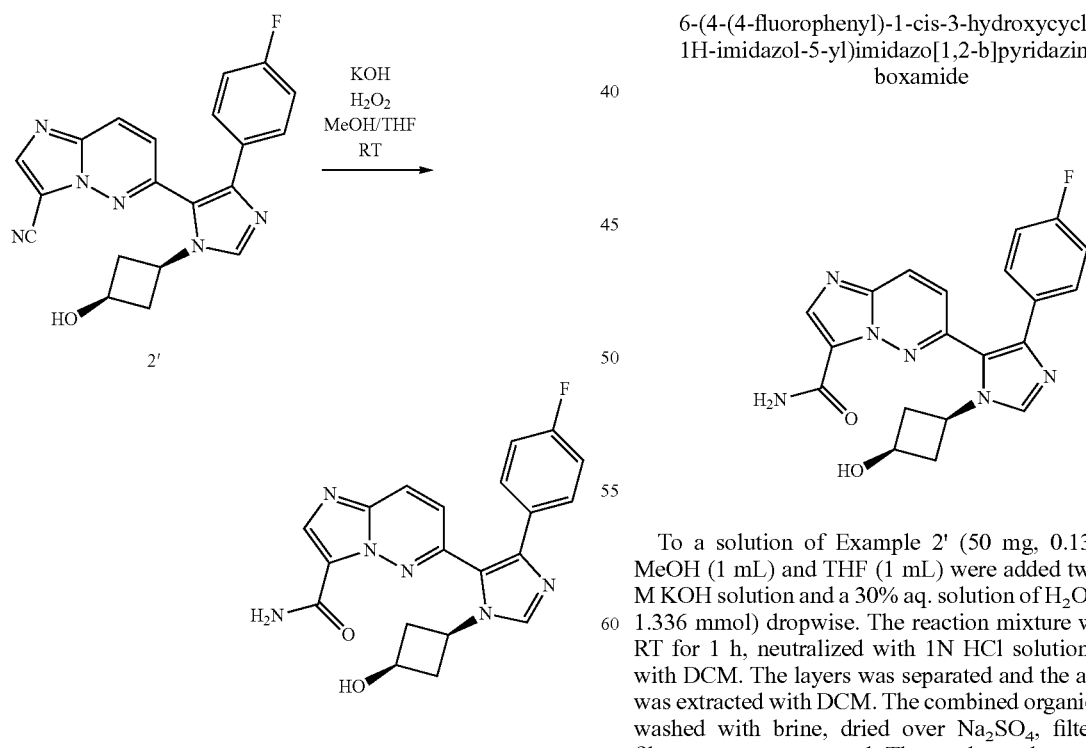

To a solution of Example 2' (50 mg, 0.134 mmol) in MeOH (1 mL) and THF (1 mL) were added two drops of 4 M KOH solution and a 30% aq. solution of $H_2O_2$ (0.041 mL, 1.336 mmol) dropwise. The reaction mixture was stirred at RT for 1 h, neutralized with 1N HCl solution and diluted with DCM. The layers was separated and the aqueous layer was extracted with DCM. The combined organic layers were washed with brine, dried over $Na_2SO_4$, filtered and the filtrate was concentrated. The crude product was dissolved in a mixture of DMF and methanol and purified via preparative HPLC. Fractions containing the desired product were combined and evaporated to afford Example 123' (12.5 mg, 24% yield). MS (ES): m/z=393.1 [M+H]+; HPLC Ret. Time 0.954 min. and 1.096 min. (HPLC Methods A and B, respectively); $^1$H NMR (500 MHz, DMSO-d$_6$) δ ppm 8.35 (s, 1H), 8.30 (d, J=9.5 Hz, 1H), 8.02 (s, 1H), 7.85 (s, 2H), 7.49 (dd, J=8.8, 5.5 Hz, 2H), 7.25 (d, J=9.5 Hz, 1H), 7.13 (t, J=8.8 Hz, 2H), 4.30-4.19 (m, 2H), 1.72-1.52 (m, 2H), 0.96 (s, 6H).

Compounds shown in Table 9 have been prepared in a manner similar to Example 123' using potassium hydroxide, hydrogen peroxide, and the corresponding cyano compounds.

TABLE 9

| Ex. | Structure | Name | [M + H]+ | Ret Time (min.) | HPLC Method |
|---|---|---|---|---|---|
| 124' | 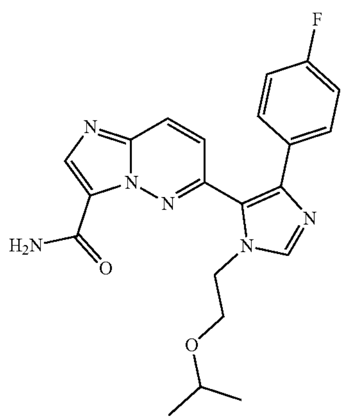 [SMILES: CC(C)OCCn1cnc(-c2ccc(F)cc2)c1-c1ccc2ncc(C(N)=O)n2n1] | 6-(4-(4-fluorophenyl)-1-(2-isopropoxyethyl)-1H-imidazol-5-yl)imidazo[1,2-b]pyridazine-3-carboxamide | 409.1 | 1.048<br>1.415 | A<br>B |
| 125' | 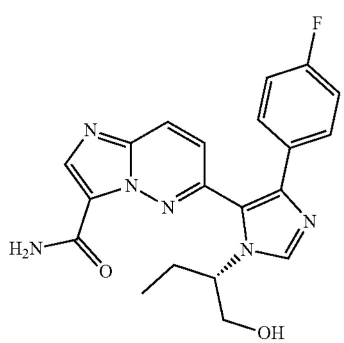 [SMILES: CC[C@@H](CO)n1cnc(-c2ccc(F)cc2)c1-c1ccc2ncc(C(N)=O)n2n1] | (S)-6-(4-(4-fluorophenyl)-1-(1-hydroxybutan-2-yl)-1H-imidazol-5-yl)imidazo[1,2-b]pyridazine-3-carboxamide | 395.1 | 0.896<br>1.055 | A<br>B |
| 126' | 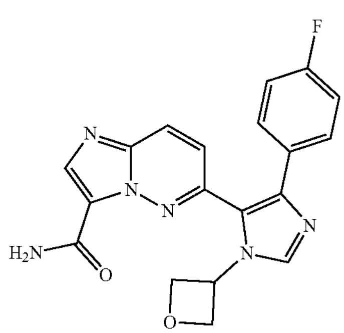 [SMILES: NC(=O)c1cnc2ccc(-c3c(-c4ccc(F)cc4)ncn3C3COC3)nn12] | 6-(4-(4-fluorophenyl)-1-(oxetan-3-yl)-1H-imidazol-5-yl)imidazo[1,2-b]pyridazine-3-carboxamide | 379.1 | 0.884<br>1.071 | A<br>B |

TABLE 9-continued

| Ex. | Structure | Name | [M + H]+ | Ret Time (min.) | HPLC Method |
|---|---|---|---|---|---|
| 127' | 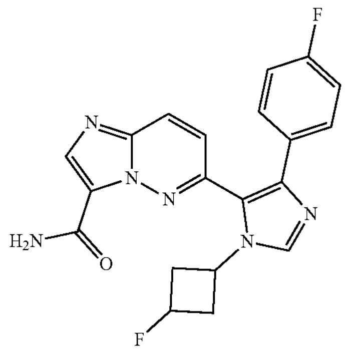 [SMILES: NC(=O)c1cnc2ccc(-c3c(-c4ccc(F)cc4)ncn3C3CC(F)C3)nn12] | 6-(1-(3-fluorocyclobutyl)-4-(4-fluorophenyl)-1H-imidazol-5-yl)imidazo[1,2-b]pyridazine-3-carboxamide | 395.1 | 1.038<br>1.218 | A<br>B |
| 128' | 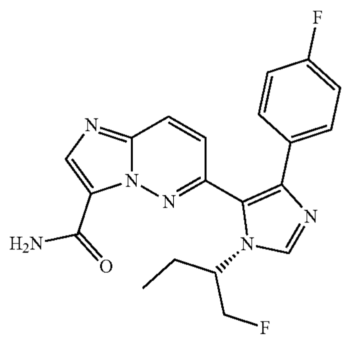 | (S)-6-(1-(1-fluorobutan-2-yl)-4-(4-fluorophenyl)-1H-imidazol-5-yl)imidazo[1,2-b]pyridazine-3-carboxamide | 397.1 | 1.094<br>1.29 | A<br>B |
| 129' | 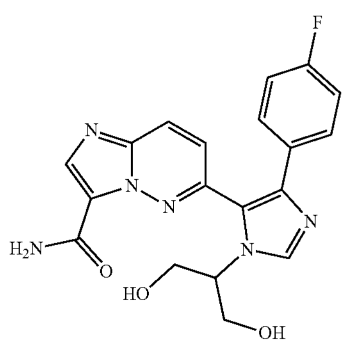 [SMILES: NC(=O)c1cnc2ccc(-c3c(-c4ccc(F)cc4)ncn3C(CO)CO)nn12] | 6-(1-(1,3-dihydroxypropan-2-yl)-4-(4-fluorophenyl)-1H-imidazol-5-yl)imidazo[1,2-b]pyridazine-3-carboxamide | 397.1 | 0.824<br>1.076 | A<br>B |
| 130' | 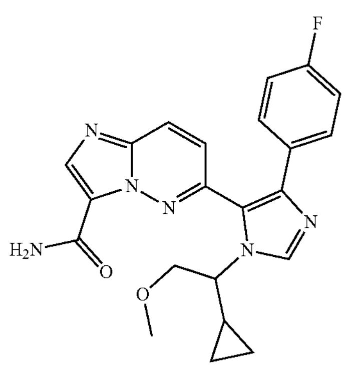 [SMILES: COCC(C1CC1)n1cnc(-c2ccc(F)cc2)c1-c1ccc2ncc(C(N)=O)n2n1] | 6-(1-(1-cyclopropyl-2-methoxyethyl)-4-(4-fluorophenyl)-1H-imidazol-5-yl)imidazo[1,2-b]pyridazine-3-carboxamide | 421.1 | 1.0<br>1.416 | A<br>B |

TABLE 9-continued

| Ex. | Structure | Name | [M + H]+ | Ret Time (min.) | HPLC Method |
|---|---|---|---|---|---|
| 131' | 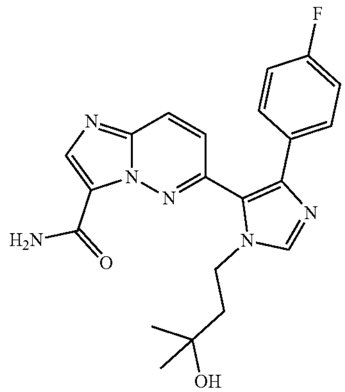 [SMILES: CC(C)(O)CCn1cnc(-c2ccc(F)cc2)c1-c1ccc2ncc(C(N)=O)n2n1] | 6-(4-(4-fluorophenyl)-1-(3-hydroxy-3-methylbutyl)-1H-imidazol-5-yl)imidazo[1,2-b]pyridazine-3-carboxamide | 409.1 | 0.906<br>1.215 | A<br>B |
| 132' | 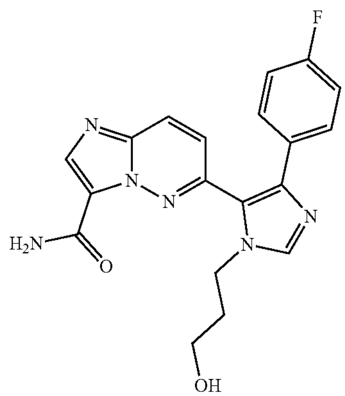 [SMILES: NC(=O)c1cnc2ccc(-c3c(-c4ccc(F)cc4)ncn3CCCO)nn12] | 6-(4-(4-fluorophenyl)-1-(3-hydroxypropyl)-1H-imidazol-5-yl)imidazo[1,2-b]pyridazine-3-carboxamide | 363.1 | 1.054<br>1.274 | A<br>B |
| 133' | 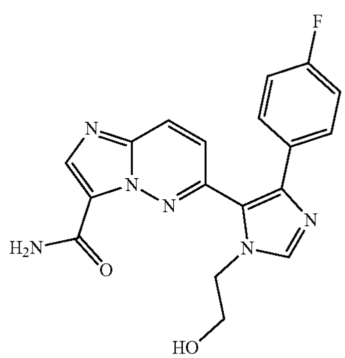 [SMILES: NC(=O)c1cnc2ccc(-c3c(-c4ccc(F)cc4)ncn3CCO)nn12] | 6-(4-(4-fluorophenyl)-1-(2-hydroxyethyl)-1H-imidazol-5-yl)imidazo[1,2-b]pyridazine-3-carboxamide | 349.1 | 1.135<br>1.212 | A<br>B |
| 134' | 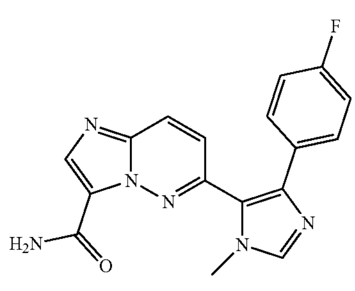 [SMILES: Cn1cnc(-c2ccc(F)cc2)c1-c1ccc2ncc(C(N)=O)n2n1] | 6-(4-(4-fluorophenyl)-1-methyl-1H-imidazol-5-yl)imidazo[1,2-b]pyridazine-3-carboxamide | 337.0 | 0.903<br>1.075 | A<br>B |

TABLE 9-continued

| Ex. | Structure | Name | [M + H]+ | Ret Time (min.) | HPLC Method |
|---|---|---|---|---|---|
| 135' | 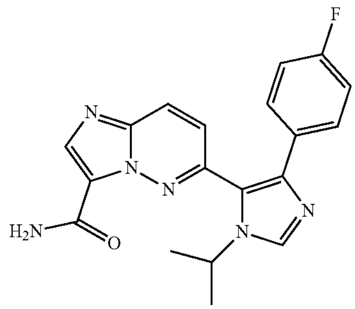 [SMILES: CC(C)n1cnc(-c2ccc(F)cc2)c1-c1ccc2ncc(C(N)=O)n2n1] | 6-(4-(4-fluorophenyl)-1-isopropyl-1H-imidazol-5-yl)imidazo[1,2-b]pyridazine-3-carboxamide | 365.1 | 0.966<br>1.227 | A<br>B |
| 136' | 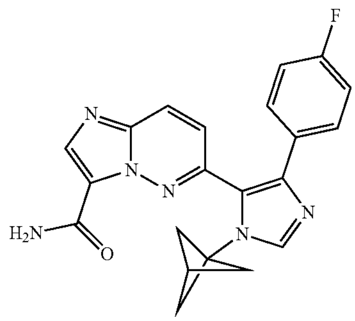 [SMILES: NC(=O)c1cnc2ccc(-c3c(-c4ccc(F)cc4)ncn3C34CC(C3)C4)nn12] | 6-(1-(bicyclo[1.1.1]pentan-1-yl)-4-(4-fluorophenyl)-1H-imidazol-5-yl)imidazo[1,2-b]pyridazine-3-carboxamide | 389.1 | 1.015<br>1.29 | A<br>B |
| 137' | 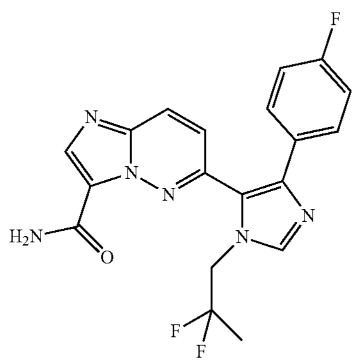 [SMILES: CC(F)(F)Cn1cnc(-c2ccc(F)cc2)c1-c1ccc2ncc(C(N)=O)n2n1] | 6-(1-(2,2-difluoropropyl)-4-(4-fluorophenyl)-1H-imidazol-5-yl)imidazo[1,2-b]pyridazine-3-carboxamide | 401.0 | 1.082<br>1.275 | A<br>B |

Compounds shown in Table 10 have been prepared in a manner similar to Example 123' using potassium hydroxide, hydrogen peroxide, and the corresponding cyano compounds.

TABLE 10

| Ex. | Structure | Name | [M + H]+ | Ret Time (min.) | HPLC Method |
|---|---|---|---|---|---|
| 138' | 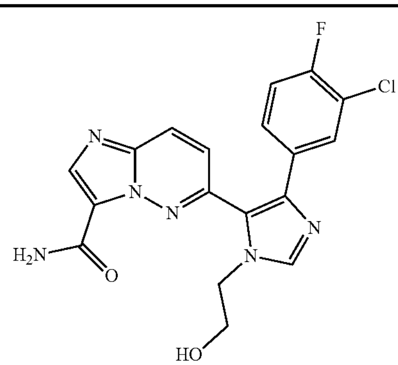 | 6-(4-(3-chloro-4-fluorophenyl)-1-(2-hydroxyethyl)-1H-imidazol-5-yl)imidazo[1,2-b]pyridazine-3-carboxamide | 401.05 | 0.7<br>0.91 | A<br>B |

TABLE 10-continued

| Ex. | Structure | Name | [M + H]+ | Ret Time (min.) | HPLC Method |
|---|---|---|---|---|---|
| 139' | 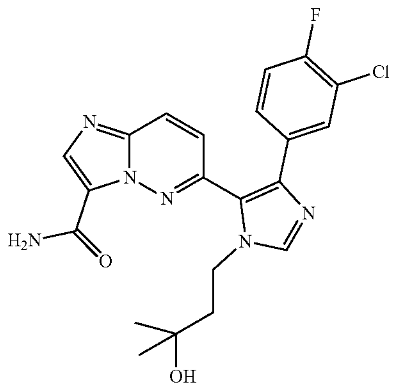 [SMILES: CC(C)(O)CCn1cnc(-c2ccc(F)c(Cl)c2)c1-c1ccc2ncc(C(N)=O)n2n1] | 6-(4-(3-chloro-4-fluorophenyl)-1-(3-hydroxy-3-methylbutyl)-1H-imidazol-5-yl)imidazo[1,2-b]pyridazine-3-carboxamide | 443.4 | 1.000<br>1.310 | A<br>B |
| 140' | 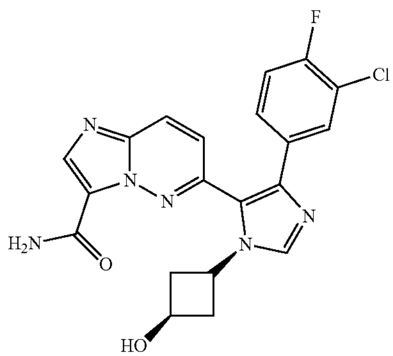 | 6-(4-(3-chloro-4-fluorophenyl)-1-((1s,3s)-3-hydroxycyclobutyl)-1H-imidazol-5-yl)imidazo[1,2-b]pyridazine-3-carboxamide | 427.1 | 1.013<br>1.252 | A<br>B |
| 141' | 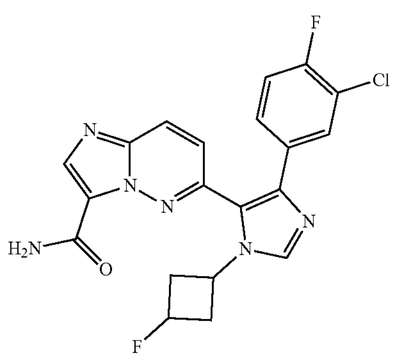 [SMILES: NC(=O)c1cnc2ccc(-c3c(-c4ccc(F)c(Cl)c4)ncn3C3CC(F)C3)nn12] | 6-(4-(3-chloro-4-fluorophenyl)-1-(3-fluorocyclobutyl)-1H-imidazol-5-yl)imidazo[1,2-b]pyridazine-3-carboxamide | 429.0 | 1.088<br>1.358 | A<br>B |
| 142' | 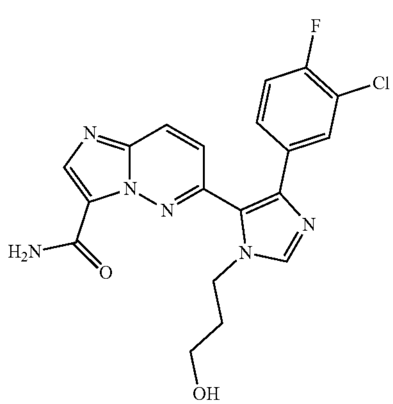 [SMILES: NC(=O)c1cnc2ccc(-c3c(-c4ccc(F)c(Cl)c4)ncn3CCCO)nn12] | 6-(4-(3-chloro-4-fluorophenyl)-1-(3-hydroxypropyl)-1H-imidazol-5-yl)imidazo[1,2-b]pyridazine-3-carboxamide | 397.1 | 1.166<br>1.53 | A<br>B |

TABLE 10-continued

| Ex. | Structure | Name | [M + H]⁺ | Ret Time (min.) | HPLC Method |
|---|---|---|---|---|---|
| 143' | 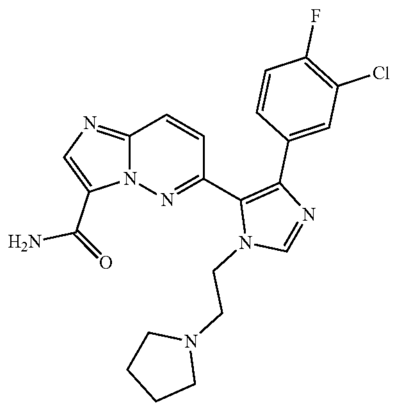 [SMILES: NC(=O)c1cnc2ccc(-c3c(-c4ccc(F)c(Cl)c4)ncn3CCN3CCCC3)nn12] | 6-(4-(3-chloro-4-fluorophenyl)-1-(2-(pyrrolidin-1-yl)ethyl)-1H-imidazol-5-yl)imidazo[1,2-b]pyridazine-3-carboxamide | 454.1 | 0.84<br>1.01 | A<br>B |
| 144' | 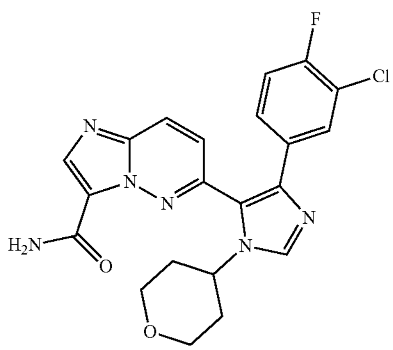 [SMILES: NC(=O)c1cnc2ccc(-c3c(-c4ccc(F)c(Cl)c4)ncn3C3CCOCC3)nn12] | 6-(4-(3-chloro-4-fluorophenyl)-1-(tetrahydro-2H-pyran-4-yl)-1H-imidazol-5-yl)imidazo[1,2-b]pyridazine-3-carboxamide | 441.2 | 0.85<br>1.18 | A<br>B |
| 145' | 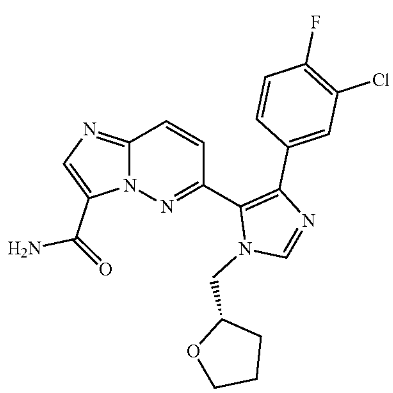 [SMILES: NC(=O)c1cnc2ccc(-c3c(-c4ccc(F)c(Cl)c4)ncn3C[C@@H]3CCCO3)nn12] | (S)-6-(4-(3-chloro-4-fluorophenyl)-1-((tetrahydrofuran-2-yl)methyl)-1H-imidazol-5-yl)imidazo[1,2-b]pyridazine-3-carboxamide | 441.1 | 0.89<br>1.22 | A<br>B |
| 146' | 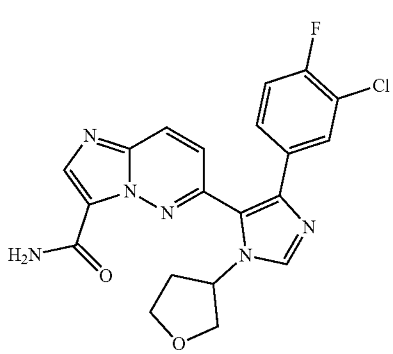 [SMILES: NC(=O)c1cnc2ccc(-c3c(-c4ccc(F)c(Cl)c4)ncn3C3CCOC3)nn12] | 6-(4-(3-chloro-4-fluorophenyl)-1-(tetrahydrofuran-3-yl)-1H-imidazol-5-yl)imidazo[1,2-b]pyridazine-3-carboxamide | 427.1 | 0.83<br>1.14 | A<br>B |

TABLE 10-continued

| Ex. | Structure | Name | [M + H]+ | Ret Time (min.) | HPLC Method |
|---|---|---|---|---|---|
| 147' | 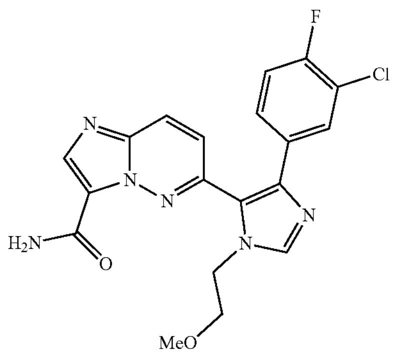 [SMILES: COCCn1cnc(-c2ccc(F)c(Cl)c2)c1-c1ccc2ncc(C(N)=O)n2n1] | 6-(4-(3-chloro-4-fluorophenyl)-1-(2-methoxyethyl)-1H-imidazol-5-yl)imidazo[1,2-b]pyridazine-3-carboxamide | 415.1 | 0.86<br>1.16 | A<br>B |
| 148' | 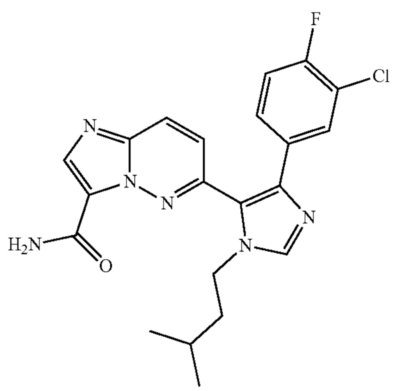 [SMILES: CC(C)CCn1cnc(-c2ccc(F)c(Cl)c2)c1-c1ccc2ncc(C(N)=O)n2n1] | 6-(4-(3-chloro-4-fluorophenyl)-1-isopentyl-1H-imidazol-5-yl)imidazo[1,2-b]pyridazine-3-carboxamide | 425.2 | 1.04<br>1.46 | A<br>B |
| 149' | 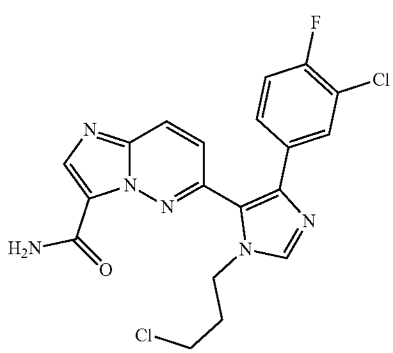 [SMILES: NC(=O)c1cnc2ccc(-c3c(-c4ccc(F)c(Cl)c4)ncn3CCCCl)nn12] | 6-(4-(3-chloro-4-fluorophenyl)-1-(3-chloropropyl)-1H-imidazol-5-yl)imidazo[1,2-b]pyridazine-3-carboxamide | 433.1 | 0.94<br>1.29 | A<br>B |
| 150' | 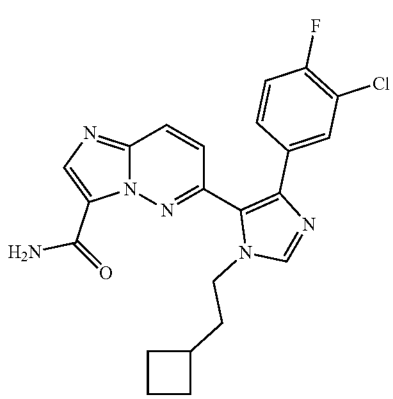 [SMILES: NC(=O)c1cnc2ccc(-c3c(-c4ccc(F)c(Cl)c4)ncn3CCC3CCC3)nn12] | 6-(4-(3-chloro-4-fluorophenyl)-1-(2-cyclobutylethyl)-1H-imidazol-5-yl)imidazo[1,2-b]pyridazine-3-carboxamide | 439.2 | 1.09<br>1.5 | A<br>B |

TABLE 10-continued

| Ex. | Structure | Name | [M + H]⁺ | Ret Time (min.) | HPLC Method |
|---|---|---|---|---|---|
| 151' | 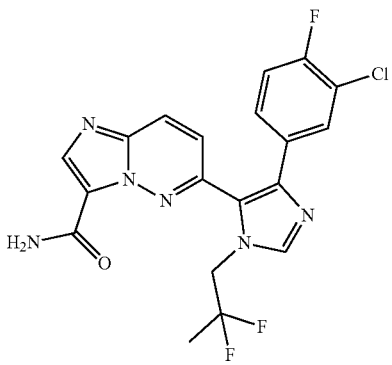 [SMILES: CC(F)(F)Cn1cnc(-c2ccc(F)c(Cl)c2)c1-c1ccc2ncc(C(N)=O)n2n1] | 6-(4-(3-chloro-4-fluorophenyl)-1-(2,2-difluoropropyl)-1H-imidazol-5-yl)imidazo[1,2-b]pyridazine-3-carboxamide | 435.1 | 1.368<br>1.526 | A<br>B |

Compounds shown in Table 11 have been prepared in a manner similar to Example 123' using potassium hydroxide, hydrogen peroxide, and the corresponding cyano compounds.

TABLE 11

| Ex. | Structure | Name | [M + H]⁺ | Ret Time (min.) | HPLC Method |
|---|---|---|---|---|---|
| 152' | 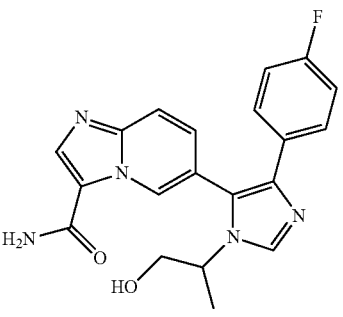 | 6-(4-(4-fluorophenyl)-1-(1-hydroxypropan-2-yl)-1H-imidazol-5-yl)imidazo[1,2-a]pyridine-3-carboxamide | 380.1 | 0.812<br>1.062 | A<br>B |
| 153' | 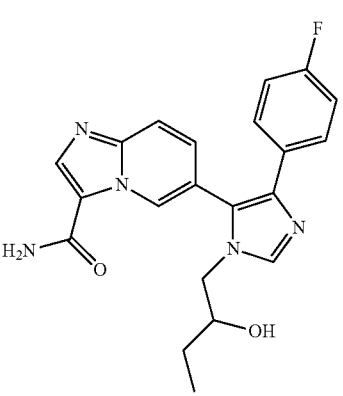 [SMILES: CCC(O)Cn1cnc(-c2ccc(F)cc2)c1-c1ccc2ncc(C(N)=O)n2c1] | 6-(4-(4-fluorophenyl)-1-(2-hydroxybutyl)-1H-imidazol-5-yl)imidazo[1,2-a]pyridine-3-carboxamide | 394.1 | 0.844<br>1.108 | A<br>B |

TABLE 11-continued

| Ex. | Structure | Name | [M + H]+ | Ret Time (min.) | HPLC Method |
|---|---|---|---|---|---|
| 154' | 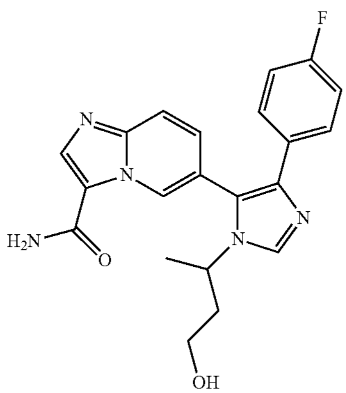 [SMILES: CC(CCO)n1cnc(-c2ccc(F)cc2)c1-c1ccc2ncc(C(N)=O)n2c1] | 6-(4-(4-fluorophenyl)-1-(4-hydroxybutan-2-yl)-1H-imidazol-5-yl)imidazo[1,2-a]pyridine-3-carboxamide | 394.1 | 0.827<br>1.086 | A<br>B |
| 155' | 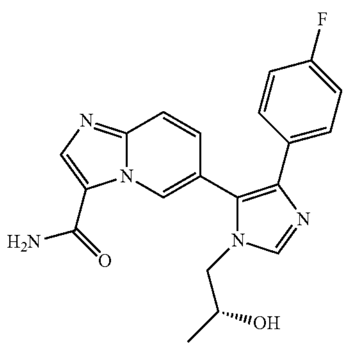 [SMILES: C[C@@H](O)Cn1cnc(-c2ccc(F)cc2)c1-c1ccc2ncc(C(N)=O)n2c1] | (R)-6-(4-(4-fluorophenyl)-1-(2-hydroxypropyl)-1H-imidazol-5-yl)imidazo[1,2-a]pyridine-3-carboxamide | 380.1 | 0.784<br>1.067 | A<br>B |
| 156' | 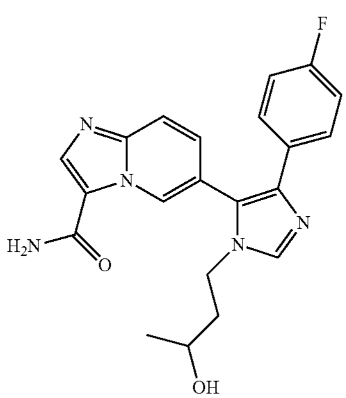 [SMILES: CC(O)CCn1cnc(-c2ccc(F)cc2)c1-c1ccc2ncc(C(N)=O)n2c1] | 6-(4-(4-fluorophenyl)-1-(3-hydroxybutyl)-1H-imidazol-5-yl)imidazo[1,2-a]pyridine-3-carboxamide | 394.1 | 0.846<br>1.098 | A<br>B |
| 157' | 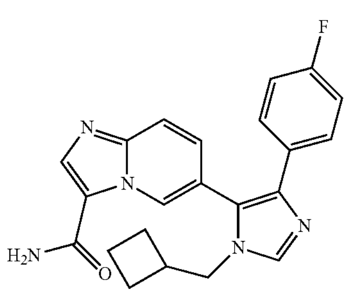 [SMILES: NC(=O)c1cnc2ccc(-c3c(-c4ccc(F)cc4)ncn3CC3CCC3)cn12] | 6-(1-(cyclobutylmethyl)-4-(4-fluorophenyl)-1H-imidazol-5-yl)imidazo[1,2-a]pyridine-3-carboxamide | 390.0 | 1.065<br>1.284 | A<br>B |

TABLE 11-continued

| Ex. | Structure | Name | [M + H]+ | Ret Time (min.) | HPLC Method |
|---|---|---|---|---|---|
| 158' | 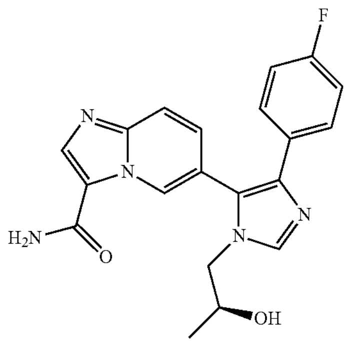 [SMILES: C[C@H](O)Cn1cnc(-c2ccc(F)cc2)c1-c1ccc2ncc(C(N)=O)n2c1] | (S)-6-(4-(4-fluorophenyl)-1-(2-hydroxypropyl)-1H-imidazol-5-yl)imidazo[1,2-a]pyridine-3-carboxamide | 380.1 | 0.819<br>1.046 | A<br>B |
| 159' | 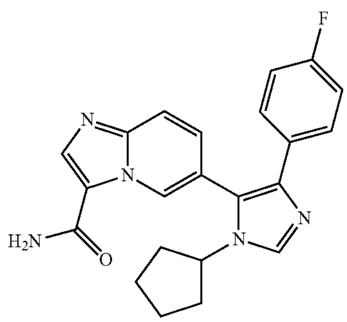 [SMILES: NC(=O)c1cnc2ccc(-c3c(-c4ccc(F)cc4)ncn3C3CCCC3)cn12] | 6-(1-cyclopentyl-4-(4-fluorophenyl)-1H-imidazol-5-yl)imidazo[1,2-a]pyridine-3-carboxamide | 390.1 | 0.928<br>1.352 | A<br>B |
| 160' | 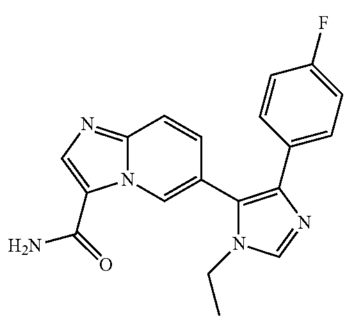 [SMILES: CCn1cnc(-c2ccc(F)cc2)c1-c1ccc2ncc(C(N)=O)n2c1] | 6-(1-ethyl-4-(4-fluorophenyl)-1H-imidazol-5-yl)imidazo[1,2-a]pyridine-3-carboxamide | 350.1 | 0.831<br>1.144 | A<br>B |
| 161' | 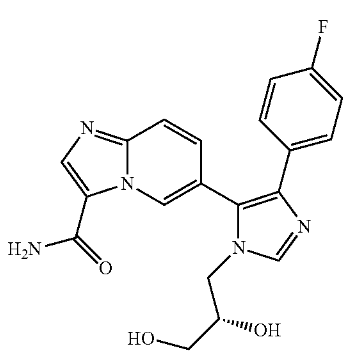 [SMILES: NC(=O)c1cnc2ccc(-c3c(-c4ccc(F)cc4)ncn3C[C@H](O)CO)cn12] | (S)-6-(1-(2,3-dihydroxypropyl)-4-(4-fluorophenyl)-1H-imidazol-5-yl)imidazo[1,2-a]pyridine-3-carboxamide | 396.1 | 0.686<br>0.996 | A<br>B |

TABLE 11-continued

| Ex. | Structure | Name | [M + H]+ | Ret Time (min.) | HPLC Method |
|---|---|---|---|---|---|
| 162' | 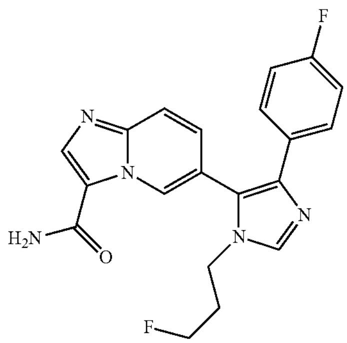 [SMILES: NC(=O)c1cnc2ccc(-c3c(-c4ccc(F)cc4)ncn3CCCF)cn12] | 6-(4-(4-fluorophenyl)-1-(3-fluoropropyl)-1H-imidazol-5-yl)imidazo[1,2-a]pyridine-3-carboxamide | 382.1 | 0.844<br>1.168 | A<br>B |
| 163' | 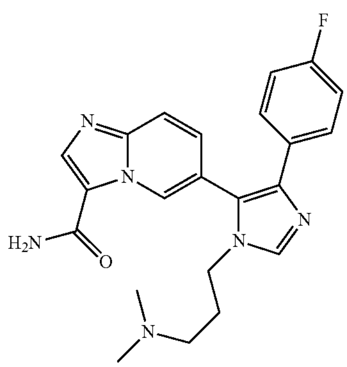 [SMILES: CN(C)CCCn1cnc(-c2ccc(F)cc2)c1-c1ccc2ncc(C(N)=O)n2c1] | 6-(1-(3-(dimethylamino)propyl)-4-(4-fluorophenyl)-1H-imidazol-5-yl)imidazo[1,2-a]pyridine-3-carboxamide | 407.1 | 0.676<br>1.006 | A<br>B |
| 164' | 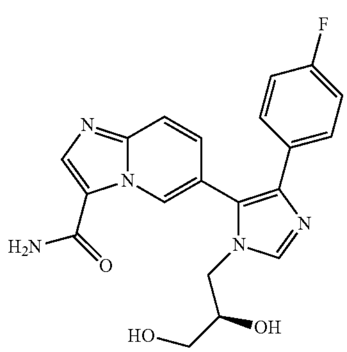 [SMILES: NC(=O)c1cnc2ccc(-c3c(-c4ccc(F)cc4)ncn3C[C@@H](O)CO)cn12] | (R)-6-(1-(2,3-dihydroxypropyl)-4-(4-fluorophenyl)-1H-imidazol-5-yl)imidazo[1,2-a]pyridine-3-carboxamide | 396.1 | 0.782<br>0.982 | A<br>B |
| 165' | 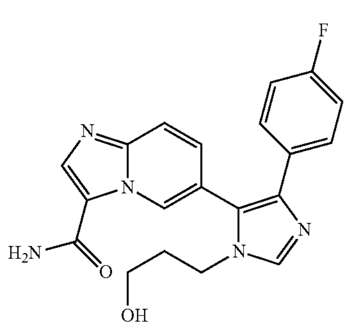 [SMILES: NC(=O)c1cnc2ccc(-c3c(-c4ccc(F)cc4)ncn3CCCO)cn12] | 6-(4-(4-fluorophenyl)-1-(3-hydroxypropyl)-1H-imidazol-5-yl)imidazo[1,2-a]pyridine-3-carboxamide | 380.1 | 0.907<br>1.048 | A<br>B |

TABLE 11-continued

| Ex. | Structure | Name | [M + H]+ | Ret Time (min.) | HPLC Method |
|---|---|---|---|---|---|
| 166' | 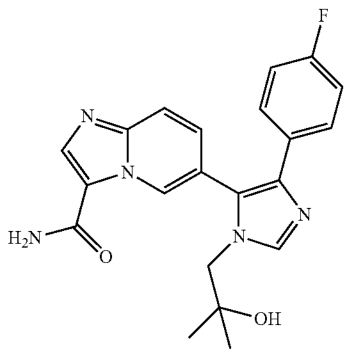 [SMILES: CC(C)(O)Cn1cnc(-c2ccc(F)cc2)c1-c1ccc2ncc(C(N)=O)n2c1] | 6-(4-(4-fluorophenyl)-1-(2-hydroxy-2-methyl-propyl)-1H-imidazol-5-yl)imidazo[1,2-a]pyridine-3-carboxamide | 394.1 | 0.84<br>1.074 | A<br>B |
| 167' | 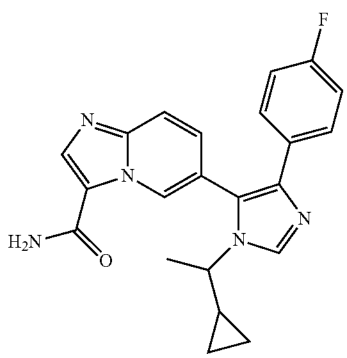 [SMILES: CC(C1CC1)n1cnc(-c2ccc(F)cc2)c1-c1ccc2ncc(C(N)=O)n2c1] | 6-(1-(1-cyclopropylethyl)-4-(4-fluorophenyl)-1H-imidazol-5-yl)imidazo[1,2-a]pyridine-3-carboxamide | 390.0 | 1.059<br>1.228 | A<br>B |
| 168' | 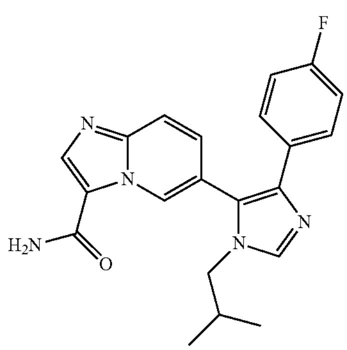 [SMILES: CC(C)Cn1cnc(-c2ccc(F)cc2)c1-c1ccc2ncc(C(N)=O)n2c1] | 6-(4-(4-fluorophenyl)-1-isobutyl-1H-imidazol-5-yl)imidazo[1,2-a]pyridine-3-carboxamide | 378.1 | 0.912<br>1.316 | A<br>B |
| 169' | 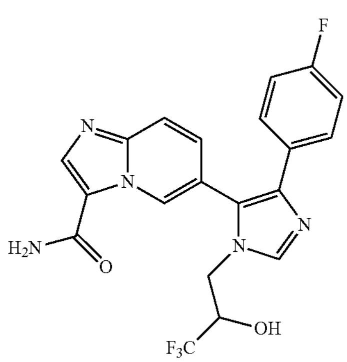 [SMILES: NC(=O)c1cnc2ccc(-c3c(-c4ccc(F)cc4)ncn3CC(O)C(F)(F)F)cn12] | 6-(4-(4-fluorophenyl)-1-(3,3,3-trifluoro-2-hydroxy-propyl)-1H-imidazol-5-yl)imidazo[1,2-a]pyridine-3-carboxamide | 434.0 | 0.875<br>1.164 | A<br>B |

TABLE 11-continued

| Ex. | Structure | Name | [M + H]+ | Ret Time (min.) | HPLC Method |
|---|---|---|---|---|---|
| 170' | 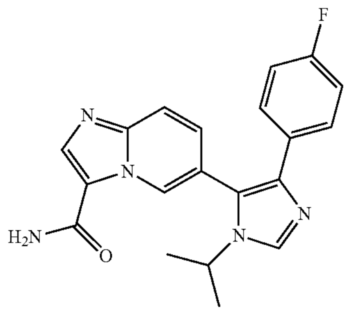 [SMILES: CC(C)n1cnc(-c2ccc(F)cc2)c1-c1ccc2ncc(C(N)=O)n2c1] | 6-(4-(4-fluorophenyl)-1-isopropyl-1H-imidazol-5-yl)imidazo[1,2-a]pyridine-3-carboxamide | 364.1 | 0.859<br>1.214 | A<br>B |
| 171' | 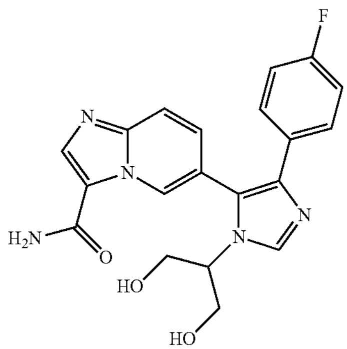 [SMILES: NC(=O)c1cnc2ccc(-c3c(-c4ccc(F)cc4)ncn3C(CO)CO)cn12] | 6-(1-(1,3-dihydroxypropan-2-yl)-4-(4-fluorophenyl)-1H-imidazol-5-yl)imidazo[1,2-a]pyridine-3-carboxamide | 396.1 | 0.787<br>0.978 | A<br>B |
| 172' | 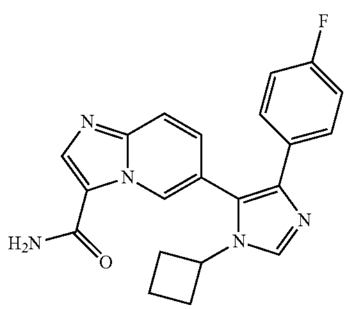 [SMILES: NC(=O)c1cnc2ccc(-c3c(-c4ccc(F)cc4)ncn3C3CCC3)cn12] | 6-(1-cyclobutyl-4-(4-fluorophenyl)-1H-imidazol-5-yl)imidazo[1,2-a]pyridine-3-carboxamide | 376.1 | 0.878<br>1.278 | A<br>B |
| 173' | 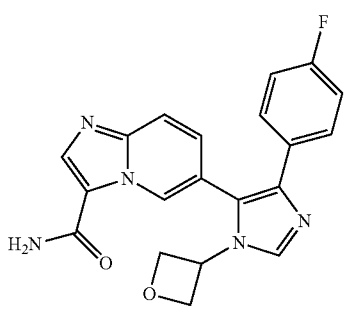 [SMILES: NC(=O)c1cnc2ccc(-c3c(-c4ccc(F)cc4)ncn3C3COC3)cn12] | 6-(4-(4-fluorophenyl)-1-(oxetan-3-yl)-1H-imidazol-5-yl)imidazo[1,2-a]pyridine-3-carboxamide | 378.1 | 0.82<br>1.079 | A<br>B |
| 174' | 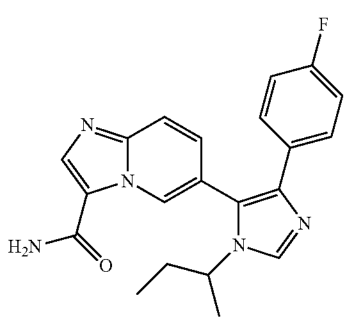 [SMILES: CCC(C)n1cnc(-c2ccc(F)cc2)c1-c1ccc2ncc(C(N)=O)n2c1] | 6-(1-(sec-butyl)-4-(4-fluorophenyl)-1H-imidazol-5-yl)imidazo[1,2-a]pyridine-3-carboxamide | 378.1 | 0.91<br>1.288 | A<br>B |

TABLE 11-continued

| Ex. | Structure | Name | [M + H]+ | Ret Time (min.) | HPLC Method |
|---|---|---|---|---|---|
| 175' | 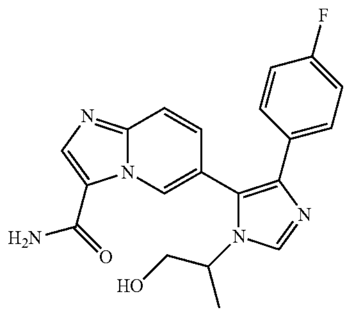 [SMILES: CC(CO)n1cnc(-c2ccc(F)cc2)c1-c1ccc2ncc(C(N)=O)n2c1] | 6-(4-(4-fluorophenyl)-1-(1-hydroxypropan-2-yl)-1H-imidazol-5-yl)imidazo[1,2-a]pyridine-3-carboxamide | 380.1 | 0.816<br>1.063 | A<br>B |
| 176' | 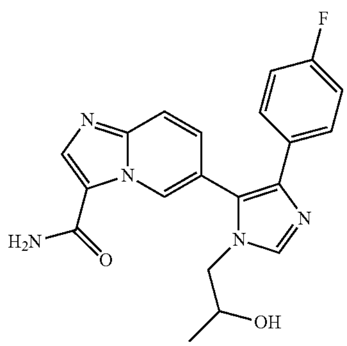 [SMILES: CC(O)Cn1cnc(-c2ccc(F)cc2)c1-c1ccc2ncc(C(N)=O)n2c1] | 6-(4-(4-fluorophenyl)-1-(2-hydroxypropyl)-1H-imidazol-5-yl)imidazo[1,2-a]pyridine-3-carboxamide | 360.1 | 0.598<br>1.056 | A<br>B |
| 177' | 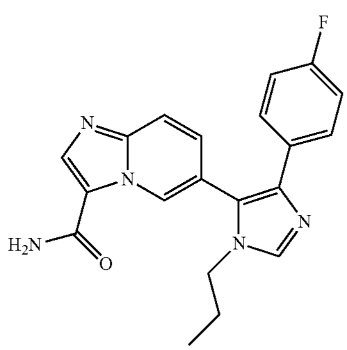 [SMILES: CCCn1cnc(-c2ccc(F)cc2)c1-c1ccc2ncc(C(N)=O)n2c1] | 6-(4-(4-fluorophenyl)-1-propyl-1H-imidazol-5-yl)imidazo[1,2-a]pyridine-3-carboxamide | 364.1 | 0.874<br>1.231 | A<br>B |
| 178' | 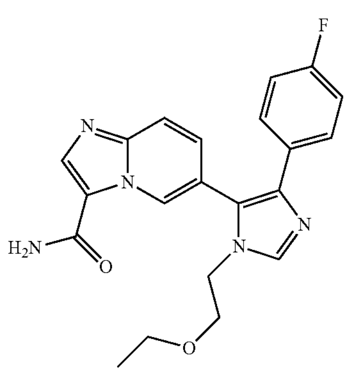 [SMILES: CCOCCn1cnc(-c2ccc(F)cc2)c1-c1ccc2ncc(C(N)=O)n2c1] | 6-(1-(2-ethoxyethyl)-4-(4-fluorophenyl)-1H-imidazol-5-yl)imidazo[1,2-a]pyridine-3-carboxamide | 394.1 | 0.899<br>1.21 | A<br>B |

TABLE 11-continued

| Ex. | Structure | Name | [M + H]+ | Ret Time (min.) | HPLC Method |
|---|---|---|---|---|---|
| 179' | 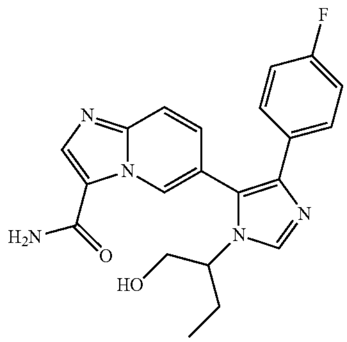 [SMILES: CCC(CO)n1cnc(-c2ccc(F)cc2)c1-c1ccc2ncc(C(N)=O)n2c1] | 6-(4-(4-fluorophenyl)-1-(1-hydroxybutan-2-yl)-1H-imidazol-5-yl)imidazo[1,2-a]pyridine-3-carboxamide | 394.1 | 0.855<br>1.126 | A<br>B |
| 180' | 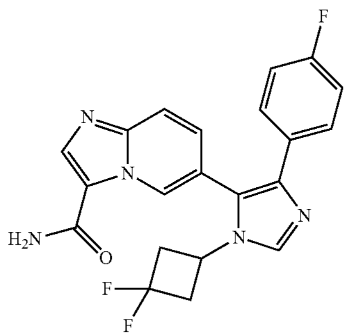 [SMILES: NC(=O)c1cnc2ccc(-c3c(-c4ccc(F)cc4)ncn3C3CC(F)(F)C3)cn12] | 6-(1-(3,3-difluorocyclobutyl)-4-(4-fluorophenyl)-1H-imidazol-5-yl)imidazo[1,2-a]pyridine-3-carboxamide | 412 | 1.047<br>1.199 | A<br>B |

Compounds shown in Table 12 have been prepared in a manner similar to Example 1', if the amine is a free base, or in a manner similar to Example 2', if the amine is an HCl salt, using imidazo[1,2-a]pyridine-6-carbaldehyde and intermediate 32C'.

TABLE 12

| Ex. | Structure | Name | [M + H]+ | Ret. Time (min.) | HPLC Method |
|---|---|---|---|---|---|
| 181' | 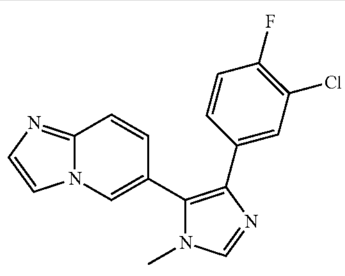 [SMILES: Cn1cnc(-c2ccc(F)c(Cl)c2)c1-c1ccc2nccn2c1] | 6-(4-(3-chloro-4-fluorophenyl)-1-methyl-1H-imidazol-5-yl)imidazo[1,2-a]pyridine | 327.1 | 1.494 0.911 | A<br>B |
| 182' | 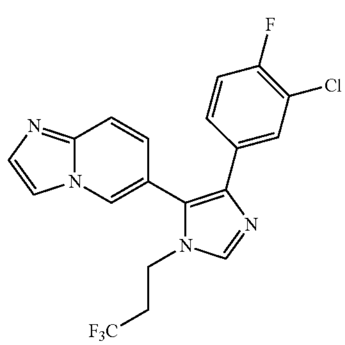 [SMILES: Fc1ccc(-c2ncn(CCC(F)(F)F)c2-c2ccc3nccn3c2)cc1Cl] | 6-(4-(3-chloro-4-fluorophenyl)-1-(3,3,3-trifluoropropyl)-1H-imidazol-5-yl)imidazo[1,2-a]pyridine | 409.2 | 1.636 1.058 | A<br>B |

TABLE 12-continued

| Ex. | Structure | Name | [M + H]+ | Ret. Time (min.) | HPLC Method |
|---|---|---|---|---|---|
| 183' | 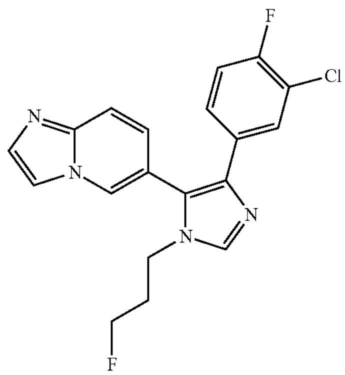 [SMILES: FCCCn1cnc(-c2ccc(F)c(Cl)c2)c1-c1ccc2nccn2c1] | 6-(4-(3-chloro-4-fluoro-phenyl)-1-(3-fluoropropyl)-1H-imidazol-5-yl)imidazo[1,2-a]pyridine | 373.2 | 1.603 0.955 | A B |
| 184' | 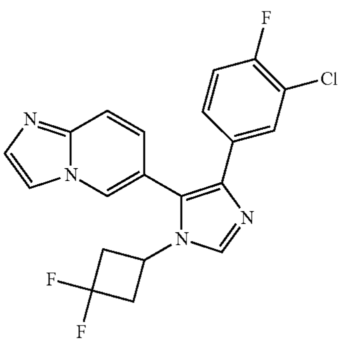 [SMILES: Fc1ccc(-c2ncn(C3CC(F)(F)C3)c2-c2ccc3nccn3c2)cc1Cl] | 6-(4-(3-chloro-4-fluoro-phenyl)-1-(3,3-difluoro-cyclobutyl)-1H-imidazol-5-yl)imidazo[1,2-a]pyridine | 403.2 | 1.634 1.039 | A B |
| 185' | 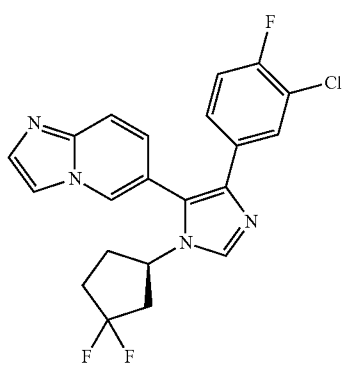 [SMILES: Fc1ccc(-c2ncn([C@@H]3CCC(F)(F)C3)c2-c2ccc3nccn3c2)cc1Cl] | (R)-6-(4-(3-chloro-4-fluorophenyl)-1-(3,3-difluorocyclopentyl)-1H-imidazol-5-yl)imidazo[1,2-a]pyridine | 417.3 | 1.782 0.960 | A B |
| 186' | 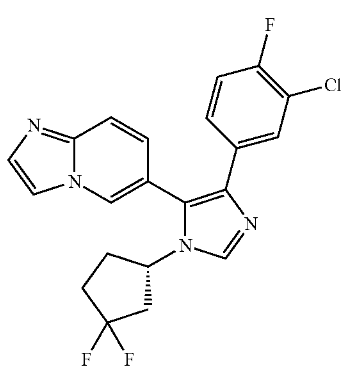 [SMILES: Fc1ccc(-c2ncn([C@H]3CCC(F)(F)C3)c2-c2ccc3nccn3c2)cc1Cl] | (S)-6-(4-(3-chloro-4-fluorophenyl)-1-(3,3-difluorocyclopentyl)-1H-imidazol-5-yl)imidazo[1,2-a]pyridine | 417.0 | 1.784 1.066 | A B |

TABLE 12-continued

| Ex. | Structure | Name | [M + H]+ | Ret. Time (min.) | HPLC Method |
|---|---|---|---|---|---|
| 187' | 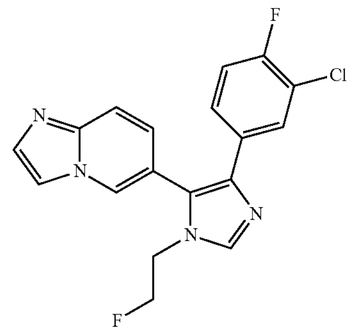 [SMILES: FCCn1cnc(-c2ccc(F)c(Cl)c2)c1-c1ccc2nccn2c1] | 6-(4-(3-chloro-4-fluoro-phenyl)-1-(2-fluoroethyl)-1H-imidazol-5-yl)imidazo[1,2-a]pyridine | 359.2 | 0.952<br>1.548 | A<br>B |

Scheme 8

Intermediate 188A': 1-((2-(4-fluorophenyl)-2-oxo-ethyl)amino)cyclopropanecarbonitrile To a solution of 2-bromo-1-(4-fluorophenyl)ethanone (3.0 g, 13.82 mmol) and DIPEA (7.24 mL, 41.5 mmol) in NMP (55.3 mL) was added 1-aminocyclopropanecarbonitrile, HCl (1.859 g, 15.20 mmol) and the reaction mixture was stirred overnight at RT. Since the starting material was not completely consumed, the mixture was heated in an oil-bath at 70° C. for 1 h, cooled to RT, diluted with water and extracted with EtOAc (2×50 mL). The combined organic layers were washed with brine and dried over anhydrous MgSO$_4$, filtered. The filtrate was concentrated under reduced pressure (water-bath temp.~25° C.) and the residue was purified by silica gel chromatography (40 g RediSep® column, eluting with 30% EtOAc in hexanes). Fractions containing the product were combined and evaporated to afford intermediate 188A' (1.66 g, 54.97% yield) as an oil. MS (ES): m/z=219.15 [M+H]$^+$; HPLC Ret. Time min. 2.903 (HPLC Method E).

Intermediate 188B': N-(1-cyanocyclopropyl)-N-(2-(4-fluorophenyl)-2-oxoethyl)formamide

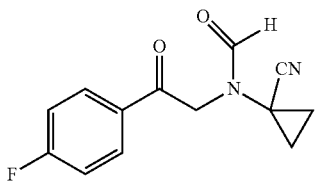

Acetic formic anhydride (reference: *Journal of Organic Chemistry*, 2007, 72(16), 6135-6142): Acetic anhydride (37.0 mL) and formic acid (18.07 mL) were heated in an oil-bath (bath temperature 55° C.) for 2 h to form acetic formic anhydride that was used in the reaction without any purification or analysis.

The above acetic formic anhydride was added to intermediate 188A' (1.66 g, 7.61 mmol) and the resultant reaction mixture was continued heating at 55-60° C. for 14 h. The mixture was then cooled in an ice-bath, very carefully basified with satd. aq. NaHCO$_3$ solution to pH~8 and extracted with EtOAc (3×50 mL). The combined organic layers were washed with brine and dried over anhydrous MgSO$_4$, and filtered. The filtrate was concentrated under reduced pressure to afford intermediate 188B' (1.787 g, 95% yield, crude) as a semi-solid. MS (ES): m/z=269.1 [M+Na]$^+$; HPLC Ret. Time min. 2.575 (HPLC Method E), which was used directly in the next step without purification.

Intermediate 188C': 1-(4-(4-fluorophenyl)-1H-imidazol-1-yl)cyclopropanecarbonitrile

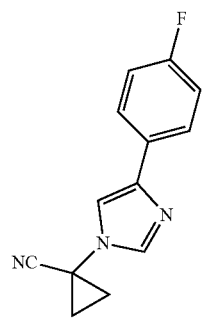 [SMILES: N#CC1(n2cnc(-c3ccc(F)cc3)c2)CC1]

A solution of intermediate 188B' (1.787 g, 7.20 mmol) and NH$_4$OAc (5.65 g, 72.6 mmol) in xylene (72.6 mL) was heated in a sealed tube in an oil-bath at 140° C. for 2 h. The solvent was concentrated to ½ the volume and the concentrated reaction mixture was purified by silica gel chromatography (40 g RediSep® column, eluting with 40% EtOAc in DCM). Fractions containing the desired product were combined and evaporated to afford intermediate 188C' (0.97 g, 58.8% yield) as a brown solid. MS (ES): m/z=228.12 [M+H]$^+$; HPLC Ret. Time 2.503 min. (HPLC Method E).

Intermediate 188D': 1-(5-bromo-4-(4-fluorophenyl)-1H-imidazol-1-yl)cyclopropanecarbonitrile

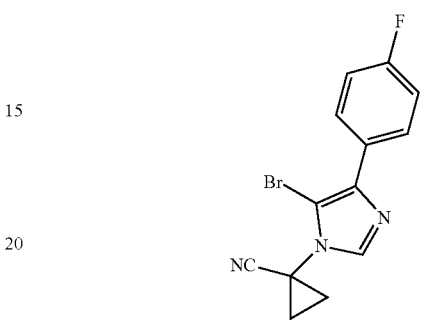

To a solution of intermediate 188C' (0.125 g, 0.550 mmol) in DCM (5.50 mL) was added NBS (0.109 g, 0.605 mmol). The reaction mixture was stirred at RT for 45 min. The solvent was evaporated and the residue was purified by silica gel chromatography (40 g RediSep® column, eluting with 20% EtOAc in DCM) to afford intermediate 188D' (0.146 g, 87% yield) as a solid. MS (ES): m/z=306/308 [M+H]$^+$; HPLC Ret. Time 3.445 min. (HPLC Method E).

Example 188'

1-(4-(4-fluorophenyl)-5-(imidazo[1,2-b]pyridazin-6-yl)-1H-imidazol-1-yl)cyclopropanecarbonitrile

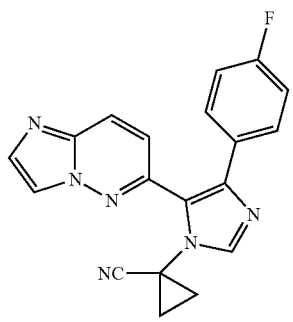 [SMILES: N#CC1(n2cnc(-c3ccc(F)cc3)c2-c2ccc3nccn3n2)CC1]

To a degassed suspension of intermediate 188D' (0.03 g, 0.098 mmol) and 6-(4,4,5,5-tetramethyl-1,3,2-dioxaborolan-2-ylimidazo[1,2-b]pyridazine (reference: US 2015/0038506 A1) (0.048 g, 0.196 mmol) in 2M aq. solution of K$_3$PO$_4$ (0.147 mL, 0.294 mmol) and 1,4-dioxane (1.0 mL) was added PdCl$_2$(dppf) (7.17 mg, 9.80 µmol). The mixture was degassed again for 2 min. and then heated in an oil-bath at 85° C. for 16 h. The reaction mixture was concentrated to dryness under reduced pressure and the residue was extracted with DCM (3×5 mL). The combined organic layers were washed with brine, dried over anhydrous MgSO$_4$, and filtered. The filtrate was concentrated under reduced pressure and the crude residue was purified via preparative HPLC. Fractions containing the desired product were combined and evaporated to afford Example 188' (0.026 g, 64.4% yield). MS (ES): m/z=345.0 [M+H]⁺; HPLC Ret. Time 1.01 min. and 1.374 min. (HPLC Methods A and B, respectively); $^1$H NMR (500 MHz, DMSO-$d_6$) δ ppm 8.40 (br. s., 1H), 8.29 (s, 1H), 8.20 (d, J=7.3 Hz, 1H), 7.95 (br. s., 1H), 7.51 (dd, J=8.6, 5.7 Hz, 2H), 7.18 (t, J=9.0 Hz, 2H), 7.10 (d, J=7.7 Hz, 1H), 1.85-1.70 (m, 4H).

Scheme 9

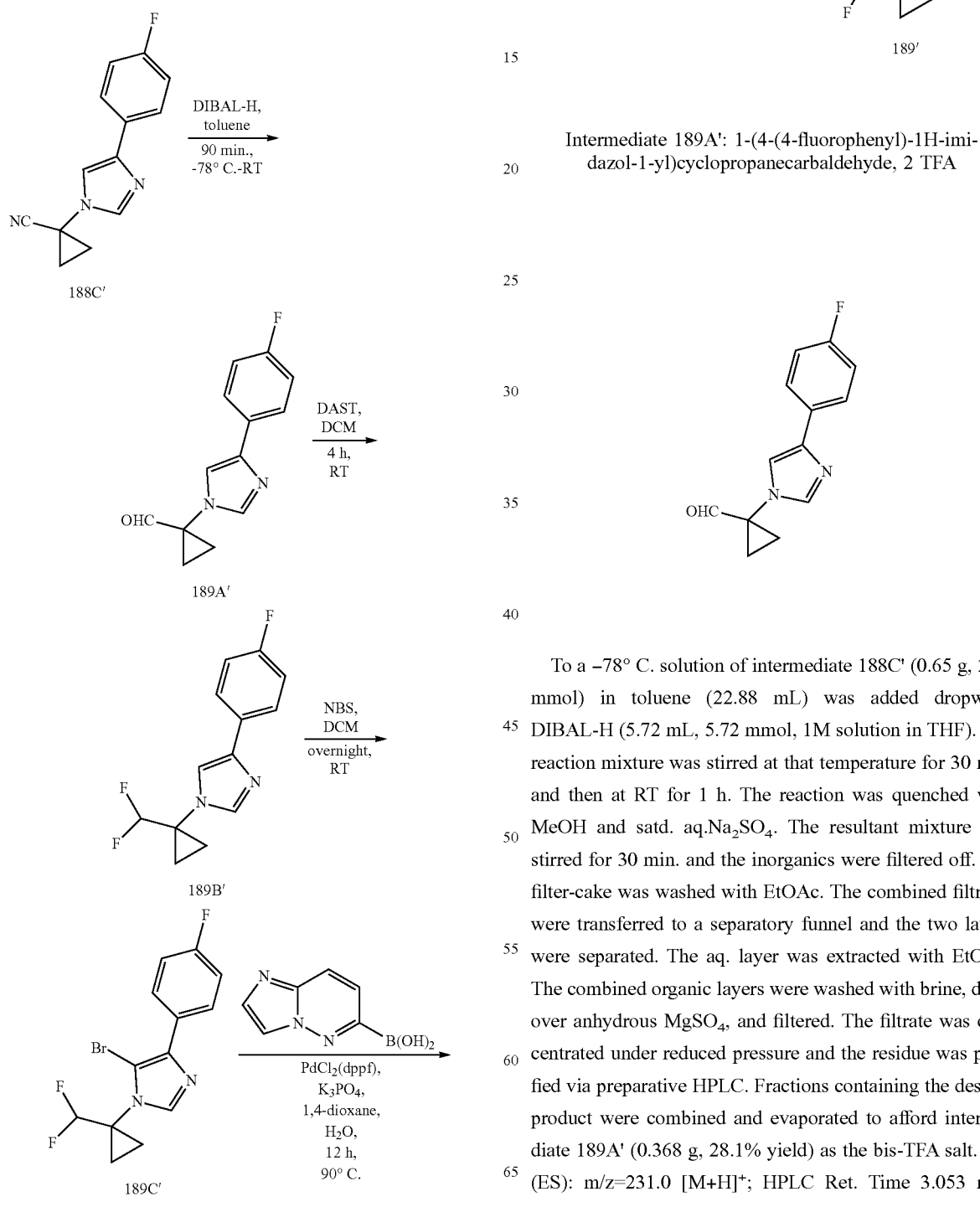

Intermediate 189A': 1-(4-(4-fluorophenyl)-1H-imidazol-1-yl)cyclopropanecarbaldehyde, 2 TFA To a −78° C. solution of intermediate 188C' (0.65 g, 2.86 mmol) in toluene (22.88 mL) was added dropwise, DIBAL-H (5.72 mL, 5.72 mmol, 1M solution in THF). The reaction mixture was stirred at that temperature for 30 min. and then at RT for 1 h. The reaction was quenched with MeOH and satd. aq.Na₂SO₄. The resultant mixture was stirred for 30 min. and the inorganics were filtered off. The filter-cake was washed with EtOAc. The combined filtrates were transferred to a separatory funnel and the two layers were separated. The aq. layer was extracted with EtOAc. The combined organic layers were washed with brine, dried over anhydrous MgSO₄, and filtered. The filtrate was concentrated under reduced pressure and the residue was purified via preparative HPLC. Fractions containing the desired product were combined and evaporated to afford intermediate 189A' (0.368 g, 28.1% yield) as the bis-TFA salt. MS (ES): m/z=231.0 [M+H]⁺; HPLC Ret. Time 3.053 min. (HPLC Method D).

Intermediate 189B': 1-(1-(difluoromethyl)cyclopropyl)-4-(4-fluorophenyl)-1H-imidazole

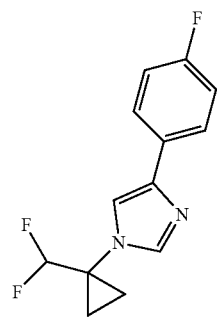 [SMILES: Fc1ccc(-c2cn(C3(C(F)F)CC3)cn2)cc1]

To a solution of intermediate 189A' (0.343 g, 0.748 mmol) in DCM (7.5 mL) was added DAST (0.3 mL, 2.245 mmol) and the reaction mixture was stirred at RT for 4 h. The mixture was quenched with some ice-water. The two layers were separated and the aq. layer was extracted with DCM. The combined organic layers were washed with satd. aq. NaHCO$_3$ solution (2×10 mL) and brine, dried over anhydrous MgSO$_4$, and filtered. The filtrate concentrated under reduced pressure and the resulting residue was purified by silica gel chromatography (24 g RediSep® column, eluting with a gradient of 30-50% EtOAc in DCM). Fractions containing the product were combined and evaporated to afford intermediate 189B' (0.15 g, 79% yield) as a colorless oil. MS (ES): m/z=253.09 [M+H]$^+$; HPLC Ret. Time 2.548 min. (HPLC Method E).

Intermediate 189C': 5-bromo-1-(1-(difluoromethyl)cyclopropyl)-4-(4-fluorophenyl)-1H-imidazole

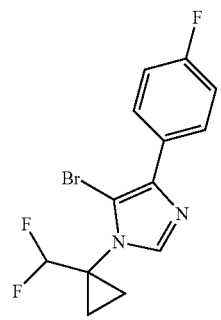 [SMILES: Fc1ccc(-c2ncn(C3(C(F)F)CC3)c2Br)cc1]

To a solution of intermediate 18913' (0.15 g, 0.595 mmol) in DCM (5.95 mL) was added NBS (0.118 g, 0.654 mmol) and the reaction mixture was stirred overnight at RT. The reaction mixture was directly purified by silica gel chromatography (40 g RediSep® column, eluting with 25% EtOAc in DCM). Fractions containing the product were combined and evaporated to afford intermediate 189C' (0.158 g, 80% yield) as a colorless oil. MS (ES): m/z=331/333 [M+H]$^+$; HPLC Ret. Time 0.97 min. (HPLC Method C).

Example 189'

6-(1-(1-(difluoromethyl)cyclopropyl)-4-(4-fluorophenyl)-1H-imidazol-5-yl)imidazo[1,2-b]pyridazine

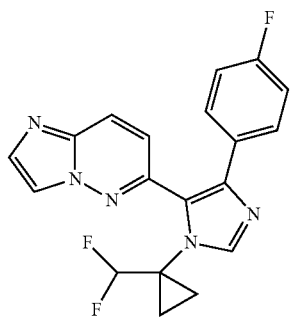 [SMILES: Fc1ccc(-c2ncn(C3(C(F)F)CC3)c2-c2ccc3nccn3n2)cc1]

Example 189' was synthesized analogous to Example 188' via a Suzuki coupling between intermediate 189C' and 6-(4,4,5,5-tetramethyl-1,3,2-dioxaborolan-2-yl)imidazo[1,2-b]pyridazine. The residue was purified via preparative HPLC. Fractions containing the desired product were combined and evaporated to afford Example 189' (0.007 g, 16.91% yield). MS (ES): m/z=370.2 [M+H]$^+$; HPLC Ret. Time 1.116 min. and 1.551 min. (HPLC Methods A and B, respectively); $^1$H NMR (500 MHz, DMSO-d$_6$) δ ppm 8.41 (s, 1H), 8.15 (d, J=9.5 Hz, 1H), 8.09 (s, 1H), 7.88 (d, J=0.7 Hz, 1H), 7.45 (dd, J=8.8, 5.5 Hz, 2H), 7.15 (t, J=8.8 Hz, 2H), 7.07 (d, J=9.5 Hz, 1H), 6.28 (s, 1H), 1.39 (br. s., 2H), 1.30-1.21 (m, 2H).

Scheme 10

435
-continued

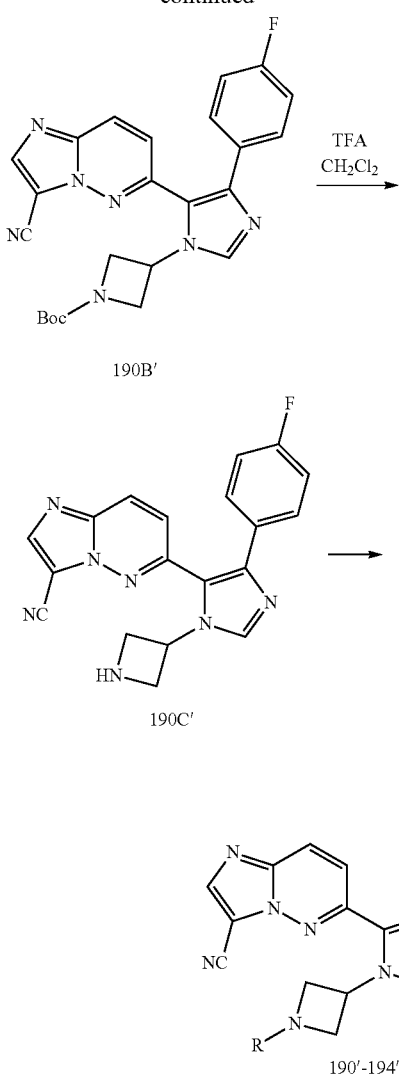

Intermediate 190A': tert-butyl 3-(((3-cyanoimidazo[1,2-b]pyridazin-6-yl)methylene)amino)azetidine-1-carboxylate

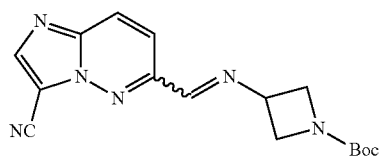 [SMILES: CC(C)(C)OC(=O)N1CC(N=Cc2ccc3ncc(C#N)n3n2)C1]

To a solution of intermediate 1D' (0.81 g, 4.71 mmol) in DCM (30 mL) were added magnesium sulfate (5.66 g, 47.1 mmol) and tert-butyl 3-aminoazetidine-1-carboxylate (0.851 g, 4.94 mmol). The suspension was stirred at RT overnight, filtered and washed with DCM. The combined filtrates were concentrated and the crude product was used directly in the next step without purification. MS (ES): m/z=325.2 [M−H]⁺; HPLC Ret. Time 1.573 min. (HPLC Method D).

436

Intermediate 190B': tert-butyl 3-(5-(3-cyanoimidazo[1,2-b]pyridazin-6-yl)-4-(4-fluorophenyl)-1H-imidazol-1-yl)azetidine-1-carboxylate

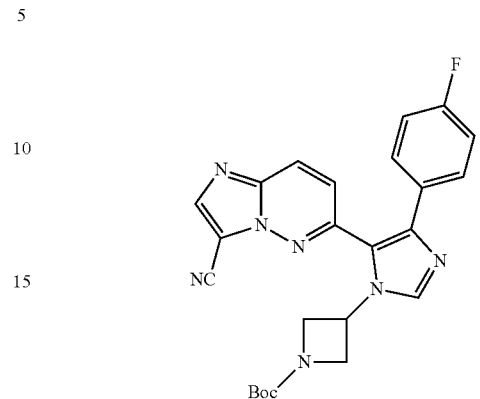

To a solution of intermediate 190A' (1.52 g, 4.7 mmol) in DMF (10 mL) were added potassium carbonate (0.780 g, 5.65 mmol) and 1-fluoro-4-(isocyano(tosyl)methyl)benzene (1.361 g, 4.71 mmol). The reaction mixture was stirred at RT overnight, and diluted with EtOAc and water. The layers were separated and the aqueous layer was extracted with EtOAc. The combined organic layers were washed with brine, dried over Na₂SO₄ and filtered. The filtrate was concentrated and the crude product was purified by silica gel chromatography (80 g RediSep® column, eluting with a gradient from 10-100% B in DCM, B: 10% MeOH in DCM). Fractions containing the product were combined and evaporated to afford intermediate 190B' (1.1 g, 51% yield). MS (ES): m/z=460.1 [M+H]⁺; HPLC Ret. Time 0.78 min. (HPLC Method C); ¹H NMR (400 MHz, CDCl₃) δ ppm 8.30 (s, 1H), 8.11 (s, 1H), 7.92 (d, J=9.5 Hz, 1H), 7.53-7.43 (m, 2H), 7.20-7.03 (m, 3H), 5.40 (ddd, J=7.8, 5.1, 2.6 Hz, 1H), 4.56 (t, J=8.7 Hz, 2H), 4.25 (dd, J=9.8, 5.0 Hz, 2H), 1.50 (s, 9H).

Intermediate 190C': 6-(1-(azetidin-3-yl)-4-(4-fluorophenyl)-1H-imidazol-5-yl)imidazo[1,2-b]pyridazine-3-carbonitrile

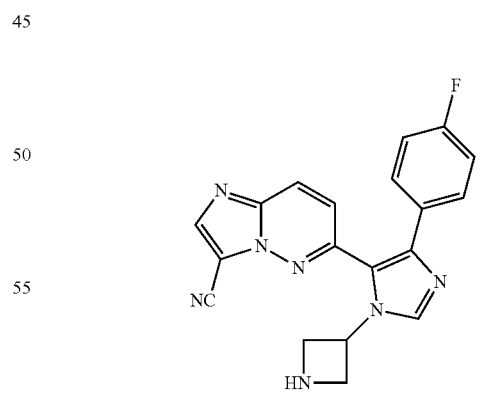

To a solution of intermediate 190B' (500 mg, 1.008 mmol) in DCM was added TFA (2 mL). The reaction mixture was stirred at RT overnight and concentrated. The residue was diluted with DCM and sat'd aq. NaHCO₃ solution. The layers were separated and the aqueous layer was extracted with DCM twice. The combined organic layers were washed with brine, dried over Na₂SO₄, and filtered. The filtrate was concentrated and the crude product was used in the next step. A small amount of the crude material was purified via preparative HPLC. Fractions containing the desired product were combined and dried under vacuum to afford Example 190C'. MS (ES): m/z=360.1 [M+H]⁺; HPLC Ret. Time 1.076 min. and 1.092 min. (HPLC Methods A and B, respectively).

Example 190' methyl 3-(5-(3-cyanoimidazo[1,2-b]pyridazin-6-yl)-4-(4-fluorophenyl)-1H-imidazol-1-yl)azetidine-1-carboxylate

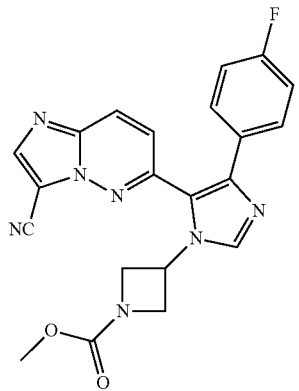 [SMILES: COC(=O)N1CC(n2cnc(-c3ccc(F)cc3)c2-c2ccc3ncc(C#N)n3n2)C1]

To a solution of Example 190C' (45 mg, 0.114 mmol) and Hunig's base (0.060 mL, 0.341 mmol) in THF (4 mL) was added methyl carbonochloridate (12.89 mg, 0.136 mmol). The reaction mixture was stirred at RT overnight and concentrated. The residue was dissolved in a mixture of DMF and methanol and purified via preparative HPLC. Fractions containing the desired product were combined and dried under vacuum to afford Example 190' (15.8 mg, 33% yield). MS (ES): m/z=418.1 [M+H]⁺; HPLC Ret. Time 1.26 min. and 1.404 min. (HPLC Methods A and B, respectively); ¹H NMR (500 MHz, DMSO-d₆) δ ppm 8.64 (s, 1H), 8.53 (s, 1H), 8.32 (d, J=9.5 Hz, 1H), 7.54 (dd, J=8.8, 5.5 Hz, 2H), 7.27 (d, J=9.5 Hz, 1H), 7.16 (t, J=8.8 Hz, 2H), 5.28 (t, J=7.0 Hz, 1H), 4.36 (br. s., 4H), 3.59 (s, 3H).

Example 191'

6-(1-(1-acetylazetidin-3-yl)-4-(4-fluorophenyl)-1H-imidazol-5-yl)imidazo[1,2-b]pyridazine-3-carbonitrile

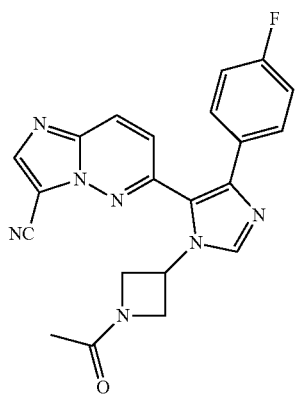 [SMILES: CC(=O)N1CC(n2cnc(-c3ccc(F)cc3)c2-c2ccc3ncc(C#N)n3n2)C1]

To a solution of intermediate 190C' (45 mg, 0.064 mmol) in THF were added pyridine (31.1 μL, 0.385 mmol) and acetyl chloride (15.11 mg, 0.192 mmol). The reaction mixture was stirred at RT overnight and then concentrated. The residue was dissolved in a mixture of DMF and methanol and purified via preparative HPLC. Fractions containing the desired product were combined and dried under vacuum to afford Example 191' (10.5 mg, 39% yield). MS (ES): m/z=402.1 [M+H]⁺; HPLC Ret. Time 1.066 min. and 1.244 min. (HPLC Methods A and B, respectively); ¹H NMR (500 MHz, DMSO-d₆) δ ppm 8.65 (s, 1H), 8.52 (s, 1H), 8.32 (d, J=9.2 Hz, 1H), 7.55 (dd, J=8.6, 5.7 Hz, 2H), 7.27 (d, J=9.5 Hz, 1H), 7.17 (t, J=8.8 Hz, 2H), 5.27 (t, J=5.9 Hz, 1H), 4.65-4.51 (m, 2H), 4.35-4.24 (m, 2H), 1.81 (s, 3H).

Example 192'

6-(1-(1-(cyclopropanecarbonyl)azetidin-3-yl)-4-(4-fluorophenyl)-1H-imidazol-5-yl)imidazo[1,2-b]pyridazine-3-carbonitrile

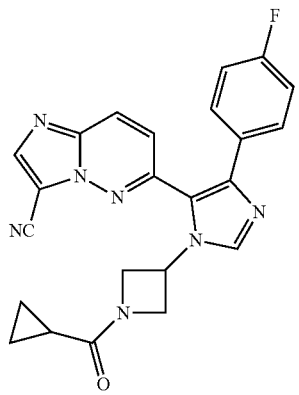 [SMILES: N#Cc1cnc2ccc(-c3c(-c4ccc(F)cc4)ncn3C3CN(C(=O)C4CC4)C3)nn12]

To a solution of intermediate 190C' (45 mg, 0.125 mmol) in THF (5 mL) were added pyridine (0.051 mL, 0.626 mmol) and cyclopropanecarbonyl chloride (13.09 mg, 0.125 mmol). The reaction mixture was stirred at RT overnight and then concentrated. The residue was dissolved in a mixture of DMF and methanol and purified via preparative HPLC. Fractions containing the desired product were combined and dried under vacuum to afford Example 192' (10.5 mg, 39% yield). MS (ES): m/z=428.1 [M+H]⁺; HPLC Ret. Time 1.186 min. and 1.402 min. (HPLC Methods A and B, respectively); ¹H NMR (500 MHz, DMSO-d₆) δ ppm 8.65 (s, 1H), 8.54 (s, 1H), 8.33 (d, J=9.5 Hz, 1H), 7.55 (dd, J=8.8, 5.5 Hz, 2H), 7.29 (d, J=9.5 Hz, 1H), 7.17 (t, J=8.8 Hz, 2H), 5.34 (t, J=7.5 Hz, 1H), 4.81-4.70 (m, 1H), 4.66 (br. s., 1H), 4.32 (br. s., 2H), 1.63-1.47 (m, 1H), 0.81-0.64 (m, 4H).

Example 193'

N-(tert-butyl)-3-(5-(3-cyanoimidazo[1,2-b]pyridazin-6-yl)-4-(4-fluorophenyl)-1H-imidazol-1-yl)azetidine-1-carboxamide

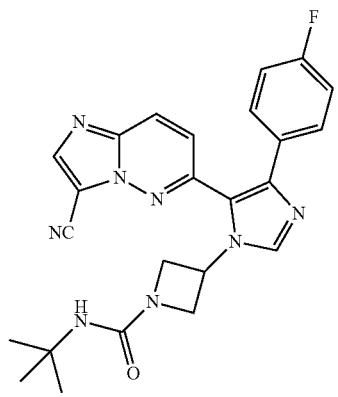 [SMILES: CC(C)(C)NC(=O)N1CC(n2cnc(-c3ccc(F)cc3)c2-c2ccc3ncc(C#N)n3n2)C1]

To a solution of intermediate 190C' (40 mg, 0.101 mmol) in DMF (1 mL) were added Hunig's base (0.053 mL, 0.303 mmol) and 2-isocyanato-2-methylpropane (15.03 mg, 0.152 mmol). The reaction mixture was stirred at RT for 2 h. The residue was dissolved a mixture of DMF and methanol and purified via preparative HPLC. Fractions containing the desired product were combined and dried under vacuum to afford Example 193' (21.4 mg, 46% yield). MS (ES): m/z=459.1 [M+H]$^+$; HPLC Ret. Time 1.4 min. and 1.576 min. (HPLC Methods A and B, respectively); $^1$H NMR (500 MHz, DMSO-d$_6$) δ ppm 8.65 (s, 1H), 8.41 (s, 1H), 8.33 (d, J=9.5 Hz, 1H), 7.55 (dd, J=8.8, 5.5 Hz, 2H), 7.28 (d, J=9.5 Hz, 1H), 7.17 (t, J=9.0 Hz, 2H), 5.19 (t, J=5.5 Hz, 1H), 4.23 (t, J=8.4 Hz, 2H), 4.10 (dd, J=8.8, 5.5 Hz, 2H), 1.24 (s, 9H).

Example 194'

6-(1-(1-(cyanomethyl)azetidin-3-yl)-4-(4-fluorophenyl)-1H-imidazol-5-yl)imidazo[1,2-b]pyridazine-3-carbonitrile

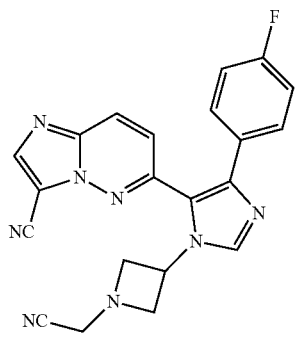 [SMILES: N#CCN1CC(n2cnc(-c3ccc(F)cc3)c2-c2ccc3ncc(C#N)n3n2)C1]

To a solution of intermediate 190C' (45 mg, 0.125 mmol) in DMF were added 2-bromoacetonitrile (45.1 mg, 0.376 mmol) and potassium carbonate (34.6 mg, 0.250 mmol). The reaction mixture was stirred at RT overnight, filtered and washed with MeOH. The filtrate was concentrated and the residue was dissolved in a mixture of DMF and methanol, and purified via preparative HPLC. Fractions containing the desired product were combined and dried under vacuum to afford Example 194' (25.6 mg, 51% yield). MS (ES): m/z=399.1 [M+H]$^+$; HPLC Ret. Time 1.12 min. and 1.384 min. (HPLC Methods A and B, respectively); $^1$H NMR (500 MHz, DMSO-d$_6$) δ ppm 8.64 (s, 1H), 8.38 (s, 1H), 8.31 (d, J=9.5 Hz, 1H), 7.54 (dd, J=8.8, 5.5 Hz, 2H), 7.27 (d, J=9.2 Hz, 1H), 7.17 (t, J=8.8 Hz, 2H), 5.03 (t, J=6.6 Hz, 1H), 3.88-3.71 (m, 2H), 3.77 (s, 2H), 3.71-3.52 (m, 2H).

Scheme 11

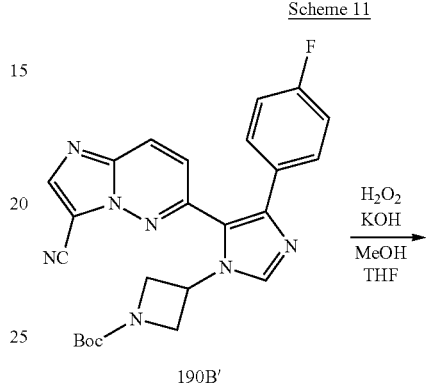

190B'

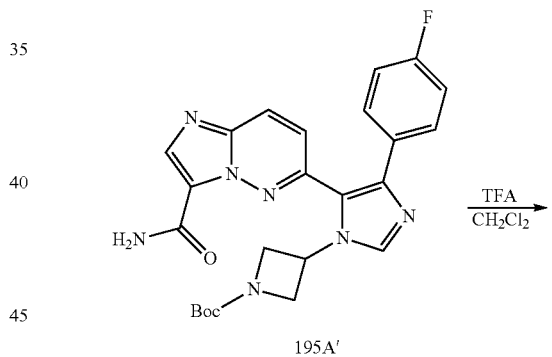

195A'

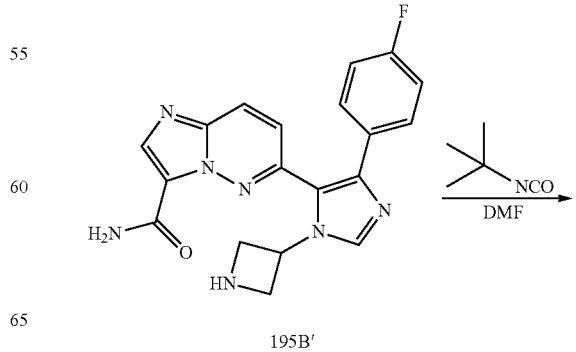

195B'

-continued

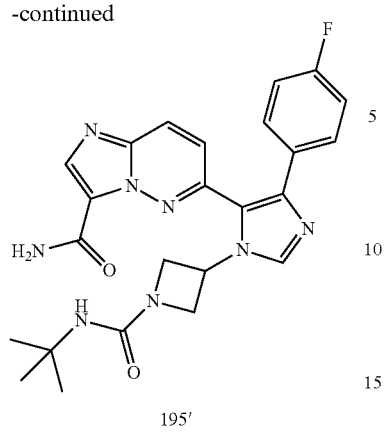

195'

Intermediate 195A': tert-butyl 3-(5-(3-carbamoylimidazo[1,2-b]pyridazin-6-yl)-4-(4-fluorophenyl)-1H-imidazol-1-yl)azetidine-1-carboxylate

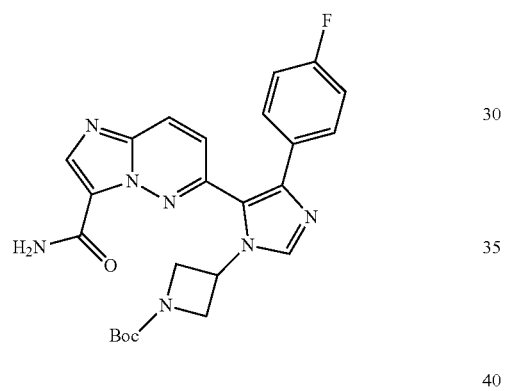

To a solution of intermediate 190B' (300 mg, 0.653 mmol) in MeOH (10 mL) and THF (10 mL) were added 4 M solution of potassium hydroxide (0.326 mL, 1.306 mmol) and 30% solution of $H_2O_2$ (0.667 mL, 6.53 mmol). The reaction mixture was stirred at RT overnight and concentrated. The residue was carefully neutralized with 1 N HCl to pH 7, diluted with DCM and sat'd aq. NaHCO$_3$. The layers were separated and the aqueous layer was extracted with DCM. The combined organic layers were washed with brine, dried over $Na_2SO_4$, and filtered. The filtrate was concentrated and the residue was dissolved in a mixture of DMF and methanol and purified via preparative HPLC. Fractions containing the desired product were combined and dried under vacuum to afford Example 195A' (248 mg, 79% yield). MS (ES): m/z=478.1 [M+H]$^+$; HPLC Ret. Time 1.162 min. and 1.387 min. (HPLC Methods A and B, respectively); $^1$H NMR (500 MHz, DMSO-d$_6$) δ ppm 8.47 (s, 1H), 8.36 (s, 1H), 8.30 (d, J=9.2 Hz, 1H), 7.83 (br. s., 2H), 7.50 (dd, J=8.8, 5.5 Hz, 2H), 7.22 (d, J=9.2 Hz, 1H), 5.27 (t, J=7.0 Hz, 1H), 4.22 (d, J=8.1 Hz, 4H), 1.38 (s, 9H).

Intermediate 195B': 6-(1-(azetidin-3-yl)-4-(4-fluorophenyl)-1H-imidazol-5-yl)imidazo[1,2-b]pyridazine-3-carboxamide

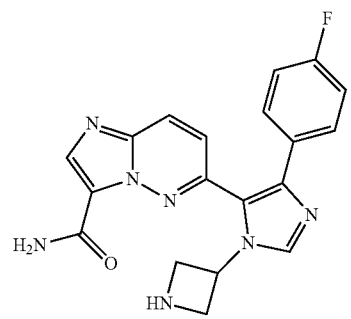 [SMILES: NC(=O)c1cnc2ccc(-c3c(-c4ccc(F)cc4)ncn3C3CNC3)nn12]

To a solution of intermediate 195A' (248 mg, 0.52 mmol) in DCM (12 mL) was added TFA (1 mL). The reaction mixture was stirred at RT overnight and concentrated. The crude material was dissolved in a mixture of DMF and methanol and purified via preparative HPLC. Fractions containing the desired product were combined and dried under vacuum to afford Example 195B' (248 mg, 79% yield). MS (ES): m/z=378.1 [M+H]$^+$; HPLC Ret. Time 0.825 min. and 0.962 min. (HPLC Methods A and B, respectively); $^1$H NMR (500 MHz, DMSO-d$_6$) δ ppm 8.36 (s, 1H), 8.38 (s, 1H), 8.30 (d, J=9.2 Hz, 1H), 7.88 (br. s., 2H, NH$_2$), 7.81 (br. s., 1H, NH), 7.54-7.45 (m, 2H), 7.21 (d, J=9.5 Hz, 1H), 7.18-7.08 (m, 2H), 5.24-5.12 (m, 1H), 3.87-3.76 (m, 2H), 3.76-3.60 (m, 2H).

Example 195'

6-(1-(1-(tert-butylcarbamoyl)azetidin-3-yl)-4-(4-fluorophenyl)-1H-imidazol-5-yl)imidazo[1,2-b]pyridazine-3-carboxamide

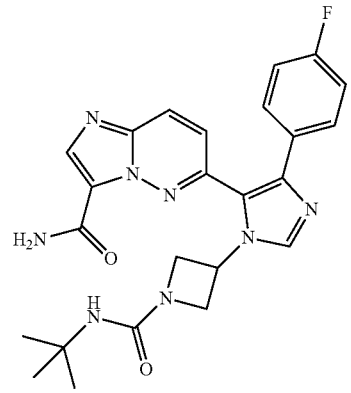 [SMILES: CC(C)(C)NC(=O)N1CC(n2cnc(-c3ccc(F)cc3)c2-c2ccc3ncc(C(N)=O)n3n2)C1]

To a solution of Example 195B' (30 mg, 0.042 mmol) in DMF (1 mL) were added TEA (5.81 µL, 0.042 mmol) and 2-isocyanato-2-methylpropane (4.13 mg, 0.042 mmol). The reaction mixture was stirred at RT for 2 h and purified via preparative HPLC. Fractions containing the desired product were combined and dried under vacuum to afford Example 195' (15.7 mg, 79% yield). MS (ES): m/z=477.1 [M+H]$^+$; HPLC Ret. Time 1.058 min. and 1.252 min. (HPLC Methods A and B, respectively); $^1$H NMR (500 MHz, DMSO-d$_6$) δ ppm 8.36 (d, J=2.2 Hz, 2H), 8.30 (d, J=9.2 Hz, 1H), 7.83 (s, 2H), 7.51 (dd, J=8.8, 5.5 Hz, 2H), 7.23 (d, J=9.5 Hz, 1H), 7.15 (t, J=8.8 Hz, 2H), 5.24 (s, 1H), 4.22-4.07 (m, 2H), 4.02 (dd, J=8.8, 5.5 Hz, 2H), 1.28-1.13 (m, 9H).

Scheme 12

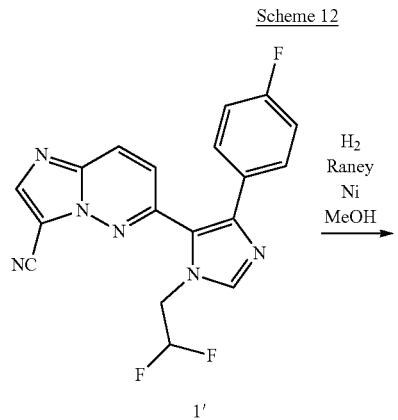

1'

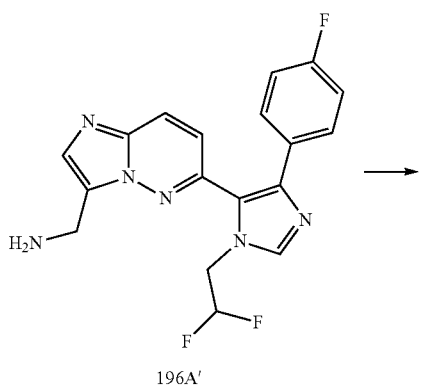

196A'

196'-202'

Intermediate 196A': (6-(1-(2,2-difluoroethyl)-4-(4-fluorophenyl)-1H-imidazol-5-yl)imidazo[1,2-b]pyridazin-3-yl)methanamine

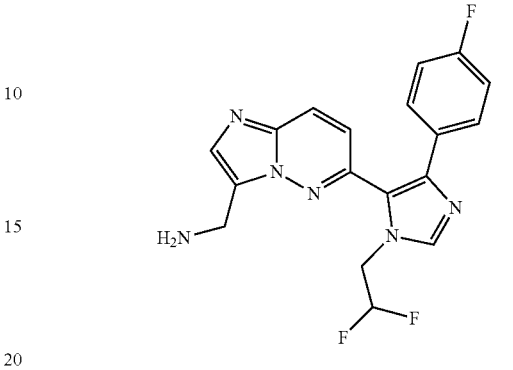

To a suspension of Example 1' (110 mg, 0.299 mmol) in MeOH (60 mL) (2 M $NH_3$ MeOH solution) was added Raney Nickel under nitrogen. The reaction mixture was exposed to 50 psi hydrogen at RT overnight. The reaction mixture was passed through a pad of Celite® and washed with MeOH. The filtrate was concentrated and the crude material was dissolved in MeOH and purified via preparative HPLC. Fractions containing the desired product were combined and dried under vacuum to afford intermediate 196A'. MS (ES): m/z=373.1 $[M+H]^+$; HPLC Ret. Time 0.926 min. and 1.103 min. (HPLC Methods A and B, respectively); $^1$H NMR (500 MHz, DMSO-$d_6$) δ ppm 8.13-7.97 (m, 2H), 7.75 (br. s., 1H), 7.50 (dd, J=8.4, 5.5 Hz, 2H), 7.18 (t, J=8.8 Hz, 2H), 6.93 (d, J=8.4 Hz, 1H), 6.41 (t, J=14.7 Hz, 1H), 4.77 (t, J=14.7 Hz, 2H), 4.11 (br. s., 2H).

Example 196'

(6-(1-(2,2-difluoroethyl)-4-(4-fluorophenyl)-1H-imidazol-5-yl)imidazo[1,2-b]pyridazin-3-yl)methanamine

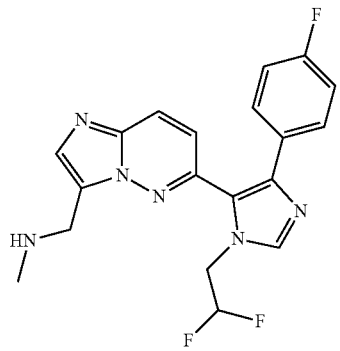 [SMILES: CNCc1cnc2ccc(-c3c(-c4ccc(F)cc4)ncn3CC(F)F)nn12]

A solution of intermediate 196A' (35 mg, 0.072 mmol) in ethyl formate (267 mg, 3.60 mmol) was heated at 70° C. for 6 h, cooled to RT and concentrated. The residue was dissolved in THF (5 mL). $BH_3$-dimethyl sulfide (0.014 mL, 0.144 mmol) was added and the reaction mixture was heated at 70° C. for 2 h. The reaction mixture was cooled to RT and carefully quenched with MeOH. The reaction mixture was stirred at RT for 1 h and then concentrated. The crude material was dissolved in a mixture of DMF and methanol and purified via preparative HPLC. Fractions containing the desired product were combined and dried under vacuum to afford Example 196' (10.4 mg, 37% yield). MS (ES): m/z=387.2 [M+H]⁺; HPLC Ret. Time 0.952 min. and 1.063 min. (HPLC Methods A and B, respectively); ¹H NMR (500 MHz, DMSO-$d_6$) δ ppm 8.09-7.98 (m, 2H), 7.86-7.72 (m, 1H), 7.49 (dd, J=8.8, 5.5 Hz, 2H), 7.17 (t, J=8.8 Hz, 2H), 6.96 (d, J=9.5 Hz, 1H), 6.41 (m, 1H), 4.85-4.67 (m, 2H), 4.07 (s, 1H), 3.1 (s, 3H).

Example 197'

N-((6-(1-(2,2-difluoroethyl)-4-(4-fluorophenyl)-1H-imidazol-5-yl)imidazo[1,2-b]pyridazin-3-yl)methyl)acetamide

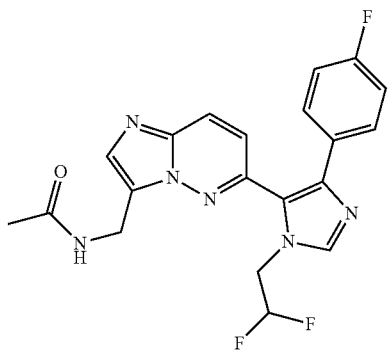 [SMILES: CC(=O)NCc1cnc2ccc(-c3c(-c4ccc(F)cc4)ncn3CC(F)F)nn12]

To a solution of intermediate 196A' (30 mg, 0.081 mmol) in THF (5 mL) were added pyridine (0.014 mL, 0.177 mmol) and acetic anhydride (9.87 mg, 0.097 mmol). The reaction mixture was stirred at RT overnight, quenched with MeOH and concentrated. The residue was dissolved in a mixture of DMF and methanol and purified via preparative HPLC. Fractions containing the desired product were combined and dried under vacuum to afford Example 197' (19.8 mg, 59% yield). MS (ES): m/z=415.1 [M+H]⁺; HPLC Ret. Time 0.982 min. and 1.247 min. (HPLC Methods A and B, respectively); ¹H NMR (500 MHz, DMSO-$d_6$) δ ppm 8.09 (d, J=9.5 Hz, 1H), 8.04 (s, 1H), 7.77 (s, 1H), 7.56-7.45 (m, 2H), 7.18 (t, J=8.8 Hz, 2H), 6.95 (d, J=9.5 Hz, 1H), 6.39 (m, 1H), 4.90-4.74 (m, 2H), 4.66 (d, J=5.1 Hz, 2H), 1.86 (s, 3H).

Example 198'

N-((6-(1-(2,2-difluoroethyl)-4-(4-fluorophenyl)-1H-imidazol-5-yl)imidazo[1,2-b]pyridazin-3-yl)methyl)cyclopropanecarboxamide

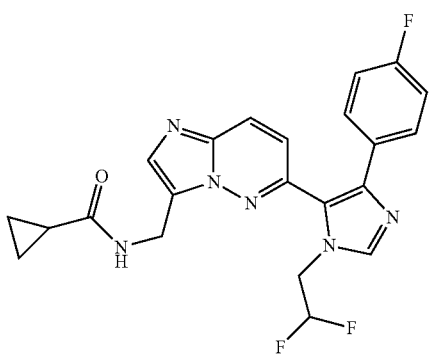 [SMILES: O=C(NCc1cnc2ccc(-c3c(-c4ccc(F)cc4)ncn3CC(F)F)nn12)C1CC1]

To a solution of 196A' (30 mg, 0.081 mmol) in THF (5 mL) were added pyridine (0.014 mL, 0.177 mmol) and cyclopropanecarbonyl chloride (10.11 mg, 0.097 mmol). The reaction mixture was stirred at RT for 2 h, quenched with MeOH and concentrated. The residue was dissolved in a mixture of DMF and methanol and purified via preparative HPLC. Fractions containing the desired product were combined and dried under vacuum to afford Example 198' (25 mg, 70% yield). MS (ES): m/z=441.1 [M+H]⁺; HPLC Ret. Time 1.066 min. and 1.378 min. (HPLC Methods A and B, respectively); ¹H NMR (500 MHz, DMSO-$d_6$) δ ppm 8.09 (d, J=9.5 Hz, 1H), 8.04 (s, 1H), 7.77 (s, 1H), 7.50 (dd, J=8.8, 5.5 Hz, 2H), 7.18 (t, J=8.8 Hz, 2H), 6.96 (d, J=9.5 Hz, 1H), 6.35 (m, 1H), 4.88-4.74 (m, 2H), 4.70 (d, J=5.5 Hz, 2H), 1.65-1.51 (m, 1H), 0.73-0.63 (m, 4H).

Example 199'

1-(tert-butyl)-3-((6-(1-(2,2-difluoroethyl)-4-(4-fluorophenyl)-1H-imidazol-5-yl)imidazo[1,2-b]pyridazin-3-yl)methyl)urea

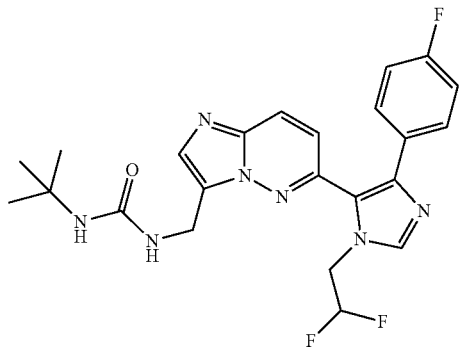 [SMILES: CC(C)(C)NC(=O)NCc1cnc2ccc(-c3c(-c4ccc(F)cc4)ncn3CC(F)F)nn12]

To a solution of intermediate 196A' (25 mg, 0.067 mmol) in THF (3 mL) was added 2-isocyanato-2-methylpropane (6.66 mg, 0.067 mmol). The reaction mixture was stirred at RT for 30 min, quenched with MeOH and concentrated. The residue was dissolved in a mixture of DMF and methanol and purified via preparative HPLC. Fractions containing the desired product were combined and dried under vacuum to afford Example 199' (14.4 mg, 45% yield). MS (ES): m/z=472.1 [M+H]⁺; HPLC Ret. Time 1.203 min. and 1.515 min. (HPLC Methods A and B, respectively); ¹H NMR (500 MHz, DMSO-$d_6$) δ ppm 8.13-7.96 (m, 2H), 7.70 (s, 1H), 7.50 (dd, J=8.8, 5.5 Hz, 2H), 7.18 (t, J=8.8 Hz, 2H), 6.94 (d, J=9.5 Hz, 1H), 6.39 (m, 1H), 6.18 (t, J=5.9 Hz, 1H), 5.76 (s, 1H), 4.89-4.72 (m, 2H), 4.59 (d, J=5.5 Hz, 2H), 1.21 (s, 9H).

Example 200'

Methyl ((6-(1-(2,2-difluoroethyl)-4-(4-fluorophenyl)-1H-imidazol-5-yl)imidazo[1,2-b]pyridazin-3-yl)methyl)carbamate

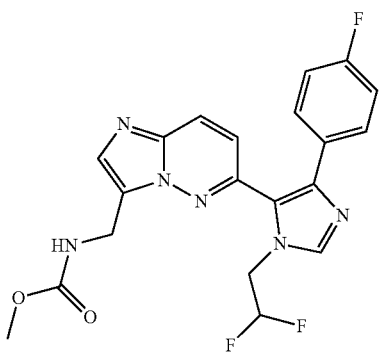 [SMILES: COC(=O)NCc1cnc2ccc(-c3c(-c4ccc(F)cc4)ncn3CC(F)F)nn12]

To a solution of intermediate 196A' (30 mg, 0.081 mmol) in THF (1 mL) were added Hunig's base (0.028 mL, 0.161 mmol) and methyl carbonochloridate (11.42 mg, 0.121 mmol). The reaction mixture was stirred at RT for 1 h and concentrated. The residue was dissolved in a mixture of DMF and methanol, purified via preparative HPLC. Fractions containing the desired product were combined and dried under vacuum to afford Example 200' (21.2 mg, 60% yield). MS (ES): m/z=431.1 [M+H]$^+$; HPLC Ret. Time 1.046 min. and 1.362 min. (HPLC Methods A and B, respectively); $^1$H NMR (500 MHz, DMSO-d$_6$) δ ppm 8.14-7.96 (m, 2H), 7.82-7.66 (m, 2H), 7.50 (dd, J=8.8, 5.5 Hz, 2H), 7.18 (t, J=8.8 Hz, 2H), 6.95 (d, J=9.5 Hz, 1H), 6.37 (m, 1H), 4.88-4.72 (m, 2H), 4.62 (d, J=5.5 Hz, 2H), 2.55 (s, 3H).

Example 201'

Isopropyl ((6-(1-(2,2-difluoroethyl)-4-(4-fluorophenyl)-1H-imidazol-5-yl)imidazo[1,2-b]pyridazin-3-yl)methyl)carbamate

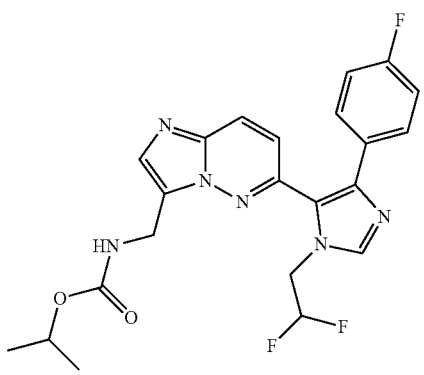 [SMILES: CC(C)OC(=O)NCc1cnc2ccc(-c3c(-c4ccc(F)cc4)ncn3CC(F)F)nn12]

To a solution of intermediate 196A' (30 mg, 0.081 mmol) in THF (1 mL) were added Hunig's base (0.028 mL, 0.161 mmol) and isopropyl carbonochloridate (0.121 mL, 0.121 mmol, 1M solution in toluene). The reaction mixture was stirred at RT overnight, quenched with MeOH and concentrated. The residue was dissolved in a mixture of DMF and methanol and purified via preparative HPLC. Fractions containing the desired product were combined and dried under vacuum to afford Example 201' (25.6 mg, 69% yield). MS (ES): m/z=459.1 [M+H]$^+$; HPLC Ret. Time 1.223 min. and 1.568 min. (HPLC Methods A and B, respectively); $^1$H NMR (500 MHz, DMSO-d$_6$) δ ppm 8.14-7.92 (m, 2H), 7.73 (s, 1H), 7.60 (br. s., 1H), 7.50 (dd, J=8.8, 5.5 Hz, 2H), 7.18 (t, J=9.0 Hz, 2H), 6.95 (d, J=9.5 Hz, 1H), 6.38 (m, 1H), 4.89-4.73 (m, 3H), 4.60 (d, J=5.5 Hz, 2H), 3.39 (d, J=7.0 Hz, 1H), 1.15 (d, J=6.2 Hz, 6H).

Example 202'

N-((6-(1-(2,2-difluoroethyl)-4-(4-fluorophenyl)-1H-imidazol-5-yl)imidazo[1,2-b]pyridazin-3-yl)methyl)pivalamide

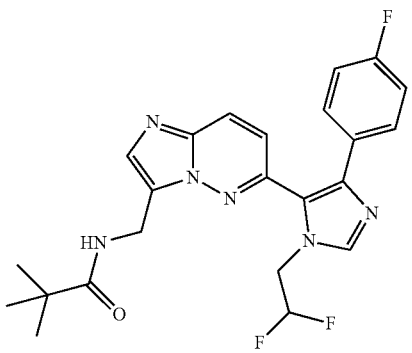 [SMILES: CC(C)(C)C(=O)NCc1cnc2ccc(-c3c(-c4ccc(F)cc4)ncn3CC(F)F)nn12]

To a solution of intermediate 196A' (30 mg, 0.081 mmol) in CH$_2$Cl$_2$ (5 mL) were added pyridine (0.013 mL, 0.161 mmol) and pivaloyl chloride (14.57 mg, 0.121 mmol). The reaction mixture was stirred at RT for 1 h, quenched with MeOH and concentrated. The residue was dissolved in a mixture of DMF and methanol and purified via preparative HPLC. Fractions containing the desired product were combined and dried under vacuum to afford Example 202' (22.5 mg, 61% yield). MS (ES): m/z=457.1 [M+H]$^+$; HPLC Ret. Time 1.21 min. and 1.579 min. (HPLC Methods A and B, respectively); $^1$H NMR (500 MHz, DMSO-d$_6$) δ ppm 8.09 (d, J=9.5 Hz, 1H), 8.05-7.96 (m, 2H), 7.68 (s, 1H), 7.48 (dd, J=8.6, 5.7 Hz, 2H), 7.18 (t, J=9.0 Hz, 2H), 6.95 (d, J=9.2 Hz, 1H), 4.79 (d, J=3.3 Hz, 2H), 4.68 (d, J=5.5 Hz, 2H), 1.11 (s, 9H).

Scheme 13

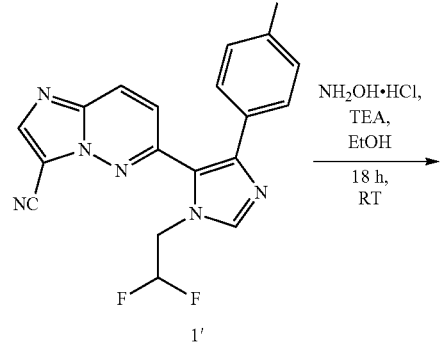

Example 203'

6-(1-(2,2-difluoroethyl)-4-(4-fluorophenyl)-1H-imidazol-5-yl)-N-hydroxyimidazo[1,2-b]pyridazine-3-carboximidamide

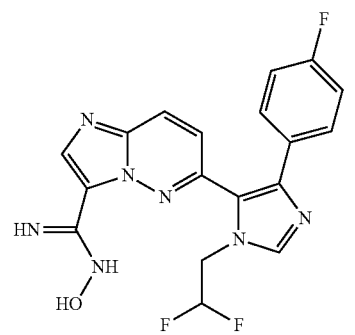 [SMILES: N=C(NO)c1cnc2ccc(-c3c(-c4ccc(F)cc4)ncn3CC(F)F)nn12]

203'

To a suspension of Example 1' (0.045 g, 0.122 mmol) in EtOH (1.2 mL) was added TEA (0.026 mL, 0.183 mmol) and hydroxylamine hydrochloride (9.34 mg, 0.134 mmol). The reaction mixture was stirred at RT for 18 h and then purified via preparative HPLC. Fractions containing the product were combined and evaporated to afford Example 203' (0.043 g, 83% yield). MS (ES): m/z=402.1 [M+H]$^+$; HPLC Ret. Time 0.943 min. and 1.269 min. (HPLC Methods A and B, respectively); $^1$H NMR (500 MHz, DMSO-d$_6$) δ ppm 8.13 (d, J=9.2 Hz, 1H), 8.04 (d, J=8.4 Hz, 2H), 7.51 (dd, J=8.8, 5.5 Hz, 2H), 7.18 (t, J=8.8 Hz, 2H), 7.00 (d, J=9.5 Hz, 1H), 6.46 (s, 1H), 6.02 (s, 2H), 4.76 (t, J=15.2 Hz, 2H).

Scheme 14

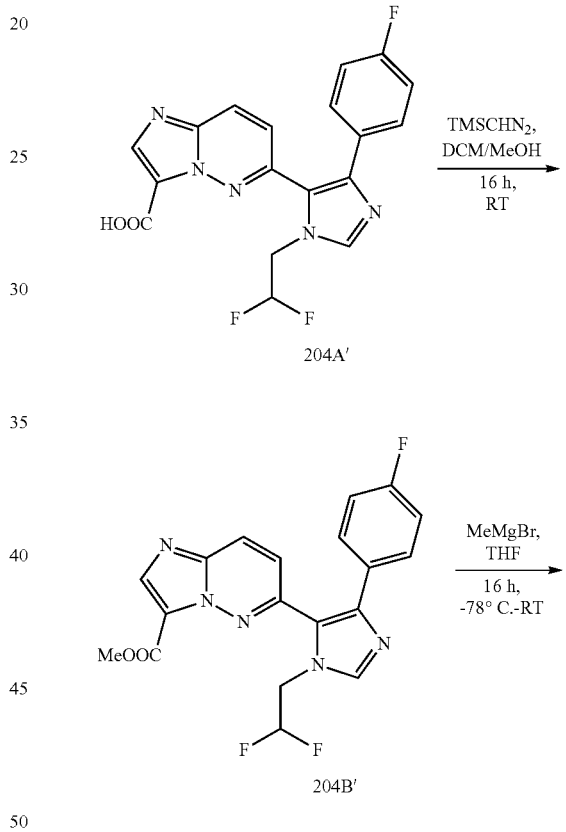

Intermediate 204A': 6-(1-(2,2-difluoroethyl)-4-(4-fluorophenyl)-1H-imidazol-5-yl)imidazo[1,2-b]pyridazine-3-carboxylic acid, 3 TFA

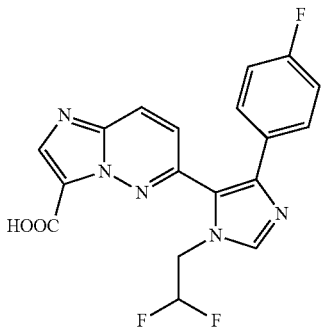 [SMILES: O=C(O)c1cnc2ccc(-c3c(-c4ccc(F)cc4)ncn3CC(F)F)nn12]

A solution of Example 1' (1.145 g, 3.11 mmol) in conc. HCl (0.77 mL, 9.33 mmol) was heated in an oil bath at 100° C. for 1 h. The reaction mixture was then cooled to RT, diluted with aq. acetonitrile and purified by reverse phase column chromatography (240 g reverse phase Commodity® column, eluting with a gradient of 0-50% acetonitrile in water containing 0.1% TFA). Fractions containing the product were combined and evaporated to afford Example 204A' (1.29 g, 57% yield). MS (ES): m/z=388.0 [M+H]$^+$; HPLC Ret. Time 1.032 min. (HPLC Method A).

Intermediate 204B': methyl 6-(1-(2,2-difluoroethyl)-4-(4-fluorophenyl)-1H-imidazol-5-yl)imidazo[1,2-b]pyridazine-3-carboxylate

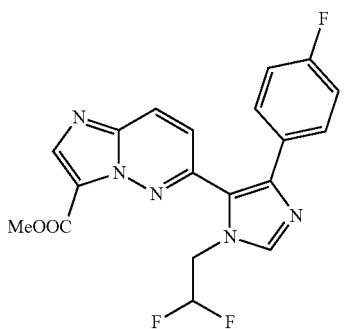 [SMILES: COC(=O)c1cnc2ccc(-c3c(-c4ccc(F)cc4)ncn3CC(F)F)nn12]

To a suspension of intermediate 204A' (0.1 g, 0.258 mmol) in DCM (1.3 mL) and MeOH (1.3 mL) was added TMS-diazomethane (0.775 mL, 1.549 mmol, 2M solution in hexanes). During the addition, bubbling was observed and the reaction mixture became homogenous. The reaction mixture was stirred at RT for 16 h and then concentrated under reduced pressure. The residue was purified by silica gel chromatography (12 g RediSep® column, eluting with 96-100% EtOAc in hexanes). Fractions containing the product were combined and evaporated to afford intermediate 204B' (0.063 g, 61% yield) as a pale yellow solid. MS (ES): m/z=402.0 [M+H]$^+$; HPLC Ret. Time 0.72 min. (HPLC Method C).

Example 204'

2-(6-(1-(2,2-difluoroethyl)-4-(4-fluorophenyl)-1H-imidazol-5-yl)imidazo[1,2-b]pyridazin-3-yl)propan-2-ol

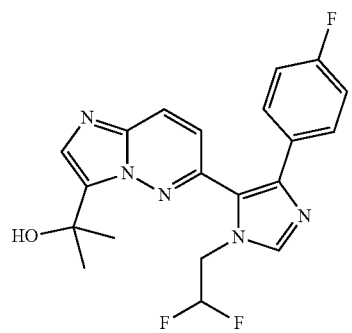 [SMILES: CC(C)(O)c1cnc2ccc(-c3c(-c4ccc(F)cc4)ncn3CC(F)F)nn12]

To a −78° C. solution of intermediate 204B' (0.045 g, 0.112 mmol) in THF (1.12 mL) was added, dropwise, methylmagnesium bromide (0.187 mL, 0.561 mmol, 3M solution in Et$_2$O). The reaction mixture was gradually allowed to warm to RT, stirred for 18 h, and quenched with satd. aq. NH$_4$Cl solution. The resulting two layers were separated and the aq. layer back-extracted with EtOAc (2×10 mL). The combined organic layers were washed with water and brine, dried over anhydrous MgSO$_4$, and filtered. The filtrate was concentrated under reduced pressure to give an oil, which was purified via preparative HPLC. Fractions containing the product were combined and evaporated to afford Example 204' (0.03 g, 71.6% yield). MS (ES): m/z=402.1 [M+H]$^+$; HPLC Ret. Time 1.064 min. and 1.386 min. (HPLC Methods A and B, respectively); $^1$H NMR (500 MHz, DMSO-d$_6$) δ ppm 8.08 (d, J=9.2 Hz, 1H), 8.03 (s, 1H), 7.71 (s, 1H), 7.53-7.43 (m, 2H), 7.17 (t, J=8.8 Hz, 2H), 6.98 (d, J=9.5 Hz, 1H), 6.38 (s, 1H), 4.85-4.70 (m, 2H), 1.65 (s, 6H).

Scheme 15

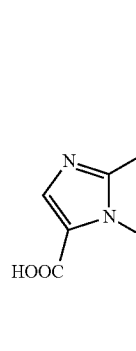

204A'

N₂H₄·HCl, HATU, DIPEA, DMF
1 h, RT
→

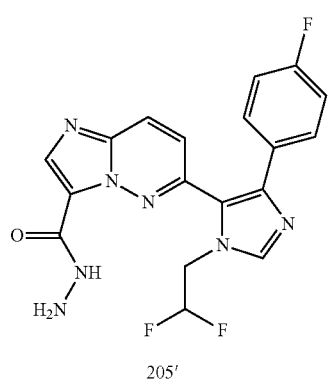

205'

Example 205'

6-(1-(2,2-difluoroethyl)-4-(4-fluorophenyl)-1H-imidazol-5-yl)imidazo[1,2-b]pyridazine-3-carbohydrazide

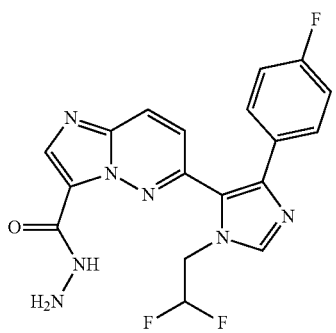 [SMILES: NNC(=O)c1cnc2ccc(-c3c(-c4ccc(F)cc4)ncn3CC(F)F)nn12]

A solution of intermediate 204A' (0.045 g, 0.062 mmol), hydrazine hydrochloride (8.45 mg, 0.123 mmol), HATU (0.047 g, 0.123 mmol) and DIPEA (0.065 mL, 0.370 mmol) in DMF (0.62 mL) was stirred at RT for 1 h. The mixture was then purified via preparative HPLC. Fractions containing the product were combined and evaporated to afford Example 205' (0.011 g, 41.8% yield). MS (ES): m/z=402.3 [M+H]$^+$; HPLC Ret. Time 0.978 min. and 1.204 min. (HPLC Methods A and B, respectively); $^1$H NMR (500 MHz, DMSO-d$_6$) δ ppm 8.30 (s, 1H), 8.22 (d, J=9.5 Hz, 1H), 8.05 (s, 1H), 7.52 (dd, J=8.8, 5.5 Hz, 2H), 7.22-7.08 (m, 3H), 4.86-4.68 (m, 2H), 4.04 (s, 2H).

Compounds shown in Table 13 have been synthesized analogous to Example 205' by amide bond coupling between intermediate 204A' and corresponding amines.

TABLE 13

| Ex. | Structure | Name | [M + H]$^+$ | Ret. Time (min.) | HPLC Method |
|---|---|---|---|---|---|
| 206' | 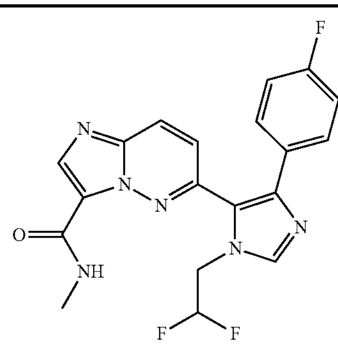 | 6-(1-(2,2-difluoroethyl)-4-(4-fluorophenyl)-1H-imidazol-5-yl)-N-methyl-imidazo[1,2-b]pyridazine-3-carboxamide | 401.3 | 1.348, 1.107 | A B |
| 207' | 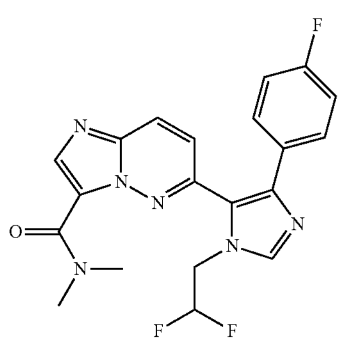 [SMILES: CN(C)C(=O)c1cnc2ccc(-c3c(-c4ccc(F)cc4)ncn3CC(F)F)nn12] | 6-(1-(2,2-difluoroethyl)-4-(4-fluorophenyl)-1H-imidazol-5-yl)-N,N-dimethylimidazo[1,2-b]pyridazine-3-carboxamide | 415.2 | 1.078, 1.30 | A B |

TABLE 13-continued

| Ex. | Structure | Name | [M + H]+ | Ret. Time (min.) | HPLC Method |
|---|---|---|---|---|---|
| 208' | 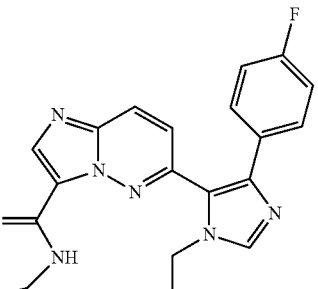 | N-cyclopropyl-6-(1-(2,2-difluoroethyl)-4-(4-fluorophenyl)-1H-imidazol-5-yl)imidazo[1,2-b]pyridazine-3-carboxamide | 427.05 | 1.447, 1.195 | A B |
| 209' | 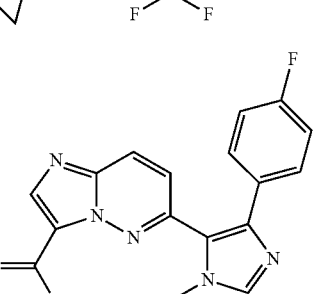 | 6-(1-(2,2-difluoroethyl)-4-(4-fluorophenyl)-1H-imidazol-5-yl)-N-methoxy-imidazo[1,2-b]pyridazine-3-carboxamide | 417.3 | 1.342, 1.066 | A B |

Scheme 16

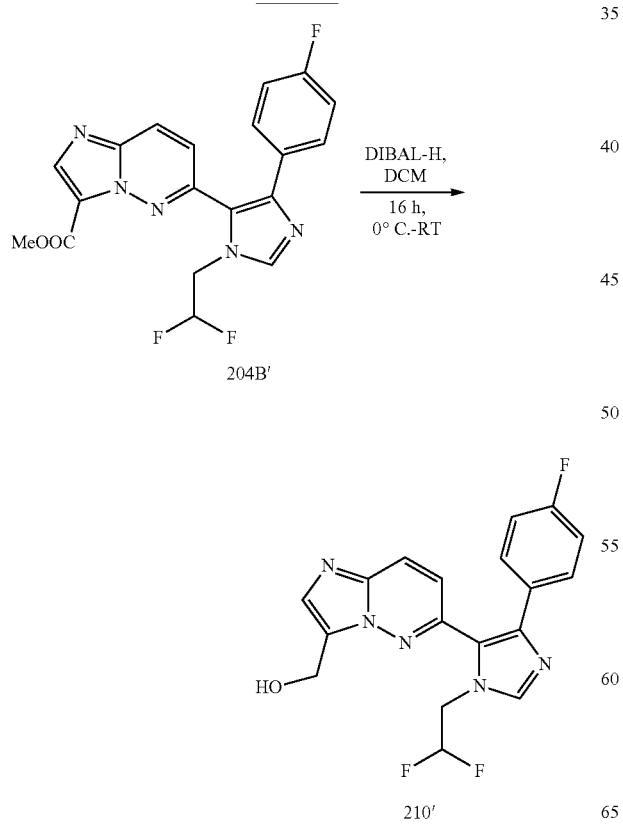

Example 210'

(6-(1-(2,2-difluoroethyl)-4-(4-fluorophenyl)-1H-imidazol-5-yl)imidazo[1,2-b]pyridazin-3-yl)methanol

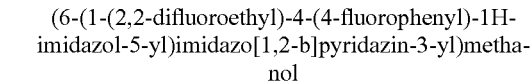

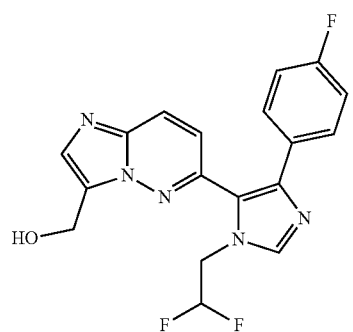 [SMILES: OCc1cnc2ccc(-c3c(-c4ccc(F)cc4)ncn3CC(F)F)nn12]

To a 0° C. solution of intermediate 204B' (0.133 g, 0.331 mmol) in DCM (3.31 mL) was added DIBAL-H (1.16 mL, 1.16 mmol, 1M solution in hexanes). The reaction was allowed to stir at RT for 16 h, quenched with satd. aq. sodium potassium tartrate at RT. After the mixture was stirred for 10 min, it was extracted with DCM (2×10 mL). The combined organic layers were washed with water, brine, dried over anhydrous MgSO$_4$, and filtered. The filtrate was concentrated under reduced pressure and the residue was purified by preparative HPLC. Fractions containing the product were combined and evaporated to afford Example 210' (0.018 g, 51.4% yield). MS (ES): m/z=374.0 [M+H]+; HPLC Ret. Time 1.007 min. and 1.340 min. (HPLC Methods A and B, respectively); ¹H NMR (500 MHz, DMSO-d₆) δ ppm 8.09 (d, J=9.2 Hz, 1H), 8.04 (s, 1H), 7.80 (s, 1H), 7.51 (dd, J=8.8, 5.5 Hz, 2H), 7.18 (t, J=9.0 Hz, 2H), 6.96 (d, J=9.5 Hz, 1H), 6.44 (s, 1H), 4.88 (d, J=3.7 Hz, 2H), 4.83-4.71 (m, 2H).

Example 211' methyl (6-(1-(2,2-difluoroethyl)-4-(4-fluorophenyl)-1H-imidazol-5-yl)imidazo[1,2-b]pyridazin-3-yl) carbamate

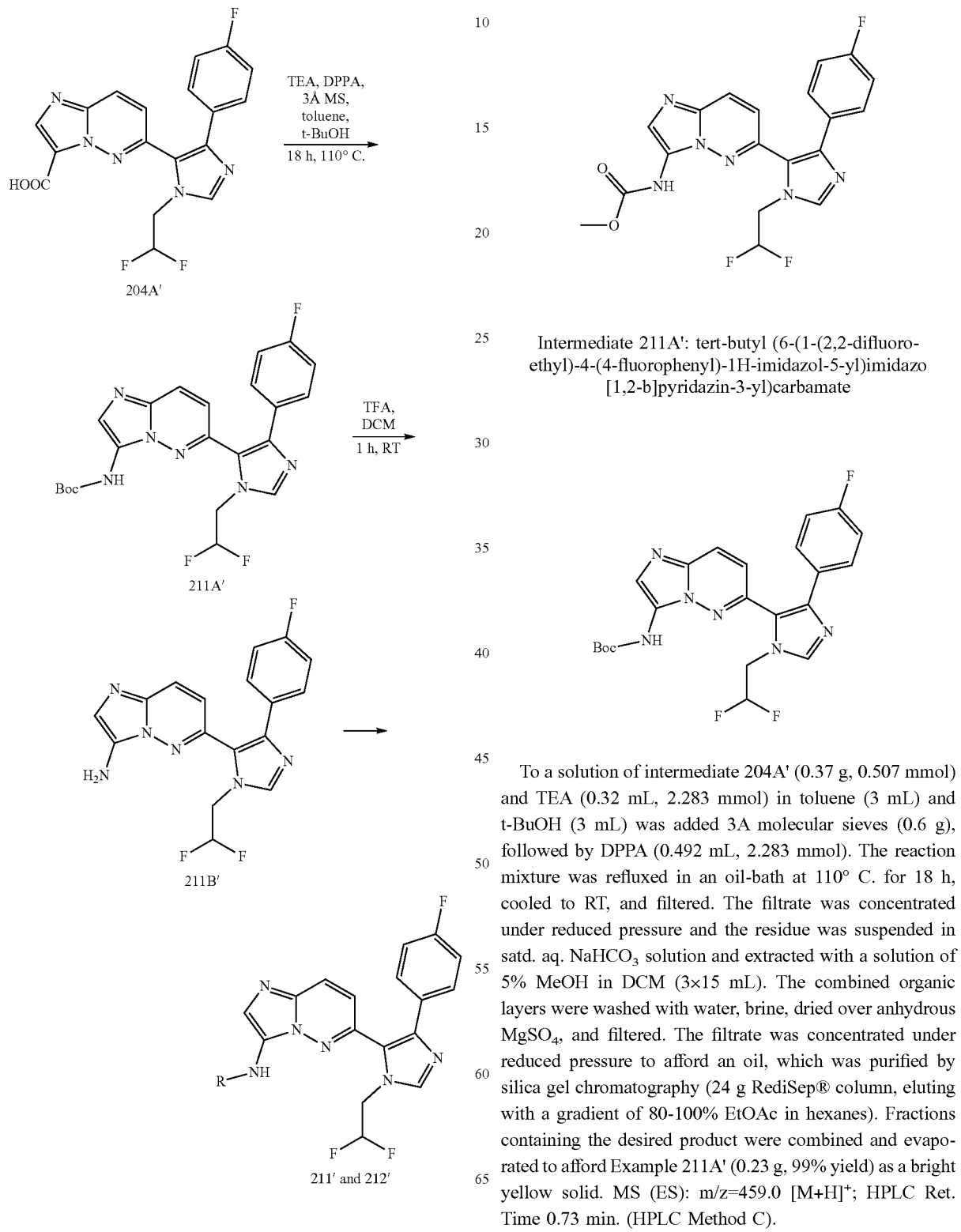

Intermediate 211A': tert-butyl (6-(1-(2,2-difluoro-ethyl)-4-(4-fluorophenyl)-1H-imidazol-5-yl)imidazo[1,2-b]pyridazin-3-yl)carbamate To a solution of intermediate 204A' (0.37 g, 0.507 mmol) and TEA (0.32 mL, 2.283 mmol) in toluene (3 mL) and t-BuOH (3 mL) was added 3A molecular sieves (0.6 g), followed by DPPA (0.492 mL, 2.283 mmol). The reaction mixture was refluxed in an oil-bath at 110° C. for 18 h, cooled to RT, and filtered. The filtrate was concentrated under reduced pressure and the residue was suspended in satd. aq. NaHCO₃ solution and extracted with a solution of 5% MeOH in DCM (3×15 mL). The combined organic layers were washed with water, brine, dried over anhydrous MgSO₄, and filtered. The filtrate was concentrated under reduced pressure to afford an oil, which was purified by silica gel chromatography (24 g RediSep® column, eluting with a gradient of 80-100% EtOAc in hexanes). Fractions containing the desired product were combined and evaporated to afford Example 211A' (0.23 g, 99% yield) as a bright yellow solid. MS (ES): m/z=459.0 [M+H]⁺; HPLC Ret. Time 0.73 min. (HPLC Method C).

Intermediate 211B': 6-(1-(2,2-difluoroethyl)-4-(4-fluorophenyl)-1H-imidazol-5-yl)imidazo[1,2-b]pyridazin-3-amine

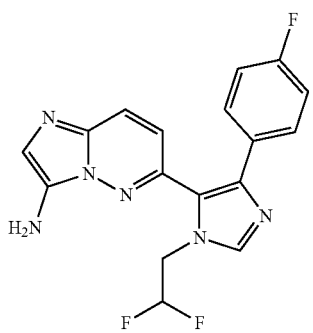 [SMILES: Nc1cnc2ccc(-c3c(-c4ccc(F)cc4)ncn3CC(F)F)nn12]

To a solution of intermediate 211A' (0.03 g, 0.065 mmol) in DCM (1.3 mL) was added TFA (0.050 mL, 0.654 mmol) and the reaction was stirred at RT for 1 h. The volatiles were concentrated under reduced pressure to afford a residue, which was basified with satd. aq. NaHCO$_3$ solution and extracted with a solution of 5% MeOH in DCM (2×10 mL). The combined organic layers were washed with water, brine, dried, and concentrated to give an oil. The oil was purified via preparative HPLC. Fractions containing the product were combined and evaporated to afford intermediate 211B' (0.023 g, 96% yield) as a bright yellow solid. MS (ES): m/z=359.0 [M+H]$^+$; HPLC Ret. Time 0.966 min. and 1.260 min. (HPLC Methods A and B, respectively); $^1$H NMR (500 MHz, DMSO-d$_6$) δ ppm 8.00 (s, 1H), 7.85 (d, J=9.2 Hz, 1H), 7.49 (dd, J=8.8, 5.5 Hz, 2H), 7.22-7.09 (m, 3H), 6.60 (d, J=9.2 Hz, 1H), 6.45 (s, 1H), 5.63 (s, 2H), 4.82-4.69 (m, 2H).

Example 211' methyl (6-(1-(2,2-difluoroethyl)-4-(4-fluorophenyl)-1H-imidazol-5-yl)imidazo[1,2-b]pyridazin-3-yl)carbamate

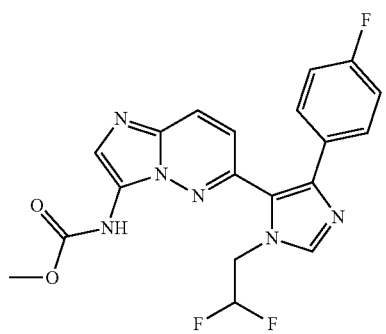 [SMILES: COC(=O)Nc1cnc2ccc(-c3c(-c4ccc(F)cc4)ncn3CC(F)F)nn12]

To a solution of intermediate 211B' (0.03 g, 0.084 mmol) and DIPEA (0.044 mL, 0.251 mmol) in DMF (0.8 mL) was added methyl carbonochloridate (0.016 mL, 0.209 mmol). The reaction was stirred at RT for 1 h and then purified via preparative HPLC. Fractions containing the product were combined and evaporated to afford Example 211' (0.007 g, 17% yield). MS (ES): m/z=417.1 [M+H]$^+$; HPLC Ret. Time 1.092 min. and 1.418 min. (HPLC Methods A and B, respectively); $^1$H NMR (500 MHz, DMSO-d$_6$) δ ppm 8.11-7.97 (m, 2H), 7.76 (s, 1H), 7.49 (dd, J=8.8, 5.5 Hz, 2H), 7.18 (t, J=9.0 Hz, 2H), 6.93 (d, J=9.2 Hz, 1H), 4.80 (t, J=15.2 Hz, 2H), 3.72 (br. s., 1H), 2.55 (s, 3H).

Example 212'

N-(6-(1-(2,2-difluoroethyl)-4-(4-fluorophenyl)-1H-imidazol-5-yl)imidazo[1,2-b]pyridazin-3-yl)acetamide

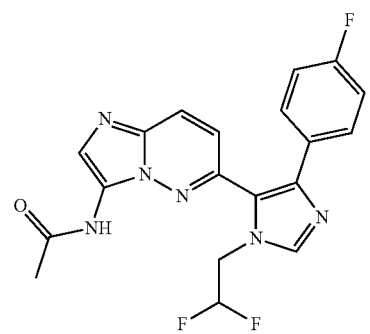 [SMILES: CC(=O)Nc1cnc2ccc(-c3c(-c4ccc(F)cc4)ncn3CC(F)F)nn12]

To a solution of intermediate 211B' (0.03 g, 0.084 mmol) and DIPEA (0.058 mL, 0.335 mmol) in DMF (0.84 mL) was added acetyl chloride (0.209 mL, 0.209 mmol, 1M solution in DCM). The reaction was stirred at RT for 1 h and purified via preparative HPLC. Fractions containing the product were combined and evaporated to afford Example 212' (0.007 g, 21.8% yield). MS (ES): m/z=401.3 [M+H]$^+$; HPLC Ret. Time 0.972 min. and 1.290 min. (HPLC Methods A and B, respectively); $^1$H NMR (500 MHz, DMSO-d$_6$) δ ppm 10.45 (s, 1H), 8.13-7.97 (m, 2H), 7.88 (s, 1H), 7.50 (dd, J=8.8, 5.5 Hz, 2H), 7.17 (t, J=8.8 Hz, 2H), 6.91 (d, J=9.2 Hz, 1H), 6.39 (s, 1H), 4.86-4.69 (m, 2H), 2.19 (s, 3H).

Scheme 18

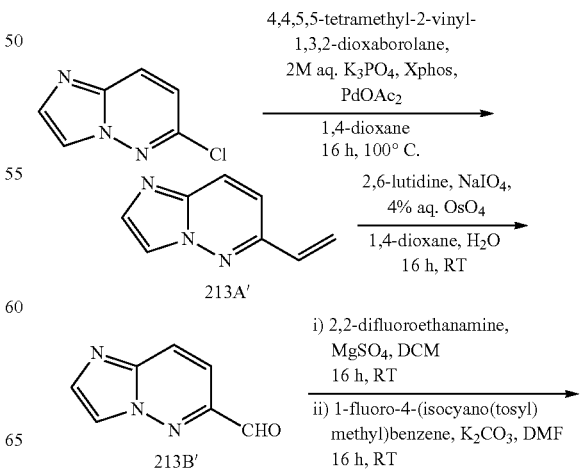

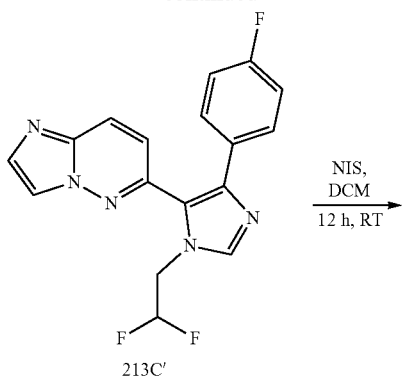

213C'

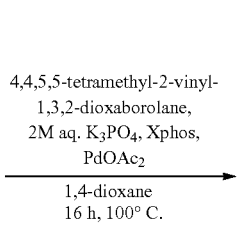

213D'

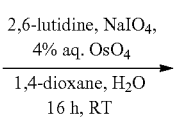

213E'

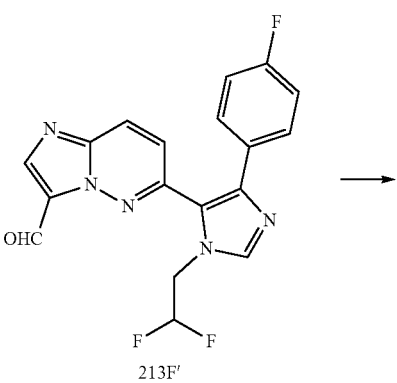

213F'

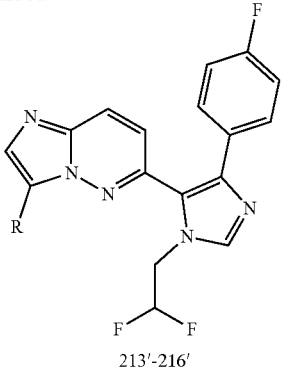

213'-216'

Intermediate 213A':
6-vinylimidazo[1,2-b]pyridazine

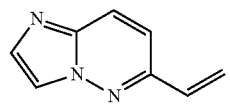

To a degassed solution of 6-chloroimidazo[1,2-b]pyridazine (7.1 g, 45.3 mmol), 4,4,5,5-tetramethyl-2-vinyl-1,3,2-dioxaborolane (16.18 mL, 91 mmol) and Xphos (6.48 g, 13.59 mmol) in 2M aq. $K_3PO_4$ (68.0 mL, 136 mmol) and 1,4-dioxane (227 mL) was added $Pd(OAc)_2$ (1.017 g, 4.53 mmol). The reaction mixture was again degassed for 2 min. and the sealed tube was heated in an oil-bath at 100° C. for 16 h. The reaction mixture was then cooled to RT and concentrated under reduced pressure to give a residue that was suspended in water and extracted with a solution of 5% MeOH in DCM (3×100 mL). The combined organic layers were washed with water, brine, dried over anhydrous $MgSO_4$, and filtered. The filtrate was concentrated under reduced pressure to give a solid, which was purified by silica gel chromatography (220 g RediSep® column, eluting with a gradient of 10-90% EtOAc in hexanes). Fractions containing the product were combined and evaporated to afford intermediate 213A' (5.38 g, 82% yield) as a pale yellow solid. MS (ES): m/z=146.1 [M+H]$^+$; $^1$H NMR (400 MHz, DMSO-$d_6$) δ ppm 8.28-8.21 (m, 1H), 8.11 (d, J=9.5 Hz, 1H), 7.76 (d, J=1.0 Hz, 1H), 7.60 (d, J=9.5 Hz, 1H), 6.83 (dd, J=17.8, 11.0 Hz, 1H), 6.32 (d, J=17.8 Hz, 1H), 5.76 (d, J=2.0 Hz, 1H).

Intermediate 213B':
imidazo[1,2-b]pyridazine-6-carbaldehyde

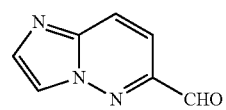 [SMILES: O=Cc1ccc2nccn2n1]

Intermediate 213B' was synthesized analogous to intermediate 1D' (Scheme 1) by reacting intermediate 213A' with $NaIO_4/OsO_4$. The crude product was purified by silica gel chromatography (220 g RediSep® column, eluting with a gradient of 10-90% EtOAc in hexanes). Fractions containing the product were combined and evaporated to afford Example 213B' (3.85 g, 70.6% yield) as a yellow solid. MS (ES): m/z=148.1 [M+H]$^+$; HPLC Ret. Time 0.972 min. and 1.232 min. (HPLC Method D); $^1$H NMR (400 MHz, DMSO-d$_6$) δ ppm 9.99 (s, 1H), 8.55 (s, 1H), 8.31 (d, J=9.3 Hz, 1H), 8.03 (d, J=1.3 Hz, 1H), 7.62 (d, J=9.5 Hz, 1H).

Intermediate 213C': 6-(1-(2,2-difluoroethyl)-4-(4-fluorophenyl)-1H-imidazol-5-yl)imidazo[1,2-b]pyridazine

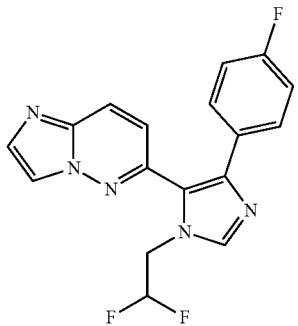 [SMILES: Fc1ccc(-c2ncn(CC(F)F)c2-c2ccc3nccn3n2)cc1]

Intermediate 213C' was synthesized analogous to Example 1' (Scheme 1) by treating intermediate 213B' with 2,2-difluoroethanamine to first form the corresponding imine, followed by reacting the intermediate imine with commercially available 1-fluoro-4-(isocyano(tosyl)methyl)benzene. The crude product was purified by silica gel chromatography (120 g RediSep® column, eluting with a gradient of 20-100% EtOAc in hexanes). Fractions containing the product were combined and evaporated to afford intermediate 213C' (2.98 g, 88% yield) as a semi-solid. MS (ES): m/z=344.1 [M+H]$^+$; HPLC Ret. Time 0.56 min. (HPLC Method C); $^1$H NMR (400 MHz, DMSO-d$_6$) δ ppm 8.40 (s, 1H), 8.12 (dd, J=9.5, 0.5 Hz, 1H), 8.03 (s, 1H), 7.87 (d, J=1.3 Hz, 1H), 7.55-7.44 (m, 2H), 7.24-7.11 (m, 2H), 6.99 (d, J=9.5 Hz, 1H), 6.38 (t, J=3.4 Hz, 1H), 4.73 (dd, J=15.5, 3.1 Hz, 2H).

Intermediate 213D': 6-(1-(2,2-difluoroethyl)-4-(4-fluorophenyl)-1H-imidazol-5-yl)-3-iodoimidazo[1,2-b]pyridazine

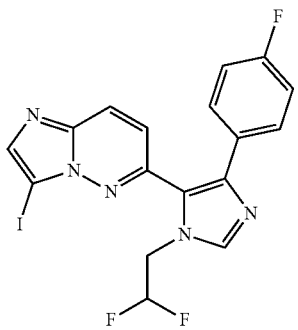 [SMILES: Fc1ccc(-c2ncn(CC(F)F)c2-c2ccc3ncc(I)n3n2)cc1]

To a solution of intermediate 213C' (2.4 g, 6.99 mmol) in DCM (46 mL) and MeOH (23 mL) was added NIS (1.651 g, 7.34 mmol). The reaction mixture was stirred at RT for 12 h, concentrated to dryness and the residue was purified by silica gel chromatography (120 g RediSep® column, eluting with a gradient of 60-100% EtOAc in hexanes). Fractions containing the product were combined and evaporated to afford intermediate 213D' (2.21 g, 67.4% yield) as a yellow solid. MS (ES): m/z=469.9 [M+H]$^+$; HPLC Ret. Time 0.77 min. (HPLC Method C).

Intermediate 213E': 6-(1-(2,2-difluoroethyl)-4-(4-fluorophenyl)-1H-imidazol-5-yl)-3-vinylimidazo[1,2-b]pyridazine

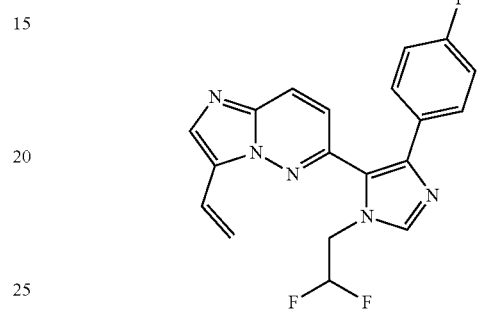

To a degassed solution of intermediate 213D' (2.622 g, 5.59 mmol), 4,4,5,5-tetramethyl-2-vinyl-1,3,2-dioxaborolane (1.954 mL, 11.18 mmol) and Xphos (0.799 g, 1.676 mmol) in 2M aq. K$_3$PO$_4$ (8.38 mL, 16.76 mmol) and 1,4-dioxane (27.9 mL) was added Pd(OAc)$_2$ (0.125 g, 0.559 mmol). The mixture was degassed again for 2 min. and the sealed tube was heated in an oil-bath at 100° C. for 16 h. The reaction was cooled to RT and concentrated under reduced pressure. The residue was suspended in water and extracted with a solution of 5% MeOH in DCM (3×25 mL). The combined organic layers were washed with water and brine, dried over anhydrous MgSO$_4$, and filtered. The filtrate was concentrated under reduced pressure and the resulting residue was purified by silica gel chromatography (80 g RediSep® column, eluting with 100% EtOAc). Fractions containing the product were combined and evaporated to afford Example 213E' (1.127 g, 54.6% yield) as a yellowish brown semi-solid. MS (ES): m/z=370.2 [M+H]$^+$; HPLC Ret. Time 2.283 min. (HPLC Method D).

Intermediate 213F': 6-(1-(2,2-difluoroethyl)-4-(4-fluorophenyl)-1H-imidazol-5-yl)imidazo[1,2-b]pyridazine-3-carbaldehyde

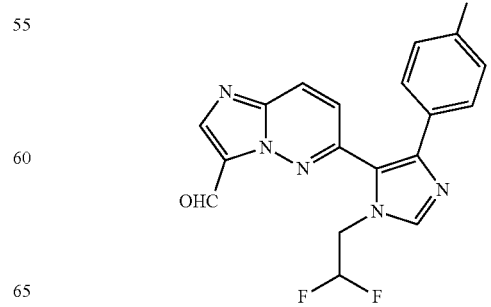

To a solution of intermediate 213E' (1.126 g, 3.05 mmol) in 1,4-dioxane (21.8 mL) and water (7.3 mL) were added 2,6-lutidine (0.71 mL, 6.10 mmol), sodium periodate (2.61 g, 12.19 mmol) and a 4% aq. solution of OsO$_4$ (0.72 mL, 0.091 mmol). The reaction mixture was stirred at RT for 16 h, diluted with water and extracted with EtOAc (3×30 mL). The combined organic layers were washed with water and brine, dried over anhydrous MgSO$_4$, and filtered. The filtrate was concentrated under reduced pressure and the resulting residue was purified by silica gel chromatography (80 g RediSep® column, eluting with 100% EtOAc). Fractions containing the product were combined and evaporated to afford intermediate 213F' (0.793 g, 70.1% yield) as a brown solid. MS (ES): m/z=372.0 [M+H]$^+$; HPLC Ret. Time 0.68 min. (HPLC Method C); $^1$H NMR (400 MHz, DMSO-d$_6$) δ ppm 10.22 (s, 1H), 8.60 (s, 1H), 8.29 (d, J=9.5 Hz, 1H), 8.08 (s, 1H), 7.61-7.49 (m, 2H), 7.27 (d, J=9.5 Hz, 1H), 7.19 (t, J=8.9 Hz, 2H), 6.65 (t, J=3.8 Hz, 1H), 4.82 (dd, J=14.8, 3.5 Hz, 2H).

Example 213'

1-(6-(1-(2,2-difluoroethyl)-4-(4-fluorophenyl)-1H-imidazol-5-yl)imidazo[1,2-b]pyridazin-3-yl)-2,2,2-trifluoroethanol

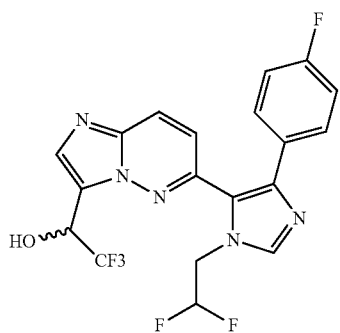 [SMILES: OC(c1cnc2ccc(-c3c(-c4ccc(F)cc4)ncn3CC(F)F)nn12)C(F)(F)F]

To an ice-cold solution of intermediate 213F' (0.04 g, 0.108 mmol) in THF (1.0 mL) was added trimethyl(trifluoromethyl)silane (0.024 mL, 0.162 mmol). The reaction mixture was then stirred at RT for 2 h, solvent was evaporated and the residue was and then purified by preparative HPLC. Fractions containing the product were combined and evaporated to afford Example 213' (0.016 g, 33.0% yield) as a solid. MS (ES): m/z=442.0 [M+H]$^+$; HPLC Ret. Time 1.211 min. and 1.470 min. (HPLC Methods A and B, respectively); $^1$H NMR (500 MHz, DMSO-d$_6$) δ ppm 8.17 (d, J=9.5 Hz, 1H), 8.06 (s, 1H), 7.94 (s, 1H), 7.50 (dd, J=8.8, 5.5 Hz, 2H), 7.18 (t, J=9.0 Hz, 2H), 7.05 (d, J=9.2 Hz, 1H), 5.84 (q, J=7.1 Hz, 1H), 4.86-4.71 (m, 2H).

Example 214'

1-(6-(1-(2,2-difluoroethyl)-4-(4-fluorophenyl)-1H-imidazol-5-yl)imidazo[1,2-b]pyridazin-3-yl)ethanol

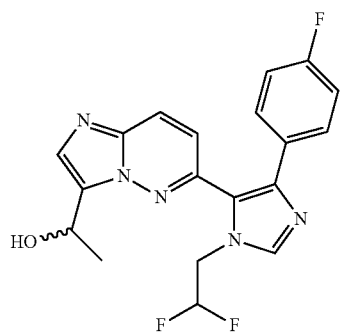

To an ice-cold solution of intermediate 213F' (0.05 g, 0.135 mmol) in THF (1.35 mL) was slowly added methylmagnesium bromide (0.090 mL, 0.269 mmol, 3M solution in Et$_2$O), The reaction mixture was stirred at RT for 3 h, quenched with satd. aq. NH$_4$Cl solution and diluted with EtOAc. The two layers were separated and the aq. layer was back-extracted with EtOAc. The combined organic layers were washed with water and brine, dried over anhydrous MgSO$_4$, and filtered. The filtrate was concentrated under reduced pressure and the resulting residue was purified via preparative HPLC. Fractions containing the product were combined and evaporated to afford Example 214' (0.045 g, 87% yield) as a solid. MS (ES): m/z=388.0 [M+H]$^+$; HPLC Ret. Time 0.988 min. and 1.298 min. (HPLC Methods A and B, respectively).

Example 215'

6-(1-(2,2-difluoroethyl)-4-(4-fluorophenyl)-1H-imidazol-5-yl)-3-(difluoromethyl)imidazo[1,2-b]pyridazine

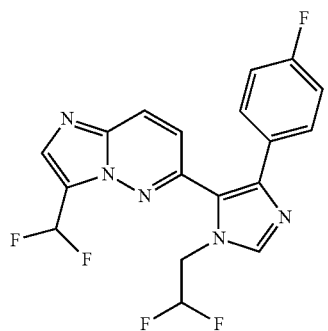 [SMILES: Fc1ccc(-c2ncn(CC(F)F)c2-c2ccc3ncc(C(F)F)n3n2)cc1]

To an ice-cold solution of intermediate 213F' (0.04 g, 0.108 mmol) in DCM (1.2 mL) was added DAST (0.043 mL, 0.323 mmol). The reaction mixture was stirred at RT for 16 h and carefully quenched with satd. aq. NaHCO$_3$ solution. The two layers were separated and the aq. layer was back-extracted with a solution of 5% MeOH in DCM (2×10 mL). The combined organic layers were washed with water and brine, dried over anhydrous MgSO$_4$, and filtered. The filtrate was concentrated under reduced pressure and the resulting residue was purified via preparative HPLC. Fractions containing the product were combined and evaporated to afford Example 215' (0.037 g, 88.1% yield) as a solid. MS (ES): m/z=394.05 [M+H]+; HPLC Ret. Time 1.04 min. and 1.081 min. (HPLC Methods A and B, respectively); $^1$H NMR (500 MHz, DMSO-$d_6$) δ ppm 8.21 (d, J=9.5 Hz, 1H), 8.16 (s, 1H), 8.06 (s, 1H), 7.60 (s, 1H), 7.58-7.45 (m, 2H), 7.19 (t, J=8.8 Hz, 2H), 7.12 (d, J=9.5 Hz, 1H), 6.40 (s, 1H), 4.87-4.71 (m, 2H).

Example 216'

5-(6-(1-(2,2-difluoroethyl)-4-(4-fluorophenyl)-1H-imidazol-5-yl)imidazo[1,2-b]pyridazin-3-yl)oxazole

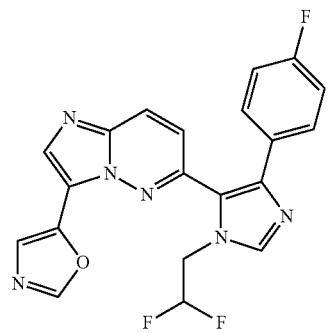 [SMILES: Fc1ccc(-c2ncn(CC(F)F)c2-c2ccc3ncc(-c4cnco4)n3n2)cc1]

A suspension of intermediate 213F' (0.04 g, 0.108 mmol), TosMIC (0.024 g, 0.124 mmol) and potassium carbonate (0.017 g, 0.124 mmol) in MeOH (1.08 mL) was refluxed in an oil-bath for 4 h. The methanol was evaporated under reduced pressure and the residue was purified via preparative HPLC. Fractions containing the product were combined and evaporated to afford Example 216' (0.036 g, 81.36% yield). MS (ES): m/z=411.0 [M+H]+; HPLC Ret. Time 1.339 min. (HPLC Method B); $^1$H NMR (500 MHz, DMSO-$d_6$) δ 8.60 (s, 1H), 8.32-8.22 (m, 2H), 8.08 (s, 1H), 7.74 (s, 1H), 7.52 (dd, J=8.8, 5.5 Hz, 2H), 7.26-7.08 (m, 3H), 6.30 (s, 1H), 4.91-4.72 (m, 2H).

Scheme 19

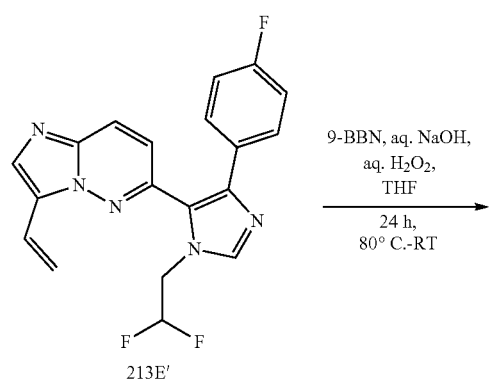

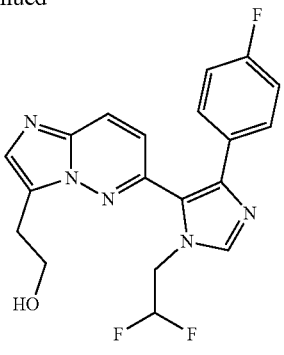

217'

Example 217'

2-(6-(1-(2,2-difluoroethyl)-4-(4-fluorophenyl)-1H-imidazol-5-yl)imidazo[1,2-b]pyridazin-3-yl)ethanol

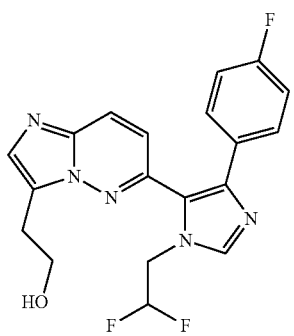 [SMILES: OCCc1cnc2ccc(-c3c(-c4ccc(F)cc4)ncn3CC(F)F)nn12]

To a stirred solution of intermediate 213E' (20 mg, 0.054 mmol) in THF (5 mL) was added 9-BBN (0.217 mL, 0.108 mmol, 0.5M solution in THF). The reaction mixture was heated at 80° C. for 14 h and cooled to RT. Following the sequential addition of 3M aq. solution of NaOH (0.108 mL, 0.325 mmol) and 30% aq. solution of $H_2O_2$ (0.111 mL, 1.083 mmol), the resultant mixture was stirred at RT for an additional 14 h. The volatiles were evaporated under reduced pressure and the resulting residue was diluted with water and extracted with ethyl acetate (2×5 mL). The combined organic layers were washed with water and brine, dried over anhydrous MgSO$_4$, and filtered. The filtrate was concentrated under reduced pressure and the residue was purified via preparative HPLC. Fractions containing the product were combined and evaporated to afford Example 217' (1.2 mg, 5.72% yield) as a solid. MS (ES): m/z=388.1 [M+H]+; HPLC Ret. Time 1.018 min. and 1.336 min. (HPLC Methods A and B, respectively); $^1$H NMR (500 MHz, DMSO-$d_6$) δ ppm 8.11-7.97 (m, 2H), 7.72 (s, 1H), 7.49 (dd, J=8.6, 5.7 Hz, 2H), 7.17 (t, J=8.8 Hz, 2H), 6.92 (d, J=9.2 Hz, 1H), 4.92-4.81 (m, 1H), 4.81-4.69 (m, 2H), 3.84-3.74 (m, 2H), 3.15 (t, J=6.6 Hz, 2H).

Scheme 20

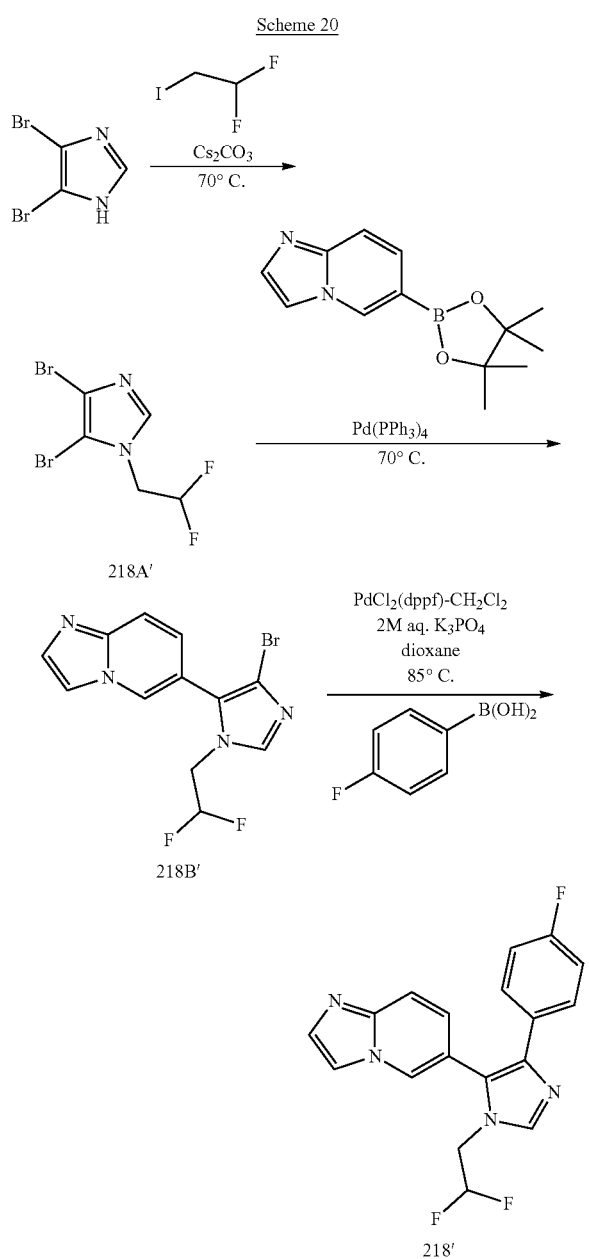

residue was purified by silica gel chromatography (80 g RediSep® column, eluting with a gradient from 10-65% EtOAc in hexanes). Fractions containing the product were combined and evaporated to afford intermediate 218A' (0.34 g, 72% yield). MS (ES): m/z=288/290 [M+H]$^+$; HPLC Ret. Time 0.68 min. (HPLC Method C); $^1$H NMR (400 MHz, CDCl$_3$) δ ppm 7.61 (s, 1H), 6.00 (t, J=3.9 Hz, 1H), 4.36 (dd, J=13.7, 3.9 Hz, 2H).

Intermediate 218B': 6-(4-bromo-1-(2,2-difluoro-ethyl)-1H-imidazol-5-yl)imidazo[1,2-a]pyridine

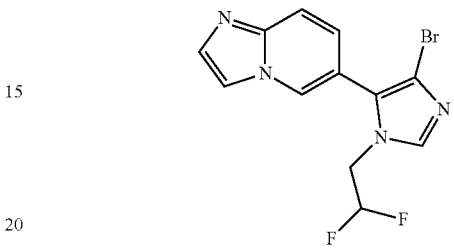

To a vial were added intermediate 218A' (104 mg, 0.359 mmol), imidazo[1,2-a]pyridin-6-ylboronic acid (58.1 mg, 0.359 mmol), potassium carbonate (149 mg, 1.076 mmol), THF (3 mL), and water (1 mL). The reaction mixture was purged with nitrogen and Pd(Ph$_3$P)$_4$ (41.5 mg, 0.036 mmol) was added. The reaction mixture was heated at 70° C. for 2 days, cooled to RT, diluted with water and extracted with DCM. The combined organic layers were washed with brine, dried over Na$_2$SO$_4$, and filtered. The filtrate was concentrated and the crude product was purified by silica gel chromatography (24 g RediSep® column, eluting with a gradient from 10-80% B in DCM; B: 10% MeOH in DCM). Fractions containing the product were combined and evaporated to afford intermediate 218B' (65 mg, 0.199 mmol, 55.4% yield). MS (ES): m/z=327/329 [M+H]$^+$; HPLC Ret. Time 0.34 min. (HPLC Method C); $^1$H NMR (400 MHz, CDCl$_3$) δ ppm 8.33-8.18 (m, 1H), 7.81-7.66 (m, 3H), 7.63 (s, 1H), 7.07 (dd, J=9.3, 1.8 Hz, 1H), 5.90 (t, J=3.3 Hz, 1H), 4.27 (dd, J=14.7, 3.3 Hz, 2H).

Example 218'

6-(1-(2,2-difluoroethyl)-4-(4-fluorophenyl)-1H-imidazol-5-yl)imidazo[1,2-a]pyridine

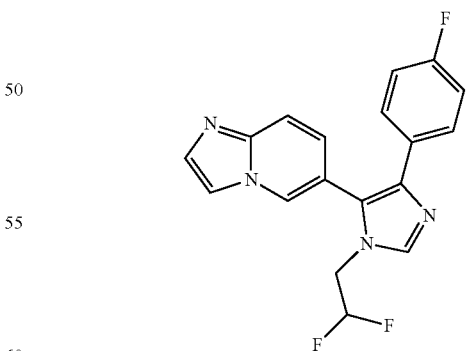

Intermediate 218A': 4,5-dibromo-1-(2,2-difluoroethyl)-1H-imidazole

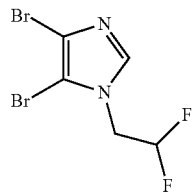 [SMILES: FC(F)Cn1cnc(Br)c1Br]

To a solution of 4,5-dibromo-1H-imidazole (0.37 g, 1.64 mmol) in acetonitrile (15 mL) were added 1,1-difluoro-2-iodoethane (0.47 g, 2.46 mmol) and cesium carbonate (0.64 g, 1.97 mmol). The suspension was heated at 70° C. overnight and then allowed to cool to RT. The reaction mixture was passed through a pad of Celite® and washed with EtOAc. The combined filtrates were concentrated and the To a vial were added intermediate 218B' (25 mg, 0.076 mmol), (4-fluorophenyl)boronic acid (16.04 mg, 0.115 mmol), 2M aq. solution of K$_3$PO$_4$ (48.7 mg, 0.229 mmol) and 1,4-dioxane (2 mL). The reaction mixture was purged with nitrogen and PdCl$_2$(dppf)-CH$_2$Cl$_2$ adduct (62.4 mg, 0.076 mmol) was added. After heating the reaction at 85° C.

for 4 h, the dark mixture was cooled to RT, passed through a pad of Celite® and washed the filter-cake with DCM. The combined filtrates were concentrated under reduced pressure. The crude product was dissolved in a mixture of DMF and methanol and purified by preparative HPLC. Fractions containing the desired product were combined and evaporated to afford Example 218' (17.7 mg, 67% yield). MS (ES): m/z=343.0 [M+H]⁺; HPLC Ret. Time 0.920 min. and 1.342 min. (HPLC Methods A and B, respectively); ¹H NMR (500 MHz, DMSO-$d_6$) δ ppm 8.67 (s, 1H), 7.98 (s, 1H), 7.93 (s, 1H), 7.76-7.63 (m, 2H), 7.46 (dd, J=8.8, 5.5 Hz, 2H), 7.22-7.02 (m, 3H), 6.23 (s, 1H), 4.52-4.31 (m, 2H).

Compounds shown in Table 14 have been prepared in a manner similar to Example 218' using intermediate 218B' and the corresponding boronic acids.

TABLE 14

| Ex. | Structure | Name | [M + H]⁺ | Ret Time (min.) | HPLC Method |
|---|---|---|---|---|---|
| 219' | 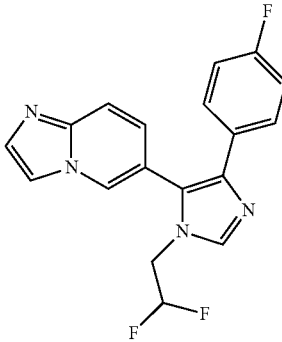 | 6-(4-(3-chloro-4-fluorophenyl)-1-(2,2-difluoroethyl)-1H-imidazol-5-yl)imidazo[1,2-a]pyridine | 376.9 | 1.978<br>1.791 | A<br>B |
| 220' | 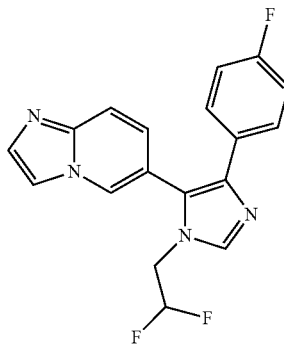 | 6-(1-(2,2-difluoroethyl)-4-(3,4-difluorophenyl)-1H-imidazol-5-yl)imidazo[1,2-a]pyridine | 361.1 | 0.964<br>1.499 | A<br>B |
| 221' | 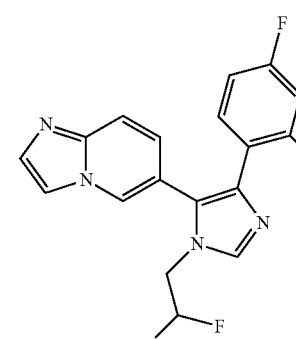 | 6-(1-(2,2-difluoroethyl)-4-(2,4-difluorophenyl)-1H-imidazol-5-yl)imidazo[1,2-a]pyridine | 361.0 | 0.907<br>1.353 | A<br>B |
| 222' | 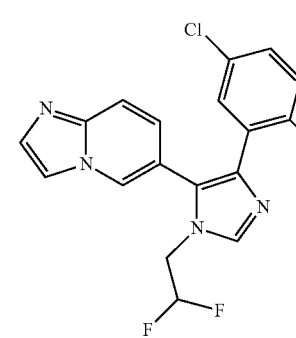 | 6-(4-(5-chloro-2-fluorophenyl)-1H-(2,2-difluoroethyl)-1H-imidazol-5-yl)imidazo[1,2-a]pyridine | 376.9 | 0.940<br>1.426 | A<br>B |

TABLE 14-continued

| Ex. | Structure | Name | [M + H]+ | Ret Time (min.) | HPLC Method |
|---|---|---|---|---|---|
| 223' | 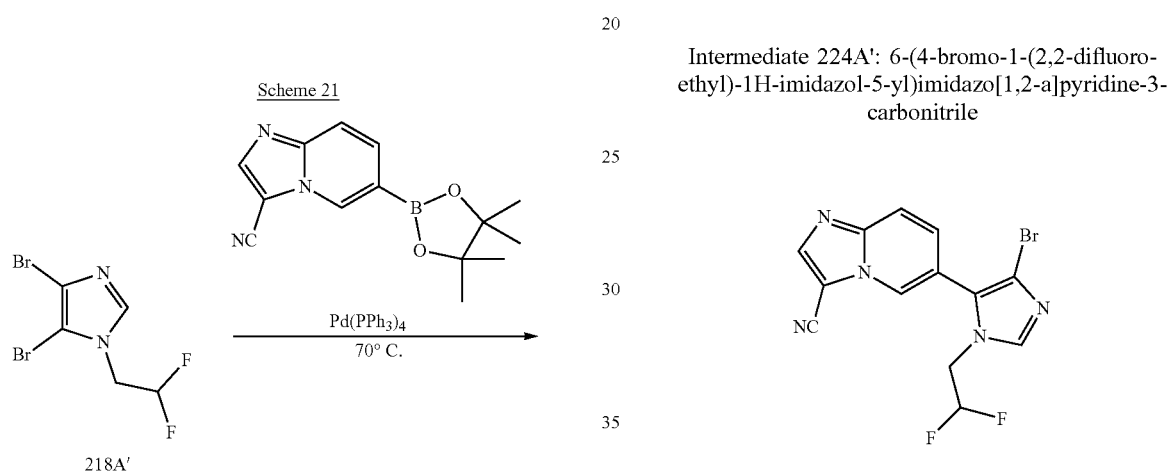 | 6-(4-(5-chloro-2,4-difluorophenyl)-1-(2,2-difluoroethyl)-1H-imidazol-5-yl)imidazo[1,2-a]pyridine | 395.0 | 1.029<br>1.444 | A<br>B |

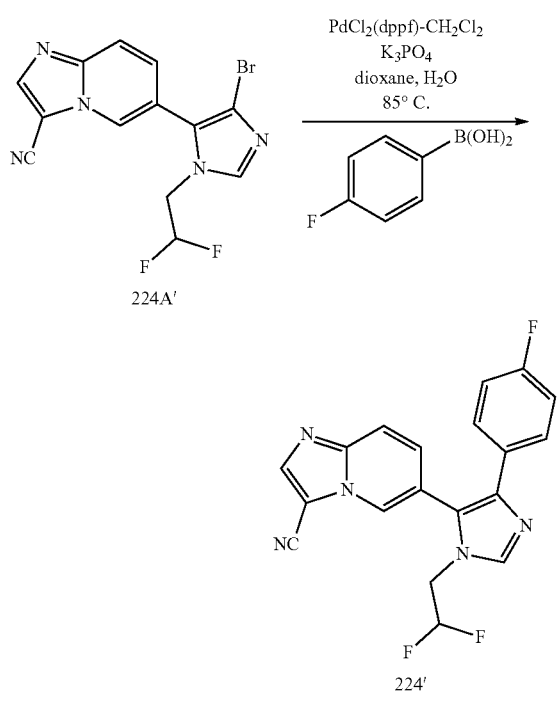

Intermediate 224A': 6-(4-bromo-1-(2,2-difluoroethyl)-1H-imidazol-5-yl)imidazo[1,2-a]pyridine-3-carbonitrile To a pressure bottle were added intermediate 218A' (420 mg, 1.449 mmol), (3-cyanoimidazo[1,2-a]pyridin-6-yl)boronic acid (271 mg, 1.449 mmol), potassium carbonate (601 mg, 4.35 mmol), THF (12 mL) and water (4 mL). The reaction mixture was purged with nitrogen and Pd(Ph$_3$P)$_4$ (167 mg, 0.145 mmol) was added. After purging the mixture again with nitrogen, reaction was heated at 70° C. for 36 h and cooled to RT, diluted with DCM and water. The layers were separated. The aqueous layer was extracted with DCM. The combined organic layers were washed with brine, dried over Na$_2$SO$_4$, and filtered. The filtrate was concentrated and the crude product was purified by silica gel chromatography (40 g RediSep column, eluting with a gradient from 40-100% EtOAc in DCM, the 50-100% B in DCM, B: 10% MeOH in DCM)). Fractions containing the product were combined and evaporated to afford 224A' (220 mg, 0.625 mmol, 43.1% yield). MS (ES): m/z=353.9 [M+H]+; HPLC Ret. Time 0.68 min. (HPLC Method C); $^1$H NMR (400 MHz, CDCl$_3$) δ ppm 8.50-8.40 (m, 1H), 8.28 (s, 1H), 7.97-7.87 (m, 1H), 7.70 (s, 1H), 7.43 (dd, J=9.3, 1.5 Hz, 1H), 5.95 (t, J=3.0 Hz, 1H), 4.30 (dd, J=14.8, 3.0 Hz, 2H).

Example 224'

6-(1-(2,2-difluoroethyl)-4-(4-fluorophenyl)-1H-imidazol-5-yl)imidazo[1,2-a]pyridine-3-carbonitrile

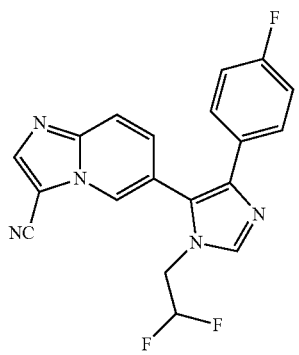 [SMILES: N#Cc1cnc2ccc(-c3c(-c4ccc(F)cc4)ncn3CC(F)F)cn12]

To a vial were added (4-fluorophenyl)boronic acid (14.9 mg, 0.106 mmol), intermediate 224A' (25 mg, 0.07 mmol), a 2 M aq. solution of $K_3PO_4$ (0.1 mL, 0.213 mmol) and 1,4-dioxane (1 mL). The reaction mixture was purged with nitrogen for 2 min and $PdCl_2(dppf)$-$CH_2Cl_2$ adduct (10.67 mg, 0.013 mmol) was added. The reaction mixture was heated at 85° C. for 6 h. The dark reaction mixture was cooled to RT, passed through a pad of Celite®, washed with DCM and concentrated in vacuo. The crude product was dissolved in a mixture of DMF and methanol and purified by preparative HPLC. Fractions containing the desired product were combined and dried under vacuum to afford Example 224' (44.4 mg, 0.100 mmol, 63% yield). MS (ES): m/z=368.0 [M+H]$^+$; HPLC Ret. Time 1.233 min. and 1.408 min. (HPLC Methods A and B, respectively); $^1$H NMR (500 MHz, DMSO-$d_6$) δ ppm 8.77 (s, 1H), 8.54 (s, 1H), 8.02-7.83 (m, 2H), 7.47 (dd, J=8.8, 5.5 Hz, 2H), 7.39 (dd, J=9.2, 1.5 Hz, 1H), 7.08 (t, J=9.0 Hz, 2H), 6.20 (m, 1H), 4.59-4.37 (m, 2H).

Compounds shown in Table 15 have been prepared in a manner similar to Example 224' using intermediate 224A' and the corresponding boronic acids.

TABLE 15

| Ex. | Structure | Name | [M + H]$^+$ | Ret Time (min.) | HPLC Method |
|---|---|---|---|---|---|
| 225' | 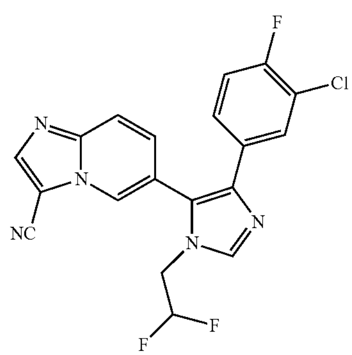 [SMILES: N#Cc1cnc2ccc(-c3c(-c4ccc(F)c(Cl)c4)ncn3CC(F)F)cn12] | 6-(4-(3-chloro-4-fluorophenyl)-1-(2,2-difluoroethyl)-1H-imidazol-5-yl)imidazo[1,2-a]pyridine-3-carbonitrile | 376.9 | 1.791<br>1.978 | A<br>B |
| 226' | 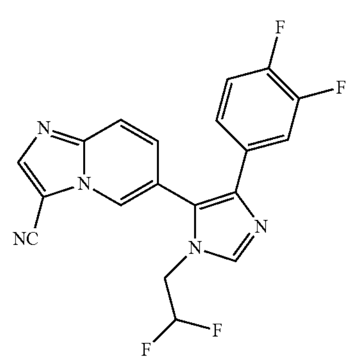 [SMILES: N#Cc1cnc2ccc(-c3c(-c4ccc(F)c(F)c4)ncn3CC(F)F)cn12] | 6-(1-(2,2-difluoroethyl)-4-(3,4-difluorophenyl)-1H-imidazol-5-yl)imidazo[1,2-a]pyridine-3-carbonitrile | 386.1 | 1.275<br>1.592 | A<br>B |

TABLE 15-continued

| Ex. | Structure | Name | [M + H]+ | Ret Time (min.) | HPLC Method |
|---|---|---|---|---|---|
| 227' | 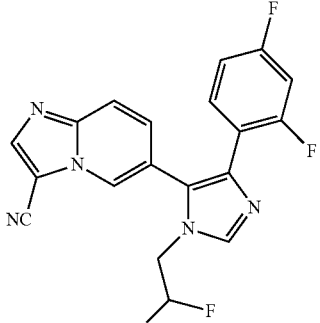 | 6-(1-(2,2-difluoroethyl)-4-(2,4-difluorophenyl)-1H-imidazol-5-yl)imidazo[1,2-a]pyridine-3-carbonitrile | 386.9 | 1.189<br>1.483 | A<br>B |
| 228' | 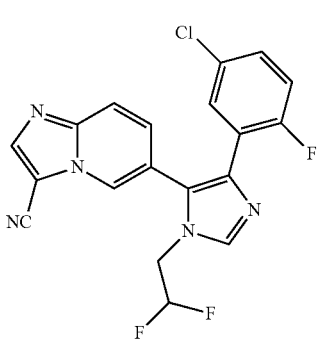 [SMILES: N#Cc1cnc2ccc(-c3c(-c4cc(Cl)ccc4F)ncn3CC(F)F)cn12] | 6-(4-(5-chloro-2-fluorophenyl)-1-(2,2-difluoroethyl)-1H-imidazol-5-yl)imidazo[1,2-a]pyridine-3-carbonitrile | 401.9 | 1.307<br>1.566 | A<br>B |
| 229' | 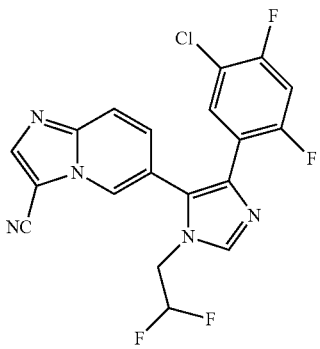 [SMILES: N#Cc1cnc2ccc(-c3c(-c4cc(Cl)c(F)cc4F)ncn3CC(F)F)cn12] | 6-(4-(5-chloro-2,4-difluorophenyl)-1-(2,2-difluoroethyl)-1H-imidazol-5-yl)imidazo[1,2-a]pyridine-3-carbonitrile | 419.9 | 1.029<br>1.444 | A<br>B |

Compounds shown in Table 16 have been prepared in a manner similar to Example 105' (Scheme 6) by heating the corresponding cyano compounds with TFA and sulfuric acid.

TABLE 16

| Ex. | Structure | Name | [M + H]+ | Ret Time (min.) | HPLC Method |
|---|---|---|---|---|---|
| 230' | 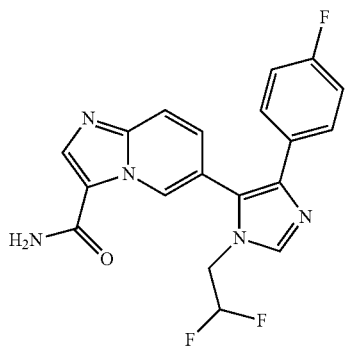 [SMILES: NC(=O)c1cnc2ccc(-c3c(-c4ccc(F)cc4)ncn3CC(F)F)cn12] | 6-(1-(2,2-difluoroethyl)-4-(4-fluorophenyl)-1H-imidazol-5-yl)imidazo[1,2-a]pyridine-3-carboxamide | 386.1 | 0.823<br>1.187 | A<br>B |

TABLE 16-continued

| Ex. | Structure | Name | [M + H]⁺ | Ret Time (min.) | HPLC Method |
|---|---|---|---|---|---|
| 231' | 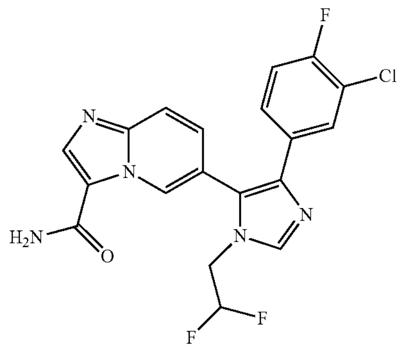 [SMILES: NC(=O)c1cnc2ccc(-c3c(-c4ccc(F)c(Cl)c4)ncn3CC(F)F)cn12] | 6-(4-(3-chloro-4-fluorophenyl)-1-(2,2-difluoroethyl)-1H-imidazol-5-yl)imidazo[1,2-a]pyridine-3-carboxamide | 419.9 | 1.516<br>1.876 | A<br>B |
| 232' | 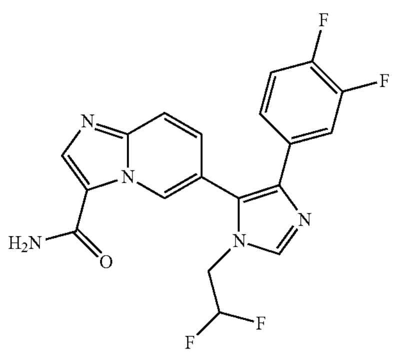 [SMILES: NC(=O)c1cnc2ccc(-c3c(-c4ccc(F)c(F)c4)ncn3CC(F)F)cn12] | 6-(1-(2,2-difluoroethyl)-4-(3,4-difluorophenyl)-1H-imidazol-5-yl)imidazo[1,2-a]pyridine-3-carboxamide | 404.0 | 0.994<br>1.360 | A<br>B |
| 233' | 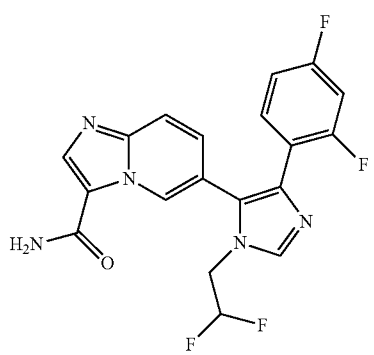 [SMILES: NC(=O)c1cnc2ccc(-c3c(-c4ccc(F)cc4F)ncn3CC(F)F)cn12] | 6-(1-(2,2-difluoroethyl)-4-(2,4-difluorophenyl)-1H-imidazol-5-yl)imidazo[1,2-a]pyridine-3-carboxamide | 404.0 | 0.923<br>1.229 | A<br>B |
| 234' | 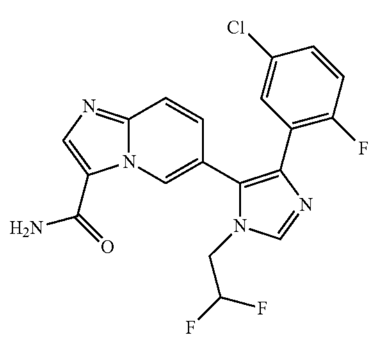 [SMILES: NC(=O)c1cnc2ccc(-c3c(-c4cc(Cl)ccc4F)ncn3CC(F)F)cn12] | 6-(4-(5-chloro-2-fluorophenyl)-1-(2,2-difluoroethyl)-1H-imidazol-5-yl)imidazo[1,2-a]pyridine-3-carboxamide | 419.9 | 0.959<br>1.299 | A<br>B |

TABLE 16-continued

| Ex. | Structure | Name | [M + H]⁺ | Ret Time (min.) | HPLC Method |
|---|---|---|---|---|---|
| 235' | 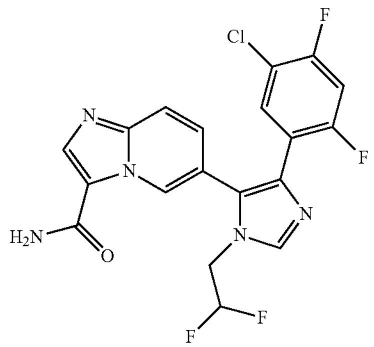 [SMILES: NC(=O)c1cnc2ccc(-c3c(-c4cc(Cl)c(F)cc4F)ncn3CC(F)F)cn12] | 6-(4-(5-chloro-2,4-difluorophenyl)-1-(2,2-difluoroethyl)-1H-imidazol-5-yl)imidazo[1,2-a]pyridine-3-carboxamide | 437.9 | 1.242<br>1.403 | A<br>B |

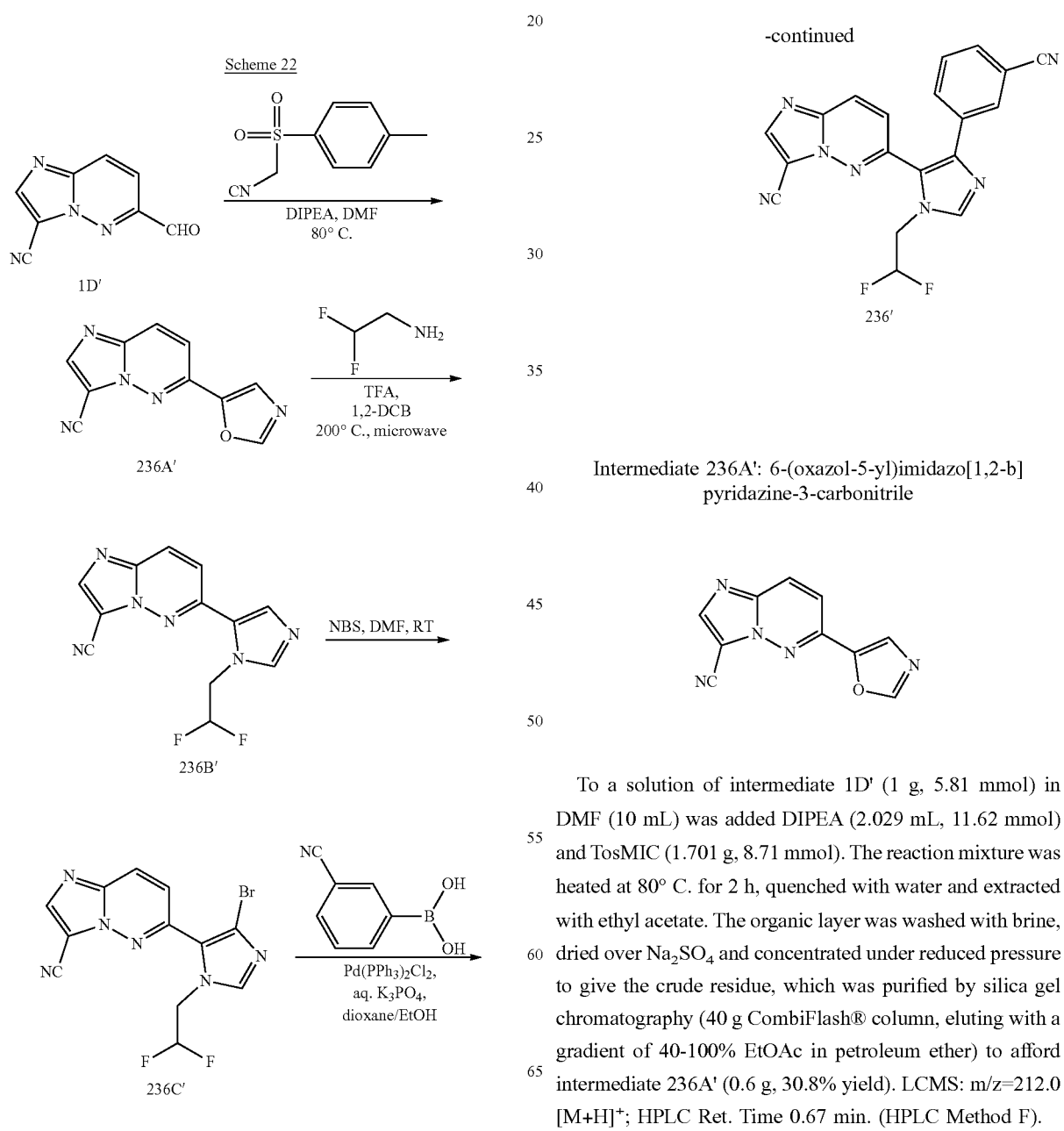

Intermediate 236A': 6-(oxazol-5-yl)imidazo[1,2-b]pyridazine-3-carbonitrile

To a solution of intermediate 1D' (1 g, 5.81 mmol) in DMF (10 mL) was added DIPEA (2.029 mL, 11.62 mmol) and TosMIC (1.701 g, 8.71 mmol). The reaction mixture was heated at 80° C. for 2 h, quenched with water and extracted with ethyl acetate. The organic layer was washed with brine, dried over $Na_2SO_4$ and concentrated under reduced pressure to give the crude residue, which was purified by silica gel chromatography (40 g CombiFlash® column, eluting with a gradient of 40-100% EtOAc in petroleum ether) to afford intermediate 236A' (0.6 g, 30.8% yield). LCMS: m/z=212.0 [M+H]⁺; HPLC Ret. Time 0.67 min. (HPLC Method F).

Intermediate 236B': 6-(1-(2,2-difluoroethyl)-1H-imidazol-5-yl)imidazo[1,2-b]pyridazine-3-carbonitrile

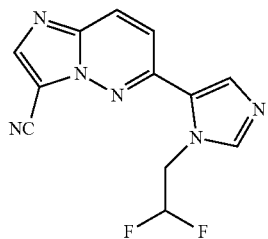 [SMILES: N#Cc1cnc2ccc(-c3cncn3CC(F)F)nn12]

To a solution of intermediate 236A' (400 mg, 1.894 mmol) in 1,2-dichlorobenzene (3 mL) was added 2,2-difluoroethanamine (0.267 mL, 3.79 mmol) and TFA (432 mg, 3.79 mmol). The reaction mixture was heated at 200° C. for 2 h in a CEM microwave instrument. The reaction mixture was quenched with 10% aqueous NaOH solution and extracted with a solution of 10% methanol in DCM. The organic layer was washed with brine, dried over Na$_2$SO$_4$, filtered and the filtrate was concentrated under reduced pressure to give the crude residue which was purified by silica gel chromatography (120 g CombiFlash® column, eluting with a gradient of 0-20% MeOH in DCM) to afford intermediate 236B' (180 mg, 32.9% yield). LCMS: m/z=275.0 [M+H]$^+$; HPLC Ret. Time 0.75 min. (HPLC Method G).

Intermediate 236C': 6-(4-bromo-1-(2,2-difluoroethyl)-1H-imidazol-5-yl)imidazo[1,2-b]pyridazine-3-carbonitrile

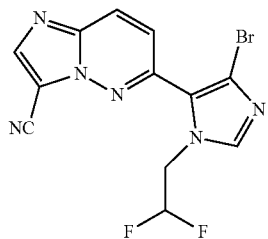 [SMILES: N#Cc1cnc2ccc(-c3c(Br)ncn3CC(F)F)nn12]

To a solution of intermediate 236B' (250 mg, 0.912 mmol) in DMF (5 mL) was added NBS (195 mg, 1.094 mmol). The reaction mixture was stirred at RT for 18 h and partitioned between water and ethyl acetate. The aqueous layer was back-extracted with ethyl acetate (2×30 mL). The combined organic layer was washed with brine, dried over Na$_2$SO$_4$, filtered and the filtrate was concentrated under reduced pressure to afford intermediate 236C' (280 mg, 34.8% yield). LCMS: m/z=352.9 [M+H]$^+$; HPLC Ret. Time 0.75 min. (HPLC Method F).

Example 236'

6-(4-(3-cyanophenyl)-1-(2,2-difluoroethyl)-1H-imidazol-5-yl)imidazo[1,2-b]pyridazine-3-carbonitrile

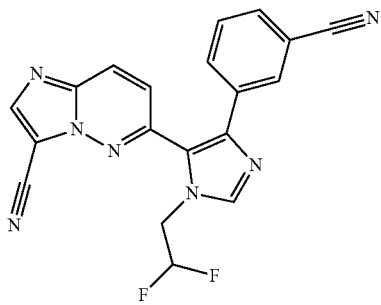 [SMILES: N#Cc1cccc(-c2ncn(CC(F)F)c2-c2ccc3ncc(C#N)n3n2)c1]

To a solution of intermediate 236C' (30 mg, 0.085 mmol) in 1,4-dioxane (1 mL), ethanol (0.5 mL) water (0.5 mL) was added 3-cyanophenylboronic acid (18 mg, 0.127 mmol), and K$_3$PO$_4$ (54.1 mg, 0.255 mmol). The reaction mixture was degassed with argon for 5 minutes and [1,1'-bis(diphenylphosphino)ferrocene]dichloropalladium(II) (6.22 mg, 8.50 μmol) was added. The reaction mixture was heated in a microwave instrument at 100° C. for 1 h. The reaction mixture was concentrated and the residue was partitioned between water and ethyl acetate. The aqueous layer was back-extracted with ethyl acetate (2×20 mL). The combined organic layer was washed with brine, dried over Na$_2$SO$_4$, filtered and the filtrate was concentrated under reduced pressure to give the crude residue, which was purified by preparative HPLC(Condition P). Fractions containing the desired product were combined and evaporated to afford Example 236' (8.5 mg, 26.65% yield). LCMS: m/z=376.2 [M+H]$^+$; HPLC Ret. Time 1.329 min. (HPLC Method H); $^1$H NMR (400 MHz, DMSO-d$_6$) δ ppm 8.66 (s, 1H), 8.35 (d, J=9.54 Hz, 1H), 8.14 (s, 1H), 7.98 (t, J=1.51 Hz, 1H), 7.81 (ddd, J=1.13, 7.91, 19.95 Hz, 2H), 7.54 (t, J=7.78 Hz, 1H), 7.32 (d, J=9.54 Hz, 1H), 6.27-6.59 (m, 1H), 4.80 (dt, J=3.51, 15.31 Hz, 2H).

The compounds shown in Table 17 have been prepared in a manner similar to Example 236' by a Suzuki coupling between intermediate 236C' and various aryl boronic acids/esters.

TABLE 17

| Ex. | Structure | Name | [M + H]$^+$ | Ret Time (min.) | HPLC Method |
|---|---|---|---|---|---|
| 237' | 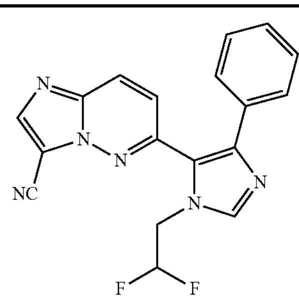 | 6-(1-(2,2-difluoroethyl)-4-phenyl-1H-imidazol-5-yl)imidazo[1,2-b]pyridazine-3-carbonitrile | 351.2 | 1.359<br>1.137 | H<br>I |

TABLE 17-continued

| Ex. | Structure | Name | [M + H]+ | Ret Time (min.) | HPLC Method |
|---|---|---|---|---|---|
| 238' | 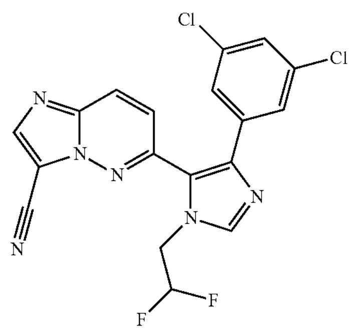 [SMILES: N#Cc1cnc2ccc(-c3c(-c4cc(Cl)cc(Cl)c4)ncn3CC(F)F)nn12] | 6-(4-(3,5-dichlorophenyl)-1-(2,2-difluoroethyl)-1H-imidazol-5-yl)imidazo[1,2-b]pyridazine-3-carbonitrile | 419.1 | 1.808<br>1.800 | H<br>I |
| 239' | 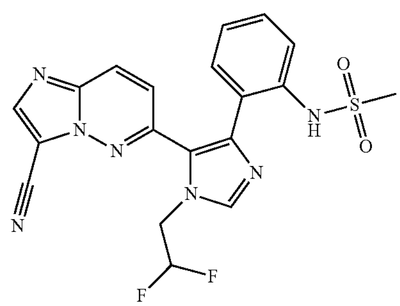 [SMILES: CS(=O)(=O)Nc1ccccc1-c1ncn(CC(F)F)c1-c1ccc2ncc(C#N)n2n1] | N-(2-(5-(3-cyanoimidazo[1,2-b]pyridazin-6-yl)-1-(2,2-difluoroethyl)-1H-imidazol-4-yl)phenyl)methanesulfonamide | 444.2 | 1.378<br>1.171 | H<br>I |
| 240' | 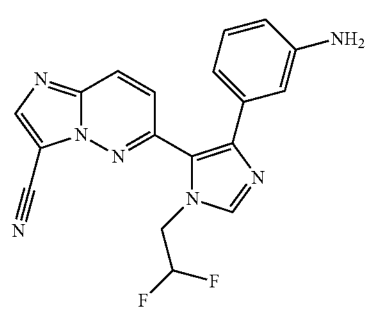 [SMILES: N#Cc1cnc2ccc(-c3c(-c4cccc(N)c4)ncn3CC(F)F)nn12] | 6-(4-(3-aminophenyl)-1-(2,2-difluoroethyl)-1H-imidazol-5-yl)imidazo[1,2-b]pyridazine-3-carbonitrile | 366.2 | 1.113<br>0.847 | H<br>I |
| 241' | 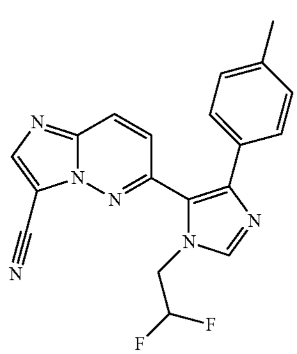 [SMILES: Cc1ccc(-c2ncn(CC(F)F)c2-c2ccc3ncc(C#N)n3n2)cc1] | 6-(1-(2,2-difluoroethyl)-4-(p-tolyl)-1H-imidazol-5-yl)imidazo[1,2-b]pyridazine-3-carbonitrile | 365.2 | 1.515<br>1.252 | H<br>I |

TABLE 17-continued

| Ex. | Structure | Name | [M + H]+ | Ret Time (min.) | HPLC Method |
|---|---|---|---|---|---|
| 242' | 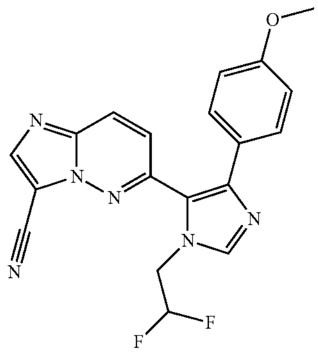 [SMILES: COc1ccc(-c2ncn(CC(F)F)c2-c2ccc3ncc(C#N)n3n2)cc1] | 6-(1-(2,2-difluoroethyl)-4-(4-methoxyphenyl)-1H-imidazol-5-yl)imidazo[1,2-b]pyridazine-3-carbonitrile | 381.2 | 1.389<br>1.133 | H<br>I |
| 243' | 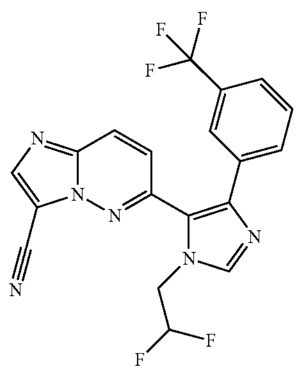 [SMILES: N#Cc1cnc2ccc(-c3c(-c4cccc(C(F)(F)F)c4)ncn3CC(F)F)nn12] | 6-(1-(2,2-difluoroethyl)-4-(3-(trifluoromethyl)phenyl)-1H-imidazol-5-yl)imidazo[1,2-b]pyridazine-3-carbonitrile | 419.2 | 1.708<br>1.627 | H<br>I |
| 244' | 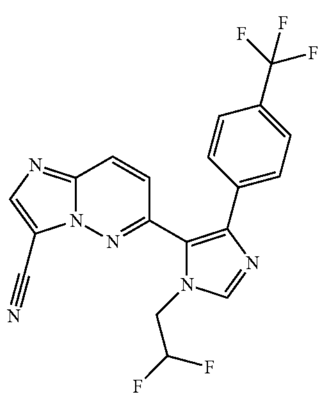 [SMILES: N#Cc1cnc2ccc(-c3c(-c4ccc(C(F)(F)F)cc4)ncn3CC(F)F)nn12] | 6-(1-(2,2-difluoroethyl)-4-(4-(trifluoromethyl)phenyl)-1H-imidazol-5-yl)imidazo[1,2-b]pyridazine-3-carbonitrile | 419.1 | 1.931<br>1.820 | H<br>I |
| 245' | 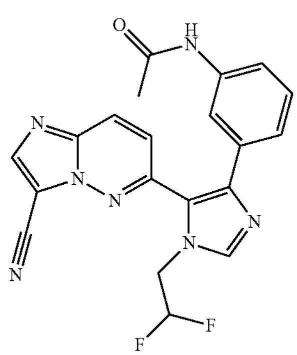 [SMILES: CC(=O)Nc1cccc(-c2ncn(CC(F)F)c2-c2ccc3ncc(C#N)n3n2)c1] | N-(3-(5-(3-cyanoimidazo[1,2-b]pyridazin-6-yl)-1-(2,2-difluoroethyl)-1H-imidazol-4-yl)phenyl)acetamide | 408.2 | 1.312<br>1.136 | H<br>I |

TABLE 17-continued

| Ex. | Structure | Name | [M + H]+ | Ret Time (min.) | HPLC Method |
|---|---|---|---|---|---|
| 246' | 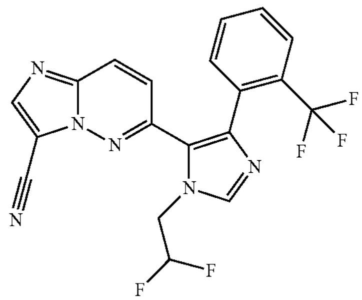 [SMILES: N#Cc1cnc2ccc(-c3c(-c4ccccc4C(F)(F)F)ncn3CC(F)F)nn12] | 6-(1-(2,2-difluoroethyl)-4-(2-(trifluoromethyl)phenyl)-1H-imidazol-5-yl)imidazo[1,2-b]pyridazine-3-carbonitrile | 419.2 | 1.528<br>1.415 | H<br>I |
| 247' | 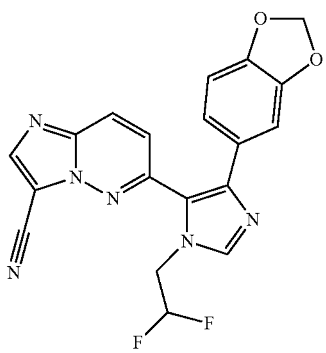 [SMILES: N#Cc1cnc2ccc(-c3c(-c4ccc5c(c4)OCO5)ncn3CC(F)F)nn12] | 6-(4-(benzo[d][1,3]dioxol-5-yl)-1-(2,2-difluoroethyl)-1H-imidazol-5-yl)imidazo[1,2-b]pyridazine-3-carbonitrile | 395.2 | 1.330<br>1.090 | H<br>I |
| 248' | 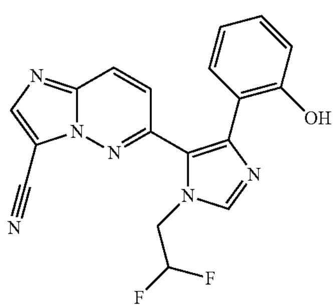 [SMILES: N#Cc1cnc2ccc(-c3c(-c4ccccc4O)ncn3CC(F)F)nn12] | 6-(1-(2,2-difluoroethyl)-4-(2-hydroxyphenyl)-1H-imidazol-5-yl)imidazo[1,2-b]pyridazine-3-carbonitrile | 367.2 | 1.422<br>1.014 | H<br>I |
| 249' | 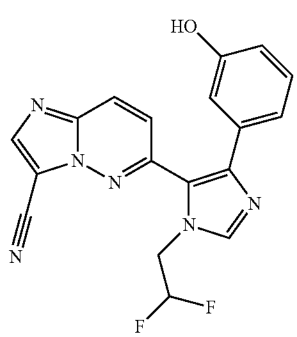 [SMILES: N#Cc1cnc2ccc(-c3c(-c4cccc(O)c4)ncn3CC(F)F)nn12] | 6-(1-(2,2-difluoroethyl)-4-(3-hydroxyphenyl)-1H-imidazol-5-yl)imidazo[1,2-b]pyridazine-3-carbonitrile | 367.1 | 1.336<br>1.124 | H<br>I |

TABLE 17-continued

| Ex. | Structure | Name | [M + H]+ | Ret Time (min.) | HPLC Method |
|---|---|---|---|---|---|
| 250' | 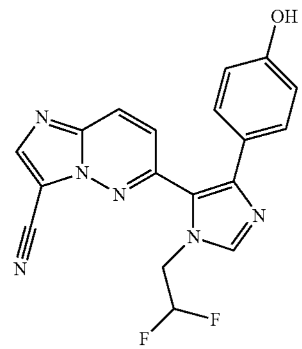 [SMILES: N#Cc1cnc2ccc(-c3c(-c4ccc(O)cc4)ncn3CC(F)F)nn12] | 6-(1-(2,2-difluoroethyl)-4-(4-hydroxyphenyl)-1H-imidazol-5-yl)imidazo[1,2-b]pyridazine-3-carbonitrile | 367.2 | 1.134<br>0.902 | H<br>I |
| 251' | 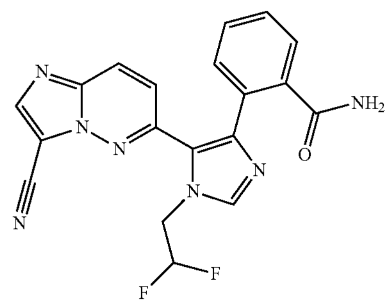 [SMILES: N#Cc1cnc2ccc(-c3c(-c4ccccc4C(N)=O)ncn3CC(F)F)nn12] | 2-(5-(3-cyanoimidazo[1,2-b]pyridazin-6-yl)-1-(2,2-difluoroethyl)-1H-imidazol-4-yl)benzamide | 394.1 | 1.153<br>0.988 | H<br>I |
| 252' | 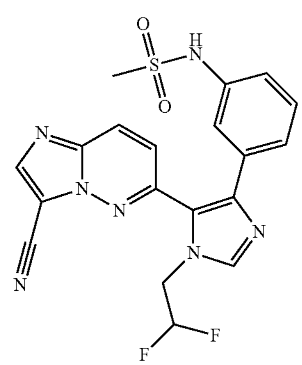 [SMILES: CS(=O)(=O)Nc1cccc(-c2ncn(CC(F)F)c2-c2ccc3ncc(C#N)n3n2)c1] | N-(3-(5-(3-cyanoimidazo[1,2-b]pyridazin-6-yl)-1-(2,2-difluoroethyl)-1H-imidazol-4-yl)phenyl)methanesulfonamide | 444.1 | 1.351<br>1.197 | H<br>I |
| 253' | 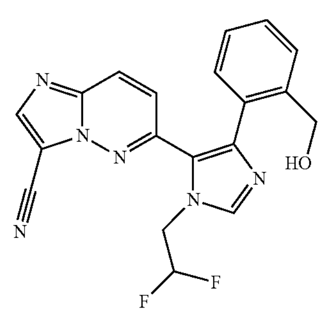 [SMILES: N#Cc1cnc2ccc(-c3c(-c4ccccc4CO)ncn3CC(F)F)nn12] | 6-(1-(2,2-difluoroethyl)-4-(2-(hydroxymethyl)phenyl)-1H-imidazol-5-yl)imidazo[1,2-b]pyridazine-3-carbonitrile | 381.2 | 1.226<br>0.994 | H<br>I |

TABLE 17-continued

| Ex. | Structure | Name | [M + H]+ | Ret Time (min.) | HPLC Method |
|---|---|---|---|---|---|
| 254' | 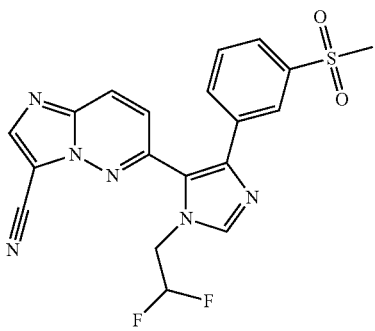 [SMILES: CS(=O)(=O)c1cccc(-c2ncn(CC(F)F)c2-c2ccc3ncc(C#N)n3n2)c1] | 6-(1-(2,2-difluoroethyl)-4-(3-(methylsulfonyl)phenyl)-1H-imidazol-5-yl)imidazo[1,2-b]pyridazine-3-carbonitrile | 429.2 | 1.179<br>1.102 | H<br>I |
| 255' | 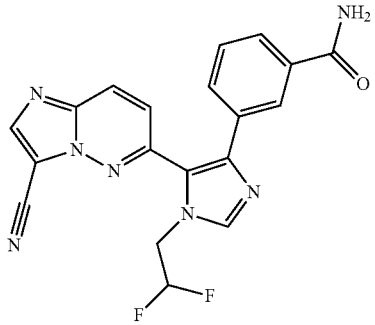 [SMILES: N#Cc1cnc2ccc(-c3c(-c4cccc(C(N)=O)c4)ncn3CC(F)F)nn12] | 3-(5-(3-cyanoimidazo[1,2-b]pyridazin-6-yl)-1-(2,2-difluoroethyl)-1H-imidazol-4-yl)benzamide | 394.2 | 0.971<br>0.848 | H<br>I |
| 256' | 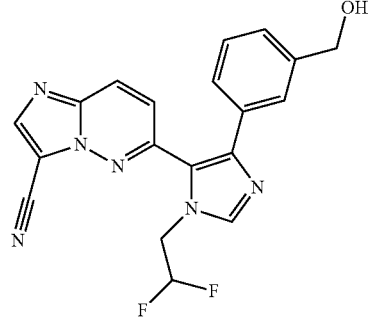 [SMILES: N#Cc1cnc2ccc(-c3c(-c4cccc(CO)c4)ncn3CC(F)F)nn12] | 6-(1-(2,2-difluoroethyl)-4-(3-(hydroxymethyl)phenyl)-1H-imidazol-5-yl)imidazo[1,2-b]pyridazine-3-carbonitrile | 381.2 | 1.105<br>0.939 | H<br>I |
| 257' | 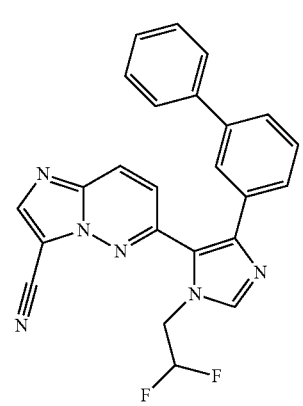 [SMILES: N#Cc1cnc2ccc(-c3c(-c4cccc(-c5ccccc5)c4)ncn3CC(F)F)nn12] | 6-(4-([1,1'-biphenyl]-3-yl)-1-(2,2-difluoroethyl)-1H-imidazol-5-yl)imidazo[1,2-b]pyridazine-3-carbonitrile | 427.2 | 1.799<br>1.625 | H<br>I |

TABLE 17-continued

| Ex. | Structure | Name | [M + H]+ | Ret Time (min.) | HPLC Method |
|---|---|---|---|---|---|
| 258' | 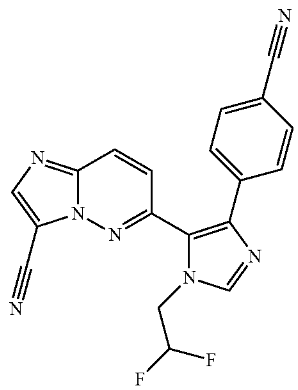 [SMILES: N#Cc1ccc(-c2ncn(CC(F)F)c2-c2ccc3ncc(C#N)n3n2)cc1] | 6-(4-(4-cyanophenyl)-1-(2,2-difluoroethyl)-1H-imidazol-5-yl)imidazo[1,2-b]pyridazine-3-carbonitrile | 376.2 | 1.318<br>1.263 | H<br>I |
| 259' | 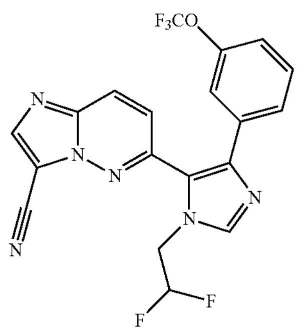 [SMILES: N#Cc1cnc2ccc(-c3c(-c4cccc(OC(F)(F)F)c4)ncn3CC(F)F)nn12] | 6-(1-(2,2-difluoroethyl)-4-(3-(trifluoromethoxy)phenyl)-1H-imidazol-5-yl)imidazo[1,2-b]pyridazine-3-carbonitrile | 435.2 | 1.732<br>1.659 | H<br>I |
| 260' | 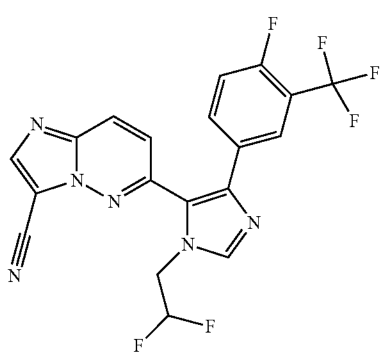 [SMILES: N#Cc1cnc2ccc(-c3c(-c4ccc(F)c(C(F)(F)F)c4)ncn3CC(F)F)nn12] | 6-(1-(2,2-difluoroethyl)-4-(4-fluoro-3-(trifluoromethyl)phenyl)-1H-imidazol-5-yl)imidazo[1,2-b]pyridazine-3-carbonitrile | 437.2 | 1.739<br>1.674 | H<br>I |
| 261' | 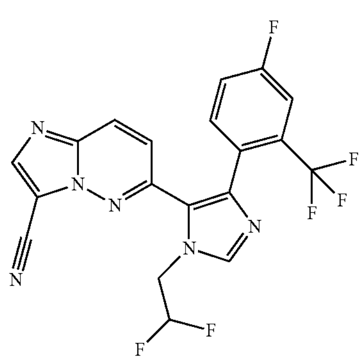 [SMILES: N#Cc1cnc2ccc(-c3c(-c4ccc(F)cc4C(F)(F)F)ncn3CC(F)F)nn12] | 6-(1-(2,2-difluoroethyl)-4-(4-fluoro-2-(trifluoromethyl)phenyl)-1H-imidazol-5-yl)imidazo[1,2-b]pyridazine-3-carbonitrile | 437.2 | 1.556<br>1.491 | H<br>I |

TABLE 17-continued

| Ex. | Structure | Name | [M + H]+ | Ret Time (min.) | HPLC Method |
|---|---|---|---|---|---|
| 262' | 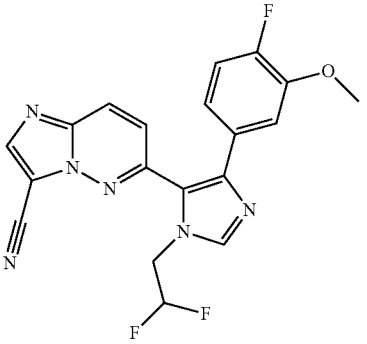 [SMILES: COc1cc(-c2ncn(CC(F)F)c2-c2ccc3ncc(C#N)n3n2)ccc1F] | 6-(1-(2,2-difluoroethyl)-4-(4-fluoro-3-methoxyphenyl)-1H-imidazol-5-yl)imidazo[1,2-b]pyridazine-3-carbonitrile | 399.2 | 1.435<br>1.275 | H<br>I |
| 263' | 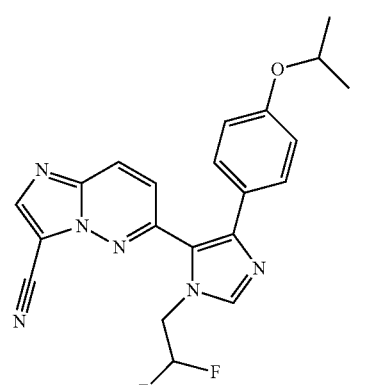 | 6-(1-(2,2-difluoroethyl)-4-(4-isopropoxyphenyl)-1H-imidazol-5-yl)imidazo[1,2-b]pyridazine-3-carbonitrile | 409.3 | 1.648<br>1.377 | H<br>I |
| 264' | 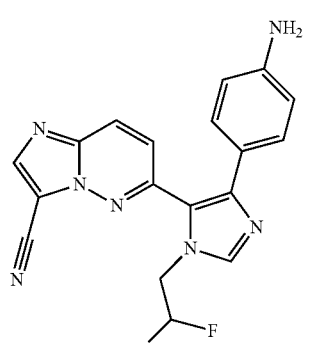 | 6-(4-(4-aminophenyl)-1-(2,2-difluoroethyl)-1H-imidazol-5-yl)imidazo[1,2-b]pyridazine-3-carbonitrile | 366.2 | 1.070<br>0.761 | H<br>I |
| 265' | 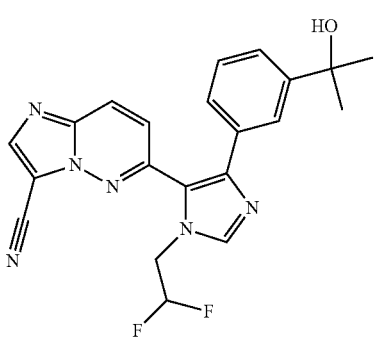 [SMILES: CC(C)(O)c1cccc(-c2ncn(CC(F)F)c2-c2ccc3ncc(C#N)n3n2)c1] | 6-(1-(2,2-difluoroethyl)-4-(3-(2-hydroxypropan-2-yl)phenyl)-1H-imidazol-5-yl)imidazo[1,2-b]pyridazine-3-carbonitrile | 409.3 | 1.253<br>1.052 | H<br>I |

TABLE 17-continued

| Ex. | Structure | Name | [M + H]+ | Ret Time (min.) | HPLC Method |
|---|---|---|---|---|---|
| 266' | 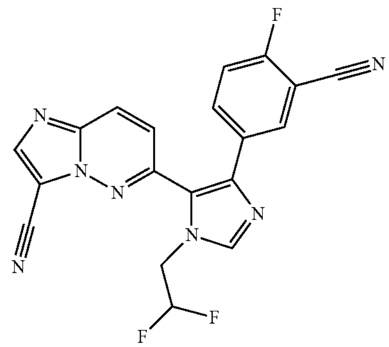 [SMILES: N#Cc1cc(-c2ncn(CC(F)F)c2-c2ccc3ncc(C#N)n3n2)ccc1F] | 6-(4-(3-cyano-4-fluorophenyl)-1-(2,2-difluoroethyl)-1H-imidazol-5-yl)imidazo[1,2-b]pyridazine-3-carbonitrile | 394.2 | 1.394<br>1.335 | H<br>I |

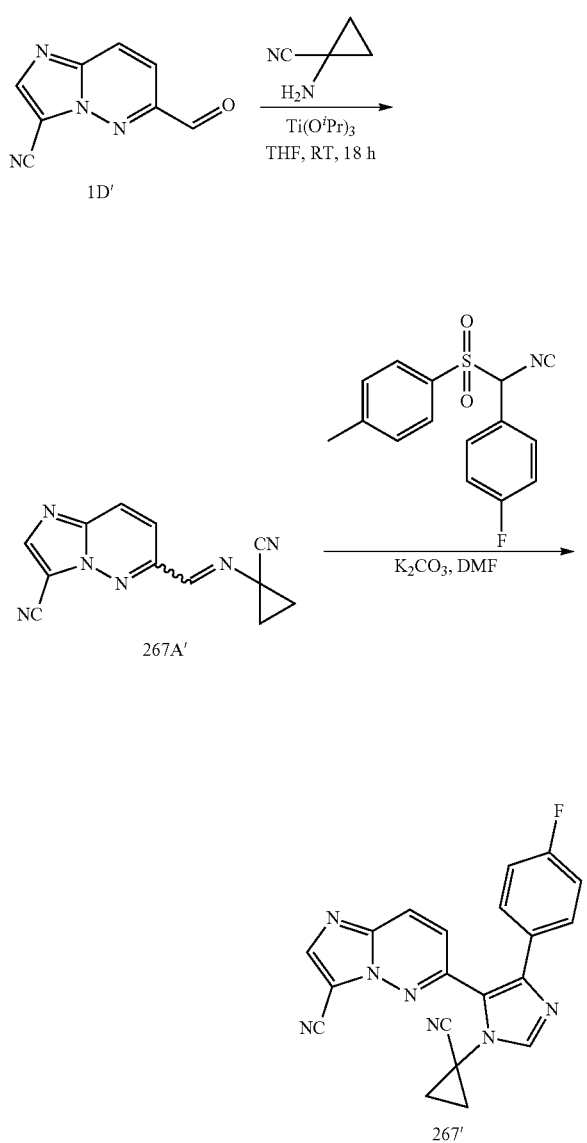

Scheme 23

Intermediate 267A': 6-(((1-cyanocyclopropyl)imino)methyl)imidazo[1,2-b]pyridazine-3-carbonitrile

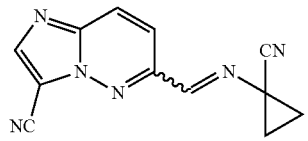 [SMILES: N#Cc1cnc2ccc(C=NC3(C#N)CC3)nn12]

To a solution of intermediate 1D' (100 mg, 0.581 mmol) in THF (10 mL) was added 1-aminocyclopropanecarbonitrile.HCl (83 mg, 0.697 mmol) and titanium (IV) isopropoxide (0.187 mL, 0.639 mmol) at RT and the mixture was stirred for 2 h. To the reaction mixture was then added water and extracted with ethyl acetate (2×30 mL). The combined organic layers were dried over $Na_2SO_4$, filtered and the filtrate was concentrated to afford intermediate 267A' (60 mg, 39.4% yield) which was used in the next step without further purification LCMS: m/z=237.3 [M+H]+; HPLC Ret. Time 0.96 min. (HPLC Method G); $^1$H NMR (400 MHz, DMSO-$d_6$) δ ppm 8.68 (s, 1H), 8.58 (s, 1H), 8.43 (d, J=9.54 Hz, 1H), 7.89 (d, J=9.54 Hz, 1H), 1.96-2.03 (m, 2H), 1.73-1.81 (m, 2H).

Example 267'

6-(1-(1-cyanocyclopropyl)-4-(4-fluorophenyl)-1H-imidazol-5-yl)imidazo[1,2-b]pyridazine-3-carbonitrile, TFA

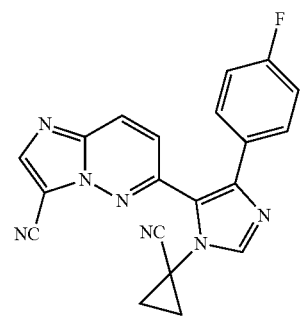 [SMILES: N#Cc1cnc2ccc(-c3c(-c4ccc(F)cc4)ncn3C3(C#N)CC3)nn12]

To a suspension of intermediate 267A' (200 mg, 0.847 mmol) in DMF (5 mL) was added potassium carbonate (176 mg, 1.270 mmol) and 1-fluoro-4-(isocyano(tosyl)methyl)benzene (294 mg, 1.016 mmol) at RT. The reaction mixture was stirred at the same temperature for 16 h, diluted with water and extracted with ethyl acetate (2×20 mL). The combined organic layers were dried over $Na_2SO_4$, and filtered. The filtrate was concentrated and the crude product was purified by preparative HPLC (Condition P) to afford Example 267' (1.2 mg, 0.290% yield) as the TFA salt. LCMS: m/z=370.0 [M+H]$^+$; HPLC Ret. Time 1.53 min. (HPLC Method H); $^1$H NMR (400 MHz, DMSO-d$_6$) δ ppm 8.68 (s, 1H), 8.32-8.42 (m, 2H), 7.58 (dd, J=5.50, 8.44 Hz, 2H), 7.31 (d, J=9.54 Hz, 1H), 7.19 (t, J=8.80 Hz, 2H), 1.84 (d, J=7.83 Hz, 4H).

Compounds shown in Table 18 have been prepared in a manner similar to Example 267' using intermediate 1D', various amines and 1-fluoro-4-(isocyano(tosyl)methyl)benzene.

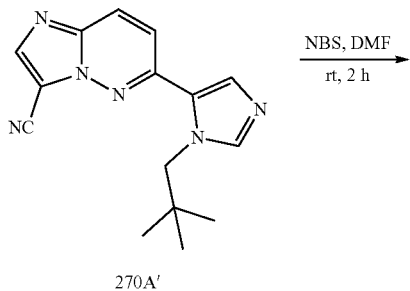

270A'

TABLE 18

| Ex. | Structure | Name | [M + H]$^+$ | Ret Time (min.) | HPLC Method |
|---|---|---|---|---|---|
| 268' | 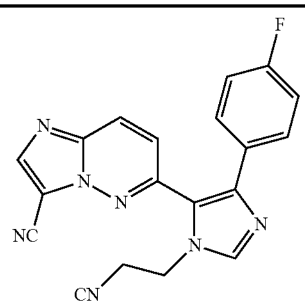 | 6-(1-(2-cyanoethyl)-4-(4-fluorophenyl)-1H-imidazol-5-yl)imidazo[1,2-b]pyridazine-3-carbonitrile | 358.0 | 1.441<br>1.208 | H<br>I |
| 269' | 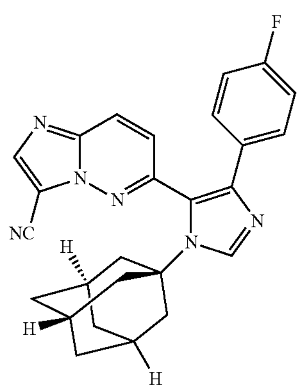 [SMILES: N#Cc1cnc2ccc(-c3c(-c4ccc(F)cc4)ncn3[C@]34CC5C[C@H](C[C@H](C5)C3)C4)nn12] | 6-(4-(4-fluorophenyl)-1-((1r,3s,5R,7S)-3-hydroxyadamantan-1-yl)-1H-imidazol-5-yl)imidazo[1,2-b]pyridazine-3-carbonitrile | 455.3 | 1.398<br>1.084 | H<br>I |

Scheme 24

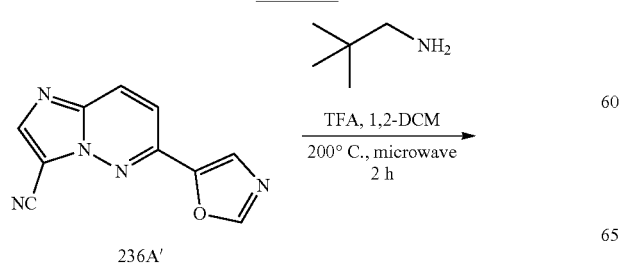

236A'

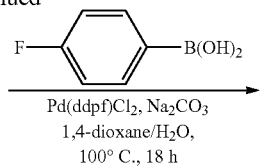

270B'

Example 270'

6-(4-(4-fluorophenyl)-1-neopentyl-1H-imidazol-5-yl)imidazo[1,2-b]pyridazine-3-carbonitrile

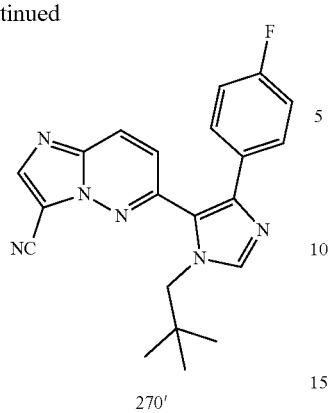

270'

Intermediate 270A': 6-(1-neopentyl-1H-imidazol-5-yl)imidazo[1,2-b]pyridazine-3-carbonitrile

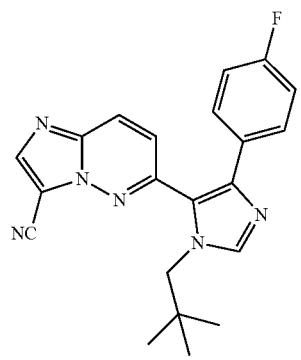 [SMILES: CC(C)(C)Cn1cnc(-c2ccc(F)cc2)c1-c1ccc2ncc(C#N)n2n1]

Intermediate 270A' was synthesized by treating intermediate 236A' with 2,2-dimethylpropan-1-amine and by employing the experimental procedure described for intermediate 236B' in Scheme 22. The crude compound was purified by silica gel chromatography (24 g CombiFlash® column, eluting with 5% MeOH in CHCl$_3$). Fractions containing the desired product were combined and evaporated to afford intermediate 270A' (160 mg, 60.3% Yield). LCMS: m/z=281.0 [M+H]$^+$; HPLC Ret. Time 2.11 min. (HPLC Method J).

Intermediate 270B': 6-(4-bromo-1-neopentyl-1H-imidazol-5-yl)imidazo[1,2-b]pyridazine-3-carbonitrile Intermediate 270B' was synthesized by treating intermediate 270A' with NBS and by employing the experimental procedure described for intermediate 236C' in Scheme 21. Intermediate 270B' (195 mg). LCMS: m/z=361.2 [M+H]$^+$; HPLC Ret. Time 1.28 min. (HPLC Method G).

To a solution of intermediate 270B' (100 mg, 0.278 mmol) and (4-fluorophenyl)boronic acid (58.4 mg, 0.418 mmol) in 1,4-dioxane (4 mL) and H$_2$O (0.2 mL) was added sodium carbonate (73.8 mg, 0.696 mmol) and the mixture was degassed for 5 minutes, then PdCl$_2$(dppf)-CH$_2$Cl$_2$ adduct (22.73 mg, 0.028 mmol) was also added. The reaction mixture was degassed again and heated at 100° C. for 12 h. The volatiles were removed under reduced pressure. The crude solid was dissolved in ethyl acetate and washed with H$_2$O. The aqueous layer was back-extracted with ethyl acetate. The combined organic layers were washed with brine, dried over Na$_2$SO$_4$, and filtered. The filtrate was concentrated under reduced pressure to obtain a brown solid (250 mg). The crude compound was purified by preparative HPLC (Condition P) to afford Example 270' (11.7 mg, 0.030 mmol, 21.8% yield). LCMS: m/z=375.3 [M+H]$^+$; HPLC Ret. Time 1.69 min. (HPLC Method H); $^1$H NMR (400 MHz, DMSO-d$_6$) δ ppm 8.65 (s, 1H), 8.31 (d, J=9.6 Hz, 1H), 7.99 (s, 1H), 7.50-7.53 (m, 2H), 7.30 (d, J=9.6 Hz, 1H), 7.12-7.16 (m, 2H), 4.17 (s, 2H), 0.73 (s, 9H) ppm.

Scheme 25

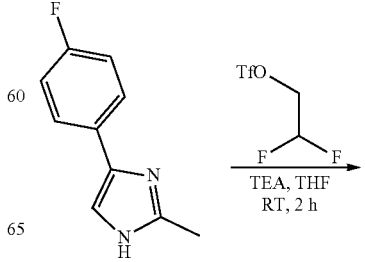

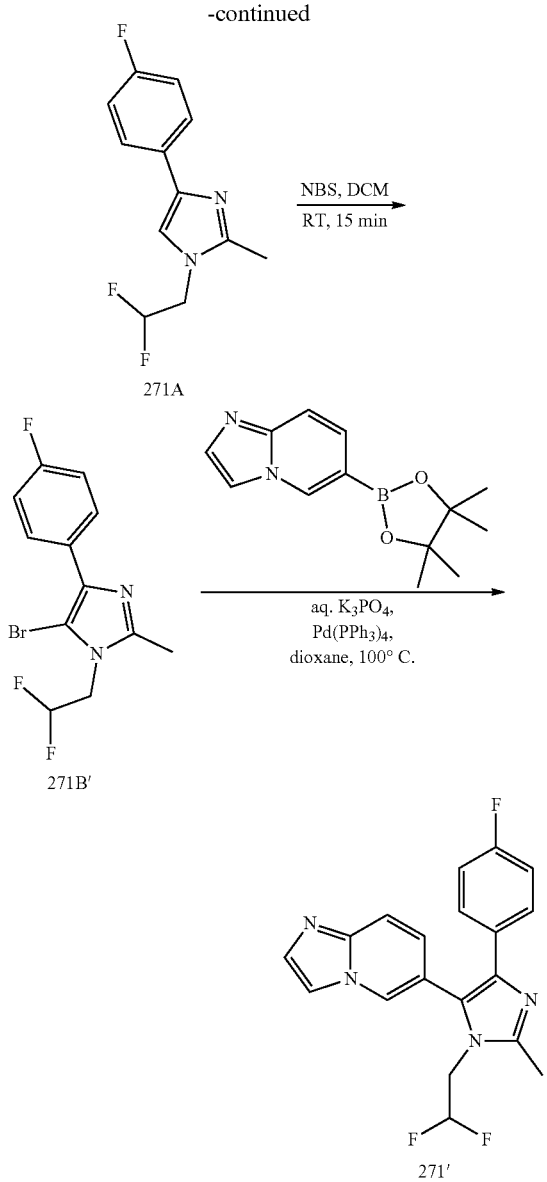

Intermediate 271A': 1-(2,2-difluoroethyl)-4-(4-fluorophenyl)-2-methyl-1H-imidazole To a solution of 4-(4-fluorophenyl)-2-methyl-1H-imidazole (reference: WO 2014100533 A1) (0.35 g, 1.986 mmol) in THF (5 mL) was added TEA (0.554 mL, 3.97 mmol). The reaction mixture was cooled to 0° C. and 2,2-difluoroethyl trifluoromethanesulfonate (0.4 mL, 2.98 mmol) was added dropwise. The reaction was stirred at RT for 2 h, concentrated under reduced pressure and the resulting residue was partitioned between water and ethyl acetate. The organic layer was washed with brine, dried over $Na_2SO_4$, and filtered. The filtrate was concentrated under reduced pressure to give the crude residue, which was purified by silica gel chromatography (24 g CombiFlash® column, eluting with a gradient of 4% MeOH in $CHCl_3$). Fractions containing the desired product were combined and evaporated to afford intermediate 271A' (0.3 g, 62.9% yield) as a yellow solid. LCMS m/z=241.2 [M+H]$^+$; HPLC Ret. Time 1.731 min. (HPLC Method J).

Intermediate 271B': 5-bromo-1-(2,2-difluoroethyl)-4-(4-fluorophenyl)-2-methyl-1H-imidazole

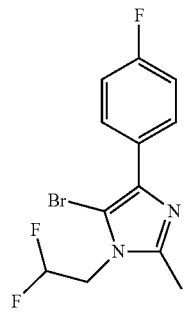 [SMILES: Cc1nc(-c2ccc(F)cc2)c(Br)n1CC(F)F]

To a solution of intermediate 271A' (0.27 g, 1.124 mmol) in DCM (5 mL) at 0° C. was added NBS (0.220 g, 1.236 mmol) portion wise. The reaction mixture was stirred at RT for 15 min. diluted with water and extracted with DCM. The combined organic layers were washed with brine, dried over $Na_2SO_4$, filtered and the filtrate was concentrated under reduced pressure to afford intermediate 271B' (0.3 g, 84% yield) as a white solid. LCMS: m/z=321.0 [M+H]$^+$; HPLC Ret. Time 1.19 min. (HPLC Method G).

Example 271'

6-(1-(2,2-difluoroethyl)-4-(4-fluorophenyl)-2-methyl-1H-imidazol-5-yl)imidazo[1,2-a]pyridine

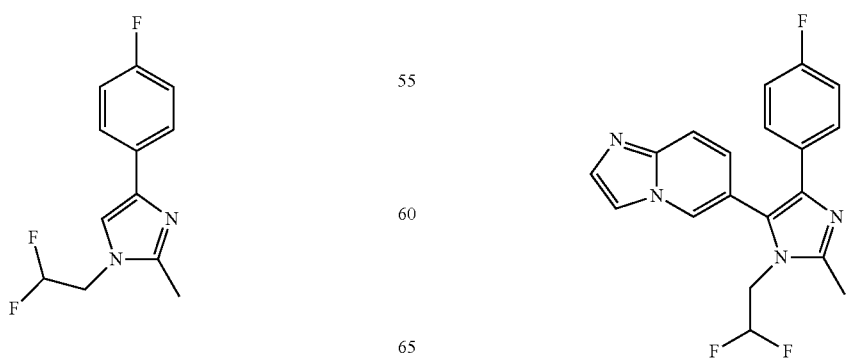

To a solution of intermediate 271B' (0.16 g, 0.501 mmol) in 1,4-dioxane (2 mL) was added imidazo[1,2-a]pyridin-6-ylboronic acid (reference: CN 103275112 A) (0.162 g, 1.003 mmol) and K₃PO₄ (0.752 mL, 1.504 mmol) and the mixture was degassed with argon for 5 minutes. Then Pd(Ph₃P)₄ (0.058 g, 0.050 mmol) was added and the reaction mixture was heated at 100° C. for 4 h. The reaction mixture was diluted with water and extracted with DCM. The organic layer was washed with brine, dried over Na₂SO₄, and filtered. The filtrate was concentrated under reduced pressure to give the crude compound, which was purified by preparative HPLC (Condition N). Fractions containing the desired product were combined and evaporated to afford Example 271' (19 mg, 11% yield). LCMS m/z=357.1 [M+H]⁺; HPLC Ret. Time 1.387 min. (HPLC Method H); ¹H NMR (400 MHz, DMSO-d₆) δ ppm 8.26 (s, 1H), 7.96 (s, 1H), 7.69-7.65 (m, 2H), 7.41 (q, J=16.00 Hz, 2H), 7.13-7.03 (m, 3H), 6.32-6.05 (m, 1H), 4.36-4.29 (m, 2H), 2.45-2.4 (m, 3H).

Scheme 26

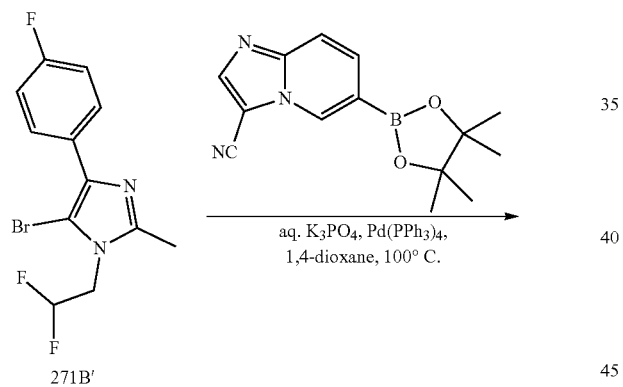

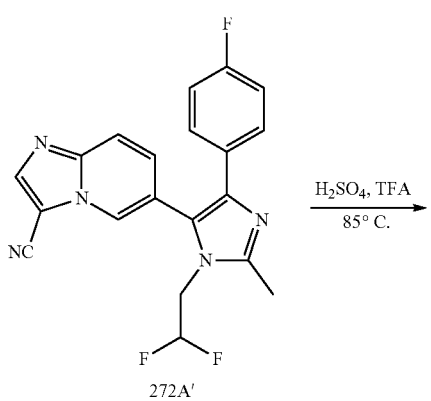

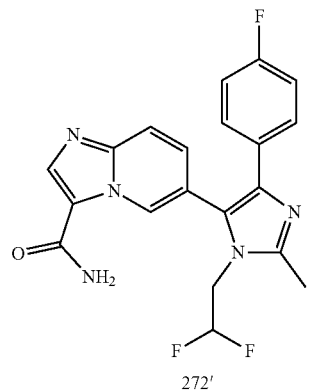

Intermediate 272A': 6-(1-(2,2-difluoroethyl)-4-(4-fluorophenyl)-2-methyl-1H-imidazol-5-yl)imidazo[1,2-a]pyridine-3-carbonitrile Intermediate 272A' was synthesized by reacting intermediate 271B' with 6-(4,4,5,5-tetramethyl-1,3,2-dioxaborolan-2-yl)imidazo[1,2-a]pyridine-3-carbonitrile (reference: WO 2014/055955 A1) and by employing the experimental procedure described for Example 271' in Scheme 25. The crude compound was purified by preparative HPLC (Condition P). Fractions containing the desired product were combined and evaporated to afford Example 272A' (150 mg, 78% yield). LCMS: m/z=382.1 [M+H]⁺; HPLC Ret. Time 1.52 min. (HPLC Method H); ¹H NMR (400 MHz, DMSO-d₆) δ ppm 8.71 (s, 1H), 8.52 (s, 1H), 7.92-7.89 (m, 1H), 7.44-7.39 (m, 3H), 7.06-7.01 (m, 2H), 6.28-6.01 (m, 1H), 4.44-4.37 (m, 2H), 2.46 (m, 3H).

Example 272'

6-(1-(2,2-difluoroethyl)-4-(4-fluorophenyl)-2-methyl-1H-imidazol-5-yl)imidazo[1,2-a]pyridine-3-carboxamide

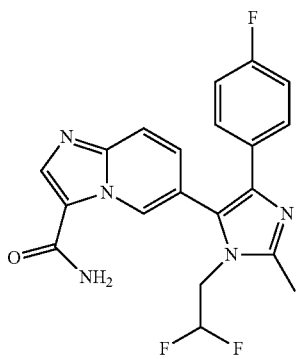 [SMILES: Cc1nc(-c2ccc(F)cc2)c(-c2ccc3ncc(C(N)=O)n3c2)n1CC(F)F]

A solution of intermediate 272A' (0.1 g, 0.262 mmol) in H₂SO₄ (0.063 ml, 1.180 mmol) and TFA (0.263 mL, 3.41 mmol) was heated at 85° C. for 2 h. The reaction mixture was diluted with water and extracted with DCM. The organic layer was washed with brine, dried over Na₂SO₄ and evaporated to give the crude compound which was purified by preparative HPLC (Condition P). Fractions containing the desired product were combined and evaporated to afford Example 272' (2 mg, 2% yield). LCMS: m/z=400.1 [M+H]⁺; HPLC Ret. Time 1.35 min. (HPLC Method H); ¹H NMR (400 MHz, DMSO-d₆) δ ppm 9.44 (s, 1H), 8.40 (s, 1H), 8.0 (bs, 1H), 7.84 (d, J=12.00 Hz, 1H), 7.41-7.36 (m, 4H), 7.06-7.01 (m, 2H), 6.31-6.04 (m, 1H), 4.38-4.25 (m, 2H) 2.45 (m, 3H).

Scheme 27

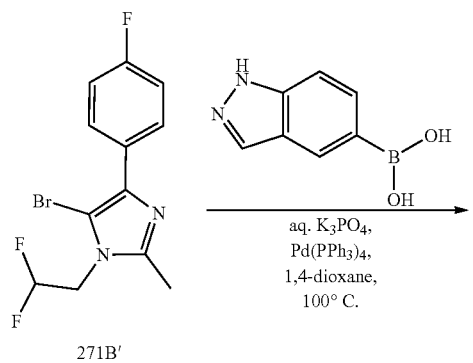

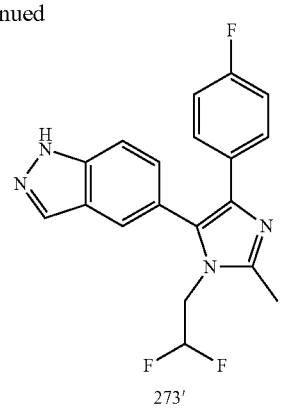

273'

Example 273'

5-(1-(2,2-difluoroethyl)-4-(4-fluorophenyl)-2-methyl-1H-imidazol-5-yl)-1H-indazole Example 273' was synthesized by reacting intermediate 271B' with (1H-indazol-5-yl)boronic acid (reference: WO 2012/078777 A1) and by employing the experimental procedure described for Example 271' in Scheme 25. The crude compound was purified by preparative HPLC (Condition P). Fractions containing the desired product were combined and evaporated to afford Example 273' (5.1 mg, 5% yield). LCMS: m/z=357.1 [M+H]⁺; HPLC Ret. Time 1.533 min. (HPLC Method H); ¹H NMR 400 MHz, DMSO-d₆) δ ppm 13.27 (s, 1H), 8.14 (s, 1H), 7.77 (s, 1H), 7.71-7.60 (m, 1H), 7.33-7.23 (m, 3H), 6.99-6.95 (m, 2H), 6.25-5.97 (m, 1H), 4.26-4.10 (m, 2H), 2.45 (s, 3H).

Scheme 28

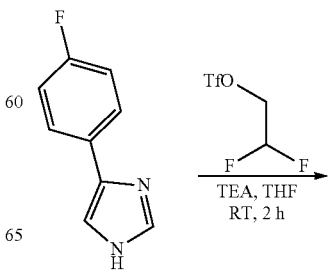

511

-continued

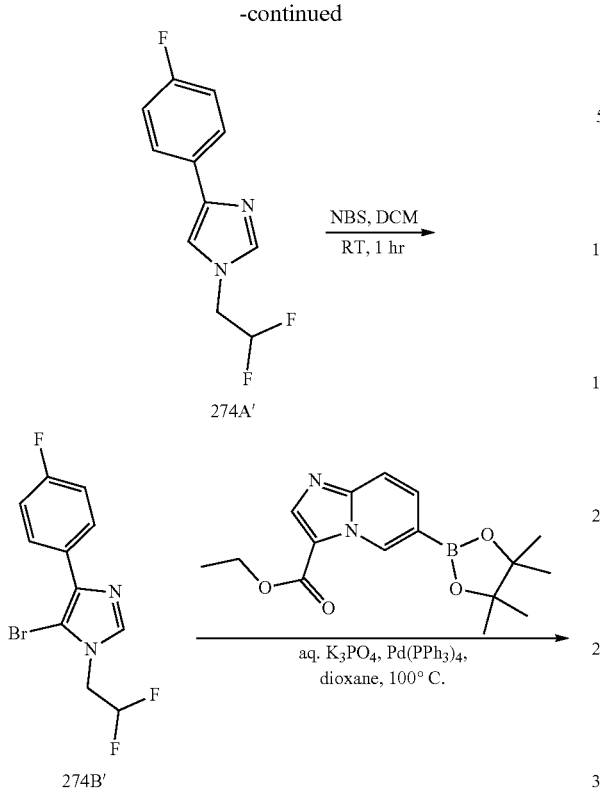

512

-continued

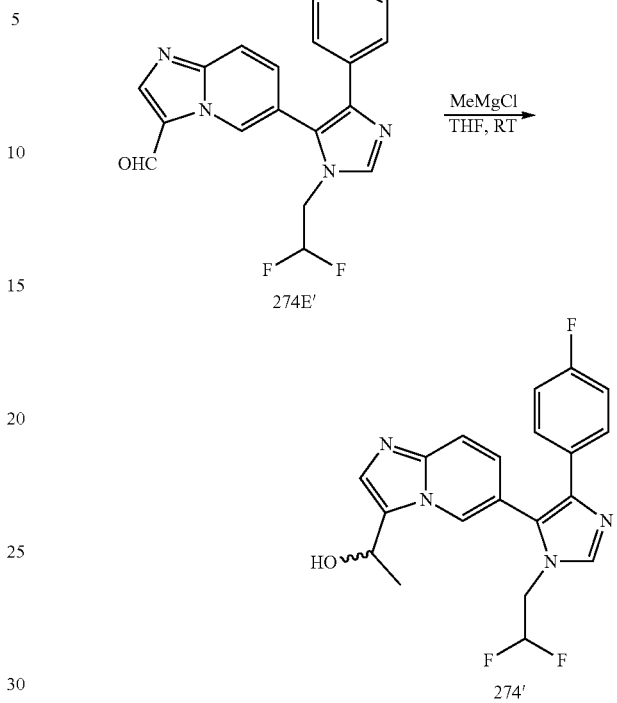

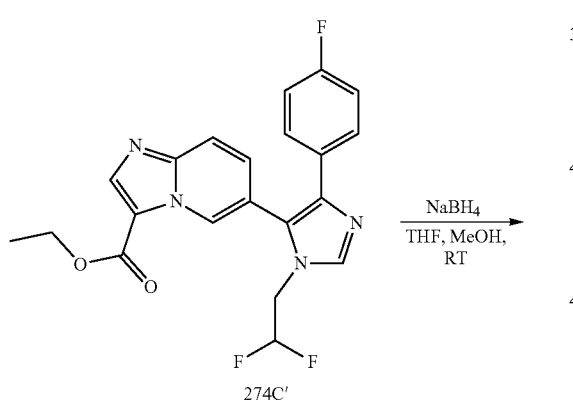

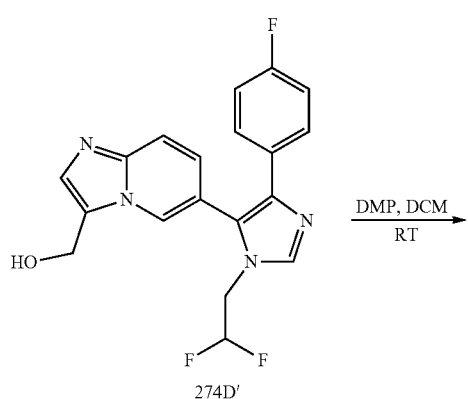

Intermediate 274A': 1-(2,2-difluoroethyl)-4-(4-fluorophenyl)-1H-imidazole

Intermediate 274A' was synthesized by reacting 4-(4-fluorophenyl)-1H-imidazole with 2,2-difluoroethyl trifluoromethanesulfonate and by employing the experimental procedure described for intermediate 271A' in Scheme 25. The crude product was purified by silica gel chromatography (40 g CombiFlash® column, eluting with a gradient of 3% MeOH in CHCl$_3$). Fractions containing the desired product were combined and evaporated to afford intermediate 274A' (3.0 g, 71.7% yield) as a brown oil. LCMS: m/z=227.0 [M+H]$^+$; HPLC Ret. Time 1.89 min. (HPLC Method J).

513

Intermediate 274B': 5-bromo-1-(2,2-difluoroethyl)-4-(4-fluorophenyl)-1H-imidazole

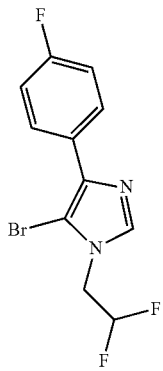 [SMILES: Fc1ccc(-c2ncn(CC(F)F)c2Br)cc1]

Intermediate 274B' was synthesized by reacting intermediate 274A' with NBS and by employing the experimental procedure described for intermediate 271B' in Scheme 25. Intermediate 274B' (3.5 g, 86% yield) as a brown oil. LCMS: m/z=307.0 [M+H]⁺; HPLC Ret. Time 2.395 min. (HPLC Method J).

Intermediate 274C': ethyl 6-(1-(2,2-difluoroethyl)-4-(4-fluorophenyl)-1H-imidazol-5-yl)imidazo[1,2-a]pyridine-3-carboxylate

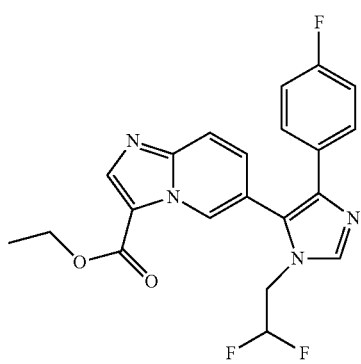 [SMILES: CCOC(=O)c1cnc2ccc(-c3c(-c4ccc(F)cc4)ncn3CC(F)F)cn12]

To a solution of 6-(4,4,5,5-tetramethyl-1,3,2-dioxaborolan-2-yl)imidazo[1,2-a] pyridine-3-carboxylate (reference: WO 2013033203 A1) (1.554 g, 4.92 mmol) in 1,4-dioxane (10 mL) was added intermediate 274B' (1 g, 3.28 mmol) and K₂CO₃ (4.92 mL, 9.83 mmol). The mixture was degassed with argon for 5 minutes and PdCl₂(dppf)-CH₂Cl₂ adduct (0.268 g, 0.328 mmol) was added. The reaction mixture was heated at 100° C. for 4 h, diluted with water and extracted with DCM. The organic layer was washed with brine, dried over Na₂SO₄, and filtered. The filtrate was concentrated under reduced pressure to give the crude compound, which was purified by preparative HPLC (Condition P). Fractions containing the desired product were combined and evaporated to afford intermediate 274C' (815 mg, 60% yield). LCMS: m/z=415.1 [M+H]⁺; HPLC Ret. Time 1.72 min. (HPLC Method H); ¹H NMR (400 MHz, DMSO-d₆) δ ppm 9.21-9.15 (m, 1H), 8.37 (s, 1H), 7.98-7.90 (m, 2H), 7.51-7.41 (m, 3H), 7.12-7.02 (m, 2H), 6.40-6.07 (m, 1H), 4.48-4.29 (m, 4H), 1.30 (s, 3H).

514

Intermediate 274D': (6-(1-(2,2-difluoroethyl)-4-(4-fluorophenyl)-1H-imidazol-5-yl)imidazo[1,2-a]pyridin-3-yl)methanol

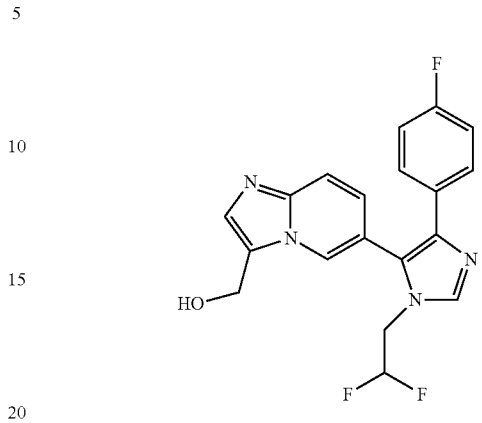

To a solution of intermediate 274C' (0.1 g, 0.241 mmol) in MeOH (1.5 mL) and THF (2.5 mL) at 0° C. was added NaBH₄ (10.96 mg, 0.290 mmol). The reaction mixture was stirred at RT for 1 h, diluted with water and extracted with ethyl acetate. The organic layer was washed with brine, dried over Na₂SO₄, filtered and the filtrate was concentrated under reduced pressure to give the crude compound, which was purified by preparative HPLC (Condition P). Fractions containing the desired product were combined and evaporated to afford intermediate 274D' (6.4 mg, 7.12% yield). LCMS: m/z=373.1 [M+H]⁺; HPLC Ret. Time 1.19 min. (HPLC Method H). ¹H NMR (400 MHz, DMSO-d₆) δ ppm 8.52-8.49 (m, 1H), 7.95-7.93 (m, 1H), 7.73-7.66 (m, 1H), 7.61-7.57 (m, 1H), 7.51-7.44 (m, 2H), 7.16-7.04 (m, 3H), 6.37-6.05 (m, 1H), 5.23-5.16 (m, 1H), 4.82-4.77 (m, 2H), 4.47-4.34 (m, 2H).

Intermediate 274E': 6-(1-(2,2-difluoroethyl)-4-(4-fluorophenyl)-1H-imidazol-5-yl)imidazo[1,2-a]pyridine-3-carbaldehyde

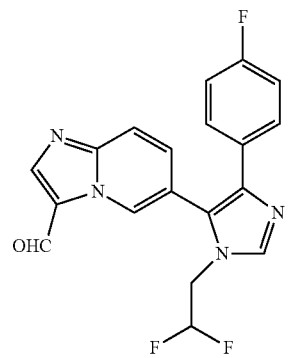 [SMILES: O=Cc1cnc2ccc(-c3c(-c4ccc(F)cc4)ncn3CC(F)F)cn12]

To a solution of intermediate 274D' (0.2 g, 0.537 mmol) in DCM (1 mL) at 0° C. was added DMP (0.342 g, 0.806 mmol). The reaction mixture was stirred at RT for 1 h, diluted with water and extracted with DCM. The organic layer was washed with brine, dried over Na₂SO₄, filtered and the filtrate was concentrated under reduced pressure to afford intermediate 274E' (0.2 g, crude). LCMS: m/z=371.4 [M+H]⁺; HPLC Ret. Time 0.97 min. (HPLC Method G).

Example 274'

1-(6-(1-(2,2-difluoroethyl)-4-(4-fluorophenyl)-1H-imidazol-5-yl)imidazo[1,2-a]pyridin-3-yl)ethanol

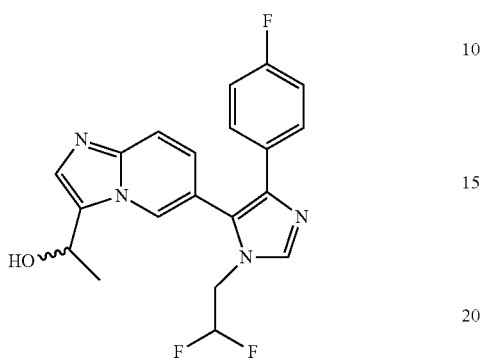

To a solution of intermediate 274E' (0.1 g, 0.270 mmol) in THF (2 mL) at 0° C. was added methylmagnesium chloride (0.900 mL, 2.70 mmol, 3M solution in THF). The reaction mixture was stirred at RT for 2 h, quenched with aqueous NH$_4$Cl solution and extracted with ethyl acetate. The organic layer was washed with brine, dried over Na$_2$SO$_4$, filtered and the filtrate was concentrated under reduced pressure to give the crude product, which was purified via preparative HPLC (condition P). Fractions containing the desired product were combined and evaporated to afford Example 274' (5.2 mg, 4.98% yield). LCMS: m/z=387.1 [M+H]$^+$; HPLC Ret. Time 1.33 min. (HPLC Method H); $^1$H NMR (400 MHz, DMSO-d$_6$) δ ppm 1.52-1.59 (m, 3H) 4.33-4.46 (m, 2H) 5.08-5.16 (m, 1H) 5.32-5.37 (m, 1H) 6.05-6.38 (m, 1H) 7.03-7.19 (m, 3H) 7.43-7.50 (m, 2H) 7.56-7.63 (m, 1H) 7.67-7.72 (m, 1H) 7.92-7.96 (m, 1H) 8.51-8.56 (m, 1H).

Scheme 29

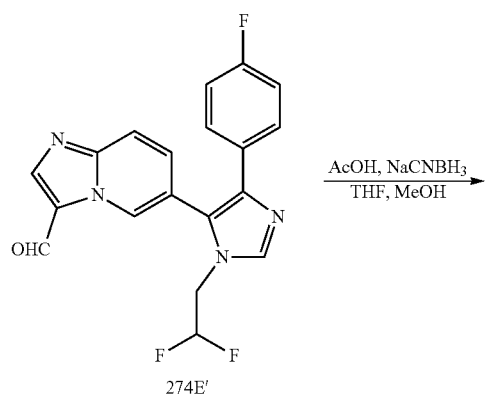

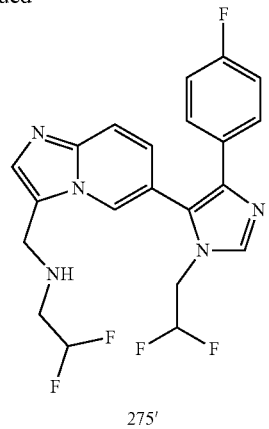

275'

Example 275'

N-((6-(1-(2,2-difluoroethyl)-4-(4-fluorophenyl)-1H-imidazol-5-yl)imidazo[1,2-a]pyridin-3-yl)methyl)-2,2-difluoroethanamine

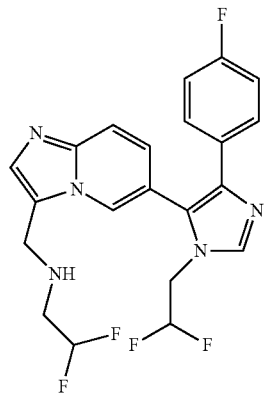 [SMILES: Fc1ccc(-c2ncn(CC(F)F)c2-c2ccc3ncc(CNCC(F)F)n3c2)cc1]

To a solution of intermediate 274E' (0.1 g, 0.270 mmol) in THF (1 mL) and MeOH (1 mL) was added 2,2-difluoroethanamine (0.024 g, 0.297 mmol) and acetic acid (0.015 mL, 0.270 mmol). The reaction mixture was stirred at RT for 16 h. After that the reaction was cooled to 0° C., NaCNBH$_3$ (0.051 g, 0.810 mmol) was added and the mixture was stirred at RT for 5 h. The reaction mixture was quenched with aq. NaHCO$_3$ and extracted with ethyl acetate. The organic layer was washed with brine, dried over Na$_2$SO$_4$, and filtered. The filtrate was concentrated under reduced pressure to give the crude product, which was purified by preparative HPLC (Condition P). Fractions containing the desired product were combined and evaporated to afford Example 275' (6.0 mg, 5.10% yield). LCMS: m/z=436.2 [M+H]$^+$; HPLC Ret. Time 1.59 min. (HPLC Method H); $^1$H NMR (400 MHz, DMSO-d$_6$) δ ppm 2.8-2.9 (m, 2H) 4.18 (s, 2H) 4.38-4.46 (m, 2H) 5.77-6.36 (m, 2H) 7.08 (t, J=8.83 Hz, 2H) 7.17 (d, J=9.17 Hz, 1H) 7.49 (dd, J=8.56, 5.75 Hz, 2H) 7.65 (s, 1H) 7.71 (d, J=9.23 Hz, 1H) 7.96 (s, 1H) 8.65 (s, 1H).

Compound shown in Table 19 has been prepared in a manner similar to Example 275' using intermediate 274E', amine and NaCNBH$_3$.

TABLE 19

| Ex. | Structure | Name | [M + H]⁺ | Ret. Time (min.) | HPLC Method |
|---|---|---|---|---|---|
| 276' | 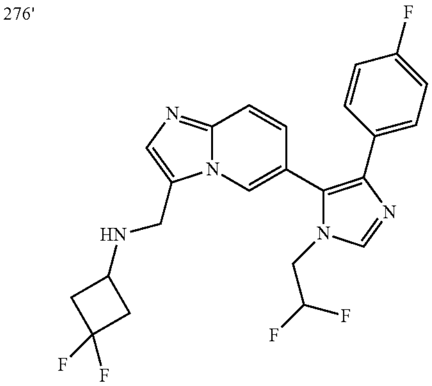 | N-((6-(1-(2,2-difluoroethyl)-4-(4-fluorophenyl)-1H-imidazol-5-yl)imidazo[1,2-a]pyridin-3-yl)methyl)-3,3-difluorocyclobutanamine | 462.1 | 1.716<br>0.935 | H<br>I |

Scheme 30

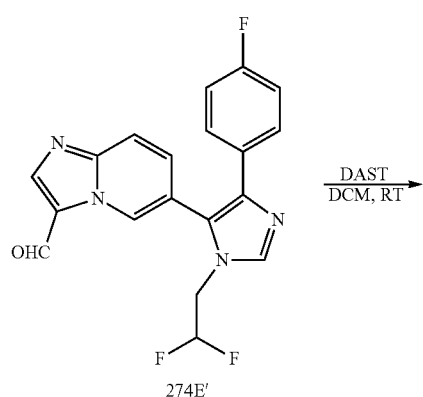

274E'

Example 277'

6-(1-(2,2-difluoroethyl)-4-(4-fluorophenyl)-1H-imidazol-5-yl)-3-(difluoromethyl)imidazo [1,2-a]pyridine

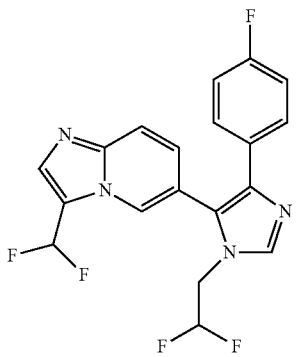 [SMILES: Fc1ccc(-c2ncn(CC(F)F)c2-c2ccc3ncc(C(F)F)n3c2)cc1]

277'

To a solution of intermediate 274E' (0.1 g, 0.270 mmol) in DCM (2 mL) at 0° C. was added DAST (0.071 mL, 0.540 mmol). The reaction mixture was stirred at RT for 2 h, quenched with aqueous NaHCO₃ solution and extracted with DCM. The organic layer was washed with brine, dried over Na₂SO₄, filtered and the filtrate concentrated under reduced pressure to give the crude product, which was purified by preparative HPLC (Condition L). Fractions containing the desired product were combined and evaporated to afford Example 277' (0.026 g, 24.54% yield). LCMS m/z=393.1 [M+H]⁺; HPLC Ret. Time 1.65 min. (HPLC Method H); ¹H NMR (400 MHz, DMSO-d₆) δ ppm 8.64-8.68 (m, 1H) 8.04-8.11 (m, 2H) 7.83-7.88 (m, 1H) 7.39-7.49 (m, 2H) 6.92-7.23 (m, 4H) 6.07-6.39 (m, 1H) 4.36-4.50 (m, 2H).

519

Scheme 31

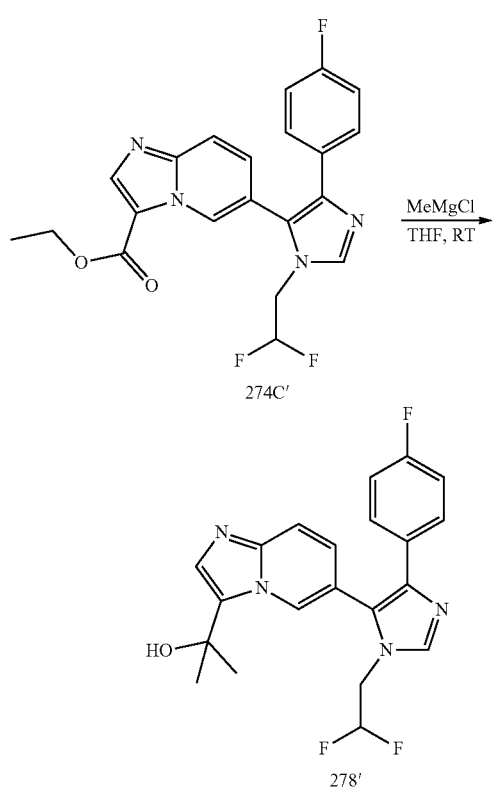

Example 278'

1-(6-(1-(2,2-difluoroethyl)-4-(4-fluorophenyl)-1H-imidazol-5-yl)imidazo[1,2-a]pyridin-3-yl)ethanol To a solution of intermediate 274C' (0.1 g, 0.241 mmol) in THF (2 mL) at 0° C. was added methylmagnesium chloride (0.804 mL, 2.413 mmol; 3M solution in THF). The reaction was warmed to RT, stirred for 2 h, quenched with aqueous NH₄Cl solution and extracted with ethyl acetate. The organic layer was washed with brine, dried over Na₂SO₄, filtered and the filtrate was concentrated under reduced pressure to give the crude product, which was purified by preparative HPLC (Condition N). Fractions containing the desired product were combined and evaporated to afford Example 278' (4.2 mg, 4.35% yield). LCMS:

520 m/z=401.1 [M+H]$^+$; HPLC Ret. Time 1.35 min. (HPLC Method H); $^1$H NMR (400 MHz, DMSO-d$_6$) δ ppm 9.07-9.01 (m, 1H), 8.10-7.99 (m, 3H), 7.79-7.72 (m, 1H), 7.51-7.42 (m, 2H), 7.14-7.04 (m, 2H), 6.43-6.09 (m, 1H), 5.7 (s, 1H), 4.50-4.36 (m, 2H), 1.64-1.59 (m, 6H).

Scheme 32

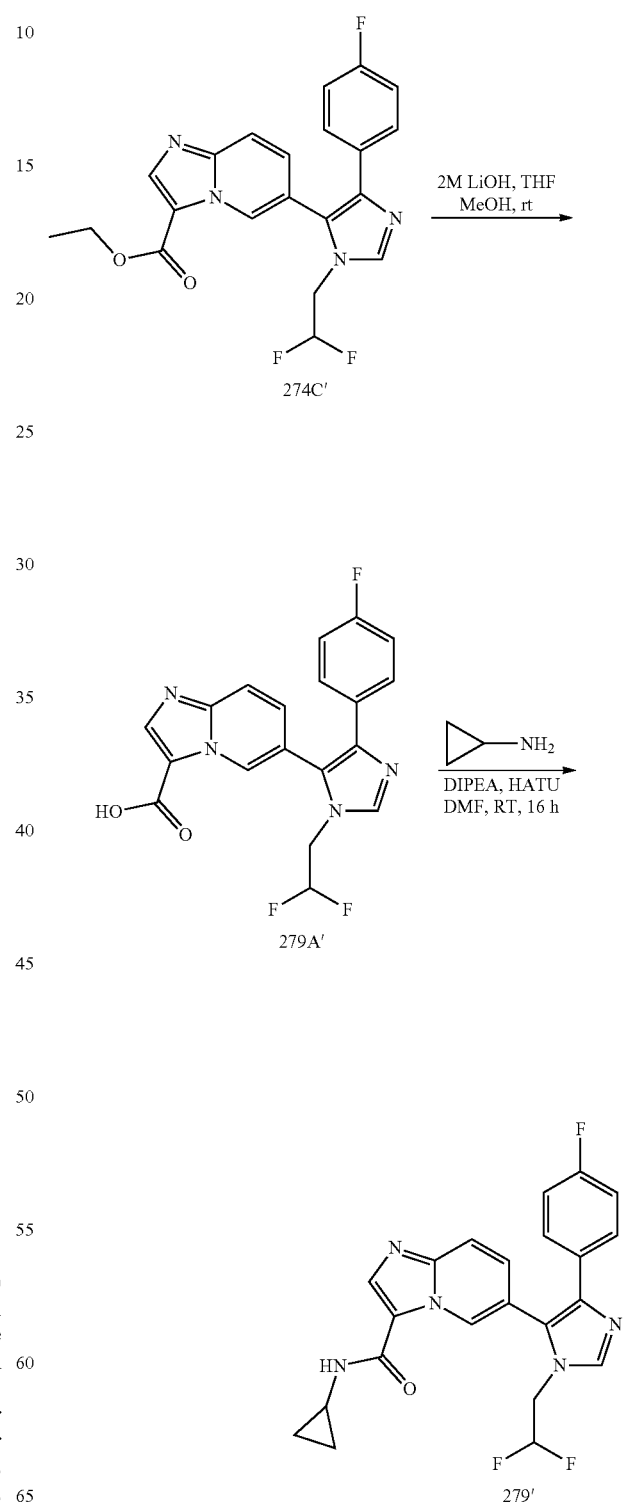

521
Intermediate 279A': 6-(1-(2,2-difluoroethyl)-4-(4-fluorophenyl)-1H-imidazol-5-yl)imidazo[1,2-a]pyridine-3-carboxylic acid

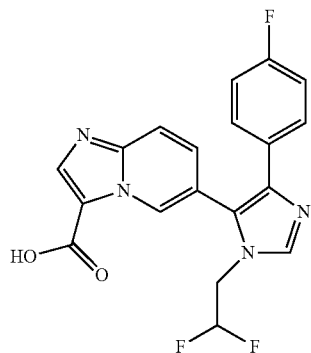 [SMILES: O=C(O)c1cnc2ccc(-c3c(-c4ccc(F)cc4)ncn3CC(F)F)cn12]

To a solution of intermediate 274C' (0.2 g, 0.483 mmol) in THF (4 mL) and MeOH (2 mL) was added 2M aq. LiOH (0.724 mL, 1.448 mmol) solution. The reaction mixture was stirred at RT for 16 h concentrated to dryness, and the resulting residue was suspended in water and acidified with 1.5 N aq. HCl. The solid precipitated out was filtered and dried to afford intermediate 279A' (0.15 g, 80% yield) as a pale yellow solid. LCMS: m/z=387.2 [M+H]$^+$; HPLC Ret. Time 1.87 min. (HPLC Method J).

522
Example 279'

N-cyclopropyl-6-(1-(2,2-difluoroethyl)-4-(4-fluorophenyl)-1H-imidazol-5-yl)imidazo[1,2-a]pyridine-3-carboxamide

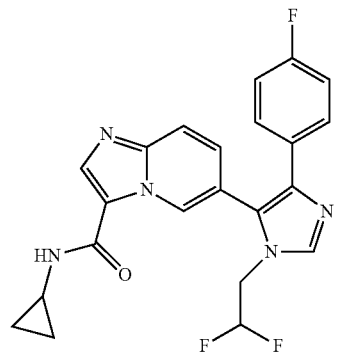 [SMILES: O=C(NC1CC1)c1cnc2ccc(-c3c(-c4ccc(F)cc4)ncn3CC(F)F)cn12]

To a solution of intermediate 279A' (0.05 g, 0.129 mmol) in DMF (1 mL) was added cyclopropanamine (0.011 g, 0.194 mmol), DIPEA (0.068 mL, 0.388 mmol) and HATU (0.098 g, 0.259 mmol). The reaction mixture was stirred at RT for 16 h, diluted with water and extracted with ethyl acetate. The organic layer was washed with brine, dried over Na$_2$SO$_4$, filtered and the filtrate was concentrated under reduced pressure to give the crude product, which was purified by preparative HPLC (Condition L). Fractions containing the desired product were combined and evaporated to afford Example 279' (0.015 g, 27.2% yield). LCMS: m/z=426.2 [M+H]$^+$; HPLC Ret. Time 1.29 min. (HPLC Method H); $^1$H NMR (400 MHz, DMSO-d$_6$) δ ppm 9.53 (d, J=0.79 Hz, 1H) 8.6-8.61 (m, 1H) 8.41 (s, 1H) 8.29 (s, 1H) 7.86-7.91 (m, 1H) 7.42-7.48 (m, 3H) 7.08-7.15 (m, 2H) 6.09-6.41 (m, 1H) 4.39-4.52 (m, 2H) 2.76-2.87 (m, 1H) 0.71-0.77 (m, 2H) 0.53-0.60 (m, 2H).

The compound shown in Table 20 has been prepared in a manner similar to Example 279' by amide bond coupling between intermediate 279A' and the amine.

TABLE 20

| Ex. | Structure | Name | [M + H]$^+$ | Ret. Time (min.) | HPLC Method |
|---|---|---|---|---|---|
| 280' | 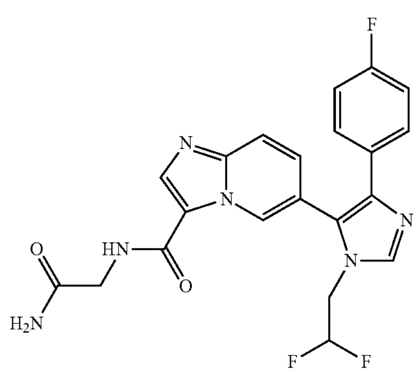 [SMILES: NC(=O)CNC(=O)c1cnc2ccc(-c3c(-c4ccc(F)cc4)ncn3CC(F)F)cn12] | N-(2-amino-2-oxoethyl)-6-(1-(2,2-difluoroethyl)-4-(4-fluorophenyl)-1H-imidazol-5-yl)imidazo[1,2-a]pyridine-3-carboxamide | 443.2 | 0.989 0.597 | H I |

Scheme 33

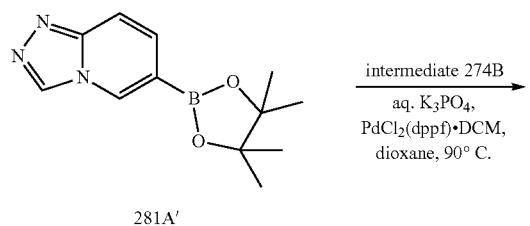

Scheme 34

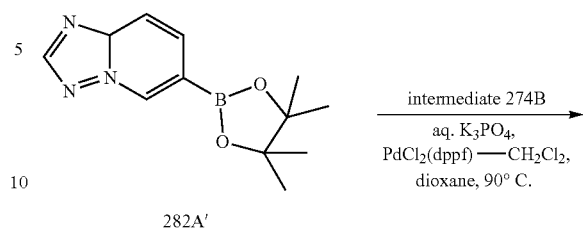

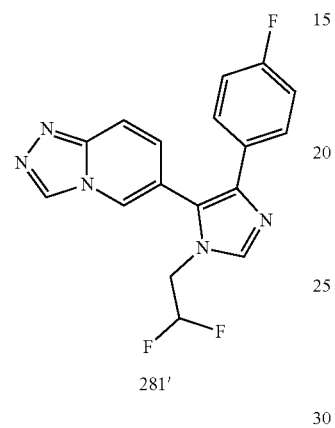

Example 281'

6-(1-(2,2-difluoroethyl)-4-(4-fluorophenyl)-1H-imidazol-5-yl)-[1,2,4]triazolo[4,3-a]pyridine

Example 282'

7-(1-(2,2-difluoroethyl)-4-(4-fluorophenyl)-1H-imidazol-5-yl)-[1,2,4]triazolo[1,5-a]pyridine

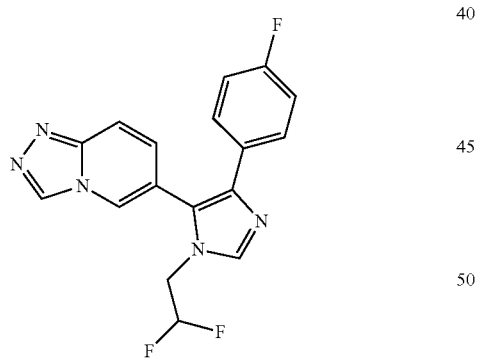

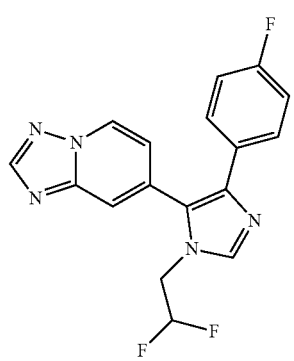 [SMILES: Fc1ccc(-c2ncn(CC(F)F)c2-c2ccn3ncnc3c2)cc1]

Example 281' was synthesized by reacting intermediate 281A' (reference: WO2013086397 A1) with intermediate 274B' and by employing the experimental procedure described for Example 271' in Scheme 25. The crude compound was purified by preparative HPLC (Condition O). Fractions containing the desired product were combined and evaporated to afford Example 281' (0.02 g, 0.058 mmol, 17.77% yield). LCMS m/z=344.1 [M+H]$^+$; HPLC Ret. Time 1.13 min. (HPLC Method H); $^1$H NMR (400 MHz, DMSO-d$_6$) δ ppm 9.26 (s, 1H), 8.68 (s, 1H), 7.94 (s, 2H), 7.52-7.43 (m, 2H), 7.26-7.18 (m, 1H), 7.09 (s, 2H), 6.38-6.05 (m, 1H), 4.51-4.37 (m, 2H).

Example 282' was synthesized by reacting intermediate 282A' (reference: WO 2013086397 A1) with intermediate 274B' and by employing the experimental procedure described for Example 271' in Scheme 25. The crude compound was purified by preparative HPLC (Condition O). Fractions containing the desired product were combined and evaporated to afford Example 282' (0.023 g, 20.44% yield). LCMS: m/z=344.1 [M+H]$^+$; HPLC Ret. Time 1.31 min. (HPLC Method H); $^1$H NMR (400 MHz, DMSO-d$_6$) δ ppm 9.04 (d, J=6.8 Hz, 1H), 8.60 (s, 1H), 7.97 (s, 2H), 7.43 (dd, J=8.8, 5.6 Hz, 2H), 7.09 (t, J=8.9 Hz, 3H), 6.38-6.05 (m, 1H), 4.54-4.41 (m, 2H).

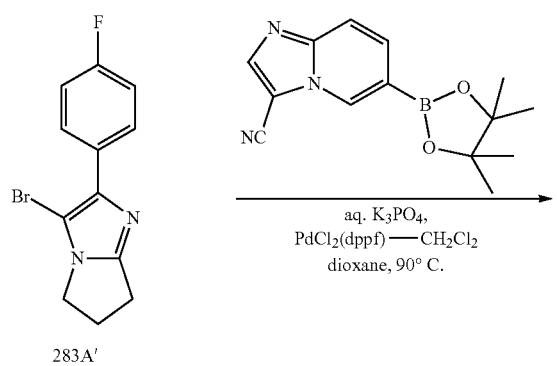

25 for Example 271'. The crude compound was purified by preparative HPLC (Condition P). Fractions containing the desired product were combined and evaporated to afford intermediate 283B' (156 mg, 64.57% yield). LCMS m/z=344.1 [M+H]+; HPLC Ret. Time 1.139 min. (HPLC Method H); $^1$H NMR 400 MHz, DMSO-$d_6$) δ ppm 8.72 (s, 1H), 8.50 (s, 1H), 7.87-7.89 (m, 1H), 7.48-7.52 (m, 2H), 7.43-7.45 (m, 1H), 7.10 (t, J=16.00 Hz, 2H), 4.03 (t, J=12.00 Hz, 2H), 2.88 (t, J=16.00 Hz, 2H), 2.55-2.61 (m, 2H).

Compound 283B': 6-(2-(4-fluorophenyl)-6,7-di-hydro-5H-pyrrolo[1,2-a]imidazol-3-yl)imidazo[1,2-a]pyridine-3-carboxamide

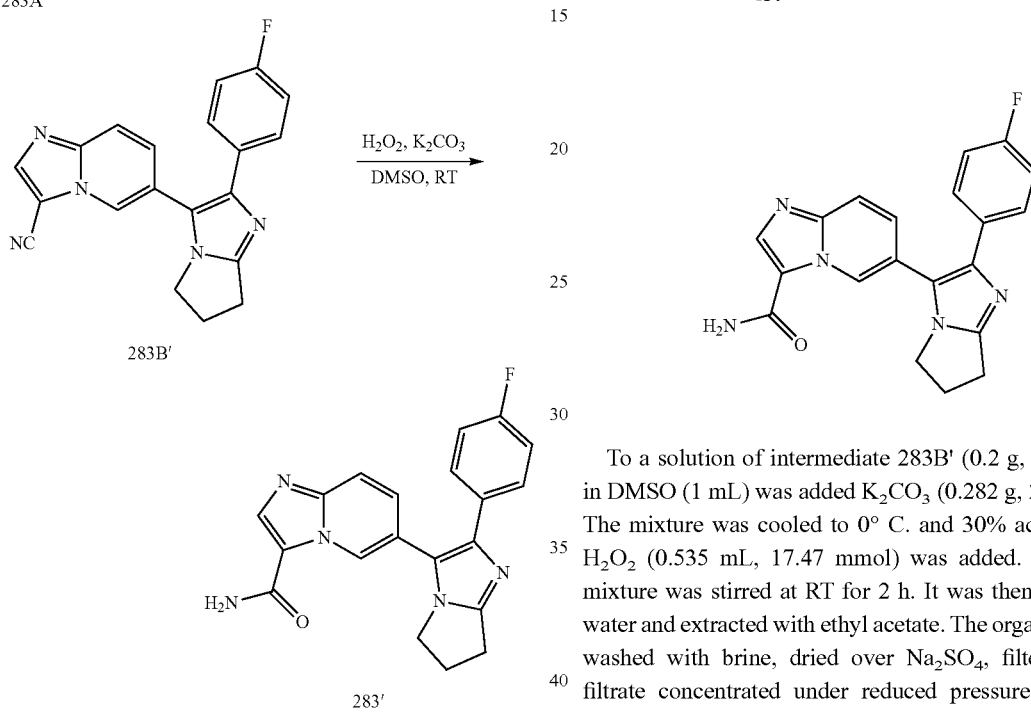

Intermediate 283B': 6-(2-(4-fluorophenyl)-6,7-di-hydro-5H-pyrrolo[1,2-a]imidazol-3-yl)imidazo[1,2-a]pyridine-3-carbonitrile To a solution of intermediate 283B' (0.2 g, 0.582 mmol) in DMSO (1 mL) was added $K_2CO_3$ (0.282 g, 2.039 mmol). The mixture was cooled to 0° C. and 30% aq. solution of $H_2O_2$ (0.535 mL, 17.47 mmol) was added. The reaction mixture was stirred at RT for 2 h. It was then diluted with water and extracted with ethyl acetate. The organic layer was washed with brine, dried over $Na_2SO_4$, filtered and the filtrate concentrated under reduced pressure to give the crude product, which was purified by preparative HPLC (Condition N). Fractions containing the desired product were combined and evaporated to afford Example 283' (9 mg, 4.28% yield). LCMS: m/z=362.1 [M+H]+; HPLC Ret. Time 1.256 min. (HPLC Method H); $^1$H NMR (400 MHz, DMSO-$d_6$) δ ppm 9.53-9.57 (m, 1H) 8.35-8.39 (m, 1H) 8.0 (bs, 1H) 7.73-7.80 (m, 1H) 7.45-7.52 (m, 2H) 7.36-7.41 (m, 2H) 7.04-7.12 (m, 2H) 3.92-3.99 (m, 2H) 2.82-2.91 (m, 2H) 2.54-2.60 (m, 2H).

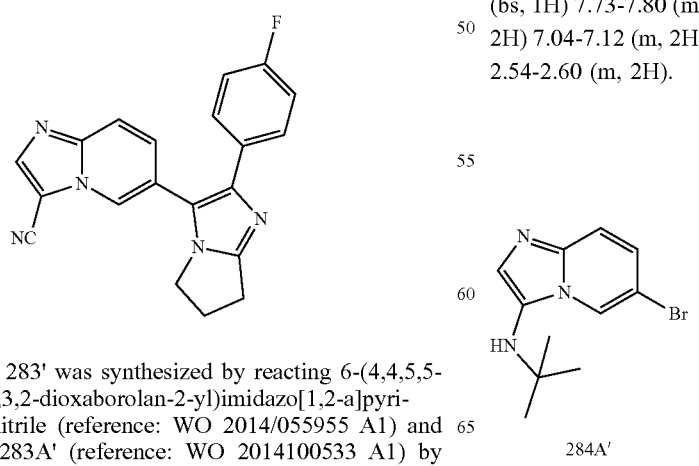

Compound 283' was synthesized by reacting 6-(4,4,5,5-tetramethyl-1,3,2-dioxaborolan-2-yl)imidazo[1,2-a]pyridine-3-carbonitrile (reference: WO 2014/055955 A1) and intermediate 283A' (reference: WO 2014100533 A1) by employing the experimental procedure described in Scheme Scheme 36

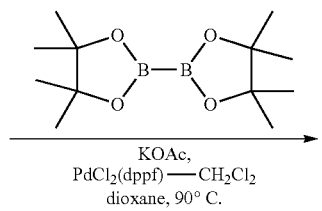

-continued

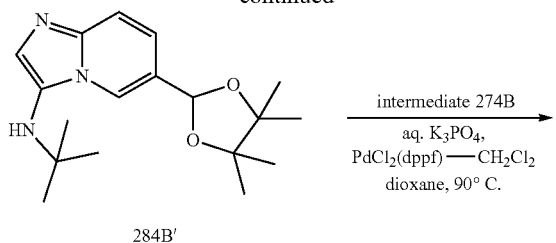

284B' intermediate 274B
aq. K₃PO₄,
PdCl₂(dppf)—CH₂Cl₂
dioxane, 90° C.

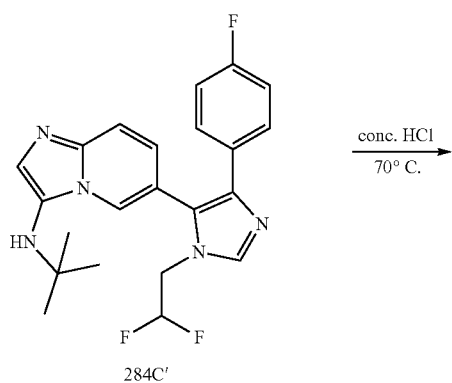

284C' conc. HCl
70° C.

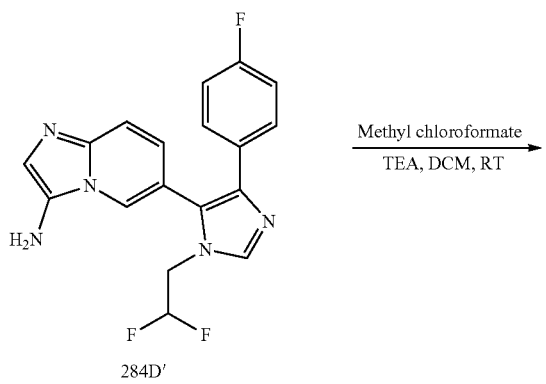

284D'

Methyl chloroformate
TEA, DCM, RT

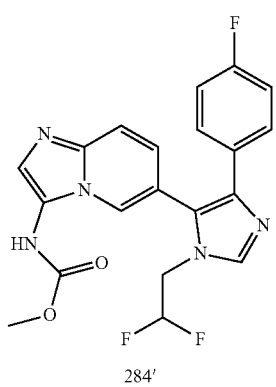

284'

Intermediate 284B': N-(tert-butyl)-6-(4,4,5,5-tetramethyl-1,3,2-dioxaborolan-2-yl)imidazo[1,2-a]pyridin-3-amine

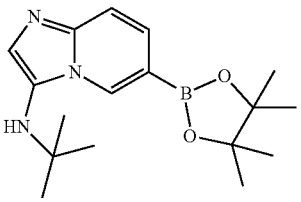 [SMILES: CC(C)(C)Nc1cnc2ccc(B3OC(C)(C)C(C)(C)O3)cn12]

To a solution of intermediate 284A' (reference: WO2013/64984 A1) (1.2 g, 4.48 mmol) in dioxane (10 mL) was added 4,4,4',4',5,5,5',5'-octamethyl-2,2'-bi(1,3-dioxolane) (1.136 g, 4.48 mmol), K₃PO₄ (1.318 g, 13.43 mmol) and PdCl₂(dppf)-CH₂Cl₂ adduct (0.110 g, 0.134 mmol). After degassing with argon, the reaction mixture was heated at 90° C. for 16 h. The reaction mixture was filtered through a pad of Celite® and the pad was washed with DCM (500 mL). The combined filtrates were concentrated under reduced pressure to afford 284B' as a dark brown oil, which was used in the next step without further purification. LCMS: m/z=316.1 [M+H]⁺; HPLC Ret. Time 0.82 min. (HPLC Method G).

Intermediate 284C': N-(tert-butyl)-6-(1-(2,2-difluoroethyl)-4-(4-fluorophenyl)-1H-imidazol-5-yl)imidazo[1,2-a]pyridin-3-amine

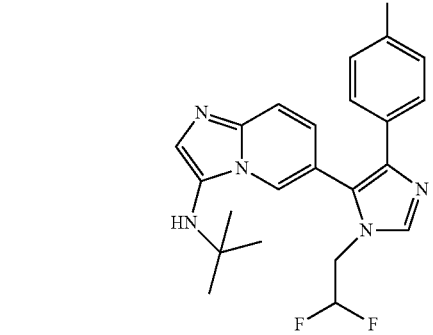

Intermediate 284C' was synthesized by reacting intermediate 284B' with intermediate 274B' and by employing the experimental procedure described for Example 271' in Scheme 25. The crude compound was purified by preparative HPLC (Condition P). Fractions containing the desired product were combined and evaporated to afford intermediate 284C' (305 mg, 45% yield). LCMS: m/z=414.3 [M+H]⁺; HPLC Ret. Time 1.60 min. (HPLC Method H); ¹H NMR (400 MHz, DMSO-d₆) δ ppm 8.35-8.41 (m, 1H) 7.90-7.97 (m, 1H) 7.59-7.66 (m, 1H) 7.40-7.47 (m, 2H) 7.27-7.32 (m, 1H) 7.02-7.16 (m, 3H) 6.05-6.37 (m, 1H) 4.57-4.60 (m, 1H) 4.31-4.44 (m, 2H) 1.06-1.10 (m, 9H).

Intermediate 284D': 6-(1-(2,2-difluoroethyl)-4-(4-fluorophenyl)-1H-imidazol-5-yl)imidazo[1,2-a]pyridin-3-amine

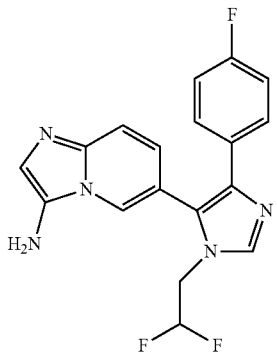 [SMILES: Nc1cnc2ccc(-c3c(-c4ccc(F)cc4)ncn3CC(F)F)cn12]

A solution of Example 284C' (0.2 g, 0.484 mmol) in conc. aqueous HCl (1.2 mL, 4.84 mmol) was stirred at 70° C. for 1 h. The reaction mixture was basified using 10% NaOH solution and extracted with ethyl acetate. The organic layer was washed with brine, dried over Na₂SO₄, filtered and the filtrate concentrated under reduced pressure to afford intermediate 284D' (0.1 g, 57.9% yield) as a red oil. LCMS: m/z=358.3 [M+H]⁺; HPLC Ret. Time 0.87 min. (HPLC Method G).

Example 284' methyl (6-(1-(2,2-difluoroethyl)-4-(4-fluorophenyl)-1H-imidazol-5-yl)imidazo[1,2-a]pyridin-3-yl)carbamate

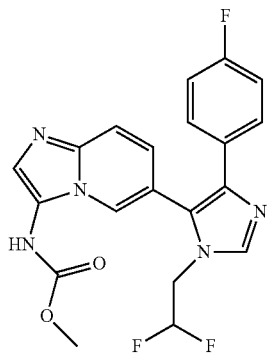 [SMILES: COC(=O)Nc1cnc2ccc(-c3c(-c4ccc(F)cc4)ncn3CC(F)F)cn12]

To a solution of intermediate 284D' in DCM (1 mL) was added TEA (0.047 mL, 0.336 mmol). The reaction mixture was cooled to 0° C. and methyl chloroformate (8.67 µL, 0.112 mmol) was added. The reaction mixture was stirred at RT for 1 h, quenched with aq. NaHCO₃ solution and extracted with ethyl acetate. The organic layer was washed with brine, dried over Na₂SO₄, filtered and the filtrate was concentrated under reduced pressure to give the crude compound, which was purified by preparative HPLC (Condition P). Fractions containing the desired product were combined and evaporated to afford Example 284' (6.0 mg, 13% yield). LCMS: m/z=416.3 [M+H]⁺; HPLC Ret. Time 1.26 min. (HPLC Method H); ¹H NMR (400 MHz, DMSO-d₆) δ ppm 9.6 (bs, 1H), 8.31-8.36 (m, 1H) 7.94 (s, 1H) 7.65-7.70 (m, 1H) 7.52 (s, 3H) 7.06-7.14 (m, 3H) 6.06-6.39 (m, 1H) 4.32-4.45 (m, 2H) 3.64-3.70 (m, 3H).

Scheme 37

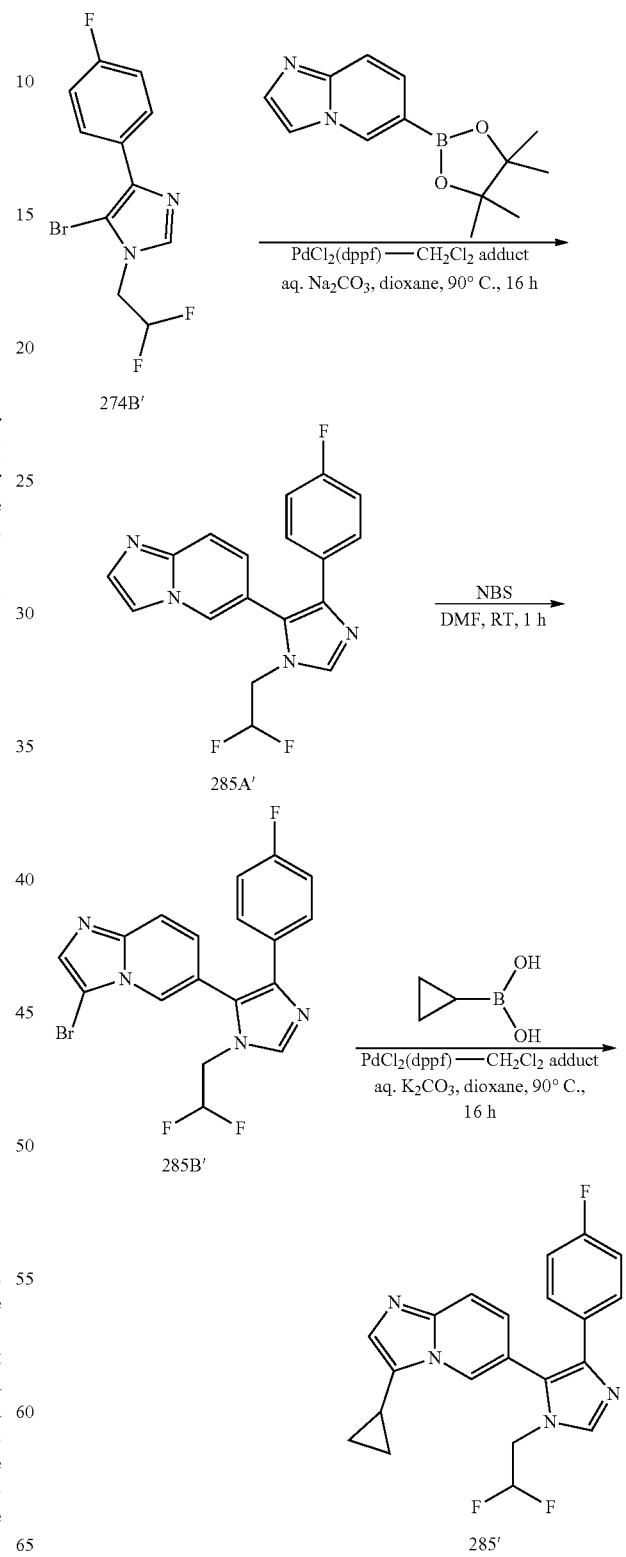

Intermediate 285A': 6-(1-(2,2-difluoroethyl)-4-(4-fluorophenyl)-1H-imidazol-5-yl)imidazo[1,2-a]pyridine

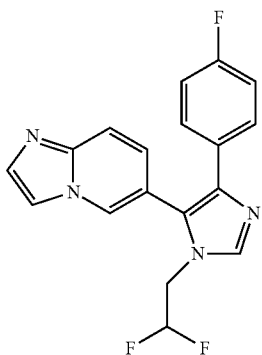 [SMILES: Fc1ccc(-c2ncn(CC(F)F)c2-c2ccc3nccn3c2)cc1]

Intermediate 285A' was synthesized by reacting 6-(4,4,5,5-tetramethyl-1,3,2-dioxaborolan-2-yl)imidazo[1,2-a]pyridine (reference: CN 103275112 A) with intermediate 274B' and by employing the experimental procedure described for Example 271' in Scheme 25. The crude product was purified by silica gel chromatography (40 g CombiFlash® column, eluting with a gradient of 4% MeOH in CHCl₃). Fractions containing the desired product were combined and evaporated to afford intermediate 285A' (0.4 g, 35.7% yield) as a pale yellow solid. LCMS: m/z=343.0 [M+H[⁻; HPLC Ret. Time 1.345 min. (HPLC Method J).

Intermediate 285B': 3-bromo-6-(1-(2,2-difluoroethyl)-4-(4-fluorophenyl)-1H-imidazol-5-yl)imidazo[1,2-a]pyridine

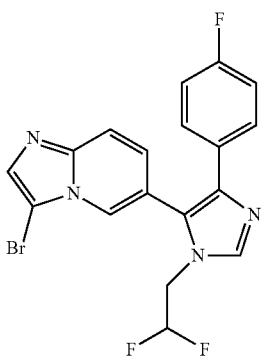 [SMILES: Fc1ccc(-c2ncn(CC(F)F)c2-c2ccc3ncc(Br)n3c2)cc1]

Intermediate 285B' was synthesized by reacting Example 285A' with NBS and by employing the experimental procedure described for intermediate 236C' in Scheme 22. Intermediate 285B' was obtained as a brown oil. LCMS: m/z=423.2 [M+H]⁺; HPLC Ret. Time 1.08 min. (HPLC Method G).

Example 285'

3-cyclopropyl-6-(1-(2,2-difluoroethyl)-4-(4-fluorophenyl)-1H-imidazol-5-yl)imidazo[1,2-a]pyridine

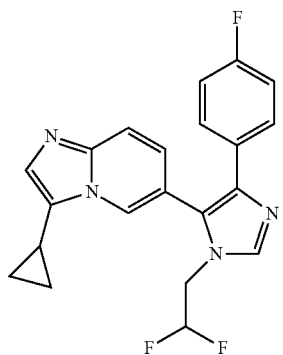 [SMILES: Fc1ccc(-c2ncn(CC(F)F)c2-c2ccc3ncc(C4CC4)n3c2)cc1]

Example 285' was synthesized by a Suzuki coupling reaction between intermediate 285B' and cyclopropylboronic acid and by employing the experimental procedure described for Example 271' in Scheme 25. The crude compound was purified by preparative HPLC (Condition N). Fractions containing the desired product were combined and evaporated to afford Example 285' (5 mg, 3.67% yield). LCMS: m/z=383.2 [M+H]⁺; HPLC Ret. Time 1.49 min. (HPLC Method H); ¹H NMR (400 MHz, DMSO-d₆) δ ppm 8.54 (dd, J=1.51, 1.00 Hz, 1H) 7.95 (s, 1H) 7.66 (dd, J=9.22, 0.88 Hz, 1H) 7.50 (dd, J=9.00, 5.62 Hz, 2H) 7.42 (d, J=0.88 Hz, 1H) 7.05-7.17 (m, 3H) 6.08-6.41 (m, 1H) 4.37-4.49 (m, 2H) 1.95-2.04 (m, 1H) 0.96 (dd, J=8.16, 2.13 Hz, 2H) 0.66 (dd, J=5.05, 2.10 Hz, 2H).

Scheme 38

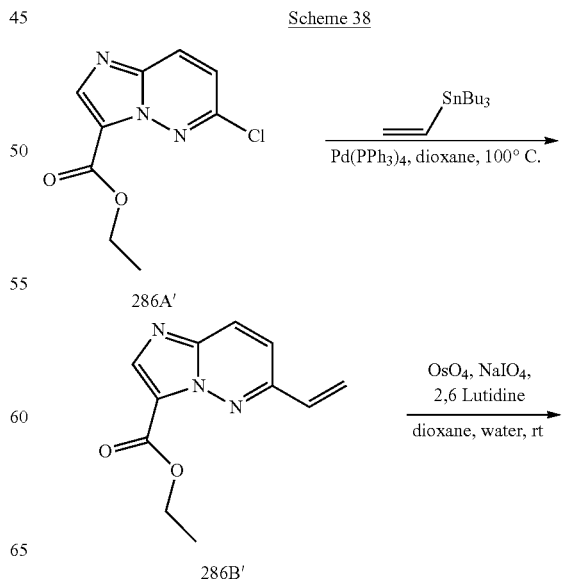

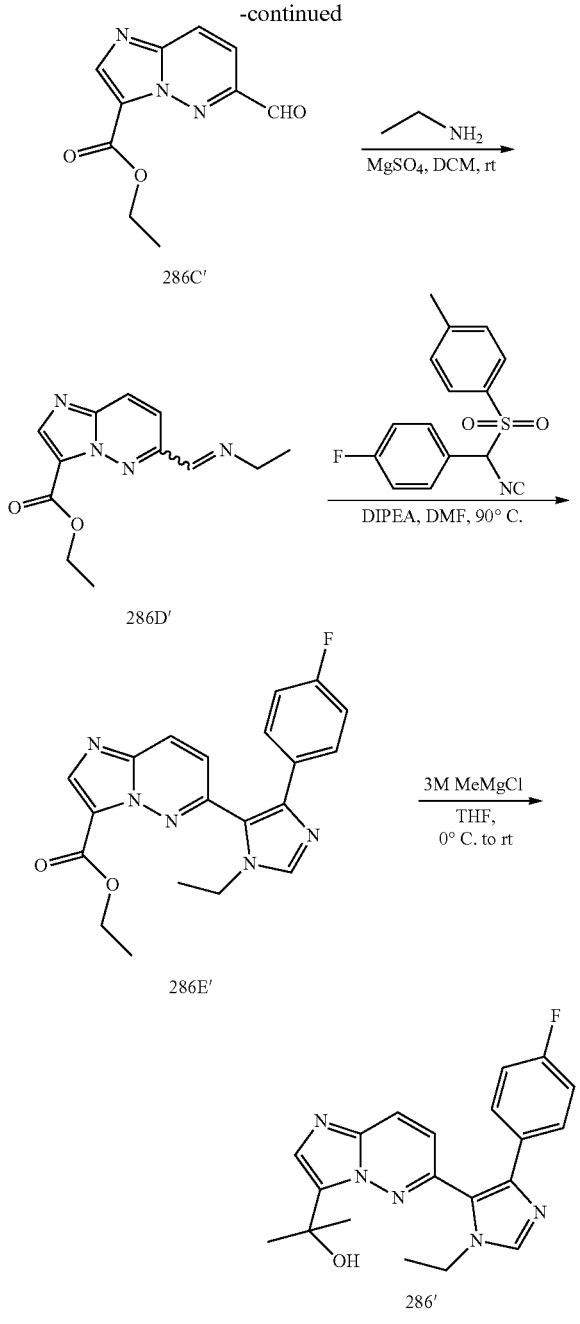

Intermediate 286B': ethyl 6-vinylimidazo[1,2-b]
pyridazine-3-carboxylate

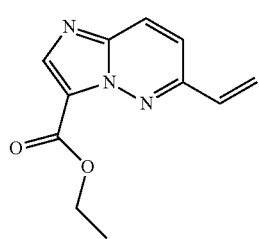 [SMILES: C=Cc1ccc2ncc(C(=O)OCC)n2n1]

To a solution of intermediate 286A' (reference: WO 2015026574 A1) (3.0 g, 13.30 mmol) in 1,4-dioxane (10 mL) was added tributyl(vinyl)tin (4.68 mL, 15.96 mmol). The mixture was degassed with argon for 5 minutes and Pd(PPh$_3$)$_4$ (0.768 g, 0.665 mmol) was added. The reaction mixture was heated at 100° C. for 12 h and concentrated under reduced pressure to give the crude residue, which was purified by silica gel chromatography (80 g CombiFlash® column, eluting with a gradient of 20-30% EtOAc in petroleum ether). Fractions containing the desired product were combined and evaporated to afford intermediate 286B' (3.0 g, 8.98 mmol, 67.5% yield) as a pale yellow solid. LCMS: m/z=218.0 [M+H]$^+$; HPLC Ret. Time 1.528 min. (HPLC Method J).

Intermediate 286C': ethyl 6-formylimidazo[1,2-b]
pyridazine-3-carboxylate

To a solution of intermediate 286B' (2.0 g, 18.41 mmol) in dioxane (60 mL) and water (17.4 mL) were added 2,6-lutidine (2.145 mL, 18.41 mmol), sodium periodate (7.88 g, 36.8 mmol), and 4% aq. solution of osmium tetroxide (2.312 mL, 0.184 mmol). The reaction mixture was stirred at RT for 4 h, diluted with water and DCM. The layers were separated. The aqueous layer was extracted with DCM. The combined organic layers were washed with brine, dried over Na$_2$SO$_4$, and filtered. The filtrate was concentrated and the residue was purified by silica gel chromatography (40 g RediSep® column, eluting with a gradient from 40-50% EtOAc in hexanes). Fractions containing the product were combined and evaporated to afford 286C' (1.2 g, 5.47 mmol, 59.5% yield). $^1$H NMR (300 MHz, DMSO-d$_6$) δ ppm 10.02 (d, J=0.8 Hz, 1H), 8.58 (s, 1H), 8.47 (dd, J=9.4, 0.8 Hz, 1H), 7.83 (d, J=9.4 Hz, 1H), 4.40 (q, J=7.2 Hz, 2H), 1.37 (t, J=7.2 Hz, 3H).

Intermediate 286D': ethyl 6-((ethylimino)methyl)imidazo[1,2-b]pyridazine-3-carboxylate

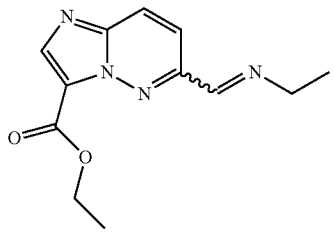 [SMILES: CCN=Cc1ccc2ncc(C(=O)OCC)n2n1]

Intermediate 286D' was synthesized from intermediate 286C' and ethylamine by employing the experimental procedure described for intermediate 1E in Scheme 1. Intermediate 286D' (0.2 g, 80% yield) was obtained as an off white solid. LCMS: m/z=247.0 [M+H]+; HPLC Ret. Time 0.98 min. (HPLC Method G).

Intermediate 286E': ethyl 6-(1-ethyl-4-(4-fluorophenyl)-1H-imidazol-5-yl)imidazo[1,2-b]pyridazine-3-carboxylate

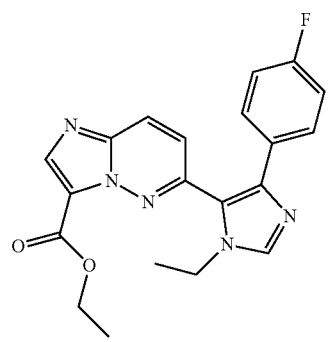 [SMILES: CCOC(=O)c1cnc2ccc(-c3c(-c4ccc(F)cc4)ncn3CC)nn12]

Intermediate 286E' was synthesized by reacting 286D' with 1-fluoro-4-(isocyano(tosyl)methyl)benzene and by employing the experimental procedure described for Example 1' in Scheme 1. Intermediate 286E' (154 mg, 33.0% yield). LCMS: m/z=380.3 [M+H]+; HPLC Ret. Time 1.10 min. (HPLC Method G).

Example 286'

2-(6-(1-ethyl-4-(4-fluorophenyl)-1H-imidazol-5-yl)imidazo[1,2-b]pyridazin-3-yl)propan-2-ol

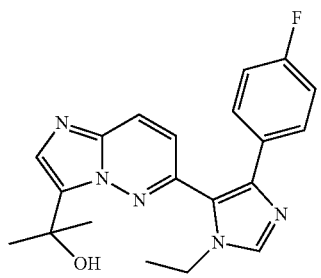 [SMILES: CCn1cnc(-c2ccc(F)cc2)c1-c1ccc2ncc(C(C)(C)O)n2n1]

Example 286' was synthesized from intermediate 286E' by employing the experimental procedure described for Example 278' in Scheme 31. The crude residue was purified by preparative HPLC (Condition L). Fractions containing the desired product were combined and evaporated to afford Example 286' (48.8 mg, 38.6% yield). LCMS: m/z=366.1 [M+H]+; HPLC Ret. Time 1.397 min. (HPLC Method H); $^1$H NMR (400 MHz, DMSO-$d_6$) δ ppm 8.11 (d, J=9.5 Hz, 1H), 8.04 (s, 1H), 7.72 (s, 1H), 7.48-7.41 (m, 2H), 7.17-7.09 (m, 2H), 7.04 (d, J=9.5 Hz, 1H), 5.38 (br. s., 1H), 4.19 (q, J=7.2 Hz, 2H), 1.63 (s, 6H), 1.24 (t, J=7.1 Hz, 3H).

The compound shown in Table 21 has been prepared in a manner similar to Example 286' using intermediate 286C', cyclopropylamine, 1-fluoro-4-(isocyano(tosyl)methyl)benzene and then reacting with MeMgBr.

TABLE 21

| Ex. | Structure | Name | [M + H]+ | Ret. Time (min.) | HPLC Method |
|---|---|---|---|---|---|
| 287' | 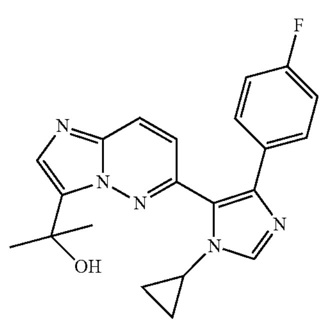 [SMILES: CC(C)(O)c1cnc2ccc(-c3c(-c4ccc(F)cc4)ncn3C3CC3)nn12] | 2-(6-(1-cyclopropyl-4-(4-fluorophenyl)-1H-imidazol-5-yl)imidazo[1,2-b]pyridazin-3-yl)propan-2-ol | 378.1 | 1.462<br>0.935 | H<br>I |

Scheme 39

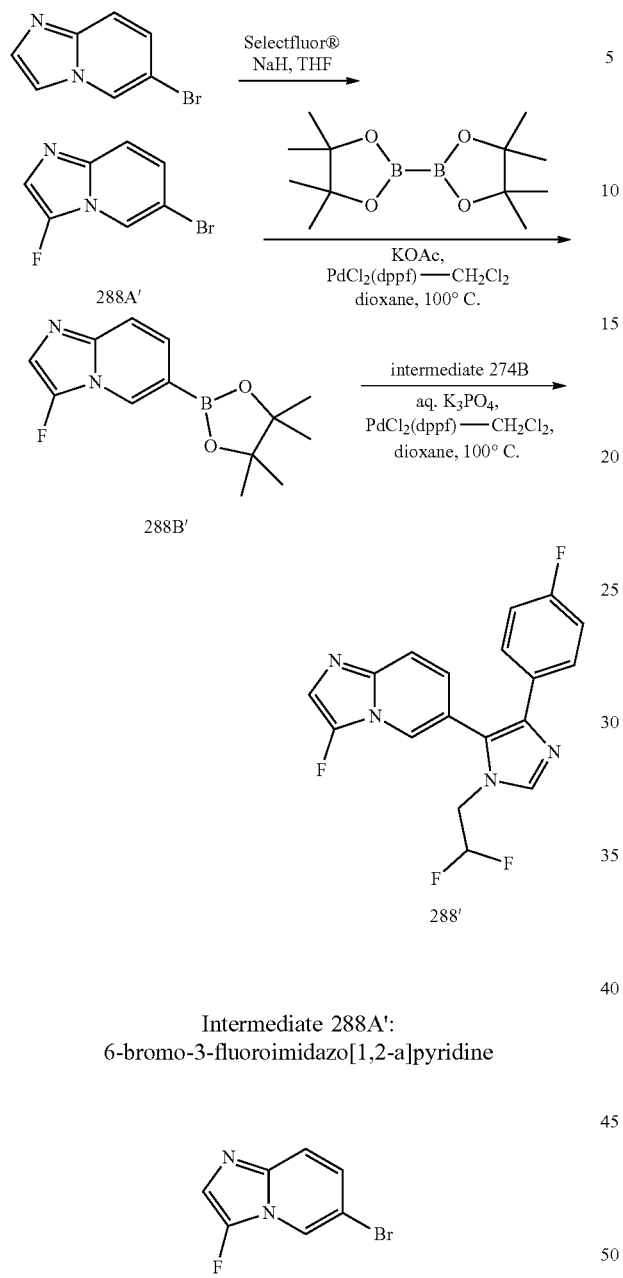

288A'

288B'

288'

Intermediate 288A':
6-bromo-3-fluoroimidazo[1,2-a]pyridine

To a solution of 6-bromoimidazo[1,2-a]pyridine (0.1 g, 0.508 mmol) in THF (10 mL) at 0° C. was added NaH (0.018 g, 0.750 mmol, 60% in mineral oil). The reaction mixture was stirred at RT for 30 min. and to it was added Selectfluor® (0.387 g, 1.092 mmol) in acetonitrile (5 mL). The reaction mixture was stirred at RT for 18 h, quenched with saturated aq. NH$_4$Cl solution and extracted with ethyl acetate. The organic layer was washed with brine, dried over Na$_2$SO$_4$, filtered and the filtrate concentrated under reduced pressure to give intermediate 288A' (110 mg, 40.3% yield). LCMS: m/z=215.3 [M+H]$^+$; HPLC Ret. Time 1.06 min. (HPLC Method G).

Intermediate 288B': 3-fluoro-6-(4,4,5,5-tetramethyl-1,3,2-dioxaborolan-2-yl)imidazo[1,2-a]pyridine

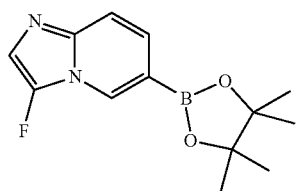 [SMILES: CC1(C)OB(c2ccc3ncc(F)n3c2)OC1(C)C]

Intermediate 288B' was synthesized by reacting intermediate 288A' with 4,4,4',4',5,5,5',5'-octamethyl-2,2'-bi(1,3-dioxolane) and by employing the experimental procedure described for intermediate 284B' in Scheme 36. Intermediate 288B' (230 mg, 75% yield). LCMS: m/z=263.4 [M+H]$^+$; HPLC Ret. Time 1.28 min. (HPLC Method G).

Example 288'

6-(1-(2,2-difluoroethyl)-4-(4-fluorophenyl)-1H-imidazol-5-yl)-3-fluoroimidazo[1,2-a]pyridine

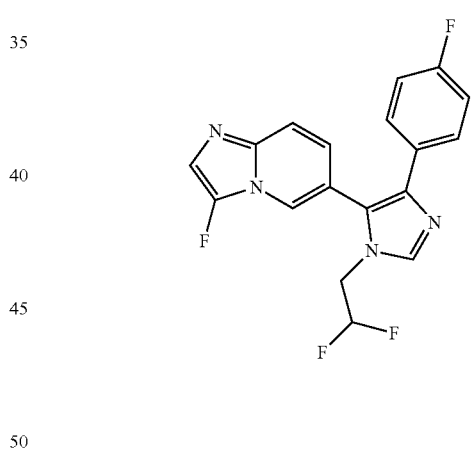

Example 288' was synthesized by reacting intermediate 288B' with intermediate 274B' and by employing the experimental procedure described for intermediate 274C' in Scheme 28. The crude residue which was purified by preparative HPLC (Condition 0). Fractions containing the desired product were combined and evaporated to afford Example 288'. LCMS: m/z=361.1 [M+H]$^+$; HPLC Ret. Time 1.55 min. (HPLC Method H); $^1$H NMR (400 MHz, DMSO-d$_6$) δ ppm 8.45 (s, 1H), 7.92 (s, 1H), 7.65-7.59 (m, 1H), 7.51-7.41 (m, 3H), 7.13-7.01 (m, 3H), 6.38-6.01 (m, 1H), 4.43 (dd, J=16.0, 3.1 Hz, 1H).

Scheme 40

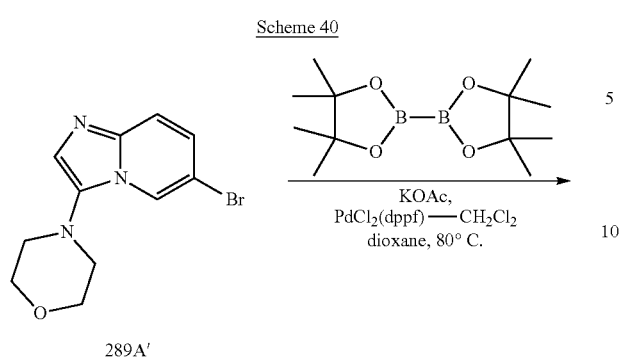

289A'

289B'

289'

Intermediate 289B': 4-(6-(4,4,5,5-tetramethyl-1,3,2-dioxaborolan-2-yl)imidazo[1,2-a]pyridin-3-yl)morpholine

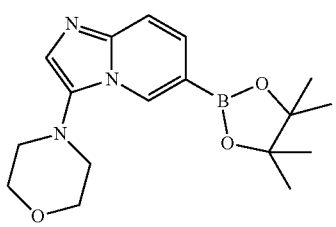 [SMILES: CC1(C)OB(c2ccc3ncc(N4CCOCC4)n3c2)OC1(C)C]

Intermediate 289B' was synthesized by reacting intermediate 289A' (reference: *J. Med. Chem.* 2011, 54, 2455-2466) with 4,4,4',4',5,5,5',5'-octamethyl-2,2'-bi(1,3-dioxolane) and by employing the experimental procedure described for intermediate 284B' in Scheme 36. LCMS: m/z=330.5 [M+H]$^+$; HPLC Ret. Time 1.13 min. (HPLC Method G).

Example 289'

4-(6-(1-(2,2-difluoroethyl)-4-(4-fluorophenyl)-1H-imidazol-5-yl)imidazo[1,2-a]pyridin-3-yl)morpholine

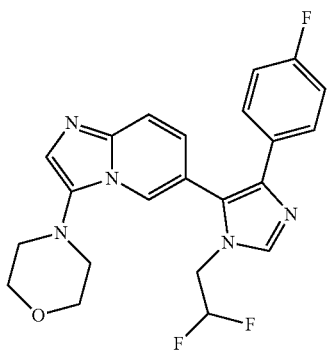 [SMILES: Fc1ccc(-c2ncn(CC(F)F)c2-c2ccc3ncc(N4CCOCC4)n3c2)cc1]

Example 289' was synthesized by reacting intermediate 299B' with intermediate 274B' and by employing the experimental procedure described for Example 271' in Scheme 25. The crude compound was purified by preparative HPLC (Condition-P). Fractions containing the desired product were combined and evaporated to afford Example 289'. LCMS: m/z=428.1 [M+H]$^+$; HPLC Ret. Time 1.586 min. (HPLC Method H); $^1$H NMR (400 MHz, DMSO-d$_6$) δ ppm 8.23 (s, 1H), 7.93 (s, 1H), 7.62 (d, J=9.29 Hz, 1H), 7.45 (dd, J=5.62, 8.80 Hz, 2H), 7.37 (s, 1H), 7.00-7.15 (m, 3H), 6.03-6.42 (m, 1H), 4.32-4.45 (m, 2H), 3.69-3.77 (m, 4H), 2.90-3.01 (m, 4H).

Scheme 41

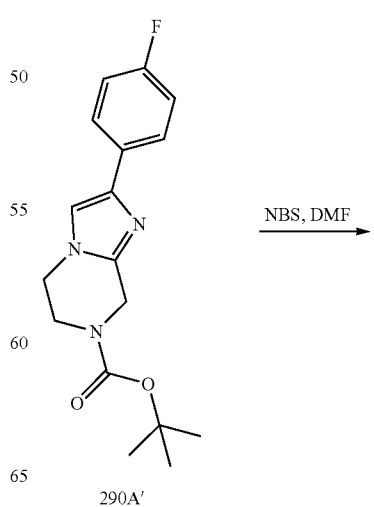

290A'

541
-continued

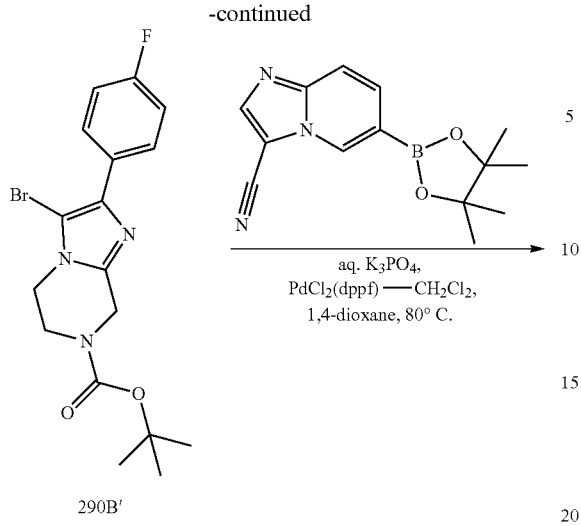

290B'

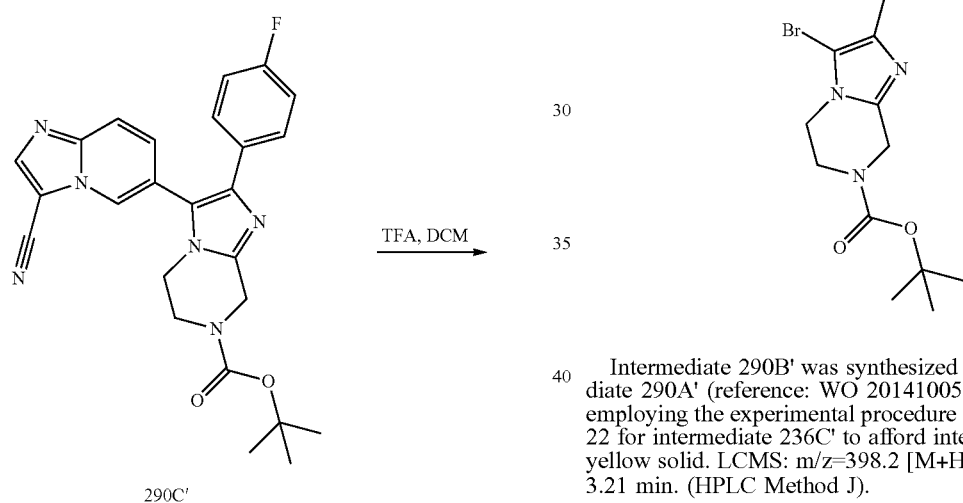

290C'

290D'

542
-continued

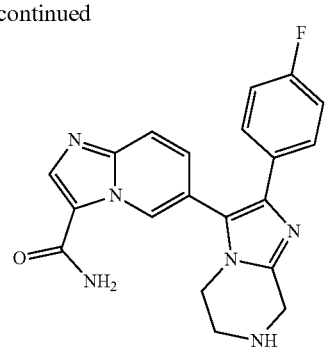

290'

Intermediate 290B': tert-butyl 3-bromo-2-(4-fluorophenyl)-5,6-dihydroimidazo[1,2-a]pyrazine-7(8H)-carboxylate Intermediate 290B' was synthesized by reacting intermediate 290A' (reference: WO 2014100533 A1) and NBS by employing the experimental procedure described in Scheme 22 for intermediate 236C' to afford intermediate 290B' as a yellow solid. LCMS: m/z=398.2 [M+H]$^+$; HPLC Ret. Time 3.21 min. (HPLC Method J).

Intermediate 290C': tert-butyl 3-(3-cyanoimidazo[1,2-a]pyridin-6-yl)-2-(4-fluorophenyl)-5,6-dihydroimidazo[1,2-a]pyrazine-7(8H)-carboxylate

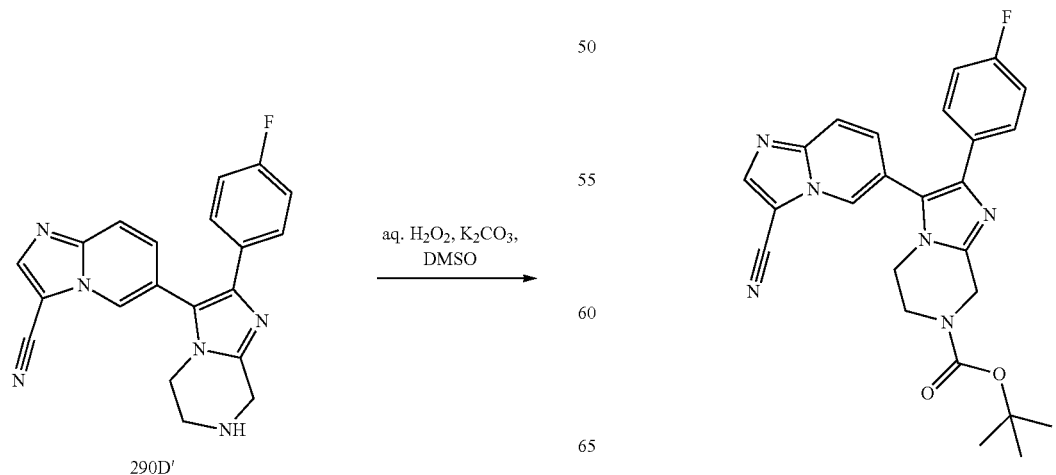

Intermediate 290C' was synthesized by reacting 6-(4,4,5,5-tetramethyl-1,3,2-dioxaborolan-2-yl)imidazo[1,2-a]pyridine-3-carbonitrile (reference: WO 2014/055955 A1) and intermediate 290B' by employing the experimental procedure described in Scheme 25 for Example 271'. The crude residue was purified by silica gel chromatography (24 g CombiFlash° column, eluting with a gradient of 60-100% EtOAc in petroleum ether). Fractions containing the desired product were combined and evaporated to afford example 290C' as a brown solid. LCMS: m/z=459.1 [M+H]$^+$; HPLC Ret. Time 1.25 min. (HPLC Method G).

Intermediate 290D': 6-(2-(4-fluorophenyl)-5,6,7,8-tetrahydroimidazo[1,2-a]pyrazin-3-yl)imidazo[1,2-a]pyridine-3-carbonitrile

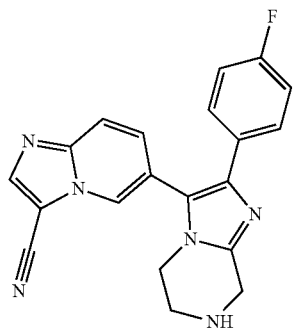 [SMILES: N#Cc1cnc2ccc(-c3c(-c4ccc(F)cc4)nc4n3CCNC4)cn12]

To a solution of intermediate 290C' (30 mg, 0.065 mmol) in DCM (2 mL) was added TFA (0.1 mL, 1.298 mmol) and the reaction mixture was stirred at RT for 15 h and then concentrated to give the crude residue. It was purified by preparative HPLC (Condition P). Fractions containing the desired product were combined and evaporated to afford example 290D'. LCMS: m/z=359.1 [M+H]$^+$; HPLC Ret. Time 1.37 min. (HPLC Method H); $^1$H NMR (400 MHz, DMSO-d$_6$) δ ppm 8.73-8.75 (m, 1H) 8.52 (s, 1H) 7.92 (dd, J=9.29, 0.98 Hz, 1H) 7.43-7.49 (m, 3H) 7.02-7.09 (m, 2H) 3.97 (s, 2H) 3.73 (t, J=5.26 Hz, 2H) 3.06 (t, J=5.26 Hz, 2H).

Example 290'

6-(2-(4-fluorophenyl)-5,6,7,8-tetrahydroimidazo[1,2-a]pyrazin-3-yl)imidazo[1,2-a]pyridine-3-carboxamide

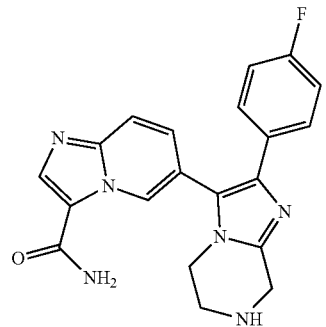 [SMILES: NC(=O)c1cnc2ccc(-c3c(-c4ccc(F)cc4)nc4n3CCNC4)cn12]

Example 290' was synthesized by reacting intermediate 290D' and K$_2$CO$_3$/H$_2$O$_2$ by employing the experimental procedure described in Scheme 35 for example 283'. The crude residue was purified by preparative HPLC (Condition P). Fractions containing the desired product were combined and evaporated to afford Example 290'. LCMS: m/z=377.1 [M+H]$^+$; HPLC Ret. Time 1.049 min. (HPLC Method H); $^1$H NMR (400 MHz, DMSO-d$_6$) δ ppm 9.49 (dd, J=1.71, 0.98 Hz, 1H) 8.40 (s, 1H) 8.02 (br. s., 1H) 7.82 (dd, J=9.29, 0.98 Hz, 1H) 7.39-7.47 (m, 3H) 7.02-7.08 (m, 2H) 3.95 (s, 2H) 3.65 (t, J=5.26 Hz, 2H) 3.05 (t, J=5.26 Hz, 2H).

Scheme 42

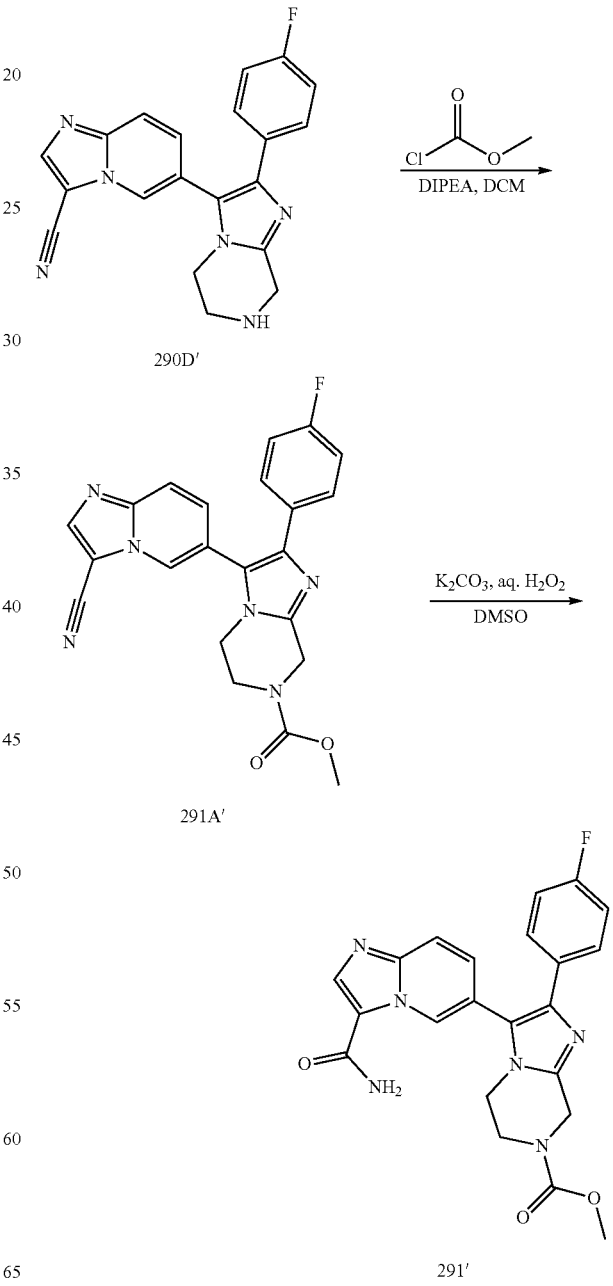

545

Intermediate 291A': methyl 3-(3-cyanoimidazo[1,2-a]pyridin-6-yl)-2-(4-fluorophenyl)-5,6-dihydroimidazo[1,2-a]pyrazine-7(8H)-carboxylate

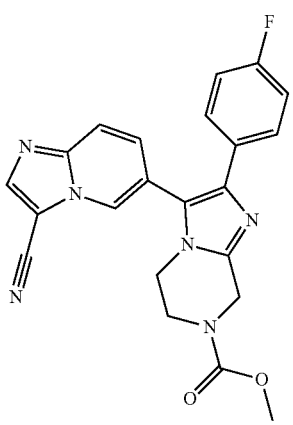 [SMILES: COC(=O)N1CCn2c(nc(-c3ccc(F)cc3)c2-c2ccc3ncc(C#N)n3c2)C1]

Intermediate 291A' was synthesized from intermediate 290D' by employing the experimental procedure described in Scheme 36 for example 284'. The crude compound was purified by preparative HPLC (Condition P). Fractions containing the desired product were combined and evaporated to afford intermediate 291A'. LCMS: m/z=417.1 [M+H]$^+$; HPLC Ret. Time 1.539 min. (HPLC Method H).

546

Example 291' methyl 3-(3-carbamoylimidazo[1,2-a]pyridin-6-yl)-2-(4-fluorophenyl)-5,6-dihydroimidazo[1,2-a]pyrazine-7(8H)-carboxylate

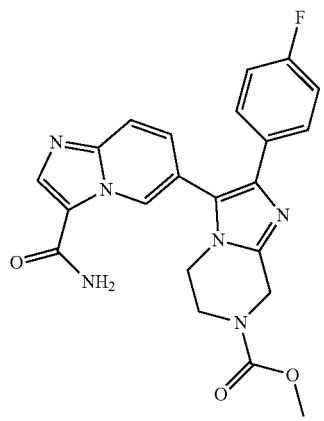 [SMILES: COC(=O)N1CCn2c(nc(-c3ccc(F)cc3)c2-c2ccc3ncc(C(N)=O)n3c2)C1]

Example 291' was synthesized from intermediate 291A' by employing the experimental procedure described in Scheme 35 for example 283'. The crude compound was purified by preparative HPLC (Condition P). Fractions containing the desired product were combined and evaporated to afford Example 291'. LCMS: m/z=435.1 [M+H]$^+$; HPLC Ret. Time 1.280 min. (HPLC Method H); $^1$H NMR (400 MHz, DMSO-d$_6$) δ ppm 9.49 (dd, J=1.71, 0.98 Hz, 1H) 8.40 (s, 1H) 8.01 (br. s., 1H) 7.84 (dd, J=9.29, 0.98 Hz, 1H) 7.42-7.48 (m, 3H) 7.04-7.10 (m, 2H) 4.71 (s, 2H) 3.80 (br. s., 4H) 3.69 (s, 3H).

The compound shown in Table 22 has been prepared similar to example 291' using intermediate 291A', acetyl chloride and then the oxidation of the cyano group with K$_2$CO$_3$/H$_2$O$_2$.

TABLE 22

| Ex. | Structure | Name | [M + H]$^+$ | Ret. Time (min.) | HPLC Method |
|---|---|---|---|---|---|
| 292' | 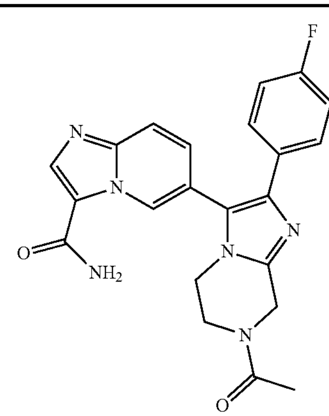 | 6-(7-acetyl-2-(4-fluorophenyl)-5,6,7,8-tetrahydroimidazo[1,2-a]pyrazin-3-yl)imidazo[1,2-a]pyridine-3-carboxamide | 419.2 | 0.935<br>0.600 | H<br>I |

Scheme 43

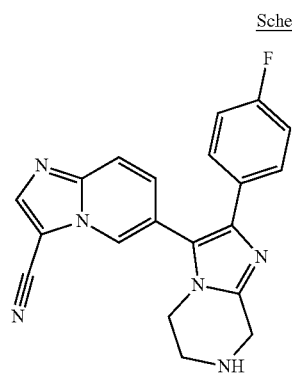

290D'

HCHO
NaCNBH₃, TEA,
MeOH
→

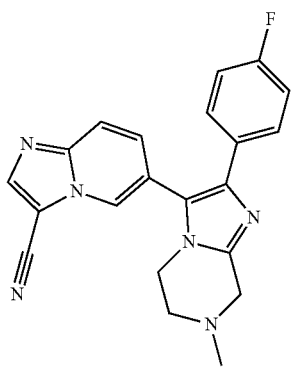 [SMILES: CN1CCn2c(nc(-c3ccc(F)cc3)c2-c2ccc3ncc(C#N)n3c2)C1]

K₂CO₃, aq. H₂O₂
DMSO
→

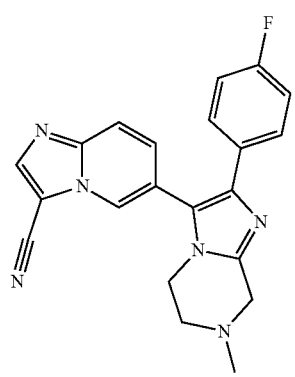

293A'

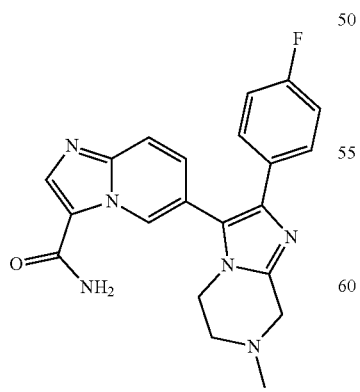

293'

Intermediate 293A': 6-(2-(4-fluorophenyl)-7-methyl-5,6,7,8-tetrahydroimidazo[1,2-a]pyrazin-3-yl)imidazo[1,2-a]pyridine-3-carbonitrile

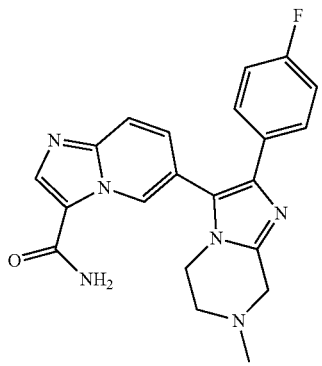 [SMILES: CN1CCn2c(nc(-c3ccc(F)cc3)c2-c2ccc3ncc(C(N)=O)n3c2)C1]

To a solution of intermediate 290D' (50 mg, 0.140 mmol) in methanol (5 mL) at 0° C. was added formaldehyde (0.021 mL, 0.279 mmol, 37% aqueous solution), TEA (0.039 mL, 0.279 mmol) and sodium cyanoborohydride (17.54 mg, 0.279 mmol). The reaction mixture was stirred at RT for 1 h and then partitioned between water and DCM. The organic layer was washed with brine, dried over Na₂SO₄, filtered and the filtrate was concentrated under reduced pressure to give the crude residue. It was purified by preparative HPLC (Condition P). Fractions containing the desired product were combined and evaporated to afford intermediate 293A' (2.1 mg, 5.6 µmol, 3.1% yield). LCMS: m/z=373.2 [M+H]⁺; HPLC Ret. Time 1.213 min. (HPLC Method I); ¹H NMR (400 MHz, DMSO-d₆) δ ppm 9.12 (s, 1H), 8.81 (s, 1H), 8.21 (d, J=9.05 Hz, 1H), 7.68-7.78 (m, 3H), 6.95-7.20 (m, 4H), 7.22 (s, 1H), 4.02 (br. s., 4H), 2.91-2.95 (m, 2H), 2.26 (s, 3H).

Example 293'

6-(2-(4-fluorophenyl)-7-methyl-5,6,7,8-tetrahydroimidazo[1,2-a]pyrazin-3-yl)imidazo[1,2-a]pyridine-3-carboxamide Example 293' was synthesized by reacting intermediate 293A' and H₂O₂/K₂CO₃ by employing the experimental procedure described in Scheme 35 for Example 283'. The crude compound was purified by preparative HPLC (Condition Q). Fractions containing the desired product were combined and evaporated to afford example 293'. LCMS: m/z=391.2 [M+H]+; HPLC Ret. Time 0.982 min. (HPLC Method H); 1H NMR (400 MHz, DMSO-d6) δ ppm 9.49 (s, 1H), 8.40 (s, 1H), 8.01 (br. s., 1H), 7.85 (d, J=9.54 Hz, 1H), 7.43-7.47 (m, 3H), 7.07 (t, J=9.05 Hz, 2H), 3.78 (br. s., 4H), 2.86 (br. s., 2H), 2.6 (s, 3H).

Intermediate 294A': 6-(7-(2,2-difluoroethyl)-2-(4-fluorophenyl)-5,6,7,8-tetrahydroimidazo[1,2-a]pyrazin-3-yl)imidazo[1,2-a]pyridine-3-carbonitrile

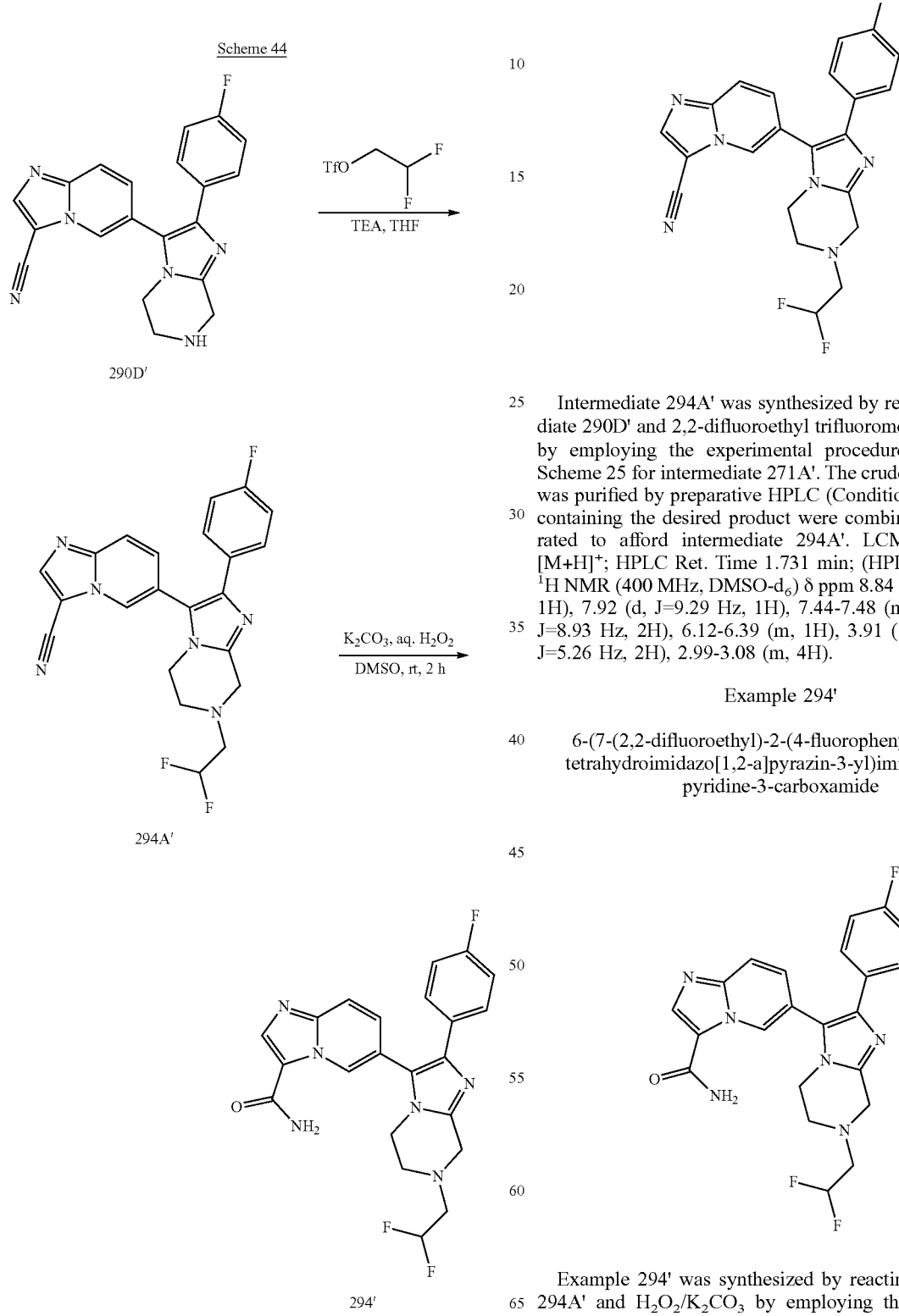

Intermediate 294A' was synthesized by reacting intermediate 290D' and 2,2-difluoroethyl trifluoromethanesulfonate by employing the experimental procedure described in Scheme 25 for intermediate 271A'. The crude residue which was purified by preparative HPLC (Condition P). Fractions containing the desired product were combined and evaporated to afford intermediate 294A'. LCMS: m/z=423.1 [M+H]+; HPLC Ret. Time 1.731 min; (HPLC Method H); 1H NMR (400 MHz, DMSO-d6) δ ppm 8.84 (s, 1H), 8.51 (s, 1H), 7.92 (d, J=9.29 Hz, 1H), 7.44-7.48 (m, 3H), 7.06 (t, J=8.93 Hz, 2H), 6.12-6.39 (m, 1H), 3.91 (s, 2H), 3.85 (t, J=5.26 Hz, 2H), 2.99-3.08 (m, 4H).

Example 294'

6-(7-(2,2-difluoroethyl)-2-(4-fluorophenyl)-5,6,7,8-tetrahydroimidazo[1,2-a]pyrazin-3-yl)imidazo[1,2-a]pyridine-3-carboxamide Example 294' was synthesized by reacting intermediate 294A' and H2O2/K2CO3 by employing the experimental procedure described in Scheme 35 for Example 283'. The crude compound was purified by preparative HPLC (Condition Q). Fractions containing the desired product were combined and evaporated to afford example 294'. LCMS: m/z=441.3 [M+H]$^+$; HPLC Ret. Time 1.160 min. (HPLC Method I). $^1$H NMR (400 MHz, DMSO-d$_6$) δ ppm 9.49 (dd, J=1.71, 0.98 Hz, 1H) 8.40 (s, 1H) 8.01 (br. s., 1H) 7.83 (dd, J=9.17, 0.86 Hz, 1H) 7.42-7.50 (m, 3H) 7.03-7.10 (m, 2H) 6.09-6.41 (m, 1H) 3.92 (s, 2H) 3.77 (t, J=5.38 Hz, 2H) 2.98-3.09 (m, 4H).

Scheme 45

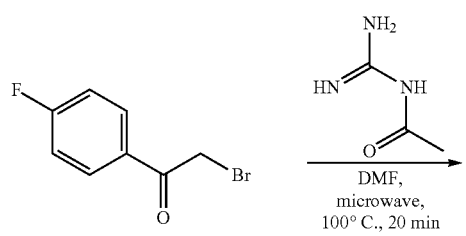

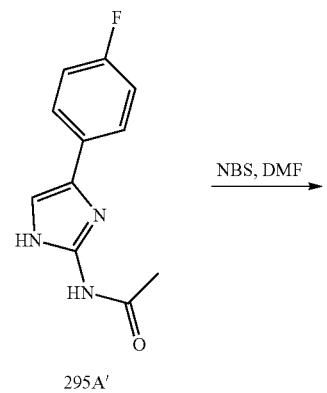

295A'

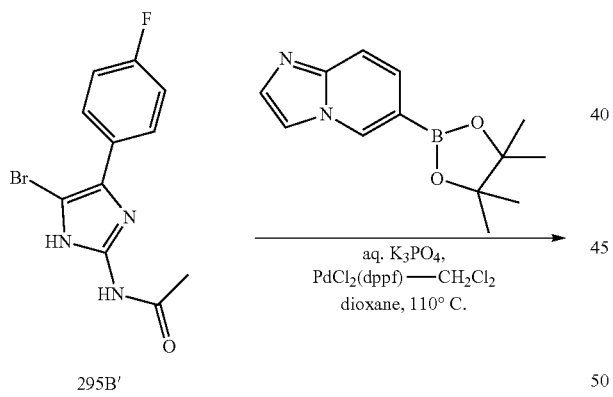

295B'

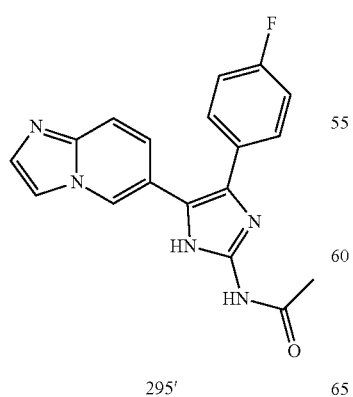

295'

Intermediate 295A': N-(4-(4-fluorophenyl)-1H-imidazol-2-yl)acetamide

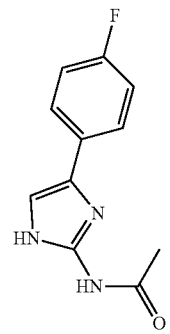

To a solution of 2-bromo-1-(4-fluorophenyl)ethanone (5.0 g, 23.04 mmol) in DMF (50 mL) was added N-carbamimidoylacetamide (6.99 g, 69.1 mmol). The reaction mixture was irradiated in a microwave oven at 100° C. for 20 min. The reaction mixture was concentrated and water was added to the residue. The solid thus obtained was filtered and dried under suction to afford intermediate 295A' (4.0 g, 79% yield). LCMS: m/z=220.2 [M+H]$^+$; HPLC Ret. Time 1.396 min. (HPLC Method J).

Intermediate 295B': N-(5-bromo-4-(4-fluorophenyl)-1H-imidazol-2-yl)acetamide

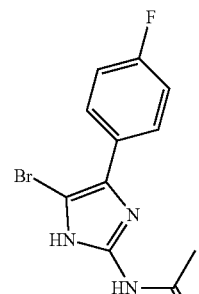

Intermediate 295B' was synthesized by reacting intermediate 295A' with NBS and by employing the experimental procedure described for intermediate 236C' in Scheme 22. LCMS: m/z=300.0 [M+2H]$^+$; HPLC Ret. Time 0.99 min. (HPLC Method G).

Example 295'

N-(4-(4-fluorophenyl)-5-(imidazo[1,2-a]pyridin-6-yl)-1H-imidazol-2-yl)acetamide

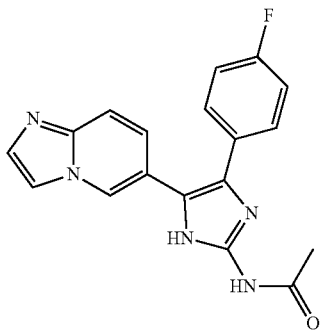 [SMILES: CC(=O)Nc1nc(-c2ccc(F)cc2)c(-c2ccc3nccn3c2)[nH]1]

Example 295' was synthesized by reacting intermediate 295B' with 6-(4,4,5,5-tetramethyl-1,3,2-dioxaborolan-2-yl)imidazo[1,2-a]pyridine (reference: CN 103275112 A) and by employing the experimental procedure described for example 271' in Scheme 25. The crude residue was purified by preparative HPLC (Condition R). Fractions containing the desired product were combined and evaporated to afford Example 295' (2.2 mg, 1.88% yield). LCMS: m/z=336.1 [M+H]$^+$; HPLC Ret. Time 1.345 min; (HPLC Method H); $^1$H NMR (400 MHz, DMSO-d$_6$) δ ppm 8.63 (br. s., 1H), 7.96 (s, 1H), 7.57 (br. s., 1H), 7.54-7.46 (m, 3H), 7.23-7.09 (m, 3H), 2.10 (s, 3H).

Scheme 46

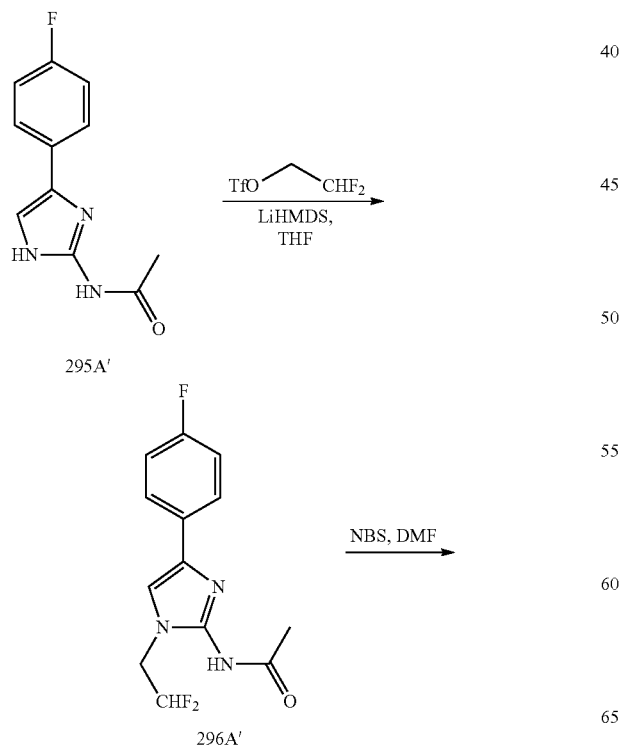

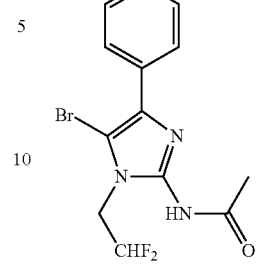

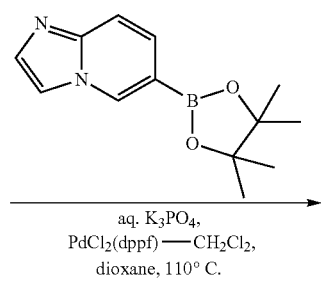

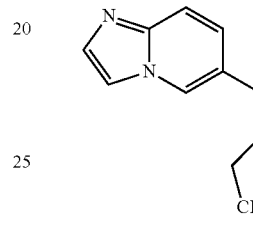

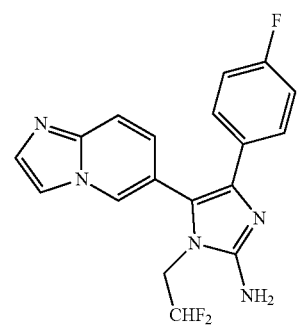

Intermediate 296A': N-(1-(2,2-difluoroethyl)-4-(4-fluorophenyl)-1H-imidazol-2-yl)acetamide To a solution of intermediate 296A' (800 mg, 3.65 mmol) in anhydrous THF (20 mL) at 0° C. was added LiHMDS (7.30 mL, 7.30 mmol, 1M solution in THF) dropwise. The reaction mixture was stirred at 0° C. for 15 min and 2,2-difluoroethyl trifluoromethanesulfonate (0.485 mL, 3.65 mmol) was added. The mixture was stirred at 0° C. for an additional 2 h, quenched with saturated aq. NH$_4$Cl solution and extracted with ethyl acetate. The organic layer was washed with brine, dried over Na$_2$SO$_4$, and filtered. The filtrate was concentrated under reduced pressure to give the crude residue, which was purified by silica gel chromatography (24 g CombiFlash® column, eluting with a gradient of 30-50% EtOAc in petroleum ether). Fractions containing the desired product were combined and evaporated to afford intermediate 296A' (600 mg, 58.0% yield). LCMS: m/z=282.0 [M−H]$^+$; HPLC Ret. Time 1.410 min. (HPLC Method J).

Intermediate 296B': N-(5-bromo-1-(2,2-difluoroethyl)-4-(4-fluorophenyl)-1H-imidazol-2-yl)acetamide

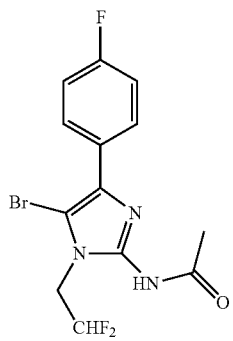

Intermediate 296B' was synthesized by reacting intermediate 296A' with NBS and by employing the experimental procedure described for intermediate 236C' in Scheme 22. LCMS: m/z=362.0 [M+H]$^+$; HPLC Ret. Time 1.988 min. (HPLC Method J).

Intermediate 296C': N-(1-(2,2-difluoroethyl)-4-(4-fluorophenyl)-5-(imidazo[1,2-a]pyridin-6-yl)-1H-imidazol-2-yl)acetamide

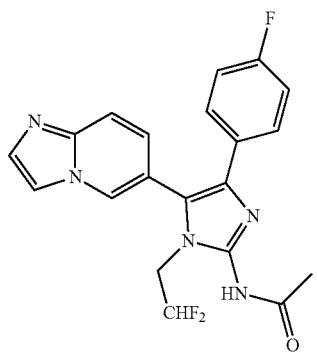 [SMILES: CC(=O)Nc1nc(-c2ccc(F)cc2)c(-c2ccc3nccn3c2)n1CC(F)F]

Intermediate 296C' was synthesized by reacting 6-(4,4,5,5-tetramethyl-1,3,2-dioxaborolan-2-yl)imidazo[1,2-a]pyridine (reference: CN 103275112 A) with intermediate 296B' and by employing the experimental procedure described for Example 236' in Scheme 22. The crude compound was purified by preparative HPLC (Condition R). Fractions containing the desired product were combined and evaporated to afford intermediate 296C' (20 mg, 18.14% yield). LCMS: m/z=400.1 [M+H]$^+$; HPLC Ret. Time 1.257 min. (HPLC Method H); $^1$H NMR (400 MHz, DMSO-d$_6$) δ ppm 8.97 (s, 1H), 7.95 (s, 1H), 7.75 (d, J=9.3 Hz, 1H), 7.62 (s, 1H), 7.32-7.42 (m, 2H), 7.12-7.22 (m, 3H), 5.98-6.26 (m, 1H), 4.24 (t, J=14.7 Hz, 2H), 2.37 (s, 3H).

Example 296'

1-(2,2-difluoroethyl)-4-(4-fluorophenyl)-5-(imidazo[1,2-a]pyridin-6-yl)-1H-imidazol-2-amine, 2 HCl

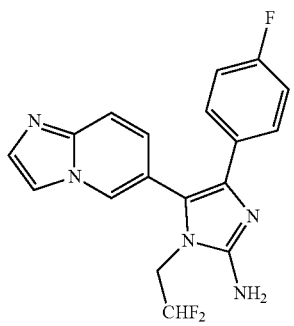 [SMILES: Nc1nc(-c2ccc(F)cc2)c(-c2ccc3nccn3c2)n1CC(F)F]

A solution of intermediate 296C' (45 mg, 0.113 mmol) and HCl (0.2 mL, 6.58 mmol) in MeOH (10 mL) was heated at 80° C. for 5 h. The reaction mixture was concentrated to give the crude residue, which was purified by preparative HPLC (HPLC Method 0). Fractions containing the desired product were combined and evaporated to afford Example 296' (15.4 mg, 31.8% yield). (Preparation of HCl salt of Example 296': 2 mL of 1M HCl was added to intermediate 296C' and concentrated by Genevac and the analytical data was recorded as the bis HCl salt). LCMS: m/z=358.1 [M+H]$^+$; HPLC Ret. Time 1.092 min; (HPLC Method H); $^1$HNMR (400 MHz, DMSO-d$_6$) δ ppm 9.08 (s, 1H) 8.34 (d, J=2.01 Hz, 1H) 8.15-8.22 (m, 1H) 8.04 (d, J=9.04 Hz, 1H) 7.75 (d, J=10.04 Hz, 1H) 7.37-7.43 (m, 2H) 7.34 (s, 1H) 7.17-7.23 (m, 2H) 7.09 (s, 1H) 6.03-6.33 (m, 1H) 4.36-4.47 (m, 2H).

The compound shown in Table 23 has been prepared in a manner similar to intermediate 296C' using intermediate 296B' and 6-(4,4,5,5-tetramethyl-1,3,2-dioxaborolan-2-yl)imidazo[1,2-a]pyridine-3-carbonitrile.

TABLE 23
| Ex. | Structure | Name | [M + H]+ | Ret. Time (min.) | HPLC Method |
|---|---|---|---|---|---|
| 297' | 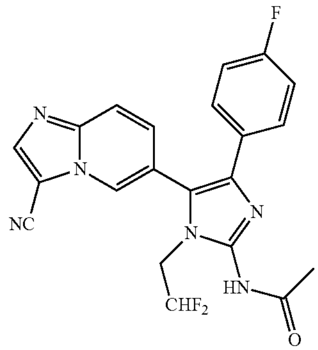 [SMILES: CC(=O)Nc1nc(-c2ccc(F)cc2)c(-c2ccc3ncc(C#N)n3c2)n1CC(F)F] | N-(5-(3-cyanoimidazo[1,2-a]pyridin-6-yl)-1-(2,2-difluoroethyl)-4-(4-fluorophenyl)-1H-imidazol-2-yl)acetamide | 425.1 | 1.403<br>1.339 | H<br>I |
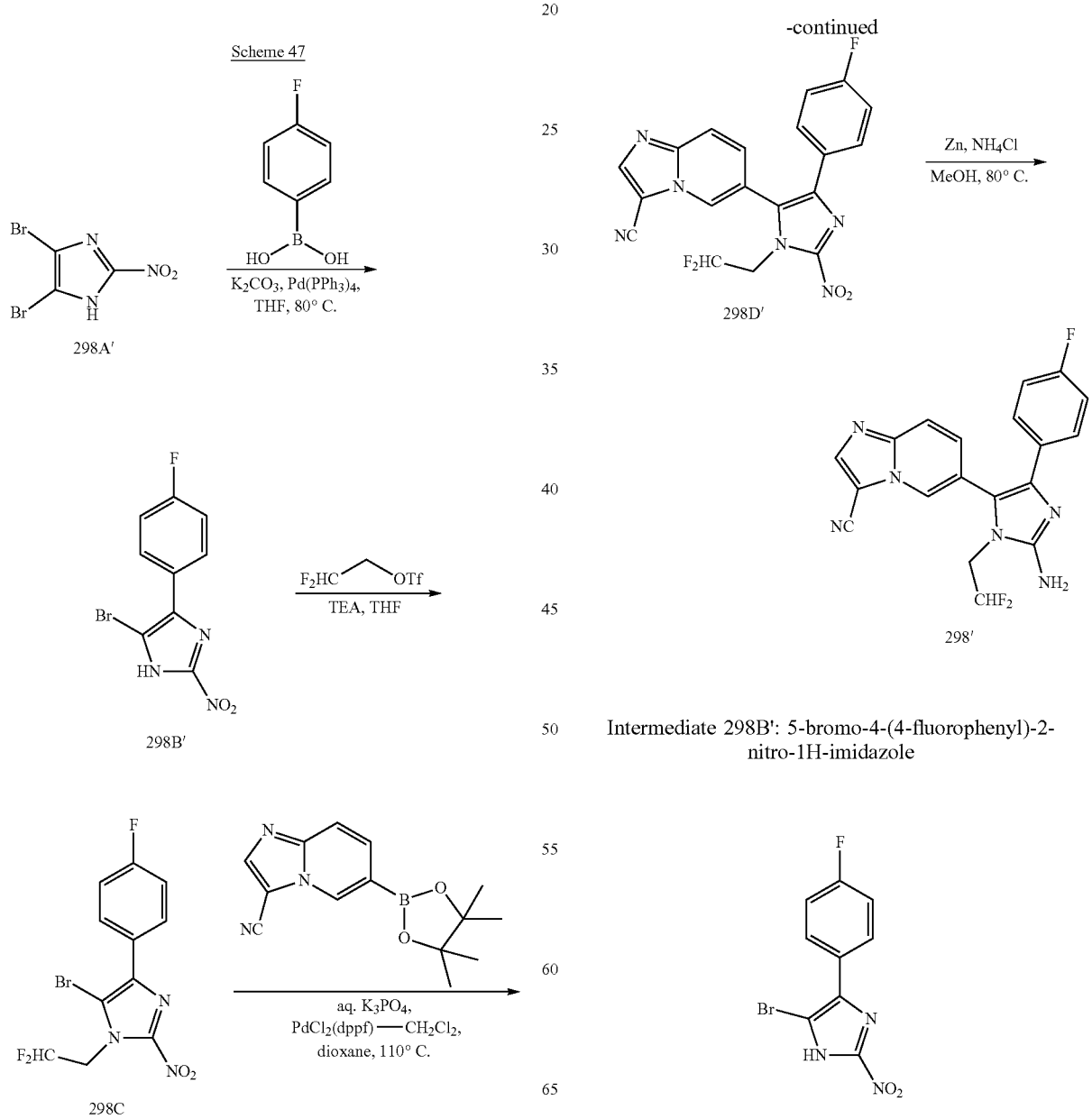
Intermediate 298B': 5-bromo-4-(4-fluorophenyl)-2-nitro-1H-imidazole To a solution of intermediate 298A' (reference: *Organic and Bio-Organic Chemistry* (1972-1999), 1989, 95-99) (1.0 g, 3.69 mmol) in THF (150 mL) was added (4-fluorophenyl)boronic acid (1.033 g, 7.38 mmol) and K₂CO₃ (0.510 g, 3.69 mmol in 10 mL water). The reaction mixture was degassed with argon for 5 minutes and Pd(PPh₃)₄ (0.213 g, 0.185 mmol) was added. The reaction mixture was heated at 80° C. for 15 h. The solvent was then evaporated and the residue was partitioned between water and ethyl acetate. The organic layer was washed with brine, dried over Na₂SO₄, and filtered. The filtrate was concentrated under reduced pressure to give the crude residue, which was purified by reverse phase silica chromatography (mobile phase A: 10 mM NH₄OAc:acetonitrile (95:5), mobile phase B: 10 mM NH₄OAc:acetonitrile (5:95), eluting with a gradient of 20-90% B). Fractions containing the desired product were combined and evaporated to afford intermediate 298B' (500 mg, 23.67% yield). LCMS: m/z=286.1 [M–H]⁺; HPLC Ret. Time 0.86 min. (HPLC Method G).

Intermediate 298C': 5-bromo-1-(2,2-difluoroethyl)-4-(4-fluorophenyl)-2-nitro-1H-imidazole

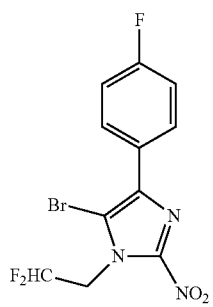

Intermediate 298C' was synthesized by reacting intermediate 298B' with NBS and by employing the experimental procedure described for intermediate 236C' in Scheme 22. The crude residue was purified by silica gel chromatography (12 g CombiFlash® column, eluting with a gradient of 25-50% EtOAc in petroleum ether). Fractions containing the desired product were combined and evaporated to afford intermediate 298C'. LCMS: m/z=352.0 [M+2H]⁺; HPLC Ret. Time 2.520 min. (HPLC Method J).

Intermediate 298D': 6-(1-(2,2-difluoroethyl)-4-(4-fluorophenyl)-2-nitro-1H-imidazol-5-yl)imidazo[1,2-a]pyridine-3-carbonitrile

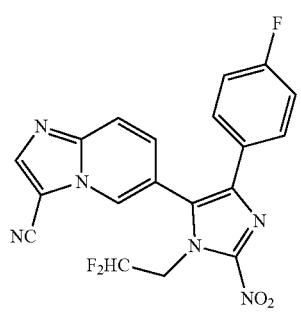 [SMILES: N#Cc1cnc2ccc(-c3c(-c4ccc(F)cc4)nc([N+](=O)[O-])n3CC(F)F)cn12]

Intermediate 298D' was synthesized by reacting 6-(4,4,5,5-tetramethyl-1,3,2-dioxaborolan-2-yl)imidazo[1,2-a]pyridine-3-carbonitrile (reference: WO 2014/055955 A1) with intermediate 298C' and by employing the experimental procedure described for Example 271' in Scheme 25. The crude compound was purified by silica gel chromatography (12 g CombiFlash® column, eluting with a gradient of 5-10% MeOH in CHCl₃). Fractions containing the desired product were combined and evaporated to afford intermediate 298D' (60 mg, 25.5% yield). LCMS: m/z=413.1 [M+H]⁺; HPLC Ret. Time 0.91 min. (HPLC Method F).

Example 298'

6-(2-amino-1-(2,2-difluoroethyl)-4-(4-fluorophenyl)-1H-imidazol-5-yl)imidazo[1,2-a]pyridine-3-carbonitrile

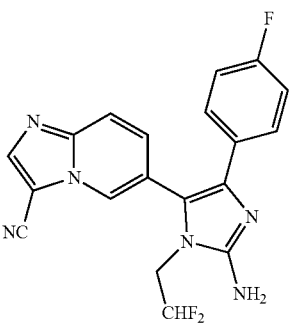 [SMILES: N#Cc1cnc2ccc(-c3c(-c4ccc(F)cc4)nc(N)n3CC(F)F)cn12]

To a solution of intermediate 298D' (25 mg, 0.061 mmol) in methanol (2.5 mL) was added ammonium chloride (6.49 mg, 0.121 mmol) and zinc (39.6 mg, 0.606 mmol). The reaction mixture was stirred at 80° C. for 1 h, filtered through a Celite® pad, and the pad was washed with DCM. The combined filtrates were evaporated to give the crude residue, which was purified by preparative HPLC (HPLC Method M). Fractions containing the desired product were combined and evaporated to afford example 298' (4.8 mg, 20.71% yield). LCMS: m/z=383.1 [M+H]⁺; HPLC Ret. Time 1.451 min. (HPLC Method H); ¹H NMR (400 MHz, DMSO-d₆) δ ppm 8.61 (s, 1H), 8.50 (s, 1H), 7.88 (d, J=9.05 Hz, 1H), 7.30-7.41 (m, 3H), 7.00 (t, J=8.93 Hz, 2H), 5.86-6.28 (m, 3H), 4.12-4.27 (m, 2H).

Example 4

Biological Assay

Assays for the compounds reported below were conducted in 1536-well plates and 2 mL reactions are prepared from addition of HIS-TGF-βR1 T204D or HIS-TGF-βR2 WT, anti-HIS detection antibody, a labeled small molecule probe ($K_d$=<100 nM; $k_{off}$=<0.001 s⁻¹) and test compounds in assay buffer (20 mM HEPES pH 7.4, 10 mM MgCl₂, 0.015% Brij35, 4 mM DTT, and 0.05 mg/ml BSA). The reaction is incubated for 1 hour at room temperature and the HTRF signal was measured on an Envision plate reader (Ex: 340 nm; Em: 520 nm/495 nm). Inhibition data were calculated by comparison to no enzyme control reactions for 100% inhibition and vehicle-only reactions for 0% inhibition. The final concentration of reagents in the assay are 1 nM HIS-TGF-βR1 T204D or HIS-TGF-βR2 WT, 0.2 nM anti-HIS detection antibody, labeled small molecule prode (at $K_d$) and 0.5% DMSO. Dose response curves were generated to determine the concentration required inhibiting 50% of kinase activity ($IC_{50}$). Compounds were dissolved at 10 mM in dimethylsulfoxide (DMSO) and evaluated at eleven concentrations. $IC_{50}$ values were derived by non-linear regression analysis.

| No. | TGFbr1 IC50 (μM) | TGFBr2 IC50 (μM) |
|---|---|---|
| 1' | 0.0016 | |
| 2' | 0.0023 | 2.2201 |
| 3' | 0.0142 | >15 > 15 |
| 4' | 0.0068 | — |
| 5' | 0.0055 | — |
| 6' | 0.0050 | 10.2377 |
| 7' | 0.0024 | 6.3338 |
| 8' | 0.0179 | >15 |
| 9' | 0.0019 | 11.1563 |
| 10' | 0.0025 | 7.1720 |
| 11' | 0.0030 | 3.1990 |
| 12' | 0.0021 | — |
| 13' | 0.0170 | >15 |
| 14' | 0.0053 | — |
| 15' | 0.0020 | 7.3009 |
| 16' | 0.0023 | >15 |
| 17' | 0.0035 | >15 |
| 18' | 0.0105 | 0.1289 |
| 19' | 0.0099 | >15 |
| 20' | 0.0022 | 4.8708 |
| 21' | 0.0019 | 4.4252 |
| 22' | 0.0012 | 3.1110 |
| 23' | 0.0019 | 9.4813 |
| 24' | 0.0004 | 2.1937 |
| 25' | 0.0026 | 3.7219 |
| 26' | 0.0926 | >15 |
| 27' | 0.0006 | 2.2513 |
| 28' | 0.0010 | >15 |
| 29' | 0.0064 | >15 |
| 30' | 0.0092 | >15 |
| 31' | 0.0019 | 3.7101 |
| 32' | 0.0018 | — |
| 33' | 0.0010 | — |
| 34' | 0.0009 | 7.7063 |
| 35' | 0.0026 | 11.0508 |
| 36' | 0.0013 | 5.7988 |
| 37' | 0.0025 | 10.7414 |
| 38' | 0.0010 | >15 |
| 39' | 0.0009 | 4.4730 |
| 40' | 0.0006 | 3.0319 |
| 41' | 0.0009 | 0.8753 |
| 42' | 0.0018 | 11.5255 |
| 43' | 0.0027 | 11.5430 |
| 44' | 0.0012 | 5.0893 |
| 45' | 0.0023 | 8.8598 |
| 46' | 0.0015 | 17.2311 |
| 47' | 0.0015 | 6.7145 |
| 48' | 0.0031 | >15 |
| 49' | 0.0014 | 2.3019 |
| 50' | 0.0023 | >15 |
| 51' | 0.0006 | 1.9862 |
| 52' | 0.0009 | 6.8860 |
| 53' | 0.0021 | 5.4685 |
| 54' | 0.0008 | 5.9937 |
| 55' | 0.0067 | >15 |
| 56' | 0.0008 | 6.8237 |
| 57' | 0.0015 | 9.3393 |
| 58' | 0.0008 | 3.5799 |
| 59' | 0.0011 | 7.5544 |
| 60' | 0.0009 | 5.5574 |
| 61' | 0.0008 | 6.4575 |
| 62' | 0.0016 | 8.9964 |
| 63' | 0.0009 | 8.7715 |
| 64' | 0.0051 | >15 |
| 65 | 0.0632 | >15 |
| 66' | 0.4185 | >15 |
| 67' | 0.0558 | >15 |
| 68' | 0.3007 | >15 |
| 69' | 0.1512 | >15 |
| 70' | 0.1226 | >15 |
| 71' | 0.1697 | >15 |
| 72' | 0.0678 | >15 |
| 73' | 0.0362 | >15 |
| 74' | 0.1519 | >15 |
| 75' | 0.1995 | >15 |
| 76' | 0.9993 | >15 |
| 77' | 0.0198 | >15 |
| 78' | 0.5684 | >15 |
| 79' | 0.0553 | >15 |
| 80' | 0.0310 | >15 |
| 81' | 0.0885 | >15 |
| 82' | 0.0716 | >15 |
| 83' | 0.1888 | >15 |
| 84' | 0.1212 | >15 |
| 85' | 0.1443 | >15 |
| 86' | 0.0947 | >15 |
| 87' | 0.0403 | >15 |
| 88' | 0.0193 | >15 |
| 89' | 0.1269 | >15 |
| 90' | 0.1072 | >15 |
| 91' | 0.0188 | >15 |
| 92' | 0.2659 | >15 |
| 93' | 0.5763 | >15 |
| 94' | 0.0131 | >15 |
| 95' | 0.0768 | >15 |
| 96' | 0.0944 | >15 |
| 97' | 0.1396 | >15 |
| 98' | 0.0173 | >15 |
| 99' | 0.0657 | >15 |
| 100' | 0.0116 | >15 |
| 101' | 0.0232 | >15 |
| 102 | 0.0024 | 0.5854 |
| 103' | 0.0018 | >15 |
| 104' | 0.0005 | 3.9544 |
| 105 | 0.0009 | 2.9308 |
| 106' | 0.0061 | >15 |
| 107' | 0.0019 | 7.6130 |
| 108' | 0.0021 | >15 |
| 109' | 0.0025 | 2.2749 |
| 110' | 0.0205 | >15 |
| 111' | 0.0008 | 3.3244 |
| 112' | 0.0007 | 9.7831 |
| 113' | 0.0009 | 3.3656 |
| 114' | 0.0013 | 3.1522 |
| 115' | 0.0046 | >15 |
| 116' | 0.0009 | 1.8896 |
| 117' | 0.0006 | 9.8046 |
| 118' | 0.0014 | >15 |
| 119' | 0.0004 | 5.8633 |
| 120' | 0.0065 | >15 |
| 121' | 0.0011 | >15 |
| 122' | 0.0018 | >15 |
| 123' | 0.0042 | 1.8551 |
| 124' | 0.0025 | 1.5908 |
| 125' | 0.0026 | >15 |
| 126' | 0.0074 | >15 |
| 127' | 0.0049 | 1.1498 |
| 128' | 0.0015 | 8.4646 |
| 129' | 0.0051 | >15 |
| 130' | 0.0021 | >15 |
| 131' | 0.0281 | >15 |
| 132' | 0.0047 | >15 |
| 133' | 0.0031 | 14.3697 |
| 134' | 0.0039 | 7.3702 |
| 135' | 0.0007 | 3.2657 |
| 136' | 0.0124 | >15 |
| 137' | 0.0006 | 6.5998 |
| 138' | 0.0007 | 5.9843 |
| 139' | 0.0052 | >15 |
| 140' | 0.0028 | 9.7851 |
| 141' | 0.0008 | 4.6352 |
| 142' | 0.0016 | >15 |
| 143' | 0.0091 | >15 |
| 144' | 0.0041 | >15 |

| No. | TGFbr1 IC50 (μM) | TGFBr2 IC50 (μM) | No. | TGFbr1 IC50 (μM) | TGFBr2 IC50 (μM) |
|---|---|---|---|---|---|
| 145' | 0.0022 | 2.2237 | 221' | 0.0068 | >15 |
| 146' | 0.0017 | 7.1990 | 222' | 0.0029 | >15 |
| 147' | 0.0013 | 1.5180 | 223' | 0.0022 | >15 |
| 148' | 0.0011 | 2.6284 | 224' | 0.0667 | >15 |
| 149' | 0.0017 | 3.6157 | 225' | 0.0100 | >15 |
| 150' | 0.0012 | 1.1117 | 226' | 0.0732 | >15 |
| 151' | 0.0006 | 3.8554 | 227' | 0.0081 | >15 |
| 152' | 0.0011 | >15 | 228' | 0.0037 | >15 |
| 153' | 0.0063 | >15 | 229' | 0.0086 | >15 |
| 154' | 0.0023 | >15 | 230' | 0.0017 | 5.9767 |
| 155' | 0.0055 | >15 | 231' | 0.0006 | 6.3016 |
| 156' | 0.0043 | 9.2537 | 232' | 0.0018 | 5.1875 |
| 157' | 0.0008 | 6.5893 | 233' | 0.0010 | >15 |
| 158' | 0.0027 | >15 | 234' | 0.0011 | 7.9394 |
| 159' | 0.0008 | >15 | 235' | 0.0010 | >15 |
| 160' | 0.0008 | 7.0201 | 236 | 0.0021 | >15 |
| 161' | 0.0067 | >15 | 237' | 0.0029 | >15 |
| 162' | 0.0019 | 11.2231 | 238' | 0.0397 | >15 |
| 163' | 0.0319 | >15 | 239' | 0.5213 | >15 |
| 164' | 0.0057 | >15 | 240' | 0.0143 | >15 |
| 165' | 0.0049 | >15 | 241' | 0.1734 | >15 |
| 166' | 0.0091 | >15 | 242' | 0.0050 | >15 |
| 167' | 0.0006 | 4.6700 | 243' | 0.0018 | >15 |
| 168' | 0.0011 | 13.2538 | 244' | 0.5459 | >15 |
| 169' | 0.0213 | >15 | 245' | 0.0491 | >15 |
| 170' | 0.0005 | 4.2962 | 246' | 0.1435 | >15 |
| 171' | 0.0084 | >15 | 247' | 0.0143 | >15 |
| 172' | 0.0005 | 1.7386 | 248' | 0.0007 | 0.1444 |
| 173' | 0.0066 | >15 | 249' | 0.0022 | >15 |
| 174' | 0.0006 | 5.5480 | 250' | 0.1359 | >15 |
| 175' | 0.0020 | >15 | 251' | 0.0735 | >15 |
| 176' | 0.0052 | >15 | 252' | 0.0077 | >15 |
| 177' | 0.0011 | 9.0826 | 253' | 0.0070 | 4.5788 |
| 178' | 0.0019 | 5.0774 | 254' | 0.7517 | >15 |
| 179' | 0.0022 | >15 | 255' | 0.8668 | >15 |
| 180' | 0.0037 | >15 | 256' | 0.0050 | >15 |
| 181' | 0.0060 | >15 | 257' | 0.0642 | >15 |
| 182' | 0.0508 | >15 | 258' | 0.3560 | >15 |
| 183' | 0.0216 | >15 | 259' | 0.0010 | >15 |
| 184' | 0.0545 | >15 | 260' | 0.0088 | >15 |
| 185' | 0.0301 | >15 | 261' | 0.0894 | >15 |
| 186' | 0.2277 | >15 | 262' | 0.0052 | >15 |
| 187' | 0.0033 | >15 | 263' | 0.1710 | >15 |
| 188' | 0.0020 | 1.4660 | 264' | 0.5161 | >15 |
| 189' | 0.0016 | 3.5554 | 265' | 0.0098 | >15 |
| 190' | 0.0527 | >15 | 266' | 0.0079 | >15 |
| 191' | 0.0727 | >15 | 267' | 0.0003 | 1.7536 |
| 192' | 0.2289 | >15 | 268' | 0.0190 | >15 |
| 193' | 0.2269 | >15 | 269' | 1.2000 | >15 |
| 194' | 0.0102 | 7.0868 | 270' | 0.0992 | >15 |
| 195' | 0.4358 | >15 | 271' | 0.1723 | >15 |
| 196' | 0.0238 | >15 | 272' | 0.0104 | >15 |
| 197' | 0.0119 | >15 | 273' | 0.0296 | >15 |
| 198' | 0.0053 | >15 | 274' | 0.1374 | >15 |
| 199' | 0.0095 | >15 | 275' | 0.1208 | >15 |
| 200' | 0.0120 | >15 | 276' | 0.9878 | >15 |
| 201' | 0.0050 | >15 | 277' | 0.0209 | >15 |
| 202' | 0.0438 | >15 | 278' | 0.1835 | >15 |
| 203' | 0.0011 | 6.2222 | 279' | 0.0095 | >15 |
| 204' | 0.0012 | >15 | 280' | 0.0032 | >15 |
| 205' | 0.0018 | >15 | 281' | 0.5219 | >15 |
| 206' | 0.0009 | >15 | 282' | 0.0129 | >15 |
| 207' | 0.0030 | >15 | 283' | 0.0009 | 2.9356 |
| 208' | 0.0012 | >15 | 284' | 0.4262 | >15 |
| 209' | 0.0007 | 2.6841 | 285' | 0.0388 | >15 |
| 210' | 0.0022 | 7.7798 | 286' | — | — |
| 211' | 0.0045 | >15 | 287' | — | — |
| 212' | 0.0093 | >15 | 288' | 0.0567 | >15 |
| 213' | 0.0023 | >15 | 289' | 0.3764 | >15 |
| 214' | 0.0011 | >15 | 290' | 0.0216 | >15 |
| 215' | 0.0008 | 7.1973 | 291' | 0.0305 | >15 |
| 216' | 0.0009 | 7.0527 | 292' | 0.0408 | >15 |
| 217' | 0.0032 | >15 | 293' | 0.0433 | >15 |
| 218' | 0.0627 | >15 | 294' | 0.0272 | >15 |
| 219' | 0.0099 | >15 | 295' | 0.0550 | >15 |
| 220' | 0.0414 | >15 | 296' | 0.1088 | >15 |

-continued

| No. | TGFbr1 IC50 (μM) | TGFBr2 IC50 (μM) |
|---|---|---|
| 297' | 0.5418 | >15 |
| 298' | 0.0448 | >15 |
| 190C' | 0.0862 | >15 |
| 195A' | 0.2443 | >15 |
| 195B' | 0.0454 | >15 |
| 196A' | 0.0201 | >15 |
| 213E' | 0.0016 | 4.6759 |
| 272A' | 0.2506 | >15 |
| 274C' | 0.0070 | >15 |
| 274D' | 0.0926 | >15 |
| 283B' | 0.0138 | 3.9581 |
| 284D' | 0.0012 | >15 |

What is claimed:

1. A method for treating a subject afflicted with cancer associated with TGF-β activity comprising administering to the subject a therapeutically effective amount of a compound having the structure of formula (I°):

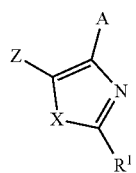

(I°)

or a pharmaceutically acceptable salt, or N-oxide thereof, or a solvate or hydrate thereof, wherein
X is —N(R')—;
R' is hydrogen, $C_1$-$C_6$alkyl, $C_1$-$C_6$haloalkyl, $C_1$-$C_6$alkyloxy, —($C_0$-$C_{12}$alkyl)-Cak or —($C_0$-$C_6$alkyl)-Hca, each optionally substituted with 1 to 3 moieties that are each independently $C_1$-$C_6$alkyl, halogen, $C_1$-$C_6$haloalkyl, —OR$^{S0}$, $C_1$-$C_6$alkyl-OR$^{S0}$, —C(O)OR$^{S0}$, —C(O)R$^{S0}$, —C(O)NR$^{S0}$$_2$, —R$^{S0}$ or cyano;
wherein each R$^{S0}$ is independently hydrogen, $C_1$-$C_6$alkyl, $C_1$-$C_6$haloalkyl, —($C_0$-$C_6$alkyl)-Ar, —($C_0$-$C_6$alkyl)-Het, —($C_0$-$C_6$alkyl)-Cak, or —($C_0$-$C_6$alkyl)-Hca, wherein Ar, Het, Cak, Hca, alkyl, and haloalkyl are optionally substituted with $C_1$-$C_6$alkyl, halogen, $C_1$-$C_6$haloalkyl or cyano;
R$^1$ is hydrogen, $C_1$-$C_6$alkyl, $C_1$-$C_6$haloalkyl, $C_1$-$C_6$alkyloxy, —OR$^{S1}$, —NR$^{S1}$$_2$, —SR$^{S1}$ or —N(R$^{S1}$)C(O)R$^{S1}$, each optionally substituted with 1 to 3 moieties that are each independently $C_1$-$C_6$alkyl, halogen, $C_1$-$C_6$haloalkyl or cyano; wherein each R$^{S1}$ is independently hydrogen, $C_1$-$C_6$alkyl, $C_1$-$C_6$haloalkyl, —($C_0$-$C_6$alkyl)-Ar, —($C_0$-$C_6$alkyl)-Het, —($C_0$-$C_6$alkyl)-Cak, or —($C_0$-$C_6$alkyl)-Hca, wherein Ar, Het, Cak, Hca, alkyl, and haloalkyl are optionally substituted with $C_1$-$C_6$alkyl, halogen, $C_1$-$C_6$haloalkyl or cyano;
or R' and R$^1$ combined with the atoms to which they are attached form a five- to eight-membered ring;
A is phenyl optionally substituted with one to five R$^2$ groups, wherein
each R$^2$ is independently halogen, —$C_1$-$C_6$alkyl, —$C_1$-$C_6$haloalkyl, —$C_1$-$C_6$alkoxy, —$C_1$-$C_6$haloalkoxy, —NO$_2$, —N(R$^{S2}$)C(O)R$^{S2}$, —OR$^{S2}$, —C(O)NR$^{S2}$$_2$, —N(R$^{S2}$)S(O)$_2$R$^{S2}$, —S(O)$_2$R$^{S2}$, —($C_0$-$C_6$alkyl)-Ar or —CN, wherein each alkyl, haloalkyl and alkoxy are optionally substituted with 1, 2, 3, or 4 groups that are each independently halogen, cyano, nitro, —OR$^{S2}$, —SR$^{S2}$, —NR$^{S2}$$_2$, —C(O)OR$^{S2}$, —C(O)NR$^{S2}$$_2$, —C(O)R$^{S2}$, —S(O)R$^{S2}$, —S(O)$_2$R$^{S2}$, —S(O)OR$^{S2}$, —S(O)$_2$OR$^{S2}$, —S(O)NR$^{S2}$$_2$, —S(O)$_2$NR$^{S2}$$_2$, —OC(O)R$^{S2}$, —OC(O)OR$^{S2}$, —OC(O)NR$^{S2}$$_2$, —N(R$^{S2}$)C(O)R$^{S2}$, —N(R$^{S2}$)C(O)OR$^{S2}$, —N(R$^{S2}$)C(O)NR$^{S2}$$_2$, —N(R$^{S2}$)S(O)R$^{S2}$, —N(R$^{S2}$)S(O)$_2$R$^{S2}$, $C_1$-$C_6$alkyl, or $C_1$-$C_6$haloalkyl;
wherein each R$^{S2}$ is independently hydrogen, $C_1$-$C_6$alkyl, $C_1$-$C_6$haloalkyl, —($C_0$-$C_6$alkyl)-Ar, —($C_0$-$C_6$alkyl)-Het, —($C_0$-$C_6$alkyl)-Cak, or —($C_0$-$C_6$alkyl)-Hca, wherein Ar, Het, Cak, Hca, alkyl, and haloalkyl are optionally substituted with $C_1$-$C_6$alkyl, halogen, $C_1$-$C_6$haloalkyl or cyano;
Z is

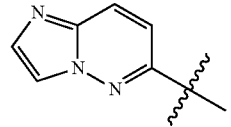

wherein
Z is optionally substituted by one or two —R$^Z$ groups that are each independently halogen, cyano, $C_{1-6}$alkyl, $C_{1-6}$haloalkyl, —$C_1$-$C_6$alkoxy, —OR$^{S3}$, —SR$^{S3}$, —C(O)R$^{S3}$, —C(O)OR$^{S3}$, —C(O)NR$^{S3}$$_2$, —S(O)$_2$NR$^{S3}$$_2$, —S(O)$_2$R$^{S3}$, —OC(O)R$^{S3}$, —OC(O)OR$^{S3}$, —OC(O)NR$^{S3}$$_2$, —N(R$^{S3}$)C(O)OR$^{S3}$, —N(R$^{S3}$)S(O)$_2$R$^{S3}$, —OP(O)(OR$^{S3}$)$_2$ or —CH$_2$—OP(O)(OR$^{S3}$), wherein each alkyl, haloalkyl and alkoxy is optionally substituted by one or two —R$^{Z2}$ groups;
wherein each R$^{S3}$ is independently hydrogen, $C_1$-$C_6$alkyl, $C_1$-$C_6$haloalkyl, —($C_0$-$C_6$alkyl)-Ar, —($C_0$-$C_6$alkyl)-Het, —($C_0$-$C_6$alkyl)-Cak, or —($C_0$-$C_6$alkyl)-Hca, wherein Ar, Het, Cak, Hca, alkyl, and haloalkyl are optionally substituted with $C_1$-$C_6$alkyl, halogen, $C_1$-$C_6$haloalkyl, or cyano; and
each —R$^{Z2}$ is independently halogen, cyano, $C_{1-6}$alkyl, $C_{1-6}$haloalkyl, —$C_1$-$C_6$alkoxy, —OR$^{S4}$, —SR$^{S4}$, —NR$^{S4}$$_2$, —C(O)R$^{S4}$, —C(O)OR$^{S4}$, —C(O)NR$^{S4}$$_2$, —S(O)$_2$NR$^{S4}$$_2$, —S(O)$_2$R$^{S4}$, —OC(O)R$^{S4}$, —N(R$^{S4}$)C(O)R$^{S4}$, —OC(O)OR$^{S4}$, —OC(O)NR$^{S4}$$_2$, —N(R$^{S4}$)C(O)OR$^{S4}$, —N(R$^{S4}$)C(O)NR$^{S4}$$_2$, —N(R$^{S4}$)S(O)$_2$R$^{S4}$, —OP(O)(OR$^{S4}$)$_2$ or —CH$_2$—OP(O)(OR$^{S4}$); and
wherein each R$^{S4}$ is independently hydrogen, $C_1$-$C_6$alkyl, $C_1$-$C_6$haloalkyl, —($C_0$-$C_6$alkyl)-Ar, —($C_0$-$C_6$alkyl)-Het, —($C_0$-$C_6$alkyl)-Cak, or —($C_0$-$C_6$alkyl)-Hca, wherein Ar, Het, Cak, Hca, alkyl, and haloalkyl are optionally substituted with one or two $C_1$-$C_6$alkyl, halogen, $C_1$-$C_6$haloalkyl or cyano.

2. The method according to claim 1, wherein compound is of structure of formula (I):

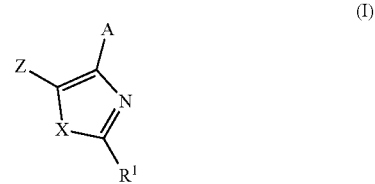

(I)

or a pharmaceutically acceptable salt, or N-oxide thereof, or a solvate or hydrate thereof, wherein X is —N(R')—;

R' is hydrogen, $C_1$-$C_6$alkyl, $C_1$-$C_6$haloalkyl, $C_1$-$C_6$alkyloxy, each optionally substituted with 1 to 3 moieties that are each independently $C_1$-$C_6$alkyl, halogen, $C_1$-$C_6$haloalkyl or cyano;

$R^1$ is hydrogen, $C_1$-$C_6$alkyl, $C_1$-$C_6$haloalkyl, $C_1$-$C_6$alkyloxy, —$OR^{S1}$, —$NR^{S1}{}_2$, —$SR^{S1}$, each optionally substituted with 1 to 3 moieties that are each independently $C_1$-$C_6$alkyl, halogen, $C_1$-$C_6$haloalkyl or cyano;

wherein each $R^{S1}$ is independently hydrogen, $C_1$-$C_6$alkyl, $C_1$-$C_6$haloalkyl, —($C_0$-$C_6$alkyl)-Ar, —($C_0$-$C_6$alkyl)-Het, —($C_0$-$C_6$alkyl)-Cak, or —($C_0$-$C_6$alkyl)-Hca, wherein Ar, Het, Cak, Hca, alkyl, and haloalkyl are optionally substituted with $C_1$-$C_6$alkyl, halogen, $C_1$-$C_6$haloalkyl or cyano;

A is phenyl optionally substituted with one to five $R^2$ groups, wherein each $R^2$ is independently halogen, —$C_1$-$C_6$alkyl, —$C_1$-$C_6$haloalkyl, —$C_1$-$C_6$alkoxy, —$NO_2$ or —CN, wherein each alkyl, haloalkyl and alkoxy are optionally substituted with 1, 2, 3, or 4 groups that are each independently halogen, cyano, nitro, —$OR^{S2}$, —$SR^{S2}$, —$NR^{S2}{}_2$, —C(O)$OR^{S2}$, —C(O)$NR^{S2}{}_2$, —C(O)$R^{S2}$, —S(O)$R^{S2}$, —S(O)$_2R^{S2}$, —S(O)$OR^{S2}$, —S(O)$_2OR^{S2}$, —S(O)$NR^{S2}{}_2$, —S(O)$_2$$NR^{S2}{}_2$, —OC(O)$R^{S2}$, —OC(O)$OR^{S2}$, —OC(O)$NR^{S2}{}_2$, —N($R^{S2}$)C(O)$R^{S2}$, —N($R^{S2}$)C(O)$OR^{S2}$, —N($R^{S2}$)C(O)$NR^{S2}{}_2$, N($R^{S2}$)S(O)$R^{S2}$, —N($R^{S2}$)S(O)$_2R^{S2}$, $C_1$-$C_6$alkyl, or $C_1$-$C_6$haloalkyl;

wherein each $R^{S2}$ is independently hydrogen, $C_1$-$C_6$alkyl, $C_1$-$C_6$haloalkyl, —($C_0$-$C_6$alkyl)-Ar, —($C_0$-$C_6$alkyl)-Het, —($C_0$-$C_6$alkyl)-Cak, or —($C_0$-$C_6$alkyl)-Hca, wherein Ar, Het, Cak, Hca, alkyl, and haloalkyl are optionally substituted with $C_1$-$C_6$alkyl, halogen, $C_1$-$C_6$haloalkyl or cyano;

Z is

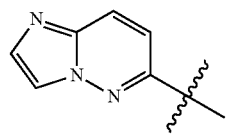

wherein

Z is optionally substituted by one or two —$R^Z$ groups that are each independently halogen, cyano, $C_{1-6}$alkyl, $C_{1-6}$haloalkyl, —$C_1$-$C_6$alkoxy, —$OR^{S3}$, —$SR^{S3}$, —C(O)$R^{S3}$, —C(O)$OR^{S3}$, —C(O)$NR^{S3}{}_2$, —S(O)$_2NR^{S3}{}_2$, —S(O)$_2R^{S3}$, —OC(O)$R^{S3}$, —OC(O)$OR^{S3}$, —OC(O)$NR^{S3}{}_2$, —N($R^{S3}$)C(O)$OR^{S3}$, —N($R^{S3}$)S(O)$_2R^{S3}$, —OP(O)(O$R^{S3}$) 2 or —CH$_2$—OP(O)(O$R^{S3}$), wherein each alkyl, haloalkyl and alkoxy is optionally substituted by one or two —$R^{Z2}$ groups;

wherein each $R^{S3}$ is independently hydrogen, $C_1$-$C_6$alkyl, $C_1$-$C_6$haloalkyl, —($C_0$-$C_6$alkyl)-Ar, —($C_0$-$C_6$alkyl)-Het, —($C_0$-$C_6$alkyl)-Cak, or —($C_0$-$C_6$alkyl)-Hca, wherein Ar, Het, Cak, Hca, alkyl, and haloalkyl are optionally substituted with $C_1$-$C_6$alkyl, halogen, $C_1$-$C_6$haloalkyl or cyano; and each —$R^{Z2}$ is independently halogen, cyano, $C_{1-6}$alkyl, $C_{1-6}$haloalkyl, —$C_1$-$C_6$alkoxy, —$OR^{S4}$, —$SR^{S4}$, —$NR^{S4}{}_2$, —C(O)$R^{S4}$, —C(O)$OR^{S4}$, —C(O)$NR^{S4}{}_2$, —S(O)$_2$NR$^{S4}{}_2$, —S(O)$_2R^{S4}$, —OC(O)$R^{S4}$, —N($R^{S4}$)C(O)$R^{S4}$, —OC(O)$OR^{S4}$, —OC(O)$NR^{S4}{}_2$, —N($R^{S4}$)C(O)$OR^{S4}$, —N($R^{S4}$)C(O)$NR^{S4}{}_2$, —N($R^{S4}$)S(O)$_2R^{S4}$, —OP(O)(O$R^{S4}$)$_2$ or —CH$_2$—OP(O)(O$R^{S4}$); and wherein each $R^{S4}$ is independently hydrogen, $C_1$-$C_6$alkyl, $C_1$-$C_6$haloalkyl, —($C_0$-$C_6$alkyl)-Ar, —($C_0$-$C_6$alkyl)-Het, —($C_0$-$C_6$alkyl)-Cak, or —($C_0$-$C_6$alkyl)-Hca, wherein Ar, Het, Cak, Hca, alkyl, and haloalkyl are optionally substituted with $C_1$-$C_6$alkyl, halogen, $C_1$-$C_6$haloalkyl or cyano.

3. The method of claim 1, wherein the compound has the structure of one of the following formulae:

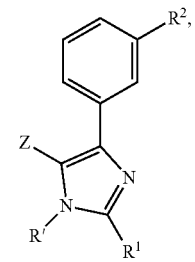
(Ie)

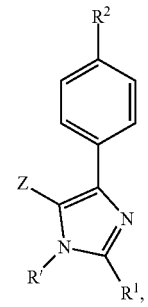
(If)

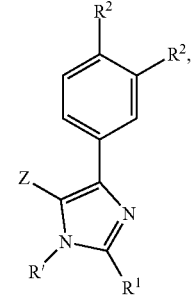
(Ig)

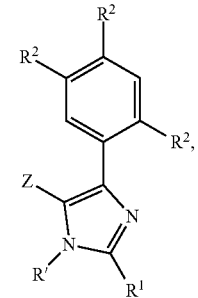
(Ii)

-continued

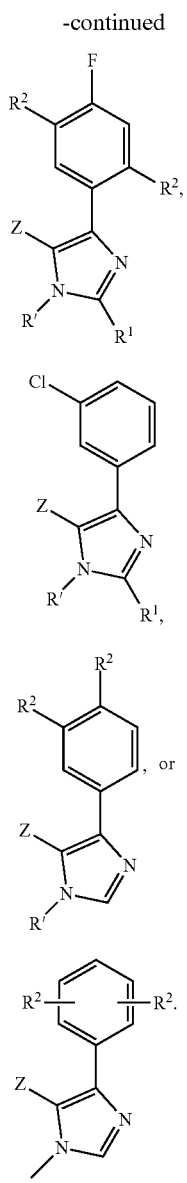

4. The method according to claim 1, wherein the compound is:
6-(1-(2,2-difluoroethyl)-4-(4-fluorophenyl)-1H-imidazol-5-yl)imidazo[1,2-b]pyridazine-3-carbonitrile,
6-(4-(4-fluorophenyl)-1-cis-3-hydroxycyclobutyl)-1H-imidazol-5-yl)imidazo[1,2-b]pyridazine-3-carbonitrile,
6-(1-(3,3-difluorocyclobutyl)-4-(4-fluorophenyl)-1H-imidazol-5-yl)imidazo[1,2-b]pyridazine-3-carbonitrile,
6-(4-(4-fluorophenyl)-1-(3,3,3-trifluoropropyl)-1H-imidazol-5-yl)imidazo[1,2-b]pyridazine-3-carbonitrile,
6-(1-(3,3-difluorocyclopentyl)-4-(4-fluorophenyl)-1H-imidazol-5-yl)imidazo[1,2-b]pyridazine-3-carbonitrile,
6(S)-6-(4-(4-fluorophenyl)-1-(1-hydroxybutan-2-yl)-1H-imidazol-5-yl)imidazo[1,2-b]pyridazine-3-carbonitrile,
6-(1-cyclopropyl-4-(4-fluorophenyl)-1H-imidazol-5-yl)imidazo[1,2-b]pyridazine-3-carbonitrile,
6-(1-(4,4-difluorocyclohexyl)-4-(4-fluorophenyl)-1H-imidazol-5-yl)imidazo[1,2-b]pyridazine-3-carbonitrile,
6-(1-(2-fluoroethyl)-4-(4-fluorophenyl)-1H-imidazol-5-yl)imidazo[1,2-b]pyridazine-3-carbonitrile,
6-(1-ethyl-4-(4-fluorophenyl)-1H-imidazol-5-yl)imidazo[1,2-b]pyridazine-3-carbonitrile,
6-(4-(4-fluorophenyl)-1-(2-isopropoxyethyl)-1H-imidazol-5-yl)imidazo[1,2-b]pyridazine-3-carbonitrile,
6-(4-(4-fluorophenyl)-1-(3-hydroxy-3-methylbutyl)-1H-imidazol-5-yl)imidazo[1,2-b]pyridazine-3-carbonitrile,
6-(4-(4-fluorophenyl)-1-(oxetan-3-yl)-1H-imidazol-5-yl)imidazo[1,2-b]pyridazine-3-carbonitrile,
6-(4-(4-fluorophenyl)-1-(2-hydroxyethyl)-1H-imidazol-5-yl)imidazo[1,2-b]pyridazine-3-carbonitrile,
6-(4-(4-fluorophenyl)-1-(3-hydroxypropyl)-1H-imidazol-5-yl)imidazo[1,2-b]pyridazine-3-carbonitrile,
6-(1-(1-cyclopropyl-2-methoxyethyl)-4-(4-fluorophenyl)-1H-imidazol-5-yl)imidazo[1,2-b]pyridazine-3-carbonitrile,
6-(4-(4-fluorophenyl)-1-(2-hydroxycyclohexyl)-1H-imidazol-5-yl)imidazo[1,2-b]pyridazine-3-carbonitrile,
6-(4-(4-fluorophenyl)-1H-imidazol-5-yl)imidazo[1,2-b]pyridazine-3-carbonitrile,
6-(4-(4-fluorophenyl)-1-methyl-1H-imidazol-5-yl)imidazo[1,2-b]pyridazine-3-carbonitrile,
6-(1-(3,3-difluoropropyl)-4-(4-fluorophenyl)-1H-imidazol-5-yl)imidazo[1,2-b]pyridazine-3-carbonitrile,
6-(4-(4-fluorophenyl)-1-(3-fluoropropyl)-1H-imidazol-5-yl)imidazo[1,2-b]pyridazine-3-carbonitrile,
6-(1-(2,2-difluoropropyl)-4-(4-fluorophenyl)-1H-imidazol-5-yl)imidazo[1,2-b]pyridazine-3-carbonitrile,
6-(1-(2-fluoro-2-methylpropyl)-4-(4-fluorophenyl)-1H-imidazol-5-yl)imidazo[1,2-b]pyridazine-3-carbonitrile,
6-(4-(4-fluorophenyl)-1-isopropyl-1H-imidazol-5-yl)imidazo[1,2-b]pyridazine-3-carbonitrile,
6-(1-(bicyclo[1.1.1]pentan-1-yl)-4-(4-fluorophenyl)-1H-imidazol-5-yl)imidazo[1,2-b]pyridazine-3-carbonitrile,
6-(4-(4-fluorophenyl)-1-(2-hydroxy-2-methylpropyl)-1H-imidazol-5-yl)imidazo[1,2-b]pyridazine-3-carbonitrile,
6-(4-(4-fluorophenyl)-1-(3-(hydroxymethyl)cyclobutyl)-1H-imidazol-5-yl)imidazo[1,2-b]pyridazine-3-carbonitrile,
(R)-6-(4-(4-fluorophenyl)-1-(4,4,4-trifluoro-1-hydroxybutan-2-yl)-1H-imidazol-5-yl)imidazo[1,2-b]pyridazine-3-carbonitrile,
(S)-6-(4-(4-fluorophenyl)-1-(4,4,4-trifluoro-1-hydroxybutan-2-yl)-1H-imidazol-5-yl)imidazo[1,2-b]pyridazine-3-carbonitrile,
6-(4-(4-fluorophenyl)-1-(tert-pentyl)-1H-imidazol-5-yl)imidazo[1,2-b]pyridazine-3-carbonitrile,
6-(4-(4-fluorophenyl)-1-((tetrahydrofuran-2-yl)methyl)-1H-imidazol-5-yl)imidazo[1,2-b]pyridazine-3-carbonitrile,
6-(4-(3-chloro-4-fluorophenyl)-1-(2-hydroxyethyl)-1H-imidazol-5-yl)imidazo[1,2-b]pyridazine-3-carbonitrile,
6-(4-(3-chloro-4-fluorophenyl)-1-(2,2-difluoroethyl)-1H-imidazol-5-yl)imidazo[1,2-b]pyridazine-3-carbonitrile,
6-(4-(3-chloro-4-fluorophenyl)-1-(2-fluoroethyl)-1H-imidazol-5-yl)imidazo[1,2-b]pyridazine-3-carbonitrile,
6-(4-(3-chloro-4-fluorophenyl)-1-(3,3,3-trifluoropropyl)-1H-imidazol-5-yl)imidazo[1,2-b]pyridazine-3-carbonitrile,
6-(4-(3-chloro-4-fluorophenyl)-1-cyclopropyl-1H-imidazol-5-yl)imidazo[1,2-b]pyridazine-3-carbonitrile,
6-(4-(3-chloro-4-fluorophenyl)-1-(3-hydroxy-3-methylbutyl)-1H-imidazol-5-yl)imidazo[1,2-b]pyridazine-3-carbonitrile,
6-(4-(3-chloro-4-fluorophenyl)-1-(3-hydroxypropyl)-1H-imidazol-5-yl)imidazo[1,2-b]pyridazine-3-carbonitrile,
6-(4-(3-chloro-4-fluorophenyl)-1-((cis)-3-hydroxycyclobutyl)-1H-imidazol-5-yl)imidazo[1,2-b]pyridazine-3-carbonitrile, 6-(4-(3-chloro-4-fluorophenyl)-1-(2-cyclobutylethyl)-1H-imidazol-5-yl)imidazo[1,2-b]pyridazine-3-carbonitrile,
6-(4-(3-chloro-4-fluorophenyl)-1-(1-methylcyclopropyl)-1H-imidazol-5-yl)imidazo[1,2-b]pyridazine-3-carbonitrile,
(S)-6-(4-(3-chloro-4-fluorophenyl)-1-((tetrahydrofuran-2-yl)methyl)-1H-imidazol-5-yl)imidazo[1,2-b]pyridazine-3-carbonitrile,
6-(4-(3-chloro-4-fluorophenyl)-1-(3-methyloxetan-3-yl)-1H-imidazol-5-yl)imidazo[1,2-b]pyridazine-3-carbonitrile,
6-(4-(3-chloro-4-fluorophenyl)-1-(3-chloropropyl)-1H-imidazol-5-yl)imidazo[1,2-b]pyridazine-3-carbonitrile,
6-(4-(3-chloro-4-fluorophenyl)-1-((3-methyloxetan-3-yl)methyl)-1H-imidazol-5-yl)imidazo[1,2-b]pyridazine-3-carbonitrile,
6-(4-(3-chloro-4-fluorophenyl)-1-(tetrahydrofuran-3-yl)-1H-imidazol-5-yl)imidazo[1,2-b]pyridazine-3-carbonitrile,
6-(4-(3-chloro-4-fluorophenyl)-1-(2-methoxyethyl)-1H-imidazol-5-yl)imidazo[1,2-b]pyridazine-3-carbonitrile,
6-(4-(3-chloro-4-fluorophenyl)-1-(tetrahydro-2H-pyran-4-yl)-1H-imidazol-5-yl)imidazo[1,2-b]pyridazine-3-carbonitrile,
6-(4-(3-chloro-4-fluorophenyl)-1-isopentyl-1H-imidazol-5-yl)imidazo[1,2-b]pyridazine-3-carbonitrile,
6-(4-(3-chloro-4-fluorophenyl)-1-methyl-1H-imidazol-5-yl)imidazo[1,2-b]pyridazine-3-carbonitrile,
6-(4-(3-chloro-4-fluorophenyl)-1-isopropyl-1H-imidazol-5-yl)imidazo[1,2-b]pyridazine-3-carbonitrile,
6-(4-(3-chloro-4-fluorophenyl)-1-ethyl-1H-imidazol-5-yl)imidazo[1,2-b]pyridazine-3-carbonitrile,
6-(4-(3-chloro-4-fluorophenyl)-1-(3,3-difluorocyclobutyl)-1H-imidazol-5-yl)imidazo[1,2-b]pyridazine-3-carbonitrile,
6-(4-(3-chloro-4-fluorophenyl)-1-(3-fluoropropyl)-1H-imidazol-5-yl)imidazo[1,2-b]pyridazine-3-carbonitrile,
6-(4-(3-chloro-4-fluorophenyl)-1-(3,3,3-trifluoro-2-hydroxypropyl)-1H-imidazol-5-yl)imidazo[1,2-b]pyridazine-3-carbonitrile,
6-(4-(3-chloro-4-fluorophenyl)-1-(2,2-difluoropropyl)-1H-imidazol-5-yl)imidazo[1,2-b]pyridazine-3-carbonitrile,
6-(4-(3-chloro-4-fluorophenyl)-1-(2-fluoro-2-methylpropyl)-1H-imidazol-5-yl)imidazo[1,2-b]pyridazine-3-carbonitrile,
6-(4-(3-chloro-4-fluorophenyl)-1-cyclobutyl-1H-imidazol-5-yl)imidazo[1,2-b]pyridazine-3-carbonitrile,
6-(1-(bicyclo[1.1.1]pentan-1-yl)-4-(3-chloro-4-fluorophenyl)-1H-imidazol-5-yl)imidazo[1,2-b]pyridazine-3-carbonitrile,
6-(4-(3-chloro-4-fluorophenyl)-1-(2-chloroethyl)-1H-imidazol-5-yl)imidazo[1,2-b]pyridazine-3-carbonitrile,
6-(4-(3-chloro-4-fluorophenyl)-1-(2-cyclopropylethyl)-1H-imidazol-5-yl)imidazo[1,2-b]pyridazine-3-carbonitrile,
6-(4-(3-chloro-4-fluorophenyl)-1-((1-methylcyclopropyl)methyl)-1H-imidazol-5-yl)imidazo[1,2-b]pyridazine-3-carbonitrile,
(R)-6-(4-(3-chloro-4-fluorophenyl)-1-(3,3-difluorocyclopentyl)-1H-imidazol-5-yl)imidazo[1,2-b]pyridazine-3-carbonitrile,
(S)-6-(4-(3-chloro-4-fluorophenyl)-1-(3,3-difluorocyclopentyl)-1H-imidazol-5-yl)imidazo[1,2-b]pyridazine-3-carbonitrile,
6-(1-(3-fluorocyclobutyl)-4-(4-fluorophenyl)-1H-imidazol-5-yl)imidazo[1,2-b]pyridazine-3-carbonitrile,
(S)-6-(1-(1-fluorobutan-2-yl)-4-(4-fluorophenyl)-1H-imidazol-5-yl)imidazo[1,2-b]pyridazine-3-carbonitrile,
6-(4-(3-chloro-4-fluorophenyl)-1-(3-fluorocyclobutyl)-1H-imidazol-5-yl)imidazo[1,2-b]pyridazine-3-carbonitrile,
6-(1-(2,2-difluoroethyl)-4-(4-fluorophenyl)-1H-imidazol-5-yl)imidazo[1,2-b]pyridazine-3-carboxamide,
6-(1-(3,3-difluorocyclobutyl)-4-(4-fluorophenyl)-1H-imidazol-5-yl)imidazo[1,2-b]pyridazine-3-carboxamide,
6-(4-(4-fluorophenyl)-1-(3,3,3-trifluoropropyl)-1H-imidazol-5-yl)imidazo[1,2-b]pyridazine-3-carboxamide,
6-(1-(3,3-difluorocyclopentyl)-4-(4-fluorophenyl)-1H-imidazol-5-yl)imidazo[1,2-b]pyridazine-3-carboxamide,
6-(1-cyclopropyl-4-(4-fluorophenyl)-1H-imidazol-5-yl)imidazo[1,2-b]pyridazine-3-carboxamide,
6-(1-(4,4-difluorocyclohexyl)-4-(4-fluorophenyl)-1H-imidazol-5-yl)imidazo[1,2-b]pyridazine-3-carboxamide,
6-(1-(2-fluoroethyl)-4-(4-fluorophenyl)-1H-imidazol-5-yl)imidazo[1,2-b]pyridazine-3-carboxamide,
6-(1-ethyl-4-(4-fluorophenyl)-1H-imidazol-5-yl)imidazo[1,2-b]pyridazine-3-carboxamide,
6-(4-(3-chloro-4-fluorophenyl)-1-(2,2-difluoroethyl)-1H-imidazol-5-yl)imidazo[1,2-b]pyridazine-3-carboxamide,
6-(4-(3-chloro-4-fluorophenyl)-1-(2-fluoroethyl)-1H-imidazol-5-yl)imidazo[1,2-b]pyridazine-3-carboxamide,
6-(4-(3-chloro-4-fluorophenyl)-1-(3,3,3-trifluoropropyl)-1H-imidazol-5-yl)imidazo[1,2-b]pyridazine-3-carboxamide,
6-(4-(3-chloro-4-fluorophenyl)-1-isopropyl-1H-imidazol-5-yl)imidazo[1,2-b]pyridazine-3-carboxamide,
6-(4-(3-chloro-4-fluorophenyl)-1-ethyl-1H-imidazol-5-yl)imidazo[1,2-b]pyridazine-3-carboxamide,
6-(4-(3-chloro-4-fluorophenyl)-1-(3,3-difluorocyclobutyl)-1H-imidazol-5-yl)imidazo[1,2-b]pyridazine-3-carboxamide,
6-(4-(4-fluorophenyl)-1-cis-3-hydroxycyclobutyl)-1H-imidazol-5-yl)imidazo[1,2-b]pyridazine-3-carboxamide,
6-(4-(4-fluorophenyl)-1-(2-isopropoxyethyl)-1H-imidazol-5-yl)imidazo[1,2-b]pyridazine-3-carboxamide,
(S)-6-(4-(4-fluorophenyl)-1-(1-hydroxybutan-2-yl)-1H-imidazol-5-yl)imidazo[1,2-b]pyridazine-3-carboxamide,
6-(4-(4-fluorophenyl)-1-(oxetan-3-yl)-1H-imidazol-5-yl)imidazo[1,2-b]pyridazine-3-carboxamide,
6-(1-(3-fluorocyclobutyl)-4-(4-fluorophenyl)-1H-imidazol-5-yl)imidazo[1,2-b]pyridazine-3-carboxamide,
(S)-6-(1-(1-fluorobutan-2-yl)-4-(4-fluorophenyl)-1H-imidazol-5-yl)imidazo[1,2-b]pyridazine-3-carboxamide,
6-(1-(1,3-dihydroxypropan-2-yl)-4-(4-fluorophenyl)-1H-imidazol-5-yl)imidazo[1,2-b]pyridazine-3-carboxamide,
6-(1-(1-cyclopropyl-2-methoxyethyl)-4-(4-fluorophenyl)-1H-imidazol-5-yl)imidazo[1,2-b]pyridazine-3-carboxamide,
6-(4-(4-fluorophenyl)-1-(3-hydroxy-3-methylbutyl)-1H-imidazol-5-yl)imidazo[1,2-b]pyridazine-3-carboxamide, 6-(4-(4-fluorophenyl)-1-(3-hydroxypropyl)-1H-imidazol-5-yl)imidazo[1,2-b]pyridazine-3-carboxamide, 6-(4-(4-fluorophenyl)-1-(2-hydroxyethyl)-1H-imidazol-5-yl)imidazo[1,2-b]pyridazine-3-carboxamide, 6-(4-(4-fluorophenyl)-1-methyl-1H-imidazol-5-yl)imidazo[1,2-b]pyridazine-3-carboxamide, 6-(4-(4-fluorophenyl)-1-isopropyl-1H-imidazol-5-yl)imidazo[1,2-b]pyridazine-3-carboxamide, 6-(1-(bicyclo[1.1.1]pentan-1-yl)-4-(4-fluorophenyl)-1H-imidazol-5-yl)imidazo[1,2-b]pyridazine-3-carboxamide, 6-(1-(2,2-difluoropropyl)-4-(4-fluorophenyl)-1H-imidazol-5-yl)imidazo[1,2-b]pyridazine-3-carboxamide, 6-(4-(3-chloro-4-fluorophenyl)-1-(2-hydroxyethyl)-1H-imidazol-5-yl)imidazo[1,2-b]pyridazine-3-carboxamide, 6-(4-(3-chloro-4-fluorophenyl)-1-(3-hydroxy-3-methylbutyl)-1H-imidazol-5-yl)imidazo[1,2-b]pyridazine-3-carboxamide, 6-(4-(3-chloro-4-fluorophenyl)-1-((1s,3s)-3-hydroxycyclobutyl)-1H-imidazol-5-yl)imidazo[1,2-b]pyridazine-3-carboxamide, 6-(4-(3-chloro-4-fluorophenyl)-1-(3-fluorocyclobutyl)-1H-imidazol-5-yl)imidazo[1,2-b]pyridazine-3-carboxamide, 6-(4-(3-chloro-4-fluorophenyl)-1-(3-hydroxypropyl)-1H-imidazol-5-yl)imidazo[1,2-b]pyridazine-3-carboxamide, 6-(4-(3-chloro-4-fluorophenyl)-1-(2-(pyrrolidin-1-yl)ethyl)-1H-imidazol-5-yl)imidazo[1,2-b]pyridazine-3-carboxamide, 6-(4-(3-chloro-4-fluorophenyl)-1-(tetrahydro-2H-pyran-4-yl)-1H-imidazol-5-yl)imidazo[1,2-b]pyridazine-3-carboxamide, (S)-6-(4-(3-chloro-4-fluorophenyl)-1-((tetrahydrofuran-2-yl)methyl)-1H-imidazol-5-yl)imidazo[1,2-b]pyridazine-3-carboxamide, 6-(4-(3-chloro-4-fluorophenyl)-1-(tetrahydrofuran-3-yl)-1H-imidazol-5-yl)imidazo[1,2-b]pyridazine-3-carboxamide, 6-(4-(3-chloro-4-fluorophenyl)-1-(2-methoxyethyl)-1H-imidazol-5-yl)imidazo[1,2-b]pyridazine-3-carboxamide, 6-(4-(3-chloro-4-fluorophenyl)-1-isopentyl-1H-imidazol-5-yl)imidazo[1,2-b]pyridazine-3-carboxamide, 6-(4-(3-chloro-4-fluorophenyl)-1-(3-chloropropyl)-1H-imidazol-5-yl)imidazo[1,2-b]pyridazine-3-carboxamide, 6-(4-(3-chloro-4-fluorophenyl)-1-(2-cyclobutylethyl)-1H-imidazol-5-yl)imidazo[1,2-b]pyridazine-3-carboxamide, 6-(4-(3-chloro-4-fluorophenyl)-1-(2,2-difluoropropyl)-1H-imidazol-5-yl)imidazo[1,2-b]pyridazine-3-carboxamide, 1-(4-(4-fluorophenyl)-5-(imidazo[1,2-b]pyridazin-6-yl)-1H-imidazol-1-yl)cyclopropanecarbonitrile, 6-(1-(1-(difluoromethyl)cyclopropyl)-4-(4-fluorophenyl)-1H-imidazol-5-yl)imidazo[1,2-b]pyridazine, methyl 3-(5-(3-cyanoimidazo[1,2-b]pyridazin-6-yl)-4-(4-fluorophenyl)-1H-imidazol-1-yl)azetidine-1-carboxylate, 6-(1-(1-acetylazetidin-3-yl)-4-(4-fluorophenyl)-1H-imidazol-5-yl)imidazo[1,2-b]pyridazine-3-carbonitrile, 6-(1-(1-(cyclopropanecarbonyl)azetidin-3-yl)-4-(4-fluorophenyl)-1H-imidazol-5-yl)imidazo[1,2-b]pyridazine-3-carbonitrile, N-(tert-butyl)-3-(5-(3-cyanoimidazo[1,2-b]pyridazin-6-yl)-4-(4-fluorophenyl)-1Himidazol-1-yl)azetidine-1-carboxamide, 6-(1-(1-(cyanomethyl)azetidin-3-yl)-4-(4-fluorophenyl)-1H-imidazol-5-yl)imidazo[1,2-b]pyridazine-3-carbonitrile, 6-(1-(1-(tert-butylcarbamoyl)azetidin-3-yl)-4-(4-fluorophenyl)-1H-imidazol-5-yl)imidazo[1,2-b]pyridazine-3-carboxamide, (6-(1-(2,2-difluoroethyl)-4-(4-fluorophenyl)-1H-imidazol-5-yl)imidazo[1,2-b]pyridazin-3-yl)methanamine, N-((6-(1-(2,2-difluoroethyl)-4-(4-fluorophenyl)-1H-imidazol-5-yl)imidazo[1,2-b]pyridazin-3-yl)methyl)acetamide, N-((6-(1-(2,2-difluoroethyl)-4-(4-fluorophenyl)-1H-imidazol-5-yl)imidazo[1,2-b]pyridazin-3-yl)methyl)cyclopropanecarboxamide, 1-(tert-butyl)-3-((6-(1-(2,2-difluoroethyl)-4-(4-fluorophenyl)-1H-imidazol-5-yl)imidazo[1,2-b]pyridazin-3-yl)methyl)urea, methyl ((6-(1-(2,2-difluoroethyl)-4-(4-fluorophenyl)-1H-imidazol-5-yl)imidazo[1,2-b]pyridazin-3-yl)methyl) carbamate, isopropyl ((6-(1-(2,2-difluoroethyl)-4-(4-fluorophenyl)-1H-imidazol-5-yl)imidazo[1,2-b]pyridazin-3-yl)methyl)carbamate, N-((6-(1-(2,2-difluoroethyl)-4-(4-fluorophenyl)-1H-imidazol-5-yl)imidazo[1,2-b]pyridazin-3-yl)methyl)pivalamide, 2-(6-(1-(2,2-difluoroethyl)-4-(4-fluorophenyl)-1H-imidazol-5-yl)imidazo[1,2-b]pyridazin-3-yl)propan-2-ol, 6-(1-(2,2-difluoroethyl)-4-(4-fluorophenyl)-1H-imidazol-5-yl)-N-methylimidazo[1,2-b]pyridazine-3-carboxamide, 6-(1-(2,2-difluoroethyl)-4-(4-fluorophenyl)-1H-imidazol-5-yl)-N,Ndimethylimidazo[1,2-b]pyridazine-3-carboxamide, N-cyclopropyl-6-(1-(2,2-difluoroethyl)-4-(4-fluorophenyl)-1H-imidazol-5-yl)imidazo[1,2-b]pyridazine-3-carboxamide, (6-(1-(2,2-difluoroethyl)-4-(4-fluorophenyl)-1H-imidazol-5-yl)imidazo[1,2-b]pyridazin-3-yl)methanol, methyl (6-(1-(2,2-difluoroethyl)-4-(4-fluorophenyl)-1H-imidazol-5-yl)imidazo[1,2-b]pyridazin-3-yl)carbamate, 1-(6-(1-(2,2-difluoroethyl)-4-(4-fluorophenyl)-1H-imidazol-5-yl)imidazo[1,2-b]pyridazin-3-yl)-2,2,2-trifluoroethanol, 1-(6-(1-(2,2-difluoroethyl)-4-(4-fluorophenyl)-1H-imidazol-5-yl)imidazo[1,2-b]pyridazin-3-yl)ethanol, 6-(1-(2,2-difluoroethyl)-4-(4-fluorophenyl)-1H-imidazol-5-yl)-3-(difluoromethyl) imidazo[1,2-b]pyridazine, 2-(6-(1-(2,2-difluoroethyl)-4-(4-fluorophenyl)-1H-imidazol-5-yl)imidazo[1,2-b]pyridazin-3-yl)ethanol, 6-(4-(3-cyanophenyl)-1-(2,2-difluoroethyl)-1H-imidazol-5-yl)imidazo[1,2-b]pyridazine-3-carbonitrile, 6-(1-(2,2-difluoroethyl)-4-phenyl-1H-imidazol-5-yl)imidazo[1,2-b]pyridazine-3-carbonitrile, 6-(4-(3,5-dichlorophenyl)-1-(2,2-difluoroethyl)-1H-imidazol-5-yl)imidazo[1,2-b]pyridazine-3-carbonitrile, N-(2-(5-(3-cyanoimidazo[1,2-b]pyridazin-6-yl)-1-(2,2-difluoroethyl)-1H-imidazol-4-yl)phenyl)methanesulfonamide, 6-(1-(2,2-difluoroethyl)-4-(p-tolyl)-1H-imidazol-5-yl)imidazo[1,2-b]pyridazine-3-carbonitrile, 6-(1-(2,2-difluoroethyl)-4-(4-methoxyphenyl)-1H-imidazol-5-yl)imidazo[1,2-b]pyridazine-3-carbonitrile, 6-(1-(2,2-difluoroethyl)-4-(3-(trifluoromethyl)phenyl)-1H-imidazol-5-yl)imidazo[1,2-b]pyridazine-3-carbonitrile,
6-(1-(2,2-difluoroethyl)-4-(4-(trifluoromethyl)phenyl)-1H-imidazol-5-yl)imidazo[1,2-b]pyridazine-3-carbonitrile,
N-(3-(5-(3-cyanoimidazo[1,2-b]pyridazin-6-yl)-1-(2,2-difluoroethyl)-1H-imidazol-4-yl)phenyl)acetamide,
6-(1-(2,2-difluoroethyl)-4-(2-(trifluoromethyl)phenyl)-1H-imidazol-5-yl)imidazo[1,2-b]pyridazine-3-carbonitrile,
6-(1-(2,2-difluoroethyl)-4-(2-hydroxyphenyl)-1H-imidazol-5-yl)imidazo[1,2-b]pyridazine-3-carbonitrile,
6-(1-(2,2-difluoroethyl)-4-(3-hydroxyphenyl)-1H-imidazol-5-yl)imidazo[1,2-b]pyridazine-3-carbonitrile,
6-(1-(2,2-difluoroethyl)-4-(4-hydroxyphenyl)-1H-imidazol-5-yl)imidazo[1,2-b]pyridazine-3-carbonitrile,
2-(5-(3-cyanoimidazo[1,2-b]pyridazin-6-yl)-1-(2,2-difluoroethyl)-1H-imidazol-4-yl)benzamide,
N-(3-(5-(3-cyanoimidazo[1,2-b]pyridazin-6-yl)-1-(2,2-difluoroethyl)-1H-imidazol-4-yl)phenyl)methanesulfonamide,
6-(1-(2,2-difluoroethyl)-4-(2-(hydroxymethyl)phenyl)-1H-imidazol-5-yl)imidazo[1,2-b]pyridazine-3-carbonitrile,
6-(1-(2,2-difluoroethyl)-4-(3-(methylsulfonyl)phenyl)-1H-imidazol-5-yl)imidazo[1,2-b]pyridazine-3-carbonitrile,
3-(5-(3-cyanoimidazo[1,2-b]pyridazin-6-yl)-1-(2,2-difluoroethyl)-1H-imidazol-4-yl)benzamide,
6-(1-(2,2-difluoroethyl)-4-(3-(hydroxymethyl)phenyl)-1H-imidazol-5-yl)imidazo[1,2-b]pyridazine-3-carbonitrile,
6-(4-([1,1'-biphenyl]-3-yl)-1-(2,2-difluoroethyl)-1H-imidazol-5-yl)imidazo[1,2-b]pyridazine-3-carbonitrile,
6-(4-(4-cyanophenyl)-1-(2,2-difluoroethyl)-1H-imidazol-5-yl)imidazo[1,2-b]pyridazine-3-carbonitrile,
6-(1-(2,2-difluoroethyl)-4-(3-(trifluoromethoxy)phenyl)-1H-imidazol-5-yl)imidazo[1,2-b]pyridazine-3-carbonitrile,
6-(1-(2,2-difluoroethyl)-4-(4-fluoro-3-(trifluoromethyl)phenyl)-1H-imidazol-5-yl)imidazo[1,2-b]pyridazine-3-carbonitrile,
6-(1-(2,2-difluoroethyl)-4-(4-fluoro-2-(trifluoromethyl)phenyl)-1H-imidazol-5-yl)imidazo[1,2-b]pyridazine-3-carbonitrile,
6-(1-(2,2-difluoroethyl)-4-(4-fluoro-3-methoxyphenyl)-1H-imidazol-5-yl)imidazo[1,2-b]pyridazine-3-carbonitrile,
6-(1-(2,2-difluoroethyl)-4-(4-isopropoxyphenyl)-1H-imidazol-5-yl)imidazo[1,2-b]pyridazine-3-carbonitrile,
6-(1-(2,2-difluoroethyl)-4-(3-(2-hydroxypropan-2-yl)phenyl)-1H-imidazol-5-yl)imidazo[1,2-b]pyridazine-3-carbonitrile,
6-(4-(3-cyano-4-fluorophenyl)-1-(2,2-difluoroethyl)-1H-imidazol-5-yl)imidazo[1,2-b]pyridazine-3-carbonitrile,
6-(1-(1-cyanocyclopropyl)-4-(4-fluorophenyl)-1H-imidazol-5-yl)imidazo[1,2-b]pyridazine-3-carbonitrile,
6-(1-(2-cyanoethyl)-4-(4-fluorophenyl)-1H-imidazol-5-yl)imidazo[1,2-b]pyridazine-3-carbonitrile,
6-(4-(4-fluorophenyl)-1-((1r,3s,5R,7S)-3-hydroxyadamantan-1-yl)-1H-imidazol-5-yl)imidazo[1,2-b]pyridazine-3-carbonitrile,
6-(4-(4-fluorophenyl)-1-neopentyl-1H-imidazol-5-yl)imidazo[1,2-b]pyridazine-3-carbonitrile,
2-(6-(1-ethyl-4-(4-fluorophenyl)-1H-imidazol-5-yl)imidazo[1,2-b]pyridazin-3-yl)propan-2-ol,
2-(6-(1-cyclopropyl-4-(4-fluorophenyl)-1H-imidazol-5-yl)imidazo[1,2-b]pyridazin-3-yl)propan-2-ol,
6-(1-(azetidin-3-yl)-4-(4-fluorophenyl)-1H-imidazol-5-yl)imidazo[1,2-b]pyridazine-3-carbonitrile,
tert-butyl 3-(5-(3-carbamoylimidazo[1,2-b]pyridazin-6-yl)-4-(4-fluorophenyl)-1Himidazol-1-yl)azetidine-1-carboxylate,
6-(1-(azetidin-3-yl)-4-(4-fluorophenyl)-1H-imidazol-5-yl)imidazo[1,2-b]pyridazine-3-carboxamide,
(6-(1-(2,2-difluoroethyl)-4-(4-fluorophenyl)-1H-imidazol-5-yl)imidazo[1,2-b]pyridazin-3-yl)methanamine, or
6-(1-(2,2-difluoroethyl)-4-(4-fluorophenyl)-1H-imidazol-5-yl)-3-vinylimidazo[1,2-b]pyridazine, or a pharmaceutically acceptable salt thereof.

5. The method according to claim 1, wherein the compound is of structure of formula (II°):

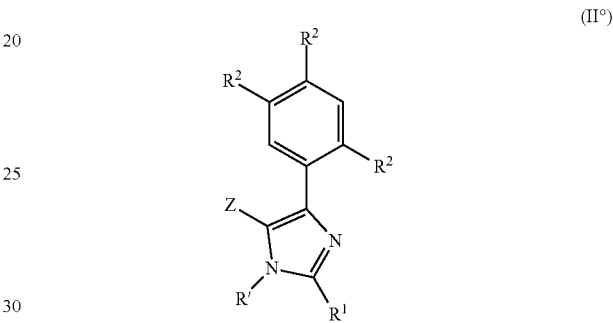

(II°)

or a pharmaceutically acceptable salt, or N-oxide thereof, or solvate or hydrate thereof, wherein
R' is hydrogen, $C_1$-$C_6$alkyl, $C_1$-$C_6$haloalkyl, —($C_0$-$C_{12}$alkyl)-Cak or —($C_0$-$C_6$alkyl)-Hca, each optionally substituted with 1 to 3 moieties that are each independently $C_1$-$C_6$alkyl, halogen, $C_1$-$C_6$haloalkyl, $C_1$-$C_6$alkyl-OR$^{S0}$, —OR$^{S0}$, —R$^{S0}$ or cyano;
wherein each R$^{S0}$ is independently hydrogen, $C_1$-$C_6$alkyl, $C_1$-$C_6$haloalkyl, —($C_0$-$C_6$alkyl)-Ar, —($C_0$-$C_6$alkyl)-Het, —($C_0$-$C_6$alkyl)-Cak, or —($C_0$-$C_6$alkyl)-Hca, wherein Ar, Het, Cak, Hca, alkyl, and haloalkyl are optionally substituted with $C_1$-$C_6$alkyl, halogen, $C_1$-$C_6$haloalkyl or cyano;
R$^1$ is hydrogen or $C_1$-$C_6$alkyl;
or R' and R$^1$ combined with the atoms to which they are attached form a five- to eight-membered Hca; and
each R$^2$ is independently hydrogen, halogen, —$C_1$-$C_6$alkyl, —$C_1$-$C_6$alkyl-OR$^{S2}$ or —OR$^{S2}$.

6. The method according to claim 1, wherein the compound is of structural formula (III°):

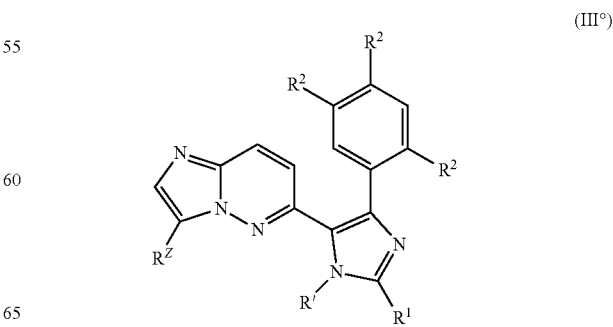

(III°)

or a pharmaceutically acceptable salt, or N-oxide thereof, or solvate or hydrate thereof, wherein R' is hydrogen, $C_1$-$C_6$alkyl, $C_1$-$C_6$haloalkyl, —($C_0$-$C_{12}$alkyl)-Cak or —($C_0$-$C_6$alkyl)-Hca, each optionally substituted with 1 to 3 moieties that are each independently $C_1$-$C_6$alkyl, halogen, $C_1$-$C_6$haloalkyl, $C_1$-$C_6$alkyl-OR$^{S0}$, —OR$^{S0}$, —R$^{S0}$ or cyano;

wherein each R$^{S0}$ is independently hydrogen, $C_1$-$C_6$alkyl, $C_1$-$C_6$haloalkyl, —($C_0$-$C_6$alkyl)-Ar, —($C_0$-$C_6$alkyl)-Het, —($C_0$-$C_6$alkyl)-Cak, or —($C_0$-$C_6$alkyl)-Hca, wherein Ar, Het, Cak, Hca, alkyl, and haloalkyl are optionally substituted with $C_1$-$C_6$alkyl, halogen, $C_1$-$C_6$haloalkyl or cyano;

R$^1$ is hydrogen or $C_1$-$C_6$alkyl;

or R' and R$^1$ combined with the atoms to which they are attached form a five- to eight-membered Hca; and each R$^2$ is independently hydrogen, halogen, —$C_1$-$C_6$alkyl, —$C_1$-$C_6$alkyl-OR$^{S2}$ or —OR$^{S2}$.

7. The method according to claim 1, wherein the compound is 6-(4-(4-fluorophenyl)-1-cis-3-hydroxycyclobutyl)-1H-imidazol-5-yl)imidazo[1,2-b]pyridazine-3-carbonitrile,

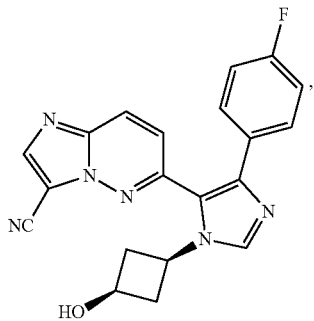 [SMILES: N#Cc1cnc2ccc(-c3c(-c4ccc(F)cc4)ncn3[C@H]3C[C@@H](O)C3)nn12 ; ","]

or a pharmaceutically acceptable salt thereof;

6-(4-(4-fluorophenyl)-1-(3-hydroxy-3-methylbutyl)-1H-imidazol-5-yl)imidazo[1,2-b]pyridazine-3-carbonitrile,

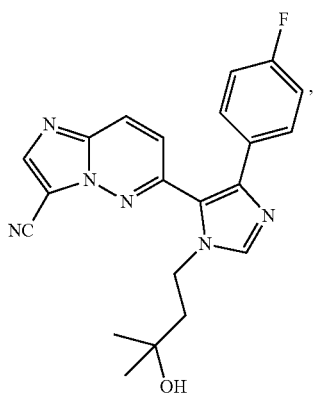 [SMILES: CC(C)(O)CCn1cnc(-c2ccc(F)cc2)c1-c1ccc2ncc(C#N)n2n1 ; ","]

or a pharmaceutically acceptable salt thereof;

6-(4-(4-fluorophenyl)-1-(2-hydroxyethyl)-1H-imidazol-5-yl)imidazo[1,2-b]pyridazine-3-carbonitrile,

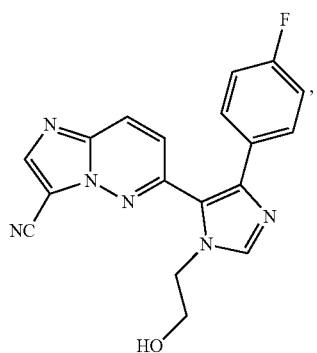 [SMILES: N#Cc1cnc2ccc(-c3c(-c4ccc(F)cc4)ncn3CCO)nn12 ; ","]

or a pharmaceutically acceptable salt thereof; or 6-(4-(4-fluorophenyl)-1-isopropyl-1H-imidazol-5-yl)imidazo[1,2-b]pyridazine-3-carbonitrile,

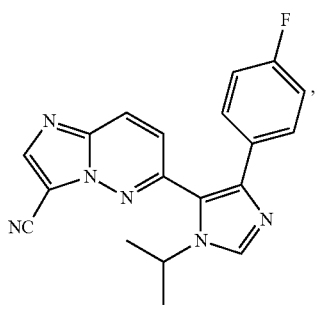 [SMILES: CC(C)n1cnc(-c2ccc(F)cc2)c1-c1ccc2ncc(C#N)n2n1 ; ","]

or a pharmaceutically acceptable salt thereof.

8. The method according to claim 1, wherein the compound is 6-(4-(3-chloro-4-fluorophenyl)-1-(2-hydroxyethyl)-1H-imidazol-5-yl)imidazo[1,2-b]pyridazine-3-carbonitrile,

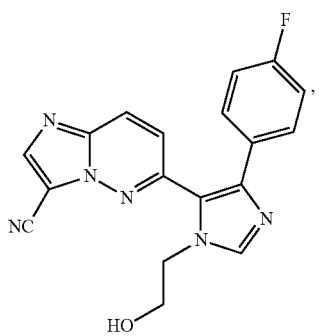 [SMILES: N#Cc1cnc2ccc(-c3c(-c4ccc(F)cc4)ncn3CCO)nn12 ; ","]

or a pharmaceutically acceptable salt thereof.

9. The method according to claim 1, wherein the compound is 6-(1-(2,2-difluoroethyl)-4-(4-fluorophenyl)-1H-imidazol-5-yl)imidazo[1,2-b]pyridazine-3-carboxamide,

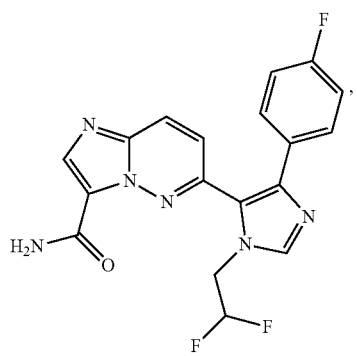 [SMILES: NC(=O)c1cnc2ccc(-c3c(-c4ccc(F)cc4)ncn3CC(F)F)nn12 ; ","]

or a pharmaceutically acceptable salt thereof; or
2-(6-(1-(2,2-difluoroethyl)-4-(4-fluorophenyl)-1H-imidazol-5-yl)imidazo[1,2-b]pyridazin-3-yl)propan-2-ol,

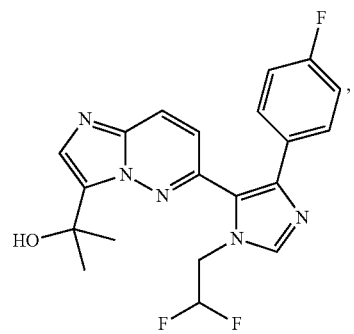 [SMILES: CC(C)(O)c1cnc2ccc(-c3c(-c4ccc(F)cc4)ncn3CC(F)F)nn12 ; ","]

or a pharmaceutically acceptable salt thereof.

10. The method of claim 1, wherein the cancer is selected from malignant tumor, brain carcinoma, kidney, liver, adrenal gland, bladder, breast, stomach, gastric tumors, ovaries, colon, rectum, prostate, pancreas, lung, vagina, thyroid, sarcoma, glioblastomas, multiple myeloma, gastrointestinal cancer, colorectal adenoma, head and neck carcinoma, melanoma, psoriasis, prostate hyperplasia, a neoplasia of epithelial character, lymphomas, a mammary carcinoma, or a leukemia.

11. The method of claim 1, wherein the cancer is melanoma, lung cancer, kidney cancer, bladder cancer, head and neck carcinoma and lymphomas.

12. The method of claim 4, wherein the cancer is selected from malignant tumor, brain carcinoma, kidney, liver, adrenal gland, bladder, breast, stomach, gastric tumors, ovaries, colon, rectum, prostate, pancreas, lung, vagina, thyroid, sarcoma, glioblastomas, multiple myeloma, gastrointestinal cancer, colorectal adenoma, head and neck carcinoma, melanoma, psoriasis, prostate hyperplasia, a neoplasia of epithelial character, lymphomas, a mammary carcinoma, or a leukemia.

13. The method of claim 4, wherein the cancer is melanoma, lung cancer, kidney cancer, bladder cancer, head and neck carcinoma and lymphomas.

14. The method of claim 6, wherein the cancer is selected from malignant tumor, brain carcinoma, kidney, liver, adrenal gland, bladder, breast, stomach, gastric tumors, ovaries, colon, rectum, prostate, pancreas, lung, vagina, thyroid, sarcoma, glioblastomas, multiple myeloma, gastrointestinal cancer, colorectal adenoma, head and neck carcinoma, melanoma, psoriasis, prostate hyperplasia, a neoplasia of epithelial character, lymphomas, a mammary carcinoma, or a leukemia.

15. The method of claim 6, wherein the cancer is melanoma, lung cancer, kidney cancer, bladder cancer, head and neck carcinoma and lymphomas.

16. The method of claim 7, wherein the cancer is selected from malignant tumor, brain carcinoma, kidney, liver, adrenal gland, bladder, breast, stomach, gastric tumors, ovaries, colon, rectum, prostate, pancreas, lung, vagina, thyroid, sarcoma, glioblastomas, multiple myeloma, gastrointestinal cancer, colorectal adenoma, head and neck carcinoma, melanoma, psoriasis, prostate hyperplasia, a neoplasia of epithelial character, lymphomas, a mammary carcinoma, or a leukemia.

17. The method of claim 7, wherein the cancer is melanoma, lung cancer, kidney cancer, bladder cancer, head and neck carcinoma and lymphomas.

18. The method of claim 8, wherein the cancer is selected from malignant tumor, brain carcinoma, kidney, liver, adrenal gland, bladder, breast, stomach, gastric tumors, ovaries, colon, rectum, prostate, pancreas, lung, vagina, thyroid, sarcoma, glioblastomas, multiple myeloma, gastrointestinal cancer, colorectal adenoma, head and neck carcinoma, melanoma, psoriasis, prostate hyperplasia, a neoplasia of epithelial character, lymphomas, a mammary carcinoma, or a leukemia.

19. The method of claim 8, wherein the cancer is melanoma, lung cancer, kidney cancer, bladder cancer, head and neck carcinoma and lymphomas.

20. The method of claim 9, wherein the cancer is selected from benign or malignant tumor, brain carcinoma, kidney, liver, adrenal gland, bladder, breast, stomach, gastric tumors, ovaries, colon, rectum, prostate, pancreas, lung, vagina, thyroid, sarcoma, glioblastomas, multiple myeloma, gastrointestinal cancer, colorectal adenoma, head and neck carcinoma, melanoma, psoriasis, prostate hyperplasia, a neoplasia of epithelial character, lymphomas, a mammary carcinoma, or a leukemia.

21. The method of claim 9, wherein the cancer is melanoma, lung cancer, kidney cancer, bladder cancer, head and neck carcinoma and lymphomas.

* * * * *